US012258332B2

(12) United States Patent
Busch et al.

(10) Patent No.: US 12,258,332 B2
(45) Date of Patent: Mar. 25, 2025

(54) ASGPR CELL SURFACE RECEPTOR BINDING COMPOUNDS AND CONJUGATES

(71) Applicant: Lycia Therapeutics, Inc., South San Francisco, CA (US)

(72) Inventors: Brett Bradley Busch, San Diego, CA (US); Justin Thomas Ernst, San Diego, CA (US); Garrick K. Packard, San Diego, CA (US); Jason G. Lewis, Castro Valley, CA (US); Eric D. Turtle, Belmont, CA (US)

(73) Assignee: Lycia Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 18/301,025

(22) Filed: Apr. 14, 2023

(65) Prior Publication Data

US 2023/0250091 A1 Aug. 10, 2023

Related U.S. Application Data

(63) Continuation of application No. PCT/US2022/037227, filed on Jul. 14, 2022.

(60) Provisional application No. 63/221,918, filed on Jul. 14, 2021.

(51) Int. Cl.
*C07D 405/04* (2006.01)
*C07D 405/12* (2006.01)
*C07D 405/14* (2006.01)
*C07D 493/08* (2006.01)

(52) U.S. Cl.
CPC .......... *C07D 405/04* (2013.01); *C07D 405/12* (2013.01); *C07D 405/14* (2013.01); *C07D 493/08* (2013.01)

(58) Field of Classification Search
CPC .. C07D 405/04; C07D 405/12; C07D 405/14; C07D 493/08
See application file for complete search history.

(56) References Cited

U.S. PATENT DOCUMENTS

| | | | |
|---|---|---|---|
| 6,844,319 B1 | 1/2005 | Poelstra et al. |
| 7,422,902 B1 | 9/2008 | Wheeler et al. |
| 8,716,239 B2 | 5/2014 | DeFrees et al. |
| 8,741,291 B2 | 6/2014 | Bhat et al. |
| 8,834,842 B2 | 9/2014 | Endocyte |
| 8,962,573 B2 | 2/2015 | Garcia et al. |
| 9,340,553 B2 | 5/2016 | Liras et al. |
| 9,493,545 B2 | 11/2016 | Finnis et al. |
| 9,545,450 B2 | 1/2017 | Do |
| 9,545,451 B2 | 1/2017 | Papadopoulos et al. |
| 9,617,293 B2 | 4/2017 | Liras et al. |
| 9,993,546 B2 | 6/2018 | August et al. |
| 10,385,320 B2 | 8/2019 | Kay et al. |
| 10,633,428 B2 | 4/2020 | Delahay et al. |
| 11,555,061 B2 | 1/2023 | Finnis et al. |
| 11,787,865 B2 | 10/2023 | Bertozzi et al. |
| 2002/0107224 A1* | 8/2002 | Tomiyama ......... A61K 31/7048 514/79 |
| 2003/0049203 A1 | 3/2003 | Elmaleh et al. |
| 2003/0152560 A1 | 8/2003 | Selden et al. |
| 2003/0211113 A1 | 11/2003 | Kakkis et al. |
| 2004/0009907 A1 | 1/2004 | Alsobrook et al. |
| 2004/0180046 A1 | 9/2004 | Himawan |
| 2006/0286087 A1 | 12/2006 | Kakkis et al. |
| 2007/0077197 A1 | 4/2007 | Wedeking et al. |
| 2007/0249682 A1 | 10/2007 | Zheng et al. |
| 2008/0081831 A1 | 4/2008 | Bour et al. |
| 2009/0238818 A1 | 9/2009 | Kakkis et al. |
| 2009/0258420 A1 | 10/2009 | van Vlijmen et al. |
| 2010/0247548 A1 | 9/2010 | Shepard et al. |
| 2011/0104076 A1 | 5/2011 | Shull |
| 2011/0104103 A1 | 5/2011 | Heetebrij et al. |

(Continued)

FOREIGN PATENT DOCUMENTS

| | | |
|---|---|---|
| CN | 112236169 A | 1/2021 |
| CN | 117915956 A | 4/2024 |

(Continued)

OTHER PUBLICATIONS

Yoo et al, N-Acetylgalactosamino dendrons as clearing agents to enhance liver targeting of model antibody-fusion protein, 2013, Bioconjugate Chemistry, vol. 24, No. 12, p. 2088-2103 (Year: 2013).*

Ahn, G. et al., "Lysosome Targeting Chimeras (LYTACs) That Engage a Liver-Specific Asialoglycoprotein Receptor for Targeted Protein Degradation" Jul. 30, 2020, pp. 1-23.

Ahn, G. et al., "LYTACs that engage the asialoglycoprotein receptor for targeted protein degradation," Nature Chemical Biology, vol. 17, No. 9, Mar. 25, 2021, pp. 937-946.

Aldhoun, M. et al., "Click Azide-Nitrile Cycloaddition as a New Ligation Tool for the Synthesis of Tetrazole-Tethered C-Glycosyl α-Amino Acids," The Journal of Organic Chemistry, vol. 73, No. 24, Dec. 19, 2008, pp. 9565-9575.

Attia, A.M.E., "Synthesis of thiopyridines and their hydrogenated thioglycosides via piperidinium salts," Tetrahedron, vol. 58, No. 7, Feb. 11, 2002, pp. 1399-1405.

(Continued)

*Primary Examiner* — Kamal A Saeed
*Assistant Examiner* — Karen Cheng
(74) *Attorney, Agent, or Firm* — Sheppard Mullin Richter & Hampton LLP

(57) ABSTRACT

The present disclosure provides a class of compounds including a ligand moiety that specifically binds to a cell surface asialoglycoprotein receptor (ASGPR). The cell surface ASGPR binding compounds can trigger the receptor to internalize into the cell of a bound compound. The ligand moieties of this disclosure can be linked to a variety of moieties of interest without impacting the specific binding to, and function of, the cell surface receptor ASGPR. Also provided are compounds that are conjugates of the ligand moieties linked to a biomolecule, such as an antibody, which conjugates can harness cellular pathways to remove specific proteins of interest from the cell surface or from the extracellular milieu. Also provided herein methods of using the conjugates to target a polypeptide of interest for sequestration and/or lysosomal degradation.

18 Claims, 6 Drawing Sheets

(56) References Cited

U.S. PATENT DOCUMENTS

| | | |
|---|---|---|
| 2011/0250195 A1 | 10/2011 | Matthews et al. |
| 2011/0275576 A1 | 11/2011 | Chang et al. |
| 2011/0294980 A1 | 12/2011 | Nakanishi et al. |
| 2012/0121592 A1 | 5/2012 | Sangkon et al. |
| 2013/0144045 A1 | 6/2013 | Papot et al. |
| 2014/0065066 A1 | 3/2014 | Low et al. |
| 2014/0212423 A1 | 7/2014 | Hanzatian et al. |
| 2015/0094334 A1 | 4/2015 | Barnham et al. |
| 2015/0329555 A1 | 11/2015 | Liras et al. |
| 2016/0002343 A1 | 1/2016 | Hanzatian et al. |
| 2016/0060354 A1 | 3/2016 | Avila et al. |
| 2016/0082112 A1 | 3/2016 | Spiegel et al. |
| 2016/0108133 A1 | 4/2016 | Armstrong et al. |
| 2016/0136299 A1 | 5/2016 | Avila et al. |
| 2016/0166679 A1 | 6/2016 | Low et al. |
| 2016/0207953 A1 | 7/2016 | Liras et al. |
| 2016/0297861 A1 | 10/2016 | Poelstra et al. |
| 2016/0362450 A1 | 12/2016 | Schteingart et al. |
| 2017/0066832 A1 | 3/2017 | Pardridge et al. |
| 2017/0218378 A1 | 8/2017 | Muro Galindo et al. |
| 2017/0232076 A1 | 8/2017 | Concino et al. |
| 2018/0265534 A1 | 9/2018 | Morere et al. |
| 2018/0318440 A1 | 11/2018 | Khan et al. |
| 2018/0355017 A1 | 12/2018 | Baik et al. |
| 2019/0002852 A1 | 1/2019 | Vitalis et al. |
| 2019/0038777 A1 | 2/2019 | Donsante et al. |
| 2019/0060481 A1 | 2/2019 | Avila et al. |
| 2019/0112588 A1 | 4/2019 | Baik et al. |
| 2019/0224282 A1 | 7/2019 | LeBowitz et al. |
| 2019/0328902 A1 | 10/2019 | Park et al. |
| 2019/0345248 A1 | 11/2019 | Ab et al. |
| 2021/0145974 A1 | 5/2021 | Spiegel et al. |
| 2021/0189392 A1 | 6/2021 | Beigelman et al. |
| 2022/0025057 A1 | 1/2022 | Bertozzi et al. |
| 2022/0177604 A1 | 6/2022 | Saunders et al. |
| 2022/0195011 A1 | 6/2022 | Baik et al. |
| 2022/0023434 A1 | 7/2022 | Bertozzi et al. |
| 2022/0332789 A1 | 10/2022 | Owen et al. |
| 2023/0097256 A1 | 3/2023 | Saulnier et al. |
| 2023/0158155 A1 | 5/2023 | Busch et al. |
| 2023/0226214 A1 | 7/2023 | Aivazian et al. |
| 2023/0279426 A1 | 9/2023 | Aivazian et al. |

FOREIGN PATENT DOCUMENTS

| | | |
|---|---|---|
| EP | 2171071 B1 | 8/2015 |
| EP | 2448600 | 3/2016 |
| EP | 2009990 B1 | 9/2016 |
| EP | 3350192 | 8/2019 |
| EP | 3036257 B1 | 10/2019 |
| EP | 3773727 A1 | 2/2021 |
| EP | 4359414 | 5/2024 |
| EP | 4359430 | 5/2024 |
| EP | 4370156 | 5/2024 |
| JP | 2019504888 A | 2/2019 |
| WO | WO 1991014438 A1 | 10/1991 |
| WO | WO 1993006216 A1 | 4/1993 |
| WO | WO 199513095 A | 5/1995 |
| WO | WO 1995014036 A1 | 5/1995 |
| WO | WO 1999/040214 A2 | 8/1999 |
| WO | WO 2001050127 A2 | 7/2001 |
| WO | WO 2003/031464 A2 | 4/2003 |
| WO | WO 2004104015 A2 | 12/2004 |
| WO | WO 2005021064 A2 | 3/2005 |
| WO | WO 2006045505 A1 | 5/2006 |
| WO | WO 2006052668 A2 | 5/2006 |
| WO | WO 2007011217 A2 | 1/2007 |
| WO | WO 2008089339 | 7/2008 |
| WO | WO 2010033733 A1 | 3/2010 |
| WO | WO 2010075010 | 7/2010 |
| WO | WO 2010125445 | 11/2010 |
| WO | WO 2011000958 A1 | 1/2011 |
| WO | WO 2011038234 A2 | 3/2011 |
| WO | WO 2011058245 A1 | 5/2011 |
| WO | WO 2013/138400 A1 | 9/2013 |
| WO | WO 2014082080 A2 | 5/2014 |
| WO | WO2015/042447 * | 3/2015 |
| WO | WO 2015069587 A2 | 5/2015 |
| WO | WO 2015/140648 A2 | 9/2015 |
| WO | WO 2016/025519 A1 | 2/2016 |
| WO | WO 2016040305 A1 | 3/2016 |
| WO | WO 2017/007796 A1 | 1/2017 |
| WO | WO 2017/046535 A1 | 3/2017 |
| WO | WO 2017058944 | 4/2017 |
| WO | WO 2017134197 | 8/2017 |
| WO | WO 2017136202 A1 | 8/2017 |
| WO | WO 2017212019 A1 | 12/2017 |
| WO | WO 2019/199634 A1 | 10/2019 |
| WO | WO 2019199621 A1 | 10/2019 |
| WO | WO 2020/093053 A1 | 5/2020 |
| WO | WO 2020/132100 A1 | 6/2020 |
| WO | WO 2020257760 A1 | 12/2020 |
| WO | WO 2021005210 A1 | 1/2021 |
| WO | WO2021/072246 * | 4/2021 |
| WO | WO 2021/072246 A1 | 4/2021 |
| WO | WO 2021/072269 A1 | 4/2021 |
| WO | WO 2021/142377 A2 | 7/2021 |
| WO | WO 2021/155317 A1 | 8/2021 |
| WO | WO 2021/156792 A1 | 8/2021 |
| WO | WO 2021/263060 A2 | 12/2021 |
| WO | WO 2021/263061 A2 | 12/2021 |
| WO | WO 2021262693 A1 | 12/2021 |
| WO | WO 2022/035997 A1 | 2/2022 |
| WO | WO 2022/150721 A1 | 7/2022 |
| WO | WO 2022/157626 A1 | 7/2022 |
| WO | WO 2022/178425 A1 | 8/2022 |
| WO | WO 2022/178428 A1 | 8/2022 |
| WO | WO 2022/192478 A1 | 9/2022 |
| WO | WO 202212593 A1 | 10/2022 |
| WO | WO 2022/235699 A2 | 11/2022 |
| WO | WO 2023288015 A1 | 1/2023 |
| WO | WO 2023009554 A1 | 2/2023 |
| WO | WO 2023/028338 A2 | 3/2023 |
| WO | WO 2023028590 A1 | 3/2023 |
| WO | WO 2023028597 A1 | 3/2023 |
| WO | WO 2023178202 A2 | 9/2023 |
| WO | WO 2024098039 A2 | 5/2024 |

OTHER PUBLICATIONS

Baenziger, J.U. et al., "Galactose and N-acetylgalactosamine-specific endocytosis of glycopeptides by isolated rat hepatocytes," Cell 22(2 pt. 2), Nov. 1980, pp. 611-620.

Banik, S. et al., "Lysosome Targeting Chimeras (LYTACs) for the Degradation of Secreted and Membrane Proteins," Nov. 20, 2019, pp. 1-64. doi.org/10.26434/chemrxiv.7927061.v2.

Banik, S.M. et al., "Lysosome-targeting chimaeras for degradation of extracellular proteins" Nature, vol. 584, Jul. 29, 2020, pp. 291-297.

Bannister, B., "The Synthesis and Biological Activities of Some Analogs of Streptozotocin," The Journal of Antibiotics, vol. 25, No. 7, Jul. 25, 1972, pp. 377-386.

Barragan, V. et al., "A mannose-6-phosphonate-cholesterylamine conjugate as a specific molecular adhesive linking cancer cells with vesicles," Chemical Communications, No. 1, Jan. 1, 2001, pp. 85-86.

Caianiello, D. et al., "Bifunctional small molecules that mediate the degradation of extracellular proteins" Aug. 4, 2020, pp. 1-17. 10.26434/chemrxiv.12732689.v2.

D'Souza, A.A. et al., "Asialoglycoprotein receptor mediated hepatocyte targeting—strategies and applications," Journal of Controlled Release, vol. 203, Apr. 10, 2015, pp. 126-139.

Gary-Bobo, M et al., "Mannose 6-phosphate receptor targeting and its applications in human diseases," Current Medicinal Chemistry 14(28), Feb. 2007, pp. 2945-2953.

Ghosh, P. et al., "Mannose 6-Phosphate Receptors: New Twists in the Tale," Nature, vol. 4, Mar. 2003, pp. 202-212.

Giguère, D. et al., "Synthesis of stable and selective inhibitors of human galectins-1 and -3," Bioorganic & Medicinal Chemistry, vol. 16, Jun. 26, 2008, pp. 7811-7823.

(56) References Cited

OTHER PUBLICATIONS

Huang, X. et al., "Well-Defined Multivalent Ligands for Hepatocytes Targeting via Asialoglycoprotein Receptor" Bioconjug Chem., 28(2), Dec. 14, 2016, pp. 283-295.
Li, S. et al., "Gram-scale production of sugar nucleotides and their derivatives," Green Chemistry, vol. 23, No. 7, Mar. 12, 2021, pp. 2628-2633.
Liu, C., "Design, Synthesis and Evaluation of Bivalent Inhibitors of Trehalose-6-Phosphate Phosphatase," Doctor of Philosophy Dissertation, The University of New Mexico, Jun. 2015, pp. 1-232.
Mamidyala, S.K. et al., "Glycomimetic Ligands for the Human Asialoglycoprotein Receptor," J. Am. Chem. Soc. 134(4), Jan. 24, 2012, pp. 1978-1981.
Nair, J.K. et al., "Multivalent N-Acetylgalactosamine-Conjugated siRNA Localizes in Hepatocytes and Elicits Robust RNAi-Mediated Gene Silencing," Journal of the American Chemical Society, vol. 136, Dec. 1, 2014, pp. 16958-16961.
PCT International Search Report and Written Opinion, PCT Application No. PCT/US2022/037227, Nov. 2, 2022, 30 pages.
PCT International Search Report and Written Opinion, PCT Application No. PCT/US2022/037196, Oct. 26, 2022, 21 pages.
PCT International Search Report and Written Opinion, PCT Application No. PCT/US21/12846, May 3, 2021, 18 pages.
PCT International Search Report and Written Opinion, PCT Application No. PCT/US2019/067228, Mar. 11, 2020, eight pages.
Rensen, P.C.N et al., "Design and Synthesis of Novel N-Acetylgalactosamine-Terminated Glycolipids for Targeting of Lipoproteins to the Hepatic Asialoglycoprotein Receptor," Journal of Medicinal Chemistry, vol. 47, No. 23, Oct. 6, 2004, pp. 5798-5808.
Rensen, P.C.N. et al., "Determination of the Upper Size Limit for Uptake and Processing of Ligands by the Asialoglycoprotein Receptor on Hepatocytes in Vitro and in Vivo," Glycobiology and Extracellular Matrices, vol. 276, Iss. 40, Oct. 2001, pp. P37577-37584.
Sanhueza, C.A. et al., "Efficient Liver Targeting by Polyvalent Display of a Compact Ligand for the Asialoglycoprotein Receptor," Journal of the American Chemical Society.
Schwartz, A.L. et al., "Characterization of the asialoglycoprotein receptor in a continuous hepatoma line", Journal of Biological Chemistry, vol. 256, Iss. 17, Sep. 10, 1981, pp. 8878-8881.
Stokmaier, D. et al., "Design, synthesis and evaluation of monovalent ligands for the asialoglycoprotein receptor (ASGP-R)," Bioorganic & Medical Chemistry, vol. 17, No. 20, Aug. 29, 2009, pp. 7254-7264.
Stokmaier, D., "Targeting Hepatocytes via the Asialoglycoprotein-Receptor," Inaugural Dissertation, Basel, Dec. 14, 2010, pp. 3-149.
Wang, Y. et al., "Pharmacokinetics and Clinical Pharmacology Considerations of GalNAc3-Conjugated Antisense Oligonucleotides," Expert Opinion on Drug Metabolism & Toxicology, vol. 15, No. 6, Jun. 2019, pp. 475-485.
Yang, N. et al., "HPMA Polymer-Based Site-Specific Delivery of Oligonucleotides to Hepatic Stellate Cells," Bioconjugate Chem. vol. 20, Jan. 9, 2009, pp. 213-221.
Ye, Z. et al., "Targeted Delivery of a Triplex-Forming Oligonucleotide to Hepatic Stellate Cells," Biochemistry, vol. 44, Feb. 25, 2005, pp. 4466-4476.
Zhou, Y. et al. "Development of Triantennary N-Acetylgalactosamine Conjugates as Degraders for Extracellular Proteins" ACS Cent. Sci. Vol. 7, No. 3, Mar. 4, 2021, pp. 499-506.
Agarwal, V. et al., "Enhancing the efficacy of cation-independent mannose 6-phosphate receptor inhibitors by intracellular delivery," Chemical Communications, vol. 52, Oct. 19, 2015, DD. 327-330.
Andreev, J. et al., "Bispecific Antibodies and Antibody-Drug Conjugates (ADCs) Bridging HER2 and Prolactin Receptor Improve Efficacy of HER2 ADCs," Molecular Cancer Therapeutics, Jan. 20, 2017, DD. 681-693.
Beljaars, L. et al., "Albumin Modified With Mannose 6-Phosphate: A Potential Carrier for Selective Delivery of Antifibrotic Drugs to Rat and Human Hepatic Stellate Cells," Hepatology vol. 29, No. 5, May 1999, pp. 1486-1493.

Borden et al. (1990) "Acidification-dependent Dissociation of Endocytosed Insulin Precedes That of Endocytosed Oroteins Bearing the Mannose 6-Phosphate Recognition Marker" The Journal of Bio. Chem. 1265(15):8497-8504_.
Braulke, T. et al., "Sorting of lysosomal proteins," Biochimica et Biophysica Acta, vol. 1793, Nov. 12, 2008, DD. 605-614.
Cotton, A. et al. "Development of Antibody-Based PROTACs for the Degradation of the Cell-Surface Immune Checkpoint Protein PD-L1" Journal of the American Chemical Society 2021, 143, 593-598.
Das, S. et al., "Controlled Synthesis of End-Functionalized Mannose-6-phosphate Glycopolypeptides for Lysosome Targeting," ACS Macro Letters, vol. 5, Jun. 22, 2016, DD. 809-813.
De Goeij, B. et al., "Efficient Payload Delivery by a Bispecific Antibody-Drug Conjugate Targeting HER2 and CD63," Molecular Cancer Therapeutics 15(11 ), Aug. 24, 2016, pp. 2688-2697.
Devanaboyina, S.C. et al., "Engineered clearing agents for the selective depletion of antigen-specific antibodies," Nature Communications 8(15314), May 31, 2017, pp. 1-6.
Distler, J.J. et al., "The Binding Specificity of High and Low Molecular Weight Phosphomannosyl Receptors from Bovine Testes," The Journal of Biological Chemistry, vol. 266, No. 32, Nov. 15, 1991, pp. 21687-21692.
Ganesan et al., (2011) "Rapid and Efficient Clearance of Blood-borne Virus by Liver Sinusoidal Endothelium" PLoS, 7(p): e1002281.
Jeanjean, A. et al., "Synthesis of new sulfonate and phosphonate derivatives for cation-independent mannose 6-phosphate receptor targeting," Bioorg Med Chem Lett 18(23), Nov. 20, 2008, DD. 6240-6243.
Kang, J-Y. et al., "Lysosomal Targeting Enhancement by Conjugation of Glycopeptides Containing Mannose-6-phosphate Glycans Derived from Glvcoengineered Yeast," Scientific Reports 8(8730), Jun. 7, 2018, pp. 1-14.
Kim, K-W. et al., "Macrophage migration inhibitory factor: a potential therapeutic target for rheumatoid arthritis", The Korean Journal of Internal Medicine, vol. 31, Jul. 2016, DD. 634-642.
Kroetsch, A. et al., "Engineered pH-dependent recycling antibodies enhance elimination of Staphylococcal enterotoxin B superantigen in mice," MABS, vol. 11, No. Dec. 2018, pp. 411-421.
Lee, J.H. et al., "Receptor mediated uptake of peptides that bind the human transferrin receptor", European Journal of Biochemistry, 268(7), Dec. 20, 2001, pp. 2004-2012.
Maga, J.A. et al., "Glycosylation-independent Lysosomal Targeting of Acid a-Glucosidase Enhances Muscle Glycogen Clearance in Pompe Mice," The Journal of Biological Chemistry, vol. 288, No. 3, Jan. 18, 2013, DD. 1428-1438.
Matsuda, S. et al., "siRNA conjugates carrying sequentially assembled trivalent N-acetylgalactosamine linked through nucleosides elicit robust gene silencing in vivo in hepatocytes," ACS Chem Biol., vol. 10, Mar. 2, 2015, DD. 1181-1187.
Mezo, A.R. et al., "Reduction of lgG in nonhuman primates by a peptide antagonist of the neonatal Fe receptor FcRn", Proceedings of the National Academy of Sciences 105(7), Feb. 19, 2008, DD. 2337-2342.
Mu, L-M. et al., "Lipid vesicles containing transferrin receptor binding peptide TfR-T12 and octa-arginine conjugate stearyl-R8 efficiently treat brain glioma along with glioma stem cells", Scientific Reports, 7(1), Jun. 14, 2017, DD. 1-12.
Palaniappan, K.K. et al., "Chemical Glycoproteomics," Chemical Reviews, vol. 116, Nov. 18, 2016, pp. 14277-14306.
Prakash, J. et al., "Tumor-targeted intracellular delivery of anticancer drugs through the mannose-6-phosphate/insulin-like growth factor II receptor," International Journal of Cancer, vol. 126, Sep. 30, 2009, DD. 1966-1981.
Pujol, A.M. et al., "Hepatocyte Targeting and Intracellular Copper Chelation by a Thiol-Containing Glycocyclopeptide," J. Am. Chem. Soc., vol. 133, No. 2, Dec. 14, 2010, pp. 286-296.
Reddy Bonam, S. et al., "Lysosomes as a therapeutic target," Nature Reviews, vol. 18, Dec. 2019, pp. 923-948.
Reidy, T. et al., "Homotrimeric macrophage migration inhibitory factor (MIF) drives inflammatory responses in the corneal epithe-

(56) References Cited

OTHER PUBLICATIONS lium by promoting caveolin-rich platform assembly in response to infection", Journal of Biological Chemistry, vol. 288, Iss. 12, Mar. 2013, DD. 8269-8278.
Ribeiro, S.M.F. et al., "The Activation Sequence of Thrombospondin-1 Inter-acts with the Latency-associated Peptide to Regulate Activation of Latent Transforming Growth Factor", The Journal of Biological Chemistry, vol. 274, Iss. 19, May 1999, pp. 13586-13593.
Roseng, L. et al., "Uptake, intracellular transport, and degradation of polyethylene glycol-modified asialofetuin in hepatocytes," The Journal of Biological Chemistry 267(32), Nov. 1992, pp. 22987-22993.
Rullo, A.F. et al., "Re-engineering the Immune Response to Metastatic Cancer: Antibody-Recruiting Small Molecules Targeting the Urokinase Receptor", Angew. Chem. Int. Ed, Feb. 15, 2016, pp. 3642-3646.
Saftig, P. et al., "Lysosome biogenesis and lysosomal membrane proteins: trafficking meets function," Nature Reviews, vol. 10, Sep. 2009, DD. 623-635.
Sakamoto, K. et al., "A novel LRP1-binding peptide L57 that crosses the blood brain barrier", Biochemistry and Biophysics Reports, vol. 12, Dec. 2017, pp. 135-139.
Sahagian and Neufeld (1983) "Biosynthesis and Turnover of the mannose 6-Phosphate Receptor in Cultured Chinese Hamster Ovary Cells" The Journal of Bio. Chem. 258(11):7121-7128.
Segers, F.M.E. et al., "Scavenger Receptor-Al-Targeted Iron Oxide Nanoparticles for In Vivo MRI Detection of Atherosclerotic Lesions", Arteriosclerosis, Thrombosis, and Vascular BiolOQY, 32(4), Jan. 26, 2012, DD. 971-978.
Tian, W. et al., "The glycosylation design space for recombinant lysosomal replacement enzymes produced in CHO cells," Nature Communications 10(1785), Apr. 30, 2019, pp. 1-13.
Toldo, S. et al., "Low-Density Lipoprotein Receptor-Related Protein-1 is a Therapeutic Target in Acute Myocardial Infarction", JACC: Basic to Translational Science 2(5), Oct. 2017, pp. 561-574.
Tong, P.Y. et al., "Ligand Interactions of the Cation-dependent Mannose 6-Phosphate Receptor," The Journal of Biological Chemistry, vol. 264, No. 14, May 15, 1989, pp. 7970-7975.
Willis, M.S. et al., "Macrophage migration inhibitory factor mediates late cardiac dysfunction after burn injury", American Journal of Physiology-Heart and Circulatory Physiology, vol. 288, Feb. 1, 2005, pp. H795-H804.
Yang, H. et al., "Purification of human immunoglobulin G via Fe-specific small peptide ligand affinity chromatography", Journal of Chromatography A, vol. 1216, Iss. 6, Feb. 6, 2009, pp. 910-918.
Zavorka, M.E. et al., "Inhibition of insulin-like growth factor II (IGF-II)-dependent cell growth by multidentate pentamannosyl 6-phosphate-based ligands targeting the mannose 6-phosphate/IGF-II receptor," Oncotarget, vol. 7, No. 38, Aug. 22, 2016, pp. 62386-62410.
Zhang, Y. et al., "Identification of a Small Peptide That Inhibits PCSK9 Protein Binding to the Low Density Lipoprotein Receptor", The Journal of Biological Chemistry, vol. 289, Iss. 2, Jan. 2014, pp. 942-955.
Zhu, Y. et al., "Conjugation of mannose 6-phosphate-containing oligosaccharides to acid alpha-glucosidase improves the clearance of glycogen in pompe mice," The Journal of Biological Chemistry 279(48), Nov. 26, 2004, pp. 50336-50341.
Caianiello, D. et al., "Bifunctional small molecules that mediate the degradation of extracellular proteins" Nature Chemical Biology, vol. 17, Aug. 19, 2021, pp. 947-953.
Akinc, A. et al., "Targeted delivery of RNAi therapeutics with endogenous and exogenous ligand-based mechanisms," Molecular Therapy 18(7), Jul. 2010, pp. 1357-1364.
Banik, S.M. et al., "Lysosome Targeting Chimeras (LYTACs) for the Degradation of Secreted and Membrane Proteins" Mar. 29, 2019, pp. 1-68. doi.org/10.26434/chemrxiv.7927061.v1.
Bocci, V., "The role of sialic acid in determining the life-span of circulating cells and glycoproteins," Experientia, vol. 32, Feb. 1976, pp. 135-140.

Kang, H.J. et al., "Cyclic peptide ligand with high binding capacity for affinity purification of immunoglobulin G", Journal of Chromatography A, vol. 1466, Sep. 30, 2016, pp. 105-112.
Kandasamy, P. et al. "Metabolically Stable Anomeric Linkages Containing CaINAc-siRNA Conjugates: An interplay among ASGPR, Glycosidase, and RISC Pathways," J. Med. Chem. 2023, 66, pp. 2506-2523.
Kim, J.A. et al., "Presumed LRP1 -targeting transport peptide delivers 13-secretase inhibitor to neurons in vitro with limited efficiency", Scientific Reports, vol. 6, 34297, Sep. 29, 2016, DD. 1-12.
Krook, M. et al., "Novel peptides binding to the Fe-portion of immunoglobulins obtained from a combinatorial phage display peptide library", Journal of Immunological Methods, vol. 221, Iss. 1-2, Dec. 1998, pp. 151-157.
Landry, J.P. et al., "Discovering small molecule ligands of vascular endothelial growth factor that block VEGF-KDR binding using label-free microarray-based assays,", Assay and Drug Development Technologies 11 (5), Jun. 2013, pp. 326-332.
Lund, L.N. et al., "Novel peptide ligand with high binding capacity for antibody purification", Journal of Chromatography A, vol. 1225, Feb. 17, 2012, pp. 158-167.
Maxfield and McGraw (2004) "Endocytic Recycling" Nature Reviews, 5:121-132.
McEnaney, P.J. et al., "Antibody-Recruiting Molecules: An Emerging Paradigm for Engaging Immune Function in Treating Human Disease", ACS Chem. Biol. (7), Jul. 3, 2012, DD. 1139-1151.
Menegatti, S. et al., "Design of protease-resistant peptide ligands for the purification of antibodies from human plasma", Journal of Chromatography A, vol. 1445, May 6, 2016, pp. 93-104.
Menegatti, S. et al., "mRNA display selection and solid-phase synthesis of Fe-binding cyclic peptide affinity ligands", Biotechnology and Bioengineering 110(3), Mar. 2013, pp. 857-870.
Menegatti, S. et al., "Reversible cyclic peptide libraries for the discovery of affinity ligands", Anal. Chem., vol. 85, No. 19, Sep. 3, 2013, DD. 9229-9237.
Merwin, J. R. et al., "Targeted Delivery of DNA Using YEE(GaINAcAH)3, a Synthetic Glycopeptide Ligand for the Asialoglycoprotein Receptor," Bioconjugate Chem. 5(6), Nov. 1, 1994, pp. 612-620.
Molino, Y. et al., "Use of LDL receptor-targeting peptide vectors for in vitro and in vivo cargo transport across the blood-brain barrier", The FASEB Journal, 31 (5), Jan. 20, 2017, pp. 1807-1827.
Nalawansha, D.A., et al., "Targeted Protein Internalization and Degradation by ENDosome Targeting Chimeras", ACS Central Science 5(6), May 9, 2019, pp. 1079-1084.
Neven, C. et al., "Macrophage Scavenger Receptor A Mediates Adhesion to Apolipoproteins A-I and E", Biochemistry 48(50), Nov. 13, 2009, 11858-11871.
Parker, C.G. et al., "Iluminating HIV gp 120-ligand recognition through computationally-driven optimization of antibody-recruiting molecules", Chemical Science, Iss. 6, Apr. 2, 2014, DD. 2311-2317.
Ruan, H. et al., "A novel peptide ligand RAP12 of LRP1 for glioma targeted drug delivery," Journal of Controlled Release, vol. 279, Jun. 10, 2018, pp. 306-315.
Santi, M. et al., "Rational design of a transferrin-binding peptide sequence tailored to targeted nanoparticle internalization", Bioconjugate Chemistry, 28(2), Dec. 1, 2016, DD. 471-480.
Sugita, T. et al., "Screening of peptide ligands that bind to the Fe region of IgG using peptide array and its application to affinity purification of antibody", Biochemical EnQineerinQ Journal, vol. 79, Oct. 15, 2013, DD. 33-40.
Third Party Observation for International Appln No. PCT/US2019/067228, 4 pages.
Tsai, C-W. et al., "Strategy of Fe-recognizable peptide ligand design for oriented immobilization of antibody", Anal. Chem., vol. 86, No. 6, Feb. 17, 2014, pp. 2931-2938.
Verdoliva, A. "A new ligand for immunoglobulin G subdomains by screening of a synthetic peptide library", ChemBioChem 6(7), Jul. 2005, DD. 1242-1253.

(56) References Cited

OTHER PUBLICATIONS

Verdoliva, A. et al., "Affinity purification of polyclonal antibodies using a new all-D synthetic peptide ligand comparison with protein A and protein G", Journal of Immunological Methods, vol. 271, Iss. 1-2, Dec. 20, 2002, DD. 77-88.

Wangler, C. et al., "In Vitro and Initial In Vivo Evaluation of 68Ga-Labeled Transferrin Receptor (TfR) Binding Peptides as Potential Carriers for Enhanced Drug Transport into TfR Expressing Cells", Molecular Imaging and Biology, 13(2), May 15, 2010, pp. 332-341.

Watarai, H. et al., "Posttranslational modification of the glycosylation inhibiting factor (GIF) gene product generates bioactive GIF", Proceedings of the National Academy of Sciences 97(24), Nov. 21, 2000, pp. 13251-13256.

Yang, H. et al., "Hexamer peptide affinity resins that bind the Fc region of human immunoglobulin G", The Journal of Peptide Research, vol. 66, Iss. 1, Dec. 2005, pp. 120-137.

Yoo, R-J. et al., "Identification of a peptide ligand for antibody immobilization on biosensor surfaces", BioChip Journal, vol. 10, Dec. 18, 2015, DD. 88-94.

Zhang, H. et al., "Recent developments in carbohydrate-decorated targeted druq/qene delivery", Medicinal research reviews 30.2 (2010): 270-289.

Zhao, W-W. et al., "Biomimetic design of affinity peptide ligands for human IgG based on protein A-IgG complex", Biochemical Engineering Journal, vol. 88, Jul. 15, 2014, pp. 1-11.

Zhao, W-W. et al., "Dual-ligand affinity systems with octapeptide ligands for affinity chromatography of hIgG and monoclonal antibody", Journal of Chromatography A, vol. 1359, Nov. 21, 2014, pp. 64-72.

Zhao, W-W. et al., "FYWHCLDE-based affinity chromatography of IgG: effect of ligand density and purifications of human IgG and monoclonal antibody", Journal of Chromatography A, vol. 1355, Aug. 15, 2014, pp. 107-114.

Zhao, W-W. et al., "Octapeptide-based affinity chromatography of human immunoglobulin G: comparisons of three different ligands", Journal of Chromatography A, vol. 1359, Sep. 12, 2014, pp. 100-111.

Coutinho Maria Francisca et al. "Mannose-6-phosphate pathway: A review on its role in lysosomal function and dysfunction", Molecular Genetics and Metabolism, vol. 105, No. 4, pp. 542-550.

Leone Dario Armando et al., "Surface LAMP-2 is an Endocytic Receptor That Diverts Antigen Internalized by Human Dendritic Cells into Highly Immunogenic Exosomes", The Journal of Immunology, vol. 199, No. 2, Jul. 15, 2017, pp. 531-546.

\* cited by examiner

ASGPR CELL SURFACE RECEPTOR BINDING COMPOUNDS AND CONJUGATES

CROSS-REFERENCE TO RELATED APPLICATIONS

This application is a continuation of International Application No. PCT/US2022/037227, filed Jul. 14, 2022, which claims benefit of U.S. Provisional No. 63/221,918, filed Jul. 14, 2021, which are hereby incorporated in their entirety by reference.

2. INTRODUCTION

Many therapeutics act by binding a functionally important site on a target protein, thereby modulating the activity of that protein, or by recruiting immune effectors, as with many monoclonal antibody drugs, to act upon the target protein. However, there is an untapped reservoir of medically important human proteins that are considered to be "undruggable" because these proteins are not readily amenable to currently available therapeutic targeting approaches. Thus, there is a need for therapies that can target a wider range of proteins.

The asialoglycoprotein receptor (ASGPR), also known as the Ashwell Morell receptor, is the transmembrane glycoprotein receptor found primarily in hepatocytes which plays an important role in serum glycoprotein homeostasis by mediating the endocytosis and lysosomal degradation of glycoproteins with exposed terminal galactose or N-acetylgalactosamine (GalNAc) residues. ASGPR cycles between endosomes and the cell surface.

Alternative ligands that provide for binding to cell surface ASGPRs followed by transport across cell membranes are of great interest.

3. SUMMARY OF THE INVENTION

The present disclosure provides a class of compounds including a ligand moiety that specifically binds to a cell surface asialoglycoprotein receptor (ASGPR). The cell surface ASGPR binding compounds can trigger the receptor to internalize into the cell a bound compound. The ligand moieties of this disclosure can be linked to a variety of moieties of interest without impacting the specific binding to, and function of, the cell surface receptor ASGPR. Also provided are compounds that are conjugates of the ligand moieties linked to a biomolecule, such as an antibody, which conjugates can harness cellular pathways to remove specific proteins of interest from the cell surface or from the extracellular milieu. For example, the conjugates described herein may sequester and/or degrade a target molecule of interest in a cell's lysosome. Also provided herein are compositions comprising such conjugates and methods of using the conjugates to target a polypeptide of interest for sequestration and/or lysosomal degradation, and methods of using the conjugates to treat disorders or disease.

4. BRIEF DESCRIPTION OF THE SEVERAL VIEWS OF THE DRAWINGS

These and other features, aspects, and advantages of the present invention will become better understood with regard to the following description, and accompanying drawings, where:

5. DETAILED DESCRIPTION OF THE INVENTION

Figure 1:
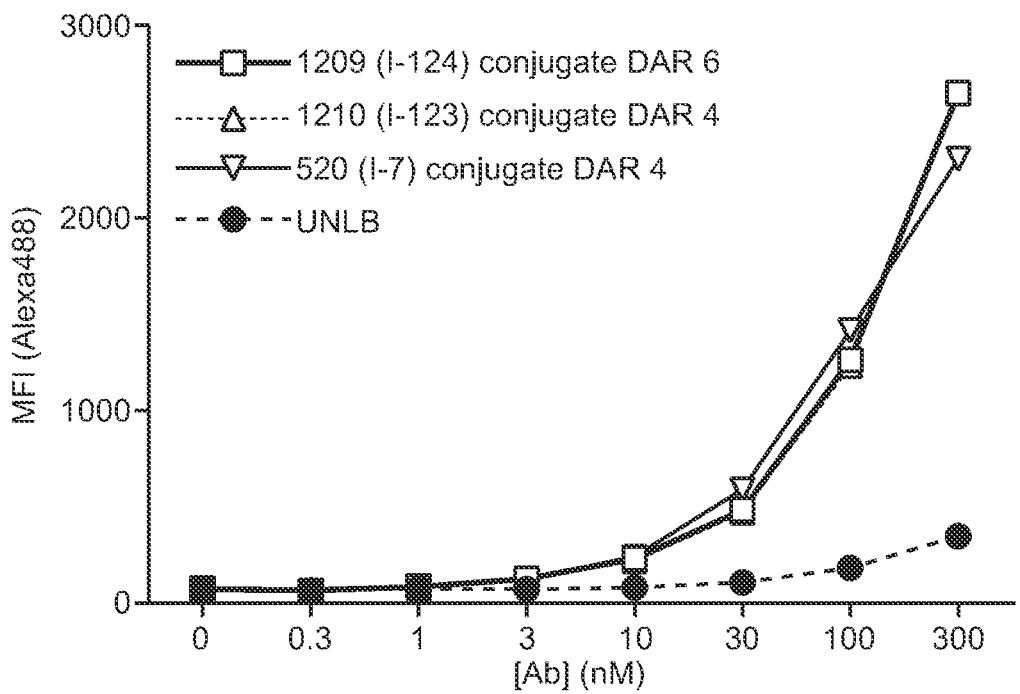
FIG. 1 shows a graph of cell fluorescence (MFI) versus antibody conjugate concentration ([Ab]) indicating that various antibody conjugates of exemplary ASGPR binding compounds, and an example M6PR binding compound (520) exhibited comparable robust uptake into HepG2 cells after one hour incubation.

As summarized above, this disclosure provides classes of compounds including a ligand moiety that specifically binds to a cell surface receptor. Also provided herein are conjugates that comprise a moiety, X, that binds to such a cell surface receptor, for example, an internalizing cell surface receptor, for example, for sequestration and/or lysosomal degradation. In certain embodiments, the cell surface receptor is ASGPR.

This disclosure includes compounds of formula (I):

$$X_n\text{-L-Y} \qquad (I)$$

or a salt thereof, wherein:
X is a moiety that binds to a ASGPR cell surface receptor (e.g., as described herein);
n is 1 to 500;
L is a linker (e.g., monovalent or multivalent, as described herein) of defined length; and
Y is a moiety of interest (e.g., as described herein).

The compounds and conjugates and methods of this disclosure are described in greater detail below. A particular class of ASGPR binding compounds is described. Also described are biomolecule conjugates that include a cell surface receptor binding moiety (X) that binds to ASGPR. Linkers (L) and moieties of interest (Y) which find use in the ASGPR binding compounds, and the biomolecule conjugates are also described. Methods in which the compounds and conjugates of this disclosure find use are also described.

5.1. ASGPR Ligands

As summarized above, this disclosure provides a class of compounds including a ligand moiety that specifically binds to a cell surface ASGPR. The ASGPR ligand moieties of this disclosure can be linked to a variety of moieties of interest without impacting the specific binding to, and function of, the cell surface ASGPR. The inventors have demonstrated that compounds of this disclosure can utilize the functions of cell surface ASGPRs in a biological system, e.g., for internalization and sequestration of a compound to the lysosome of a cell, and in some cases subsequent lysosomal degradation. The compounds of this disclosure find use in a variety of applications.

The term "asialoglycoprotein receptor" (ASGPR), also known as the Ashwell Morell receptor, means the transmembrane glycoprotein receptor found primarily in hepatocytes which plays an important role in serum glycoprotein homeostasis by mediating the endocytosis and lysosomal degradation of glycoproteins with exposed terminal galactose or N-acetylgalactosamine (GalNAc) residues. ASGPR cycles between endosomes and the cell surface. In particular embodiments, the ASGPR is *Homo sapiens* asialoglycoprotein receptor 1 (ASGR1) (see, e.g., NCBI Reference Sequence: NM_001197216).

A compound comprising such ASGPR binding moiety (X) (e.g., as described herein), may bind to other receptors, for example, may bind with lower affinity as determined by, e.g., immunoassays or other assays known in the art. In a specific embodiment, X, or a compound as described herein comprising such X specifically binds to the cell surface ASGPR with an affinity that is at least 2 logs, 2.5 logs, 3 logs, 4 logs or greater than the affinity when X or the compound or the conjugate bind to another cell surface receptor. In a specific embodiment, X or a compound as described herein comprising X, specifically binds to ASGPR with an affinity ($K_d$) 20 mM or less. In particular embodiments, such binding is with an affinity ($K_d$) is 10 mM or less, 1 mM or less, 100 uM or less, 10 uM or less, 1 uM or less, 100 nM or less, 10 nM or less, or 1 nM or less. The terms "binds," "binds to," "specifically binds" or "specifically binds to" in this context are used interchangeably.

The ASGPR binding compounds of this disclosure include a moiety (X) that specifically binds to the cell surface receptor ASGPR. The ASGPR binding compounds can be monovalent or multivalent (e.g., bivalent or trivalent or of higher valency), where a monovalent compound includes a single ASGPR ligand moiety, and a multivalent compound includes two or more such moieties.

In certain embodiments, the ASGPR binding moiety X is able to bind to a specific cell surface ASGPR, and direct (or target) the molecule to this receptor. In certain embodiments, the ASGPR binding moiety X is capable of binding to the ASGPR and directing (or targeting) a compound or conjugate described herein for internalization and sequestration to the lysosome, and/or subsequent lysosomal degradation.

In some embodiments, the ASGPR binding moiety X includes an amino sugar ring derivative of galactose (e.g., N-Acetylgalactosamine, and analogs thereof), that is linked via a linking moiety to the 1, 6 or 2-position of the sugar ring. The linking moiety can be of 1-10 atoms in length, such as 1-6, or 1-5, 1-4, or 1-3 atoms in length. In some embodiments, the amino sugar ring derivative of galactose is linked via a linking moiety to an oxygen, sulfur, nitrogen or carbon atom the 1-position of the ring. In some embodiments, the amino sugar ring derivative of galactose is linked via a linking moiety to an oxygen, sulfur, nitrogen or carbon atom the 6-position of the ring. In some embodiments, the amino sugar ring derivative of galactose is linked via a linking moiety to an oxygen, sulfur, nitrogen or carbon atom the 2-position of the ring. In certain embodiments, the amino sugar derivative of galactose is linked via a linking moiety to a heteroaryl group at the 1, 6 or 2 position of the ring. In certain embodiments, the amino sugar derivative of galactose is a bicyclic structure.

In some embodiments, the ASGPR binding compounds is monovalent (e.g., in Formula (I), n is 1), such that the ASGPR binding compound includes a single ASGPR ligand moiety (X) that is linked to a moiety of interest (Y) via a linking moiety at the 1, 6, or 2-position of (X). In certain embodiments of formula (I), n is 1, and L comprises a linear linker having a backbone of 20 or more consecutive atoms covalently linking the ASGPR ligand (X) to Y via a linking moiety at any of the 1, 2 or 6-positions of X. In certain cases, n is 20 to 100 consecutive atoms, such as 25 to 80, 25 to 60, or 25 to 50. In certain embodiments of formula (I), n is 1, and L comprises a backbone of 25 or more consecutive atoms covalently linking the ASGPR ligand (X) to Y.

In some embodiments, the ASGPR binding compounds are multivalent (e.g., in Formula (I), n is 2 or more, such that the ASGPR binding compound includes two or more ASGPR ligand binding moieties (X) that are each covalently linked to a moiety of interest (Y) via a branched linker (e.g., L is a branched linker). In certain cases, the ASGPR binding compound is divalent (e.g., n is 2 in Formula 1). In certain other cases, the ASGPR binding compound is trivalent (e.g., n is 3 in Formula 1). In certain cases, each branch of the branched linker comprises a liner linker of 14 or more consecutive atoms to covalently link a linking moiety of each X to a branching point in the linker. In certain cases, each branch of the linker includes 14 to 50 consecutive atoms, such as 14 to 40, 14 to 30, or 14 to 20 atoms. In certain cases, each branch of the linker includes a linear linker of 20 or more consecutive atoms. In certain cases, the linker comprises a linear linker of 12 or more consecutive atoms to covalently link the branching point of L to a moiety of interest (Y), such as 15 or more, 20 or more, 30 or more, or even more consecutive atoms to covalently link the branching point of L to Y.

The ASGPR binding moiety (X) of the compounds of this disclosure can be described by formula (Ia):

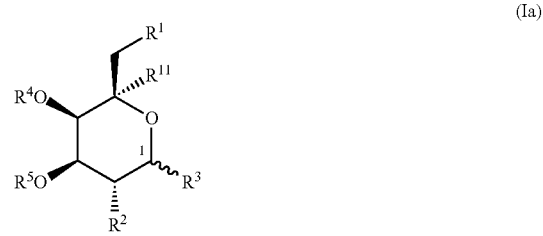

(Ia)

wherein:
$R^1$ is selected from —OH, —OC(O)R, —C(O)NHR, —$Z^1$—*, and optionally substituted triazole, where R is optionally substituted $C_{1-6}$ alkyl or optionally substituted aryl;
$R^2$ is selected from —NHCOCH$_3$, —NHCOCF$_3$, —NHCOCH$_2$CF$_3$, —OH, optionally substituted triazole, and —$Z^1$—*;
$R^3$ is selected from —H, —OH, —CH$_3$, —OCH$_3$, —OCH$_2$CH=CH and —$Z^1$—*;
one of $R^1$ to $R^3$ is —$Z^1$—* or comprises —$Z^1$—*, wherein "*" represents a point of attachment of $Z^1$ to the linker (L);
$R^4$ and $R^5$ are each independently selected from H, and a promoiety; or $R^4$ and $R^5$ are cyclically linked to form a promoiety;

$R^{11}$ is H, or a group that forms a bridge (e.g., a 2 atom bridge cyclically linked) to the 1-position carbon atom;

$Z^1$ is a linking moiety selected from $Z^{11}$, optionally substituted $Z^{11}$-heteroaryl, optionally substituted $Z^{11}$-aryl, optionally substituted heteroaryl, optionally substituted aryl, optionally substituted alkyl, optionally substituted amide, optionally substituted sulfonamide, optionally substituted urea, and optionally substituted thiourea;

$Z^{11}$ is selected from —O—, —S—, $NR^{21}$—, and —C($R^{22}$)$_2$, each $R^{21}$ is independently selected from H, and optionally substituted (C$_1$-C$_6$)alkyl; and each $R^{22}$ is independently selected from H, halogen (e.g., F) and optionally substituted (C$_1$-C$_6$)alkyl.

In some embodiments of formula (Ia):
i) when n is 3, $R^1$ is OH, $R^2$ is —NHCOCH$_3$, $R^4$-$R^5$ are H, and $R^3$ is $Z^1$, then $Z^1$ is not O;
ii) when n is 2 or 3, $R^1$ is OAc, $R^2$ is —NHCOCH$_3$, $R^4$-$R^5$ are Ac, and $R^3$ is $Z^1$, then $Z^1$ is not O;
iii) when n is 2 or 3, $R^1$ is Obz, $R^2$ is —NHCOCH$_3$, $R^4$-$R^5$ are Bz, and $R^3$ is $Z^1$, then $Z^1$ is not O;
iv) when n is 3, $R^1$ is OH, $R^2$ is —NHCOCH$_3$, $R^4$-$R^5$ are H, and $R^3$ is $Z^1$, and $Z^{11}$ is O, then L comprises a backbone of at least 16 consecutive atoms to a branching point;
v) when n is 3, $R^1$ is $Z^1$, where $Z^1$ is O, and $R^4$-$R^5$ are H, then $R^3$ is not —CH$_3$—OCH$_3$, or —OCH$_2$CH═CH; and
vi) when $R^{11}$ is a group of the formula —CH$_2$O— that forms a bridge (i.e., is cyclically linked) to the 1-position carbon atom on the sugar ring, $R^2$ is —NHCOCH$_3$, $R^4$-$R^5$ are H, then $R^1$ and $R^3$ are not $Z^1$.

In some embodiments the ASGPR binding moiety (X) of the compounds of this disclosure can be described by formula (Ia-1):

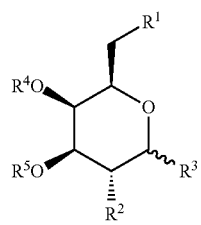

(Ia-1)

wherein:
$R^1$ is selected from —OH, —OC(O)R, —C(O)NHR, —$Z^1$—*, and optionally substituted triazole, where R is optionally substituted C$_{1-6}$ alkyl or optionally substituted aryl;
$R^2$ is selected from —NHCOCH$_3$, —NHCOCF$_3$, —NHCOCH$_2$CF$_3$, —OH, optionally substituted triazole, and —$Z^1$—*;
$R^3$ is selected from —H, —OH, —CH$_3$, —OCH$_3$, —OCH$_2$CH═CH and —$Z^1$—*;
one of $R^1$ to $R^3$ is —$Z^1$—*, wherein "*" represents a point of attachment of $Z^1$ to the linker (L);
$R^4$ and $R^5$ are each independently selected from H, and a promoiety (e.g., an ester promoiety);
$Z^1$ is a linking moiety selected from $Z^{11}$, optionally substituted $Z^{11}$-heteroaryl, optionally substituted $Z^{11}$-aryl, optionally substituted heteroaryl, optionally substituted aryl, optionally substituted amide, optionally substituted sulfonamide, optionally substituted urea, and optionally substituted thiourea;

$Z^{11}$ is selected from —O—, —S—, $NR^{21}$—, and —C($R^{22}$)$_2$, each $R^{21}$ is independently selected from H, and optionally substituted (C$_1$-C$_6$)alkyl; and each $R^{22}$ is independently selected from H, halogen (e.g., F) and optionally substituted (C$_1$-C$_6$)alkyl.

In some embodiments of formula (Ia-1):
i) when n is 3, $R^1$ is OH, $R^2$ is —NHCOCH$_3$, $R^4$-$R^5$ are H, and $R^3$ is $Z^1$, then $Z^1$ is not O;
ii) when n is 2 or 3, $R^1$ is OAc, $R^2$ is —NHCOCH$_3$, $R^4$-$R^5$ are Ac, and $R^3$ is $Z^1$, then $Z^1$ is not O;
iii) when n is 2 or 3, $R^1$ is OBz, $R^2$ is —NHCOCH$_3$, $R^4$-$R^5$ are Bz, and $R^3$ is $Z^1$, then $Z^1$ is not O;
iv) when n is 3, $R^1$ is OH, $R^2$ is —NHCOCH$_3$, $R^4$-$R^5$ are H, and $R^3$ is $Z^1$, and $Z^1$ is O, then L comprises a backbone of at least 16 consecutive atoms to a branching point; and/or
v) when n is 3, $R^1$ is $Z^1$, where $Z^1$ is O, and $R^4$-$R^5$ are H, then $R^3$ is not —CH$_3$.

In some embodiments, the ASGPR binding moiety (X) of the compounds of this disclosure can be described by formula (Ib):

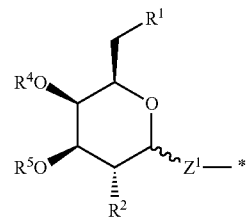

(Ib)

wherein $R^1$, $R^2$, $R^4$, $R^5$ and $Z^1$ are as defined herein.

In some embodiments of Formula (Ib), $Z^1$ is in an alpha configuration

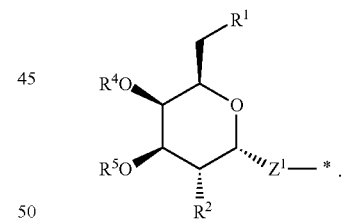

In some embodiments of Formula (Ib), $Z^1$ is in a beta configuration

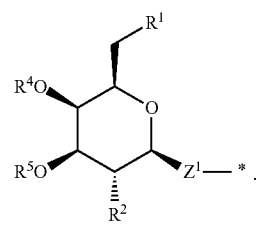

In certain embodiments of formula (Ib), $Z^1$ is $Z^{11}$—Ar, wherein Ar is or optionally substituted heteroaryl or optionally substituted aryl. In certain cases, Ar is an optionally substituted heteroaryl. In certain cases, the heteroaryl is a 5 or 6-membered heteroaryl. In certain cases, the heteroaryl is a 5-membered heteroaryl. In certain cases, the 5-membered heteroaryl is a triazole. In certain cases, the triazole is a 1,2,3-triazole moiety. In certain cases, $Z^{11}$ is —C($R^{22}$)$_2$. In certain cases, at least one $R^{22}$ is H. In certain cases, both $R^{22}$ are H. In certain cases $Z^{11}$ is —O—. In certain cases, $Z^{11}$ is —S—. In certain other cases, $Z^{11}$ is —NR$^{21}$, where $R^{21}$ is H or (C$_{1-3}$)alkyl. In certain cases, $Z^1$ is —C($R^{22}$)$_2$-triazole-. In certain cases, $Z^1$ is:

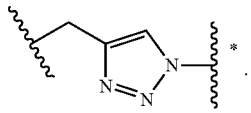 [SMILES: *Cc1cn(*)nn1]

In certain cases, $Z^1$ is:

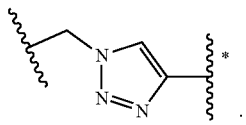 [SMILES: *Cn1cc(*)nn1]

In certain embodiments of formula (Ib), $Z^1$ is $Z^{11}$. In certain cases, $Z^{11}$ is —C($R^{22}$)$_2$. In certain cases, at least one $R^{22}$ is H. In certain cases, both $R^{22}$ are H, and $Z^{11}$ is —CH$_2$—. In certain cases $Z^{11}$ is —O—. In certain cases, $Z^{11}$ is —S—. In certain other cases, $Z^{11}$ is —NR$^{21}$, where $R^{21}$ is H or (C1-3)alkyl.

In certain embodiments of formula (Ib), $Z^1$ is monocyclic 5 or 6-membered heteroaryl or aryl. In certain cases, $Z^1$ is

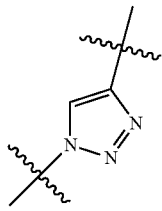

In certain cases, $Z^1$ is

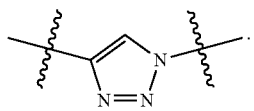 [SMILES: *c1cn(*)nn1]

In certain embodiments of formula (Ib), $Z^1$ is selected from —O—, —S—, —C($R^{22}$)$_2$—, —NR$^{21}$—, —CONR$^{21}$—, and

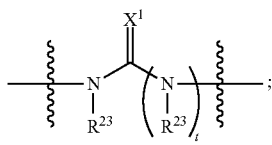

wherein:
$X^1$ is O or S;
t is 0 or 1;
$R^{21}$ and each $R^{23}$ is independently selected from H, and optionally substituted (C$_1$-C$_6$)alkyl (e.g., C$_{(1-3)}$-alkyl, such as methyl); and
each $R^{22}$ is independently selected from H, halogen (e.g., F) and optionally substituted (C$_1$-C$_6$)alkyl.

In certain embodiments of formula (Ib), $Z^1$ is optionally substituted (C$_1$-C$_6$)alkyl. In some cases of $Z^1$ the alkyl is methyl. In some cases of $Z^1$, the alkyl is ethyl. In some cases of $Z^1$, the alkyl is propyl. In some cases of $Z^1$, the alkyl is butyl. In some cases of $Z^1$, the alkyl is pentyl. In some cases of $Z^1$, the alkyl is hexyl.

In certain embodiments, the compound of formula (Ib) is selected from one of the following structures:

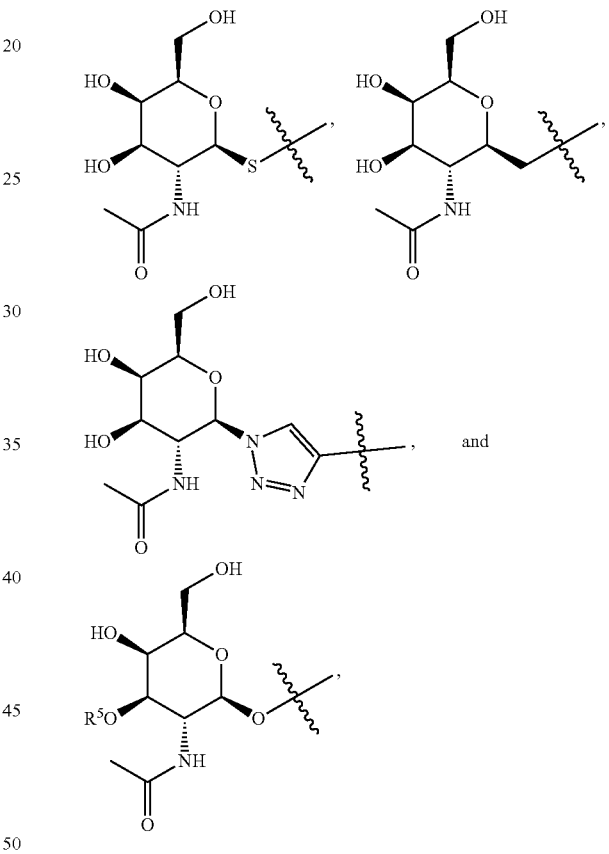

wherein $R^5$ is independently H or a promoiety.

In some embodiments, the compound of formula (Ib) is selected from one of the following structures:

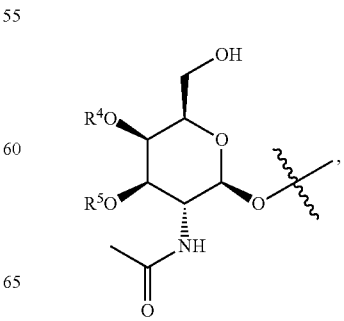

-continued

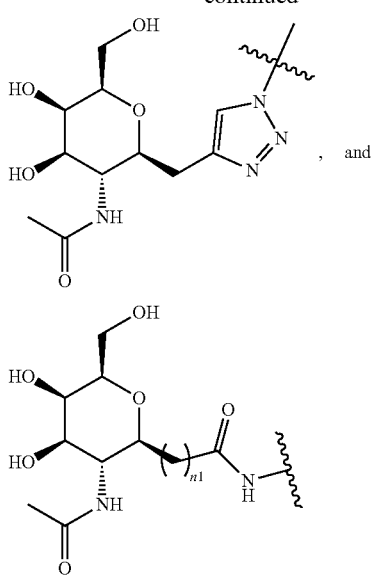
, and

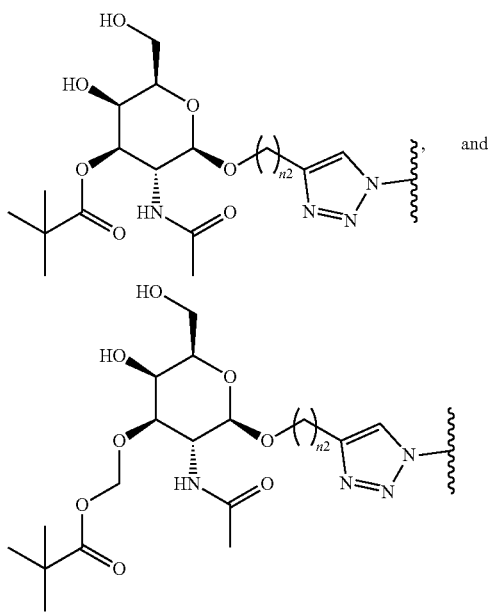

wherein $R^5$ and $R^4$ independently H or a promoiety, or $R^5$ and $R^4$ are cyclically linked to form a promoiety; and n1 is an integer from 1 to 6.

In some embodiments, at least one of $R^4$-$R^5$ is of the formula —COCH$_3$, —COCH(CH$_3$)$_2$ or —COC(CH$_3$)$_3$. In certain cases, at least one of $R^4$-$R^5$ is of the formula —CH$_2$OCOC(CH$_3$)$_3$. In certain cases, at least one of $R^4$-$R^5$ is of the formula —COC(CH$_3$)$_3$ or —CH$_2$OCOC(CH$_3$)$_3$. In certain cases, $R^4$ is H and $R^5$ is selected from —COCH$_3$, —COCH(CH$_3$)$_2$, —COC(CH$_3$)$_3$ and —CH$_2$OCOC(CH$_3$)$_3$. In certain cases, $R^4$ is H and $R^5$ is —COC(CH$_3$)$_3$. In certain cases, $R^4$ is H and $R^5$ is —CH$_2$OCOC(CH$_3$)$_3$. In some embodiments, the compound of formula (Ib) is selected from one of the following structures:

wherein n2 is an integer from 1 to 6.

In some embodiments of the compound of formula (Ib), $R^5$ and $R^4$ are cyclically linked to form a promoiety. In some cases, the compound of formula (Ib) is selected from one of the following structures:

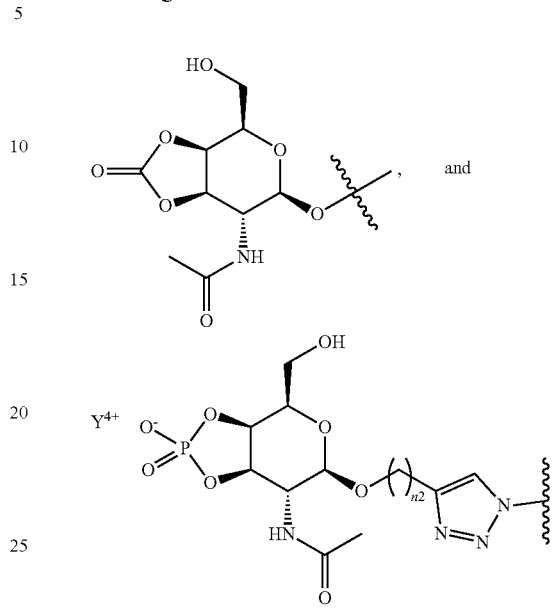

wherein n2 is an integer from 1 to 6; and $Y^4$ is a suitable counterion.

In some embodiments, the ASGPR binding moiety (X) of the compounds of this disclosure can be described by formula (Ic):

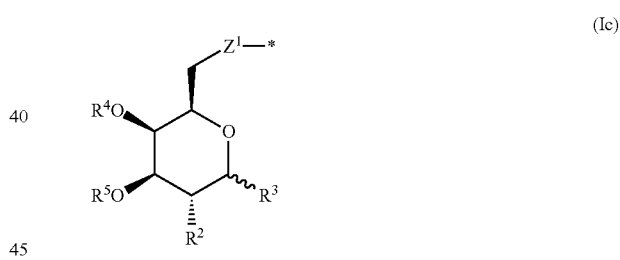

(Ic)

wherein $R^2$-$R^5$ and $Z^1$ are as defined herein.

In certain embodiments of formula (Ic), $Z^1$ is selected from —O—, —S—, —CONR$^{21}$—, and optionally substituted —(C(R$^{22}$)$_2$)$_q$-heteroaryl, wherein q is 0 or 1. In certain cases, $Z^1$ is —O—. In certain other cases, $Z^1$ is optionally substituted —(C(R$^{22}$)$_2$)$_q$-triazole wherein q is 0 or 1. In certain cases, $Z^1$ is

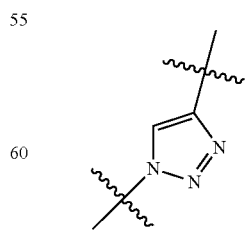

In certain embodiments of formula (Ic), $Z^1$ is $Z^{11}$—Ar, wherein Ar is or optionally substituted heteroaryl or optionally substituted aryl. In certain cases, Ar is an optionally substituted heteroaryl. In certain cases, the heteroaryl is a 5 or 6-membered heteroaryl. In certain cases, the heteroaryl is a 5-membered heteroaryl. In certain cases, the 5-membered heteroaryl is a triazole. In certain cases, the triazole is a 1,2,3-triazole moiety. In certain cases, $Z^{11}$ is —C($R^{22}$)$_2$. In certain cases, at least one $R^{22}$ is H. In certain cases, both $R^{22}$ are H. In certain cases $Z^{11}$ is —O—. In certain cases, $Z^{11}$ is —S—. In certain other cases, $Z^{11}$ is —NR$^{21}$, where $R^{21}$ is H or (C$_{1-3}$)alkyl. In certain cases, $Z^1$ is —C($R^{22}$)$_2$-triazole-. In certain cases, $Z^1$ is:

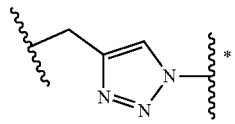

In certain embodiments of formula (Ic), $Z^1$ is $Z^{11}$. In certain cases, $Z^{11}$ is —C($R^{22}$)$_2$. In certain cases, at least one $R^{22}$ is H. In certain cases, both $R^{22}$ are H, and $Z^{11}$ is —CH$_2$—. In certain cases $Z^{11}$ is —O—. In certain cases, $Z^{11}$ is —S—. In certain other cases, $Z^{11}$ is —NR$^{21}$, where $R^{21}$ is H or (C$_1$-3)alkyl.

In certain embodiments of formula (Ic), $Z^1$ is monocyclic 5 or 6-membered heteroaryl or aryl. In certain cases, $Z^1$ is

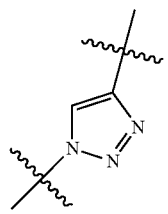

In certain embodiments of formula (Ic), $Z^1$ is selected from —O—, —S—, —C($R^{22}$)$_2$—, —NR$^{21}$—, —CONR$^{21}$—, and

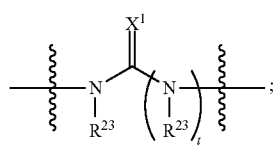

wherein:
 $X^1$ is O or S;
 t is 0 or 1;
 $R^{21}$ and each $R^{23}$ is independently selected from H, and optionally substituted (C$_1$-C$_6$)alkyl (e.g., C$_{(1-3)}$-alkyl, such as methyl); and
 each $R^{22}$ is independently selected from H, halogen (e.g., F) and optionally substituted (C$_1$-C$_6$)alkyl.

In certain embodiments, the compound of formula (Ic) is the following structure:

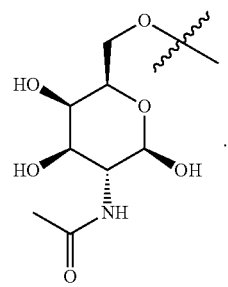 [SMILES: *OC[C@H]1O[C@@H](O)[C@H](NC(C)=O)[C@@H](O)[C@H]1O]

In certain embodiments, the compound of formula (Ic) is the following structure:

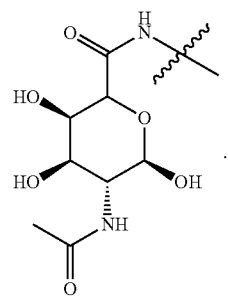 [SMILES: *NC(=O)C1O[C@@H](O)[C@H](NC(C)=O)[C@@H](O)[C@H]1O]

In some embodiments, the ASGPR binding moiety (X) of the compounds of this disclosure can be described by formula (Id):

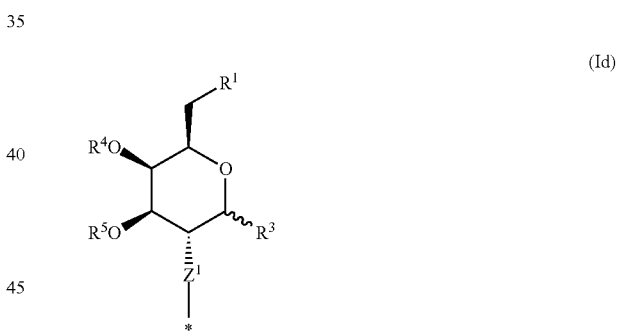

(Id)

wherein $R^1$, $R^3$-$R^5$ and $Z^1$ are as defined herein.

In some embodiments, $Z^1$ is selected from optionally substituted —(C($R^{22}$)$_2$)$_q$-heteroaryl, and

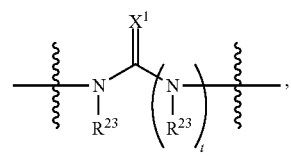

wherein q is 0 or 1.

In some embodiments, $Z^1$ is optionally substituted —(C($R^{22}$)$_2$)$_q$-triazole wherein q is 0 or 1.

In some embodiments, $Z^1$ is

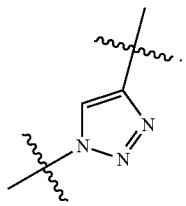 [SMILES: *c1cn(*)nn1 ; "."]

In some embodiments, $Z^1$ is

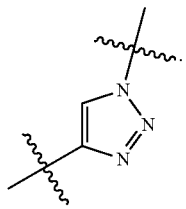 [SMILES: *c1cn(*)nn1 ; "."]

In some embodiments, $Z^1$ is

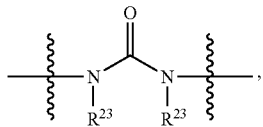

wherein $R^{23}$ is H, or $C_{(1-3)}$-alkyl.

In some embodiments, $Z^1$ is —NR$^{23}$CO—, wherein $R^{23}$ is H or $C_{(1-3)}$-alkyl.

In certain embodiments of formula (Id), $Z^1$ is selected from optionally substituted —(C(R$^{22}$)$_2$)$_q$-heteroaryl, and

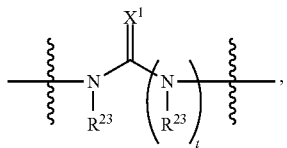

wherein q is 0 or 1.

In certain embodiments of formula (Id), $Z^1$ is optionally substituted —(C(R$^{22}$)$_2$)$_q$-triazole wherein q is 0 or 1. In certain cases, $Z^1$ is

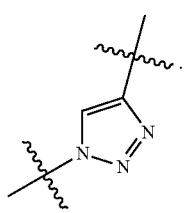 [SMILES: *c1cn(*)nn1 ; "."]

In certain cases, $Z^1$ is

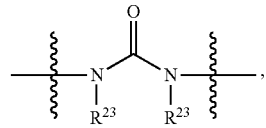

wherein $R^{23}$ is H, or $C_{(1-3)}$-alkyl.

In certain cases, $Z^1$ is —NR$^{23}$CO—, wherein $R^{23}$ is H or $C_{(1-3)}$-alkyl.

In certain embodiments of formula (Id), $Z^1$ is monocyclic 5 or 6-membered heteroaryl or aryl. In certain cases, $Z^1$ is

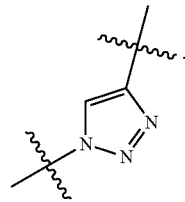 [SMILES: *c1cn(*)nn1 ; "."]

In certain embodiments of formula (Id), $Z^1$ is a monocyclic 5 or 6-membered heteroaryl of one of the following structures:

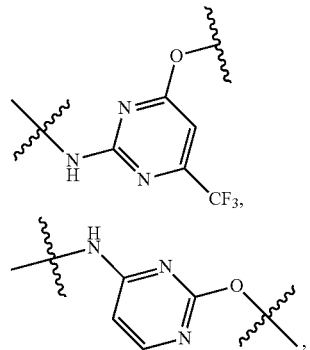

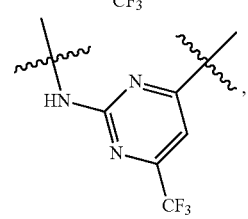

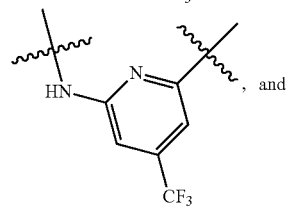, and

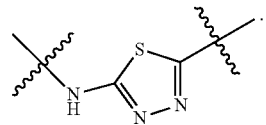

In certain embodiments of formula (Id), Z' is of one of the following structures:

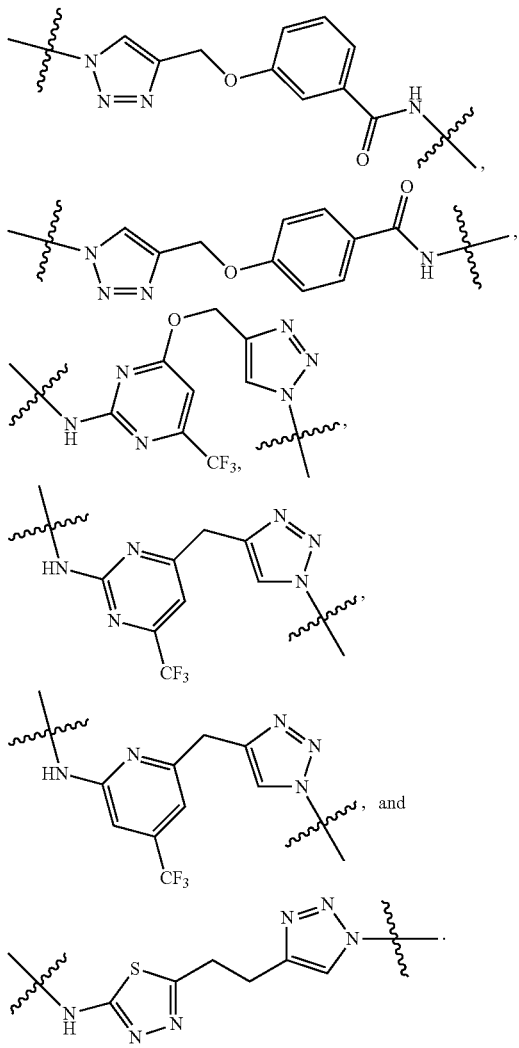

In certain embodiments of formula (Id), Z$^1$ is selected from —O—, —C(R$^{22}$)$_2$—, —NR$^{21}$—, —CONR$^{21}$—, and

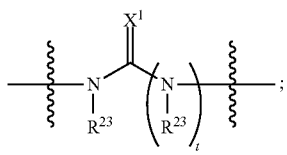

wherein:
X$^1$ is O or S;
t is 0 or 1;
R$^{21}$ and each R$^{23}$ is independently selected from H, and optionally substituted (C$_1$-C$_6$)alkyl (e.g., C$_{(1-3)}$-alkyl, such as methyl); and
each R$^{22}$ is independently selected from H, halogen (e.g., F) and optionally substituted (C$_1$-C$_6$)alkyl.

In certain embodiments, the compound of formula (Id) is selected from one of the following structures:

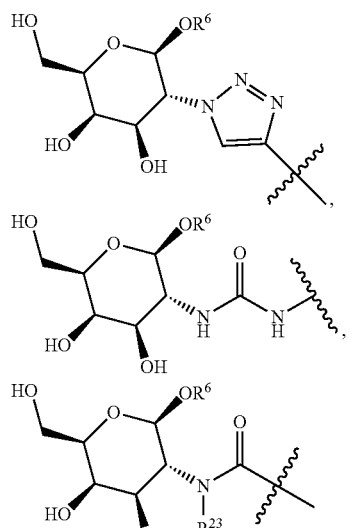

wherein R$^6$ is independently H or (C$_{1-3}$)alkyl.

In some embodiments of the compound of formula (Id) R$^3$ is H, such that the compound of formula (Id) has no non-hydrogen substituents at the 1-position of the sugar ring.

In some embodiments, the ASGPR binding moiety (X) of the compounds of this disclosure can be described by formula (Ie'):

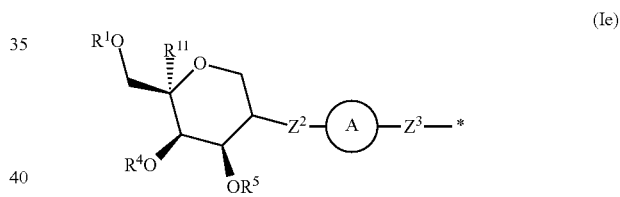

(Ie)

wherein:
R$^1$, R$^4$, R$^5$ and R$^{11}$ are as defined herein;
Z$^2$ is absent or selected from —O—, —S—, NR$^{25}$—, and —C(R$^{22}$)$_2$—;
ring A is absent or selected from a 5 or 6-membered optionally substituted aryl and a 5 or 6-membered optionally substituted heteroaryl;
Z$^3$ is a linking moiety selected from Z$^{12}$, optionally substituted alkyl, optionally substituted Z$^{12}$-alkyl, optionally substituted Z$^{12}$-heteroaryl, optionally substituted Z$^{12}$-aryl, optionally substituted heteroaryl, optionally substituted aryl, optionally substituted amide, optionally substituted sulfonamide, optionally substituted urea, and optionally substituted thiourea; and
Z$^{12}$ is selected from —CH$_2$O—, —O—, —S—, —NR$^{26}$—, and —C(R$^{22}$)$_2$—;
R$^{25}$ and R$^{26}$ are each independently selected from H, optionally substituted (C$_1$-C$_6$)alkyl (e.g., C$_{(1-3)}$-alkyl, such as methyl), and optionally substituted acyl; and
each R$^{22}$ is independently selected from H, halogen (e.g., F) and optionally substituted (C$_1$-C$_6$)alkyl.

In some embodiments of formula (Ie'), the ASGPR binding moiety (X) of the compounds of this disclosure can be described by formula (Ie"):

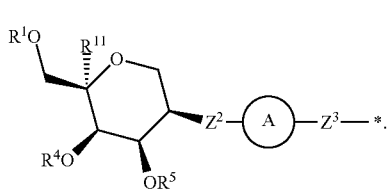

(Ie")

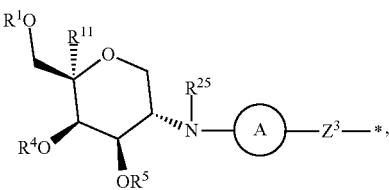

(Ig)

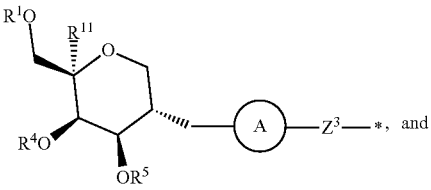

(Ih)

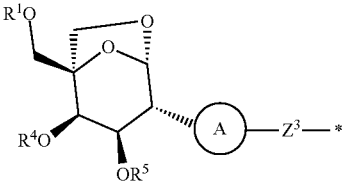

(Ii)

In some embodiments of formula (Ie'), the ASGPR binding moiety (X) of the compounds of this disclosure can be described by formula (Ie):

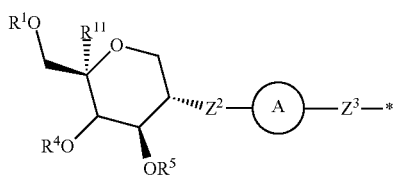

(Ie)

wherein:
R$^1$, R$^4$, R$^5$ and R$^{11}$ are as defined herein;
Z$^2$ is absent or selected from —O—, —S—, NR$^{25}$—, and —C(R$^{22}$)$_2$;
ring A is absent or selected from a 5 or 6-membered optionally substituted aryl and a 5 or 6-membered optionally substituted heteroaryl;
Z$^3$ is a linking moiety selected from Z$^{12}$, optionally substituted alkyl, optionally substituted Z$^{12}$-alkyl, optionally substituted Z$^{12}$-heteroaryl, optionally substituted Z$^{12}$-aryl, optionally substituted heteroaryl, optionally substituted aryl, optionally substituted amide, optionally substituted sulfonamide, optionally substituted urea, and optionally substituted thiourea; and
Z$^{12}$ is selected from —CH$_2$O—, —O—, —S—, —NR$^{26}$—, and —C(R$^{22}$)$_2$—;
R$^{25}$ and R$^{26}$ are each independently selected from H, optionally substituted (C$_1$-C$_6$)alkyl (e.g., C$_{(1-3)}$-alkyl, such as methyl), and optionally substituted acyl; and
each R$^{22}$ is independently selected from H, halogen (e.g., F) and optionally substituted (C$_1$-C$_6$)alkyl.

In some embodiments Z$^2$ is absent. In some embodiments, Z$^2$ is C(R$^{22}$)$_2$ where R$^{22}$ is H or optionally substituted (C$_1$-C$_3$)alkyl. In some embodiments, Z$^2$ is —CH$_2$—. In some embodiments, Z$^2$ is NR$^{25}$ where R$^{25}$ is selected from H, optionally substituted (C$_1$-C$_3$)alkyl and optionally substituted acyl. In some embodiments, Z$^2$ is —N(COCH$_3$)—. In some embodiments, Z$^2$ is —NH—. In some embodiments, Z$^2$ is —S—. In some embodiments, Z$^2$ is O.

In some embodiments, the compound of formula (Ie) is of any one of formulae (If)-(Ii):

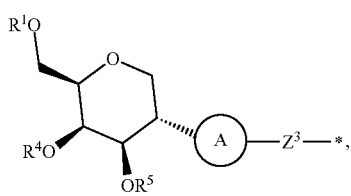

(If)

wherein the A ring, R$^1$, R$^4$, R$^5$, R$^{11}$, Z$^3$ and R$^{25}$ are as defined herein.

In some embodiments of any one of formulae (Ie)-(Ii), the A ring is a 5 or 6-membered aryl or heteroaryl. In certain cases, the A ring is a 5-membered heteroaryl selected from selected from triazole, thiadiazole, thiophene, oxazole, isoxazole, isothiazole, thiazole, oxadiazole, and furan. In certain cases, the A ring is a 6-membered heteroaryl selected from pyridine, pyrimidine, pyridazine, pyrazine, and triazine. In certain cases, the A ring is triazole. In certain cases, the A ring is pyridine. In certain cases, the A ring is pyrimidine. In certain cases, the A ring is thiadiazole.

In some embodiments of any one of formulae (Ie)-(Ii), the A ring is absent.

In some embodiments of any one of formulae (Ie)-(Ii), the A ring is phenyl or substituted phenyl.

In some embodiments of formula (If), the A ring is a 5 or 6-membered heteroaryl. In certain cases of formula (If), the A ring is a 5-membered heteroaryl. In certain embodiments of formula (If), the A ring is triazole. In certain embodiments of (If), the A ring is absent.

In some embodiments of formula (Ig), the A ring is a 5 or 6-membered heteroaryl and R$^{25}$ is H. In certain embodiments of formula (Ig), the A ring is triazole. In certain cases of formula (Ig), the A ring is pyridine. In certain cases of formula (Ig), the A ring is pyrimidine. In certain cases of formula (Ig), the A ring is thiadiazole. In some embodiments of formula (Ig), the A ring is absent and R$^{25}$ is H or optionally substituted acyl. In some cases, R$^{25}$ is —COCH$_3$. In some cases, R$^{25}$ is H.

In some embodiments of formula (Ih), the A ring is a 5 or 6-membered heteroaryl. In certain cases of formula (Ih), the A ring is a 5-membered heteroaryl. In certain embodiments of formula (Ih), the A ring is triazole. In certain embodiments of (Ih), the A ring is absent.

In some embodiments of formula (Ii), the A ring is a 5 or 6-membered heteroaryl. In certain cases of formula (Ii), the A ring is a 5-membered heteroaryl. In certain embodiments of formula (Ii), the A ring is triazole. In certain embodiments of (Ii), the A ring is absent.

In some cases, the ASGPR binding moiety (X) of the compounds of this disclosure can be described by any one of formulae (Ij)-(Im):

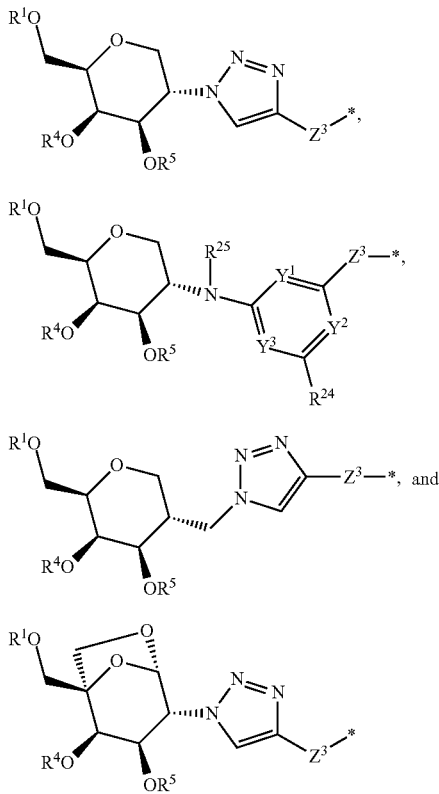

wherein:
R$^1$, R$^4$, R$^5$, RH, Z$^3$ and R$^{25}$ are as defined herein.
Y$^1$-Y$^3$ are each independently N or CR$^{27}$; and
R$^{24}$ and R$^{27}$ are each independently selected from H, optionally substituted C$_{(1-6)}$-alkyl, optionally substituted fluoroalkyl, and halogen.

In some embodiments of any one of formulae (Ie)-(Im), Z$^3$ is selected from —O—, —CH$_2$O—, —OCH$_2$—, optionally substituted —OCH$_2$-heteroaryl, optionally substituted —OCH$_2$-aryl, optionally substituted —CH$_2$O-heteroaryl, and optionally substituted —CH$_2$O-aryl.

In some embodiments, Z$^3$ is selected from:

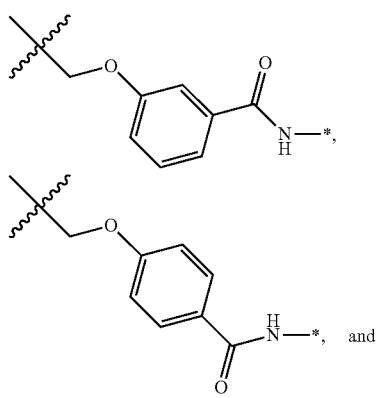

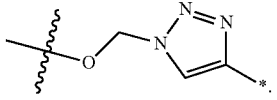

In some embodiments of any one of formulae (Ie)-(Im), Z$^3$ is selected from —C(R$^{22}$)$_2$—, optionally substituted alkyl, optionally substituted amide, optionally substituted sulfonamide, optionally substituted urea, and optionally substituted thiourea. In some embodiments, Z$^3$ is —CH$_2$—. In some embodiments, Z$^3$ is —CH$_2$CH$_2$—. In some embodiments, Z$^3$ is —CH$_2$CH$_2$CH$_2$—. In some embodiments, Z$^3$ is —NHSO$_2$—(C$_{1-3}$-alkyl). In some embodiments, Z$^3$ is —N(Ac)—(C$_{1-3}$-alkyl).

In some embodiments of any one of formulae (Ie)-(Im), Z$^3$ is selected from —S— and —NR$^{26}$—, where R$^{26}$ is selected from H and optionally substituted (C$_1$-C$_3$)alkyl.

In some embodiments of formula (Ik) at least one of Y$^1$ to Y$^3$ is N. In some cases, at least two of Y$^1$ to Y$^3$ are N. In certain cases, Y$^1$ and Y$^3$ are N and Y$^2$ is CR$^{25}$. In certain cases, Y$^1$ and Y$^2$ are N and Y$^3$ is CR$^{25}$. In certain cases, Y$^1$ and Y$^2$ are CR$^{25}$ and Y$^3$ is N. In certain cases, R$^{25}$ is H. In certain cases, R$^{25}$ is C$_{(1-3)}$-alkyl, or C$_{(1-3)}$-fluoroalkyl. In some cases, the fluoroalkyl is CF$_3$.

In certain embodiments of any one of formulae (Ie)-(Im) R$^1$ is OH.

In some embodiments of any one of formulae (Ie)-(Im), R$^4$ and R$^5$ are each H. In certain cases, at least one of R$^4$-R$^5$ is a promoiety. In certain embodiments, R$^4$ and R$^5$ are cyclically linked to form a promoiety (e.g., as described herein).

In certain embodiments, the compound of formula (Ie) is selected from one of the following structures:

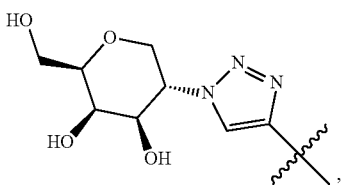

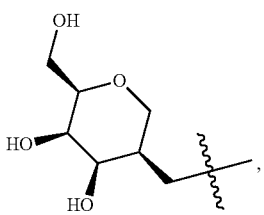

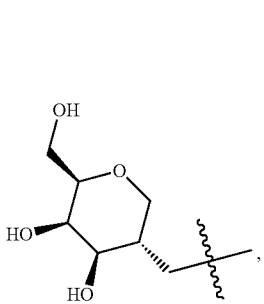

-continued

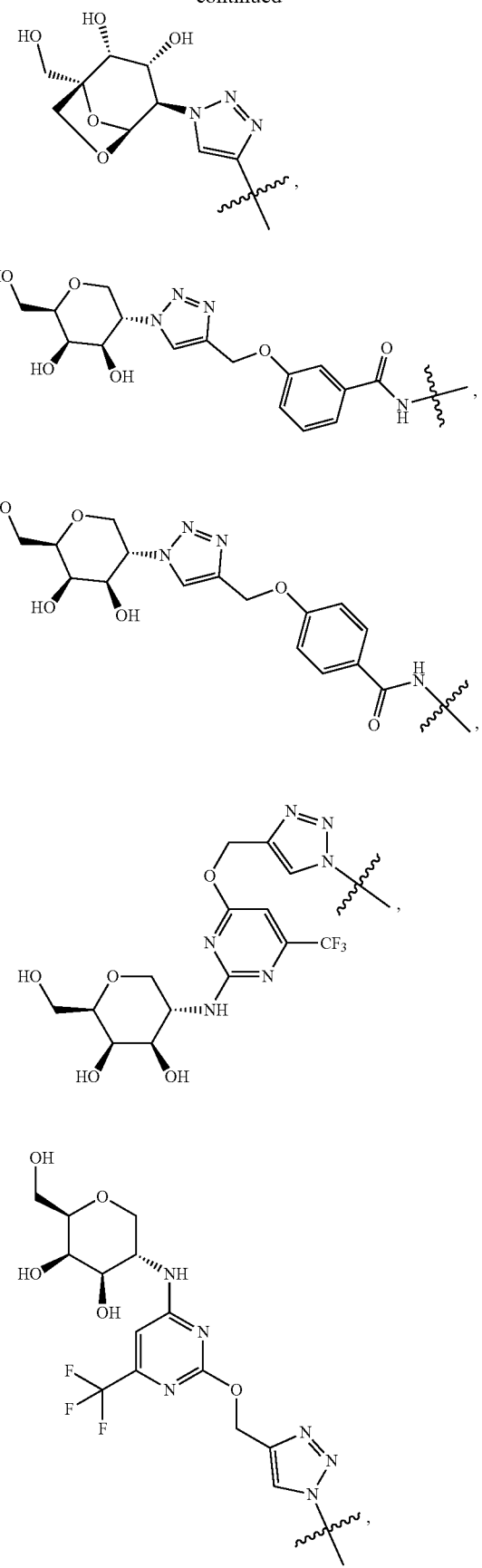

-continued

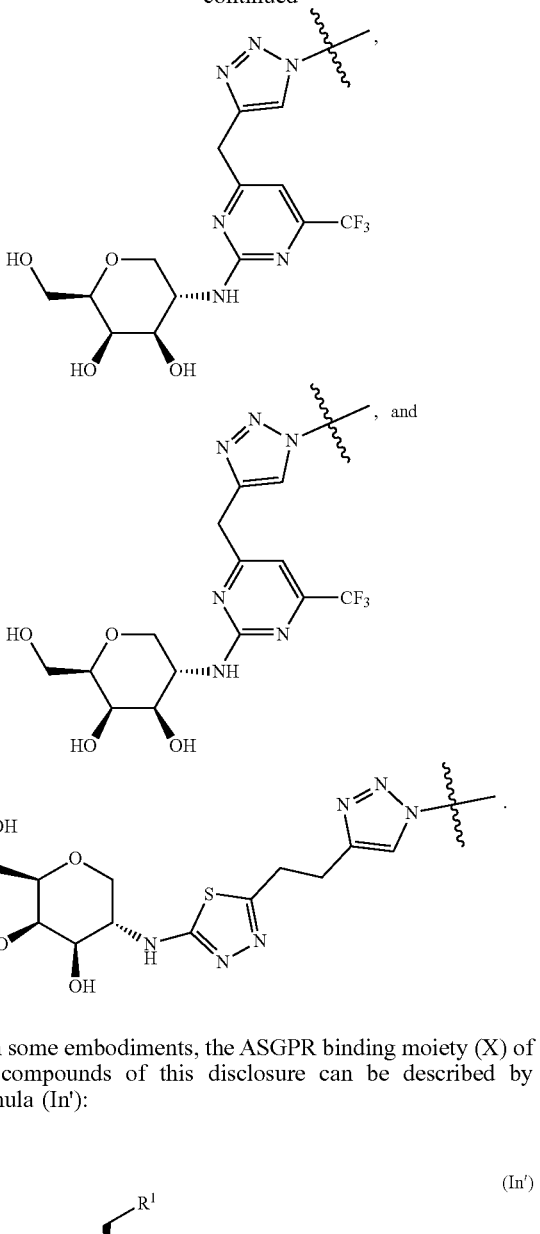

In some embodiments, the ASGPR binding moiety (X) of the compounds of this disclosure can be described by formula (In'):

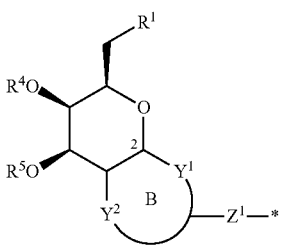

(In')

wherein:
$R^1$, $R^4$, $R^5$ and $Z^1$ are as defined herein;
$Y^1$ and $Y^2$ are each independently selected from —O—, —S—, $NR^{28}$—, and —$C(R^{22})_2$;
$R^{28}$ is selected from H, optionally substituted ($C_1$-$C_6$) alkyl, and —$C(O)R^{22}$;
each $R^{22}$ is independently selected from H, halogen and optionally substituted ($C_1$-$C_6$)alkyl;
and
ring B is a 5 or 6-membered optionally substituted cyclic group. In some embodiments of formula (In'), $Y^1$ is connected to the sugar ring via an alpha configuration. In some embodiments of formula (In'), $Y^1$ is connected to the sugar ring via a beta configuration.

In some embodiments, the ASGPR binding moiety (X) of the compounds of this disclosure can be described by formula (In):

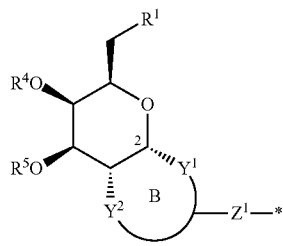

(In)

wherein:
$R^1$, $R^4$, $R^5$ and $Z^1$ are as defined herein;
$Y^1$ and $Y^2$ are each independently selected from —O—, —S—, $NR^{28}$—, and —$C(R^{22})_2$;
$R^{28}$ is selected from H, optionally substituted ($C_1$-$C_6$) alkyl, and —$C(O)R^{22}$;
each $R^{22}$ is independently selected from H, halogen and optionally substituted ($C_1$-$C_6$)alkyl;
and
ring B is a 5 or 6-membered optionally substituted cyclic group.

In some embodiments of formula (In)—(In') $Y^1$ is O. In certain cases, $Y^1$ is S. In certain cases, $Y^1$ is —$NR^{28}$—. In certain cases, $Y^1$ is —$C(R^{22})_2$ and each $R^{22}$ is H.

In some embodiments of formula (In)—(In') $Y^2$ is —$NR^{28}$— where $R^{28}$ is H. In certain cases, $Y^2$ is —$NR^{28}$— where $R^{28}$ is —$C(O)R^{22}$. In some cases, $R^{22}$ is methyl.

In some embodiments of formula (In)—(In') the B ring is a 5 or 6-membered heterocycle. In some cases, the B ring is a 5-membered heterocycle. In some cases, the B ring is a 6-membered heterocycle.

In some embodiments of formula (In)—(In') $Z^1$ is $Z^{11}$, where $Z^{11}$ is selected from —O—, —S—, $NR^{21}$—, and —$C(R^{22})_2$. In some cases, $Z^1$ is —O—. In some cases, $Z^1$ is —S—. In some cases, $Z^1$ is $NR^{21}$ where $R^{21}$ is H. In some cases, $Z^1$ is —$C(R^{22})_2$ where each $R^{22}$ is H.

In some embodiments of formula (In)—(In') $Z^1$ is optionally substituted $Z^{11}$-heteroaryl or optionally substituted $Z^{11}$-aryl. In some embodiments, $Z^1$ is $CH_2$-heteroaryl or $CH_2$-aryl. In some embodiments of formula (In)—(In') $Z^1$ is optionally substituted amide. In some embodiments of formula (In)—(In') $Z^1$ is optionally substituted sulfonamide. In some embodiments of formula (In)—(In') $Z^1$ is optionally substituted urea or optionally substituted thiourea.

In some embodiments, the compound of formula (In)—(In') has one of the following structures:

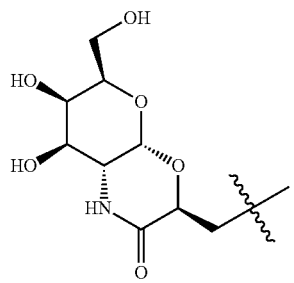

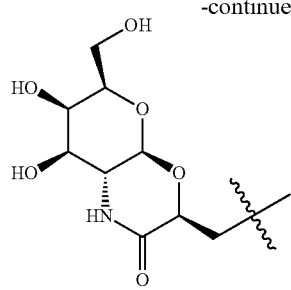

In certain embodiments of any one of formulae (Ia)-(In), n is 1, and L comprises a linear linker having a backbone of 20 or more consecutive atoms covalently linking X to Y via $Z^1$, such as a backbone of 25 or more consecutive atoms, or 30 or more consecutive atoms, and in some cases, up to 100 consecutive atoms. In certain embodiments, linker L separates X and Y (or $Z^1$) by a chain of 20 to 50 consecutive atoms. In certain embodiments, linker L separates X and Y (or $Z^1$) by a chain of 21 to 50 consecutive atoms, by a chain of 22 to 50 consecutive atoms, by a chain of 23 to 50 consecutive atoms, by a chain of 24 to 50 consecutive atoms, by a chain of 25 to 50 consecutive atoms, by a chain of 26 to 50 consecutive atoms, by a chain of 27 to 50 consecutive atoms, by a chain of 28 to 50 consecutive atoms, or by a chain of 29 to 50 consecutive atoms. In certain embodiments, linker L separates X and Y (or $Z^1$) by a chain of 30 to 60 consecutive atoms. In certain embodiments, linker L separates X and Y (or $Z^1$) by a chain of 31 to 60 consecutive atoms. In certain embodiments, linker L separates X and Y (or $Z^1$) by a chain of 32 to 60 consecutive atoms. In certain embodiments, linker L separates X and Y (or $Z^1$) by a chain of 33 to 60 consecutive atoms. In certain embodiments, linker L separates X and Y (or $Z^1$) by a chain of 34 to 60 consecutive atoms. In certain embodiments, linker L separates X and Y (or $Z^1$) by a chain of 35 to 50 consecutive atoms. In certain embodiments, linker L separates X and Y (or $Z^1$) by a chain of 36 to 50 consecutive atoms. In certain embodiments, linker L separates X and Y (or $Z^1$) by a chain of 41 to 50 consecutive atoms. In certain embodiments, linker L separates X and Y (or $Z^1$) by a chain of 46 to 50 consecutive atoms.

In certain embodiments of any one of formulae (Ia)-(In), n is 2 or more, and L is a branched linker that covalently links 2 or more X moieties to Y via the linking moiety $Z^1$.

In certain embodiments of any one of formulae (Ia)-(In), n is 2 or more and each branch of L comprises a linear linker of 14 or more consecutive atoms to covalently link via $Z^1$ each X moiety to a branching point of the linker L, such as 15 or more consecutive atoms, 16 or more consecutive atoms, or 17 or more consecutive atoms, and in some cases, up to 50 consecutive atoms. In certain cases, each branch of L comprises a linear linker of 14 to 50 consecutive atoms, such as 14 to 45, 14 to 40, 14 to 35 or 14 to 30 consecutive atoms. In certain cases, each branch of L comprises 14 to 30 consecutive atoms, such as 14 to 29, 14 to 28, 14 to 27, 14 to 26, 14 to 25, 14 to 24, 14 to 23, 14 to 22, 14 to 21, or 14 to 20 consecutive atoms. In certain cases, L comprises more than 14 consecutive atoms covalently linking each X moiety (via each $Z^1$ group) to a branching point of the linker. In certain cases, L comprises 15 consecutive atoms separating each $Z^1$ group from a branching point of L. In certain cases, L comprises 16 consecutive atoms separating each $Z^1$ group from a branching point of L. In certain cases, L comprises 17 consecutive atoms separating each $Z^1$ group from a branching point of L. In certain cases, L comprises 18 consecutive atoms separating each $Z^1$ group from a branching point of L. In certain cases, L comprises 19 consecutive atoms separating each $Z^1$ group from a branching point of L. In certain cases, L comprises 20 consecutive atoms separating each $Z^1$ group from a branching point of L. In certain other cases, L comprises a liner linker of 20 or more consecutive atoms separating each $Z^1$ group from a branching point L.

In certain embodiments of any one of formulae (Ia)-(In), n is 2, and L comprises a branched linker having 14 or more consecutive atoms separating each $Z^1$ group of X from a branching point of L.

In certain embodiments of any one of formulae (Ia)-(In), n is 3, and L comprises a branched linker having 14 or more consecutive atoms separating each $Z^1$ group of X from a branching point of L.

In certain embodiments of any one of formulae (Ia)-(In), the linker L is of the formula (II) (e.g., as described herein).

In certain embodiments of any one of formulae (Ia), (Ib) or (Id)-(In), $R^1$ is OH. In certain other cases, $R^1$ is —OC(O)R. In certain cases, $R^1$ is —C(O)NHR, where R is an optionally substituted alkyl. In certain cases, R terminates in an alkenyl or an alkynyl group. In certain other cases $R^1$ is optionally substituted triazole. In certain cases, the triazole is of the following structure:

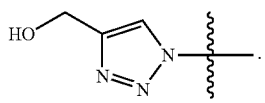

In certain embodiments of (Ia)-(Ic), $R^2$ is —NHCOCH$_3$. In certain other embodiments, $R^2$ is —NHCOCF$_3$. In certain other embodiments, $R^2$ is —NHCOCH$_2$CF$_3$. In certain cases, $R^2$ is —OH. In certain other cases, $R^2$ is an optionally substituted triazole. In certain cases, the triazole in of the following structure:

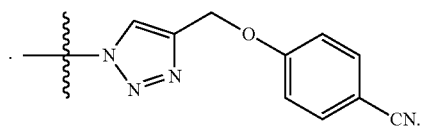 [SMILES: *n1cc(COc2ccc(C#N)cc2)nn1]

In certain embodiments when $R^1$ or $R^2$ is a substituted triazole. The triazole is a 1,2,3-trizole, and the substituent is at the 4 or 5-position. In certain cases, the substituent on the triazole moiety includes but is not limited to, an optionally substituted ($C_{1-6}$)alkyl, optionally substituted ($C_{1-6}$)alkoxy, optionally substituted aryl, optionally substituted heteroaryl, optionally substituted alkaryl, and an optionally substituted alkyheteroaryl. It will be understood that any convenient substituent can be included in the triazole moiety, see, e.g., triazole moieties disclosed in Mamidayala et al, *J. Am. Chem. Soc.* 2012, 134, 1978-1981.

In certain embodiments of any one of formulae (Ia)-(In), at least one of $R^4$-$R^5$ is a promoiety. In certain cases, the promoiety is an ester. In certain embodiments the ester of the formula —OCOCH$_3$, —OCOCH(CH$_3$)$_2$ or —OCOC(CH$_3$)$_3$. In certain cases, at least one of $R^4$-$R^5$ is of the formula —COCH$_3$, —COCH(CH$_3$)$_2$ or —COC(CH$_3$)$_3$. In certain cases, at least one of $R^4$-$R^5$ is of the formula —CH$_2$OCOC(CH$_3$)$_3$ In certain embodiments, $R^4$ is a promoiety and $R^5$ is H. In certain other cases, $R^5$ is H and $R^4$ is a promoiety. In certain cases, both $R^4$ and $R^5$ are both promoieties. In certain cases, $R^4$ and $R^5$ are cyclically linked to form a promoiety. In certain cases, $R^4$ and $R^5$ are cyclically linked to form a promoiety of formulae (Io) or (Ip):

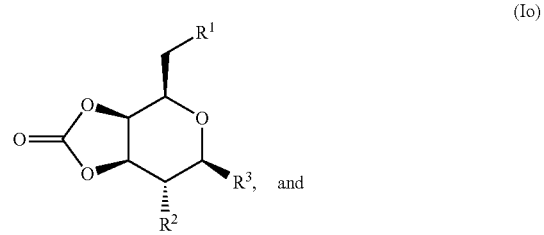

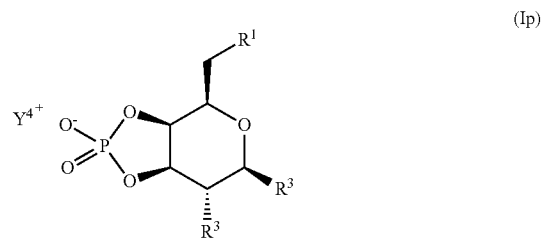

Wherein $R^1$-$R^3$ and $Y^4$ are as defined herein.

In certain embodiments of any one of formulae (Ia)-(In), both $R^4$ and $R^5$ are H.

In certain embodiments of formula (I), n is 2 or 3, and X is selected from one of the following structures:

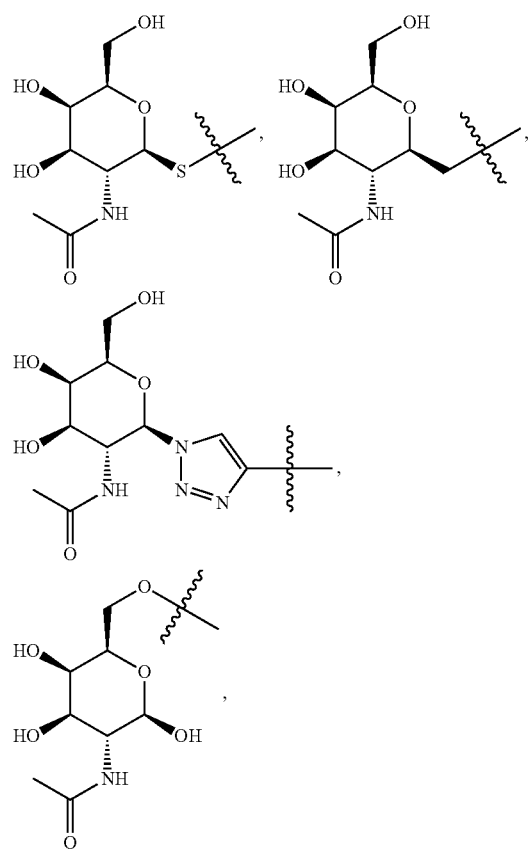

-continued

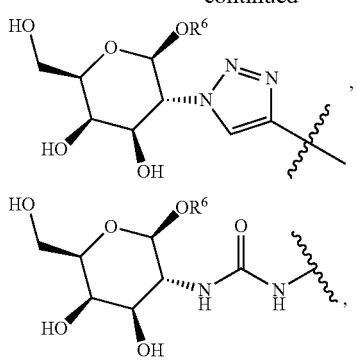

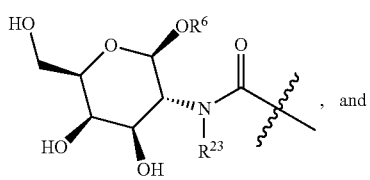

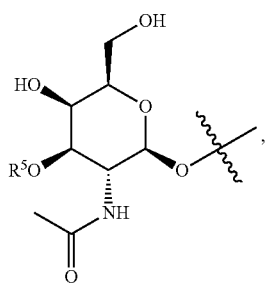

wherein $R^5$ and $R^{23}$ are independently H or $(C_{1-3})$alkyl.

In certain embodiments of formula (I), n is 1, 2 or 3, and X is selected from one of the following structures:

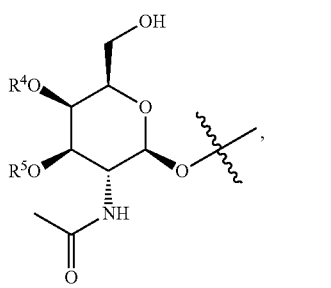

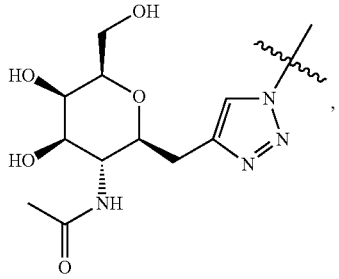

-continued

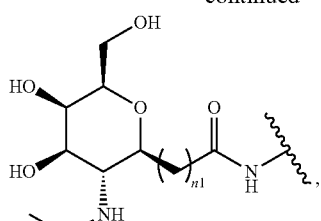

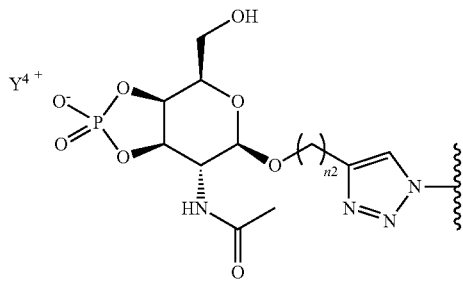

wherein $R^5$ and $R^4$ independently H or a promoiety, or $R^5$ and $R^4$ are cyclically linked to form a promoiety; n1 and n2 are each independently an integer from 1 to 6; and $Y^4$ is a suitable counterion. In some embodiments, $Y^4$ is sodium.

In certain embodiments of formula (I), n is 1, 2 or 3, and X is selected from one of the following structures:

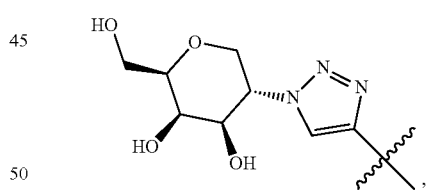

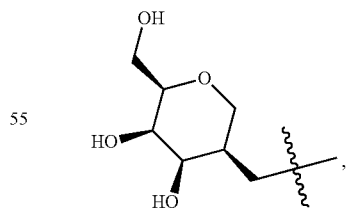

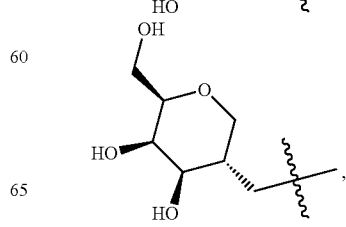

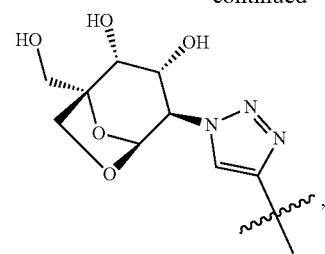
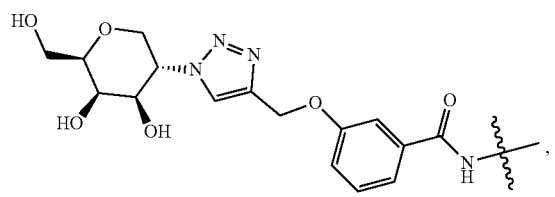
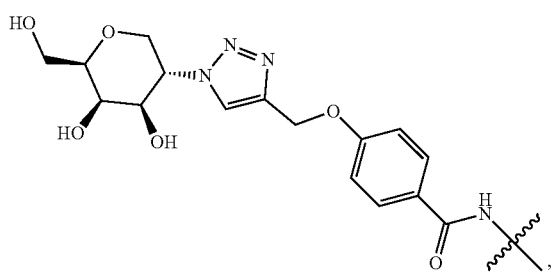
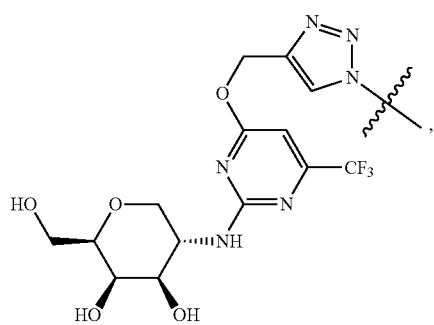
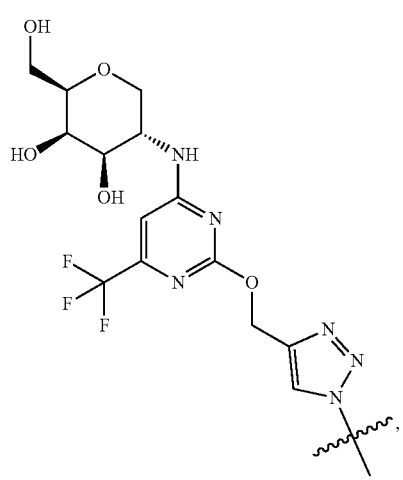
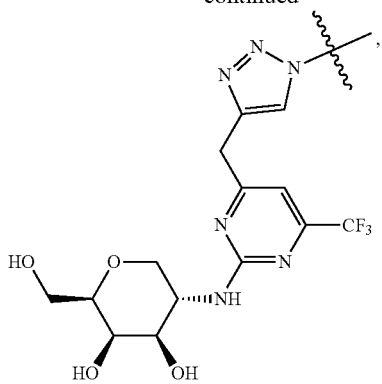
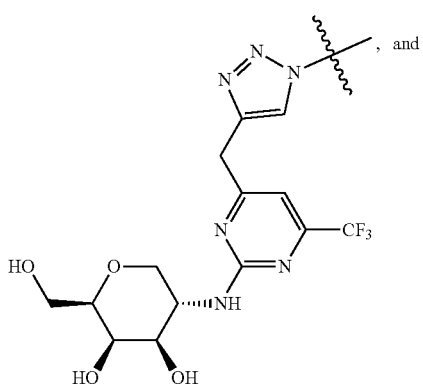
, and
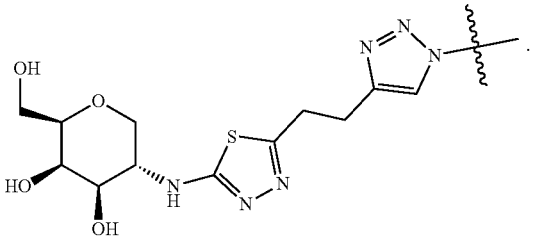 [SMILES: *n1cc(CCc2nnc(N[C@H]3CO[C@H](CO)[C@H](O)[C@@H]3O)s2)nn1]
In certain embodiments of formula (I), n is 1, 2 or 3, and X is the following structure:
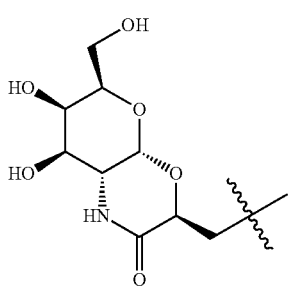
In certain embodiments of formula (I), n is 1, 2 or 3, and X is the following structure:

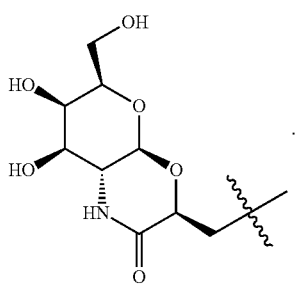 [SMILES: *C[C@@H]1O[C@H]2O[C@H](CO)[C@H](O)[C@H](O)[C@H]2NC1=O]

In certain embodiments of formula (I), n is 1 and X is

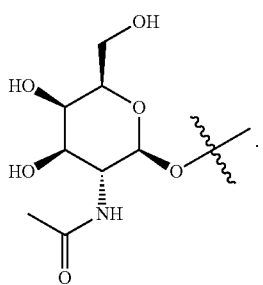 [SMILES: *O[C@@H]1O[C@H](CO)[C@H](O)[C@H](O)[C@H]1NC(C)=O]

In certain embodiments of any one of formulae (Ia)-(Ip), —$Z^1$— is linked to an -$L^1$- moiety (e.g., of the linker of any of formulae (II), (IIa) or (IIb) described herein). In some embodiments, the subject compounds comprise a —$Z^1$-$L^1$- group selected from:

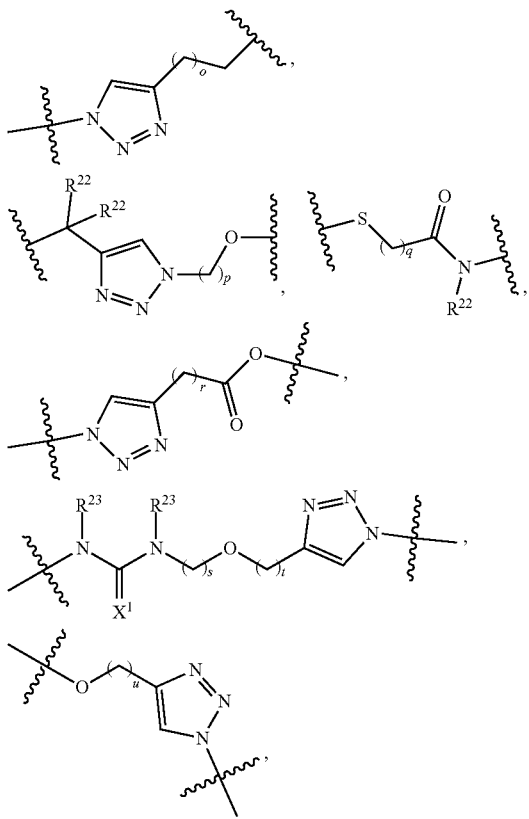

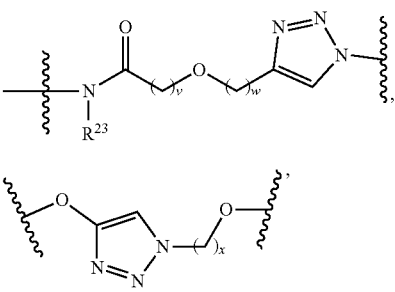

wherein o, p, q, r, s, t, u, v, w, x, y, z and z1 are each independently 1 to 6.

In certain embodiments, the $Z^1$-$L^1$- group is

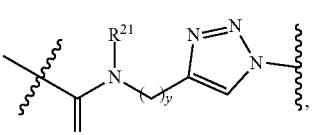

and o is 1 or 2.

In certain embodiments, the $Z^1$-$L^1$- group is

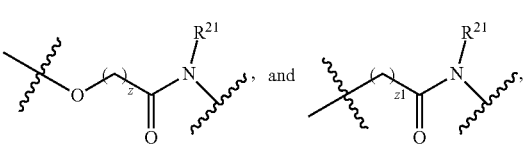

each $R^{22}$ is H, and p is 1 or 2.

In certain embodiments, the $Z^1$-$L^1$- group is

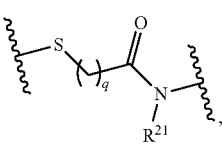

where q is 1-3.

In certain embodiments, the $Z^1$-$L^1$- group is

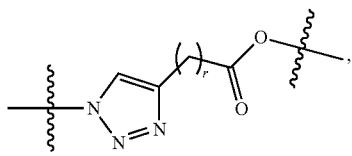

where r is 1-3.

In certain embodiments, the group is

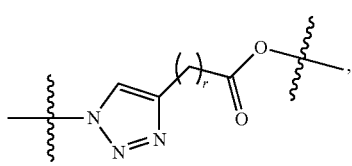

where r is 1-3.

In certain embodiments, the $Z^1$-$L^1$- group is

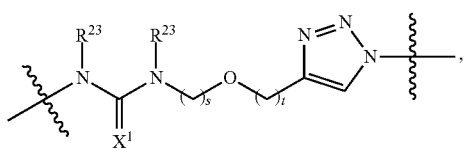

where s and t are each independently 1-3.

In certain embodiments, the $Z^1$-$L^1$- group is

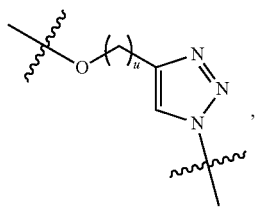

where u is 1-3.

In certain embodiments, the $Z^1$-$L^1$- group is

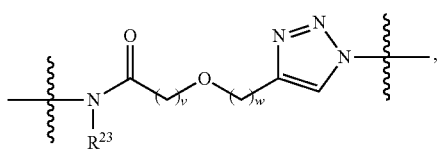

where v and w are each independently is 1-3.

In certain embodiments, the $Z^1$-$L^1$- group is

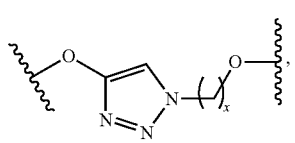

where x is 0-3.

In certain embodiments, the $Z^1$-$L^1$- group is

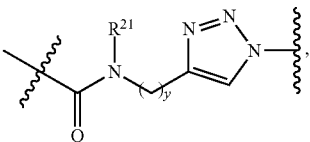

where y is 1-3.

In certain embodiments, the $Z^1$-$L^1$- group is

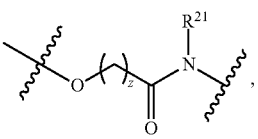

where $R^{21}$ is H, and z is 1-4.

In certain embodiments, the $Z^1$-$L^1$- group is

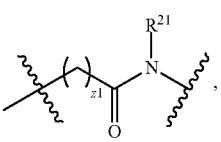

where $R^{21}$ is H, and z1 is 1-4.

In certain embodiments, the subject compounds comprise a —$Z^1$-L- group selected from:

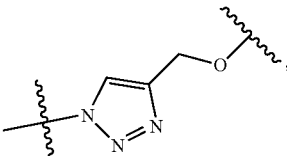

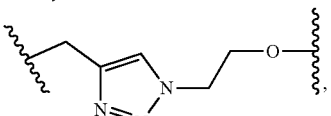

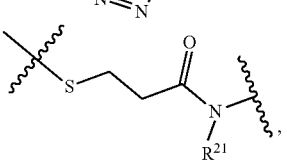

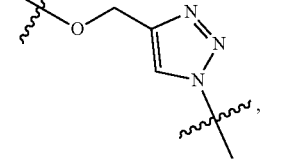

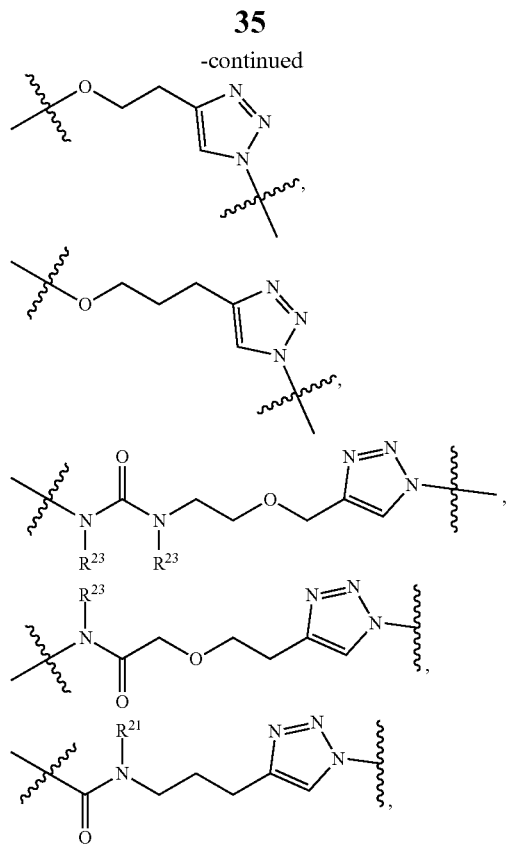
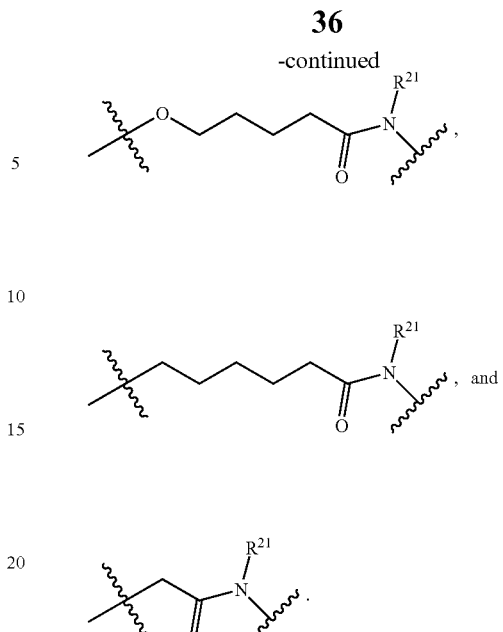

5.1.1. Exemplary ASGPR Ligands

Exemplary moieties that bind the ASGPR, and synthons which can be utilized in the preparation of compounds of this disclosure that include the ASGPR ligand of interest are shown in Tables 1-4.

In certain embodiments, the compound of formula (Ib) is a compound shown in Table 1:

TABLE 1

Exemplary ASGPR binding moieties (X) of formula (Ib)

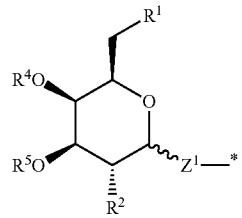

| # | $R^1$ | $R^2$ | $R^4$ | $R^5$ | $Z^1$ |
|---|---|---|---|---|---|
| X1 | —OH | —NHC(O)CH$_3$ | H | H | —O— |
| X2 | —OH | —NHC(O)CH$_3$ | H | H | —S— |
| X3 | —OH | —NHC(O)CH$_3$ | H | H | —CH$_2$— |
| X4 | —OH | —NHC(O)CH$_3$ | H | H | 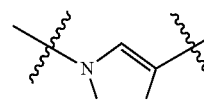 |
| X4.1 | —OH | —NHC(O)CH$_3$ | H | H | 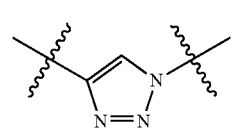 [SMILES: *c1cn(*)nn1] |
| X5 | —OH | —NHC(O)CH$_3$ | H | —C(O)CH(CH$_3$)$_2$ | —O— |
| X5.1 | —OH | —NHC(O)CH$_3$ | H | H | —NH— |

In certain embodiments, the compound of formula (Ic) is a compound shown in Table 2:

TABLE 2

Exemplary ASGPR binding moieties (X) of formula (Ic)

| # | $R^3$ | $R^2$ | $R^4$ | $R^5$ | $Z^1$ |
|---|---|---|---|---|---|
| X6 | —OH | —NHC(O)CH$_3$ | H | H | —O— |
| X7 | —OCH$_3$ | —NHC(O)CH$_3$ | H | H | —C(O)NH— |
| X8 | —OCH$_3$ | —NHC(O)CH$_3$ | H | H | —O— |

In certain embodiments, the compound of formula (Id) is a compound shown in Table 3:

TABLE 3

Exemplary ASGPR binding moieties (X) of formula (Id)

| # | $R^1$ | R3 | $R^4$ | $R^5$ | $Z^1$ |
|---|---|---|---|---|---|
| X9 | —OH | —OCH$_3$ | H | H | triazole |
| X10 | —OH | —OCH$_3$ | H | H | —NH(CO)NH— |
| X11 | —OH | —OCH$_3$ | H | H | —NHC(O)— |

In certain embodiments, the compound of formula (Id) is a compound shown in Table 4:

TABLE 4

Other exemplary ASGPR binding moieties (X) of formula (Id)

| # | $R^1$ | $R^3$ | $R^4$ | $R^5$ | $Z^1$ |
|---|---|---|---|---|---|
| X12 | —OH | H | H | H | triazole |
| X13 | —OH | H | H | H | triazole-CH$_2$-O-phenyl-C(O)NH— |
| X14 | —OH | H | H | H | triazole-CH$_2$-O-phenyl-C(O)NH— |
| X15 | —OH | H | H | H | —CH$_2$— |

TABLE 4-continued
Other exemplary ASGPR binding moieties (X) of formula (Id)
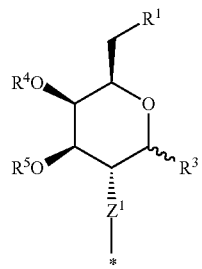
| # | R¹ | R³ | R⁴ | R⁵ | Z¹ |
|---|----|----|----|----|----|
| X16 | —OH | H | H | H | 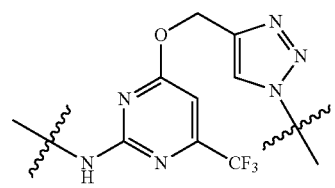 [SMILES: *Nc1nc(OCc2cn(*)nn2)cc(C(F)(F)F)n1] |
| X17 | —OH | H | H | H | 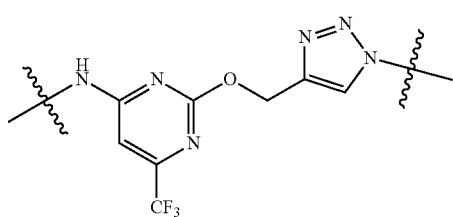 [SMILES: *Nc1cc(C(F)(F)F)nc(OCc2cn(*)nn2)n1] |
| X18 | —OH | H | H | H | 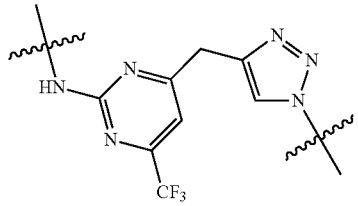 [SMILES: *Nc1nc(Cc2cn(*)nn2)cc(C(F)(F)F)n1] |
| X19 | —OH | H | H | H | 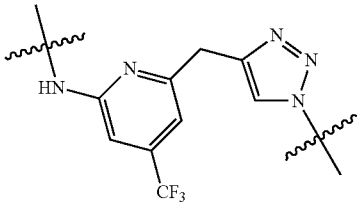 [SMILES: *Nc1cc(C(F)(F)F)cc(Cc2cn(*)nn2)n1] |
| X20 | —OH | H | H | H | 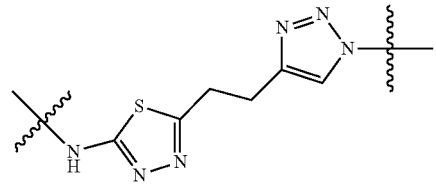 [SMILES: *Nc1nnc(CCc2cn(*)nn2)s1] |

Exemplary building blocks that can be used in the preparation of compounds of this disclosure that include ASGPR ligands (X) of interest are shown in Table 5.

TABLE 5

ASGPR binding compound X building blocks

| # | Structure |
|---|---|
| XB1 | 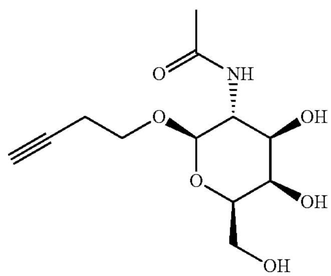 [SMILES: C#CCCO[C@@H]1O[C@H](CO)[C@H](O)[C@H](O)[C@H]1NC(C)=O] |
| XB2 | 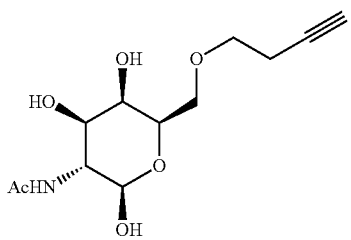 [SMILES: C#CCCOC[C@H]1O[C@@H](O)[C@H](NC(C)=O)[C@@H](O)[C@H]1O] |
| XB3 | 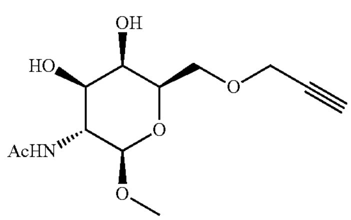 [SMILES: C#CCOC[C@H]1O[C@@H](OC)[C@H](NC(C)=O)[C@@H](O)[C@H]1O] |
| XB4 | 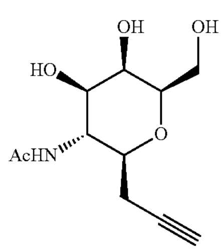 [SMILES: C#CC[C@@H]1O[C@H](CO)[C@H](O)[C@H](O)[C@H]1NC(C)=O] |
| XB4B | 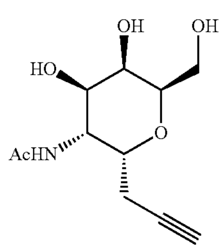 [SMILES: C#CC[C@H]1O[C@H](CO)[C@H](O)[C@H](O)[C@H]1NC(C)=O] |

TABLE 5-continued

ASGPR binding compound X building blocks

| # | Structure |
|---|---|
| XB5 | (N-acetyl-3,4,6-tri-O-acetyl-β-D-galactosaminyl)-thio-propanoic acid |
| XB5B | (N-acetyl-3,4,6-tri-O-acetyl-α-D-galactosaminyl)-thio-propanoic acid |
| XB6 | 2-acetamido-2-deoxy-β-D-galactopyranosyl azide |
| XB7 | N-acetyl-α-D-galactosaminyl pent-4-ynyl ether |
| XB8 | 3-O-isobutyryl-N-acetyl-β-D-galactosaminyl pent-4-ynyl ether |

TABLE 5-continued

ASGPR binding compound X building blocks

| # | Structure |
|---|---|
| XB9 | 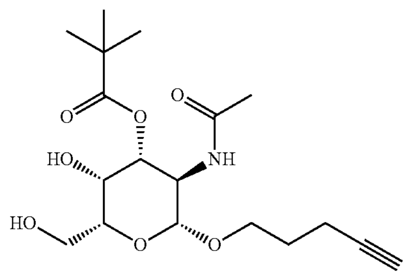 [SMILES: C#CCCCO[C@@H]1O[C@H](CO)[C@H](O)[C@H](OC(=O)C(C)(C)C)[C@H]1NC(C)=O] |
| XB10 | 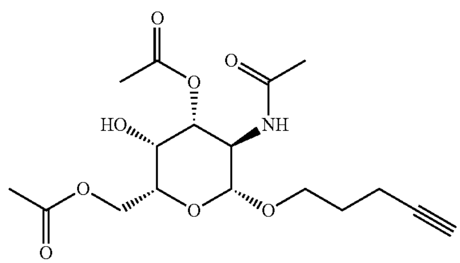 [SMILES: C#CCCCO[C@@H]1O[C@H](COC(C)=O)[C@H](O)[C@H](OC(C)=O)[C@H]1NC(C)=O] |
| XB11 | 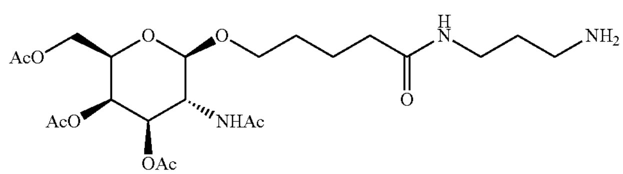 [SMILES: CC(=O)N[C@H]1[C@H](OCCCCC(=O)NCCCN)O[C@H](COC(C)=O)[C@H](OC(C)=O)[C@@H]1OC(C)=O] |
| XB12 | 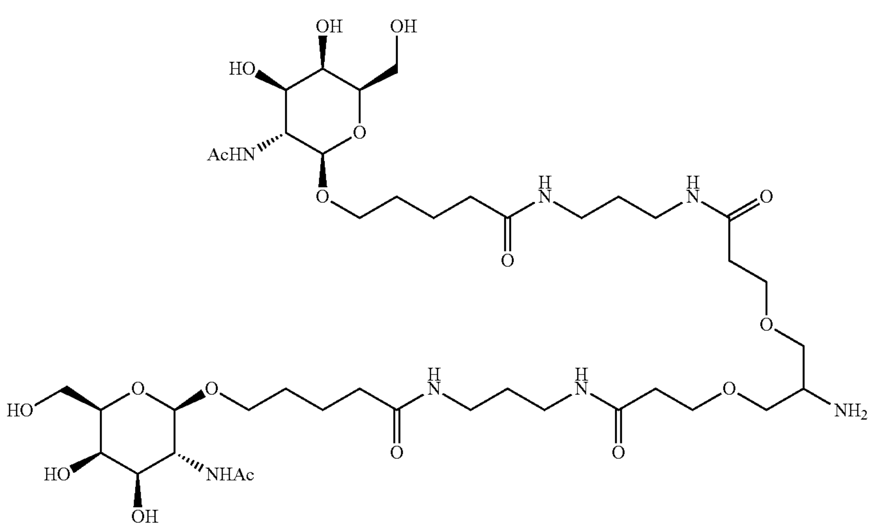 [SMILES: CC(=O)N[C@H]1[C@H](OCCCCC(=O)NCCCNC(=O)CCOCC(N)COCCC(=O)NCCCNC(=O)CCCCO[C@@H]2O[C@H](CO)[C@H](O)[C@H](O)[C@H]2NC(C)=O)O[C@H](CO)[C@H](O)[C@@H]1O] |

TABLE 5-continued
ASGPR binding compound X building blocks
| # | Structure |
|---|---|
| XB13 | 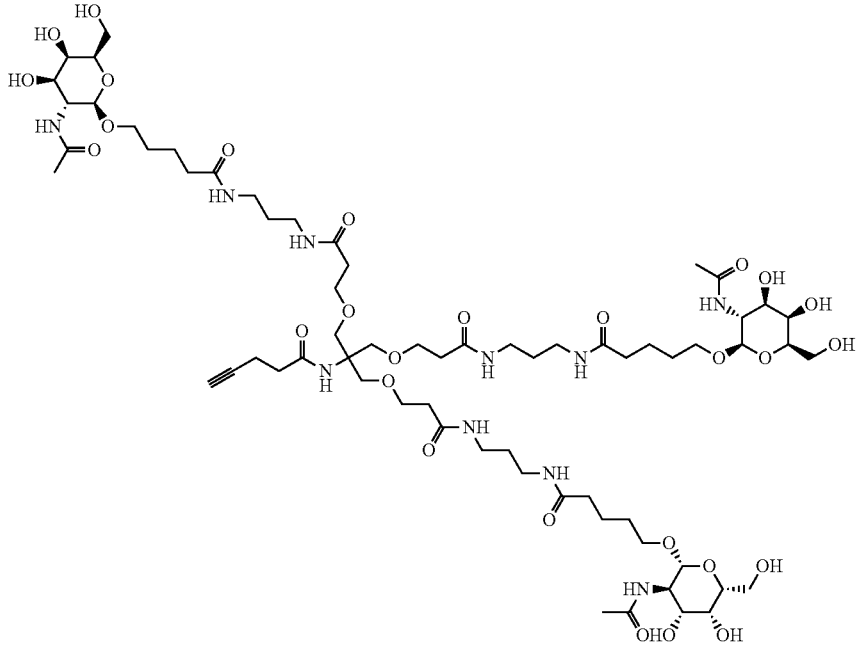 [SMILES: C#CCCC(=O)NC(COCCC(=O)NCCCNC(=O)CCCCO[C@@H]1O[C@H](CO)[C@H](O)[C@H](O)[C@H]1NC(C)=O)(COCCC(=O)NCCCNC(=O)CCCCO[C@@H]1O[C@H](CO)[C@H](O)[C@H](O)[C@H]1NC(C)=O)COCCC(=O)NCCCNC(=O)CCCCO[C@@H]1O[C@H](CO)[C@H](O)[C@H](O)[C@H]1NC(C)=O] |
| XB14 | 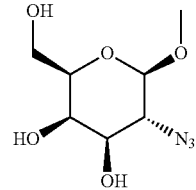 |
| XB15 | 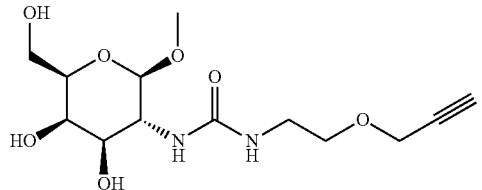 [SMILES: C#CCOCCNC(=O)N[C@H]1[C@H](OC)O[C@H](CO)[C@H](O)[C@@H]1O] |
| XB16 | 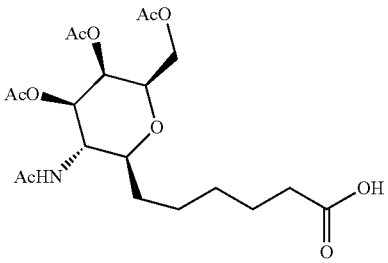 [SMILES: CC(=O)N[C@@H]1[C@@H](OC(C)=O)[C@@H](OC(C)=O)[C@@H](COC(C)=O)O[C@H]1CCCCCC(=O)O] |

TABLE 5-continued

ASGPR binding compound X building blocks

| # | Structure |
|---|---|
| XB17 | 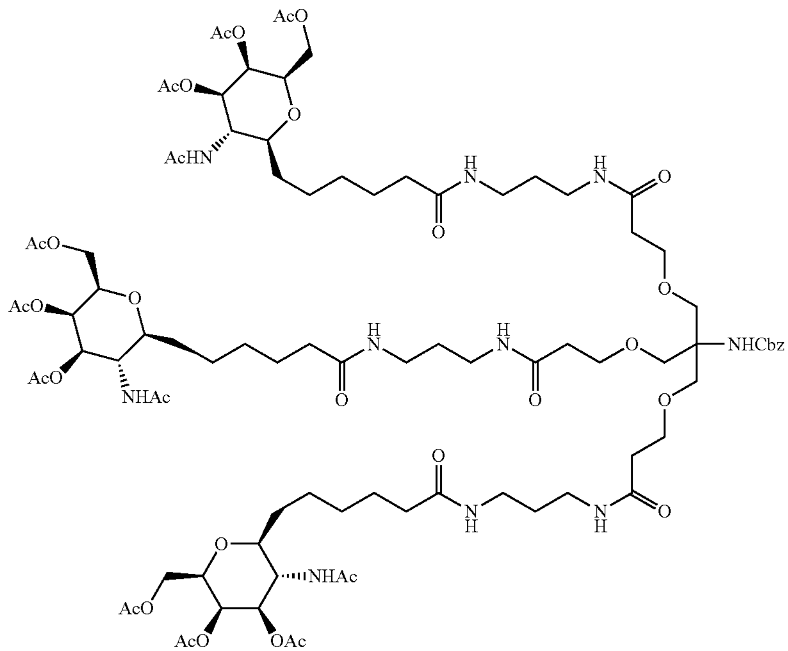 [SMILES: CC(=O)N[C@@H]1[C@@H](OC(C)=O)[C@@H](OC(C)=O)[C@@H](COC(C)=O)O[C@H]1CCCCCC(=O)NCCCNC(=O)CCOCC(COCCC(=O)NCCCNC(=O)CCCCC[C@@H]1O[C@H](COC(C)=O)[C@H](OC(C)=O)[C@H](OC(C)=O)[C@H]1NC(C)=O)(COCCC(=O)NCCCNC(=O)CCCCC[C@@H]1O[C@H](COC(C)=O)[C@H](OC(C)=O)[C@H](OC(C)=O)[C@H]1NC(C)=O)NC(=O)OCc1ccccc1] |
| XB18 | 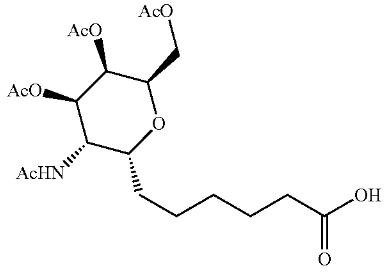 [SMILES: CC(=O)N[C@@H]1[C@@H](OC(C)=O)[C@@H](OC(C)=O)[C@@H](COC(C)=O)O[C@@H]1CCCCCC(=O)O] |

TABLE 5-continued

ASGPR binding compound X building blocks

| # | Structure |
|---|-----------|
| XB19 | *[Structure: Tri-antennary GalNAc building block with three acetyl-protected N-acetylgalactosamine units connected via pentanoyl-propylamide-propanamide-ethylene glycol linkers to a central pentaerythritol-like core bearing an NHCbz group]* |

In some embodiments of the ASGPR ligand (X) building blocks that can be used in the preparation of compounds of this disclosure, $R^3$ is H such that the ASGPR ligand (X) includes $CH_2$ at the 1-position, and $R^2$ is a linking moiety, $Z^1$. Exemplary building blocks that can be used in the preparation of compounds of this disclosure that include ASGPR ligands (X) of interest are shown in Table 6.

TABLE 6

ASGPR binding compound X building blocks

| # | Structure |
|---|-----------|
| XB20 | *[Structure: Pyranose sugar (HO-CH2, OH, OH) linked via N to 1,2,3-triazole, then CH2-O to 3-carboxyphenyl group]* |
| XB21 | *[Structure: Pyranose sugar (HO-CH2, OH, OH) linked via N to 1,2,3-triazole, then CH2-O to 4-carboxyphenyl group]* |

TABLE 6-continued
ASGPR binding compound X building blocks
| # | Structure |
|---|---|
| XB24 | 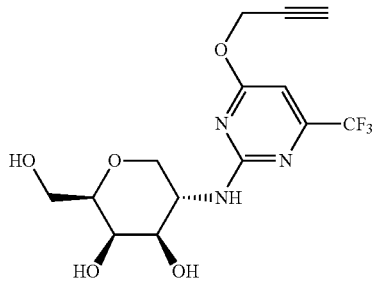 [SMILES: C#CCOc1cc(C(F)(F)F)nc(N[C@H]2CO[C@H](CO)[C@H](O)[C@@H]2O)n1] |
| XB25A | 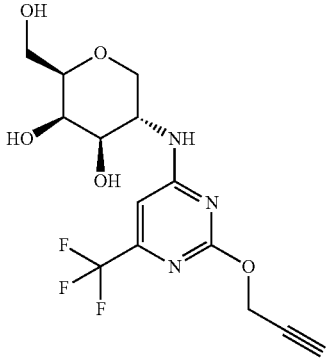 [SMILES: C#CCOc1nc(N[C@H]2CO[C@H](CO)[C@H](O)[C@@H]2O)cc(C(F)(F)F)n1] |
| XB25B | 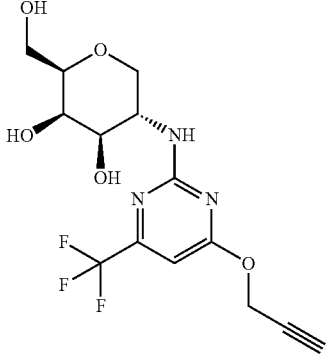 [SMILES: C#CCOc1cc(C(F)(F)F)nc(N[C@H]2CO[C@H](CO)[C@H](O)[C@@H]2O)n1] |
| XB26 | 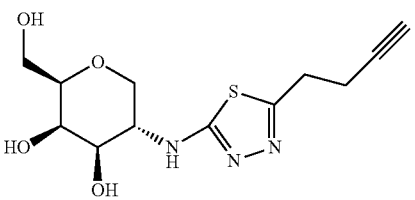 [SMILES: C#CCCc1nnc(N[C@H]2CO[C@H](CO)[C@H](O)[C@@H]2O)s1] |
| XB27 | 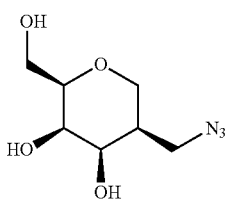 [SMILES: [N-]=[N+]=NC[C@@H]1CO[C@H](CO)[C@H](O)[C@@H]1O] |

TABLE 6-continued

ASGPR binding compound X building blocks

| # | Structure |
|---|---|
| XB28 | 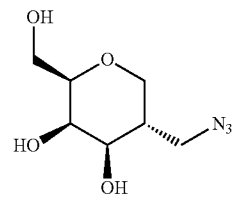 [SMILES: [N-]=[N+]=NC[C@H]1CO[C@H](CO)[C@H](O)[C@@H]1O] |
| XB29 | 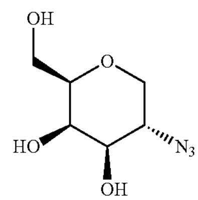 [SMILES: [N-]=[N+]=N[C@H]1CO[C@H](CO)[C@H](O)[C@@H]1O] |
| XB43 | 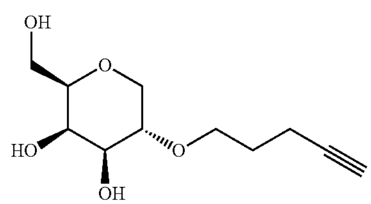 [SMILES: C#CCCCO[C@H]1CO[C@H](CO)[C@H](O)[C@@H]1O] |
| XB30 | 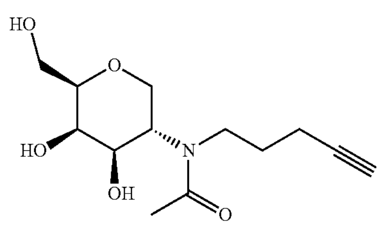 [SMILES: C#CCCCN(C(C)=O)[C@H]1CO[C@H](CO)[C@H](O)[C@@H]1O] |
| XB31 | 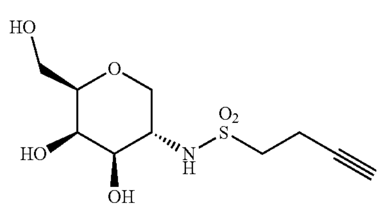 [SMILES: C#CCCS(=O)(=O)N[C@H]1CO[C@H](CO)[C@H](O)[C@@H]1O] |

TABLE 6-continued

ASGPR binding compound X building blocks

| # | Structure |
|---|---|
| XB32 | 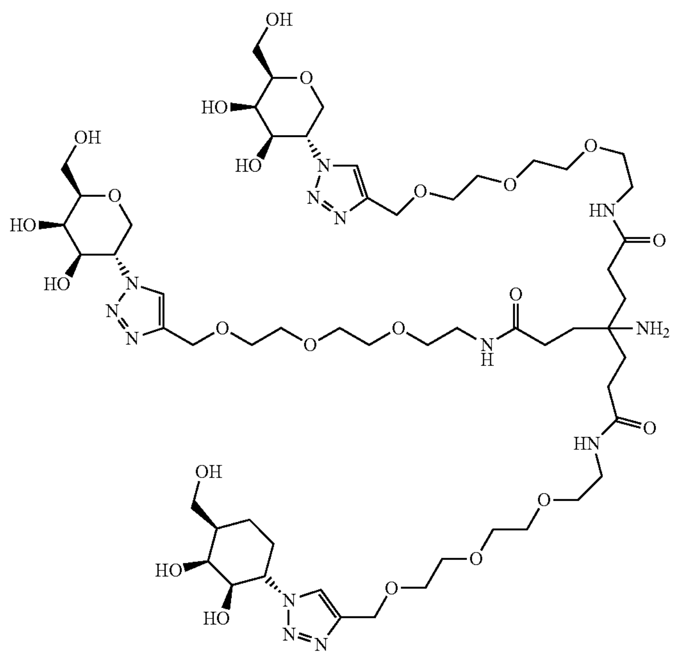 |
| XB33 | 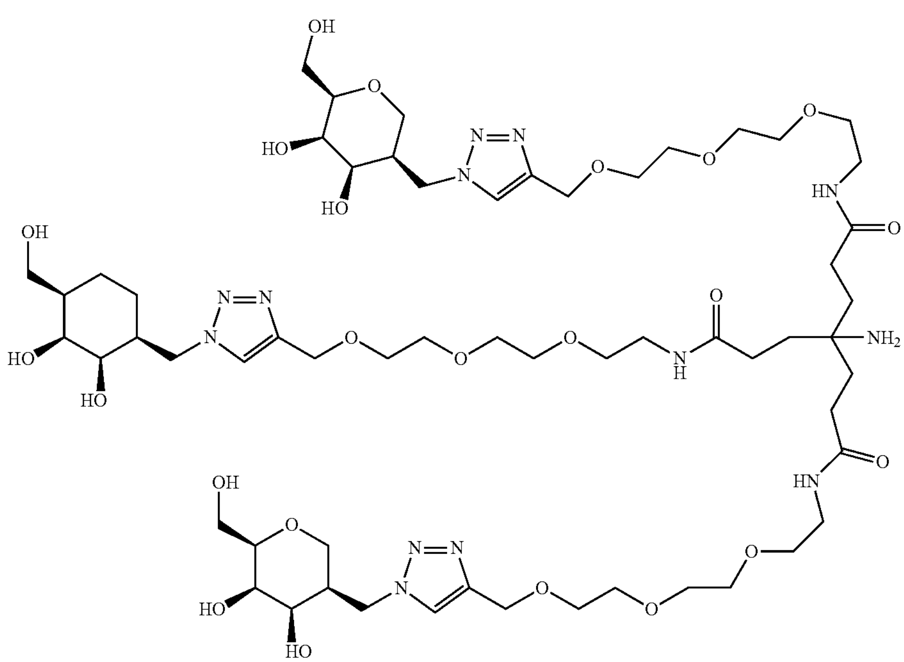 [SMILES: NC(CCC(=O)NCCOCCOCCOCc1cn(C[C@@H]2CO[C@H](CO)[C@H](O)[C@@H]2O)nn1)(CCC(=O)NCCOCCOCCOCc1cn(C[C@@H]2CO[C@H](CO)[C@H](O)[C@@H]2O)nn1)CCC(=O)NCCOCCOCCOCc1cn(C[C@@H]2CC[C@H](CO)[C@H](O)[C@@H]2O)nn1] |

TABLE 6-continued
ASGPR binding compound X building blocks
| # | Structure |
|---|---|
| XB34 | 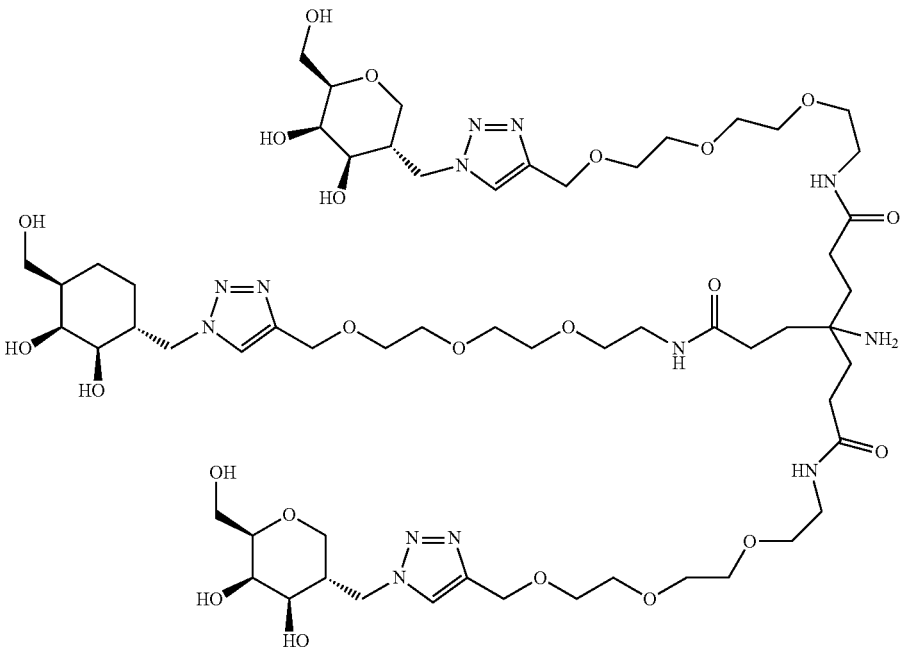 [SMILES: NC(CCC(=O)NCCOCCOCCOCc1cn(C[C@H]2CO[C@H](CO)[C@H](O)[C@@H]2O)nn1)(CCC(=O)NCCOCCOCCOCc1cn(C[C@H]2CO[C@H](CO)[C@H](O)[C@@H]2O)nn1)CCC(=O)NCCOCCOCCOCc1cn(C[C@H]2CC[C@H](CO)[C@H](O)[C@@H]2O)nn1] |
| XB35 | 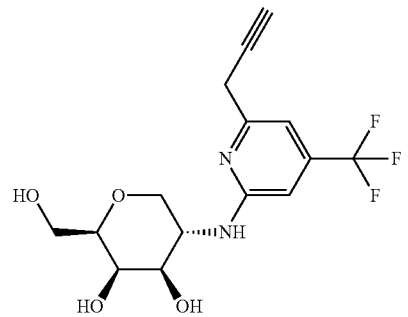 [SMILES: C#CCc1cc(C(F)(F)F)cc(N[C@H]2CO[C@H](CO)[C@H](O)[C@@H]2O)n1] |
| XB36 | 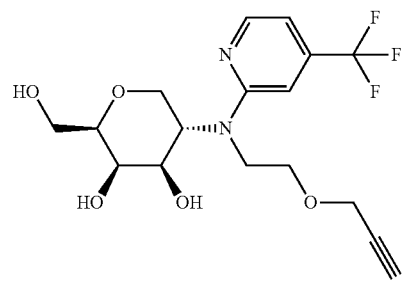 [SMILES: C#CCOCCN(c1cc(C(F)(F)F)ccn1)[C@H]1CO[C@H](CO)[C@H](O)[C@@H]1O] |

TABLE 6-continued

ASGPR binding compound X building blocks

| # | Structure |
|---|---|
| XB37 | (structure) |

In some embodiments, the ASGPR ligand (X) building blocks that can be used in the preparation of compounds of this disclosure is a bicyclic structure. Exemplary building blocks that can be used in the preparation of compounds of this disclosure that include ASGPR ligands (X) of interest are shown in Table 7.

TABLE 7

ASGPR binding compound X building blocks

| # | Structure |
|---|---|
| XB38 | (structure) |
| XB38B | (structure) |

TABLE 7-continued

ASGPR binding compound X building blocks

| # | Structure |
|---|---|
| XB39 | (structure) |
| XB40 | (structure) |
| XB41 | (structure) |
| XB42 | (structure) |

5.1.1. Prodrugs

Aspects of this disclosure include prodrugs of any of the ASGPR binding moieties described herein that are incorporated into the compounds and conjugates of this disclosure.

The term "prodrug" refers to an agent which is converted into the drug in vivo by some physiological or chemical process (e.g., a prodrug on being brought to the physiological pH is converted to the desired drug form).

Prodrugs forms of any of the ASGPR binding moieties described herein can be useful because, for example, can lead to particular therapeutic benefits as a consequence of an extension of the half-life of the resulting compound or conjugate in the body or a reduction in the active dose required.

Pro-drugs can also be useful in some situations, as they may be easier to administer than the parent drug. They may, for instance, be bioavailable by oral administration whereas the parent drug is not. The pro-drug may also have improved solubility in pharmacological compositions over the parent drug.

Prodrug derivative of a ASGPR binding moiety generally includes a promoiety substituent at a suitable labile site of the compound. The promoiety refers to the group that is removed by enzymatic or chemical reactions, when a prodrug is converted to the drug in vivo.

In some embodiments, the promoiety is a group attached via an ester linkage to a hydroxyl group of the compound or drug.

In some embodiments, a prodrug derivative of one or more of the hydroxyl groups of the sugar ring may be incorporated into the compounds. For example, an ester promoiety can be incorporated at one or more of the hydroxyl groups at the 3 and/or 4 positions of the sugar (e.g., as described herein). In some embodiments, the hydroxyl groups at the 3 and 4 positions of the sugar are cyclically linked to form a promoiety (e.g., as described herein).

5.2. Linkers

The terms "linker", "linking moiety" and "linking group" are used interchangeably and refer to a linking moiety that covalently connects two or more moieties or compounds, such as ligands and other moieties of interest. In some cases, the linker is divalent and connects two moieties. In certain cases, the linker is a branched linking group that is trivalent or of a higher multivalency. In some cases, the linker that connects the two or more moieties has a linear or branched backbone of 500 atoms or less (such as 400 atoms or less, 300 atoms or less, 200 atoms or less, 100 atoms or less, 80 atoms or less, 60 atoms or less, 50 atoms or less, 40 atoms or less, 30 atoms or less, or even 20 atoms or less) in length, e.g., as measured between the two or more moieties. A linking moiety may be a covalent bond that connects two groups or a linear or branched chain of between 1 and 500 atoms in length, for example of about 1, 2, 3, 4, 5, 6, 8, 10, 12, 14, 16, 18, 20, 30, 40, 50, 100, 150, 200, 300, 400 or 500 carbon atoms in length, where the linker may be linear, branched, cyclic or a single atom. In certain cases, one, two, three, four, five or more, ten or more, or even more carbon atoms of a linker backbone may be optionally substituted with heteroatoms, e.g., sulfur, nitrogen or oxygen heteroatom. In certain instances, when the linker includes a PEG group, every third atom of that segment of the linker backbone is substituted with an oxygen. The bonds between backbone atoms may be saturated or unsaturated, usually not more than one, two, or three unsaturated bonds will be present in a linker backbone. The linker may include one or more substituent groups, for example an alkyl, aryl or alkenyl group. A linker may include, without limitations, one or more of the following: oligo(ethylene glycol), ether, thioether, disulfide, amide, carbonate, carbamate, tertiary amine, alkyl which may be straight or branched, e.g., methyl, ethyl, n-propyl, 1-methylethyl (iso-propyl), n¬butyl, n-pentyl, 1,1-dimethylethyl (t-butyl), and the like. The linker backbone may include a cyclic group, for example, an aryl, a heterocycle, a cycloalkyl group or a heterocycle group, where 2 or more atoms, e.g., 2, 3 or 4 atoms, of the cyclic group are included in the backbone.

In some embodiments, a "linker" or linking moiety is derived from a molecule with two reactive termini, one for conjugation to a moiety of interest (Y), e.g., a biomolecule (e.g., an antibody) and the other for conjugation to a moiety (noted as X) that binds to a ASGPR cell surface receptor. When Y is a polypeptide, the polypeptide conjugation reactive terminus of the linker is in some cases a site that is capable of conjugation to the polypeptide through a cysteine thiol or lysine amine group on the polypeptide, and so is can be a thiol-reactive group such as a maleimide or a dibromomaleimide, or as defined herein, or an amine-reactive group such as an active ester (e.g., perfluorophenyl ester or tetrafluorophenyl ester), or as defined herein.

In certain embodiments of the formula described herein, the linker L comprises one or more straight or branched-chain carbon moieties and/or polyether (e.g., ethylene glycol) moieties (e.g., repeating units of —$CH_2CH_2O$—), and combinations thereof. In certain embodiments, these linkers optionally have amide linkages, urea or thiourea linkages, carbamate linkages, ester linkages, amino linkages, ether linkages, thioether linkages, sulfhydryl linkages, heteroaryl linkages, or other hetero functional linkages. In certain embodiments, the linker comprises one or more of carbon atoms, nitrogen atoms, sulfur atoms, oxygen atoms, and combinations thereof. In certain embodiments, the linker comprises one or more of an ether bond, thioether bond, amine bond, amide bond, carbon-carbon bond, carbon-nitrogen bond, carbon-oxygen bond, carbon-sulfur bond, and combinations thereof. In certain embodiments, the linker comprises a linear structure. In certain embodiments, the linker comprises a branched structure. In certain embodiments, the linker comprises a cyclic structure. In certain cases, the linker comprises one or more heteroaryl cyclic structures, e.g., a triazole, such as a 1,2,3-traizole.

In certain embodiments, L is between about 10 Å and about 20 Å in length. In certain embodiments, L is between about 15 Å and about 20 Å in length. In certain embodiments, L is about 15 Å in length. In certain embodiments, L is about 16 Å in length. In certain embodiments, L is about 17 Å in length.

In certain embodiments, L is a linker between about 5 Å and about 500 Å. In certain embodiments, L is between about 10 Å and about 400 Å. In certain embodiments, L is between about 10 Å and about 300 Å. In certain embodiments, L is between about 10 Å and about 200 Å. In certain embodiments, L is between about 10 Å and about 100 Å. In certain embodiments, L is between about 10 Å and about 20 Å, between about 20 Å and about 30 Å, between about 30 Å and about 40 Å, between about 40 Å and about 50 Å, between about 50 Å and about 60 Å, between about 60 Å and about 70 Å, between about 70 Å and about 80 Å, between about 80 Å and about 90 Å, or between about 90 Å and about 100 Å. In certain embodiments, L is a linker between about 5 Å and about 500 Å, which comprises an optionally substituted arylene linked to X, an optionally substituted heteroarylene linked to X, an alkylene group linked to X, or a heteroatom linked to X. In certain embodiments, L is a linker between about 10 Å and about 500 Å, which comprises an optionally substituted arylene linked to X, or optionally substituted heteroarylene linked to X, an alkylene group linked to X, or a heteroatom linked to X. In certain embodiments, L is a linker between about 10 Å and about 400 Å, which comprises an optionally substituted arylene linked to X, or optionally substituted heteroarylene linked to X, an alkylene group linked to X, or a heteroatom linked to X. In certain embodiments, L is a linker between about 10 Å and about 200 Å, which comprises an optionally substituted arylene linked to X, or optionally substituted heteroarylene linked to X, an alkylene group linked to X, or a heteroatom linked to X.

In certain embodiments, linker L separates X and Y (or $Z^1$) by a chain of 4 to 500 consecutive atoms. In certain embodiments, linker L separates X and Y (or $Z^1$) by a chain of 4 to 50 consecutive atoms. In certain embodiments, linker L separates X and Y (or $Z^1$) by a chain of 6 to 50 consecutive atoms, by a chain of 11 to 50 consecutive atoms, by a chain of 16 to 50 consecutive atoms, by a chain of 21 to 50 consecutive atoms, by a chain of 26 to 50 consecutive atoms, by a chain of 31 to 50 consecutive atoms, by a chain of 36 to 50 consecutive atoms, by a chain of 41 to 50 consecutive atoms, or by a chain of 46 to 50 consecutive atoms. In certain embodiments, linker L separates X and Y (or $Z^1$) by a chain of 6 to 50 consecutive atoms. In certain embodiments, linker L separates X and Y (or $Z^1$) by a chain of 11 to 50 consecutive atoms. In certain embodiments, linker L separates X and Y (or $Z^1$) by a chain of 16 to 50 consecutive atoms. In certain embodiments, linker L separates X and Y (or $Z^1$) by a chain of 21 to 50 consecutive atoms. In certain embodiments, linker L separates X and Y (or $Z^1$) by a chain of 26 to 50 consecutive atoms. In certain embodiments, linker L separates X and Y (or $Z^1$) by a chain of 31 to 50 consecutive atoms. In certain embodiments, linker L separates X and Y (or $Z^1$) by a chain of 36 to 50 consecutive atoms. In certain embodiments, linker L separates X and Y (or $Z^1$) by a chain of 41 to 50 consecutive atoms. In certain embodiments, linker L separates X and Y (or $Z^1$) by a chain of 46 to 50 consecutive atoms.

In certain embodiments, linker L separates X and Y (or $Z^1$) by a chain of 4 or 5 consecutive atoms, by a chain of 6 to 10 consecutive atoms, by a chain of 11 to 15 consecutive atoms, by a chain of 16 to 20 consecutive atoms, by a chain of 21 to 25 consecutive atoms, by a chain of 26 to 30 consecutive atoms, by a chain of 31 to 35 consecutive atoms, by a chain of 36 to 40 consecutive atoms, by a chain of 41 to 45 consecutive atoms, or by a chain of 46 to 50 consecutive atoms.

In certain embodiments, linker L is a chain of 5 to 500 consecutive atoms separating X and Y (or $Z^1$) and which comprises an optionally substituted arylene linked to X, optionally substituted heteroarylene linked to X, optionally substituted alkylene linked to X, or heteroatom linked to X. In certain embodiments, linker L is a chain of 7 to 500 consecutive atoms separating X and Y (or $Z^1$) and which comprises an optionally substituted arylene linked to X, optionally substituted heteroarylene linked to X, optionally substituted alkylene linked to X, or heteroatom linked to X. In certain embodiments, linker L is a chain of 10 to 500 consecutive atoms separating X and Y (or $Z^1$) and which comprises an optionally substituted arylene linked to X, optionally substituted heteroarylene linked to X, optionally substituted alkylene linked to X, or heteroatom linked to X. In certain embodiments, linker L is a chain of 15 to 400 consecutive atoms separating X and Y (or $Z^1$) and which comprises an optionally substituted arylene linked to X, optionally substituted heteroarylene linked to X, optionally substituted alkylene linked to X, or heteroatom linked to X.

In certain embodiments, linker L is a chain of 5 to 500 consecutive atoms separating X and Y (or $Z^1$) and which comprises an alkylene, a heteroatom, or optionally substituted heteroarylene linked to X. In certain embodiments, linker L is a chain of 7 to 500 consecutive atoms separating X and Y (or $Z^1$) and which comprises an alkylene, a heteroatom, or optionally substituted heteroarylene linked to X. In certain embodiments, linker L is a chain of 10 to 500 consecutive atoms separating X and Y (or $Z^1$) and which comprises an alkylene, a heteroatom, or optionally substituted heteroarylene linked to X. In certain embodiments, linker L is a chain of 15 to 400 consecutive atoms separating X and Y (or $Z^1$) and which comprises an alkylene, a heteroatom, or optionally substituted heteroarylene linked to X.

In certain embodiments, linker L is a chain of 5 to 500 consecutive atoms separating X and Y (or $Z^1$) and which comprises an optionally substituted triazole linked to X. In certain embodiments, linker L is a chain of 7 to 500 consecutive atoms separating X and Y (or $Z^1$) and which comprises an optionally substituted triazole linked to X. In certain embodiments, linker L is a chain of 10 to 500 consecutive atoms separating X and Y (or $Z^1$) and which comprises an optionally substituted triazole linked to X. In certain embodiments, linker L is a chain of 15 to 400 consecutive atoms separating X and Y (or $Z^1$) and which comprises an optionally substituted triazole linked to X.

In certain embodiments, linker L is a chain of 16 to 400 consecutive atoms separating X and Y (or Z) and which comprises an optionally substituted arylene linked to X, optionally substituted heteroarylene linked to X, optionally substituted alkylene linked to X, or a heteroatom linked to X.

It is understood that the linker may be considered as connecting directly to a $Z^1$ group of a ASGPR binding moiety (X) (e.g., as described herein). In some embodiments of any of formulae (Ia)-(Ip), the linker may be considered as connecting directly to the $Z^1$ group. Alternatively, the —$Z^1$-$L^1$- group (e.g., as described herein) can be considered part of a linking moiety that connects L to Y. The disclosure is meant to include all such configurations of ASGPR binding moiety (X) and linker (L).

In some embodiments of formula (I)—(Ia), L is a linker of formula (II):

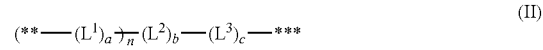

(II)

wherein
$L^1$ and $L^3$ are independently a linker, and $L^2$ is a branched linking moiety, wherein $L^1$ to $L^3$ together provide a linear or branched linker between X and Y;
a, b and c are independently 0 or 1;
** represents the point of attachment to $L^1$ of X via $Z^1$; and
*** represents the point of attachment to Y;
wherein:
when n is 1, a is 1, and b is 0;
when n is >1, a is 1, and b is 1.

In certain embodiments of the linker of formula (II), $L^1$ to $L^3$ each independently comprise one or more linking moieties independently selected from —$C_{1-20}$-alkylene-, —NHCO—$C_{1-6}$-alkylene-, —CONH—$C_{1-6}$-alkylene-, —NH $C_{1-6}$-alkylene-, —NHCONH—$C_{1-6}$-alkylene-, —NHCSNH—$C_{1-6}$-alkylene-, —$C_{1-6}$-alkylene-NHCO—, —$C_{1-6}$-alkylene-CONH—, —$C_{1-6}$-alkylene-NHCONH—, —$C_{1-6}$-alkylene-NHCSNH—, —O(CH$_2$)$_p$—, —(OCH$_2$CH$_2$)$_p$—, —NHCO—, —CONH—, —NHSO$_2$—, —SO$_2$NH—, —CO—, —SO$_2$—, —O—, —S—, monocyclic heteroaryl (e.g., 1,2,3-triazole), monocyclic aryl (e.g., phenyl, e.g., 1,4-linked phenyl or 1,3-linked phenyl), monocyclic heterocycle (e.g., pyrrolidine-2,5-dione, piperazine or piperidine ring as described herein), amino acid residue (naturally or non-naturally occurring amino acid residue), —NH—, and —NMe-, wherein each p is independently 1 to 50.

In certain embodiments of the linker of formula (II), any of $L^1$-$L^3$ comprises repeating ethylene glycol moieties (e.g., —CH$_2$CH$_2$O— or —OCH$_2$CH$_2$—). In certain cases, the linker of formula (II) comprises 1 to 25 ethylene glycol moieties, such as 3 to 25, 5 to 25, 7 to 25, 10 to 25, 15 to 25, 17 to 25, 20 to 25 or 22 to 25 ethylene glycol moieties. In some instances, the linker of formulae (II) comprises 3 or more ethylene glycol moieties, such as 5 or more, 7 or more, 10 or more, 15 or more, 20 or more, or even more ethylene glycol moieties.

In certain embodiments of the linker of formula (II), any of $L^1$-$L^3$ comprises one or more triazole linking moieties. In some instances, the linker comprises one or more 1,2,3-triazole linking moieties. In certain cases, the one or more 1,2,3-triazole moieties is selected from one of the following structures:

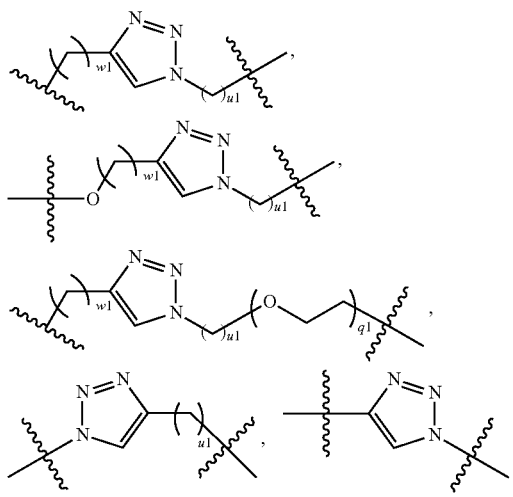

wherein w1, u1 and q1 are independently 1 to 25 (e.g., 1 to 12, such as 1 to 6).

In certain embodiments of the linker of formula (II), n is 1, such that b is 0, and the linker is of the formula (IIa):

$$-(L^1)_a-(L^3)_c-*$$ (IIa)

wherein
  $L^1$ and $L^3$ are independently a linker (e.g., as described herein), wherein $L^1$ to $L^3$ together provide a linear linker between X and Y;
  a is 1;
  c is 0 or 1;
  ** represents the point of attachment to $L^1$ of X via $Z^1$; and
  *** represents the point of attachment to Y.

In certain embodiments of the linker of formula (IIa), the linear linker has a backbone of 20 or more consecutive atoms covalently linking X to Y via $Z^1$, such as a backbone of 25 or more consecutive atoms, or 30 or more consecutive atoms, and in some cases, up to 100 consecutive atoms. In certain embodiments of formula (IIa), the linear linker separates X and Y (or $Z^1$) by a chain of 20 to 50 consecutive atoms. In certain embodiments, the linear linker separates X and Y (or $Z^1$) by a chain of 21 to 50 consecutive atoms, by a chain of 22 to 50 consecutive atoms, by a chain of 23 to 50 consecutive atoms, by a chain of 24 to 50 consecutive atoms, by a chain of 25 to 50 consecutive atoms, by a chain of 26 to 50 consecutive atoms, by a chain of 27 to 50 consecutive atoms, by a chain of 28 to 50 consecutive atoms, or by a chain of 29 to 50 consecutive atoms. In certain embodiments of formula (IIa), the linear linker separates X and Y (or $Z^1$) by a chain of 30 to 60 consecutive atoms. In certain embodiments, the linear linker separates X and Y (or $Z^1$) by a chain of 31 to 60 consecutive atoms. In certain embodiments, the linear linker separates X and Y (or $Z^1$) by a chain of 32 to 60 consecutive atoms. In certain embodiments, the linear linker separates X and Y (or $Z^1$) by a chain of 33 to 60 consecutive atoms. In certain embodiments, the linear linker separates X and Y (or $Z^1$) by a chain of 34 to 60 consecutive atoms. In certain embodiments, the linear linker L separates X and Y (or $Z^1$) by a chain of 35 to 50 consecutive atoms. In certain embodiments, the linear linker L separates X and Y (or $Z^1$) by a chain of 36 to 50 consecutive atoms. In certain embodiments, the linear linker L separates X and Y (or $Z^1$) by a chain of 41 to 50 consecutive atoms. In certain embodiments, the linear linker L separates X and Y (or $Z^1$) by a chain of 46 to 50 consecutive atoms.

In certain other embodiments of formula (II), n is 2 or more, such that $L^1$ to $L^3$ together provide a branched linker between X and Y.

In certain embodiments of formula (II), n is 2 or more, and $L^2$ is selected from:

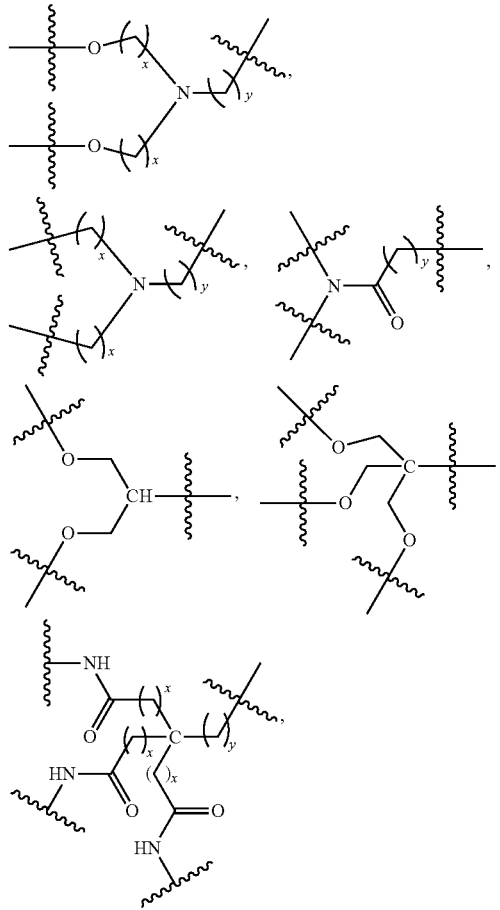

-continued

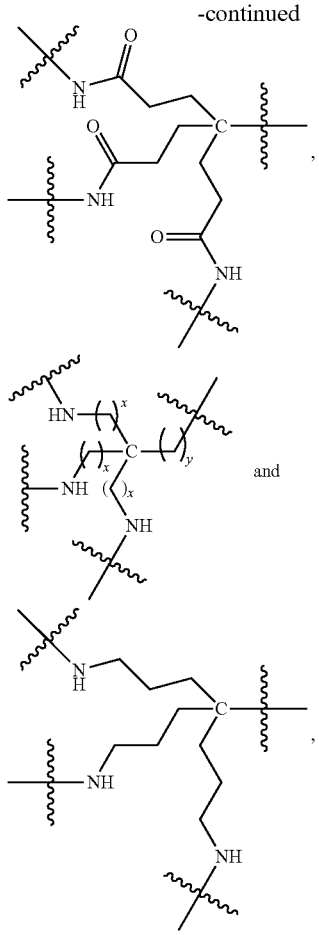

and wherein each x and y are independently 1 to 10.

In certain embodiments of formula (II), $L^1$-$L^2$ comprises a backbone of 14 or more consecutive atoms between X and the branching atom, such as 14 to 50, 14 to 40, 14 to 35 or 14 to 30 consecutive atoms between X and the branching atom.

In certain embodiments of formula (II) or (IIa), $L^3$ comprises a backbone of 10 to 80 consecutive atoms, such as 12 to 70, 12 to 60, or 12 to 50 consecutive atoms.

In certain embodiments of formula (II) or (IIa), wherein $L^3$ comprises a linking moiety selected from ($C_{10}$-$C_{20}$-alkylene (e.g., $C_{12}$-alkylene), or —(OCH$_2$CH$_2$)$_p$—, where p is 1 to 25, such as 3 to 25, 5 to 24, 7 to 25, 10 to 25, 15 to 25 or 20 to 24.

In certain embodiments, L is of formula (IIb):

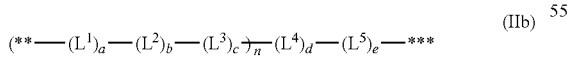

(IIb)

wherein
each $L^1$ to $L^5$ is independently a linking moiety which together provide a linear or branched linker between $Z^1$ and Y;
a, b, c, d, and e are each independently 0, 1, or 2;
** represents the point of attachment to $L^1$ of X via $Z^1$; and
*** represents the point of attachment to Y;

wherein:
when n is 1, a is 1, and c is 0; and
when n is >1, a is 1, and c is 1.

In certain embodiments of the linker of formula (IIb), $L^1$ to $L^5$ each independently comprise one or more linking moieties independently selected from —$C_{1-20}$-alkylene-, —NHCO—$C_{1-6}$-alkylene-, —CONH—$C_{1-6}$-alkylene-, —NH $C_{1-6}$-alkylene-, —NHCONH—$C_{1-6}$-alkylene-, —NHCSNH—$C_{1-6}$-alkylene-, —$C_{1-6}$-alkylene-NHCO—, —$C_{1-6}$-alkylene-CONH—, —$C_{1-6}$-alkylene-NH—, —$C_{1-6}$-alkylene-NHCONH—, —$C_{1-6}$-alkylene-NHCSNH—, —O(CH$_2$)$_p$—, —(OCH$_2$CH$_2$)$_p$—, —NHCO—, —CONH—, —NHSO$_2$—, —SO$_2$NH—, —CO—, —SO$_2$—, —O—, —S—, monocyclic heteroaryl (e.g., 1,2,3-triazole), monocyclic aryl (e.g., phenyl, e.g., 1,4-linked phenyl or 1,3-linked phenyl), monocyclic heterocycle (e.g., pyrrolidine-2,5-dione, piperazine or piperidine ring as described herein), amino acid residue (naturally or non-naturally occurring amino acid residue), —NH—, and —NMe-, wherein each p is independently 1 to 50.

In certain embodiments of formula (IIb), -($L^1$)$_a$- comprises an optionally substituted alkyl or ethylene glycol linking moiety. In certain cases, $L^1$ comprises an optionally substituted —$C_{1-6}$-alkylene-. In certain cases, $L^1$ comprises an ethylene glycol linking moiety.

In certain embodiments of formula (IIb), $L^1$ is independently selected from: —$C_{1-6}$-alkylene-, —(CH$_2$CH$_2$O)$_t$—, —$C_{1-6}$-alkylene-NR$^4$CO—, —$C_{1-6}$-alkyleneCONH—, or OCH$_2$, wherein t is 1 to 20; and $R^4$ is independently selected from H, and optionally substituted ($C_1$-$C_6$)alkyl. In certain cases, $L^1$ is —$C_{1-6}$-alkylene-, such as —$C_{1-3}$-alkylene-. In certain cases, $L^1$ is —(CH$_2$CH$_2$O)$_t$—, where t is 1 to 20, such as 1 to 15, 1 to 10, 1 to 8, 1 to 6, or 1 to 4. In certain cases, $L^1$ is —$C_{1-6}$-alkylene-NR$^4$CO—. In certain cases, $L^1$ is —$C_{1-6}$-alkyleneCONH—. In certain cases, $L^1$ is or OCH$_2$.

In some embodiments of formula (IIb), one or more $L^1$ is independently —CH$_2$O—; —(CH$_2$CH$_2$O)$_t$—, —NR$^4$CO—, —$C_{1-6}$-alkylene-,

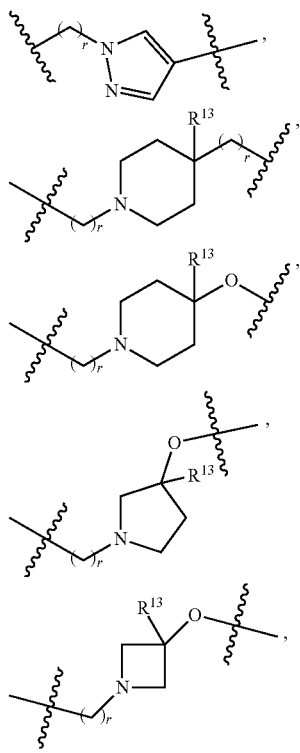

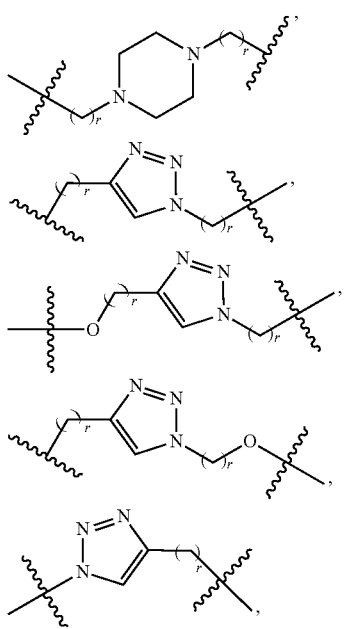

wherein: R[13] is selected from H, halogen, OH, optionally substituted $(C_1-C_6)$alkyl, optionally substituted $(C_1-C_6)$ alkoxy, COOH, NO$_2$, CN, NH$_2$, —N(R[21])$_2$, —OCOR[21], —COOR[21], —CONHR[21], and —NHCOR[21];

each r independently 0 to 20, and any of the L[1] moieties are optionally further substituted.

In certain embodiments of formula (IIb), L[2] is independently selected from: —NR[4']CO—C$_{1-6}$-alkylene-, —CONR[4']—C$_{1-6}$-alkylene,

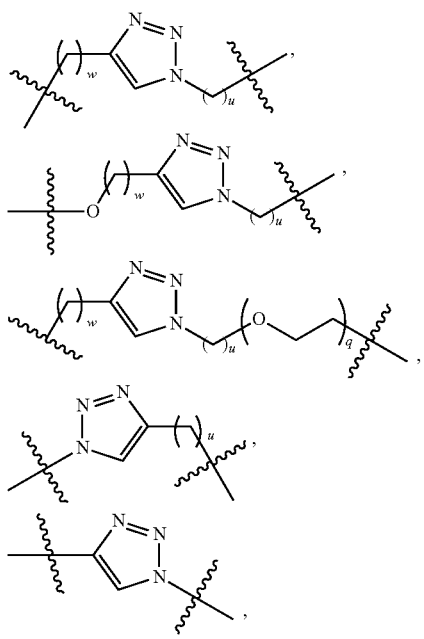

—OCH$_2$—, and —(OCH$_2$CH$_2$)$_q$—, wherein q is 1 to 10, u is 0 to 10, w is 1 to 10, and R[4'] is independently selected from H, and optionally substituted $(C_1-C_6)$alkyl. In certain cases, L[2] is —NR[4']CO—C$_{1-6}$-alkylene-. In certain cases, L[2] is —CONR[4']—C$_{1-6}$-alkylene.

In certain cases, L[2] is

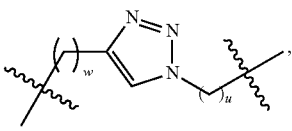

where w is 1 and u is 0 or 1.
In certain cases, L[2] is

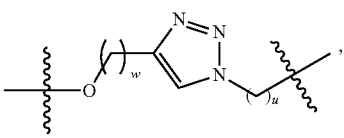

where w is 1 and u is 0 or 1.
In certain cases, L[2] is

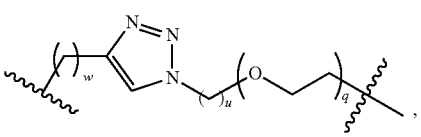

where w is 1, u is 0 or 1, and q is 1.
In certain cases, L[2] is

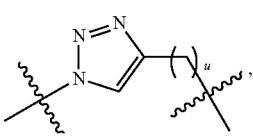

where u is 0 or 1.
In certain cases, L[2] is

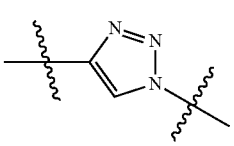 [SMILES: *c1cn(*)nn1]

In certain embodiments, L[2] is —OCH$_2$—. In certain other embodiments, L[2] is (OCH$_2$CH$_2$)$_q$—, and q is 1 to 10, 1 to 9, 1 to 8, 1 to 7, 1 to 6, 1 to 5, 1 to 4, 1 to 3 or 1 to 2. In certain cases, q is 2 to 8, such as 2 to 6, 4 to 6, or 2 to 4.

In certain embodiments of formula (IIb), L[4] is absent or independently selected from —C$_{1-6}$-alkylene-, —(CH$_2$CH$_2$O)$_t$—, —C$_{1-6}$-alkylene-NHCO—, —C$_{1-6}$-alkyleneCONH—, or OCH$_2$, wherein t is 1 to 20. In certain cases, L[4] is absent. In certain cases, L[4] is —C$_{1-6}$-alkylene-. In certain cases, L[4] is —(CH$_2$CH$_2$O)$_t$—, where t is 1 to 20, such as 1 to 15, 1 to 12, 1 to 10, 1 to 8, 1 to 6, 1 to 4 or 1 to 3. In certain cases, L[4] is —C$_{1-6}$-alkylene-NHCO—. In certain cases, L[4] is —C$_{1-6}$-alkyleneCONH—. In certain cases, L[4] is OCH$_2$.

In some embodiments of the subject compounds, n is 1 and L[3] in formula (IIb) is absent.

In certain embodiments of the subject compounds, n is 2 or more, and $L^3$ of formula (IIb) is a branched linking moiety.

Accordingly, in some embodiments of formula (IIb), $L^3$ is a branched linking moiety, e.g., a divalent, or a trivalent linking moiety. For example, an $L^3$ linking moiety can be of the one of the following general formula:

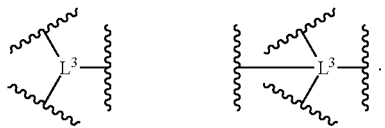

In some embodiments of formula (IIb), the branched linking moiety can be of higher valency and be described by one of the one of the following general formula:

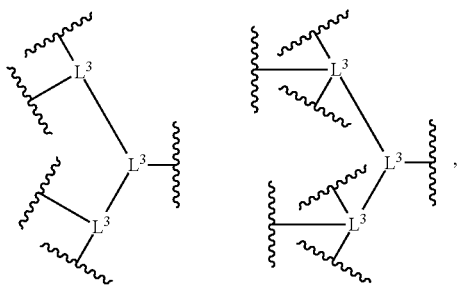

etc.

where any two $L^3$ groups can be directed linked or connected via optional linear linking moieties (e.g., as described herein).

In some embodiments of formula (IIb), the branched linking moiety can include one, two or more $L^3$ linking moieties, each being trivalent moieties, which when linked together can provide for multiple branching points for covalent attachment of the ligands and be described by the following general formula:

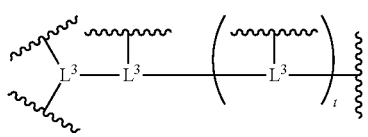

where t is 0 to 500, such as 0 to 100, 0 to 20, or 0 to 10.

In some embodiments, the branched linking moiety (e.g., $L^3$) comprises one or more of: an amino acid residue (e.g., Asp, Lys, Orn, Glu), N-substituted amido (—N(—)C (=O)—), tertiary amino, polyol (e.g., O-substituted glycerol), and the like.

In some embodiments of formula (IIb), one or more $L^3$ is a branching moiety selected from

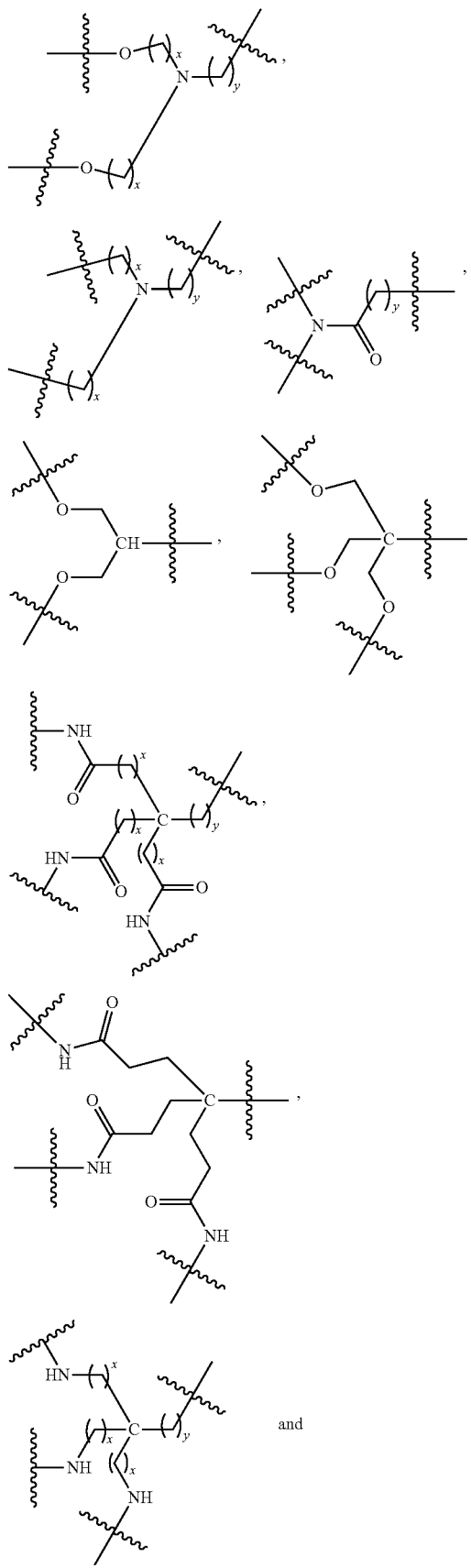

and

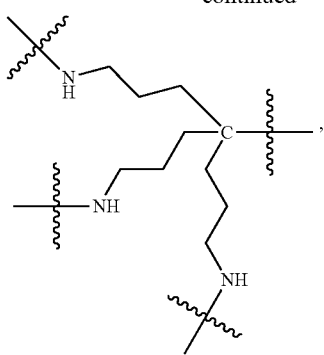

wherein each x and y are each independently 1 to 10, such as 1-6, 1-3, e.g., 1 or 2. In some cases, each x is 1, 2 or 3, e.g., 2.

In some embodiments of formula (IIb), $L^5$ is selected from —CH$_2$O—; —(CH$_2$CH$_2$O)$_1$—, —NR$^4$CO—, —C$_{1-6}$-alkylene-,

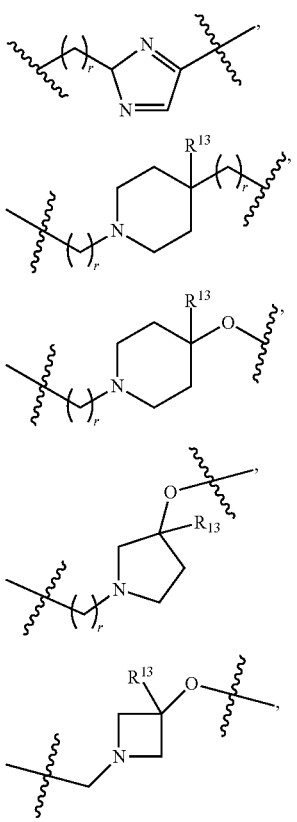

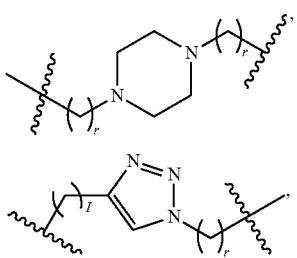

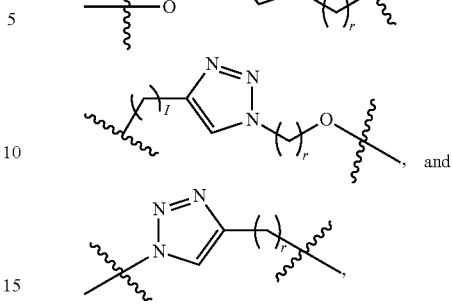

wherein:
$R^{13}$ is selected from H, halogen, OH, optionally substituted (C$_1$-C$_6$)alkyl, optionally substituted (C$_1$-C$_6$) alkoxy, COOH, NO$_2$, CN, NH$_2$, —N(R$^{21}$)$_2$, —OCOR$^{21}$, —COOR$^{21}$, —CONHR$^{21}$, and —NHCOR$^{21}$; each r independently 0 to 20, and any of the $L^5$ moieties are optionally further substituted.

In certain cases, $L^5$ is —CH$_2$O—. In certain cases, $L^5$ is —(CH$_2$CH$_2$O)$_t$—, where t is 1 to 20, such as 1-15, 1-12, 1-10, 1-8, 1-6, or 1 to 4. In certain cases, $L^5$ is —NR$^4$CO—, where $R^4$ is H, or optionally substituted (C$_1$-C$_6$)alkyl. In certain cases, $L^5$ is —C$_{1-6}$-alkylene-.

In certain cases, $L^5$ is

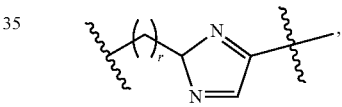

where r is 0 to 20, such as 0 to 15, 0 to 10, 0 to 8, or 0 to 5.

In certain cases, $L^5$ is

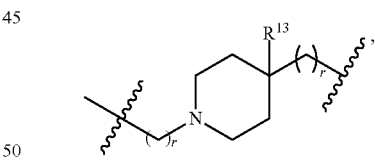

where each r is independently 0 to 20, such as 0 to 15, 0 to 10, 0 to 8, or 0 to 5 and $R^{13}$ is H, or optionally substituted (C$_1$-C$_6$)alkyl.

In certain cases, $L^5$ is

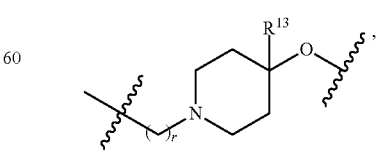

where r is 0 to 20, such as 0 to 15, 0 to 10, 0 to 8, or 0 to 5 and $R^{13}$ is H, or optionally substituted (C$_1$-C$_6$)alkyl.

In certain cases, $L^5$ is

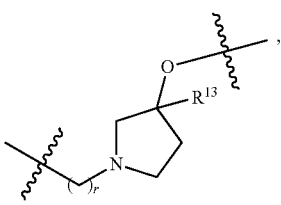

where r is 0 to 20, such as 0 to 15, 0 to 10, 0 to 8, or 0 to 5, and $R^{13}$ is H, or optionally substituted $(C_1-C_6)$alkyl.

In certain cases, $L^5$ is

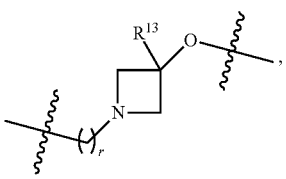

where r is 0 to 20, such as 0 to 15, 0 to 10, 0 to 8, or 0 to 5, and $R^{13}$ is H, or optionally substituted $(C_1-C_6)$alkyl.

In certain cases, $L^5$ is

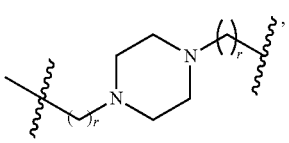

where each r is independently 0 to 20, such as 0 to 15, 0 to 10, 0 to 8, or 0 to 5.

In certain cases, $L^5$ is

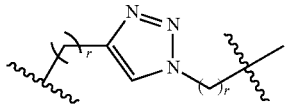

where each r is independently 0 to 20, such as 0 to 15, 0 to 10, 0 to 8, or 0 to 5.

In certain cases, $L^5$ is

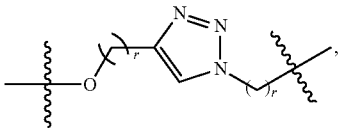

where each r is independently 0 to 20, such as 0 to 15, 0 to 10, 0 to 8, or 0 to 5.

In certain cases, $L^5$ is

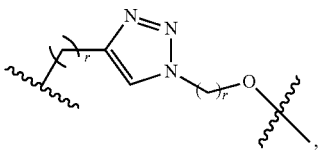

where each r is independently 0 to 20, such as 0 to 15, 0 to 10, 0 to 8, or 0 to 5.

In certain cases, $L^5$ is

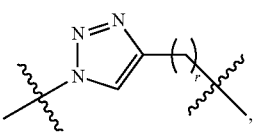

where r is 0 to 20, such as 0 to 15, 0 to 10, 0 to 8, or 0 to 5.

In some embodiments of formula (IIb), $L^5$ comprises one or more of: an amino acid residue (e.g., Asp, Lys, Orn, Glu), an amino acid analogue, N-substituted amido (—N(—)C(═O)—), tertiary amino, polyol (e.g., O-substituted glycerol), and the like. Analogs of an amino acid, include but not limited to, unnatural amino acids, as well as other modifications known in the art. The amino acid includes L-amino acids, D-amino acids, or both, and may contain any of a variety of amino acid modifications or analogs known in the art.

In some embodiments of formula (IIb), $L^1$-$L^5$ comprises one or more of the following units:

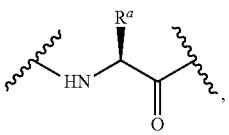

where $R^a$ is $(C_1-C_6)$alkyl or substituted $(C_1-C_6)$alkyl, e.g., a $(C_1-C_6)$alkyl optionally substituted with amine, a tertiary amine, optionally substituted alkoxy, optionally substituted carboxyl, optionally substituted aryl, or optionally substituted heteroaryl. It is understood that $R^a$ can be linked to a M6PR binding moiety.

In some embodiments, the linker includes a polypeptide scaffold where some or all of the sidechain groups of the amino acid residues have been modified to attach a ASGPR binding moiety (e.g., as described herein). It is understood that ASGPR binding moieties (e.g., as described herein) can be conjugated to amino acid residues, such as Asp, Lys, Orn, Glu, and Ser, of a polypeptide containing linker via a convenient conjugation chemistry. In some embodiments, the linker contains a polylysine polypeptide. In some embodiments, the linker contains a polyornithine polypeptide. In some embodiments, the linker contains a polyserine polypeptide. In some embodiments, the linker contains a polyaspartate polypeptide. The polypeptide can be a randomly polymerized polymer having an average length, or a polymer of defined length prepared e.g., in a controlled stepwise fashion. In some cases, the polypeptide linker segment has a length of 10-100 amino acid residues, such as 20-90, or 20-50 amino acid residues. In some embodiments, the N-terminal or C-terminal of the polypeptide linker segment is modified to include a linking unit to an additional M6PR binding moiety (e.g., as described herein). In some embodiments, the N-terminal or C-terminal of the polypeptide linker segment is modified with one or more linking units (e.g., as described herein) suitable for attachment to a Y moiety of interest.

In certain embodiments of formula (IIb), a is 1. In certain cases, at least one of b, c, d, and e is not 0. In certain cases, b is 1 or 2. In certain cases, c is 1 or 2. In certain cases, e is 1 or 2. In certain cases, b, d and e are independently 1 or 2. In certain cases, a, b, d, and e are each 1, and c is 0.

In certain embodiments of formula (II), (IIa) or (IIb), the linker comprises 20 to 100 consecutive atoms, such as 20 to 90, 20 to 80, 20 to 70, 20 to 60, 20 to 50, 20 to 40 or 20 to 30 consecutive atoms. In certain cases, the linker comprises 25 to 100 consecutive atoms, such as 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, or 95 to 100 consecutive atoms.

In certain embodiments of formula (II), (IIa) or (IIb), the linker comprises 25 or more consecutive atoms, such as 26 or more, 27 or more, 28 or more, 29 or more or 30 or more consecutive atoms. In certain embodiments of formula (II), (IIa) or (IIb), the linker comprises 30 or more consecutive atoms, such as 31 or more, 32 or more, 33 or more, 34 or more, 35 or more, 36 or more, 37, or more, 38 or more, 39 or more, 40 or even more consecutive atoms.

The inventors have demonstrated that ASGPR binding compounds of this disclosure having a particular configuration with a linker of desired valency and length can specifically bind with high affinity to both the ASGPR and a target simultaneously, and exhibit high uptake activity of a target. The conjugates of this disclosure can thus provide for sequestering of a target protein in the cell's lysosome and degrading of the target protein. For example, conjugates of trivalent ASGPR binding compounds with 14 or more atoms between the ASGPR binding moiety (e.g., $Z^1$ group) and the branching point of the linker can exhibit superior uptake of cells as compared to conjugates of trivalent ASGPR binding compounds with shorter linkers (e.g., linkers less than 14 atoms) between the ASGPR binding compound (e.g., $Z^1$ group) and the branching point. For example, the inventors observed that a conjugate having a 1-triazole moiety and a short linkage (e.g., 6 atoms) from the ASGPR ligand to the branching point of the ligand (I-157, linker length of 6 atoms to branching point) exhibited less uptake activity in HepG2 cells than the conjugate having a 1-triazole moiety and a longer linkage (e.g., 14 atoms) from the ASGPR ligand to the branching point (I-143, length of 14 atoms) (see, e.g., FIG. 2A). Based on this discovery, described herein are multivalent ASGPR binding compounds having a certain linker length range between the ASGPR binding moiety and the linker branching point which provides desirable binding and cellular uptake of a bound target.

Further, conjugates of trivalent ASGPR binding compounds (e.g., compounds of formula (I) where n=3) can exhibit superior uptake activity in cells as compared to conjugates of divalent or monovalent ASGPR binding compounds (e.g., compounds of formula (I) where n=2 or 1). The inventors observed that conjugate (I-124, n=3) showed superior uptake activity in HepG2 cells as compared to the divalent conjugate (I-144, n=2) (see, e.g., FIG. 2B).

Still further, conjugates of multivalent ASGPR binding compounds with 12 or more atoms between the branching point of the linker and the Y moiety of interest can exhibit superior uptake of cells as compared to conjugates of multivalent ASGPR binding compounds with shorter linkers (e.g., linkers less than 12 atoms) between the branching point of the linker and the Y moiety of interest. The inventors have also demonstrated that conjugates of ASGPR binding compounds having more than 12 atoms between the branching point of the linker and Y exhibit comparable uptake activity. For example, it was observed that conjugates having longer linkers between the ASGPR linker and Y (e.g., conjugates of compounds I-137, having 81 atoms between the branching point and Y; and I-129, having 33 atoms between the branching point and Y) exhibit comparable activity to a reference conjugate (e.g., conjugate of compound I-124, having 12 atoms between the branching point and Y) (see, e.g., FIG. 2B).

As such, in certain embodiments where the linker of formula (II) or (IIb) is a branched linker, each branch of the linker comprises a linear linker of 14 or more consecutive atoms to covalently link via $Z^1$ each X moiety to a branching point of the linker. In certain cases, each branch of the linker comprises a linear linker of 15 or more consecutive atoms to the branching point. In certain cases, each branch of the linker comprises a linear linker of 16 or more consecutive atoms to the branching point. In certain cases, each branch of the linker comprises a linear linker of 17 or more consecutive atoms to the branching point. In certain cases, each branch of the linker comprises a linear linker of 18 or more consecutive atoms to the branching point. In certain cases, each branch of the linker comprises a linear linker of 19 or more consecutive atoms to the branching point.

In certain embodiments of formula (II) or (IIb), the linker is a branched linker comprising branches covalently linking via $Z^1$ each X moiety to a branching point of the linker, and a linear linker covalently linking the branching point to Y. In certain cases, the linear linker covalently linking the branching point to Y is 12 or more consecutive atoms. In certain cases, the linear linker covalently linking the branching point to Y is 15 or more consecutive atoms. In certain cases, the linear linker covalently linking the branching point to Y is 20 or more consecutive atoms. In certain cases, the linear linker covalently linking the branching point to Y is 25 or more consecutive atoms. In certain cases, the linear linker covalently linking the branching point to Y is 30 or more consecutive atoms. In certain cases, the linear linker covalently linking the branching point to Y is 40 or more consecutive atoms. In certain cases, the linear linker covalently linking the branching point to Y is 50 or more consecutive atoms. In certain cases, the linear linker covalently linking the branching point to Y is 60 or more consecutive atoms. In certain cases, the linear linker covalently linking the branching point to Y is 70 or more consecutive atoms. In certain cases, the linear linker covalently linking the branching point to Y is 80 or more consecutive atoms.

5.2.1. Exemplary Linkers and Linking Moieties

Exemplary linkers and linking moieties that can be utilized in the preparation of compounds of this disclosure (e.g., that link the ASGPR ligand (X) to the moiety of interest (Y)) are shown in Tables 8-10.

In certain embodiments, the linker is a linear linker or linking moiety as shown in Table 8.

TABLE 8

Exemplary linear linkers and linking moieties

| Linker No. | Linker structure |
|---|---|
| L1 | (structure) r is 0 to 10, q is 0 to 20, s is 0 or 1, Z' is CO, NHCO, CONH or NH |
| L1.1 | (structure) |
| L1.2 | (structure) |
| L1.3 | (structure) |
| L1.4 | (structure) |
| L1.5 | (structure) |
| L1.6 | (structure) |
| L1.7 | (structure) |
| L1.8 | (structure) |
| L1.9 | (structure) |

TABLE 8-continued

Exemplary linear linkers and linking moieties

| Linker No. | Linker structure |
|---|---|
| L1.10 | (structure) |
| L1.11 | (structure) |
| L2 | (structure)<br>r is 0 to 10, p and q are 0 to 20, s is 0 or 1, Z' is CO, NHCO, CONH or NH |
| L2.1 | (structure) |
| L3 | (structure)<br>r is 0 to 10, p and q are independently 0 to 20 |
| L4 | (structure)<br>r is 0 to 10, s is 1 to 10 |
| L5 | (structure) or (structure)<br>where r is 0 to 10, q is 0 to 20 |
| L5.1 | (structure) |
| L6 | (structure) or (structure)<br>r is 0 to 10, q is 0 to 20 |

TABLE 8-continued
Exemplary linear linkers and linking moieties
| Linker No. | Linker structure |
|---|---|
| L7 | 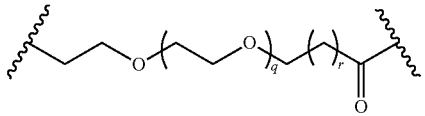<br>r is 0 to 10, q is 0 to 12 |
| L7.1 | 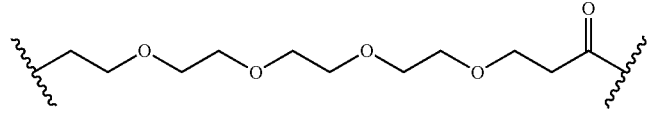 [SMILES: *CCOCCOCCOCCOCCC(*)=O] |
| L7.2 | 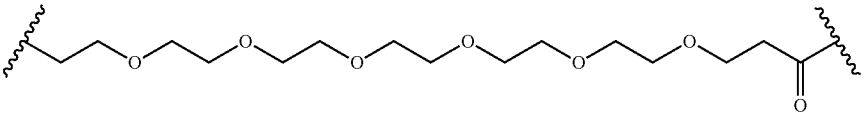 [SMILES: *CCOCCOCCOCCOCCOCCOCCC(*)=O] |
| L7.3 | 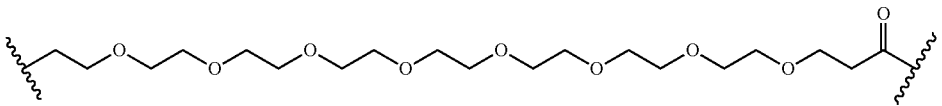 [SMILES: *CCOCCOCCOCCOCCOCCOCCOCCOCCC(*)=O] |
| L8 | 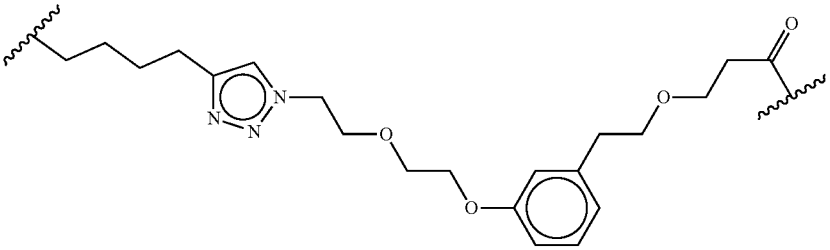 |
| L9 | 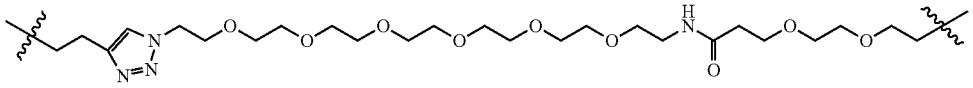 [SMILES: *CCOCCOCCC(=O)NCCOCCOCCOCCOCCOCCOCCn1cc(CC*)nn1] |
| L10 | 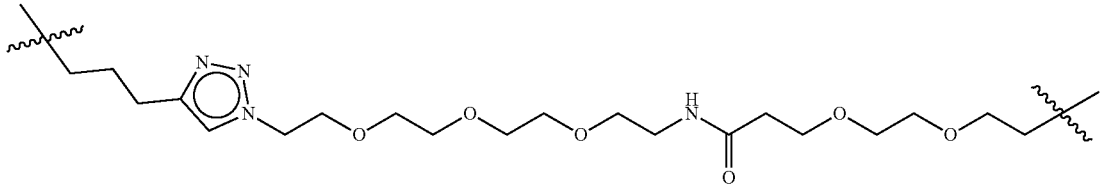 |
| L11 | 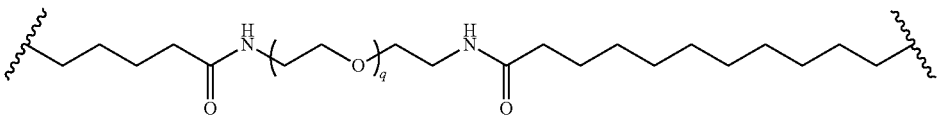<br>q is 0 to 10 |

Table 9 includes various linker component synthetic precursors (e.g., linear and branched linker precursors) that can be utilized in the preparation of the subject compounds.

TABLE 9

Linker component synthetic precursors

| Reagent # | Structure |
|---|---|
| LC1 | 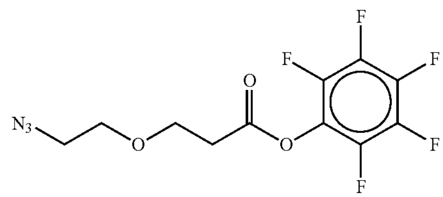 |
| LC1.1 | 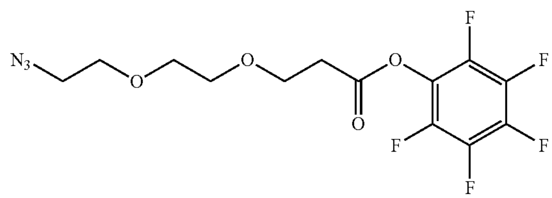 [SMILES: [N-]=[N+]=NCCOCCOCCC(=O)Oc1c(F)c(F)c(F)c(F)c1F] |
| LC2 | 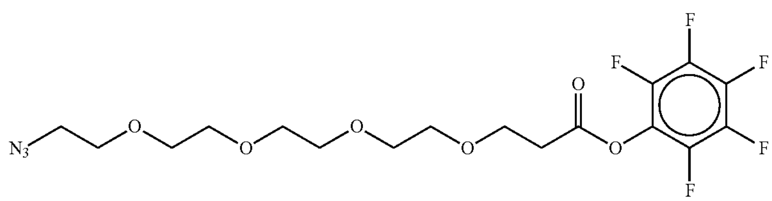 |
| LC3 | 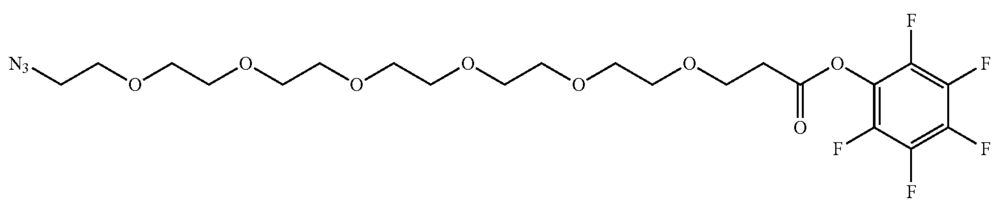 [SMILES: [N-]=[N+]=NCCOCCOCCOCCOCCOCCOCCC(=O)Oc1c(F)c(F)c(F)c(F)c1F] |
| LC3.1 | 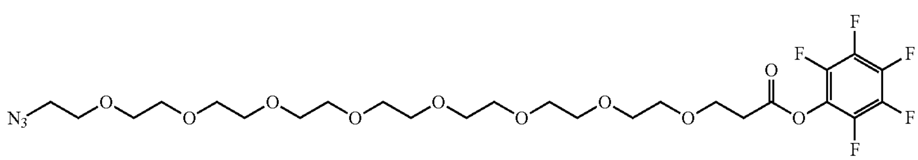 [SMILES: [N-]=[N+]=NCCOCCOCCOCCOCCOCCOCCOCCOCCC(=O)Oc1c(F)c(F)c(F)c(F)c1F] |
| LC3.2 | 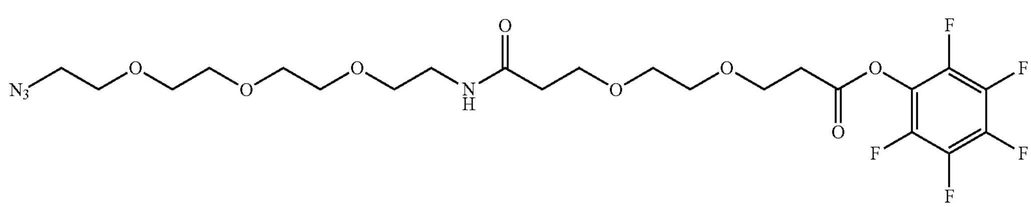 [SMILES: [N-]=[N+]=NCCOCCOCCOCCNC(=O)CCOCCOCCC(=O)Oc1c(F)c(F)c(F)c(F)c1F] |
| LC4 | 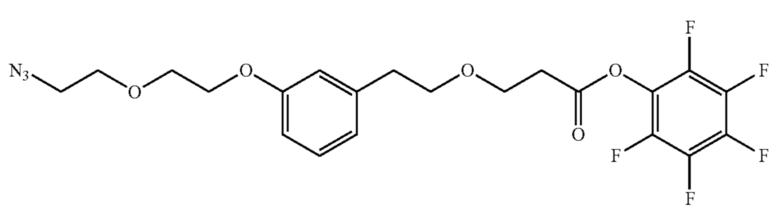 [SMILES: [N-]=[N+]=NCCOCCOc1cccc(CCOCCC(=O)Oc2c(F)c(F)c(F)c(F)c2F)c1] |

TABLE 9-continued
Linker component synthetic precursors
| Reagent # | Structure |
|---|---|
| LC5 | 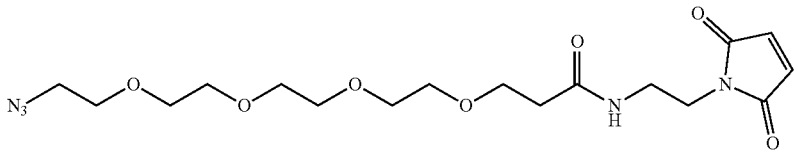 [SMILES: [N-]=[N+]=NCCOCCOCCOCCOCCC(=O)NCCN1C(=O)C=CC1=O] |
| LC6 | 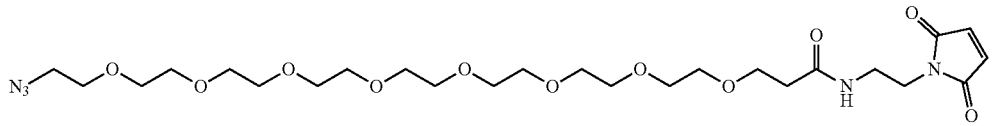 [SMILES: [N-]=[N+]=NCCOCCOCCOCCOCCOCCOCCOCCOCCC(=O)NCCN1C(=O)C=CC1=O] |
| LC7 | 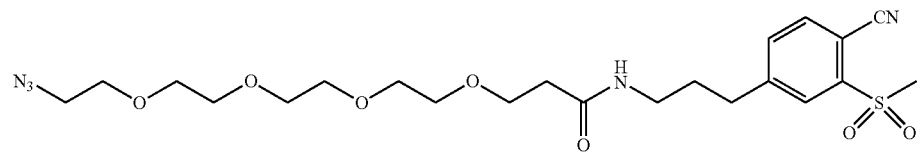 [SMILES: CS(=O)(=O)c1cc(CCCNC(=O)CCOCCOCCOCCOCCN=[N+]=[N-])ccc1C#N] |
| LC8 | 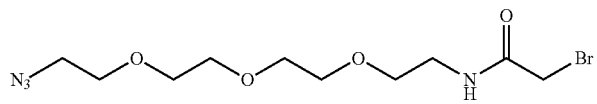 [SMILES: [N-]=[N+]=NCCOCCOCCOCCNC(=O)CBr] |
| LC9 | 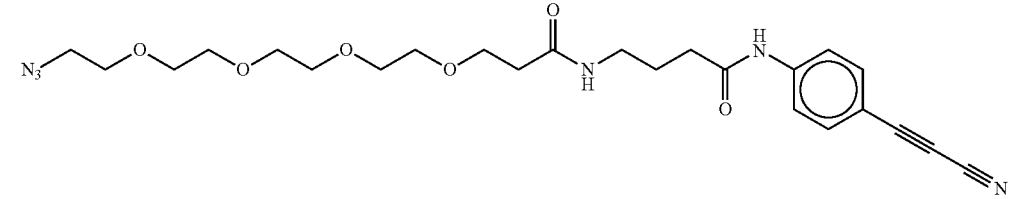 |
| LC9.1 | 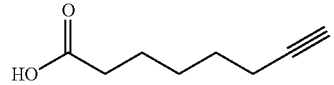 |
| LC10 | 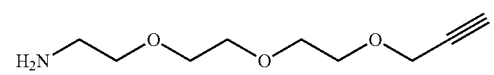 |
| LC10.1 | 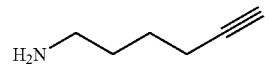 |
| LC10.2 | 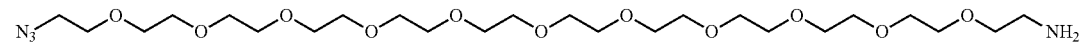 [SMILES: [N-]=[N+]=NCCOCCOCCOCCOCCOCCOCCOCCOCCOCCOCCOCCN] |
| LC10.3 | 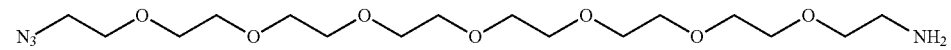 [SMILES: [N-]=[N+]=NCCOCCOCCOCCOCCOCCOCCOCCN] |
| LC10.4 | 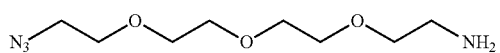 |
| LC10.5 | 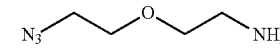 |
| LC10.6 | 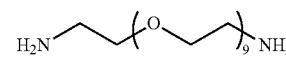 |

TABLE 9-continued

Linker component synthetic precursors

| Reagent # | Structure |
|---|---|
| LC10.7 | 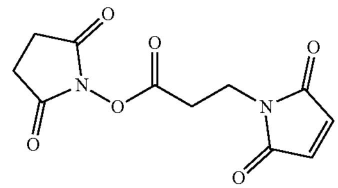 [SMILES: O=C(CCN1C(=O)C=CC1=O)ON1C(=O)CCC1=O] |
| LC10.8 | 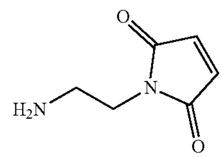 |
| LC11 | 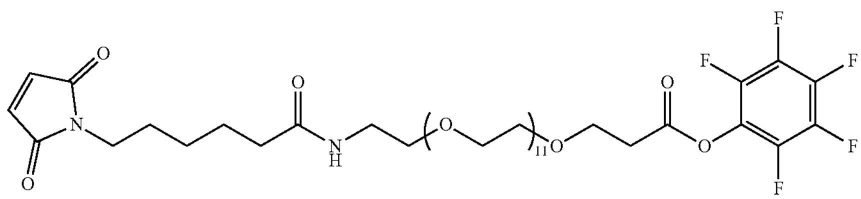 |
| LC12 | 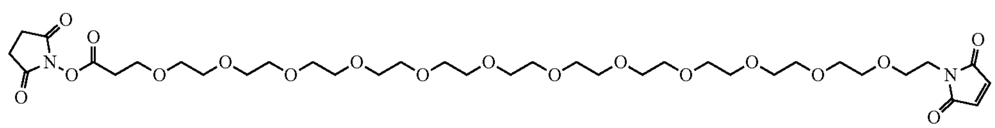 [SMILES: O=C(CCOCCOCCOCCOCCOCCOCCOCCOCCOCCOCCOCCOCCN1C(=O)C=CC1=O)ON1C(=O)CCC1=O] |
| LC13 | 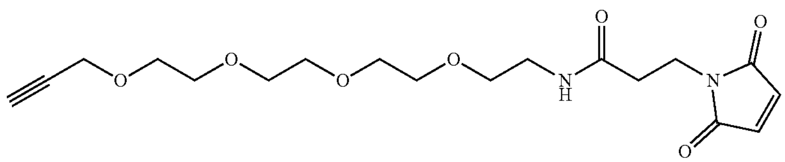 [SMILES: C#CCOCCOCCOCCOCCNC(=O)CCN1C(=O)C=CC1=O] |
| LC14 | 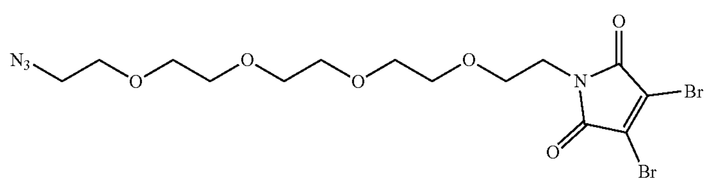 [SMILES: [N-]=[N+]=NCCOCCOCCOCCOCCN1C(=O)C(Br)=C(Br)C1=O] |
| LC15 | 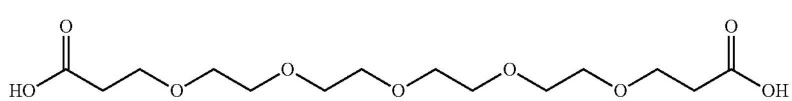 [SMILES: O=C(O)CCOCCOCCOCCOCCOCCC(=O)O] |
| LC16 | 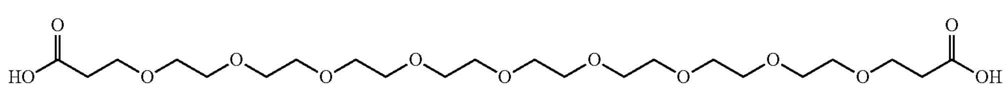 [SMILES: O=C(O)CCOCCOCCOCCOCCOCCOCCOCCOCCOCCC(=O)O] |
| LC17(1-3) | k = 4, l = 0<br>k = 0, l = 12<br>k = 2, l = 6 |

TABLE 9-continued

Linker component synthetic precursors

| Reagent # | Structure |
|---|---|
| LC18 | (structure) |
| LC19 | (structure) |
| LC19.1 | (structure) |
| LC20 | (structure) |

TABLE 9-continued

| Linker component synthetic precursors | |
|---|---|
| Reagent # | Structure |

LC21

LC22

LC23

LC24

LC25

TABLE 9-continued
Linker component synthetic precursors
| Reagent # | Structure |
|---|---|
| LC26 | 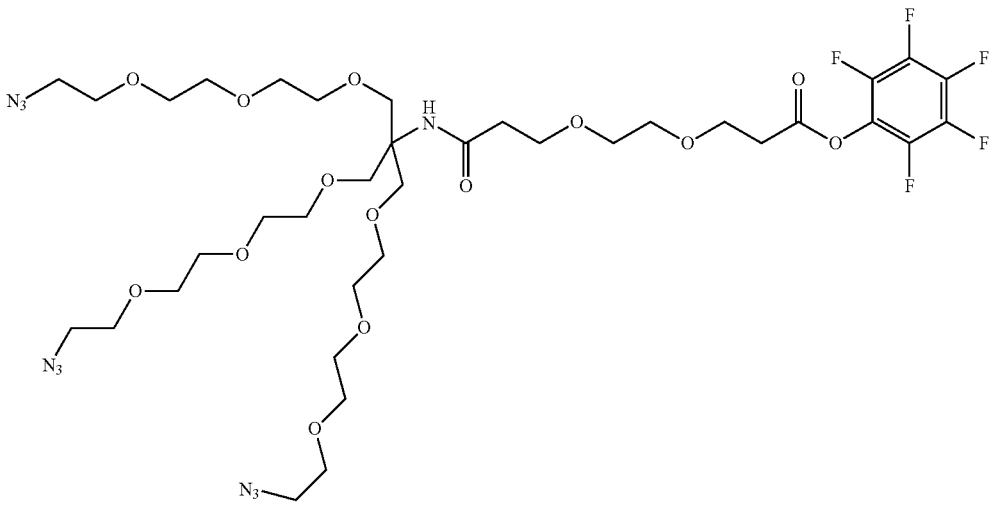 [SMILES: [N-]=[N+]=NCCOCCOCCOCC(COCCOCCOCCN=[N+]=[N-])(COCCOCCOCCN=[N+]=[N-])NC(=O)CCOCCOCCC(=O)Oc1c(F)c(F)c(F)c(F)c1F] |
| LC27 | 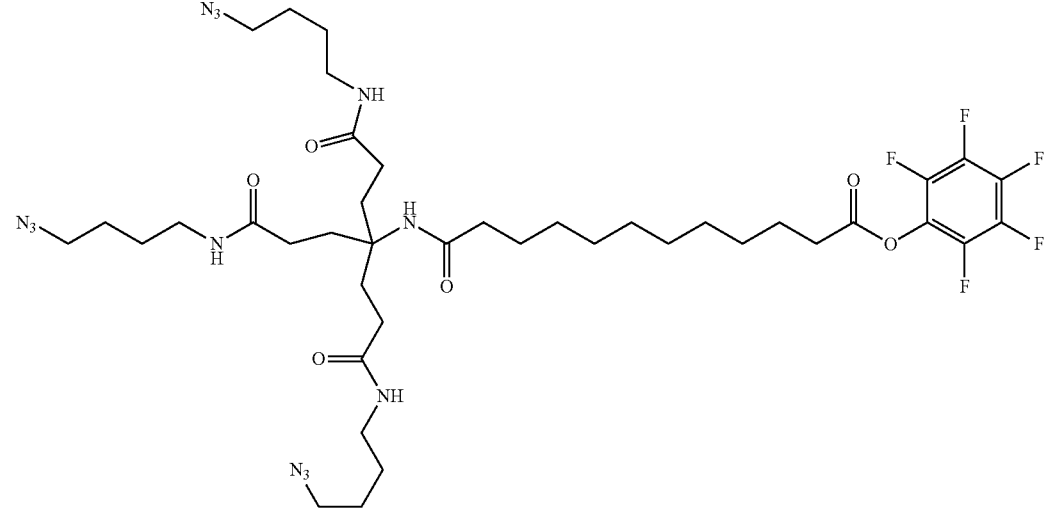 [SMILES: [N-]=[N+]=NCCCCNC(=O)CCC(CCC(=O)NCCCCN=[N+]=[N-])(CCC(=O)NCCCCN=[N+]=[N-])NC(=O)CCCCCCCCCCC(=O)Oc1c(F)c(F)c(F)c(F)c1F] |
| LC28 | 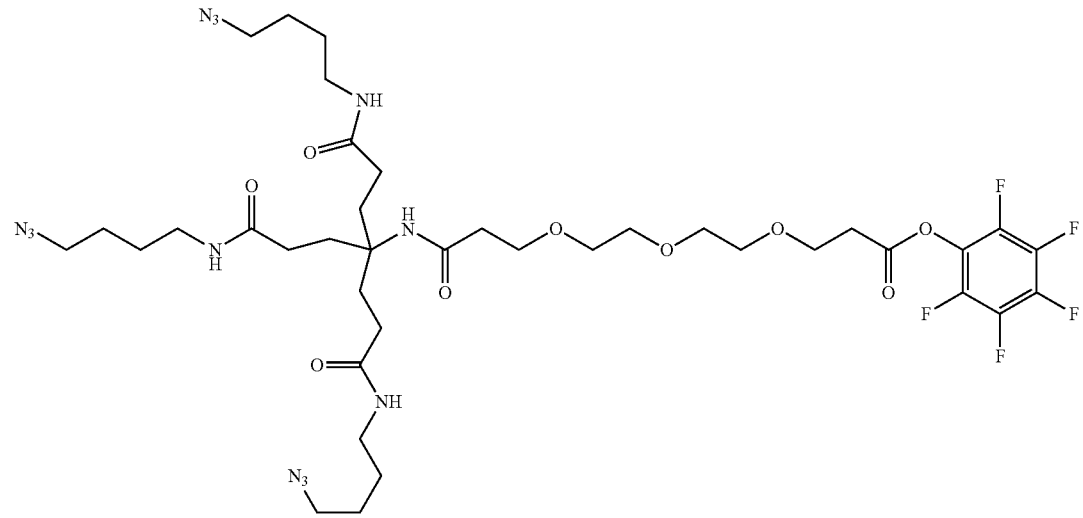 [SMILES: [N-]=[N+]=NCCCCNC(=O)CCC(CCC(=O)NCCCCN=[N+]=[N-])(CCC(=O)NCCCCN=[N+]=[N-])NC(=O)CCOCCOCCOCCC(=O)Oc1c(F)c(F)c(F)c(F)c1F] |

TABLE 9-continued
Linker component synthetic precursors
| Reagent # | Structure |
|---|---|
| LC29 | 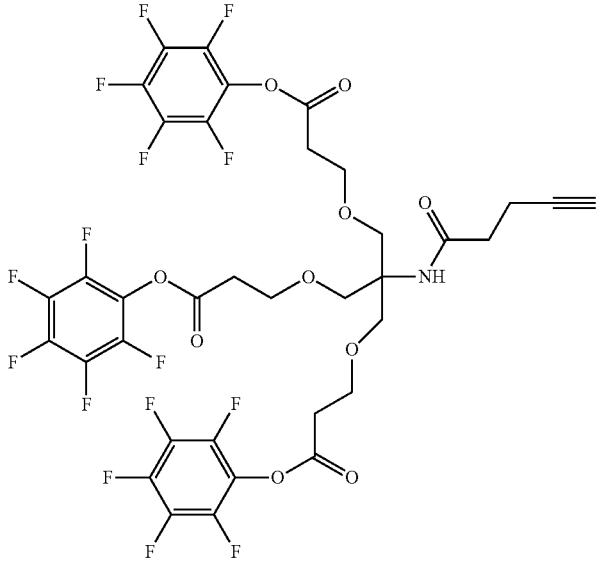 [SMILES: C#CCCC(=O)NC(COCCC(=O)Oc1c(F)c(F)c(F)c(F)c1F)(COCCC(=O)Oc1c(F)c(F)c(F)c(F)c1F)COCCC(=O)Oc1c(F)c(F)c(F)c(F)c1F] |
| LC30 | 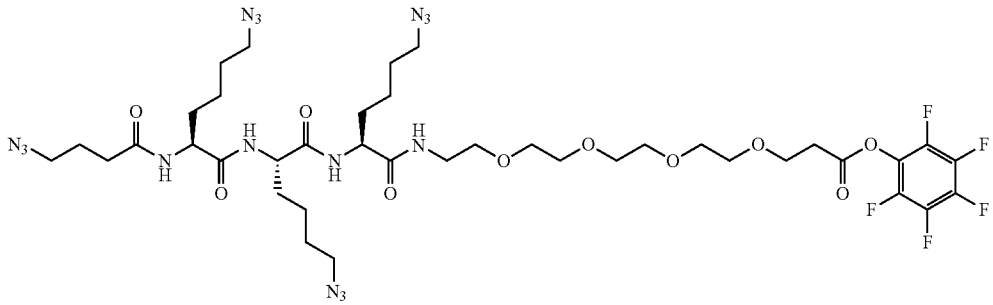 [SMILES: [N-]=[N+]=NCCCC[C@H](NC(=O)CCCN=[N+]=[N-])C(=O)N[C@@H](CCCCN=[N+]=[N-])C(=O)N[C@@H](CCCCN=[N+]=[N-])C(=O)NCCOCCOCCOCCOCCC(=O)Oc1c(F)c(F)c(F)c(F)c1F] |
| LC31 | 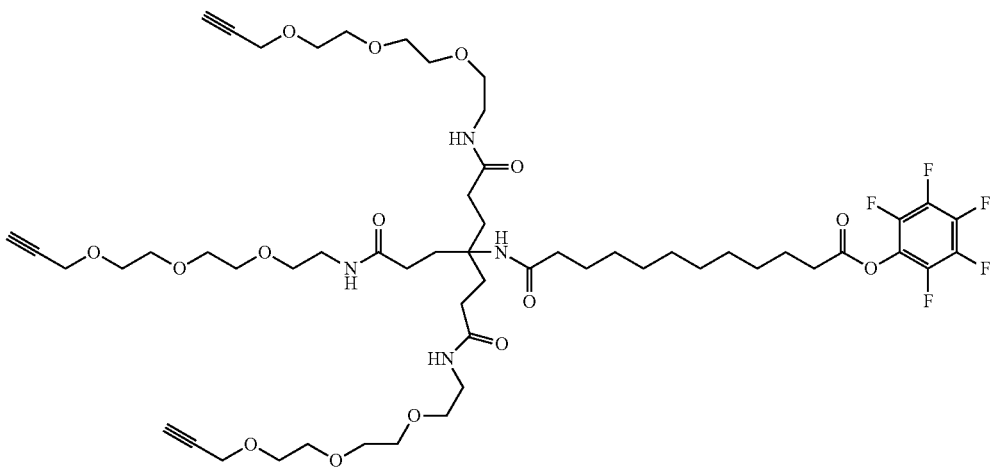 [SMILES: C#CCOCCOCCOCCNC(=O)CCC(CCC(=O)NCCOCCOCCOCC#C)(CCC(=O)NCCOCCOCCOCC#C)NC(=O)CCCCCCCCCCC(=O)Oc1c(F)c(F)c(F)c(F)c1F] |
In certain embodiments, the linker is a branched linker or linking moiety as shown in Table 10.

TABLE 10
Exemplary branched linkers and branched linking moieties
| Linker No. | Linker structure |
|---|---|
| L21 | 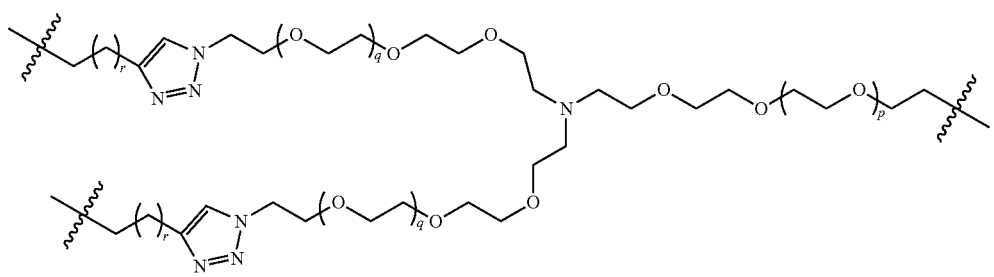
r is 0 to 10, q and p are indepenently 0 to 20 |
| L22 | 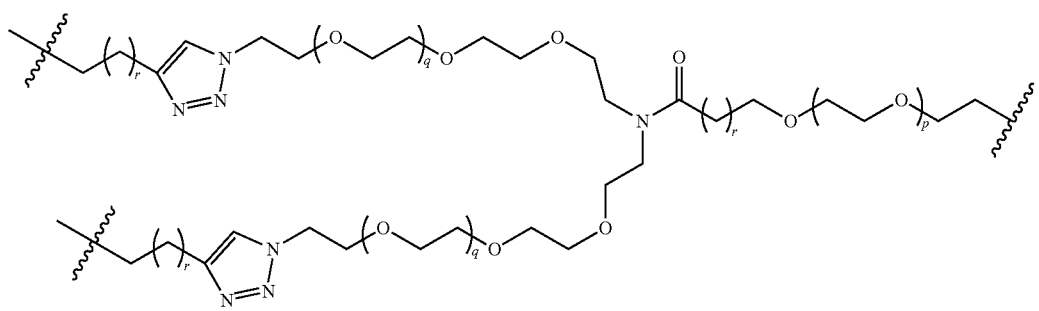
each r is independently 0 to 10, q and p are independently 0 to 20 |
| L23 | 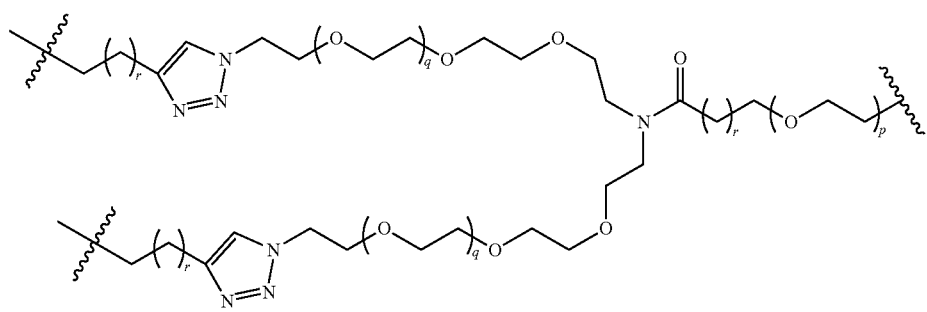
each r is independently 0 to 10, q and p are independently 0 to 20 |
| L24 | 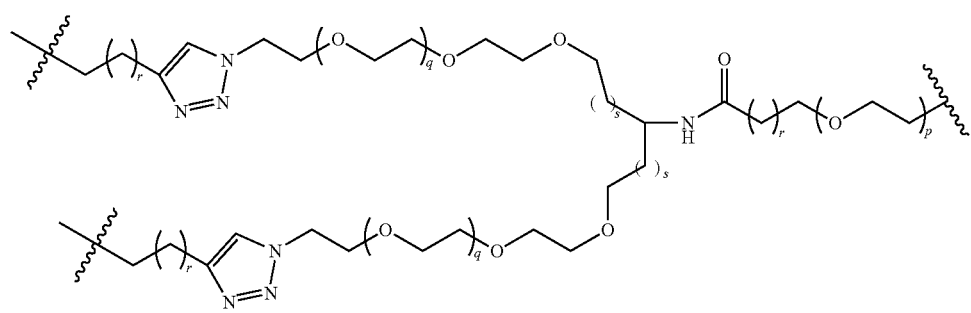
each r is independently 0 to 10, s is 0 or 1, q and p are independently 0 to 20 |

TABLE 10-continued

Exemplary branched linkers and branched linking moieties

| Linker No. | Linker structure |
|---|---|
| L25 | 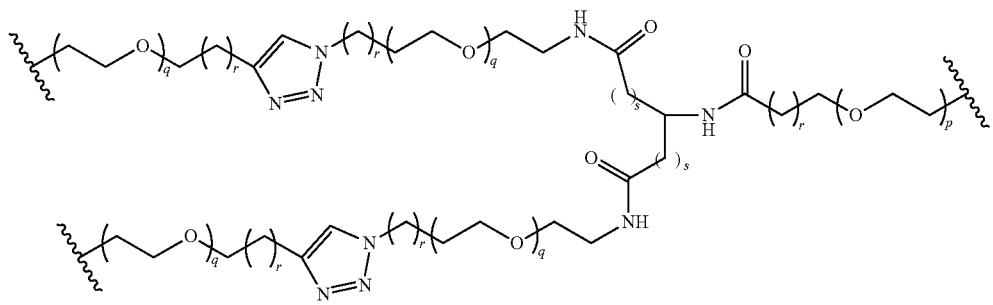 | each r is independently 0 to 10, s is 0 or 1, each q and p is independently 0 to 20

| | |
|---|---|
| L26 | 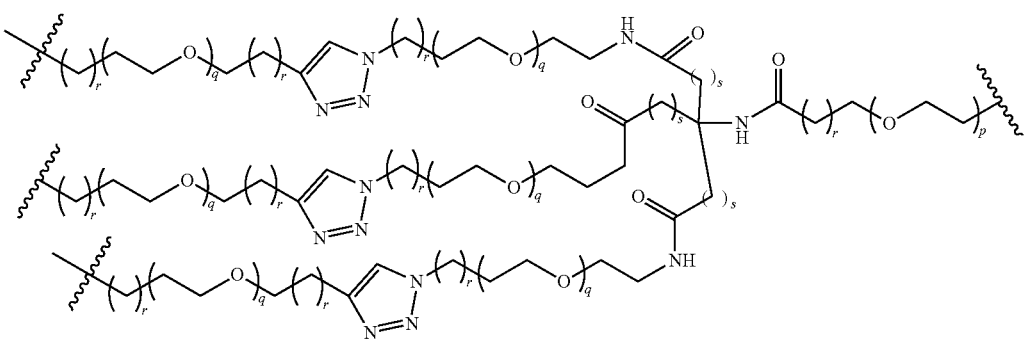 | each r is independently 0 to 10, s is 0 or 1, each q and p is independently 0 to 20

| | |
|---|---|
| L26.1 | 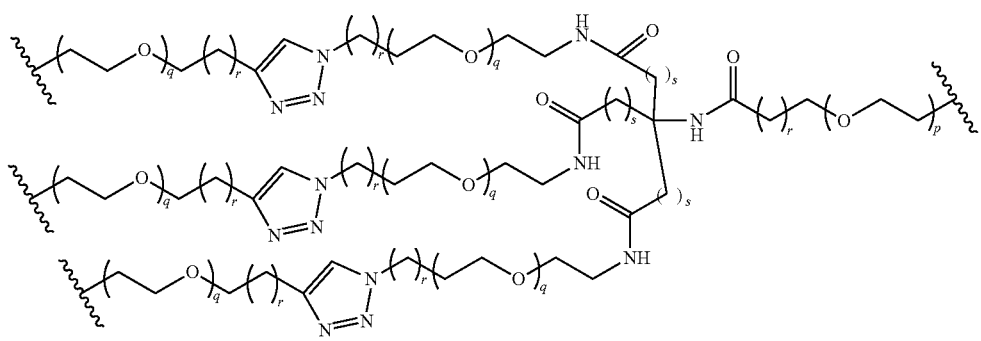 | each r is independently 0 to 10, s is 0 or 1, each q and p is independently 0 to 20

| | |
|---|---|
| L27 | 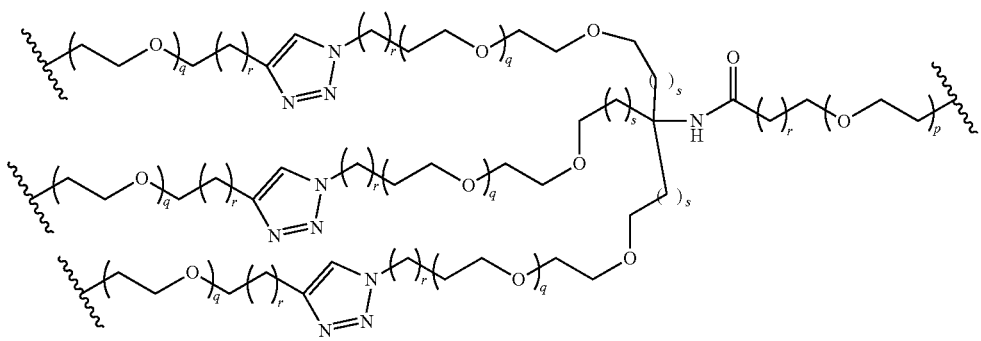 | each r is independently 0 to 10, s is 0 or 1, each q and p is independently 0 to 20

TABLE 10-continued
Exemplary branched linkers and branched linking moieties
| Linker No. | Linker structure |
|---|---|
| L28 | 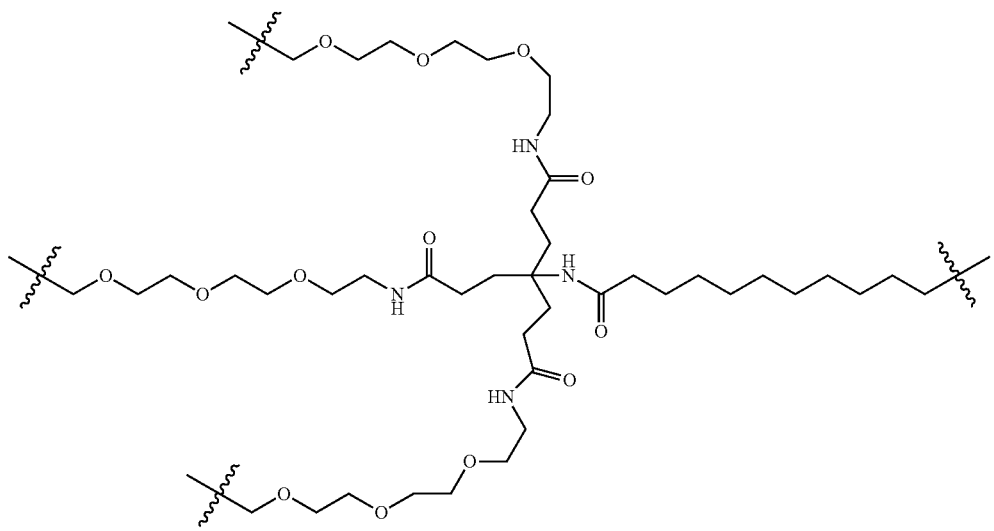 [SMILES: *CCCCCCCCCCC(=O)NC(CCC(=O)NCCOCCOCCOC*)(CCC(=O)NCCOCCOCCOC*)CCC(=O)NCCOCCOCCOC*] |
| L29 | 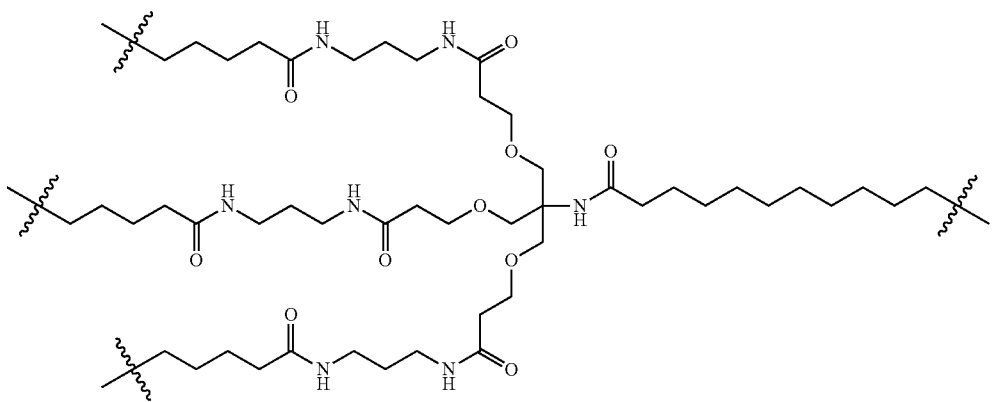 [SMILES: *CCCCCCCCCCC(=O)NC(COCCC(=O)NCCCNC(=O)CCCC*)(COCCC(=O)NCCCNC(=O)CCCC*)COCCC(=O)NCCCNC(=O)CCCC*] |
| L30 | 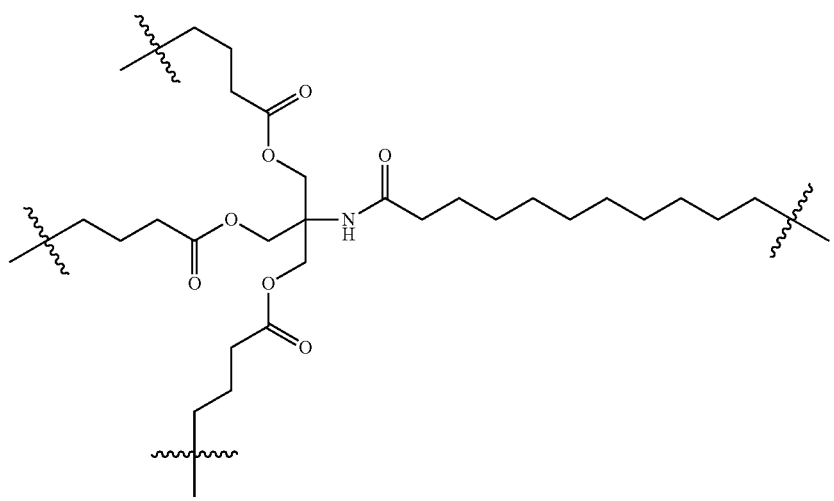 [SMILES: *CCCCCCCCCCC(=O)NC(COC(=O)CCC*)(COC(=O)CCC*)COC(=O)CCC*] |

TABLE 10-continued
Exemplary branched linkers and branched linking moieties
| Linker No. | Linker structure |
|---|---|
| L31 | 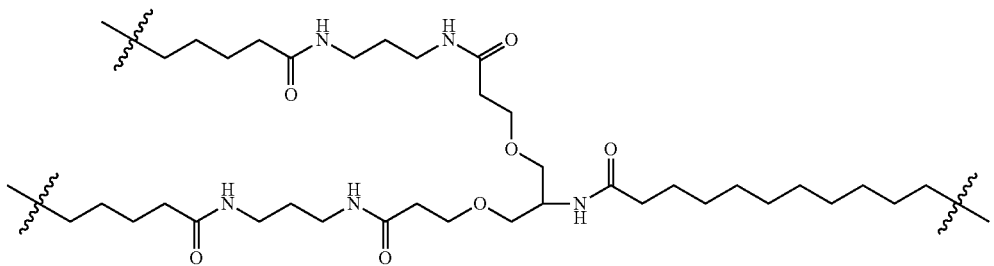 [SMILES: *CCCCCCCCCCC(=O)NC(COCCC(=O)NCCCNC(=O)CCCC*)COCCC(=O)NCCCNC(=O)CCCC*] |
| L32 | 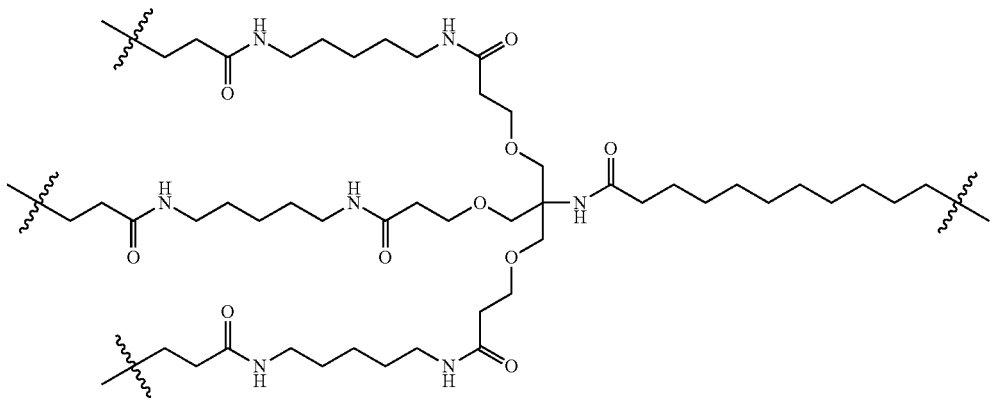 [SMILES: *CCCCCCCCCCC(=O)NC(COCCC(=O)NCCCCCNC(=O)CC*)(COCCC(=O)NCCCCCNC(=O)CC*)COCCC(=O)NCCCCCNC(=O)CC*] |
| L33 | 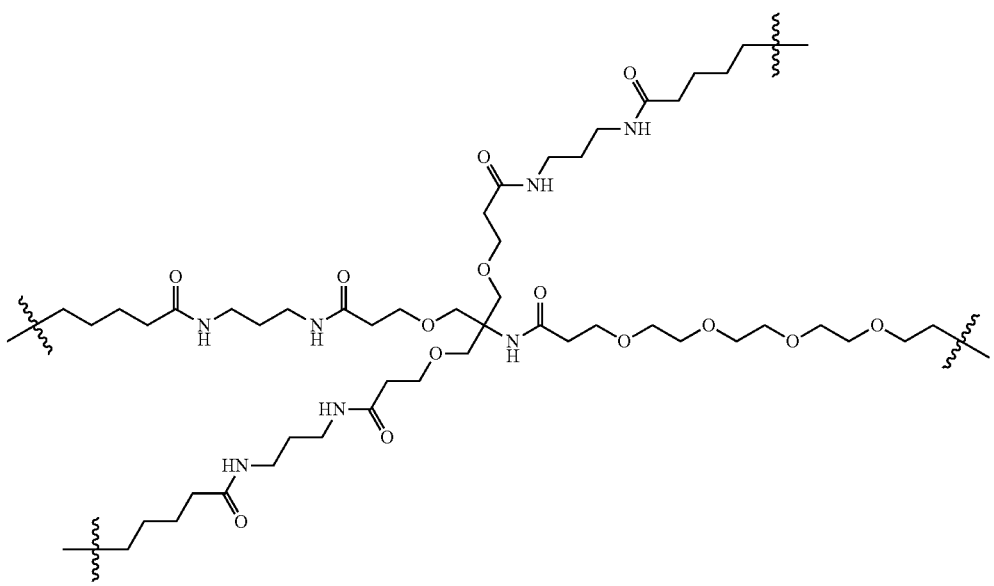 [SMILES: *CCCCC(=O)NCCCNC(=O)CCOCC(COCCC(=O)NCCCNC(=O)CCCC*)(COCCC(=O)NCCCNC(=O)CCCC*)NC(=O)CCOCCOCCOCCOCC*] |

TABLE 10-continued

Exemplary branched linkers and branched linking moieties

| Linker No. | Linker structure |
|---|---|
| L34 | |

5.3. Chemoselective Ligation Group

In certain embodiments of formula (I), Y is a chemoselective ligation group, or a precursor thereof. A chemoselective ligation group is a group having a reactive functionality or function group capable of conjugation to a compatible group of a second moiety. For example, chemoselective ligation groups (or a precursor thereof) may be one of a pair of groups associated with a conjugation chemistry such as azido-alkyne click chemistry, copper free click chemistry, Staudinger ligation, tetrazine ligation, hydrazine-iso-Pictet-Spengler (HIPS) ligation, cysteine-reactive ligation chemistry (e.g., thiol-maleimide, thiol-haloacetamide or alkyne hydrothiolation), amine-active ester coupling, tyrosine specific conjugation chemistry (e.g., e-Y-CLICK), methionine specific conjugation chemistry (e.g., oxaziridine-based or ReACT chemistry), reductive amination, dialkyl squarate chemistry, etc.

Chemoselective ligation groups that may be utilized in linking two moieties, include, but are not limited to, amino (e.g., a N-terminal amino or a lysine sidechain group of a polypeptide), azido, aryl azide, alkynyl (e.g., ethynyl or cyclooctyne or derivative), active ester (e.g., N-hydroxysuccinimide (NHS) ester, sulfo-NHS ester or PFP ester or thioester), haloacetamide (e.g., iodoacetamide or bromoacetamide), chloroacetyl, bromoacetyl, hydrazide, maleimide, vinyl sulfone, 2-sulfonyl pyridine, cyano-alkyne, thiol (e.g., a cysteine residue), disulfide or protected thiol, isocyanate, isothiocyanate, aldehyde, ketone, alkoxyamine, hydrazide, aminooxy, phosphine, HIPS hydrazinyl-indolyl group, or aza-HIPS hydrazinyl-pyrrolo-pyridinyl group, tetrazine, cyclooctene, squarate, and the like.

In some instances, chemoselective ligation group is capable of spontaneous conjugation to a compatible chemical group when the two groups come into contact under suitable conditions (e.g., copper free Click chemistry conditions). In some instances, the chemoselective ligation group is capable of conjugation to a compatible chemical group when the two groups come into contact in the presence of a catalyst or other reagent (e.g., copper catalyzed Click chemistry conditions).

In some embodiments, the chemoselective ligation group is a photoactive ligation group. For example, upon irradiation with ultraviolet light, a diazirine group can form reactive carbenes, which can insert into C—H, N—H, and O—H bonds of a second moiety.

In some instances, Y is a precursor of the reactive functionality or function group capable of conjugation to a compatible group of a second moiety. For example, a carboxylic acid is a precursor of an active ester chemoselective ligation group.

In certain embodiments of formula (I), Y is a reactive moiety capable forming a covalent bond to a polypeptide (e.g., with an amino acid sidechain of a polypeptide having a compatible reactive group). The reactive moiety can be referred to as a chemoselective ligation group.

In certain embodiments of formula (I), Y is a thio-reactive chemoselective ligation group (e.g., as described in Table 11). In some cases, Y can produce a residual moiety Z resulting from the covalent linkage of a thiol-reactive chemoselective ligation group to one or more cysteine residue(s) of a protein, e.g., Ab.

In certain embodiments of formula (I), Y is an amino-reactive chemoselective ligation group (e.g., as described in Table 11). In some cases, Y can produce a residual moiety Z resulting from the covalent linkage of an amine-reactive chemoselective ligation group to one or more lysine residue(s) a protein, e.g., Ab.

Exemplary chemoselective ligation groups, and synthetic precursors thereof, which may be adapted for use in the compounds of this disclosure are shown in Table 11.

TABLE 11
Exemplary chemoselective ligation groups and precursors
| Groups | Exemplary structures |
| --- | --- |
| carboxylic acid or active ester | 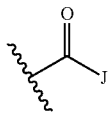 |
where J is selected from —OH, —Cl, —Br, —I, —F, —OH, —O—N-succinimide, —O-(4-nitrophenyl), —O-pentafluorophenyl, —O-tetrafluorophenyl, and —O—C(O)—OR$^{J'}$, and R$^{J'}$ is —C$_1$—C$_8$ alkyl or -aryl,
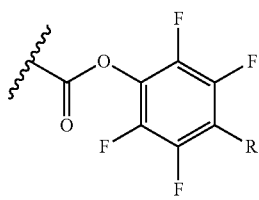
R is H or F,
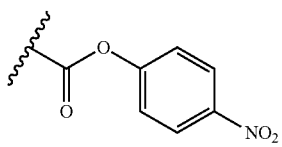
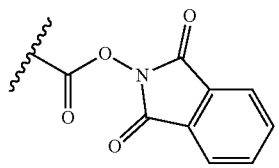
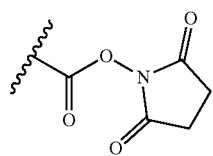
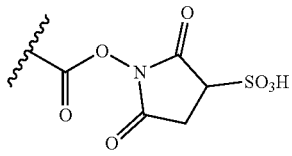
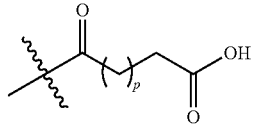
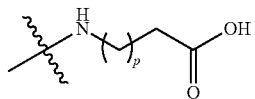
where p is 0 to 6

TABLE 11-continued

Exemplary chemoselective ligation groups and precursors

| Groups | Exemplary structures |
|---|---|
| maleimide | 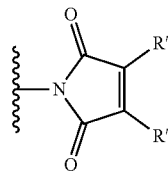<br>where each R' is independently hydrogen or halogen (e.g., bromo) |
| isocyanate or isothiocyanate | —NCS<br>—NCO<br>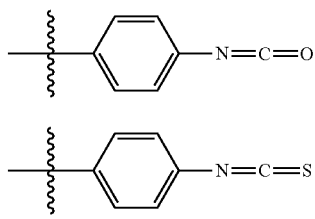 |
| alkyl halide | 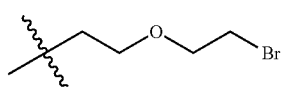 [SMILES: *CCOCCBr] |
| alkyl tosylate | 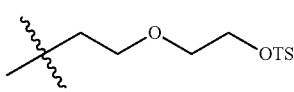 |
| aldehyde | 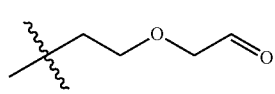 [SMILES: *CCOCC=O] |
| haloacetamide or alpha-leaving group acetamide | 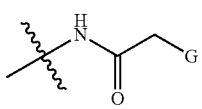<br>where G is selected from —Cl, —Br, —I, —O-mesyl, and —O-tosyl |
| 2-sulfonylpyridine | 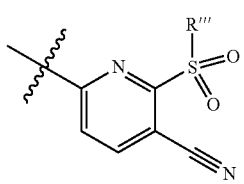<br>where R''' is alkyl |
| diazirine | 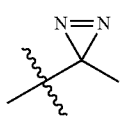 [SMILES: *C1(C)N=N1] |
| sulfonyl halide or vinyl sulfone | 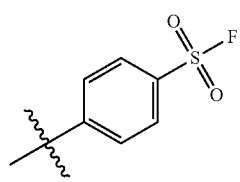 [SMILES: *c1ccc(S(=O)(=O)F)cc1] |

TABLE 11-continued
Exemplary chemoselective ligation groups and precursors
| Groups | Exemplary structures |
| --- | --- |
|  | 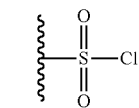 |
|  | 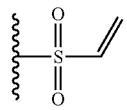 |
| hydrazide<br>hydrazino<br>hydroxylamino | 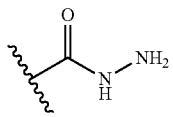 |
|  | 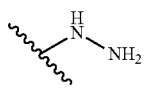 |
|  | 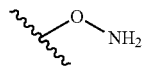 |
| pyridyl disulfide | 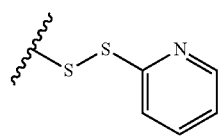 |
| (HIPS) hydrazinyl-<br>indolyl group, or<br>(aza-HIPS) hydrazinyl-<br>pyrrolo-pyridinyl group | 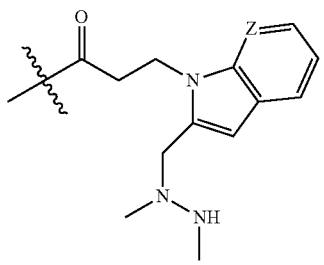<br>where Z is CH or N |
| alkyne or<br>cyclooctyne | 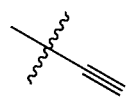 |
|  | 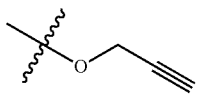 [SMILES: *OCC#C] |
|  | 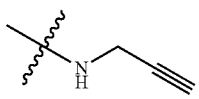 [SMILES: *NCC#C] |
|  | 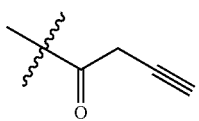 [SMILES: *C(=O)CC#C] |

TABLE 11-continued
Exemplary chemoselective ligation groups and precursors
| Groups | Exemplary structures |
| --- | --- |
| | 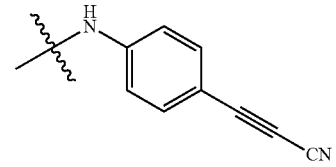 [SMILES: *Nc1ccc(C#CC#N)cc1] |
| | 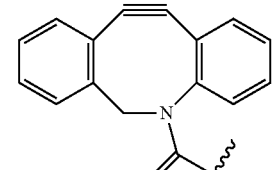 |
| | 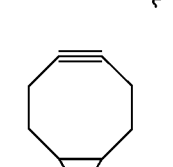 |
| azide |   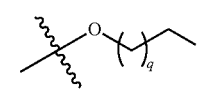 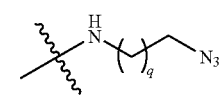 |
| | where p is 0 to 6 and where q is 1 to 6 |
| amine |   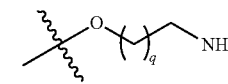 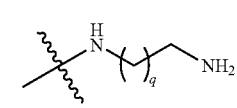 |
| | where p is 0 to 6 and where q is 1 to 6 |

In Table 11, the ⌇ can represent a point of attachment of Y to a linking moiety or a linked X moiety.

5.3.1. Exemplary Compounds with Chemoselective Ligation Group

This disclosure includes compounds of formula (I) which can include:

(1) one or more particular ASGPR ligand (X) (e.g., as described herein, such as ligands X1-X20 of Tables 1-4) or a particular ASGPR ligand (X) (e.g., as described herein), (2) a linker including one or more linking moieties (e.g., as described herein, such as any one or more of the linking moieties of Tables 8 to 10); and (3) a chemoselective ligation group (Y) e.g., as described herein, such as any one of the groups of Table 11).

Table 12 illustrates various monovalent ligand-linker compounds for use in conjugates of the disclosure.

TABLE 12

Exemplary ligand-linker compounds for use in conjugates
$X_n$-L-Y

| Cmpd # | X | L | n | effective length L to Y conjugate | Chemoselective ligation |
|---|---|---|---|---|---|
| 1101 (I-117) | X1 | | 1 | 10 | PFP ester |
| 1102 (I-115) | X1 | | 1 | 19 | PFP ester |
| 1103 | X1 | | 1 | 25 | PFP ester |
| 1104 (I-133) | X1 | | 1 | 29 | maleimide |
| 1105 | X1 | | 1 | 28 | PFP ester |
| 1106 (I-112) | X1 | | 1 | 26 | PFP ester |
| 1107 (I-146) | X1 | | 1 | 35 | PFP ester |
| 1108 (I-118) | X6 | | 1 | 10 | PFP ester |
| 1109 (I-116) | X6 | | 1 | 19 | PFP ester |
| 1110 (I-113) | X6 | | 1 | 26 | NHS ester |
| 1111 (I-147) | X5 | L10 | 1 | 27 | PFP ester |
| 1112 (I-148) | X5 | L1 | 1 | 26 | PFP ester |
| 1113 (I-149) | X1 | L11 | 1 | 23 | PFP ester |
| 1114 (I-150) | X1 | L11 | 1 | 26 | PFP ester |
| 1115 (I-151) | X1 | L11 | 1 | 29 | PFP ester |

PFP is pentafluorophenyl
TFP is tetrafluorophenyl
NHS is N-hydroxysuccinimde ester Tables 13 illustrates various multivalent ligand-linker compounds for use in conjugates of the disclosure.

TABLE 13

Exemplary Multimeric Ligand-linker compounds
$X_n$-L-Y

| Cmpd # | X | n | $X^1$ to branch length | branch to Y length | Y |
|---|---|---|---|---|---|
| 1218 (I-143) | X4 | 3 | 14 to C | 12 to C=O | PFP ester |
| 1303 (I-136) | X8 | 3 | 16 to C | 12 to C=O | PFP ester |
| 1219 (I-157) | X4 | 3 | 6 to N | 12 to C=O | PFP ester |
| 1213 (I-137) | X1 | 3 | 15 to C | 81 to C=O | PFP ester |
| 1211 (I-129) | X1 | 3 | 15 to C | 33 to C=O | PFP ester |
| 1203 (I-144) | X1 | 2 | 15 to CH | 12 to C=O | PFP ester |
| 1215 (I-141) | X2 | 3 | 15 to C | 12 to C=O | PFP ester |
| 1208 (I-145) | X1 | 3 | 15 to C | 16 to C=O | PFP ester |
| 1216 (I-140) | X3 | 3 | 18 to C | 12 to C=O | PFP ester |
| 1401 (I-153) | X10 | 3 | 14 to C | 12 to C=O | PFP ester |
| 1204 (I-111) | X1 | 2 | 16 to N | 11 to C=O | PFP ester |
| 1402 (I-154) | X11 | 3 | 19 to C | 12 to C=O | PFP ester |
| 1403 (I-155) | X12 | 3 | 19 to C | 12 to C=O | PFP ester |

Tables 14-17 illustrate several exemplary ASGPR binding compounds of this disclosure that include a chemoselective ligation group, or a precursor thereof. It is understood that this disclosure includes Y (e.g., as described herein) conjugates of each of the exemplary compounds of Tables 12-18. For example, conjugates where the chemoselective ligation group has been conjugated to a different Y, such as a biomolecule or a small molecule ligand for a target protein.

The chemoselective ligation group of such compounds can be utilized to connect to another Y moiety of interest (e.g., as described below). It is understood that any of these compounds can also be prepared de novo to include an alternative Y moiety of interest (e.g., as described below) rather than the chemoselective ligation group. In some embodiments, such compounds are referred to as a conjugate, e.g., a biomolecule conjugate that specifically binds a target protein.

TABLE 14

Example ASGPR binding compounds having chemoselective ligation group

| # | Structure |
|---|---|
| 1101 (I-117) | 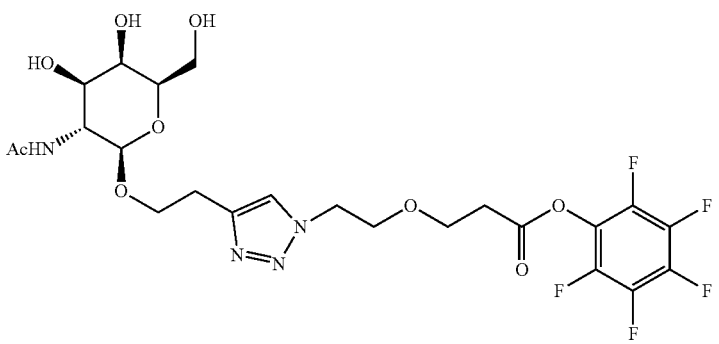 [SMILES: CC(=O)N[C@H]1[C@H](OCCc2cn(CCOCCC(=O)Oc3c(F)c(F)c(F)c(F)c3F)nn2)O[C@H](CO)[C@H](O)[C@@H]1O] |

TABLE 14-continued

Example ASGPR binding compounds having chemoselective ligation group

| # | Structure |
|---|---|
| 1102 (I-115) | 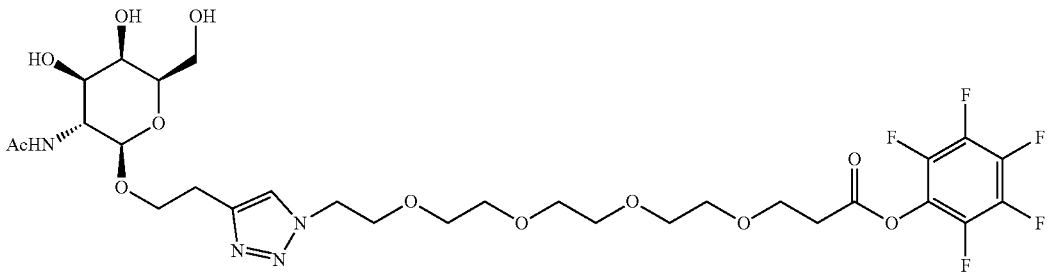 [SMILES: CC(=O)N[C@H]1[C@H](OCCc2cn(CCOCCOCCOCCOCCC(=O)Oc3c(F)c(F)c(F)c(F)c3F)nn2)O[C@H](CO)[C@H](O)[C@@H]1O] |
| 1103 | 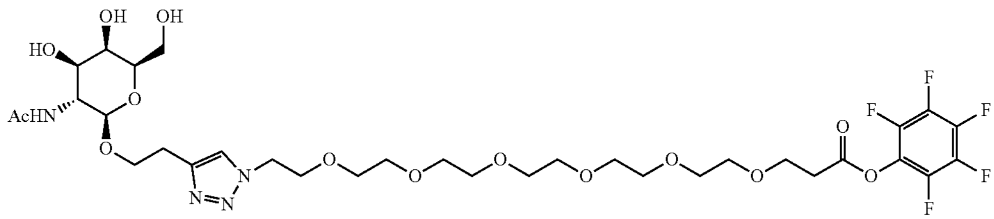 [SMILES: CC(=O)N[C@H]1[C@H](OCCc2cn(CCOCCOCCOCCOCCOCCOCCC(=O)Oc3c(F)c(F)c(F)c(F)c3F)nn2)O[C@H](CO)[C@H](O)[C@@H]1O] |
| 1104 (I-133) | 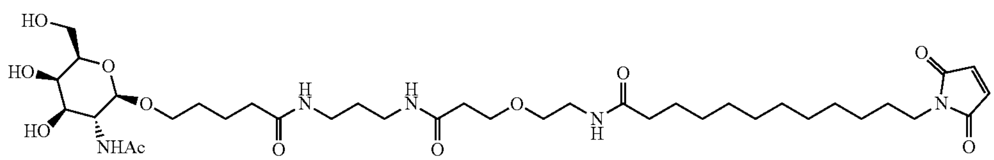 [SMILES: CC(=O)N[C@H]1[C@H](OCCCCC(=O)NCCCNC(=O)CCOCCNC(=O)CCCCCCCCCCCN2C(=O)C=CC2=O)O[C@H](CO)[C@H](O)[C@@H]1O] |
| 1105 | 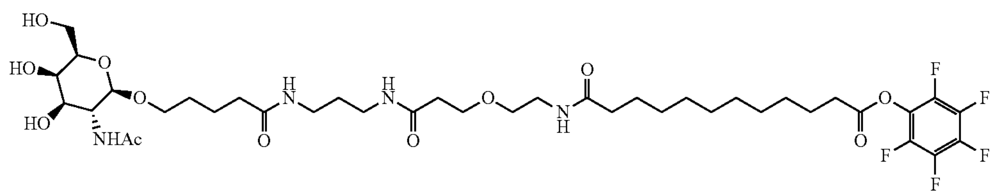 [SMILES: CC(=O)N[C@H]1[C@H](OCCCCC(=O)NCCCNC(=O)CCOCCNC(=O)CCCCCCCCCCC(=O)Oc2c(F)c(F)c(F)c(F)c2F)O[C@H](CO)[C@H](O)[C@@H]1O] |
| 1106 (I-112) | 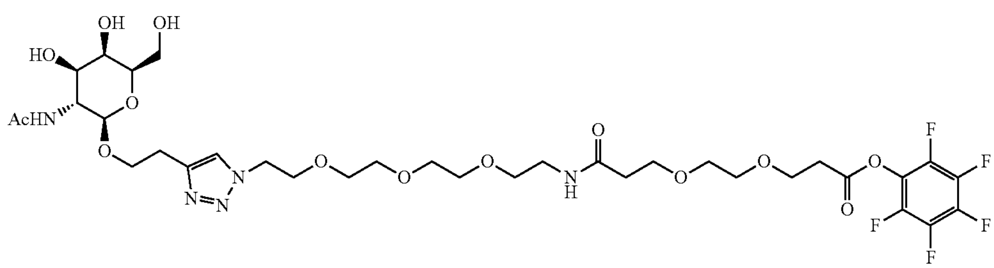 [SMILES: CC(=O)N[C@H]1[C@H](OCCc2cn(CCOCCOCCOCCNC(=O)CCOCCOCCC(=O)Oc3c(F)c(F)c(F)c(F)c3F)nn2)O[C@H](CO)[C@H](O)[C@@H]1O] |
| 1107 (I-146) | 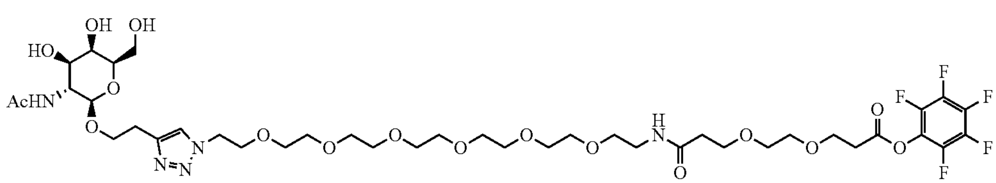 [SMILES: CC(=O)N[C@H]1[C@H](OCCc2cn(CCOCCOCCOCCOCCOCCOCCNC(=O)CCOCCOCCC(=O)Oc3c(F)c(F)c(F)c(F)c3F)nn2)O[C@H](CO)[C@H](O)[C@@H]1O] |
| 1108 (I-118) | 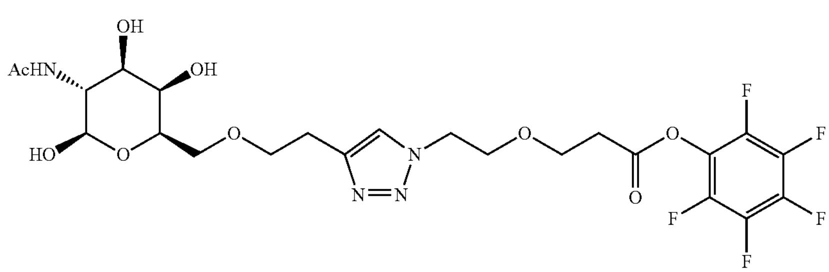 [SMILES: CC(=O)N[C@@H]1[C@@H](O)[C@@H](O)[C@@H](COCCc2cn(CCOCCC(=O)Oc3c(F)c(F)c(F)c(F)c3F)nn2)O[C@H]1O] |

TABLE 14-continued

Example ASGPR binding compounds having chemoselective ligation group

| # | Structure |
|---|---|
| 1109 (I-116) | 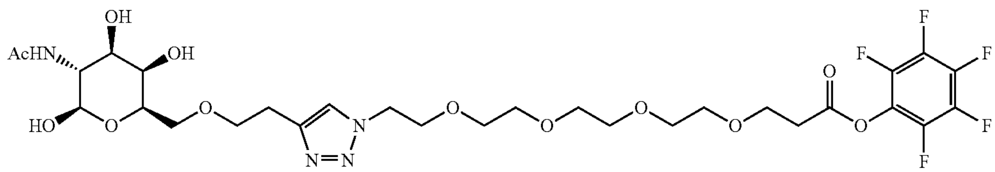 [SMILES: CC(=O)N[C@@H]1[C@@H](O)[C@@H](O)[C@@H](COCCc2cn(CCOCCOCCOCCOCCC(=O)Oc3c(F)c(F)c(F)c(F)c3F)nn2)O[C@H]1O] |
| 1110 (I-113) | 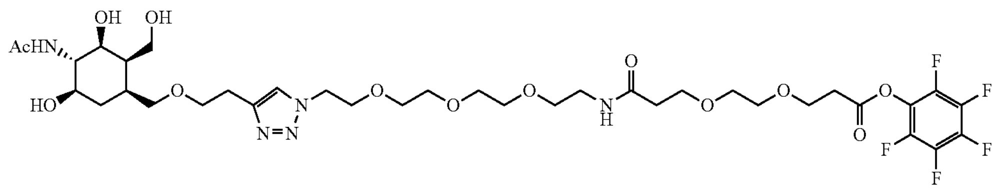 [SMILES: CC(=O)N[C@@H]1[C@@H](O)[C@@H](CO)[C@@H](COCCc2cn(CCOCCOCCOCCNC(=O)CCOCCOCCC(=O)Oc3c(F)c(F)c(F)c(F)c3F)nn2)C[C@H]1O] |
| 1111 (I-147) | 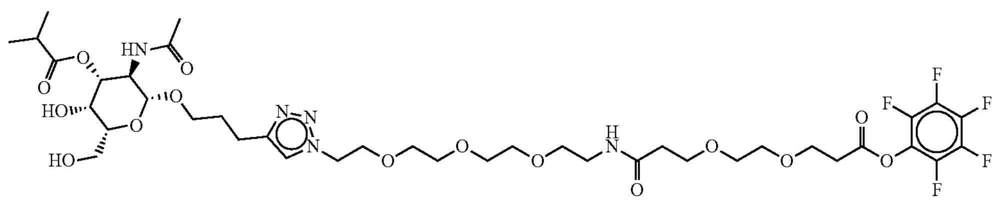 |
| 1112 (I-148) | 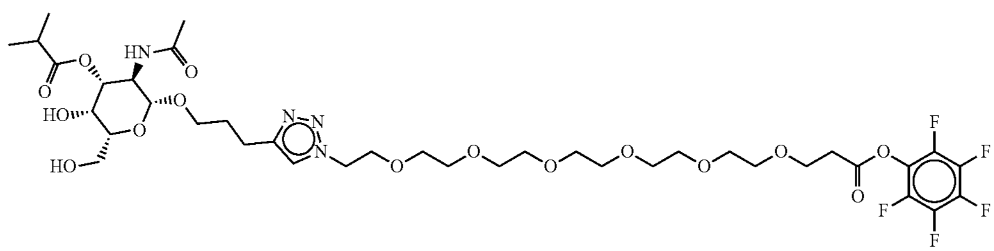 |
| 1113 (I-149) | 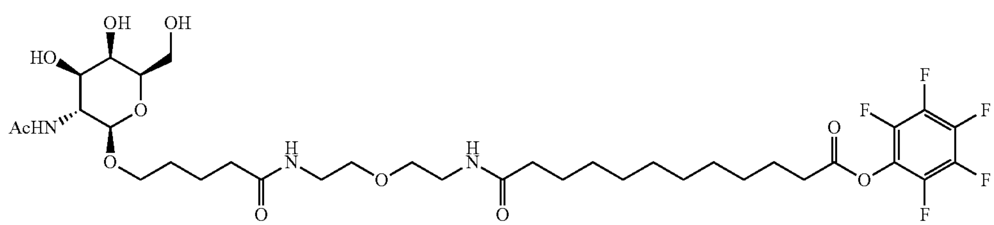 [SMILES: CC(=O)N[C@H]1[C@H](OCCCCC(=O)NCCOCCNC(=O)CCCCCCCCCCC(=O)Oc2c(F)c(F)c(F)c(F)c2F)O[C@H](CO)[C@H](O)[C@@H]1O] |
| 1114 (I-150) | 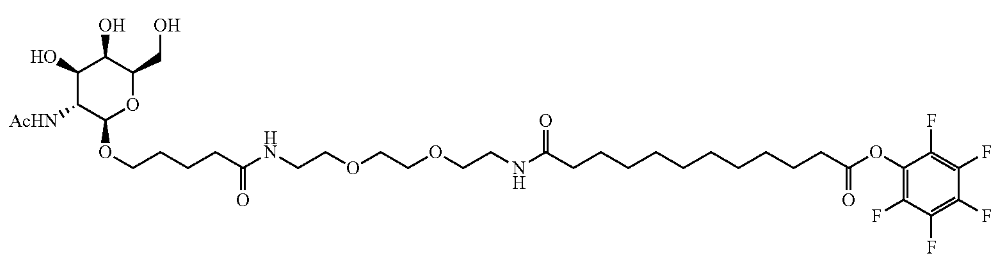 [SMILES: CC(=O)N[C@H]1[C@H](OCCCCC(=O)NCCOCCOCCNC(=O)CCCCCCCCCCC(=O)Oc2c(F)c(F)c(F)c(F)c2F)O[C@H](CO)[C@H](O)[C@@H]1O] |
| 1115 (I-151) | 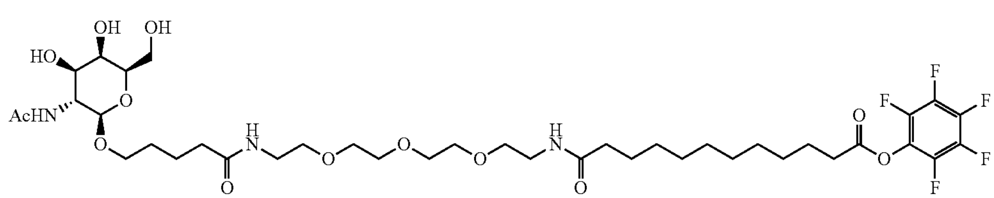 [SMILES: CC(=O)N[C@H]1[C@H](OCCCCC(=O)NCCOCCOCCOCCNC(=O)CCCCCCCCCCC(=O)Oc2c(F)c(F)c(F)c(F)c2F)O[C@H](CO)[C@H](O)[C@@H]1O] |

TABLE 14-continued

Example ASGPR binding compounds having chemoselective ligation group

| # | Structure |
|---|---|
| 1116 (I-164) | 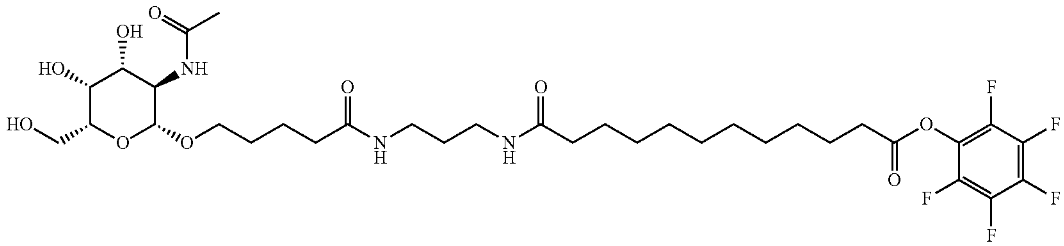 [SMILES: CC(=O)N[C@H]1[C@H](OCCCCC(=O)NCCCNC(=O)CCCCCCCCCCC(=O)Oc2c(F)c(F)c(F)c(F)c2F)O[C@H](CO)[C@H](O)[C@@H]1O] |
| 1117 (I-168) | 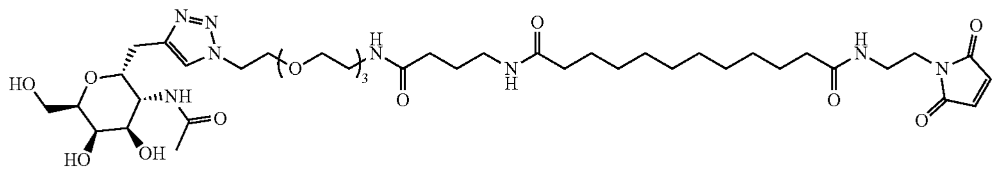 |
| 1118 (I-169) | 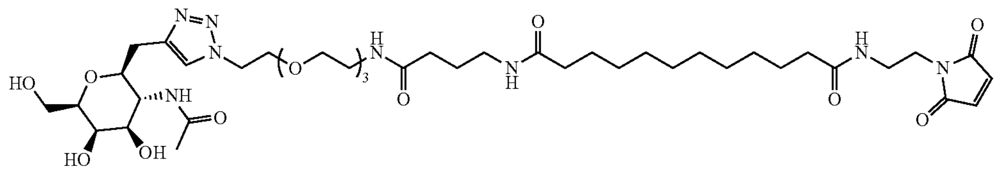 |

TABLE 15

Multivalent ASGPR binding compounds having chemoselective ligation group and X group of formula (Ib)

| # | Structure |
|---|---|
| 1201 | 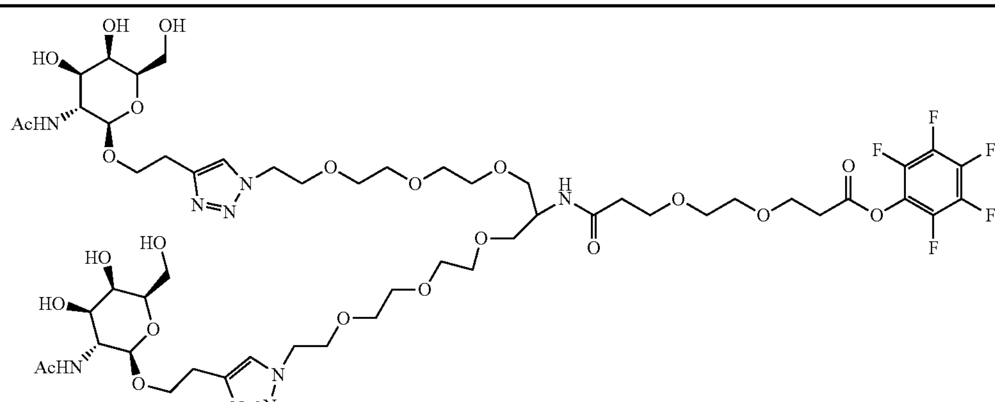 |
| 1202 (I-131) | 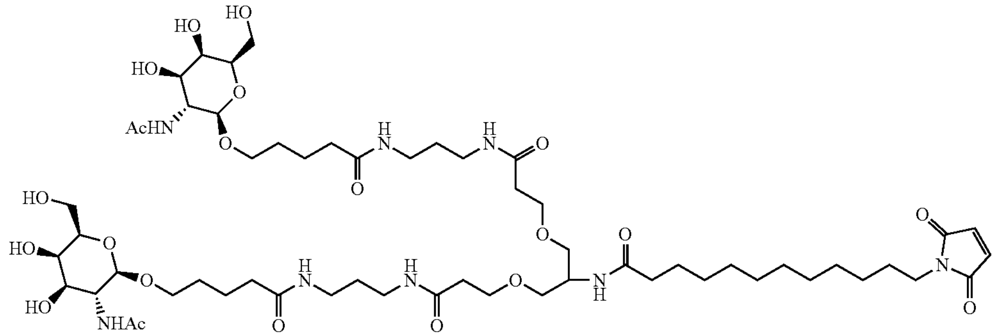 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)NC(=O)CCCCCCCCCCCN2C(=O)C=CC2=O)O[C@H](CO)[C@H](O)[C@@H]1O] |

TABLE 15-continued
Multivalent ASGPR binding compounds having chemoselective ligation group and X group of formula (Ib)
| # | Structure |
|---|---|
| 1203 (I-144) | 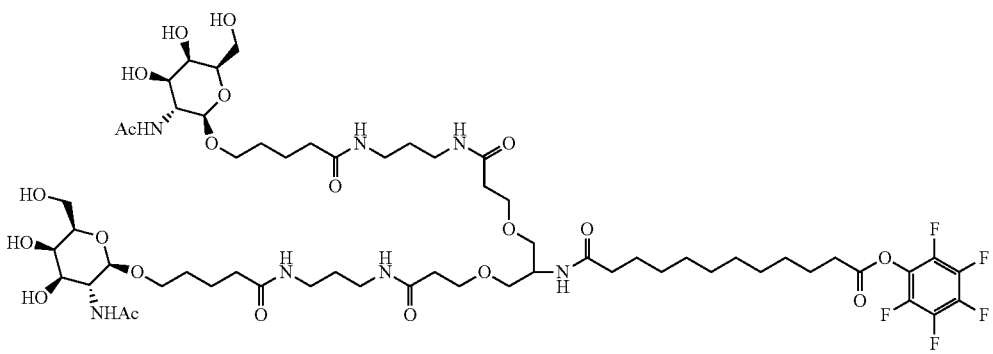 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)NC(=O)CCCCCCCCCCC(=O)Oc2c(F)c(F)c(F)c(F)c2F)O[C@H](CO)[C@H](O)[C@@H]1O] |
| 1204 (I-111) | 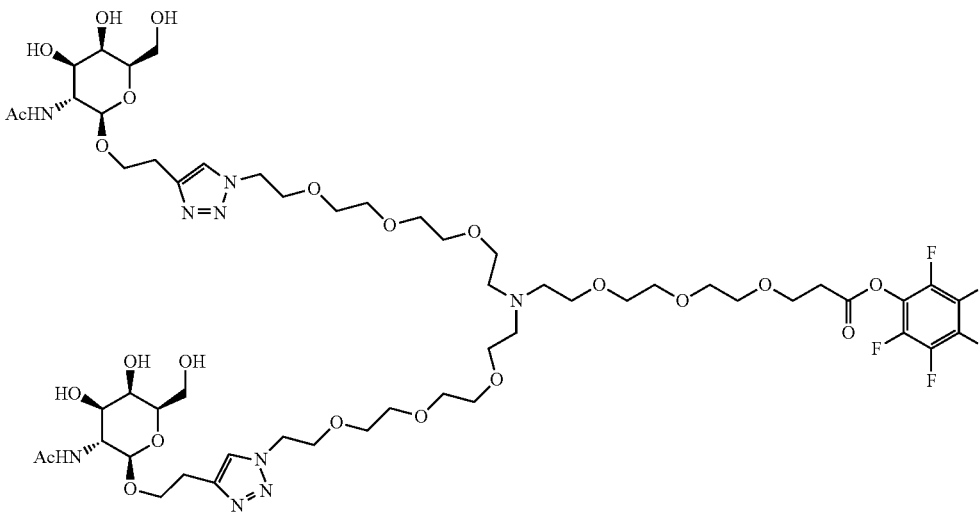 |
| 1217 | 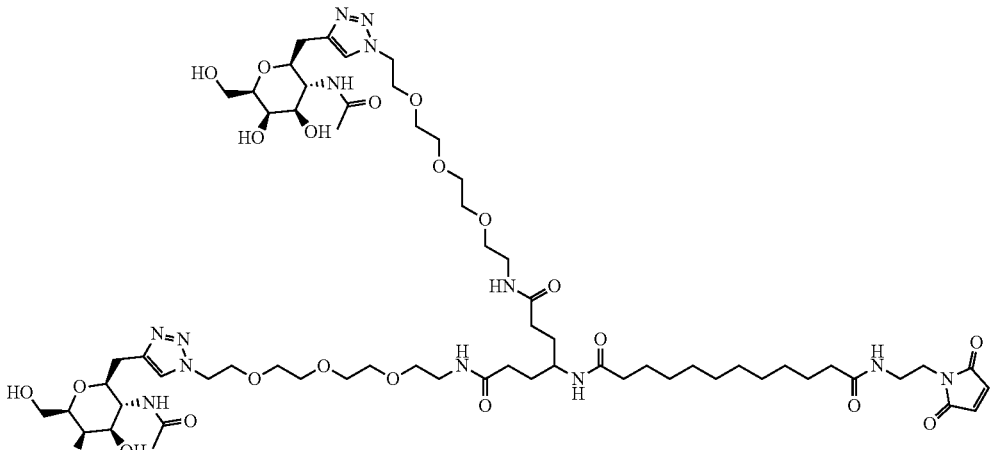 |

TABLE 15-continued
Multivalent ASGPR binding compounds having chemoselective ligation group and X group of formula (Ib)
| # | Structure |
|---|---|
| 1217 A | 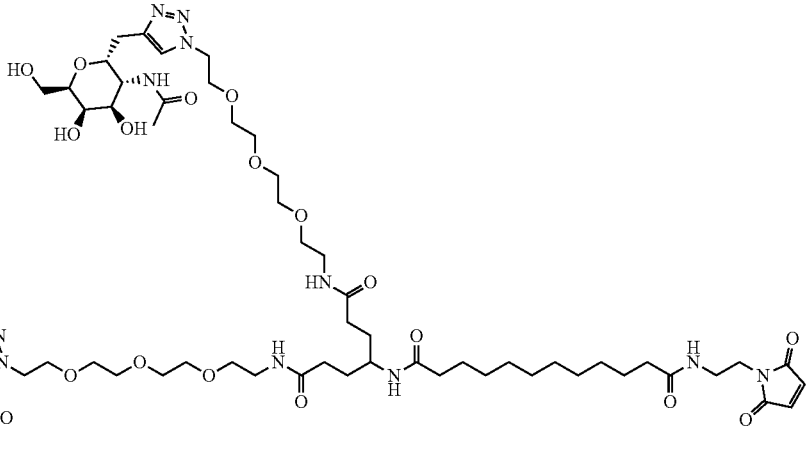 |
Trimeric ligands
| 1205 (I-127) | 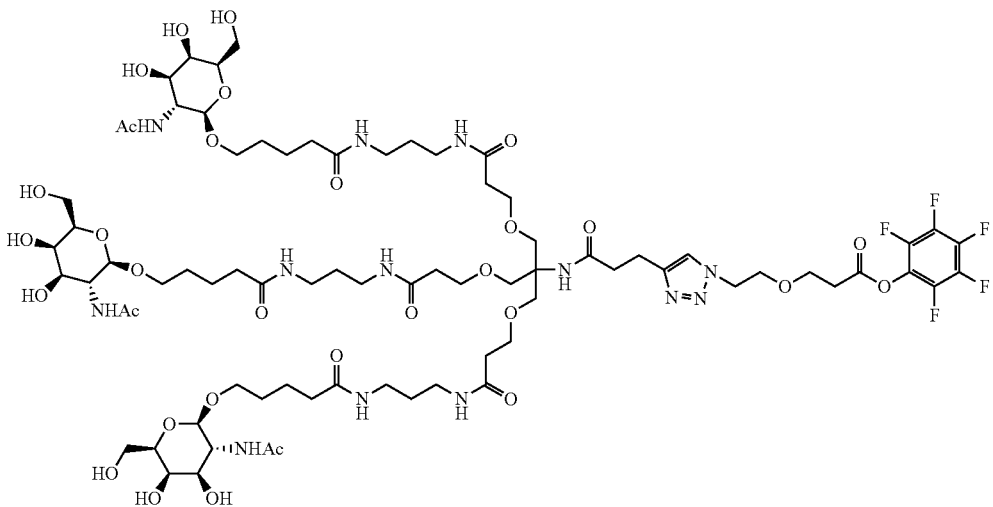 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCc2cn(CCOCCC(=O)Oc3c(F)c(F)c(F)c(F)c3F)nn2)O[C@H](CO)[C@H](O)[C@@H]1O] |
| 1206 | 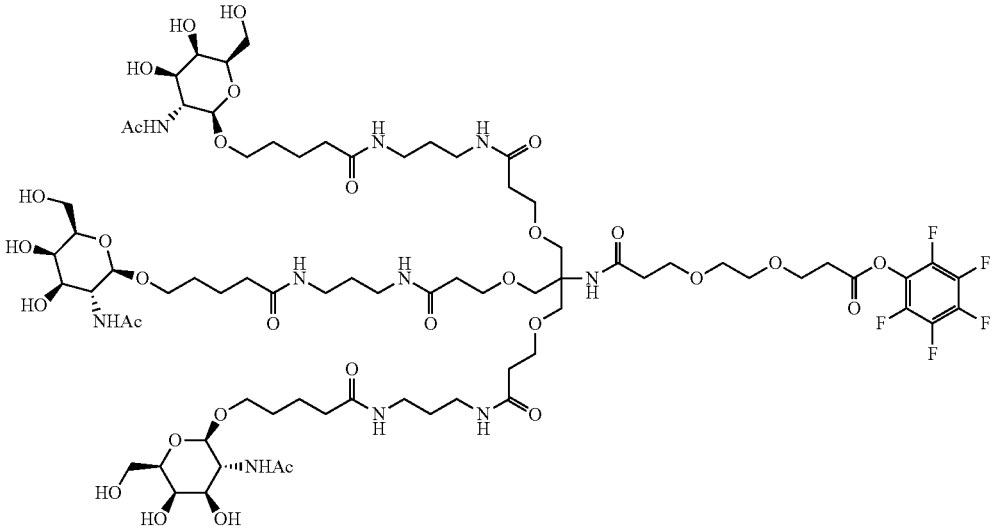 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCOCCOCCC(=O)Oc2c(F)c(F)c(F)c(F)c2F)O[C@H](CO)[C@H](O)[C@@H]1O] |

TABLE 15-continued

Multivalent ASGPR binding compounds having chemoselective ligation group and X group of formula (Ib)

| # | Structure |
|---|-----------|
| 1207 (I-107) | 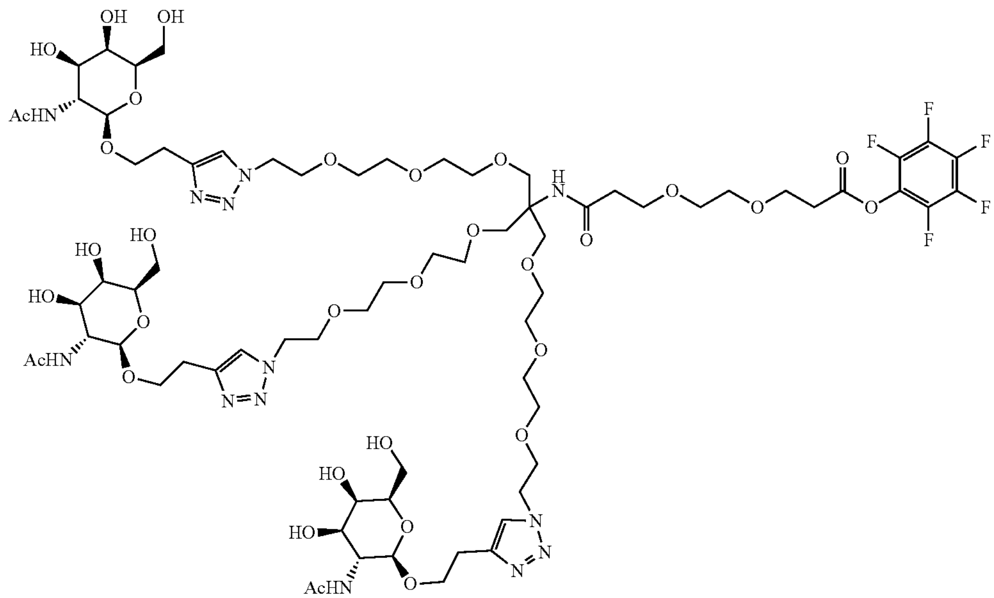 [SMILES: CC(=O)N[C@H]1[C@H](OCCc2cn(CCOCCOCCOCC(COCCOCCOCCn3cc(CCO[C@@H]4O[C@H](CO)[C@H](O)[C@H](O)[C@H]4NC(C)=O)nn3)(COCCOCCOCCn3cc(CCO[C@@H]4O[C@H](CO)[C@H](O)[C@H](O)[C@H]4NC(C)=O)nn3)NC(=O)CCOCCOCCC(=O)Oc3c(F)c(F)c(F)c(F)c3F)nn2)O[C@H](CO)[C@H](O)[C@@H]1O] |
| 1208 (I-145) | 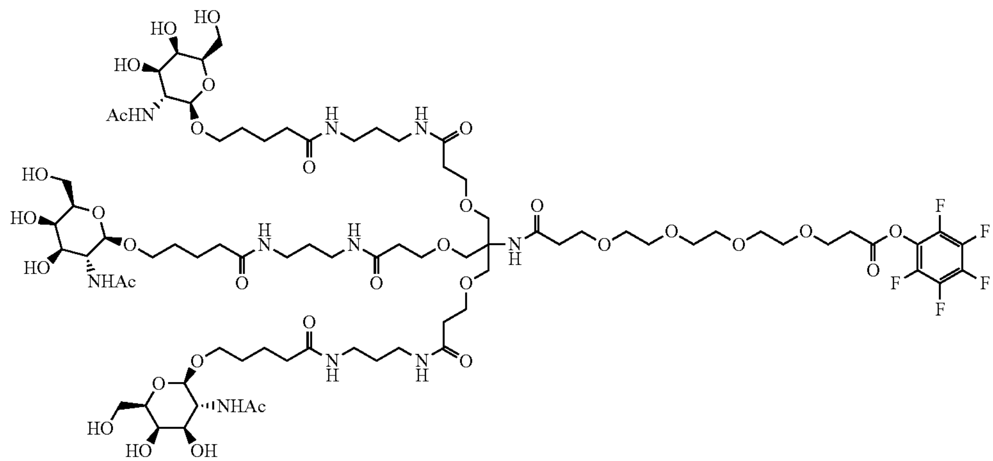 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCOCCOCCOCCOCCC(=O)Oc2c(F)c(F)c(F)c(F)c2F)O[C@H](CO)[C@H](O)[C@@H]1O] |
| 1209 (I-124) | 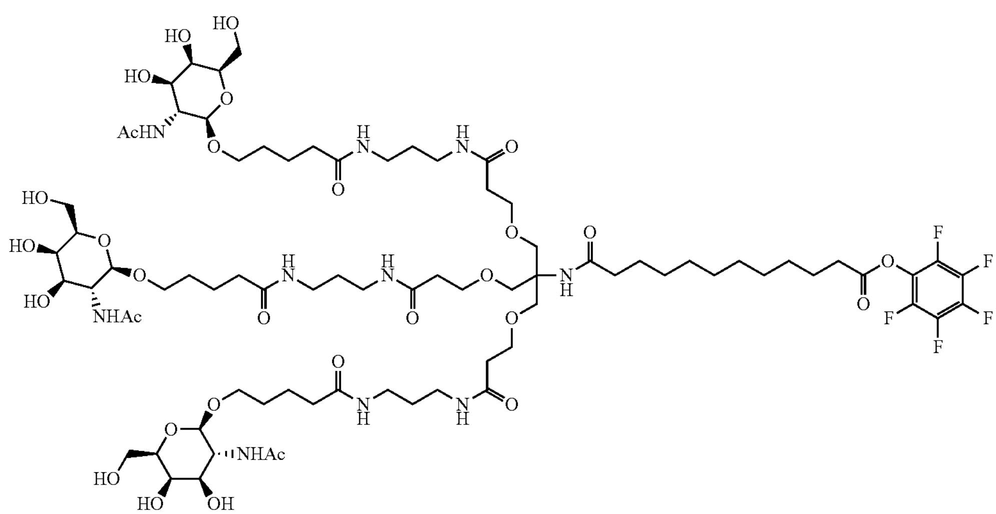 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCCCCCCCCCC(=O)Oc2c(F)c(F)c(F)c(F)c2F)O[C@H](CO)[C@H](O)[C@@H]1O] |

TABLE 15-continued
Multivalent ASGPR binding compounds having chemoselective ligation group and X group of formula (Ib)
| # | Structure |
|---|---|
| 1210 (I-123) | 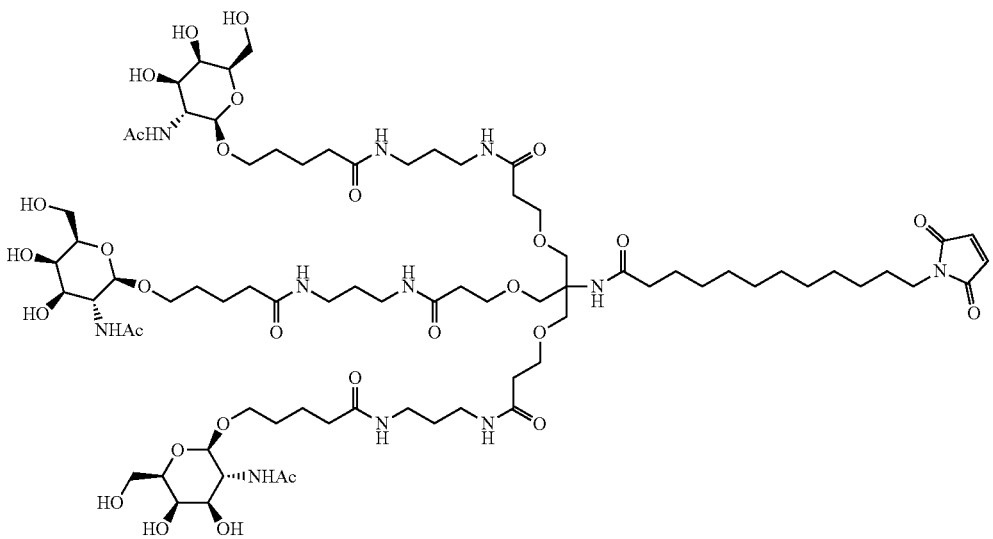 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCCCCCCCCCCN2C(=O)C=CC2=O)O[C@H](CO)[C@H](O)[C@@H]1O] |
| 1211 (I-129) | 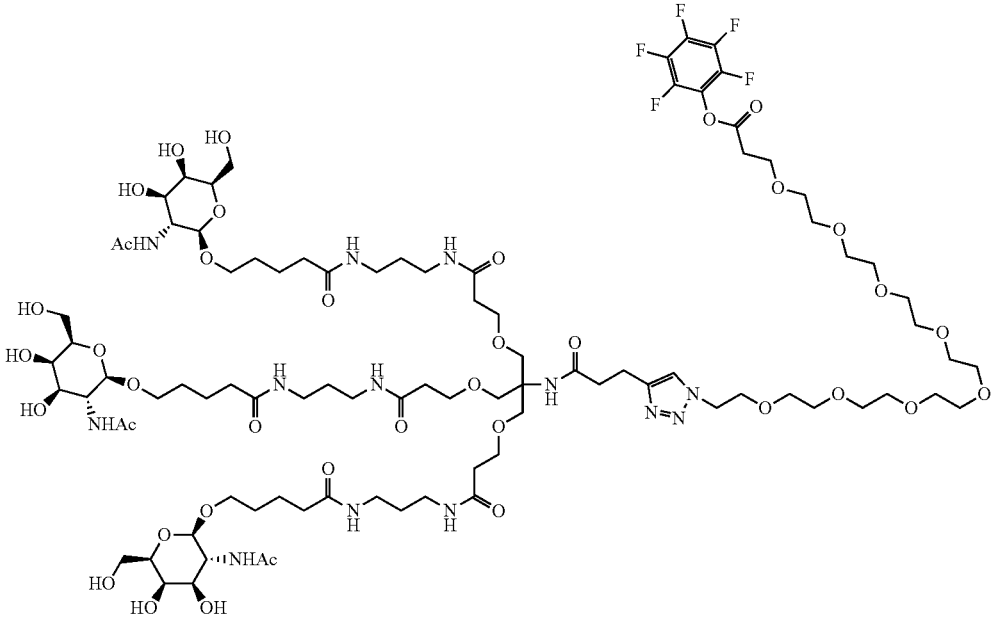 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCc2cn(CCOCCOCCOCCOCCOCCOCCOCCOCCC(=O)Oc3c(F)c(F)c(F)c(F)c3F)nn2)O[C@H](CO)[C@H](O)[C@@H]1O] |

TABLE 15-continued

Multivalent ASGPR binding compounds having chemoselective ligation group and X group of formula (Ib)

| # | Structure |
|---|---|
| 1212 I-125 | |
| 1213 (I-137) | |

TABLE 15-continued
Multivalent ASGPR binding compounds having chemoselective ligation group and X group of formula (Ib)
| # | Structure |
|---|---|
| 1214 (I-135) |  |
| 1215 (I-141) | 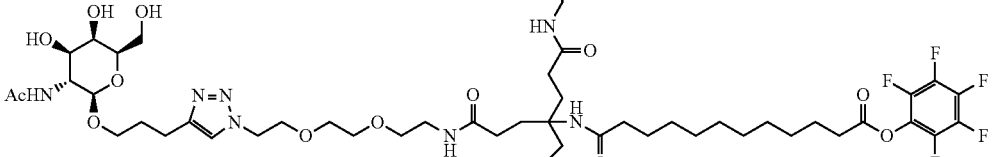 |
| 1216 (I-140) | 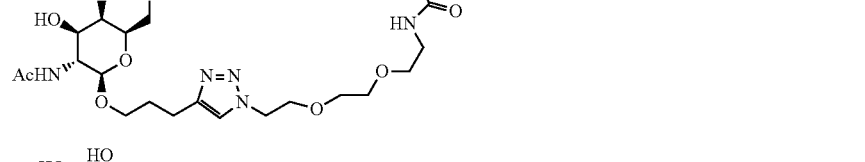 |

TABLE 15-continued
Multivalent ASGPR binding compounds having chemoselective ligation group and X group of formula (Ib)
| # | Structure |
|---|---|
| 1216 A | 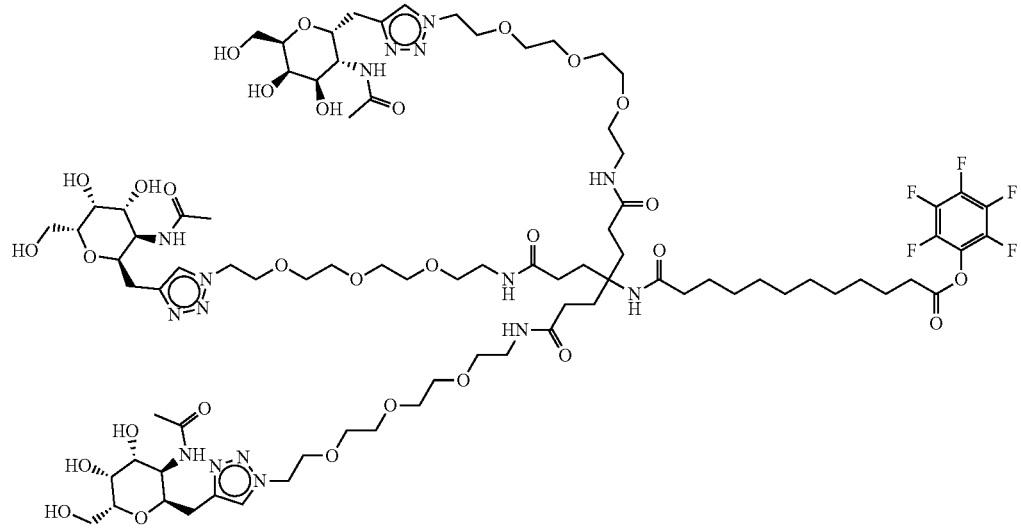 |
| 1218 (I-143) | 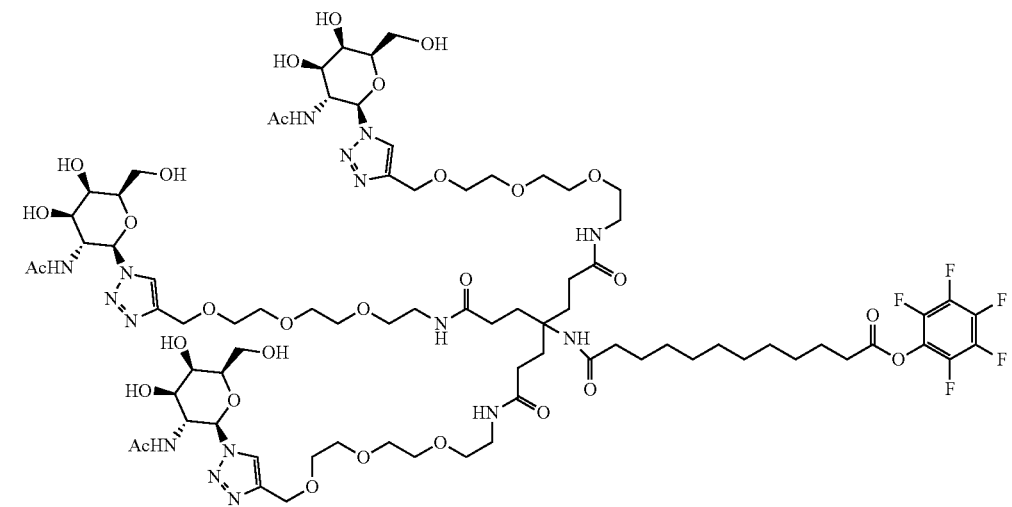 [SMILES: CC(=O)N[C@@H]1[C@@H](O)[C@@H](O)[C@@H](CO)O[C@H]1n1cc(COCCOCCOCCNC(=O)CCC(CCC(=O)NCCOCCOCCOCc2cn([C@@H]3O[C@H](CO)[C@H](O)[C@H](O)[C@H]3NC(C)=O)nn2)(CCC(=O)NCCOCCOCCOCc2cn([C@@H]3O[C@H](CO)[C@H](O)[C@H](O)[C@H]3NC(C)=O)nn2)NC(=O)CCCCCCCCCCC(=O)Oc2c(F)c(F)c(F)c(F)c2F)nn1] |

TABLE 15-continued

Multivalent ASGPR binding compounds having chemoselective ligation group and X group of formula (Ib)

| # | Structure |
|---|---|
| 1219 (I-157) | 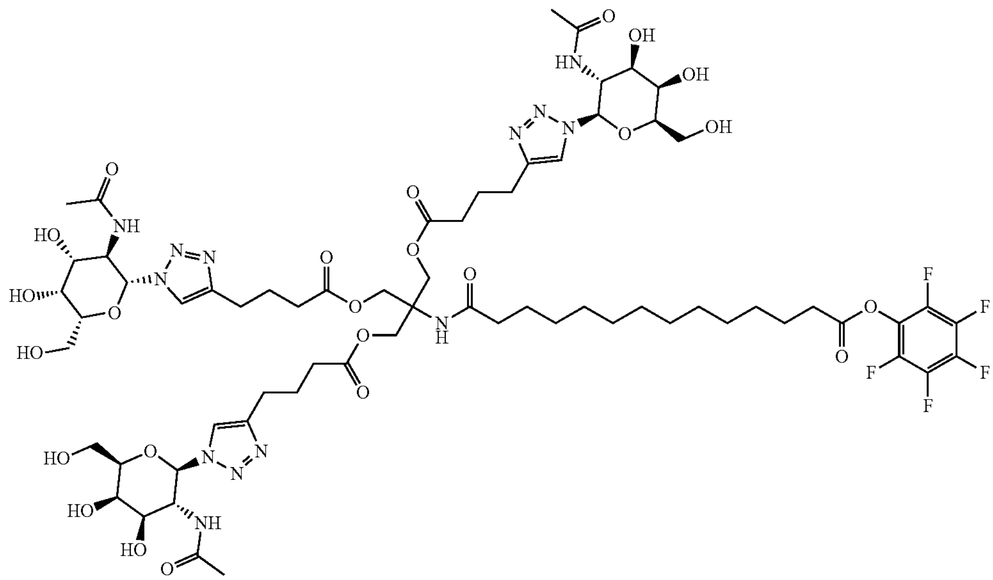 [SMILES: CC(=O)N[C@@H]1[C@@H](O)[C@@H](O)[C@@H](CO)O[C@H]1n1cc(CCCC(=O)OCC(COC(=O)CCCc2cn([C@@H]3O[C@H](CO)[C@H](O)[C@H](O)[C@H]3NC(C)=O)nn2)(COC(=O)CCCc2cn([C@@H]3O[C@H](CO)[C@H](O)[C@H](O)[C@H]3NC(C)=O)nn2)NC(=O)CCCCCCCCCCCCC(=O)Oc2c(F)c(F)c(F)c(F)c2F)nn1] |
| 1220 (I-158) | 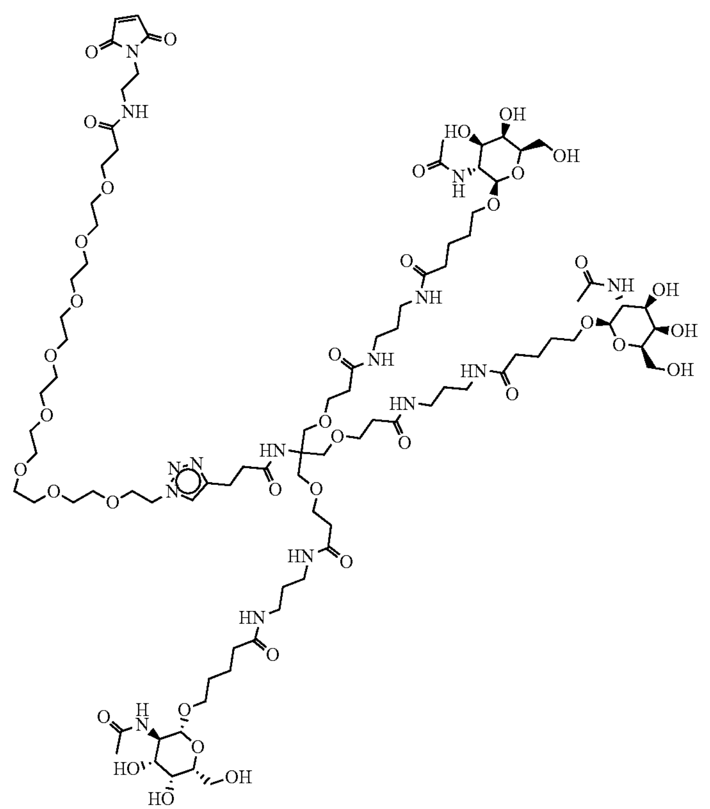 |

TABLE 15-continued

Multivalent ASGPR binding compounds having chemoselective ligation group and X group of formula (Ib)

| # | Structure |
|---|---|
| 1221 (I-138) | 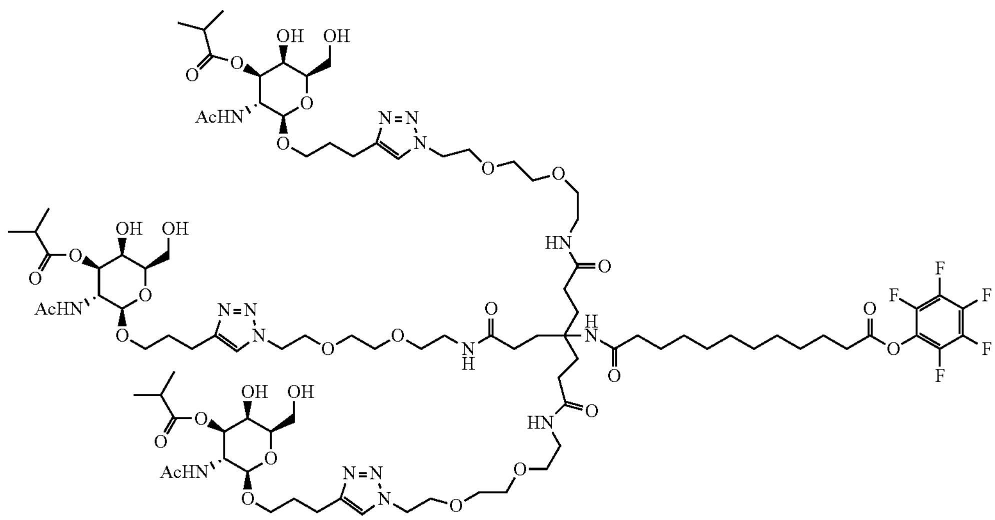 [SMILES: CC(=O)N[C@H]1[C@H](OCCCc2cn(CCOCCOCCNC(=O)CCC(CCC(=O)NCCOCCOCCn3cc(CCCO[C@@H]4O[C@H](CO)[C@H](O)[C@H](OC(=O)C(C)C)[C@H]4NC(C)=O)nn3)(CCC(=O)NCCOCCOCCn3cc(CCCO[C@@H]4O[C@H](CO)[C@H](O)[C@H](OC(=O)C(C)C)[C@H]4NC(C)=O)nn3)NC(=O)CCCCCCCCCCC(=O)Oc3c(F)c(F)c(F)c(F)c3F)nn2)O[C@H](CO)[C@H](O)[C@@H]1OC(=O)C(C)C] |
| 1222 (I-159) | 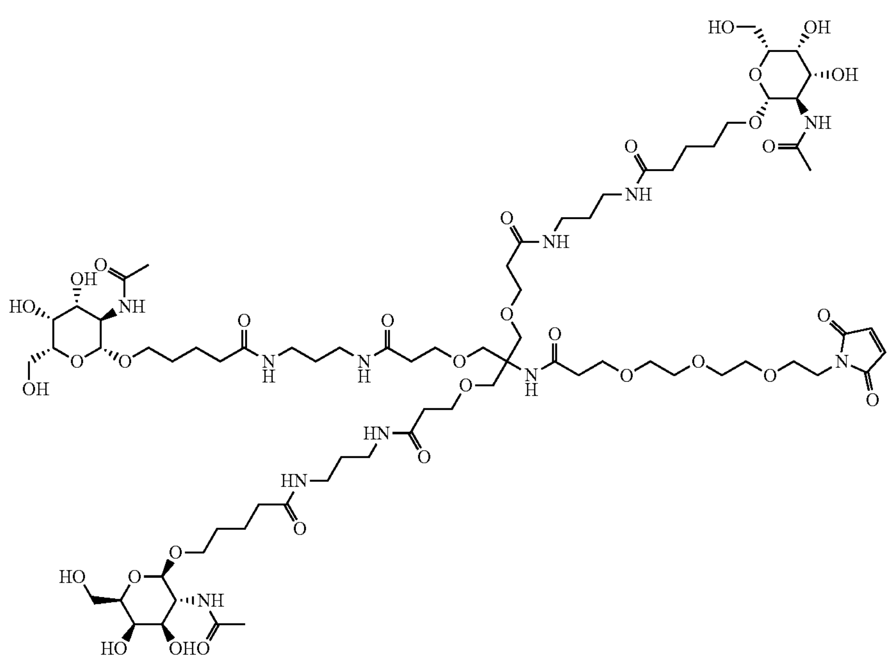 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCOCCOCCOCCN2C(=O)C=CC2=O)O[C@H](CO)[C@H](O)[C@@H]1O] |

TABLE 15-continued
Multivalent ASGPR binding compounds having chemoselective ligation group and X group of formula (Ib)
| # | Structure |
|---|---|
| 1223 (I-160) | 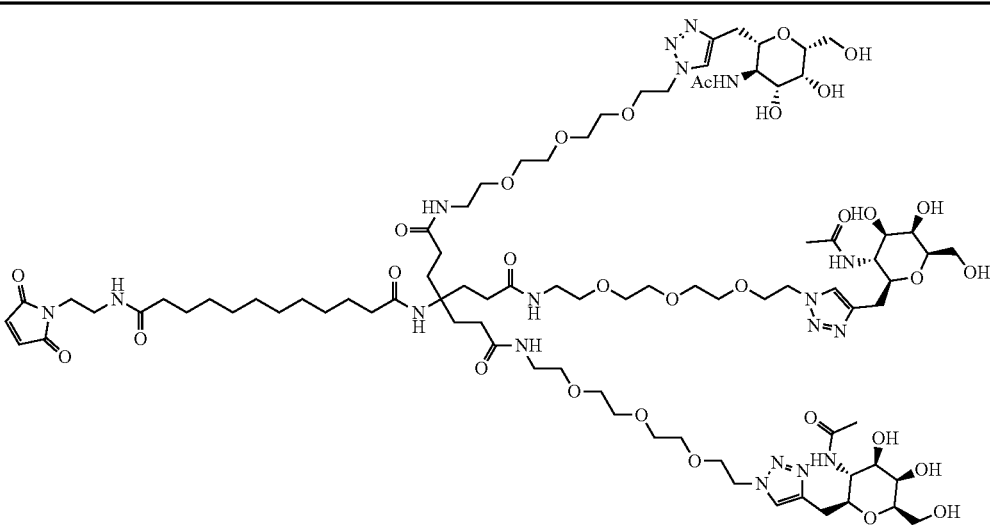 |
| 1224 (I-161) | 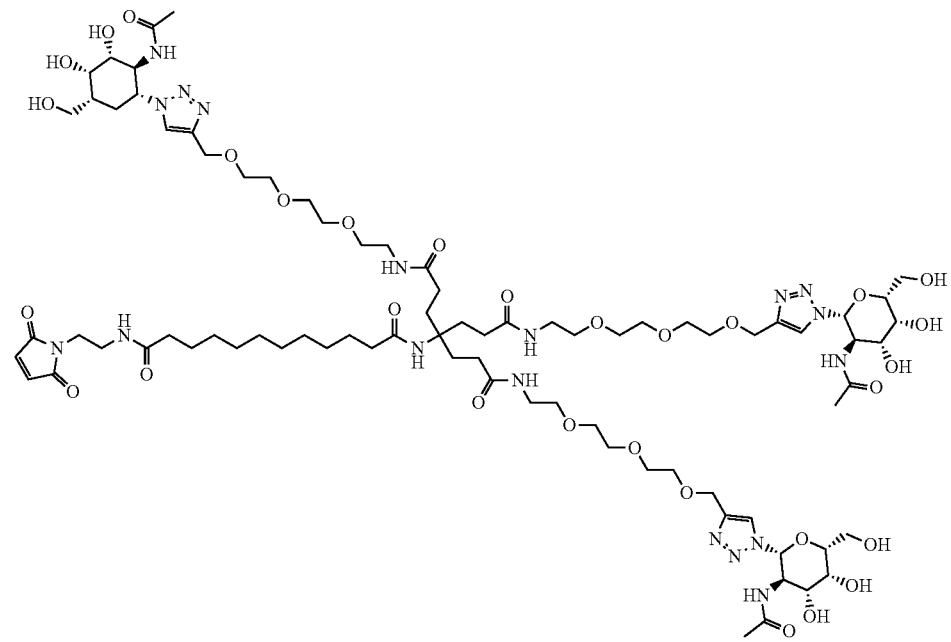 [SMILES: CC(=O)N[C@@H]1[C@@H](O)[C@@H](O)[C@@H](CO)C[C@H]1n1cc(COCCOCCOCCNC(=O)CCC(CCC(=O)NCCOCCOCCOCc2cn([C@@H]3O[C@H](CO)[C@H](O)[C@H](O)[C@H]3NC(C)=O)nn2)(CCC(=O)NCCOCCOCCOCc2cn([C@@H]3O[C@H](CO)[C@H](O)[C@H](O)[C@H]3NC(C)=O)nn2)NC(=O)CCCCCCCCCCC(=O)NCCN2C(=O)C=CC2=O)nn1] |

TABLE 15-continued
Multivalent ASGPR binding compounds having chemoselective ligation group and X group of formula (Ib)
| # | Structure |
|---|---|
| 1225 (I-162) | 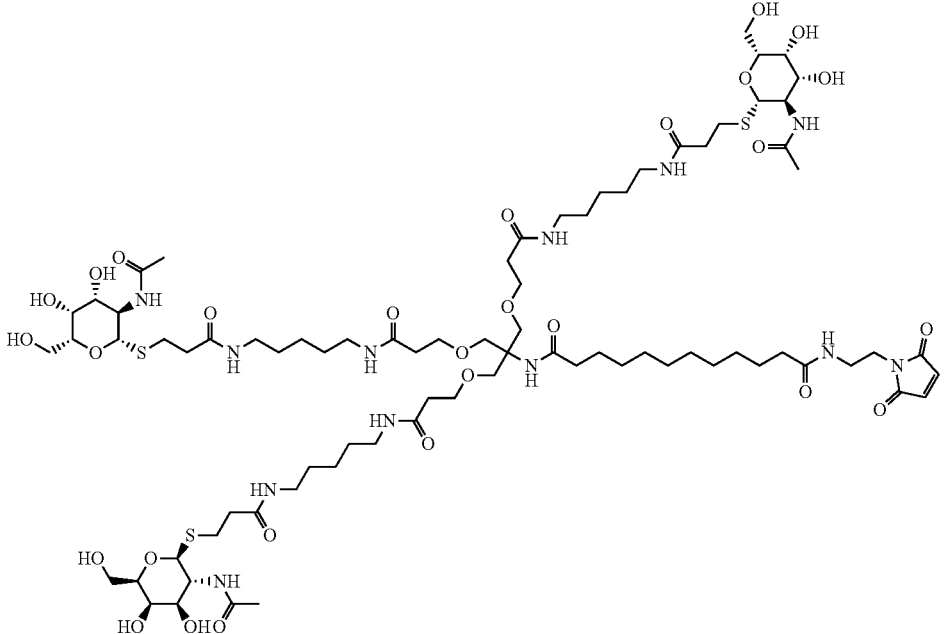 [SMILES: CC(=O)N[C@@H]1[C@@H](O)[C@@H](O)[C@@H](CO)O[C@H]1SCCC(=O)NCCCCCNC(=O)CCOCC(COCCC(=O)NCCCCCNC(=O)CCS[C@@H]1O[C@H](CO)[C@H](O)[C@H](O)[C@H]1NC(C)=O)(COCCC(=O)NCCCCCNC(=O)CCS[C@@H]1O[C@H](CO)[C@H](O)[C@H](O)[C@H]1NC(C)=O)NC(=O)CCCCCCCCCCC(=O)NCCN1C(=O)C=CC1=O] |
| 1226 (I-163) | 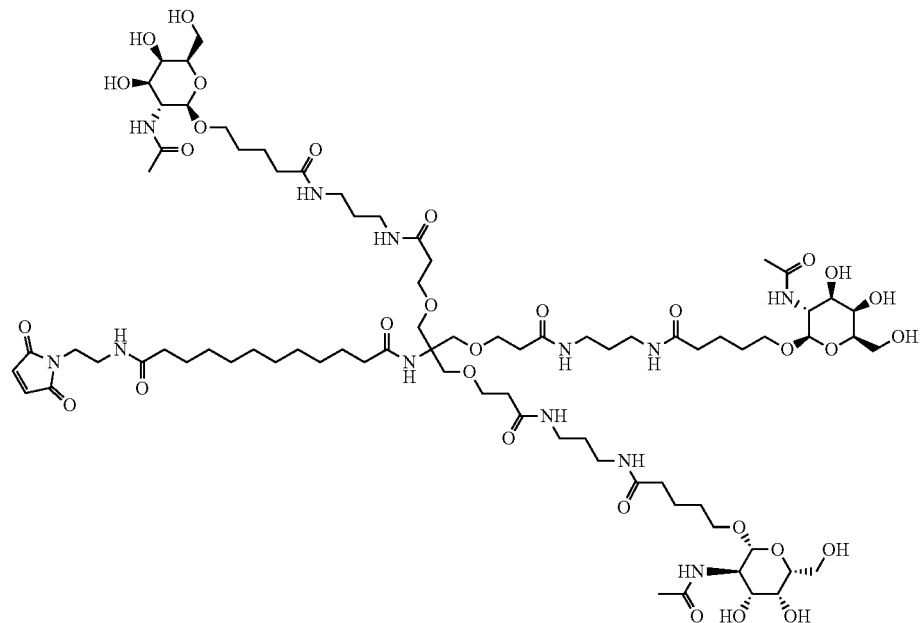 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCCCCCCCCCC(=O)NCCN2C(=O)C=CC2=O)O[C@H](CO)[C@H](O)[C@@H]1O] |

TABLE 15-continued
Multivalent ASGPR binding compounds having chemoselective ligation group and X group of formula (Ib)
| # | Structure |
|---|---|
| 1227 (I-170) | 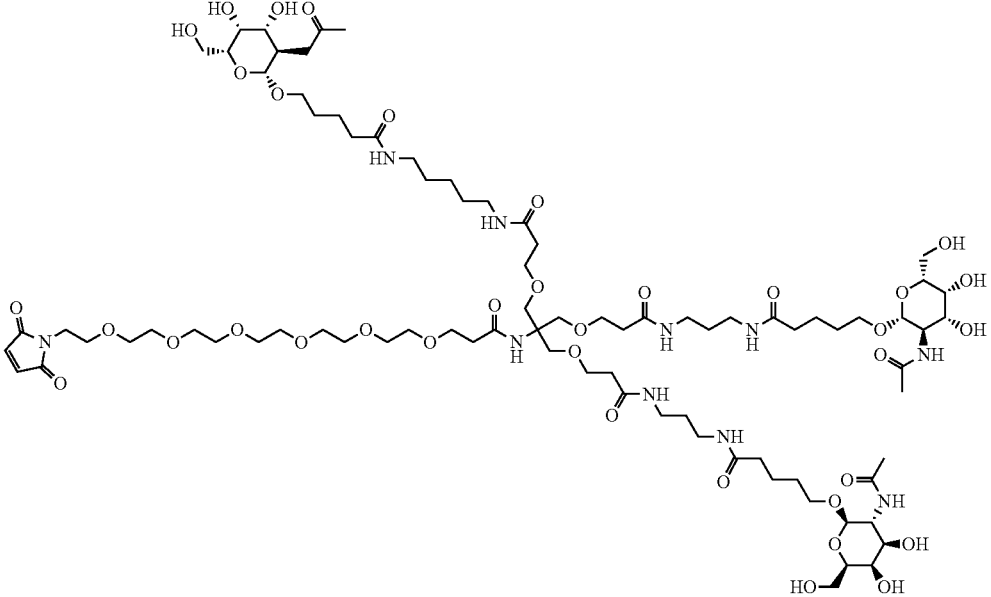 [SMILES: CC(=O)C[C@H]1[C@H](OCCCCC(=O)NCCCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCOCCOCCOCCOCCOCCOCCN2C(=O)C=CC2=O)O[C@H](CO)[C@H](O)[C@@H]1O] |
| 1228 | 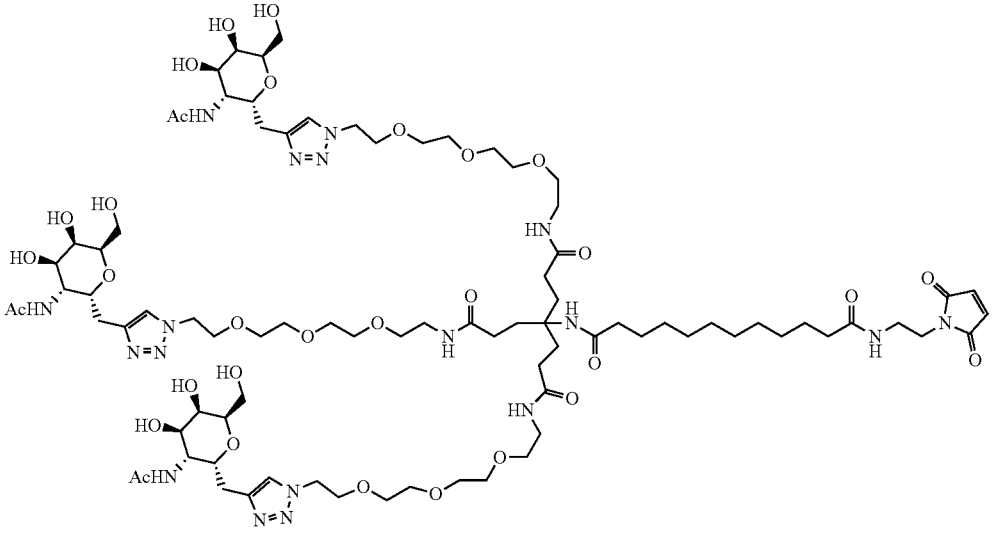 [SMILES: CC(=O)N[C@@H]1[C@@H](O)[C@@H](O)[C@@H](CO)O[C@@H]1Cc1cn(CCOCCOCCOCCNC(=O)CCC(CCC(=O)NCCOCCOCCOCCn2cc(C[C@H]3O[C@H](CO)[C@H](O)[C@H](O)[C@H]3NC(C)=O)nn2)(CCC(=O)NCCOCCOCCOCCn2cc(C[C@H]3O[C@H](CO)[C@H](O)[C@H](O)[C@H]3NC(C)=O)nn2)NC(=O)CCCCCCCCCCC(=O)NCCN2C(=O)C=CC2=O)nn1] |

TABLE 15-continued
Multivalent ASGPR binding compounds having chemoselective ligation group and X group of formula (Ib)
| # | Structure |
|---|---|
| 1229 | 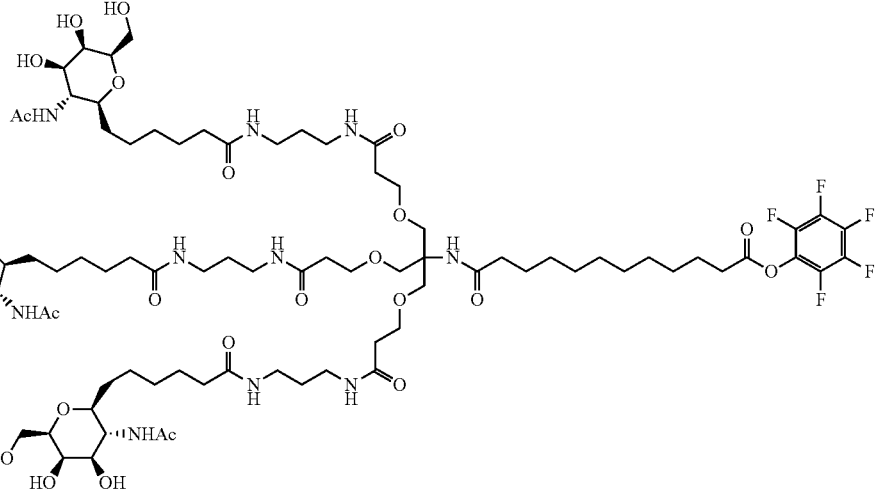 |
| 1230 | 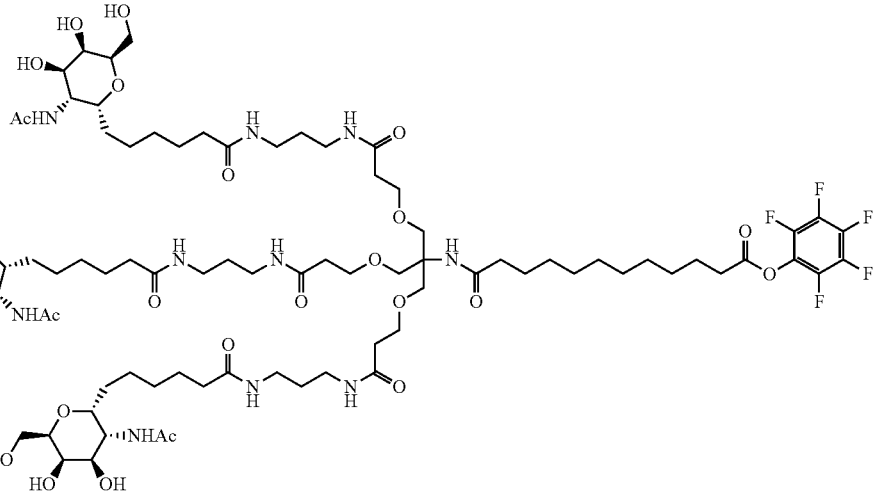 |
| 1231 | 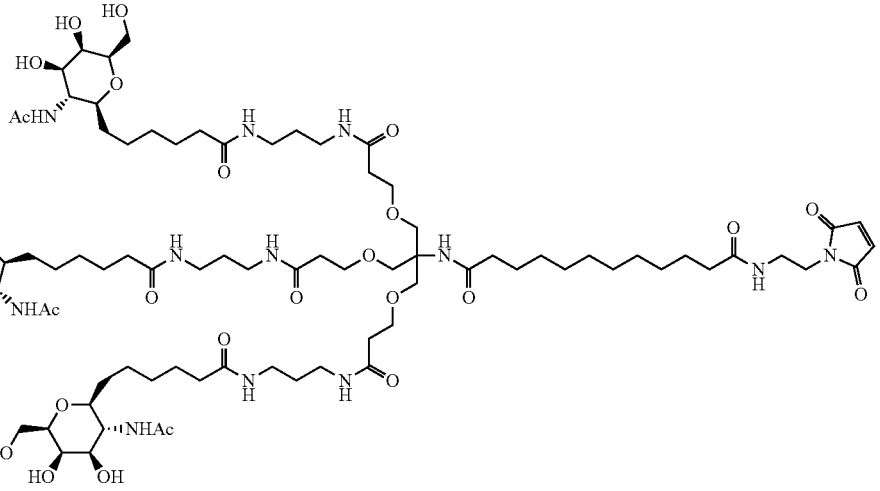 |

TABLE 15-continued
Multivalent ASGPR binding compounds having chemoselective ligation group and X group of formula (Ib)
| # | Structure |
|---|-----------|
| 1232 | 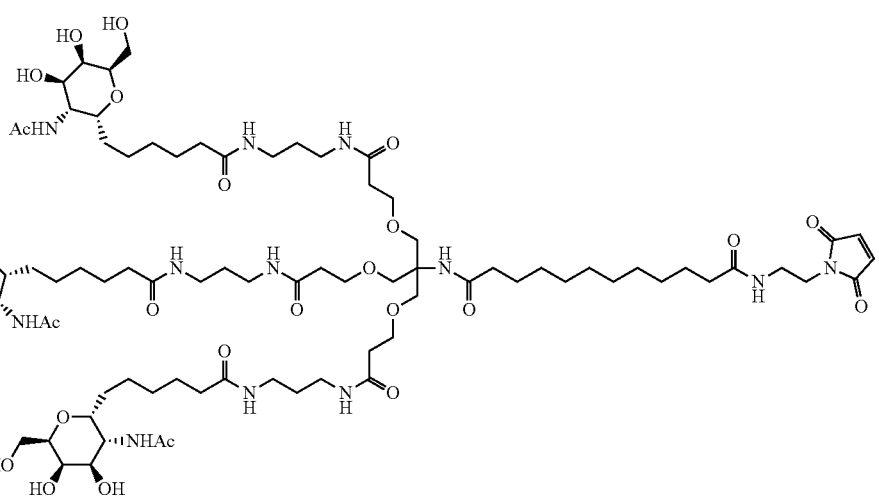 |
| 1233 | 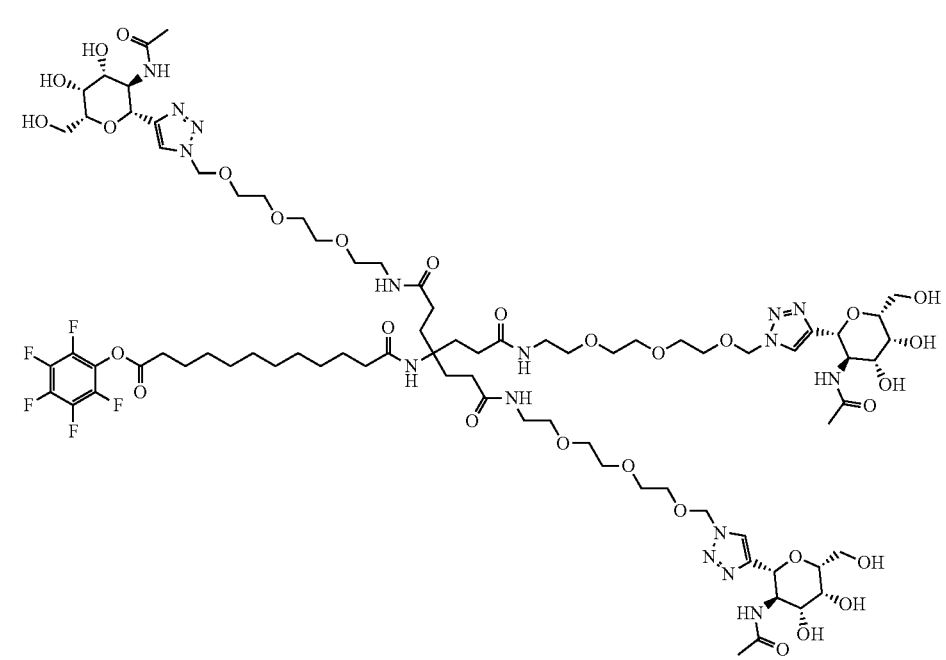 [SMILES: CC(=O)N[C@@H]1[C@@H](O)[C@@H](O)[C@@H](CO)O[C@H]1c1cn(COCCOCCOCCNC(=O)CCC(CCC(=O)NCCOCCOCCOCn2cc([C@@H]3O[C@H](CO)[C@H](O)[C@H](O)[C@H]3NC(C)=O)nn2)(CCC(=O)NCCOCCOCCOCn2cc([C@@H]3O[C@H](CO)[C@H](O)[C@H](O)[C@H]3NC(C)=O)nn2)NC(=O)CCCCCCCCCCC(=O)Oc2c(F)c(F)c(F)c(F)c2F)nn1] |

TABLE 15-continued
Multivalent ASGPR binding compounds having chemoselective ligation group and X group of formula (Ib)
| # | Structure |
|---|---|
| 1233 B | 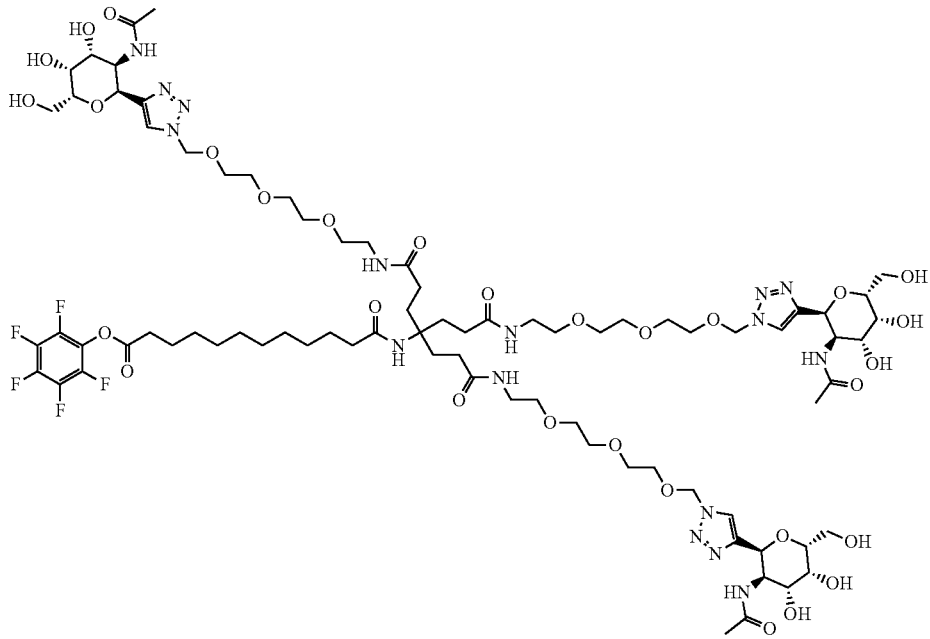 [SMILES: CC(=O)N[C@@H]1[C@@H](O)[C@@H](O)[C@@H](CO)O[C@@H]1c1cn(COCCOCCOCCNC(=O)CCC(CCC(=O)NCCOCCOCCOCn2cc([C@H]3O[C@H](CO)[C@H](O)[C@H](O)[C@H]3NC(C)=O)nn2)(CCC(=O)NCCOCCOCCOCn2cc([C@H]3O[C@H](CO)[C@H](O)[C@H](O)[C@H]3NC(C)=O)nn2)NC(=O)CCCCCCCCCCC(=O)Oc2c(F)c(F)c(F)c(F)c2F)nn1] |
| 1234 | 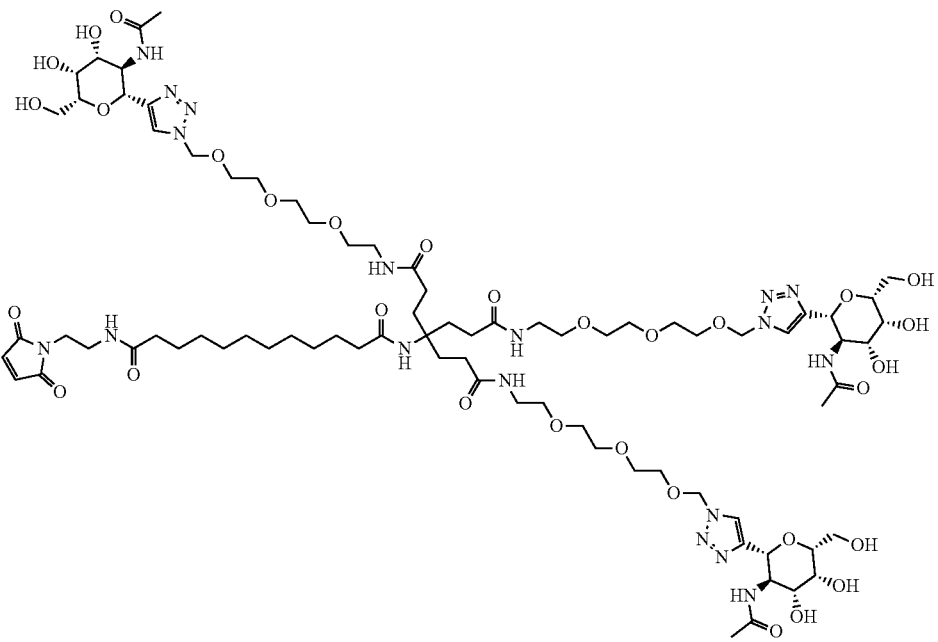 [SMILES: CC(=O)N[C@@H]1[C@@H](O)[C@@H](O)[C@@H](CO)O[C@H]1c1cn(COCCOCCOCCNC(=O)CCC(CCC(=O)NCCOCCOCCOCn2cc([C@@H]3O[C@H](CO)[C@H](O)[C@H](O)[C@H]3NC(C)=O)nn2)(CCC(=O)NCCOCCOCCOCn2cc([C@@H]3O[C@H](CO)[C@H](O)[C@H](O)[C@H]3NC(C)=O)nn2)NC(=O)CCCCCCCCCCC(=O)NCCN2C(=O)C=CC2=O)nn1] |

TABLE 15-continued
Multivalent ASGPR binding compounds having chemoselective ligation group and X group of formula (Ib)
| # | Structure |
|---|-----------|
| 1234 B | 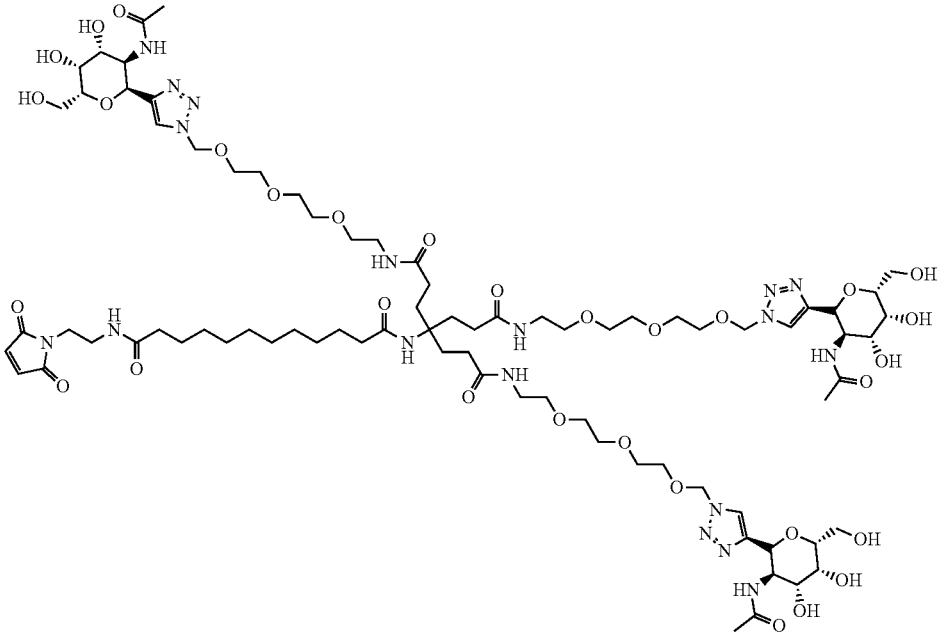 |
TABLE 16
Multivalent ASGPR binding compounds having chemoselective ligation group and X group of formula (Ic)
| # | Structure |
|---|-----------|
| 1301 (I-110) | 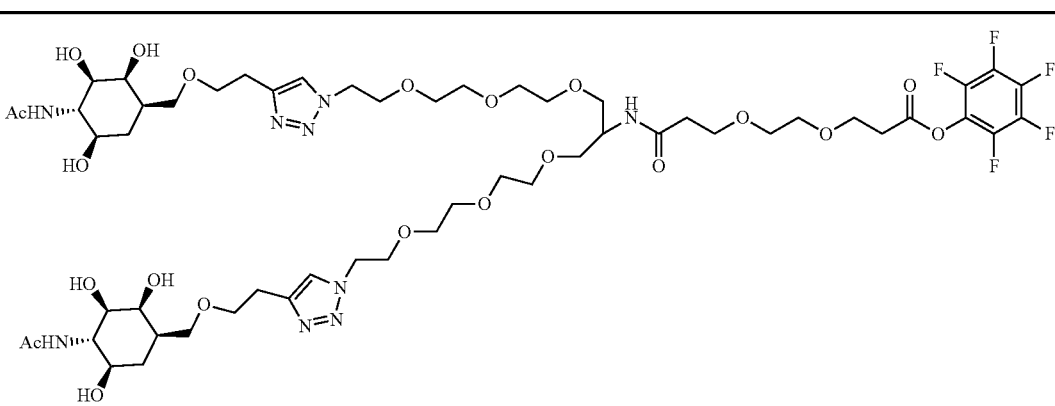 |

TABLE 16-continued
Multivalent ASGPR binding compounds having chemoselective ligation group and X group of formula (Ic)
| # | Structure |
|---|-----------|
| Trimeric ligands | |
1302
(I-108)
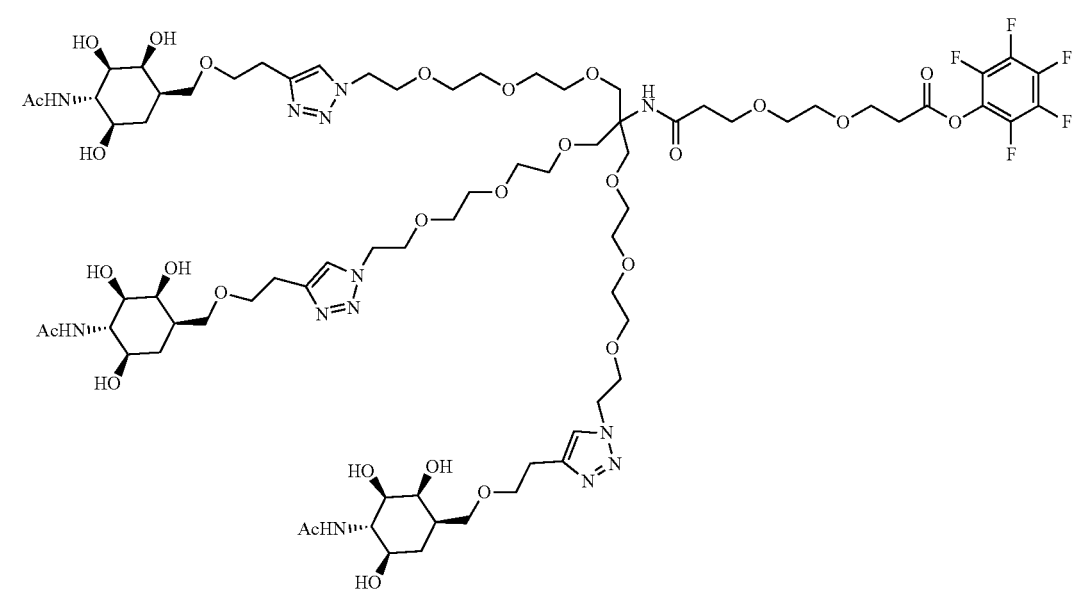 [SMILES: CC(=O)N[C@@H]1[C@@H](O)[C@@H](O)[C@@H](COCCc2cn(CCOCCOCCOCC(COCCOCCOCCn3cc(CCOC[C@H]4C[C@@H](O)[C@H](NC(C)=O)[C@@H](O)[C@H]4O)nn3)(COCCOCCOCCn3cc(CCOC[C@H]4C[C@@H](O)[C@H](NC(C)=O)[C@@H](O)[C@H]4O)nn3)NC(=O)CCOCCOCCC(=O)Oc3c(F)c(F)c(F)c(F)c3F)nn2)C[C@H]1O]
1303
(I-136)
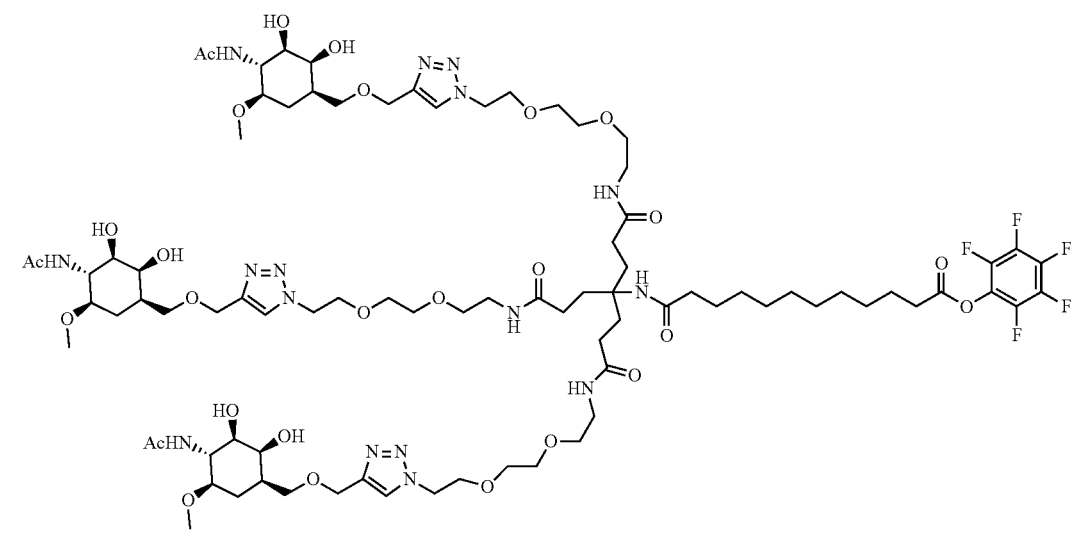 [SMILES: CO[C@@H]1C[C@H](COCc2cn(CCOCCOCCNC(=O)CCC(CCC(=O)NCCOCCOCCn3cc(COC[C@H]4C[C@@H](OC)[C@H](NC(C)=O)[C@@H](O)[C@H]4O)nn3)(CCC(=O)NCCOCCOCCn3cc(COC[C@H]4C[C@@H](OC)[C@H](NC(C)=O)[C@@H](O)[C@H]4O)nn3)NC(=O)CCCCCCCCCCC(=O)Oc3c(F)c(F)c(F)c(F)c3F)nn2)[C@H](O)[C@H](O)[C@H]1NC(C)=O]

TABLE 16-continued
Multivalent ASGPR binding compounds having chemoselective ligation group and X group of formula (Ic)
| # | Structure |
|---|---|
| 1304 (I-152) | 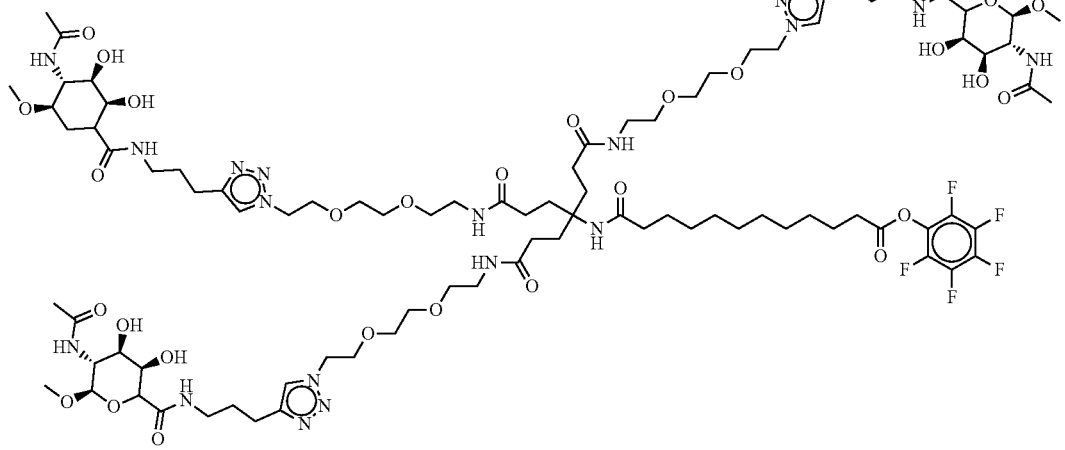 |
TABLE 17
Multivalent ASGPR binding compounds having chemoselective ligation group and X group of formula (Id)
| # | Structure |
|---|---|
| 1401 (I-153) | 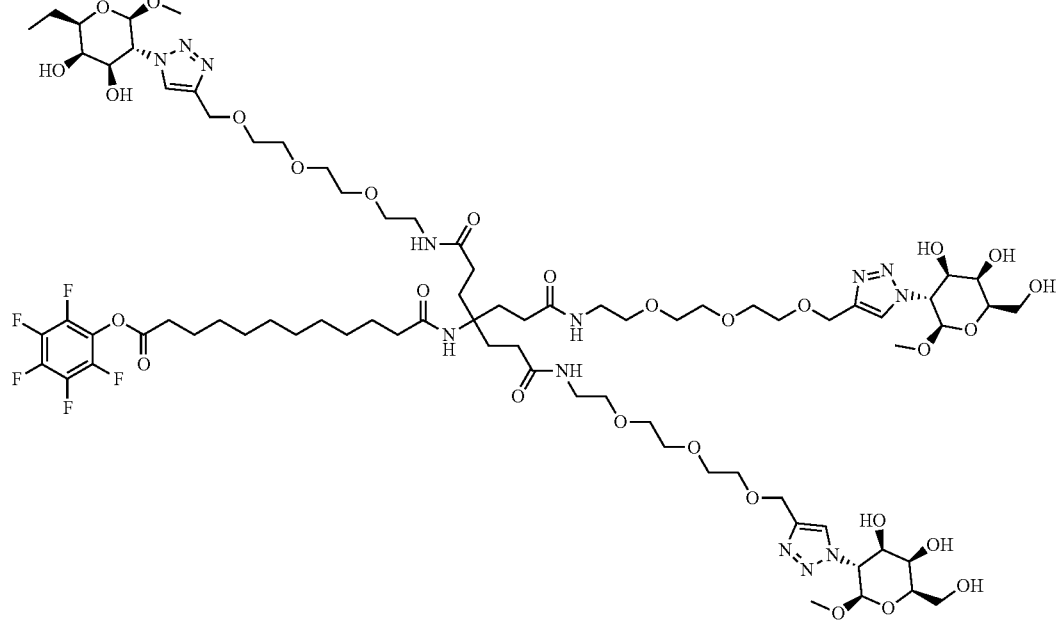 [SMILES: CC[C@H]1O[C@@H](OC)[C@H](n2cc(COCCOCCOCCNC(=O)CCC(CCC(=O)NCCOCCOCCOCc3cn([C@H]4[C@H](OC)O[C@H](CO)[C@H](O)[C@@H]4O)nn3)(CCC(=O)NCCOCCOCCOCc3cn([C@H]4[C@H](OC)O[C@H](CO)[C@H](O)[C@@H]4O)nn3)NC(=O)CCCCCCCCCCC(=O)Oc3c(F)c(F)c(F)c(F)c3F)nn2)[C@@H](O)[C@H]1O] |

TABLE 17-continued

Multivalent ASGPR binding compounds having chemoselective ligation group and X group of formula (Id)

| # | Structure |
|---|---|
| 1402 (I-154) | 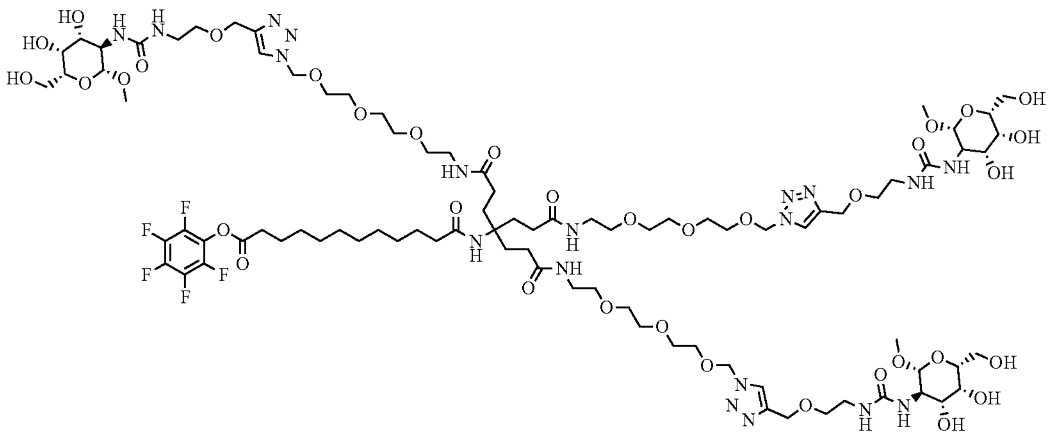 [SMILES: CO[C@@H]1O[C@H](CO)[C@H](O)[C@H](O)C1NC(=O)NCCOCc1cn(COCCOCCOCCNC(=O)CCC(CCC(=O)NCCOCCOCCOCn2cc(COCCNC(=O)N[C@H]3[C@H](OC)O[C@H](CO)[C@H](O)[C@@H]3O)nn2)(CCC(=O)NCCOCCOCCOCn2cc(COCCNC(=O)N[C@H]3[C@H](OC)O[C@H](CO)[C@H](O)[C@@H]3O)nn2)NC(=O)CCCCCCCCCCC(=O)Oc2c(F)c(F)c(F)c(F)c2F)nn1] |
| 1403 (I-155) | 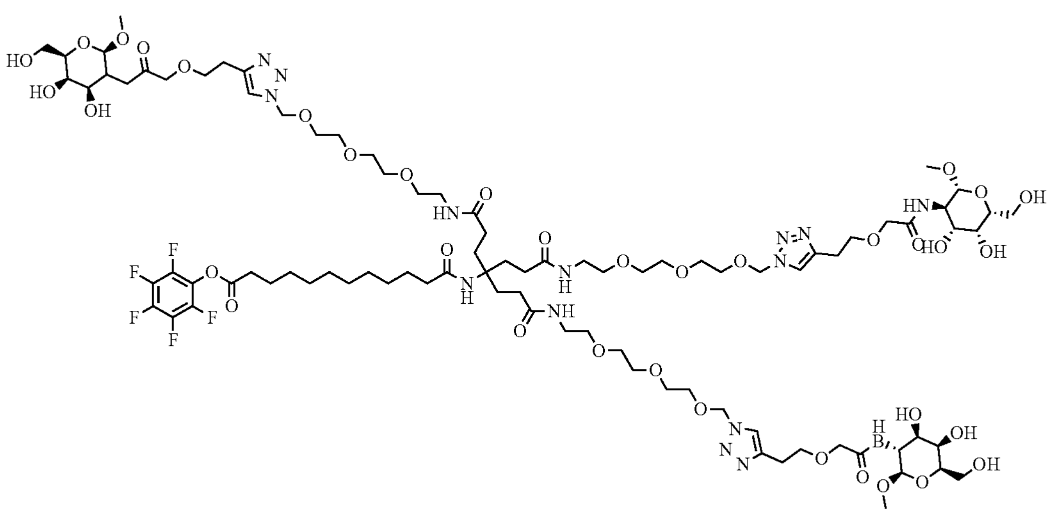 |

The present disclosure is meant to encompass stereoisomers of any one of the compounds described herein. In some instance, the compound includes an enantiomer of the D-N-acetylgalactosamine (GalNAc), or an analog or derivative of GalNAc.

5.3.2. Other Exemplary Compounds

Table 18 illustrates exemplary ASGPR binding compounds of this disclosure that include a binding moiety, or a precursor thereof.

TABLE 18

Multivalent ASGPR binding compounds having protein targeting group

| # | Structure |
|---|---|
| 1404 (I-156) | 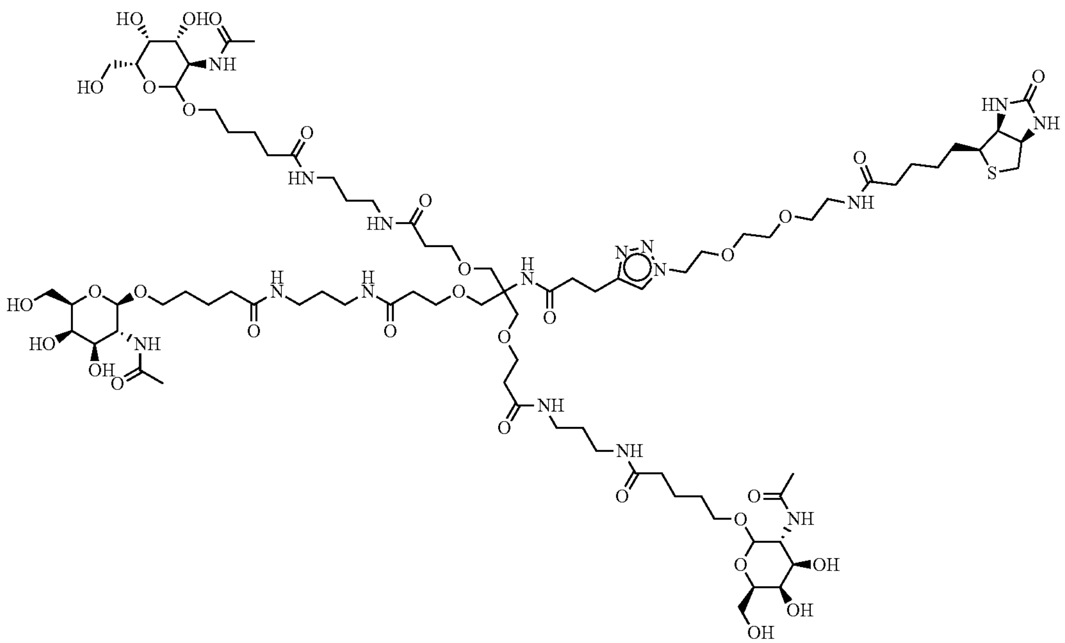 |
| 1405 (I-139) | 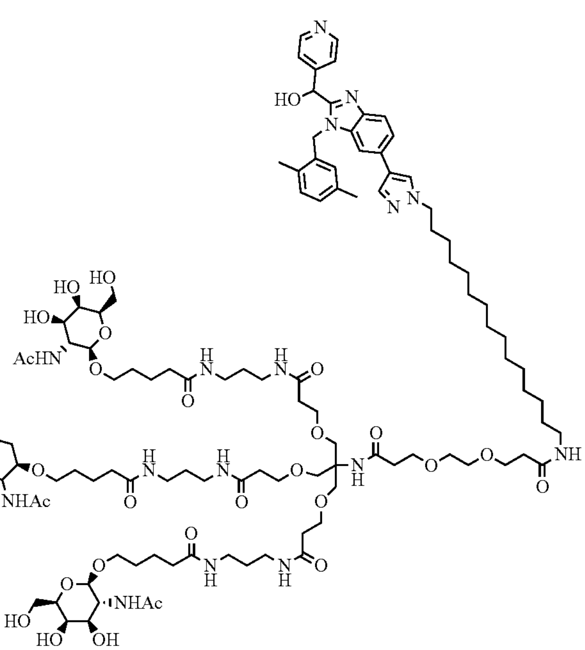 |

TABLE 18-continued
Multivalent ASGPR binding compounds having protein targeting group
| # | Structure |
|---|---|
| 1406 (I-142) | 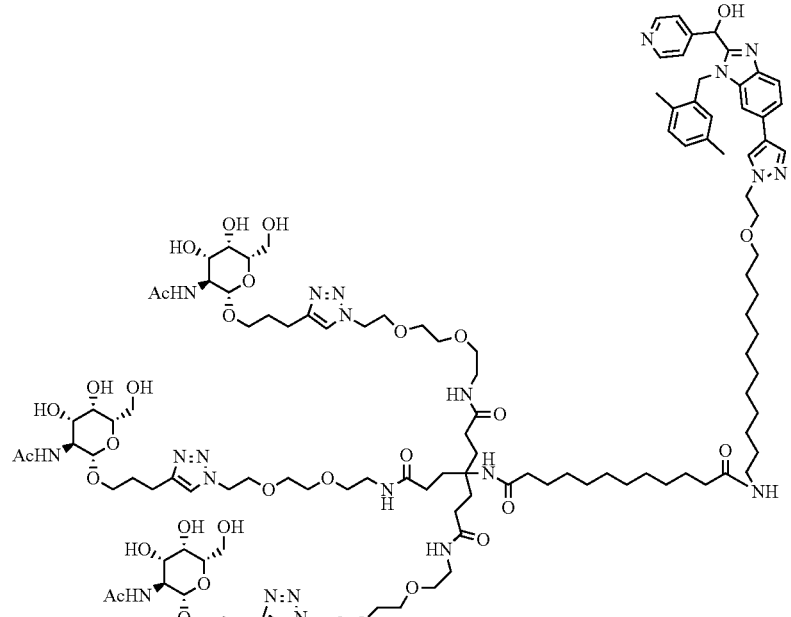 |
Table 19 illustrates exemplary trivalent ASGPR binding intermediate compounds of this disclosure including X groups of formula (Ie).
TABLE 19
Multivalent ASGPR binding compounds including X groups of formula (Ie)
| # | Structure |
|---|---|
| 1901 (I-171) | 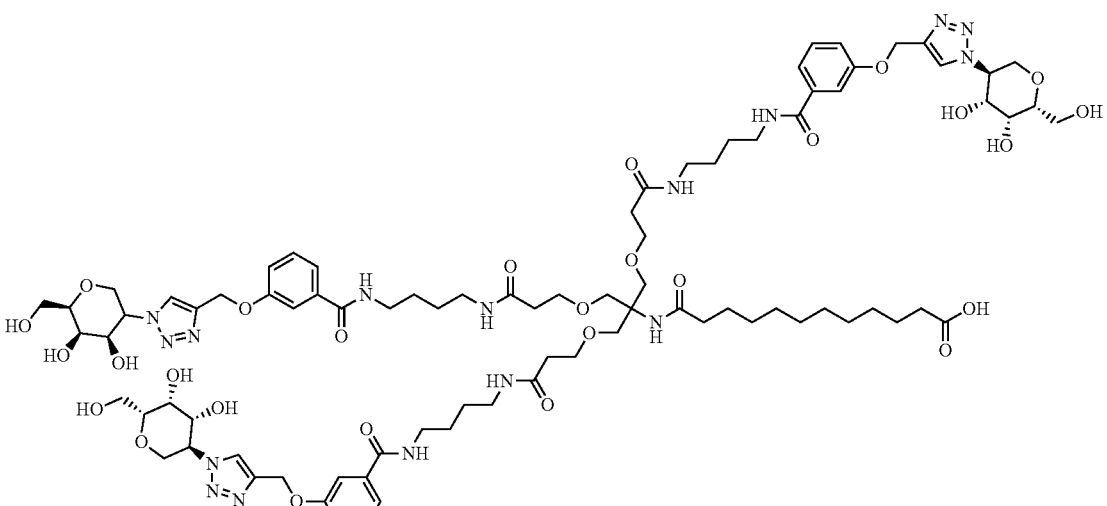 |

TABLE 19-continued
Multivalent ASGPR binding compounds including X groups of formula (Ie)
| # | Structure |
|---|---|
| 1902 (I-172) | 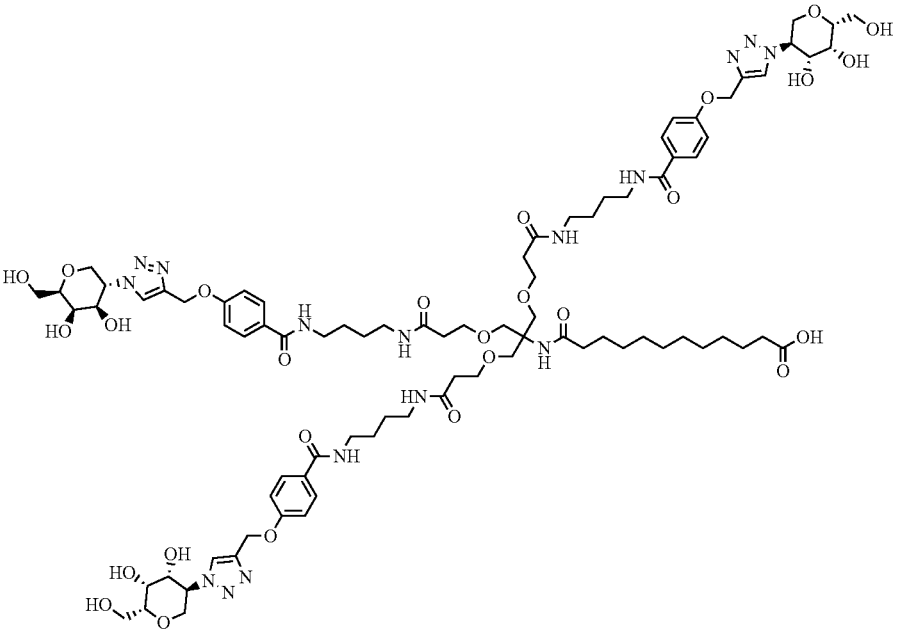 [SMILES: O=C(O)CCCCCCCCCCC(=O)NC(COCCC(=O)NCCCCNC(=O)c1ccc(OCc2cn([C@H]3CO[C@H](CO)[C@H](O)[C@@H]3O)nn2)cc1)(COCCC(=O)NCCCCNC(=O)c1ccc(OCc2cn([C@H]3CO[C@H](CO)[C@H](O)[C@@H]3O)nn2)cc1)COCCC(=O)NCCCCNC(=O)c1ccc(OCc2cn([C@H]3CO[C@H](CO)[C@H](O)[C@@H]3O)nn2)cc1] |
| 1904 | 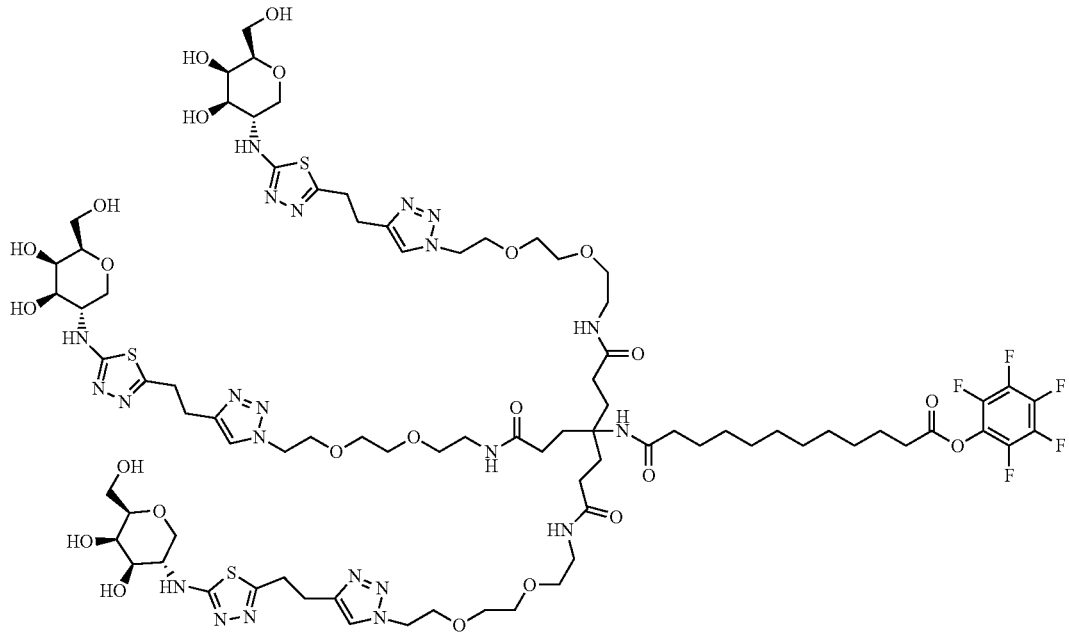 [SMILES: O=C(CCC(CCC(=O)NCCOCCOCCn1cc(CCc2nnc(N[C@H]3CO[C@H](CO)[C@H](O)[C@@H]3O)s2)nn1)(CCC(=O)NCCOCCOCCn1cc(CCc2nnc(N[C@H]3CO[C@H](CO)[C@H](O)[C@@H]3O)s2)nn1)NC(=O)CCCCCCCCCCC(=O)Oc1c(F)c(F)c(F)c(F)c1F)NCCOCCOCCn1cc(CCc2nnc(N[C@H]3CO[C@H](CO)[C@H](O)[C@@H]3O)s2)nn1] |

TABLE 19-continued
Multivalent ASGPR binding compounds including X groups of formula (Ie)
| # | Structure |
|---|---|
| 1905 | 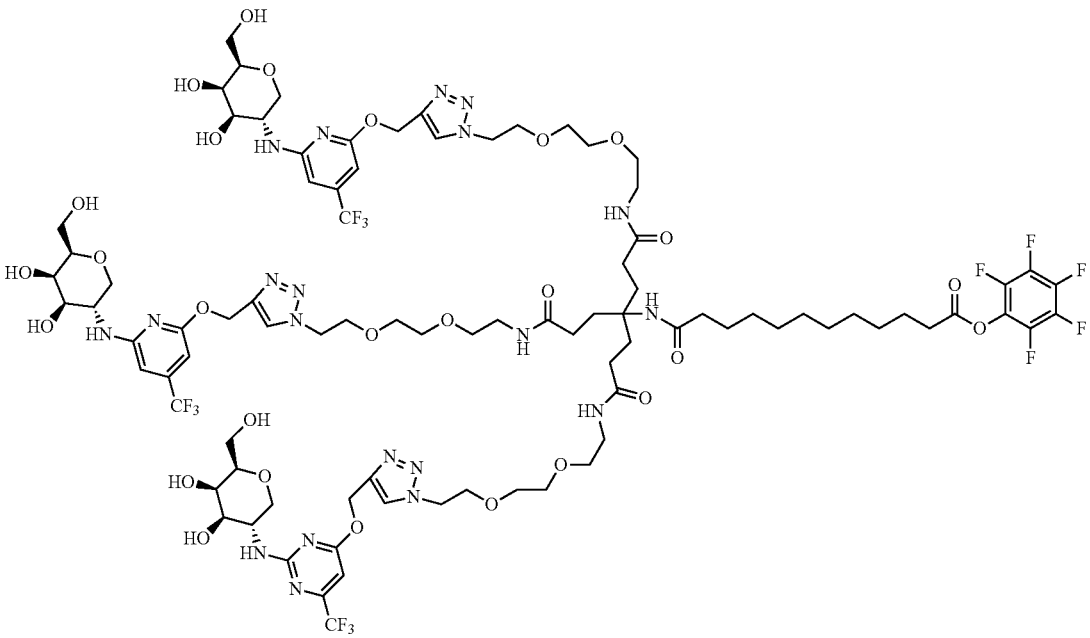 [SMILES: O=C(CCC(CCC(=O)NCCOCCOCCn1cc(COc2cc(C(F)(F)F)cc(N[C@H]3CO[C@H](CO)[C@H](O)[C@@H]3O)n2)nn1)(CCC(=O)NCCOCCOCCn1cc(COc2cc(C(F)(F)F)nc(N[C@H]3CO[C@H](CO)[C@H](O)[C@@H]3O)n2)nn1)NC(=O)CCCCCCCCCCC(=O)Oc1c(F)c(F)c(F)c(F)c1F)NCCOCCOCCn1cc(COc2cc(C(F)(F)F)cc(N[C@H]3CO[C@H](CO)[C@H](O)[C@@H]3O)n2)nn1] |
| 1906 | 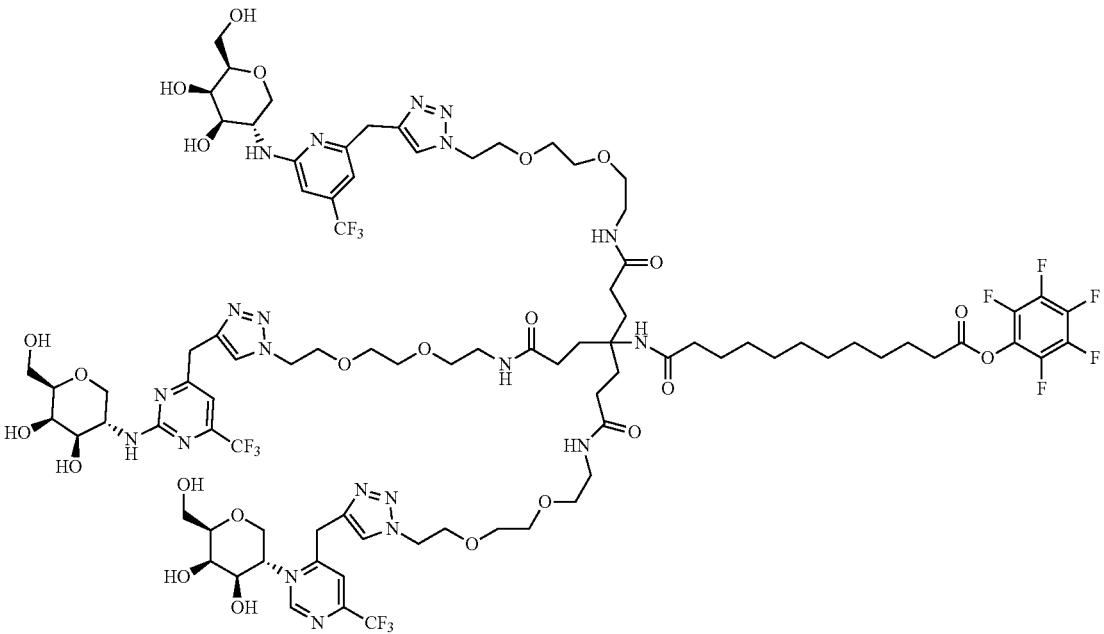 |

TABLE 19-continued

Multivalent ASGPR binding compounds including X groups of formula (Ie)

| # | Structure |
|---|-----------|
| 1907 | 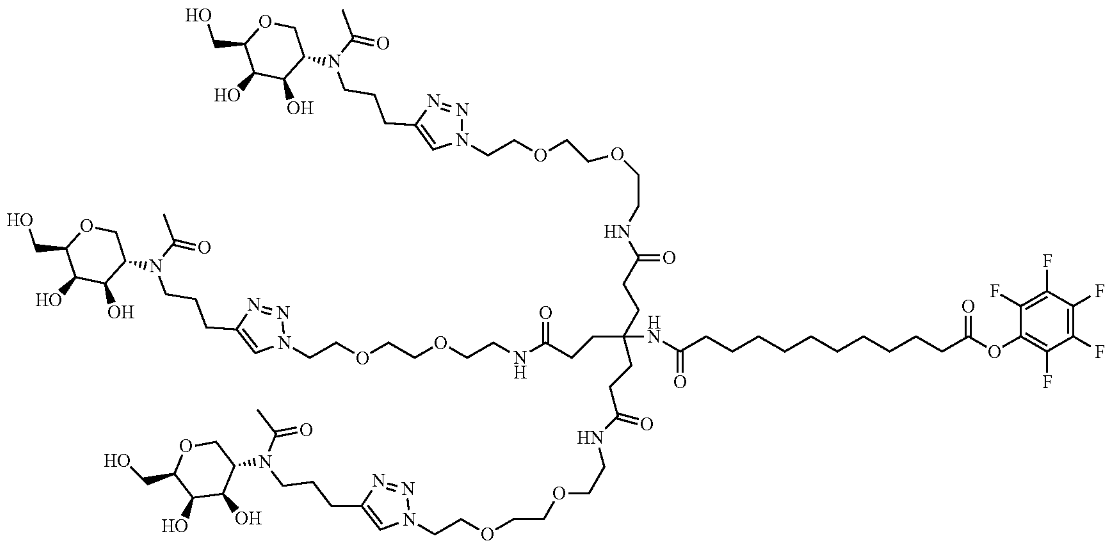 [SMILES: CC(=O)N(CCCc1cn(CCOCCOCCNC(=O)CCC(CCC(=O)NCCOCCOCCn2cc(CCCN(C(C)=O)[C@H]3CO[C@H](CO)[C@H](O)[C@@H]3O)nn2)(CCC(=O)NCCOCCOCCn2cc(CCCN(C(C)=O)[C@H]3CO[C@H](CO)[C@H](O)[C@@H]3O)nn2)NC(=O)CCCCCCCCCCC(=O)Oc2c(F)c(F)c(F)c(F)c2F)nn1)[C@H]1CO[C@H](CO)[C@H](O)[C@@H]1O] |
| 1908 | 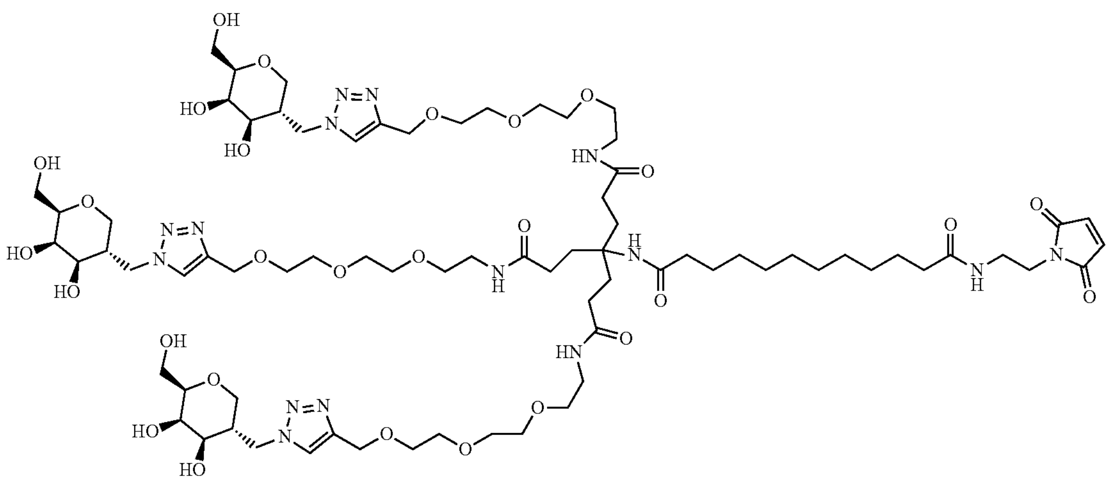 [SMILES: O=C(CCCCCCCCCCC(=O)NC(CCC(=O)NCCOCCOCCOCc1cn(C[C@H]2CO[C@H](CO)[C@H](O)[C@@H]2O)nn1)(CCC(=O)NCCOCCOCCOCc1cn(C[C@H]2CO[C@H](CO)[C@H](O)[C@@H]2O)nn1)CCC(=O)NCCOCCOCCOCc1cn(C[C@H]2CO[C@H](CO)[C@H](O)[C@@H]2O)nn1)NCCN1C(=O)C=CC1=O] |
| 1909 | 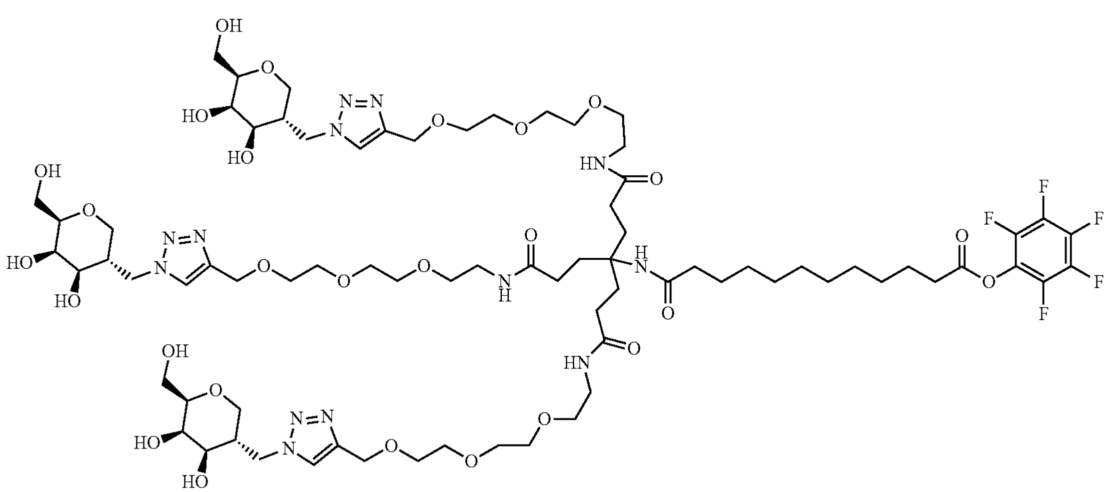 [SMILES: O=C(CCC(CCC(=O)NCCOCCOCCOCc1cn(C[C@H]2CO[C@H](CO)[C@H](O)[C@@H]2O)nn1)(CCC(=O)NCCOCCOCCOCc1cn(C[C@H]2CO[C@H](CO)[C@H](O)[C@@H]2O)nn1)NC(=O)CCCCCCCCCCC(=O)Oc1c(F)c(F)c(F)c(F)c1F)NCCOCCOCCOCc1cn(C[C@H]2CO[C@H](CO)[C@H](O)[C@@H]2O)nn1] |

TABLE 19-continued

Multivalent ASGPR binding compounds including X groups of formula (Ie)

| # | Structure |
|---|---|
| 1910 | 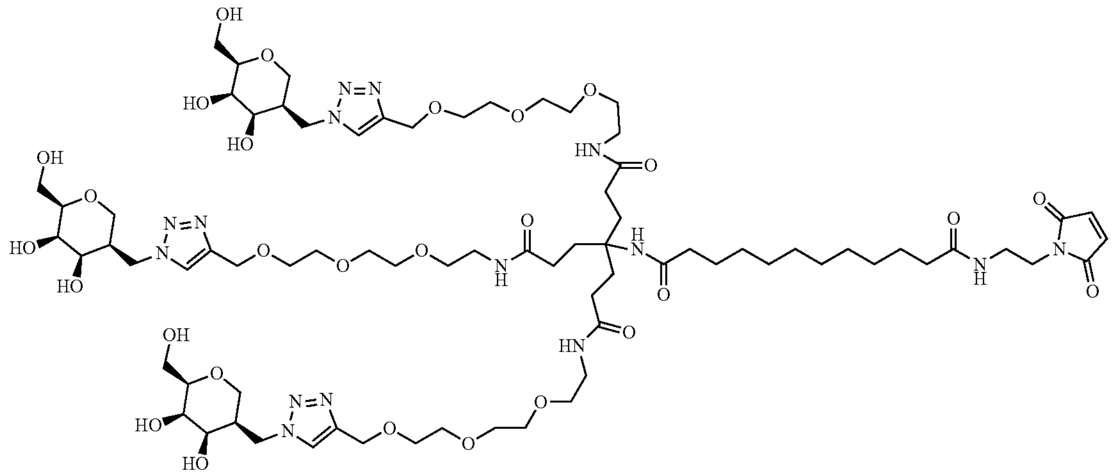 [SMILES: O=C(CCCCCCCCCCC(=O)NC(CCC(=O)NCCOCCOCCOCc1cn(C[C@@H]2CO[C@H](CO)[C@H](O)[C@@H]2O)nn1)(CCC(=O)NCCOCCOCCOCc1cn(C[C@@H]2CO[C@H](CO)[C@H](O)[C@@H]2O)nn1)CCC(=O)NCCOCCOCCOCc1cn(C[C@@H]2CO[C@H](CO)[C@H](O)[C@@H]2O)nn1)NCCN1C(=O)C=CC1=O] |
| 1911 | 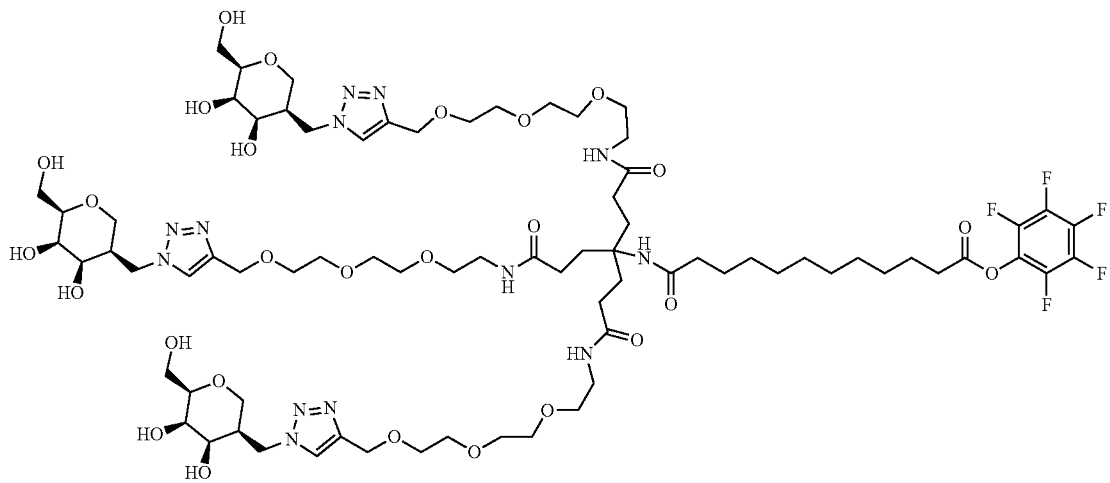 [SMILES: O=C(CCC(CCC(=O)NCCOCCOCCOCc1cn(C[C@@H]2CO[C@H](CO)[C@H](O)[C@@H]2O)nn1)(CCC(=O)NCCOCCOCCOCc1cn(C[C@@H]2CO[C@H](CO)[C@H](O)[C@@H]2O)nn1)NC(=O)CCCCCCCCCCC(=O)Oc1c(F)c(F)c(F)c(F)c1F)NCCOCCOCCOCc1cn(C[C@@H]2CO[C@H](CO)[C@H](O)[C@@H]2O)nn1] |
| 1912 | 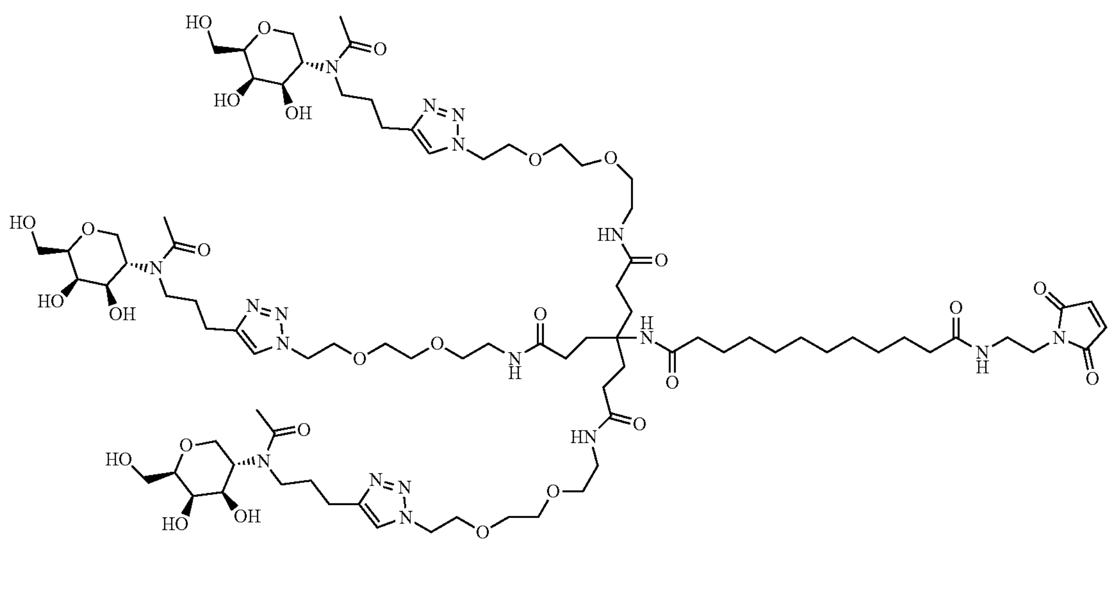 [SMILES: CC(=O)N(CCCc1cn(CCOCCOCCNC(=O)CCC(CCC(=O)NCCOCCOCCn2cc(CCCN(C(C)=O)[C@H]3CO[C@H](CO)[C@H](O)[C@@H]3O)nn2)(CCC(=O)NCCOCCOCCn2cc(CCCN(C(C)=O)[C@H]3CO[C@H](CO)[C@H](O)[C@@H]3O)nn2)NC(=O)CCCCCCCCCCC(=O)NCCN2C(=O)C=CC2=O)nn1)[C@H]1CO[C@H](CO)[C@H](O)[C@@H]1O] |

TABLE 19-continued
Multivalent ASGPR binding compounds including X groups of formula (Ie)
| # | Structure |
|---|---|
| 1913 | 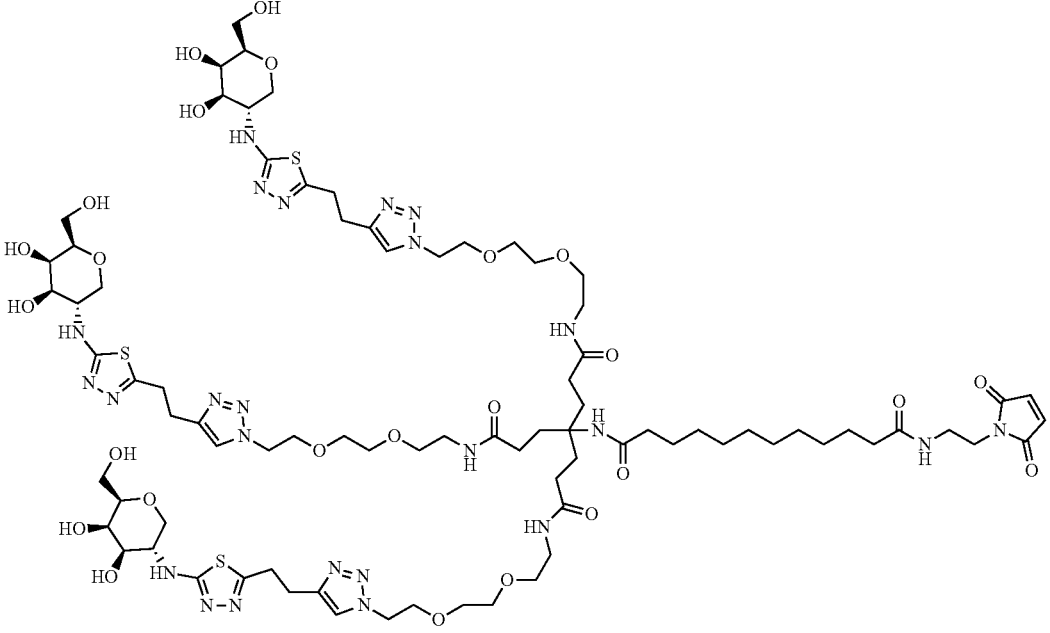 [SMILES: O=C(CCCCCCCCCCC(=O)NC(CCC(=O)NCCOCCOCCn1cc(CCc2nnc(N[C@H]3CO[C@H](CO)[C@H](O)[C@@H]3O)s2)nn1)(CCC(=O)NCCOCCOCCn1cc(CCc2nnc(N[C@H]3CO[C@H](CO)[C@H](O)[C@@H]3O)s2)nn1)CCC(=O)NCCOCCOCCn1cc(CCc2nnc(N[C@H]3CO[C@H](CO)[C@H](O)[C@@H]3O)s2)nn1)NCCN1C(=O)C=CC1=O] |
| 1914 | 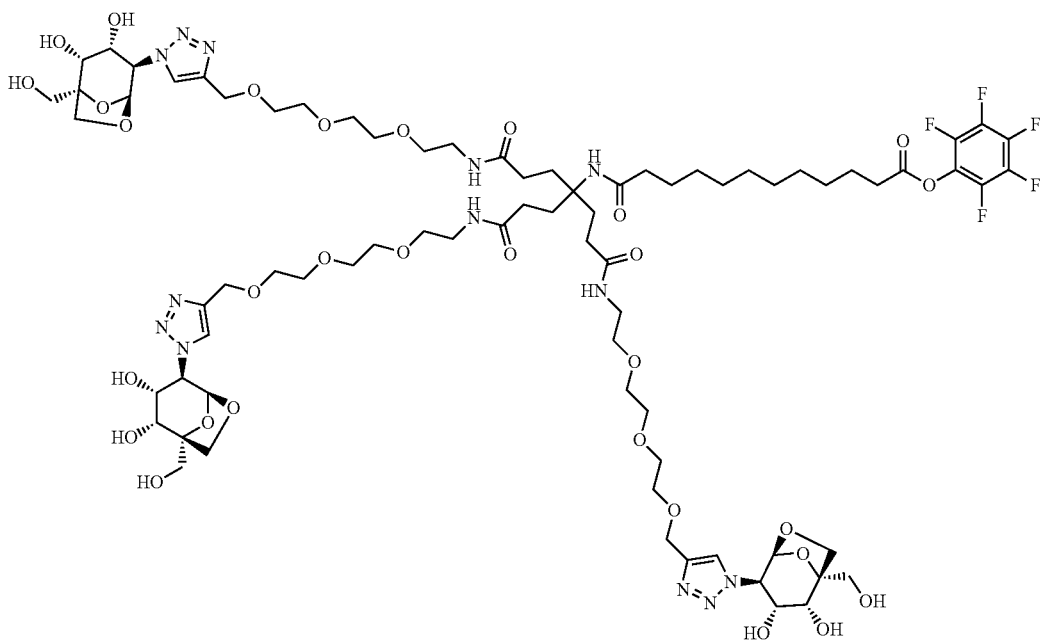 [SMILES: O=C(CCC(CCC(=O)NCCOCCOCCOCc1cn([C@H]2[C@H]3OC[C@](CO)(O3)[C@H](O)[C@@H]2O)nn1)(CCC(=O)NCCOCCOCCOCc1cn([C@H]2[C@H]3OC[C@](CO)(O3)[C@H](O)[C@@H]2O)nn1)NC(=O)CCCCCCCCCCC(=O)Oc1c(F)c(F)c(F)c(F)c1F)NCCOCCOCCOCc1cn([C@H]2[C@H]3OC[C@](CO)(O3)[C@H](O)[C@@H]2O)nn1] |

TABLE 19-continued

Multivalent ASGPR binding compounds including X groups of formula (Ie)

| # | Structure |
|---|---|
| 1915 | 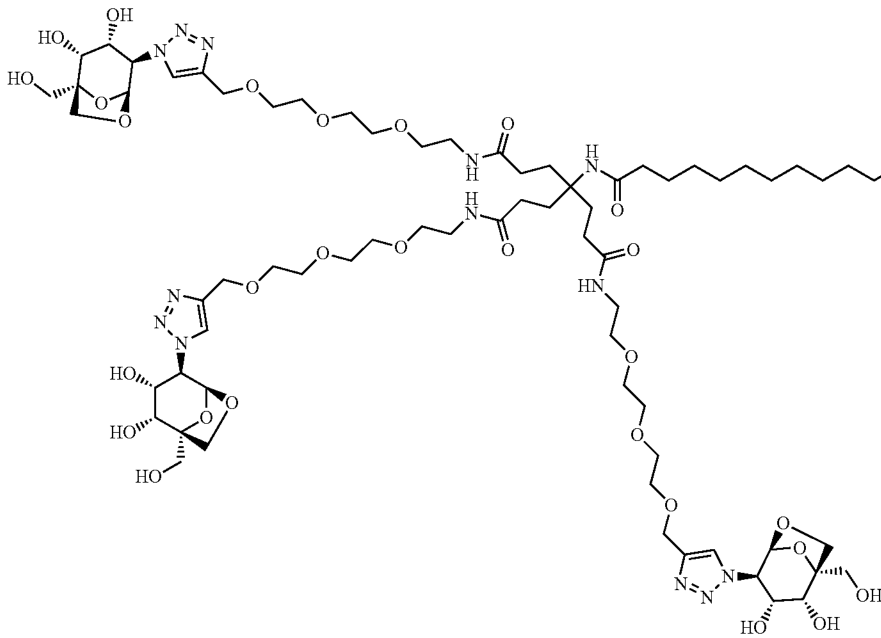 |
| 1916 | 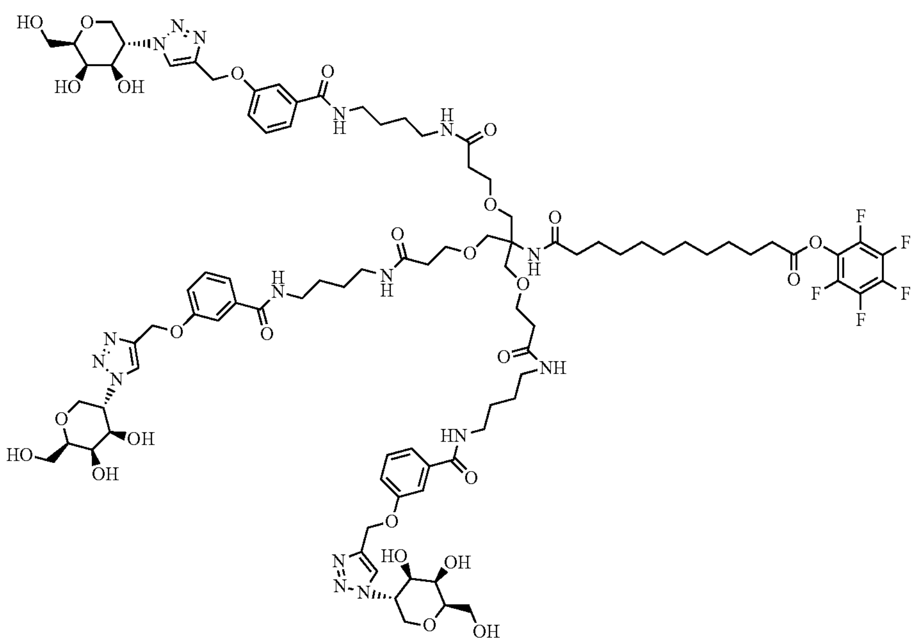 [SMILES: O=C(CCOCC(COCCC(=O)NCCCCNC(=O)c1cccc(OCc2cn([C@H]3CO[C@H](CO)[C@H](O)[C@@H]3O)nn2)c1)(COCCC(=O)NCCCCNC(=O)c1cccc(OCc2cn([C@H]3CO[C@H](CO)[C@H](O)[C@@H]3O)nn2)c1)NC(=O)CCCCCCCCCCC(=O)Oc1c(F)c(F)c(F)c(F)c1F)NCCCCNC(=O)c1cccc(OCc2cn([C@H]3CO[C@H](CO)[C@H](O)[C@@H]3O)nn2)c1] |

TABLE 19-continued

Multivalent ASGPR binding compounds including X groups of formula (Ie)

| # | Structure |
|---|---|
| 1917 | 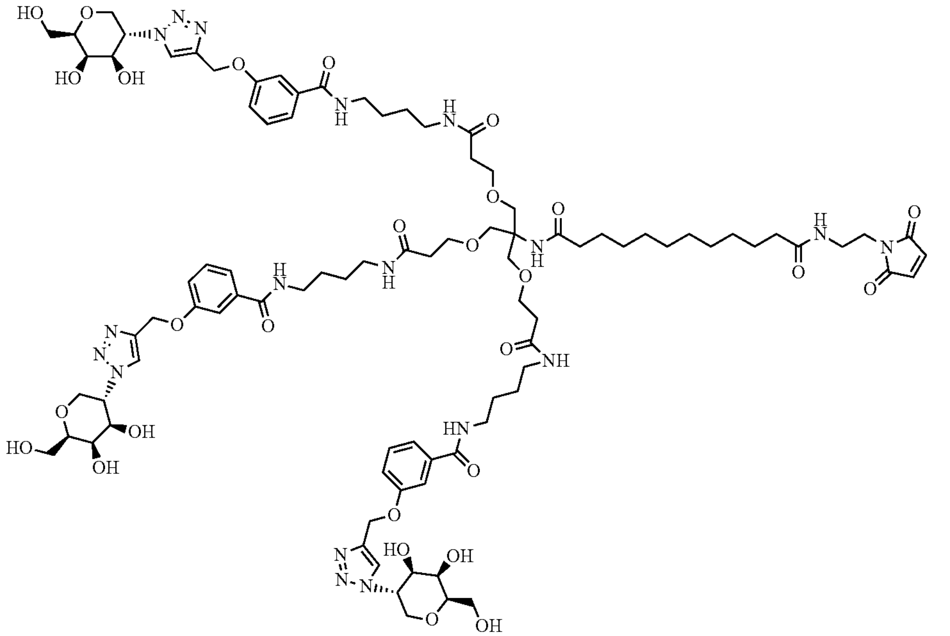 [SMILES: O=C(CCCCCCCCCCC(=O)NC(COCCC(=O)NCCCCNC(=O)c1cccc(OCc2cn([C@H]3CO[C@H](CO)[C@H](O)[C@@H]3O)nn2)c1)(COCCC(=O)NCCCCNC(=O)c1cccc(OCc2cn([C@H]3CO[C@H](CO)[C@H](O)[C@@H]3O)nn2)c1)COCCC(=O)NCCCCNC(=O)c1cccc(OCc2cn([C@H]3CO[C@H](CO)[C@H](O)[C@@H]3O)nn2)c1)NCCN1C(=O)C=CC1=O] |
| 1918 (I-165) | 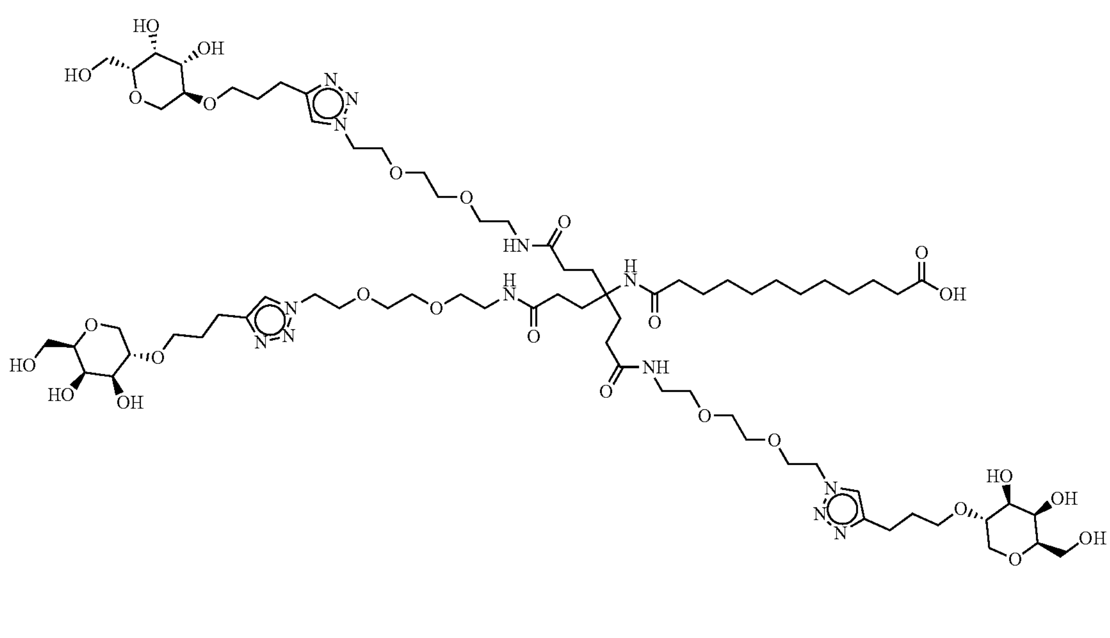 |

TABLE 19-continued
Multivalent ASGPR binding compounds including X groups of formula (Ie)
| # | Structure |
|---|---|
| 1919 (I-166) | 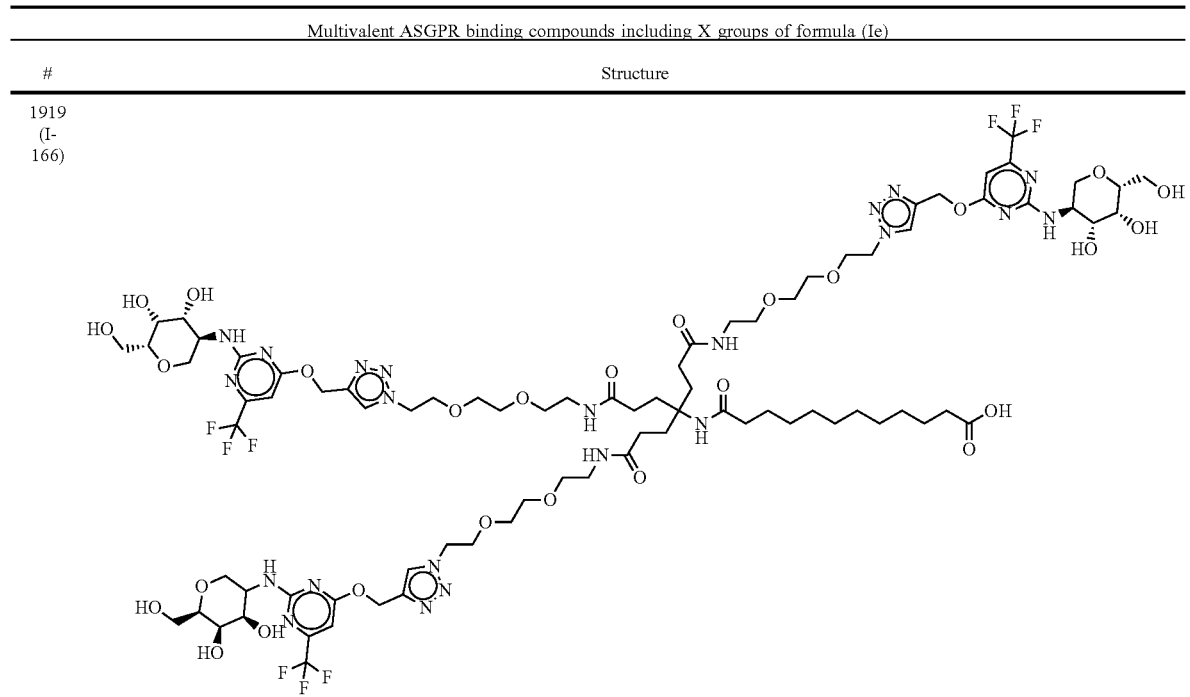 |
| 1920 (I-167) | 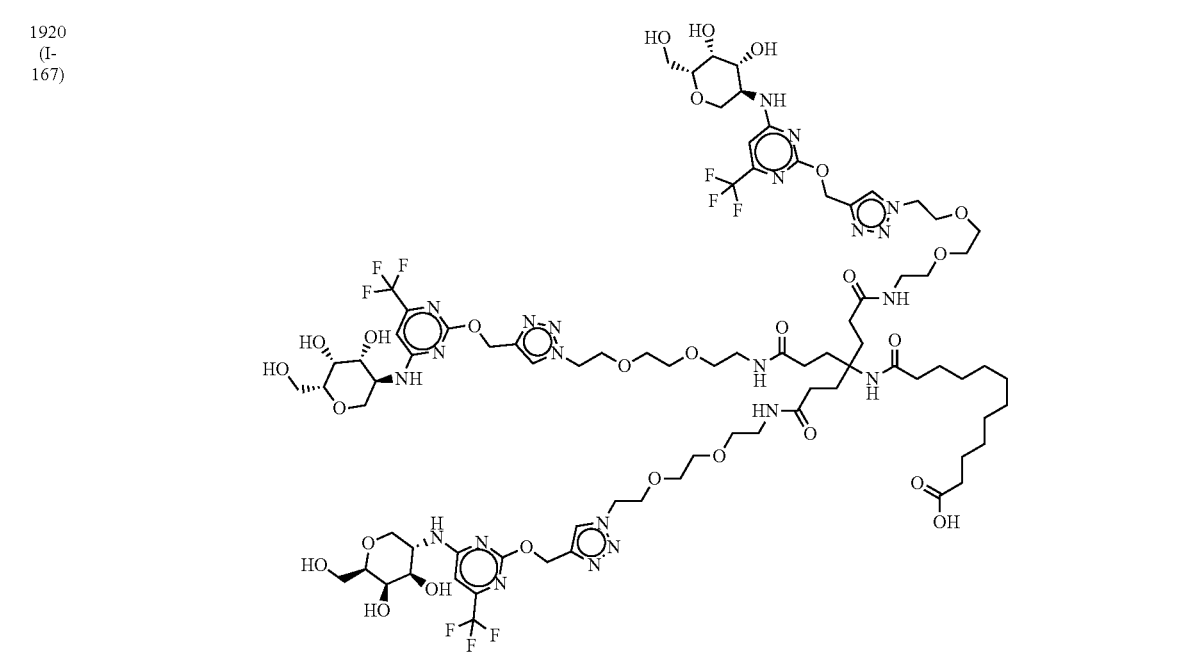 |
Table 20 illustrates exemplary monovalent ASGPR binding intermediate compounds of this disclosure that include a promoiety and X groups that are of formula (Ib).

TABLE 20

Multivalent ASGPR binding intermediate compounds of formula (Ib)

| # | Structure |
|---|---|
| 2001 (I-173) | 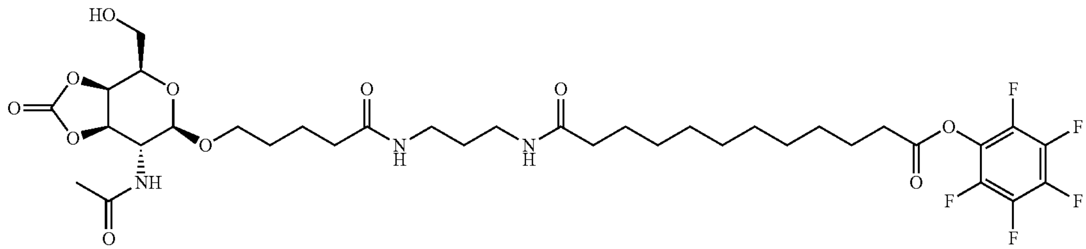 [SMILES: CC(=O)N[C@H]1[C@H](OCCCCC(=O)NCCCNC(=O)CCCCCCCCCCC(=O)Oc2c(F)c(F)c(F)c(F)c2F)O[C@H](CO)[C@@H]2OC(=O)O[C@H]12] |

Table 21 illustrates exemplary ASGPR binding intermediate compounds of this disclosure that include X groups that are of formula (In).

TABLE 21

ASGPR binding intermediate compounds including X groups of formula (In)

| # | Structure |
|---|---|
| 2101 | 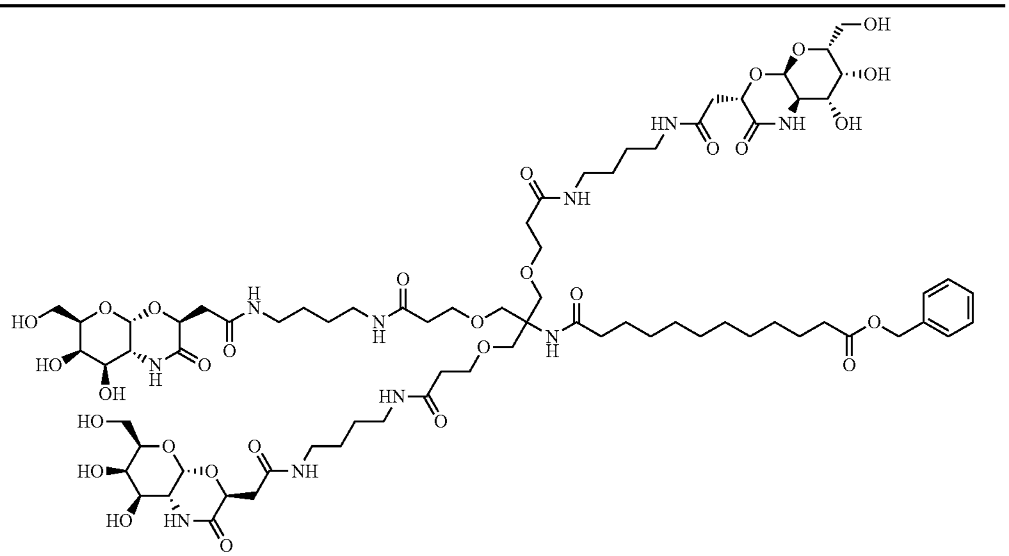 |

5.4. Conjugates with Moiety of Interest

The compounds of this disclosure can be referred to as a conjugate, e.g., when the moiety of interest (Y) is a molecule (e.g., as described herein). Such conjugates can be prepared by conjugation of a chemoselective ligation group of any one of the compounds described herein with a compatible reactive group of a molecule Y. The compatible group of the molecule Y can be introduced by modification prior to conjugation, or can be a group present in the molecule. Alternatively, such conjugates can be prepared de novo, e.g., via modification of a Y molecule of interest starting material to introduce a linker, e.g., to which a ligand X can be attached.

In some embodiments, the moiety of interest to which the ASGPR binding moiety is linked is a biomolecule. In some embodiments, the moiety of interest is a biomolecule. In some embodiments, the biomolecule is selected from peptide, protein, polynucleotide, polysaccharide, glycan, glyco- protein, lipid, enzyme, antibody, and antibody fragment. In some embodiments, the moiety of interest Y is selected from small molecule, small molecule drug, chemotherapeutic agent, cytotoxic agent, diagnostic agent, dye, fluorophore, and the like.

In preferred embodiments, the moiety of interest is a molecule that specifically binds to a target of interest, i.e., a target-binding moiety. In such cases, the conjugates of this disclosure can provide for cellular uptake of the target after it non-covalently binds to the conjugate, and/or degradation. The inventors have demonstrated that conjugates of this disclosure having a particular configuration of ASGPR binding moiety of a desired affinity, with a linker of desired valency and length can specifically bind with high affinity to both the ASGPR and the target simultaneously. The conjugates of this disclosure can thus provide for sequestering of a target protein in the cell's lysosome and degrading of the target protein.

In some embodiments, the moiety of interest is a molecule that does not bind to an extracellular target, but rather is a molecule that is itself desirable to deliver intracellularly. In some embodiments, the moiety of interest is selected from enzymes (e.g., lysosomal enzyme), a nanoparticle, a viral composition (e.g., viral particle), therapeutic protein, therapeutic antibodies and cytotoxic agents.

In some embodiments, the moiety of interest is a lysosomal enzyme for delivery to a cell for use in enzyme replacement therapy, such as acid alpha-glucosidase (GAA). Lysosomal enzymes of interest that may be adapted for use in conjugates of this disclosure include, but are not limited to, acid alpha-glucosidase, acid beta-galactosidase-1, acid sphingomyelinase, alpha-D-mannosidase, alpha-fucosidase, alpha-galactosidase A, alpha-glucosaminide acetyltransferase, alpha-glucosidase, alpha-L-iduronidase, alpha-N-acetylgalactosaminidase, alpha-acetylglucosaminidase, alpha-D-neuraminidase, arylsulfatase A, arylsulfatase B, beta-galactosidase, beta-glucuronidase, beta-mannosidase, cathepsin D, cathepsin K, ceramidase, cystinosine, ganglioside activator GM2, galactocerebrosidase, glucocerebrosidase, heparan sulfatase, hexosaminidase A, hexosaminidase B, hyaluronidase, iduronate-2-sulfatase, LAMP2, lysosomal acid lipase, N-acetylglucosamine-1-phosphotransferase, N-acetylgalactosamine 6-sulfatase, N-acetylglucosamine-1-phosphotransferase, N-acetylglucosamine-6-sulfate sulfatase, N-aspartyl-beta-glucosaminidase, palmitoyl-thioesterase-1, acid phosphatase, protected protein/cathepsin A (PPCA), sialin, tripeptidyl-peptidase 1.

Aspects of this disclosure include compounds of formula (I) where the moiety of interest Y is a selected from small molecule, dye, fluorophore, monosaccharide, disaccharide, trisaccharide, and biomolecule. In some embodiments, Y is a small molecule that specifically binds to a target molecule, such as a target protein.

In some embodiments of the compounds of this disclosure, Y is a biomolecule. In some embodiments, the biomolecule is selected from protein, polynucleotide, polysaccharide, peptide, glycoprotein, lipid, enzyme, antibody, and antibody fragment. In some embodiments, Y is a biomolecule that specifically binds to a target molecule, such as a target protein.

The compounds of this disclosure can, in some cases, be referred to as a conjugate, e.g., when the moiety of interest (Y) is a molecule such as a biomolecule, where the conjugate can be derived from a conjugation or coupling reaction between a chemoselective ligation group and a compatible group on the biomolecule. In some embodiments, the biomolecule is conjugated via a naturally occurring group of the biomolecule. In some embodiments, the biomolecule is conjugated via a compatible functional group that is introduced into the biomolecule prior to chemoselective conjugation. In such cases, the linking moiety between X and Y incorporates the residual group (e.g., Z) that is the product of the chemoselective ligation chemistry.

Aspects of this disclosure include compounds of formula (I) where the moiety of interest Y is a moiety that specifically binds to a target molecule, such as a target protein. The target protein can be the target protein is a membrane bound protein or an extracellular protein. In some embodiments of the compounds of this disclosure, Y is a biomolecule that specifically binds to a target protein. This disclosure provides conjugates of the particular ASGPR binding compounds and conjugates. In some embodiments, the conjugate includes a moiety of interest Y that specifically binds a target protein, and can find use in methods of cell uptake or internalization of the target protein via binding to the cell surface receptor, and eventual degradation of the target protein.

In some embodiments, Y is an aptamer that specifically binds to a target molecule, such as a target protein. In some embodiments, Y is a peptide or protein (e.g., peptidic binding motif, protein domain, engineered polypeptide, or glycoprotein) that specifically binds to a target molecule, such as a target protein. In some embodiments, Y is an antibody or antibody fragment that specifically binds to a target molecule, such as a target protein. In some embodiments, Y is a polynucleotide or oligonucleotide that specifically binds to a target molecule, such as a target protein or a target nucleic acid.

In some embodiments, one Y biomolecule is conjugated to a single moiety (X) that specifically binds to the cell surface receptor (e.g., ASGPR) via a linker L. In some embodiments, one Y biomolecule is conjugated to one (Xn-L)- group, wherein when n=1 the (Xn-L)- group is referred to as monovalent, and when n>1 the (Xn-L)- group is referred to as multivalent (e.g., bivalent, trivalent, etc.). It is understood that in some embodiments of formula (I), where Y is a biomolecule, Y can be conjugated to two or more (Xn-L)- groups, wherein each (Xn-L)- group may itself be monovalent or multivalent (e.g., bivalent, trivalent, etc.). In such cases, the ratio of linked (Xn-L)-groups to biomolecule can be referred to as 2 or more.

In some embodiments, Y is an antibody or antibody fragment that specifically binds the target protein and the compound is a conjugate of formula (III):

(III)

wherein:

n is 1 to 20;

m is an average loading of 1 to 80;

each X is a moiety that binds to a cell surface ASGPR;

each L is a linker;

each Z is a residual moiety resulting from the covalent linkage of a chemoselective ligation group to a compatible group of Ab; and Ab is the antibody or antibody fragment that specifically binds the target protein.

In certain embodiments of formula (III), each X is independently of formula (Ib) (e.g., as described herein). In certain cases, each X is independently selected from a compound of Table 1. In certain cases, each X is independently selected from one of the following compounds:

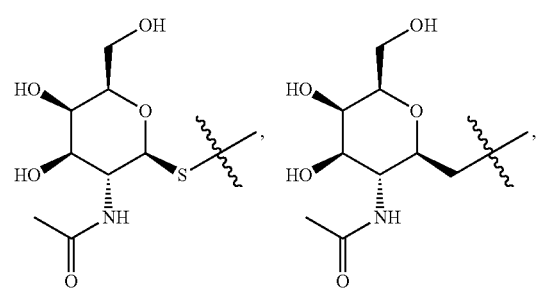

-continued

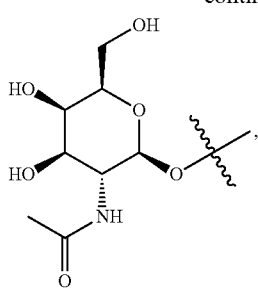

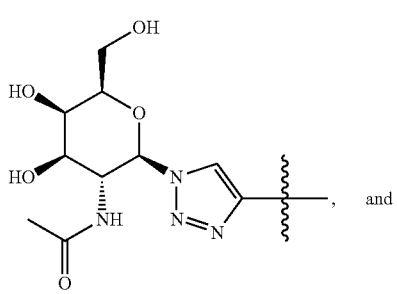, and

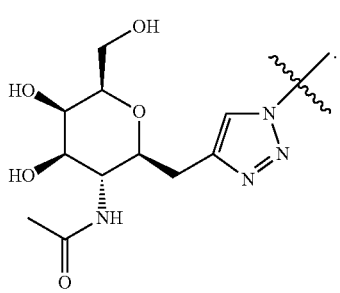

In certain embodiments of formula (III), each X is independently selected from one of the following compounds:

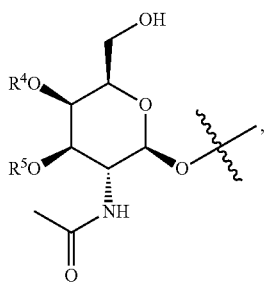,

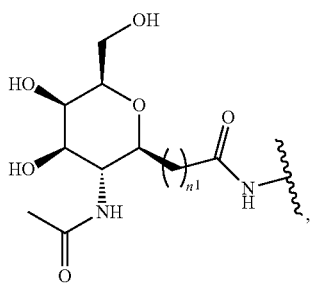,

-continued

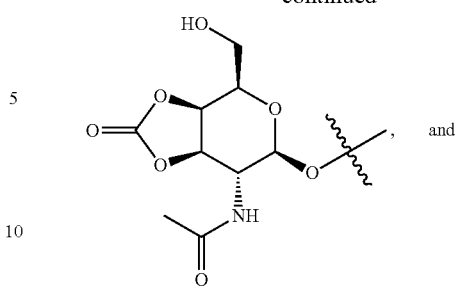, and

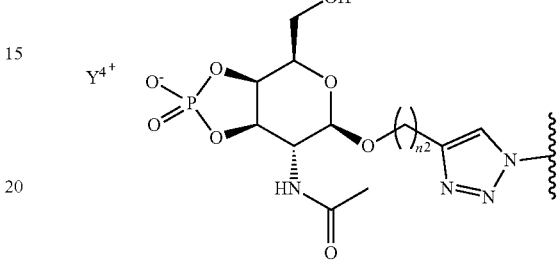

wherein $R^5$ and $R^4$ independently H or a promoiety, or $R^5$ and $R^4$ are cyclically linked to form a promoiety; n1 and n2 are each independently an integer from 1 to 6; and $Y^4$ is a suitable counterion. In some embodiments, $Y^4$ is sodium.

In certain embodiments of formula (III), n is 1 and X is:

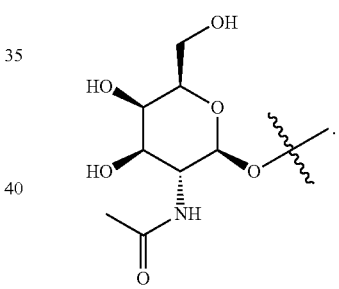.

In certain other embodiments of formula (III), each X is independently of the formula (Ic) (e.g., as described herein). In certain cases, each X is independently selected from a compound of Table 2.

In certain other embodiments of formula (III), each X is independently of formula (Id) (e.g., as described herein). In certain cases, each X is independently selected from a compound of Table 3. In certain cases, each X is independently selected from a compound of Table 4.

In certain embodiments of formula (III), each X is independently selected from one of the following compounds:

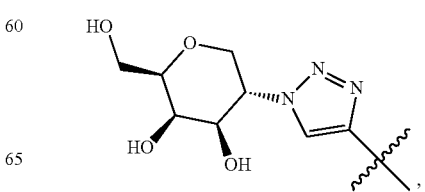,

-continued

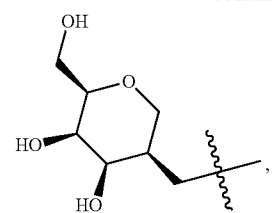

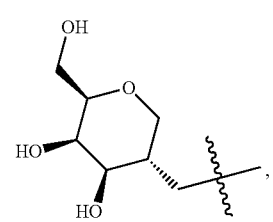

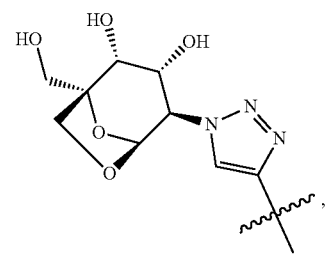

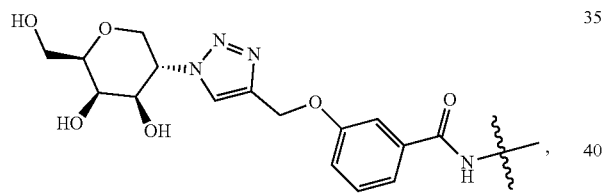

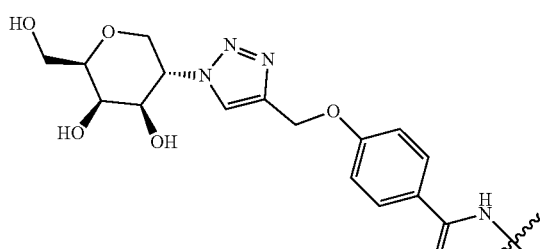

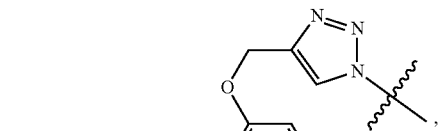

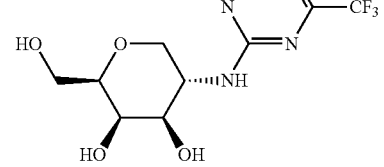

-continued

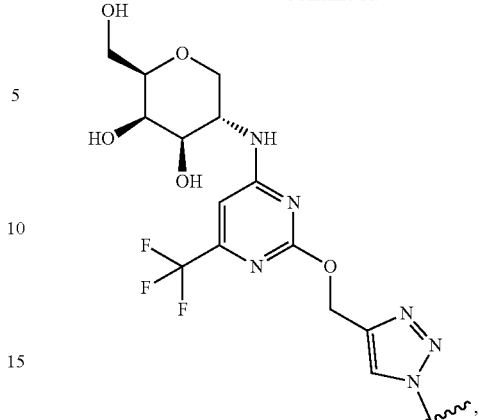

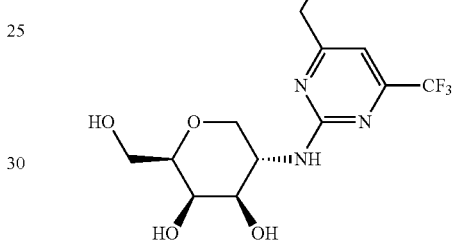

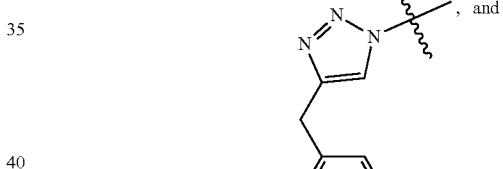, and

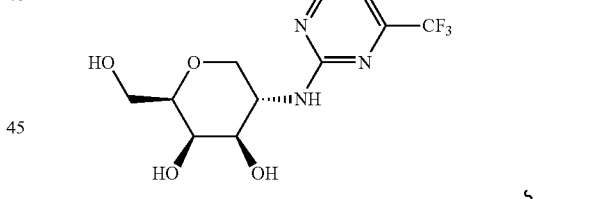

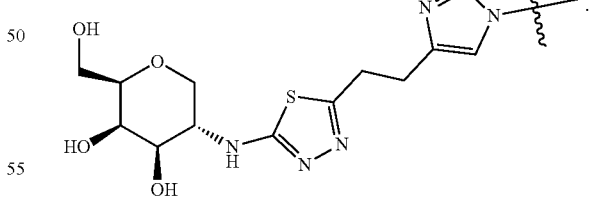

In certain embodiments of the conjugate of formula (III), L is a linker of formula (II) (e.g., as described herein).

In certain embodiments of the conjugate of formula (III), n is 1 to 6. In certain cases, n is 1, such that the antibody is conjugated to a monovalent ASGPR ligand and the linker is of the formula (IIa) (e.g., as described herein). In certain cases, n is at least 2, such that the antibody is conjugated to a multivalent ASGPR ligand. In certain cases, n is 2. In certain cases n is 3.

In certain embodiments of the conjugate of formula (III), Z is a residual moiety resulting from the covalent linkage of a chemoselective ligation moiety of Table 8.

In certain embodiments of the conjugate of formula (III), Z is a residual moiety resulting from the covalent linkage of a thiol reactive chemoselective ligation group to one or more cysteine residue(s) of Ab.

In certain other embodiments of the conjugate of formula (III), Z is a residual moiety resulting from the covalent linkage of an amine-reactive chemoselective ligation group to one or more lysine residue(s) of Ab.

In certain embodiments, the conjugates with their linker structures described herein have weaker binding affinity to cell surface receptors. Without being bound to any particular mechanism or theory, such weaker binding affinity may be corrected to longer half-life of the conjugates, and may be useful for tuning (e.g., modifying) the pharmacokinetic properties of the conjugates described herein. In certain embodiments, such weaker binding conjugates still have sufficiently robust uptake.

Conjugates of a polypeptide, e.g., an antibody (Ab) and compound (Xn-L-Y) may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present disclosure further contemplates that the conjugates described herein may be prepared using any suitable methods as disclosed in the art (see, e.g., Bioconjugate Techniques (Hermanson ed., 2d ed. 2008)).

In certain embodiments of the conjugates described herein, L is bonded through an amide bond to a lysine residue of the polypeptide. In certain embodiments of the conjugates described herein, L is bonded through a thioether bond to a cysteine residue of the polypeptide. In certain embodiments of the conjugates described herein, L is bonded through an amide bond to a lysine residue of Ab. In certain embodiments of the conjugates described herein, L is bonded through a thioether bond to a cysteine residue of Ab. In certain embodiments of the conjugates described herein, L is bonded through two thioether bonds to two cysteine residues of Ab, wherein the two cysteine residues are from an opened cysteine-cysteine disulfide bond in Ab. In certain embodiments, the opened cysteine-cysteine disulfide bond is an interchain disulfide bond.

In certain embodiments of the conjugates described herein, when L is bonded through an amide bond to a lysine residue of a polypeptide (e.g., an antibody), m is an integer from 1 to 80. In certain embodiments of the conjugates described herein, when L is bonded through a thioether bond to a cysteine residue of P, m is an integer from 1 to 8.

In certain embodiments, conjugation to the polypeptide, or the antibody Ab may be via site-specific conjugation. Site-specific conjugation may, for example, result in homogeneous loading and minimization of conjugate subpopulations with potentially altered antigen-binding or pharmacokinetics. In certain embodiments, for example, conjugation may comprise engineering of cysteine substitutions at positions on the polypeptide or antibody, e.g., on the heavy and/or light chains of an antibody that provide reactive thiol groups and do not disrupt polypeptide or antibody folding and assembly or alter polypeptide or antigen binding (see, e.g., Junutula et al., *J. Immunol. Meth.* 2008; 332: 41-52; and Junutula et al., *Nature Biotechnol.* 2008; 26: 925-32; see also WO2006/034488 (herein incorporated by reference in its entirety)). In another non-limiting approach, selenocysteine is cotranslationally inserted into a polypeptide or antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., Proc. Natl. Acad. Sci. USA 2008; 105: 12451-56; and Hofer et al., *Biochemistry* 2009; 48(50): 12047-57). Yet other non-limiting techniques that allow for site-specific conjugation to polypeptides or antibodies include engineering of non-natural amino acids, including, e.g., p-acetylphenylalanine (p-acetyl-Phe), p-azidomethyl-N-phenylalanine (p-azidomethyl-Phe), and azidolysine (azido-Lys) at specific linkage sites, and can further include engineering unique functional tags, including, e.g., LPXTG, LLQGA, sialic acid, and GlcNac, for enzyme mediated conjugation. See Jackson, *Org. Process Res. Dev.* 2016; 20: 852-866; and Tsuchikama and An, *Protein Cell* 2018; 9(1):33-46, the contents of each of which is incorporated by reference in its entirety. See also US 2019/0060481 A1 & US 2016/0060354 A1, the contents of each of which is incorporated by reference in its entirety. All such methodologies are contemplated for use in connection with making the conjugates described herein.

Loading of the compounds of formula (I) to the polypeptides (e.g., antibodies) described herein is represented by "m" in formula (III), and is the average number of units of "Xn-L-" or "Xn-" per conjugate molecule. As used herein, the term "DAR" refers to the average value of "m" or the loading of the conjugate. The number of "X" moieties (e.g., folate moieties) per each unit of "Xn-L-" or "Xn-" is represented by "n" in formula (III). As used herein, the term "valency" or "valencies" refers to the number of "X" moieties per unit ("n"). It will be understood that loading, or DAR, is not necessarily equivalent to the number of "X" moieties per conjugate molecule. By means of example, where there is one "X" moiety per unit (n=1; valency is "1"), and one "Xn-L-" unit per conjugate (m=1), there will be 1×1=1 "X" moiety per conjugate. However, where there are two "X" moieties per unit (n=2; valency is "2"), and four "Xn-L-" units per conjugate (m=4), there will be 2×4=8 "X" moieties per conjugate. Accordingly, for the conjugates described herein, the total number of "X" moieties per conjugate molecule will be n x m. As used herein, the term "total valency" or "total valencies" refers to the total number of "X" moieties per conjugate molecule (n x m; total valency).

DAR (loading) may range from 1 to 80 units per conjugate. The conjugates provided herein may include collections of polypeptides, antibodies or antigen binding fragments conjugated with a range of units, e.g., from 1 to 80. The average number of units per polypeptide or antibody in preparations of the conjugate from conjugation reactions may be characterized by conventional means such as mass spectroscopy. The quantitative distribution of DAR (loading) in terms of m may also be determined. In some instances, separation, purification, and characterization of homogeneous conjugate where m is a certain value may be achieved by means such as electrophoresis.

In certain embodiments, the DAR for a conjugate provided herein ranges from 1 to 80. In certain embodiments, the DAR for a conjugate provided herein ranges from 1 to 70. In certain embodiments, the DAR for a conjugate provided herein ranges from 1 to 60. In certain embodiments, the DAR for a conjugate provided herein ranges from 1 to 50. In certain embodiments, the DAR for a conjugate provided herein ranges from 1 to 40. In certain embodiments, the DAR for a conjugate provided herein ranges from 1 to 35. In certain embodiments, the DAR for a conjugate provided herein ranges from 1 to 30. In certain embodiments, the DAR for a conjugate provided herein ranges from 1 to 25. In certain embodiments, the DAR for a conjugate provided herein ranges from 1 to 20. In certain embodiments, the DAR for a conjugate provided herein ranges from 1 to 18. In certain embodiments, the DAR for a conjugate provided herein ranges from 1 to 15. In certain embodiments, the DAR for a conjugate provided herein ranges from 1 to 12. In certain embodiments, the DAR for a conjugate provided herein ranges from 1 to 10. In certain embodiments, the DAR for a conjugate provided herein ranges from 1 to 9. In certain embodiments, the DAR for a conjugate provided herein ranges from 1 to 8. In certain embodiments, the DAR for a conjugate provided herein ranges from 1 to 7. In certain embodiments, the DAR for a conjugate provided herein ranges from 1 to 6. In certain embodiments, the DAR for a conjugate provided herein ranges from 1 to 5. In certain embodiments, the DAR for a conjugate provided herein ranges from 1 to 4. In certain embodiments, the DAR for a conjugate provided herein ranges from 1 to 3. In certain embodiments, the DAR for a conjugate provided herein ranges from 2 to 12. In certain embodiments, the DAR for a conjugate provided herein ranges from 2 to 10. In certain embodiments, the DAR for a conjugate provided herein ranges from 2 to 9. In certain embodiments, the DAR for a conjugate provided herein ranges from 2 to 8. In certain embodiments, the DAR for a conjugate provided herein ranges from 2 to 7. In certain embodiments, the DAR for a conjugate provided herein ranges from 2 to 6. In certain embodiments, the DAR for a conjugate provided herein ranges from 2 to 5. In certain embodiments, the DAR for a conjugate provided herein ranges from 2 to 4. In certain embodiments, the DAR for a conjugate provided herein ranges from 3 to 12. In certain embodiments, the DAR for a conjugate provided herein ranges from 3 to 10. In certain embodiments, the DAR for a conjugate provided herein ranges from 3 to 9. In certain embodiments, the DAR for a conjugate provided herein ranges from 3 to 8. In certain embodiments, the DAR for a conjugate provided herein ranges from 3 to 7. In certain embodiments, the DAR for a conjugate provided herein ranges from 3 to 6. In certain embodiments, the DAR for a conjugate provided herein ranges from 3 to 5. In certain embodiments, the DAR for a conjugate provided herein ranges from 3 to 4.

In certain embodiments, the DAR for a conjugate provided herein ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7.

In certain embodiments, the DAR for a conjugate provided herein is about 1, about 2, about 3, about 4, about 5, about 6, about 7, about 8, about 9, about 10, about 11, about 12, or more. In some embodiments, the DAR for a conjugate provided herein is about 3.1, about 3.2, about 3.3, about 3.4, about 3.5, about 3.6, about 3.7, about 3.8, or about 3.9.

In some embodiments, the DAR for a conjugate provided herein ranges from 2 to 20, 2 to 19, 2 to 18, 2 to 17, 2 to 16, 2 to 15, 2 to 14, or 2 to 13. In some embodiments, the DAR for a conjugate provided herein ranges from 3 to 20, 3 to 19, 3 to 18, 3 to 17, 3 to 16, 3 to 15, 3 to 14, or 3 to 13. In some embodiments, the DAR for a conjugate provided herein is about 1. In some embodiments, the DAR for a conjugate provided herein is about 2. In some embodiments, the DAR for a conjugate provided herein is about 3. In some embodiments, the DAR for a conjugate provided herein is about 4. In some embodiments, the DAR for a conjugate provided herein is about 3.8. In some embodiments, the DAR for a conjugate provided herein is about 5. In some embodiments, the DAR for a conjugate provided herein is about 6. In some embodiments, the DAR for a conjugate provided herein is about 7. In some embodiments, the DAR for a conjugate provided herein is about 8. In some embodiments, the DAR for a conjugate provided herein is about 9. In some embodiments, the DAR for a conjugate provided herein is about 10. In some embodiments, the DAR for a conjugate provided herein is about 11. In some embodiments, the DAR for a conjugate provided herein is about 12. In some embodiments, the DAR for a conjugate provided herein is about 13. In some embodiments, the DAR for a conjugate provided herein is about 14. In some embodiments, the DAR for a conjugate provided herein is about 15. In some embodiments, the DAR for a conjugate provided herein is about 16. In some embodiments, the DAR for a conjugate provided herein is about 17. In some embodiments, the DAR for a conjugate provided herein is about 18. In some embodiments, the DAR for a conjugate provided herein is about 19. In some embodiments, the DAR for a conjugate provided herein is about 20.

In some embodiments, the DAR for a conjugate provided herein is about 25. In some embodiments, the DAR for a conjugate provided herein is about 30. In some embodiments, the DAR for a conjugate provided herein is about 35. In some embodiments, the DAR for a conjugate provided herein is about 40. In some embodiments, the DAR for a conjugate provided herein is about 50. In some embodiments, the DAR for a conjugate provided herein is about 60. In some embodiments, the DAR for a conjugate provided herein is about 70. In some embodiments, the DAR for a conjugate provided herein is about 80.

In certain embodiments, fewer than the theoretical maximum of units are conjugated to the polypeptide, e.g., antibody, during a conjugation reaction. A polypeptide may contain, for example, lysine residues that do not react with the compound or linker reagent. Generally, for example, antibodies do not contain many free and reactive cysteine thiol groups which may be linked to a drug unit; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine. In some embodiments, the compound is conjugated via a lysine residue on the antibody. In some embodiments, the linker unit or a drug unit is conjugated via a cysteine residue on the antibody.

In certain embodiments, the amino acid that attaches to a unit is in the heavy chain of an antibody. In certain embodiments, the amino acid that attaches to a unit is in the light chain of an antibody. In certain embodiments, the amino acid that attaches to a unit is in the hinge region of an antibody. In certain embodiments, the amino acid that attaches to a unit is in the Fc region of an antibody. In certain embodiments, the amino acid that attaches to a unit is in the constant region (e.g., CH1, CH2, or CH3 of a heavy chain, or CH1 of a light chain) of an antibody. In yet other embodiments, the amino acid that attaches to a unit or a drug unit is in the VH framework regions of an antibody. In yet other embodiments, the amino acid that attaches to unit is in the VL framework regions of an antibody.

The DAR (loading) of a conjugate may be controlled in different ways, e.g., by: (i) limiting the molar excess of compound or conjugation reagent relative to polypeptide, (ii) limiting the conjugation reaction time or temperature, (iii) partial or limiting reductive conditions for cysteine thiol modification, (iv) engineering by recombinant techniques the amino acid sequence of the polypeptide, such that the number and position of cysteine residues is modified for control of the number and/or position of linker-drug attachments (such as for thiomabs prepared as disclosed in WO2006/034488 (herein incorporated by reference in its entirety)).

It is to be understood that the preparation of the conjugates described herein may result in a mixture of conjugates with a distribution of one or more units attached to a polypeptide, for example, an antibody. Individual conjugate molecules may be identified in the mixture by mass spectroscopy and separated by HPLC, e.g. hydrophobic interaction chromatography, including such methods known in the art. In certain embodiments, a homogeneous conjugate with a single DAR (loading) value may be isolated from the conjugation mixture by electrophoresis or chromatography.

In certain embodiments of the conjugate of formula (III) m is 1 to 20, such as 2 to 10, 2 to 8, or 2 to 6. In certain cases, m is 10 or less. In certain cases, m is 2 to 8. In certain cases, m is 2 to 6. In certain cases, m is an average loading of about 4.

It is to be understood that the preparation of the conjugates described herein may result in a mixture of conjugates with a distribution of one or more units attached to a polypeptide, for example, an antibody. Individual conjugate molecules may be identified in the mixture by mass spectroscopy and separated by HPLC, e.g. hydrophobic interaction chromatography, including such methods known in the art. In certain embodiments, a homogeneous conjugate with a single DAR (loading) value may be isolated from the conjugation mixture by electrophoresis or chromatography.

5.4.1. Target-Binding Moieties

The target-binding moiety can be any moiety that has an affinity for the target of less than 1 μM, such as 300 nM or less, 100 nM or less, 30 nM or less, 10 nM or less, 3 nM or less, or 1 nM or less, e.g., as measured in an in vitro binding assay.

In some embodiments, the target-binding moiety is a biomolecule. In some embodiments, the target-binding moiety is a biomolecule that specifically binds to a target protein. In some embodiments, the biomolecule is selected from peptide, protein, polynucleotide, polysaccharide, glycan, glycoprotein, lipid, enzyme, antibody, and antibody fragment.

In some embodiments, the target-binding moiety is a polypeptide (e.g., peptide or protein binding motif, protein domain, engineered polypeptide, or glycoprotein) that specifically binds to a target molecule, such as a target protein. In some embodiments, the target-binding moiety of the bifunctional compound includes a polypeptide that binds to a soluble (e.g., secreted) target protein of interest. In some embodiments, the target-binding is a polypeptide ligand that includes a receptor ligand, or a receptor-binding portion or fragment of the receptor ligand, that binds a target cell surface receptor. Target-binding polypeptides may contain L-amino acids, D-amino acids, or both and may contain any of a variety of naturally occurring amino acids, non-naturally occurring amino acids, and/or amino acid modifications or analogs known in the art. Useful modifications include, e.g., N-terminal acetylation, amidation, methylation, etc.

In some embodiments, the target-binding moiety is a polynucleotide that specifically binds to a target molecule, such as a target protein or a target nucleic acid. The terms polynucleotide and nucleic acid can be used interchangeably. In some embodiments, the target-binding moiety is a nucleic acid aptamer that specifically binds to a target molecule, such as a target protein.

In some embodiments, the target-binding moiety is a glycan. In some embodiments, the target-binding moiety is a glycan epitope for an autoantibody.

5.4.1.1 Antibodies

In some embodiments, the target-binding moiety is an antibody or antibody fragment that specifically binds to a target moiety, such as a target protein.

The ASGPR binding moiety can be site-specifically covalently linked to the antibody or antibody fragment, via an optional linking moiety. ASGPR binding moiety can be covalently linked to the antibody or antibody fragment via a site-specific cysteine modification on the antibody or antibody fragment (e.g., L443C) and a thiol-reactive chemoselective ligation group. ASGPR binding moiety can be covalently linked to the antibody or antibody fragment via one or more lysine residues of the antibody or antibody fragment and an amine-reactive chemoselective ligation group.

In some embodiments, the bifunctional conjugate of this disclosure includes an antibody (Ab). In some embodiments, Ab is a monoclonal antibody. In some embodiments, Ab is a human antibody. In some embodiments, Ab is a humanized antibody. In some embodiments, Ab is a chimeric antibody. In some embodiments, Ab is a full-length antibody that includes two heavy chains and two light chains. In some embodiments, Ab is an IgG antibody, e.g., is an IgG1, IgG2, IgG3 or IgG4 antibody. In some embodiments, Ab is a single chain antibody. In some embodiments, the target-binding moiety is an antigen-binding fragment of an antibody, e.g., a Fab fragment.

In some embodiments, the antibody or antibody fragment specifically binds to a cancer antigen.

In some embodiments, the antibody or antibody fragment specifically binds to a hepatocyte antigen.

In some embodiments, the antibody or antibody fragment specifically binds to an antigen presented on a macrophage.

In some embodiments, the antibody or antibody fragment specifically binds to an intact complement or a fragment thereof. In some embodiments, the antibody or antibody fragment specifically binds to one or more immunodominant epitope(s) within intact complement or a fragment thereof.

In some embodiments, the antibody or antibody fragment specifically binds to a cell surface receptor. In some embodiments, the antibody or antibody fragment specifically binds to a cell surface receptor ligand.

In some embodiments, the antibody or antibody fragment specifically binds to an epidermal growth factor (EGF) protein, e.g., a human EGF. In some embodiments, the antibody or antibody fragment specifically binds to one or more immunodominant epitope(s) within an EGF protein.

In some embodiments, the antibody or antibody fragment specifically binds to an epidermal growth factor receptor (EGFR) protein, e.g., a human EGFR. In some embodiments, the antibody or antibody fragment specifically binds to one or more immunodominant epitope(s) within an EGFR protein. In some embodiments, the antibody or antibody fragment comprises the CDRs present in cetuximab. In some embodiments, the antibody or antibody fragment includes the variable light chain and variable heavy chain present in cetuximab. In some embodiments, the antibody is cetuximab. In some embodiments, the antibody or antibody fragment includes the CDRs present in matuzumab. In some embodiments, the antibody or antibody fragment includes the variable light chain and variable heavy chain present in matuzumab. In some embodiments, the antibody is matuzumab.

In some embodiments, the antibody or antibody fragment specifically binds to vascular endothelial growth factor (VEGF) protein, e.g., human VEGF protein. In some embodiments, the antibody or antibody fragment specifically binds to one or more immunodominant epitope(s) within a VEGF protein.

In some embodiments, the antibody or antibody fragment specifically binds to a vascular endothelial growth factor receptor (VEGFR) protein, e.g., human VEGFR protein. In some embodiments, the antibody or antibody fragment specifically binds vascular endothelial growth factor receptor 2 (VEGFR2) protein, e.g., a human VEGFR2 protein. In some embodiments, the antibody or antibody fragment specifically binds a vascular endothelial growth factor receptor 3 (VEGFR3) protein, e.g., a human VEGFR3 protein. In some embodiments, the antibody or antibody fragment specifically binds to one or more immunodominant epitope(s) within a VEGFR protein, a VEGFR2 protein or a VEGFR3 protein.

In some embodiments, the antibody or antibody fragment specifically binds to a fibroblast growth factor (FGF), e.g., a human FGF. In some embodiments, the antibody or antibody fragment specifically binds to one or more immunodominant epitope(s) within a FGF protein.

In some embodiments, the antibody or antibody fragment specifically binds to a fibroblast growth factor receptor (FGFR), e.g., a human FGFR. In some embodiments, the antibody or antibody fragment specifically binds fibroblast growth factor receptor 2 (FGFR2) protein, e.g., a human FGFR2 protein, for example, a FGFR2b protein. In some embodiments, the antibody or antibody fragment specifically binds a fibroblast growth factor receptor 3 (FGFR3) protein, e.g., a human FGFR3 protein. In some embodiments, the antibody or antibody fragment specifically binds to one or more immunodominant epitope(s) within a FGFR protein, a FGFR2 protein or a FGFR3 protein.

In some embodiments, the antibody specifically binds to a receptor tyrosine kinase cMET protein. In some embodiments, the antibody specifically binds to one or more immunodominant epitope(s) within a receptor tyrosine kinase cMET protein.

In some embodiments, the antibody specifically binds to a CD47 protein, e.g., a human CD47 protein. In some embodiments, the antibody specifically binds to one or more immunodominant epitope(s) within a CD47 protein.

In some embodiments, the antibody specifically binds to an immune checkpoint inhibitor. In some embodiments, the antibody binds to one or more immunodominant epitope(s) within an immune checkpoint inhibitor. In some embodiments, the antibody specifically binds to a programmed death protein, e.g., a human PD-1. In some embodiments, the antibody specifically binds to one or more immunodominant epitope(s) within PD-1 protein.

In some embodiments, the antibody specifically binds to a programmed death ligand-1 (PD-L$^1$) protein, e.g., a human PD-L$^1$. In some embodiments, the antibody specifically binds to one or more immunodominant epitope(s) within PD-L$^1$ protein.

In some embodiments, the antibody binds to TIM3. In some embodiments, the antibody binds to one or more immunodominant epitope(s) within TIM3.

In some embodiments, the antibody specifically binds to a lectin. In some embodiments, the antibody specifically binds to one or more immunodominant epitope(s) within a lectin. In some embodiments, the antibody binds to SIGLEC. In some embodiments, the antibody binds to one or more immunodominant epitope(s) within SIGLEC. In some embodiments, the antibody binds to a cytokine receptor. In some embodiments, the antibody binds to a one or more immunodominant epitope(s) within cytokine receptor. In some embodiments, the antibody binds to sIL6R. In some embodiments, the antibody binds to one or more immunodominant epitope(s) within sIL6R. In some embodiments, the antibody binds to a cytokine. In some embodiments, the antibody binds to one or more immunodominant epitope(s) within a cytokine. In some embodiments, the antibody binds to MCP-1, TNF (e.g., a TNF-alpha), IL1a, IL1b, IL4, IL5, IL6, IL12/IL23, IL13, IL17 or p40. In some embodiments, the antibody binds to one or more immunodominant epitope(s) within MCP-1, TNF (e.g., a TNF-alpha), IL1a, IL1b, IL4, IL5, IL6, IL12/IL23, IL13, IL17 or p40.

In some embodiments, the antibody binds to a major histocompatibility protein (e.g., a MHC class I or class II molecule). In some embodiments, the antibody binds to one or more immunodominant epitope(s) within a major histocompatibility protein (e.g., a MHC class I or class II molecule). In some embodiments, the antibody binds to beta 2 microglobulin. In some embodiments, the antibody binds to one or more immunodominant epitope(s) within beta 2 microglobulin.

5.4.1.2 Modified Viral Compositions

In specific embodiments, Y is a viral particle, viral capsid, a viral envelope or a viral protein. In some embodiments, the viral composition is a viral particle that comprises a transgene. In some embodiments, the viral protein is a viral capsid protein or a viral envelope protein.

In certain aspects, provided herein are modified viral compositions comprising a viral composition, for example, a virus particle, a virus capsid or a viral protein (e.g., a viral capsid protein or an envelope protein) attached to (e.g., conjugated to, directly or indirectly, for example via an intervening linker sequence) an ASGPR binding moiety that binds to a cell surface receptor. In certain embodiments, a modified viral composition comprises a virus particle that comprises a polynucleotide that optionally comprises a transgene, e.g., a transgene useful for therapeutic applications.

The modified viral compositions, e.g., viral conjugates, presented herein may comprise any viral composition described herein e.g., any virus particle, capsid or viral protein, for example capsid protein or envelope protein, or fragment thereof, as described herein.

In certain aspects, a viral composition described herein may comprise a virus particle. The terms "virus particle," "viral particle," "virus vector" or "viral vector" are used interchangeably herein. A "virus particle" refers to a virus capsid and a polynucleotide (DNA or RNA), which may comprise a viral genome, a portion of a viral genome, or a polynucleotide derived from a viral genome (e.g., one or more ITRs), which polynucleotide optionally comprises a transgene. In certain instances, a virus particle further comprises an envelope (which generally comprises lipid moieties and envelope proteins), surrounding or partially surrounding the capsid.

A viral particle may be referred to as a "recombinant viral particle," or "recombinant virus particle," which terms as used herein refer to a virus particle that has been genetically altered, e.g., by the deletion or other mutation of an endogenous viral gene and/or the addition or insertion of a heterologous nucleic acid construct into the polynucleotide of the virus particle. Thus, a recombinant virus particle generally refers to a virus particle comprising a capsid coat or shell (and an optional outer envelope) within which is packaged a polynucleotide sequence that comprises sequences of viral origin and sequences not of viral origin (i.e., a polynucleotide heterologous to the virus). This polynucleotide sequence is typically a sequence of interest for the genetic alteration of a cell.

In certain aspects, a viral composition described herein may comprise an "viral capsid," "empty viral particle," "empty virus particle," or "capsid," or "empty particle" when referred to herein in the context of the virus, which terms as used herein refer to a three-dimensional shell or coat comprising a viral capsid protein, optionally surrounded or partially surrounded by an outer envelope. In particular embodiments, the viral composition is a virus particle or a fragment thereof, virus capsid or fragment thereof, a viral protein, for example, a virus capsid protein or fragment thereof or envelope protein, or fragment thereof.

In some embodiments, the virus used in a modified viral composition provided herein is adenovirus (AV); adeno-associated virus (AAV); retroviruses (e.g., lentiviruses (LV), rhabdoviruses, murine leukemia virus); herpes simplex virus, coronavirus, reovirus, and the like. In some embodiments, the viral vector, viral particle or viral protein used in the present disclosure is derived from a non-enveloped virus, e.g., an adeno-associated virus (AAV).

In some embodiments, lentiviral vectors can be used for CAR-T gene delivery, vaccines, or research tools, e.g., to introduce genes into mature T cells to generate immunity to cancer through the delivery of chimeric antigen receptors (CARs) or cloned T-cell receptors.

Naturally occurring AAV forms a virus particle that comprises a three-dimensional capsid coat or shell (a "capsid") made up of capsid proteins (VP1, VP2 and VP3) and, contained within the capsid, an AAV viral genome.

The modified AAV compositions, e.g., AAV conjugates or fusions, presented herein may comprise any AAV composition described herein, e.g., any AAV particle, capsid or capsid protein, or fragment thereof, as described herein. The term "AAV capsid protein" or "AAV cap protein" refers to a protein encoded by an AAV capsid (cap) gene (e.g., VP1, VP2, and VP3) or a variant or fragment thereof. The term includes a capsid protein expressed by or derived from an AAV, e.g., a recombinant AAV, such as a chimeric AAV. For example, the term includes but not limited to a capsid protein derived from any AAV serotype such as AAV1, AAV2, AAV2i8, AAV3, AAV4, AAV5, AAV6, AAV7, AAV8, AAV9, AAV10, AAV rh10, AAV11, AAV12, AAV13, AAV-DJ, AAV3b, AAV LK03, AAV rh74, AAV Anc81, Anc82, Anc83, Anc84, Anc110, Anc113, Anc126, or Anc127, AAV_go.1, AAV hu.37, or AAV rh.8 or a variant thereof.

5.4.1.3 Bridging Moieties that Bind Virus Composition

In some embodiments, Y is a bridging moiety that specifically binds to a viral composition, for example, a viral particle, viral capsid, viral envelope or viral protein (e.g., a viral capsid protein or envelope protein), wherein the binding is not via a covalent linkage.

Any suitable moiety that binds a viral particle, viral capsid, viral envelope or viral protein (e.g., a viral capsid protein or envelope protein) can be adapted for use in the conjugates of this disclosure.

In certain embodiments, a bridging moiety is a polypeptide that specifically binds a viral composition. In some embodiments, the bridging moiety is a polypeptide that binds to a viral composition, e.g., a virus particle, virus capsid, virus envelope, or a viral protein, for example, a viral capsid protein or viral envelope protein. In certain aspects, the bridging composition binds the viral capsid protein or a viral envelope protein, when the viral protein is part of a virus particle.

In certain embodiments, a bridging moiety is an antibody or antibody fragment (e.g., an antigen binding fragment of an antibody) that specifically binds a viral composition. In certain embodiments, a bridging moiety that binds a viral protein may also bind a viral particle, for example, via binding to the viral protein incorporated in a viral particle. Likewise, in certain embodiments, a bridging moiety that binds a viral particle may also bind a viral protein even if the viral protein is not incorporated in a viral particle. The viral particle can be an AAV virus particle. The viral protein can be a AAV capsid protein.

In some embodiments, the bridging moieties of this disclosure specifically bind to an AAV composition, e.g., an AAV particle, AAV capsid, or AAV viral protein (e.g., an AAV capsid protein, for example, a VP1, VP2 or VP3 protein).

An antibody or antigen binding fragment that may be utilized in connection with the modified viral compositions provided herein, e.g., in connection with the bridging compositions and bridging moieties presented herein, includes, without limitation, monoclonal antibodies, antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof (e.g., domain antibodies).

5.4.1.4 Small Molecules

In some embodiments, the target-binding moiety of the bifunctional compound of this disclosure is a small molecule that specifically binds to a target molecule, such as a target protein. In some embodiments, the bifunctional compound includes a small molecule inhibitor or ligand of a target protein. A small molecule target-binding moiety can be covalently linked to one or more ASGPR binding moieties via a linker. The linker can be covalently attached to the small molecule via substitution at any suitable site of the small molecule such that binding to the target protein is substantially retained.

In some embodiments, the target-binding moiety is a small molecule inhibitor or antagonist of a target protein (e.g., as described herein). Any convenient small molecules known to bind a target of interest can be adapted for use in the subject compounds and conjugates.

In some embodiments, the target-binding moiety is a small molecule inhibitor or antagonist of VEGF.

In some embodiments, the target-binding moiety is a small molecule inhibitor or antagonist of PD-L$^1$.

In some embodiments, the target-binding moiety is a small molecule inhibitor or antagonist of EGFR protein, a VEGFR protein, a FGFR2 protein or a FGFR3 protein.

In some embodiments, the target-binding moiety is a small molecule inhibitor or antagonist of TNF protein (e.g., TNF-alpha). TNF-alpha (TNFα) is a soluble cytokine produced by monocytes and macrophages as part of immune and inflammatory processes and is involved in a diverse range of cellular responses including differentiation, proliferation, inflammation, and cell death. TNFα is a type II transmembrane protein that can be cleaved and secreted as a soluble form. Both the transmembrane and soluble biologically active forms of TNFα are homotrimeric complexes that can signal through TNF receptors 1 and 2 (TNF-R1 and TNF-R2). TNFα is directly involved in systemic inflammation through the regulation of the intracellular NF-κB, JNK and p38-MAPK signaling pathways.

The TNFα binding moiety can be a TNFα inhibitor, such as a competitive inhibitor of TNF receptor binding or an allosteric inhibitor of TNF signaling. The compounds of this disclosure can include a potent TNFα inhibitor, e.g., an inhibitor having sub-micromolar inhibitory activity. In some embodiments, the TNFα inhibitor is an allosteric inhibitor. In some embodiments, the TNFα binding moiety is an allosteric desymmetrization TNFα inhibitor. An allosteric desymmetrization TNFα inhibitor refers to a compound that binds to an allosteric site within TNFα and stabilizes the trimeric unit in a nonsymmetrical conformation that allows the TNFα trimer to recruit only two out of the three copies of TNF Receptor (TNFR, e.g., TNFR1), leading to an incompetent TNFα-TNFR signaling complex.

See e.g., Xiao et al. in Journal of Medicinal Chemistry 2020 63 (23), 15050-15071, and McMillan et al. in Nature Communications (2021) 12:582, which discloses an analysis of the X-ray co-crystal structure of exemplary inhibitors bound to TNFα. An allosteric desymmetrization TNFα inhibitor can act via a particular mechanism of action to provide potent inhibitory activity. For example, (a) the TNFα inhibitor binding site is a cavity within the TNFα trimer created via movement of monomer A, (b) the inhibitor stabilizes the TNFα trimer in an inactive conformation by forming key π-π and hydrogen bonding interactions, (c) an allosteric desymmetrization TNFα inhibitor binds to TNFα trimer leading to major disruption of one TNFR binding site and minor disruption of a second site, while the third site remains unchanged, and (d) the allosteric desymmetrization TNFα inhibitor modulates TNF-R activity through an allosteric mechanism rather than direct competition with TNFR. Thus, the binding of an allosteric desymmetrization TNFα inhibitor to the symmetric TNFα trimer can lead to the formation of an asymmetric trimer which prevents the recruitment of three TNF receptor molecules that are necessary for signaling.

5.4.2. Targets

As summarized above, the bifunctional compounds of this disclosure can include a moiety of interest (Y) that specifically binds a target molecule. The target molecule can be a cell surface molecule or an extracellular molecule.

In some embodiments of the compounds and methods of this disclosure, the target molecule is a cell surface molecule. By "cell surface molecule" is meant a target molecule associated with a cell membrane, e.g., because the molecule has a domain that inserts into or spans a cell membrane, e.g., a cell membrane-tethering domain or a transmembrane domain. The cell surface molecule may be any cell surface molecule which is desired for targeted degradation via the endosomal/lysosomal pathway. In some embodiments, the cell surface molecule is a cell surface receptor.

Cell surface receptors of interest include, but are not limited to, stem cell receptors, immune cell receptors, growth factor receptors, cytokine receptors, hormone receptors, receptor tyrosine kinases, a receptor in the epidermal growth factor receptor (EGFR) family (e.g., HER2 (human epidermal growth factor receptor 2), etc.), a receptor in the fibroblast growth factor receptor (FGFR) family, a receptor in the vascular endothelial growth factor receptor (VEGFR) family, a receptor in the platelet derived growth factor receptor (PDGFR) family, a receptor in the rearranged during transfection (RET) receptor family, a receptor in the Eph receptor family, a receptor in the discoidin domain receptor (DDR) family, and a mucin protein (e.g., MUC1). In some embodiments, the cell surface molecule is CD71 (transferrin receptor). In certain aspects, the cell surface receptor is an immune cell receptor selected from a T cell receptor, a B cell receptor, a natural killer (NK) cell receptor, a macrophage receptor, a monocyte receptor, a neutrophil receptor, a dendritic cell receptor, a mast cell receptor, a basophil receptor, and an eosinophil receptor.

In some embodiments, the moiety of interest (Y) specifically binds a cell surface molecule which mediates its effect not through a specific molecular interaction (and therefore is not susceptible to blocking), but rather through bulk biophysical or aggregate effects. A non-limiting example of such a cell surface molecule is a mucin. Examples of mucins include, but are not limited to, MUC1, MUC16, MUC2, MUC5AC, MUC4, CD43, CD45, GPIb, and the like.

In some embodiments, when the moiety of interest specifically binds a cell surface molecule, the cell surface molecule is present on a cancer cell. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a hematological malignancy (e.g., a leukemia cell, a lymphoma cell, a myeloma cell, etc.), a primary tumor, a metastatic tumor, and the like. In some embodiments, the cell surface molecule present on the cancer cell is a tumor-associated antigen or a tumor-specific antigen. In certain aspects, when the moiety of interest (Y) specifically binds a cell surface molecule, the cell surface molecule is present on an immune cell. In some embodiments, the cell surface molecule is present on an immune cell selected from a T cell, a B cell, a natural killer (NK) cell, a macrophage, a monocyte, a neutrophil, a dendritic cell, a mast cell, a basophil, and an eosinophil. In certain aspects, the cell surface molecule present on the immune cell is an inhibitory immune receptor. As used herein, an "inhibitory immune receptor" is a receptor present on an immune cell that negatively regulates an immune response. Examples of inhibitory immune receptors which may be inhibited according to the methods of the present disclosure include inhibitory immune receptors of the Ig superfamily, including but not limited to: CD200R, CD300a (IRp60; mouse MAIR-I), CD300f (IREM-1), CEACAM1 (CD66a), FcγRIIb, ILT-2 (LIR-1; LILRB1; CD85j), ILT-3 (LIR-5; CD85k; LILRB4), ILT-4 (LIR-2; LILRB2), ILT-5 (LIR-3; LILRB3; mouse PIR—B); LAIR-1, PECAM-1 (CD31), PILR-a (FDF03), SIRL-1, and SIRP-a. Further examples of inhibitory immune receptors which may be inhibited according to the methods of the present disclosure include sialic acid-binding Ig-like lectin (Siglec) receptors, e.g., Siglec 7, Siglec 9, and/or the like. Additional examples of inhibitory immune receptors which may be inhibited according to the methods of the present disclosure include C-type lectins, including but not limited to: CLEC4A (DCIR), Ly49Q and MICL. Details regarding inhibitory immune receptors may be found, e.g., in Steevels et al. (2011) Eur. J. Immunol. 41 (3):575-587. In some embodiments, the cell surface molecule present on the immune cell is a ligand of an inhibitory immune receptor. In certain aspects, the cell surface molecule present on the immune cell is an immune checkpoint molecule. Non-limiting examples of immune checkpoint molecules to which the moiety of interest (Y) may specifically bind include PD-1, PD-L1, CTLA4, TIM3, LAG3, TIGIT, and a member of the B7 family.

In some embodiments of the compounds and methods of this disclosure, the target molecule is an extracellular molecule. By "extracellular molecule" is meant a soluble molecule external to the cell membranes of any cells in the vicinity of the soluble molecule. The extracellular molecule may be any extracellular molecule which is desired for targeted degradation via the endosomal/lysosomal pathway.

In some embodiments, the extracellular molecule is a soluble target protein. In some embodiments, the extracellular molecule is a secreted protein that accumulates in disease (e.g., alpha-synuclein), a cholesterol carrier (e.g., ApoB), an infectious disease toxin (e.g., AB toxins, ESAT-6), an infectious particle (e.g., a whole virus, a whole bacterium, etc.), a clotting factor (e.g., Factor IX), the target of any FDA approved antibody that binds to an extracellular molecule (e.g., TNFalpha), any chemokine or cytokine (e.g., mediators of sepsis or chronic inflammation such at IL-1), a proteinaceous hormone (e.g., insulin, ACTH, etc.), a proteinaceous mediator of a mood disorder, a proteinaceous mediator of energy homeostasis (e.g., leptin, ghrelin, etc.), a proteinaceous allergen present in the bloodstream or an antibody against such an allergen (e.g., for peanut allergies), a proteinaceous toxin (e.g., snake venom hyaluronidase, etc.), an autoantibody, etc.

In some embodiments, the target molecule is an extracellular molecule that is an antibody, e.g., an antibody that specifically binds a cell surface molecule or different extracellular molecule. In some embodiments, the antibody is an autoantibody. In some embodiments, the target is a human immunoglobulin A(IgA). In some embodiments, the IgA is a particular antibody that plays a crucial role in the immune function of mucous membranes. In the blood, IgA interacts with an Fc receptor called CD89 expressed on immune effector cells, to initiate inflammatory reactions. Aberrant IgA expression has been implicated in a number of autoimmune and immune-mediated disorders. In some embodiments, the target is a human immunoglobulin G (IgG). The Fc regions of IgGs include a conserved N-glycosylation site at asparagine 297 in the constant region of the heavy chain. Various N-glycans can be attached to this site. The N-glycan IgG composition has been linked to several autoimmune, infectious and metabolic diseases. In addition, overexpression of IgG4 has been associated with IG4-related diseases. In some embodiments, the target is human immunoglobulin E (IgE). IgE is a type of immunoglobulin that plays an essential role in type I hypersensitivity, which can manifest into various allergic diseases and conditions.

In some embodiments, the extracellular molecule is a ligand for a cell surface receptor. Cell surface receptor ligands of interest include, but are not limited to, growth factors (e.g., epidermal growth factor (EGF), vascular endothelial growth factor (VEGF), and the like), cytokines (e.g., an interleukin, an interferon, a tumor necrosis factor (TNF), a transforming growth factor b (TGF-b), including any particular subtypes of such cytokines), hormones, and the like. In certain aspects, the moiety of interest (Y) specifically binds apolipoprotein E4 (ApoE4).

5.5. Pharmaceutical Compositions

In another embodiment, provided herein are pharmaceutical compositions comprising one or more conjugates disclosed herein and a pharmaceutically acceptable carrier.

In certain embodiments, the pharmaceutical compositions provided herein contain therapeutically effective amounts of one or more of the conjugates provided herein, and optionally one or more additional prophylactic or therapeutic agents, in a pharmaceutically acceptable carrier.

Pharmaceutical carriers suitable for administration of the conjugates provided herein include any such carriers known to those skilled in the art to be suitable for the particular mode of administration.

The conjugates described herein can be formulated as the sole pharmaceutically active ingredient in the composition or can be combined with other active ingredients.

In certain embodiments, the conjugate is formulated into one or more suitable pharmaceutical preparations, such as solutions, suspensions, powders, sustained release formulations or elixirs in sterile solutions or suspensions for parenteral administration, or as transdermal patch preparation and dry powder inhalers.

In compositions provided herein, a conjugate described herein may be mixed with a suitable pharmaceutical carrier. The concentration of the conjugate in the compositions can, for example, be effective for delivery of an amount, upon administration, that treats, prevents, or ameliorates a condition or disorder described herein or a symptom thereof.

In certain embodiments, the pharmaceutical compositions provided herein are formulated for single dosage administration. To formulate a composition, the weight fraction of conjugate is dissolved, suspended, dispersed or otherwise mixed in a selected carrier at an effective concentration such that the treated condition is relieved, prevented, or one or more symptoms are ameliorated.

Concentrations of the conjugate in a pharmaceutical composition provided herein will depend on, e.g., the physicochemical characteristics of the conjugate, the dosage schedule, and amount administered as well as other factors known to those of skill in the art.

Pharmaceutical compositions described herein are provided for administration to a subject, for example, humans or animals (e.g., mammals) in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals in unit dosage form, including oral or nasal solutions or suspensions and oil-water emulsions containing suitable quantities of a conjugate or pharmaceutically acceptable derivatives thereof. The conjugate is, in certain embodiments, formulated and administered in unit-dosage forms or multiple-dosage forms. Unit-dose forms as used herein refers to physically discrete units suitable for human or animal (e.g., mammal) subjects and packaged individually as is known in the art. Each unit-dose contains a predetermined quantity of a conjugate sufficient to produce the desired therapeutic effect, in association with the required pharmaceutical carrier, vehicle or diluent. Examples of unit-dose forms include ampoules and syringes and individually packaged capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of capsules or bottles. Hence, in specific aspects, multiple dose form is a multiple of unit-doses which are not segregated in packaging.

In certain embodiments, the conjugates herein are in a liquid pharmaceutical formulation. Liquid pharmaceutically administrable formulations can, for example, be prepared by dissolving, dispersing, or otherwise mixing a conjugate and optional pharmaceutical adjuvants in a carrier, such as, for example, water, saline, aqueous dextrose, glycerol, glycols, and the like, to thereby form a solution or suspension. In certain embodiments, a pharmaceutical composition provided herein to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., Remington: The Science and Practice of Pharmacy (2012) 22nd ed., Pharmaceutical Press, Philadelphia, PA Dosage forms or compositions containing antibody in the range of 0.005% to 100% with the balance made up from non-toxic carrier can be prepared.

Parenteral administration, in certain embodiments, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

In certain embodiments, intravenous or intraarterial infusion of a sterile aqueous solution containing a conjugate described herein is an effective mode of administration. Another embodiment is a sterile aqueous or oily solution or suspension containing a conjugate described herein injected as necessary to produce the desired pharmacological effect.

In certain embodiments, the pharmaceutical formulations are lyophilized powders, which can be reconstituted for administration as solutions, emulsions and other mixtures. They can also be reconstituted and formulated as solids or gels.

The lyophilized powder is prepared by dissolving a conjugate provided herein, in a suitable solvent. In some embodiments, the lyophilized powder is sterile. Suitable solvents can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. A suitable solvent can also contain a buffer, such as citrate, sodium or potassium phosphate or other such buffer known to those of skill in the art at, in certain embodiments, about neutral pH. Subsequent sterile filtration of the solution followed by lyophilization under standard conditions known to those of skill in the art provides an example of a formulation. In certain embodiments, the resulting solution will be apportioned into vials for lyophilization. Lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier.

In certain embodiments, the conjugates provided herein can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

5.6. Uses and Methods

In one aspect, provided herein are methods of using the conjugates described herein to remove a polypeptide of interest (a target protein) from a cell's surface. In one aspect, provided herein are methods of using the conjugates described herein to remove a polypeptide of interest (a target protein) from the extracellular milieu. For example, in one embodiment, provided herein are methods of using the conjugates described herein to remove a polypeptide of interest (a target protein) from the surface of a cell by sequestering the target protein in the cell's lysosome. In another embodiment, provided herein are methods of using the conjugates described herein to remove a polypeptide of interest (a target protein) from the extracellular space (the extracellular milieu) of a cell by sequestering the target protein in the cell's lysosome. In another embodiment, provided herein are methods of using the conjugates described herein to remove a polypeptide of interest (a target protein) from the surface of a cell by sequestering the target protein in the cell's lysosome and degrading the target protein. In another embodiment, provided herein are methods of using the conjugates described herein to remove a polypeptide of interest (a target protein) from the extracellular space (the extracellular milieu) of a cell by sequestering the target protein in the cell's lysosome and degrading the target protein.

Removal of a target protein may refer to reduction, or depletion, of the target protein from the cell surface or from the extracellular space, or the extracellular milieu, that is, a reduction, or depletion, of the amount of the target protein on the cell surface or in the extracellular milieu.

In one aspect, provided herein are methods of using the conjugates described herein to sequester a polypeptide of interest (a target protein) in a cell's lysosome. In one aspect, provided herein are methods of using the conjugates described herein to sequester a polypeptide of interest (a target protein) in a cell's lysosome and to degrade the polypeptide of interest.

In one aspect, provided herein are methods of using the conjugates described herein to degrade a polypeptide of interest (a target protein).

In one aspect, provided herein are methods of depleting a polypeptide of interest (a target protein) described herein by degradation through a cell's lysosomal pathway.

In another aspect, provided herein are methods of depleting a polypeptide of interest (a target protein) described herein by administering to a subject in need thereof an effective amount of a conjugate or pharmaceutically acceptable salt described herein, or a pharmaceutical composition described herein. In certain embodiments, the subject is a mammal (e.g., human).

In certain embodiments, the target protein is a VEGF protein, an EGFR protein, a VEGFR protein, a PD-L1 protein, an FGFR2 protein or an FGFR3 protein.

In another aspect, provided herein are methods of treating a disease or disorder by administering to a subject, e.g., a human, in need thereof an effective amount of a conjugate or pharmaceutically acceptable salt described herein, or a pharmaceutical composition described herein.

The terms "administer", "administration", or "administering" refer to the act of injecting or otherwise physically delivering a substance (e.g., a conjugate or pharmaceutical composition provided herein) to a subject or a patient (e.g., human), such as by mucosal, topical, intradermal, parenteral, intravenous, intramuscular delivery and/or any other method of physical delivery described herein or known in the art. In a particular embodiment, administration is by intravenous infusion.

The terms "effective amount" or "therapeutically effective amount" refer to an amount of a therapeutic (e.g., a conjugate or pharmaceutical composition provided herein) which is sufficient to treat, diagnose, prevent, delay the onset of, reduce and/or ameliorate the severity and/or duration of a given condition, disorder or disease and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy or to serve as a bridge to another therapy. In some embodiments, "effective amount" as used herein also refers to the amount of a conjugate described herein to achieve a specified result.

In certain embodiments, when the disorder or disease is cancer, "effective amount" or "therapeutically effective amount" mean that amount of a conjugate or pharmaceutical composition provided herein which, when administered to a human suffering from a cancer, is sufficient to effect treatment for the cancer. "Treating" or "treatment" of the cancer includes one or more of:

(1) limiting/inhibiting growth of the cancer, e.g. limiting its development;
(2) reducing/preventing spread of the cancer, e.g. reducing/preventing metastases;
(3) relieving the cancer, e.g. causing regression of the cancer,
(4) reducing/preventing recurrence of the cancer; and
(5) palliating symptoms of the cancer.

The terms "subject" and "patient" are used interchangeably. A subject can be a mammal such as a non-primate (e.g., cows, pigs, horses, cats, dogs, goats, rabbits, rats, mice, etc.) or a primate (e.g., monkey and human), for example a human. In certain embodiments, the subject is a mammal, e.g., a human, diagnosed with a disease or disorder provided herein. In another embodiment, the subject is a mammal, e.g., a human, at risk of developing a disease or disorder provided herein. In a specific embodiment, the subject is human.

The terms "therapies" and "therapy" can refer to any protocol(s), method(s), compositions, formulations, and/or agent(s) that can be used in the prevention, treatment, management, or amelioration of a disease or disorder or symptom thereof (e.g., a disease or disorder provided herein or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a disease or disorder or one or more symptoms thereof. In certain embodiments, the term "therapy" refers to a therapy other than a conjugate described herein or pharmaceutical composition thereof.

In certain embodiments, the disease or disorder is treated by depletion of the target protein by degradation through the lysosomal pathway.

In certain embodiments, the disease or disorder is treated by depletion of certain proteins, for example, soluble proteins, e.g., secreted proteins, cell surface proteins (for example, cell surface receptor proteins, e.g., tyrosine kinase receptors, soluble cytokine receptors, and immune checkpoint receptors, e.g., EGFR, VEGFR, FGFR, and PD-L[1]), lectins, complements, lipoproteins, transport proteins, MHC class I and class II molecules, cytokines, chemokines, and/or receptors, or fragments or subunits of any of the foregoing.

In certain embodiments, the disease or disorder is a cancer.

In certain embodiments, the cancer is selected from the group consisting of bladder cancer, breast cancer, cervical cancer, cholangiocarcinoma, endometrial cancer, hepatocellular carcinoma, kidney cancer, melanoma, myeloid neoplasms, non-small cell lung cancer (NSCLC), Ewing's sarcoma, and Hodgkin's Lymphoma.

In certain embodiments, the cancer is a solid tumor.

In certain embodiments, the disease or disorder is an inflammatory or autoimmune disease.

In certain embodiments, the disease or disorder is an inflammatory disease.

In certain embodiments, the disease or disorder is an autoimmune disease.

In certain embodiments, the disease or disorder is a viral disease. In certain cases, the viral disease is hepatitis B.

5.7. Definitions

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "protein" and "polypeptide" are used interchangeably. Proteins may include moieties other than amino acids (e.g., may be glycoproteins, etc.) and/or may be otherwise processed or modified. Those of ordinary skill in the art will appreciate that a "protein" can be a complete protein chain as produced by a cell (with or without a signal sequence), or can be a protein portion thereof. Those of ordinary skill will appreciate that a protein can sometimes include more than one protein chain, for example non-covalently or covalently attached, e.g., linked by one or more disulfide bonds or associated by other means. In certain embodiments, a polypeptide can occur as a single chain or as two or more associated chains, e.g., may be present as a multimer, e.g., dimer, a trimer. The terms also encompass an amino acid polymer that has been modified naturally or by intervention; for example, by disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. In some embodiments, proteins are antibodies, antibody fragments, biologically active portions thereof, and/or characteristic portions thereof.

The terms "antibody" and "immunoglobulin" are terms of art and can be used interchangeably herein in their broadest sense and includes certain types of immunoglobulin molecules comprising one or more antigen-binding domains that specifically bind to an antigen or epitope.

In a certain embodiments, an isolated antibody (e.g., monoclonal antibody) described herein, or an antigen-binding fragment thereof, which specifically binds to a protein of interest, for example, EGFR, is conjugated to one or more lysosomal targeting moieties, for example, via a linker.

An "antigen" is a moiety or molecule that contains an epitope to which an antibody can specifically bind. As such, an antigen is also is specifically bound by an antibody. In a specific embodiment, the antigen, to which an antibody described herein binds, is a protein of interest, for example, EGFR (e.g., human EGFR), or a fragment thereof, or for example, an extracellular domain of EGFR (e.g., human EGFR).

An "epitope" is a term known in the art and refers to a localized region of an antigen to which an antibody can specifically bind. An epitope can be a linear epitope of contiguous amino acids or can comprise amino acids from two or more non-contiguous regions of the antigen.

The terms "binds," "binds to," "specifically binds" or "specifically binds to" in the context of antibody binding refer to antibody binding to an antigen (e.g., epitope) as such binding is understood by one skilled in the art. For example, a molecule that specifically binds to an antigen may bind to other polypeptides, generally with lower affinity as determined by, e.g., immunoassays, Biacore™, KinExA 3000 instrument (Sapidyne Instruments, Boise, ID), or other assays known in the art. In a specific embodiment, molecules that specifically bind to an antigen bind to the antigen with an affinity ($K_d$) that is at least 2 logs, 2.5 logs, 3 logs, 4 logs lower (higher affinity) than the $K_d$ when the molecules bind to another antigen. In another specific embodiment, molecules that specifically bind to an antigen do not cross react with other proteins. In another specific embodiment, where EGFR is the protein of interest, molecules that specifically bind to an antigen do not cross react with other non-EGFR proteins.

An antibody specifically includes, but is not limited to, full length antibodies (e.g., intact immunoglobulins), antibody fragments, monoclonal antibodies, polyclonal antibodies recombinantly produced antibodies, monospecific antibodies, multispecific antibodies (including bispecific antibodies), human antibodies, humanized antibodies, chimeric antibodies, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain/antibody heavy chain pair, an antibody with two light chain/heavy chain pairs (e.g., identical pairs), intrabodies, heteroconjugate antibodies, single domain antibodies, monovalent antibodies, bivalent antibodies (including monospecific or bispecific bivalent antibodies), single chain antibodies, or single-chain Fvs (scFv), camelized antibodies, affybodies, Fab fragments, F(ab') fragments, F(ab')$_2$ fragments, disulfide-linked Fvs (sdFv), anti-idiotypic (anti-Id) antibodies (including, e.g., anti-anti-Id antibodies), and epitope-binding fragments of any of the above.

Antibodies can be of any type (e.g., IgG, IgE, IgM, IgD, IgA or IgY), any class, (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies (e.g., human IgG), or a class (e.g., human IgG1, IgG2, IgG3 or IgG4) or subclass thereof.

In a particular embodiment, an antibody is a 4-chain antibody unit comprising two heavy (H) chain/light (L) chain pairs, wherein the amino acid sequences of the H chains are identical and the amino acid sequences of the L chains are identical. In a specific embodiment, the H and L chains comprise constant regions, for example, human constant regions. In a yet more specific embodiment, the L chain constant region of such antibodies is a kappa or lambda light chain constant region, for example, a human kappa or lambda light chain constant region. In another specific embodiment, the H chain constant region of such antibodies comprise a gamma heavy chain constant region, for example, a human gamma heavy chain constant region. In a particular embodiment, such antibodies comprise IgG constant regions, for example, human IgG constant regions.

The term "constant region" or "constant domain" is a well-known antibody term of art (sometimes referred to as "Fc"), and refers to an antibody portion, e.g., a carboxyl terminal portion of a light and/or heavy chain which is not directly involved in binding of an antibody to antigen but which can exhibit various effector functions, such as interaction with the Fc receptor. The terms refer to a portion of an immunoglobulin molecule having a generally more conserved amino acid sequence relative to an immunoglobulin variable domain.

The term "heavy chain" when used in reference to an antibody can refer to any distinct types, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct types, e.g., kappa (κ) of lambda (λ) based on the amino acid sequence of the constant domains. Light chain amino acid sequences are well known in the art. In specific embodiments, the light chain is a human light chain.

The term "monoclonal antibody" is a well-known term of art that refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell (e.g., hybridoma or host cell producing a recombinant antibody), wherein the antibody specifically binds to an epitope as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody).

The terms "variable region" or "variable domain" refer to a portion of an antibody, generally, a portion of a light or heavy chain, typically about the amino-terminal 110 to 120 amino acids in the mature heavy chain and about 90 to 100 amino acids in the mature light chain. Variable regions comprise complementarity determining regions (CDRs) flanked by framework regions (FRs). Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope. In a specific embodiment, numbering of amino acid positions of antibodies described herein is according to the EU Index, as in Kabat et al. (1991) Sequences of Proteins of Immunological Interest, Fifth Edition, U.S. Department of Health and Human Services, NIH Publication No. 91-3242. In certain embodiments, the variable region is a human variable region.

In certain aspects, the CDRs of an antibody can be determined according to (i) the Kabat numbering system (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196: 901-917; Al-Lazikani et al., 1997, J. Mol. Biol., 273: 927-948; Chothia et al., 1992, J. Mol. Biol., 227: 799-817; Tramontano et al., 1990, J. Mol. Biol. 215(1):175-82; U.S. Pat. No. 7,709,226; and Martin, A., "Protein Sequence and Structure Analysis of Antibody Variable Domains," in Antibody Engineering, Kontermann and Dübel, eds., Chapter 31, pp. 422-439, Springer-Verlag, Berlin (2001)); or (iii) the ImMunoGeneTics (IMGT) numbering system, for example, as described in Lefranc, 1999, The Immunologist, 7: 132-136 and Lefranc et al., 1999, Nucleic Acids Res., 27: 209-212 ("IMGT CDRs"); or (iv) the AbM numbering system, which will be referred to herein as the "AbM CDRs", for example as described in MacCallum et al., 1996, J. Mol. Biol., 262: 732-745. See also, e.g., Martin, A., "Protein Sequence and Structure Analysis of Antibody Variable Domains," in Antibody Engineering, Kontermann and Dübel, eds., Chapter 31, pp. 422-439, Springer-Verlag, Berlin (2001); or (v) the Contact numbering system, which will be referred to herein as the "Contact CDRs" (the Contact definition is based on analysis of the available complex crystal structures (bioinf.org.uk/abs) (see, e.g., MacCallum et al., 1996, J. Mol. Biol., 262:732-745)).

The terms "full length antibody," "intact antibody" and "whole antibody" are used herein interchangeably to refer to an antibody in its substantially intact form, and are not antibody fragments as defined below. The terms particularly refer to an antibody with heavy chains that contain the Fc region.

"Antibody fragments" comprise only a portion of an intact antibody, wherein the portion retains at least one, two, three and as many as most or all of the functions normally associated with that portion when present in an intact antibody. In one aspect, an antibody fragment comprises an antigen binding site of the intact antibody and thus retains the ability to bind antigen. In another aspect, an antibody fragment, such as an antibody fragment that comprises the Fc region, retains at least one of the biological functions normally associated with the Fc region when present in an intact antibody. Such functions may include FcRn binding, antibody half life modulation, conjugate function and complement binding. In another aspect, an antibody fragment is a monovalent antibody that has an in vivo half life substantially similar to an intact antibody. For example, such an antibody fragment may comprise on antigen binding arm linked to an Fc sequence capable of conferring in vivo stability to the fragment. Antibody fragments suitable for use in the compounds of this disclosure include, for example, Fv fragments, Fab fragments, F(ab')$_2$ fragments, Fab' fragments, scFv (sFv) fragments, and scFv-Fc fragments.

"Polynucleotide" or "nucleic acid," as used interchangeably herein, and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. The nucleic acid molecule may be an aptamer.

The term "purified" refers to isolation of a substance (compound, polynucleotide, protein, polypeptide, polypeptide composition) such that the substance of interest comprises the majority percent of the sample in which it resides. Typically in a sample a substantially purified component comprises 50%, 80%-85%, 90-99%, such as at least 90%, 91%, 92%, 93%, 94%, 95%, 96%, 97%, 98%, 99% of the sample. Techniques for purifying polynucleotides, polypeptides and virus particles of interest are well-known in the art and include, for example, ion-exchange chromatography, affinity chromatography and sedimentation according to density.

The terms "treatment," "treating," and the like, refer to obtaining a desired pharmacologic and/or physiologic effect, such as reduction of tumor burden. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease (e.g., reduction in of tumor burden).

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

Unless specifically stated otherwise, where a compound may assume alternative tautomeric, regioisomeric and/or stereoisomeric forms, all alternative isomers, are intended to be encompassed within the scope of the claimed subject matter. For example, when a compound is described as a particular optical isomer D- or L-, it is intended that both optical isomers be encompassed herein. For example, where a compound is described as having one of two tautomeric forms, it is intended that both tautomers be encompassed herein. Thus, the compounds provided herein may be enantiomerically pure, or be stereoisomeric or diastereomeric mixtures. The compounds provided herein may contain chiral centers. Such chiral centers may be of either the (R) or (S) configurations, or may be a mixture thereof. The chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. In some embodiments, hydrogen atoms of the compounds described herein may be replaced with deuterium atoms. In certain embodiments, "deuterated" as applied to a chemical group and unless otherwise indicated, refers to a chemical group that is isotopically enriched with deuterium in an amount substantially greater than its natural abundance. Isotopic variants of the compounds according to the present disclosure can be prepared by various, including, for example, the methods described below and in the working examples, by using corresponding isotopic modifications of the particular reagents and/or starting compounds therein.

Thus, any of the embodiments described herein are meant to include a salt, a single stereoisomer, a mixture of stereoisomers and/or an isotopic form of the compounds.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

A "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

The term "pharmaceutically acceptable" means being approved by a regulatory agency of the Federal or a state government, or listed in the U.S. Pharmacopeia, European Pharmacopeia or other generally recognized Pharmacopeia for use in animals, and, more particularly in humans.

The term "pharmaceutically acceptable salt" refers to those salts which are suitable for use in contact with the tissues of humans and lower animals without undue toxicity, irritation, allergic response and the like. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the conjugate compounds, or separately by reacting the free base function or group of a compound with a suitable organic acid. Examples of pharmaceutically acceptable salts include, but are not limited to, nontoxic acid addition salts, or salts of an amino group formed with inorganic acids "Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

The term "alkyl" refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)n- (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NRaRb, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl", unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—CH($CH_3$)—$CH_2$—), hexylene (—$(CH_2)_6$—) and the like.

Similarly, the terms "alkenylene," "alkynylene," "arylene," "aralkylene," and "alkarylene" refer to di-radical alkenyl, alkynyl, aryl, aralkyl, and alkaryl groups, respectively.

The term "amino" refers to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to —$CO_2H$ or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —$SO_2$-alkyl, —$SO_2$-substituted alkyl, —$SO_2$-aryl and —$SO_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocycloalkyl" refers to a cycloalkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The terms "heterocycle," "heterocyclic" and "heterocyclyl" refer to a saturated or unsaturated group having a single ring or multiple condensed rings, including fused bridged and spiro ring systems, and having from 3 to 15 ring atoms, including 1 to 4 hetero atoms. These ring heteroatoms are selected from nitrogen, sulfur and oxygen, wherein, in fused ring systems, one or more of the rings can be cycloalkyl, heterocycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO— alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH$_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH$_2$), mono- and di-(C1-C24 alkyl)-substituted amino, mono- and di-(C5-C20 aryl)-substituted amino, C2—C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO$_2$-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH$_2$)n-O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$) alkyl), which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M+)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O) O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$) R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$) NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S) R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C (NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$ O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$) R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O) OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O) NR$^{80}$R$^{80}$, —NR$^{70}$C(NR$^{70}$)R$^{70}$ and —NR$^{70}$C(NR$^{70}$) NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

Unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 10%, 9%, 8%, 7%, 6%, 5%, 4%, 3%, 2%, 1%, 0.5%, 0.4%, 0.3%, 0.25%, 0.2%, 0.1% or 0.05% of a given value or range. In certain embodiments, where an integer is required, the term "about" means within plus or minus 10% of a given value or range, rounded either up or down to the nearest integer.

In the description herein, if there is any discrepancy between a chemical name and chemical structure, the chemical structure shall prevail.

Definitions of other terms and concepts appear throughout the detailed description.

ASGPR binding compounds and conjugates are described in International Application No. PCT/US2021/012846, filed Jan. 8, 2021, the disclosure of which is herein incorporated by reference in its entirety.

5.8. Additional Embodiments

Additional embodiments of the present disclosure are also described in the following clauses.

Clause 1. A cell surface receptor binding conjugate of formula (I):

$$X_n\text{-L-Y} \quad (I)$$

or a salt thereof,
wherein:
X is a moiety that binds to a cell surface asialoglycoprotein receptor (ASGPR);
n is 1 to 500 (e.g., n is 1 to 20, 1 to 10, 1 to 6 or 1 to 5); and
L is a linker;
Y is a biomolecule that specifically binds a target protein.

Clause 2. The conjugate of clause 1, wherein the conjugate is formula (V):

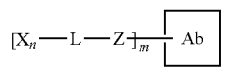
(V)

or a pharmaceutically acceptable salt thereof,
wherein:
n is 1 to 20;
m is an average loading of 1 to 80;
Ab is an antibody or antibody fragment that specifically binds the target protein; and
Z is a residual moiety resulting from the covalent linkage of a chemoselective ligation group to a compatible group of Ab.

Clause 3. The conjugate of clause 1 or 2, wherein X is a moiety that binds to ASGPR and is selected from formula (III-a) to (III-j):

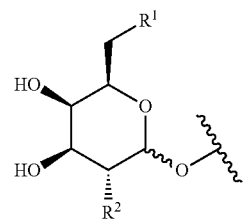
(III-a)

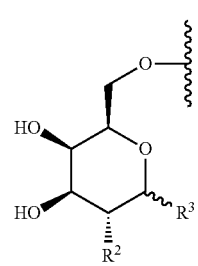
(III-b)

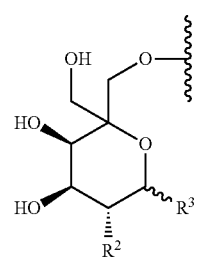
(III-c)

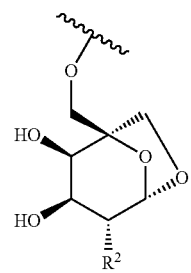
(III-d)

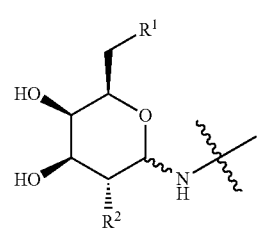
(III-e)

(III-f) 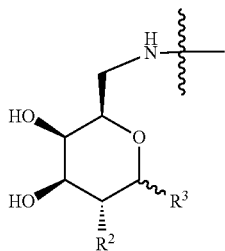

(III-g) 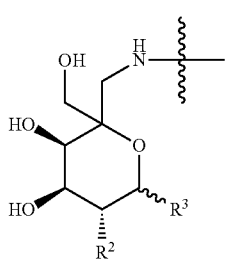

(III-h) 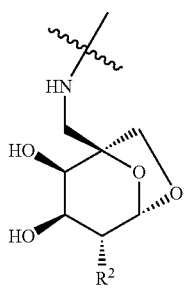

(III-i) 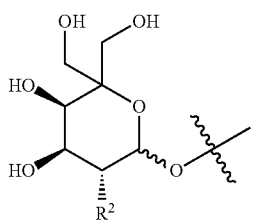

(III-j) 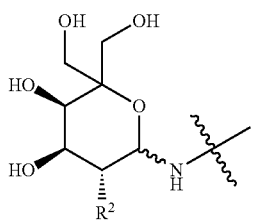

wherein:

$R^1$ is selected from —OH, —OC(O)R, and

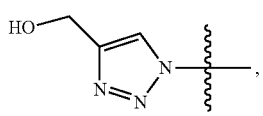

wherein R is $C_{1-6}$ alkyl;

$R^2$ is selected from —NHCOCH$_3$, —NHCOCF$_3$, —NHCOCH$_2$CF$_3$, —OH, and

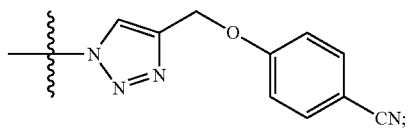 [SMILES: *n1cc(COc2ccc(C#N)cc2)nn1]

and $R^3$ is selected from —H, —OH, —CH$_3$, —OCH$_3$, and —OCH$_2$CH=CH$_2$.

Clause 4. The conjugate of clause 3, wherein X is:

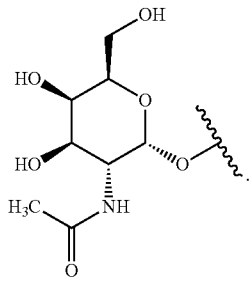 [SMILES: *O[C@H]1O[C@H](CO)[C@H](O)[C@H](O)[C@H]1NC(C)=O]

Clause 5. The conjugate of clause 3, wherein X is:

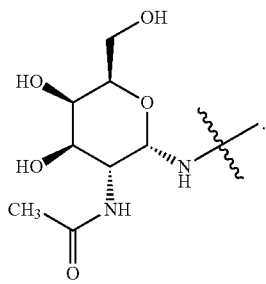 [SMILES: *N[C@H]1O[C@H](CO)[C@H](O)[C@H](O)[C@H]1NC(C)=O]

Clause 6. The conjugate of clauses 1 to 5, wherein the linker L is of formula (IIa):

$$-[(L^1)_a\text{-}(L^2)_b\text{-}(L^3)_c]_n\text{-}(L^4)_d\text{-}(L^5)_e\text{-}(L^6)_f\text{-}(L^7)_g\text{-} \quad \text{(IIa)}$$

wherein each $L^1$ to $L^7$ is independently a linking moiety and together provide a linear or branched linker between X and Y;

a is 1 or 2;

b, c, d, e, f, and g are each independently 0, 1, or 2;

n is 1 to 6 (e.g., n is 1 to 5, or 2 to 6, or 1, 2 or 3).

Clause 107. The conjugate of clause 108, wherein:

when d is 0, n is 1;

when d is 1, n is 1 to 3; and when d is 2, n is 1 to 6.

Clause 7. The conjugate of clause 6, wherein -(L$^1$)$_a$- comprises an optionally substituted aryl or heteroaryl linking moiety.

Clause 8. The conjugate of clause 6, wherein each $L^1$ is independently selected from

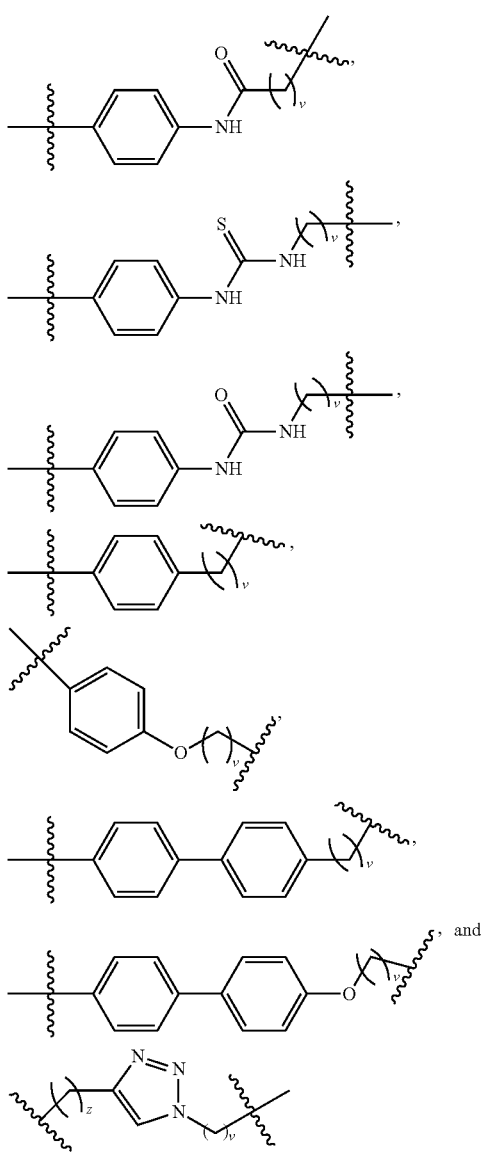

wherein v is 0 to 10 and z is 0 to 10.

Clause 9. The conjugate of any one of clauses 6 to 8, wherein:

each $L^2$ is independently selected from —$C_{1-6}$-alkylene-, —NHCO—$C_{1-6}$-alkylene-, —CONH—$C_{1-6}$-alkylene-, —O(CH$_2$)$_p$—, and —(OCH$_2$CH$_2$)$_p$—, wherein p is 1 to 10; and each $L^3$ is independently selected from:

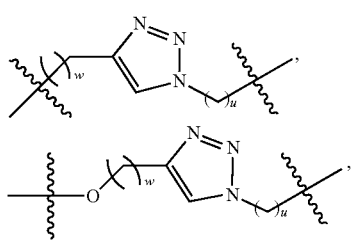

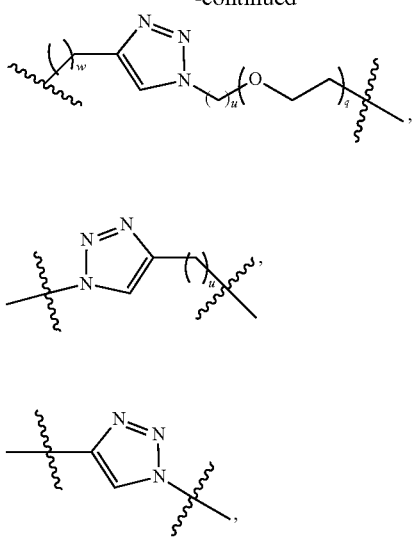

and —(OCH$_2$CH$_2$)$_q$—, wherein q is 1 to 10, u is 0 to 10, and w is 1 to 10.

Clause 10. The conjugate of any one of clauses 6 to 9, wherein when n is 2 or more, at least one $L^4$ is present and is a branched linking moiety.

Clause 11. The conjugate of any one of clauses 6 to 10, wherein each $L^4$ is independently selected from:

—OCH$_2$CH$_2$—,

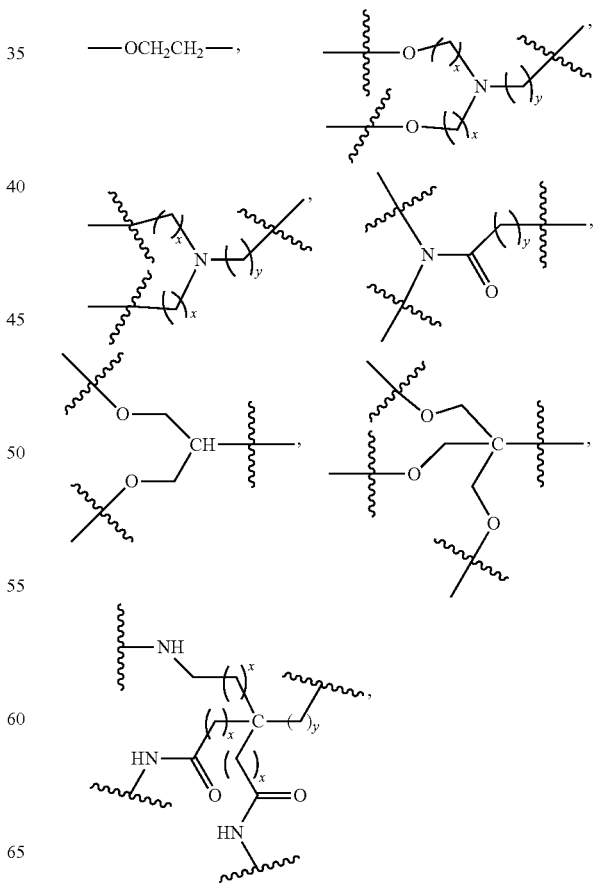

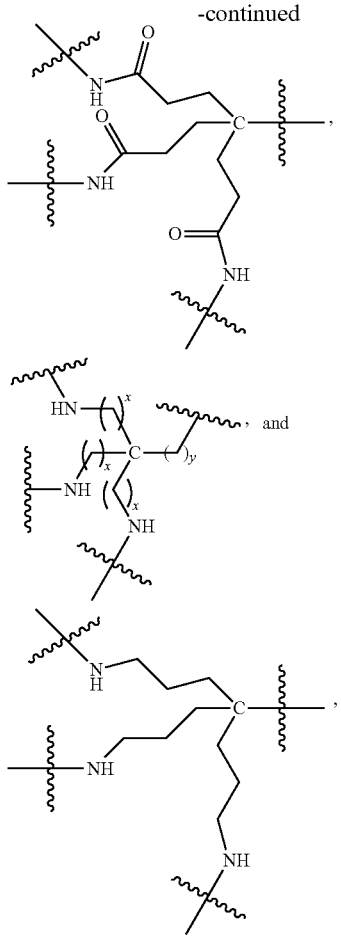

wherein each x and y are each independently 1 to 10.

Clause 12. The conjugate of any one of clauses 6 to 11, wherein:
each $L^5$ is independently —NHCO—$C_{1-6}$-alkylene-, —CONH—$C_{1-6}$-alkylene-, —$C_{1-6}$-alkylene-,

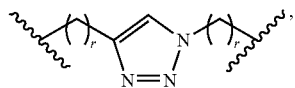

or —(OCH$_2$CH$_2$)$_r$—;
each $L^6$ is independently —NHCO—$C_{1-6}$-alkylene-, —CONH—$C_{1-6}$-alkylene-, —$C_{1-6}$-alkylene-, or —(OCH$_2$CH$_2$)$_s$—;
each $L^7$ is independently —NHCO—$C_{1-6}$-alkylene-, —CONH—$C_{1-6}$-alkylene-, —$C_{1-6}$-alkylene-, —(OCH$_2$CH$_2$)$_t$—, or —OCH$_2$—; and r, s, and t are each independently 1 to 20.

Clause 13. The conjugate of any one of clauses 6 to 12, wherein a is 1.

Clause 14. The conjugate of any one of clauses 6 to 13, wherein at least one of b, c, e, f, and g is not 0.

Clause 15. The conjugate of any one of clauses 6 to 14, wherein at least one of b or c is not 0 and at least one of e, f, and g is not 0.

Clause 16. The conjugate of any one of clauses 6 to 15, wherein a, b, and c are each independently 1 or 2.

Clause 17. The conjugate of any one of clauses 6 to 16, wherein the linker L is selected from any one of the structures of Tables 2-3.

Clause 18. The conjugate of clause 1 or 17, wherein the conjugate is selected from:
i) a conjugate derived from conjugation of a compound of any one of the structures of compound Tables described herein and a biomolecule;
ii) a conjugate derived from conjugation of a compound of any one of the structures of compound Tables described herein and a polypeptide; or
iii) a conjugate derived from conjugation of a compound of any one of the structures of compound Tables described herein and an antibody or antibody fragment.

Clause 19. The conjugate of clause 18, wherein the antibody or antibody fragment is an IgG antibody.

Clause 20. The conjugate of clause 18, wherein the antibody or antibody fragment is a humanized antibody.

Clause 21. The conjugate of any one of clauses 18 to 20, wherein the antibody or antibody fragment specifically binds to a secreted or soluble protein.

Clause 22. The conjugate of any one of clauses 18 to 20, wherein the antibody or antibody fragment specifically binds to a cell surface receptor.

Clause 23. A method of internalizing a target protein in a cell comprising a ASGPR cell surface receptor, the method comprising: contacting a cellular sample comprising the cell and the target protein with an effective amount of a conjugate according to any one of clauses 1 to 22, wherein the conjugate specifically binds the target protein and specifically binds the cell surface receptor to facilitate cellular uptake of the target protein.

Clause 24. The method of clause 23, wherein the target protein is a membrane bound protein.

Clause 25. The method of clause 24, wherein the target protein is an extracellular protein.

Clause 26. The method of any one of clauses 23 to 25, wherein the compound or conjugate comprises an antibody or antibody fragment (Ab) that specifically binds the target protein.

Clause 27. A method of reducing levels of a target protein in a biological system, the method comprising: contacting the biological system with an effective amount of a conjugate according to any one of clauses 1 to 22, wherein the conjugate specifically binds the target protein and specifically binds a ASGPR cell surface receptor of cells in the biological system to facilitate cellular uptake and degradation of the target protein.

Clause 28. The method of claim 27, wherein the biological system is a human subject.

Clause 29. The method of claim 27, wherein the biological system is an in vitro cellular sample.

Clause 30. The method of claim 28, wherein the target protein is a membrane bound protein.

Clause 31. The method of claim 29, wherein the target protein is an extracellular protein.

Clause 32. A method of treating a disease or disorder associated with a target protein, the method comprising: administering to a subject in need thereof an effective amount of a conjugate according to any one of clauses 1 to 22, wherein the conjugate specifically binds the target protein.

Clause 33. The method of clause 32, wherein the disease or disorder is an inflammatory disease.

Clause 34. The method of clause 32, wherein the disease or disorder is an autoimmune disease.

Clause 35. The method of clause 32, wherein the disease or disorder is a cancer.

Clause 36. A compound of the following formula (I):

$$X_n\text{-L-Y} \quad (I)$$

or a salt, a single stereoisomer, a mixture of stereoisomers or an isotopic form thereof, wherein:

X is a moiety that binds to a ASGPR cell surface receptor;
L is a linker of the following formula (IIa):

$$\text{-}[(L^1)_a(L^2)_b\text{-}(L^3)_c]_n\text{-}(L^4)_d\text{-}(L^5)_e\text{-}(L^6)_f\text{-}(L^7)_g\text{-} \quad (IIa); \text{ and}$$

wherein each $L^1$ is independently

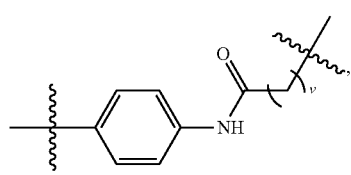

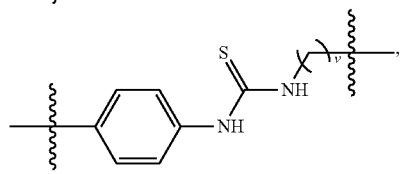

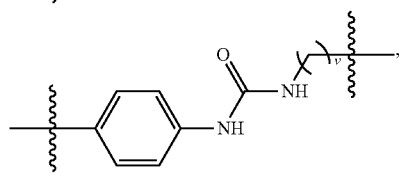

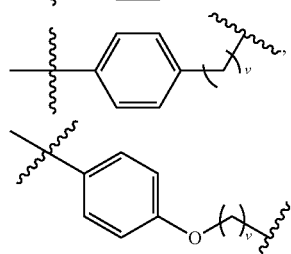

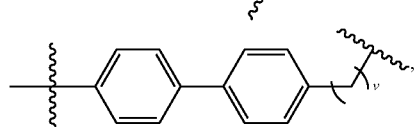

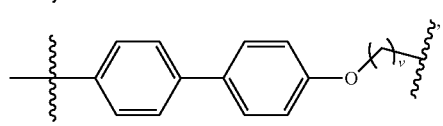

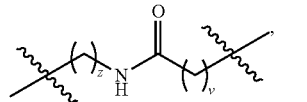

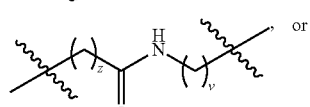

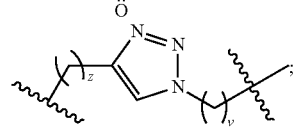

each $L^2$ is independently —$C_{1-6}$-alkylene-, —NHCO—$C_{1-6}$-alkylene-, —CONH—$C_{1-6}$-alkylene-, —$(OCH_2)_p$—, or —$(OCH_2CH_2)_p$—;

each $L^3$ is independently

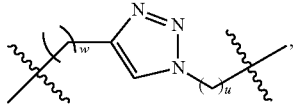

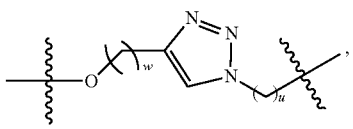

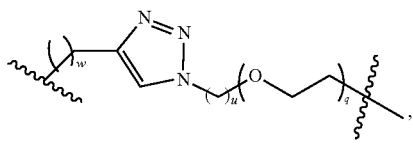

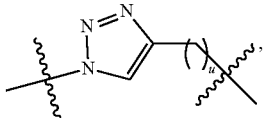

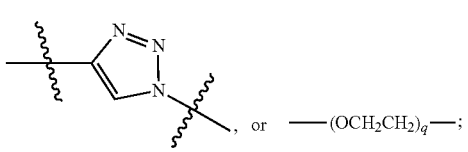, or —$(OCH_2CH_2)_q$—;

each $L^4$ is independently —$OCH_2CH_2$—,

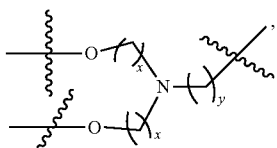

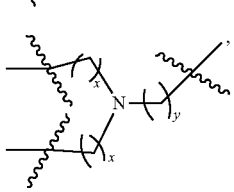 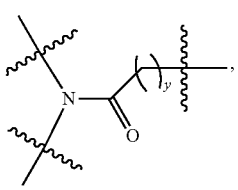

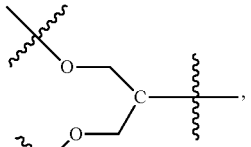

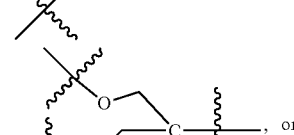, or

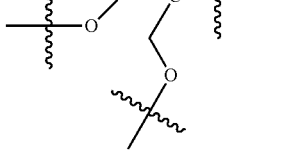

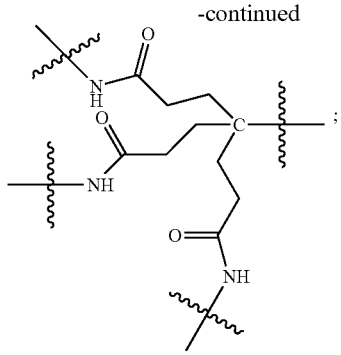

each L⁵ is independently —NHCO—C₁₋₆-alkylene-, —CONH—C₁₋₆-alkylene-, —C₁₋₆-alkylene-,

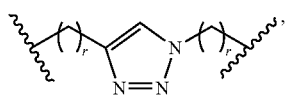

or —(OCH₂CH₂)ᵣ—;

each L⁶ is independently —NHCO—C₁₋₆-alkylene-, —CONH—C₁₋₆-alkylene-, —C₁₋₆-alkylene-, or —(OCH₂CH₂)ₛ—;

each L⁷ is independently —NHCO—C₁₋₆-alkylene-, —CONH—C₁₋₆-alkylene-, —C₁₋₆-alkylene-, —(OCH₂CH₂)ₜ—, or —OCH₂—;

p, q, r, s, and t are each independently an integer of 1 to 20; a is 1 or 2; b, c, d, e, f, and g are each independently 0, 1, or 2; u, v, w, x, y, and z are each independently an integer of 1 to 10;

n is an integer of 1 to 5; wherein when d is 0, n is 1, when d is 1, n is an integer of 1 to 3, and when d is 2, n is an integer of 1 to 5;

Y is a moiety selected from the group consisting of

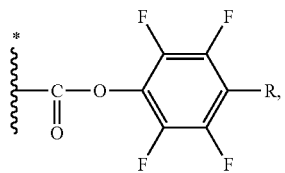

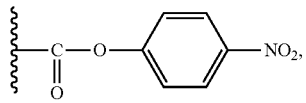

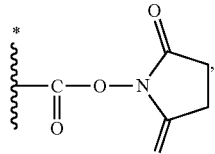

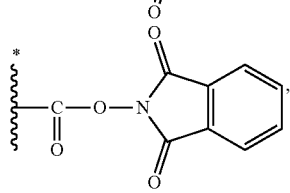

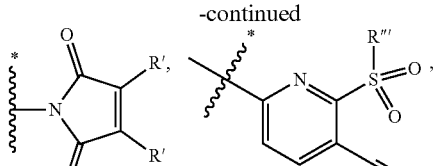

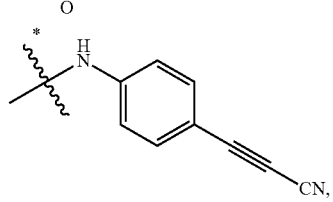

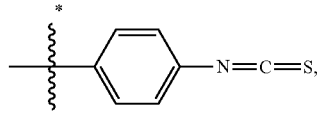

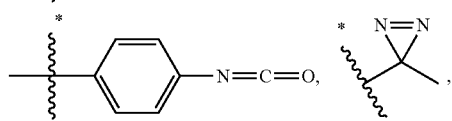

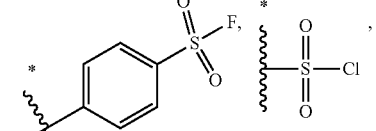

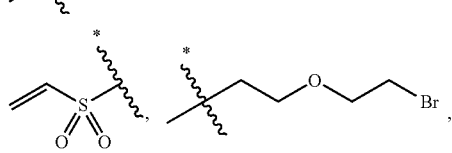

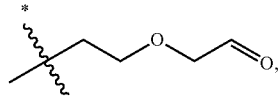

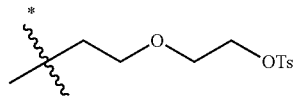

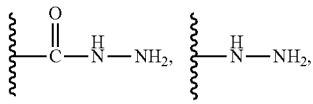

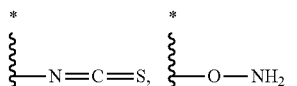

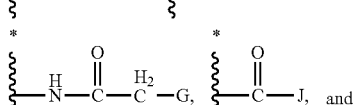, and

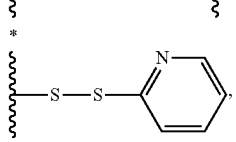

wherein § represents the point of attachment to L;
R is hydrogen or fluorine;
each R' is independently hydrogen or halo;

G is selected from —F, —Cl, —Br, —I, —O-mesyl, and —O-tosyl;

J is selected from —Cl, —Br, —I, —F, —OH, —O—N-succinimide, —O-(4-nitrophenyl), —O-pentafluorophenyl, —O-tetrafluorophenyl, and —O—C(O)—$OR^{J''}$; and $R^{J''}$ is —$C_1$-$C_8$ alkyl or -aryl.

Clause 37. The compound of clause 36, wherein a is 1.

Clause 38. The compound of clause 36, wherein at least one of b, c, e, f, and g is not 0.

Clause 39. The compound of clause 36, wherein at least one of b or c is not 0 and at least one of e, f, and g is not 0.

Clause 40. The compound of clause 36, wherein a, b, and c are each independently 1 or 2.

Clause 41. The compound of clause 36, wherein each X is independently selected from formula (III-a) to (III-j):

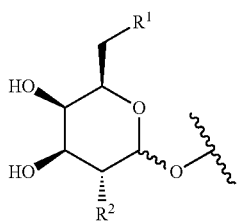
(III-a)

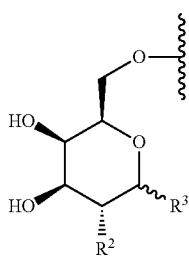
(III-b)

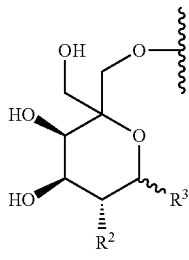
(III-c)

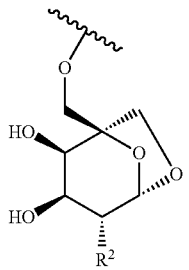
(III-d)

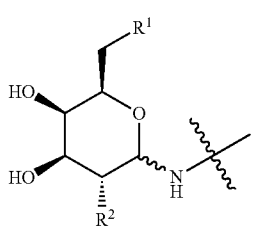
(III-e)

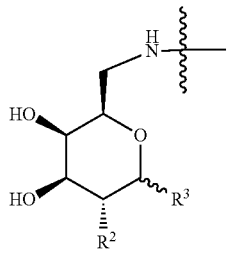
(III-f)

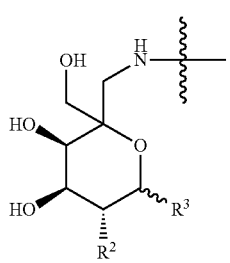
(III-g)

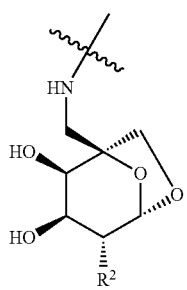
(III-h)

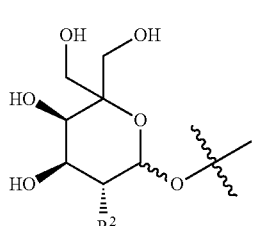
(III-i)

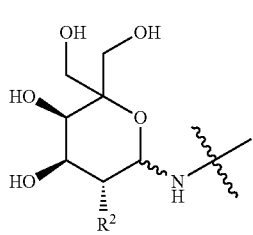
(III-j)

wherein:

$R^1$ is selected from —OH, —OC(O)R, and

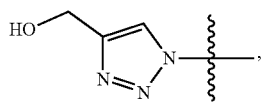

wherein R is $C_{1-6}$ alkyl;

$R^2$ is selected from —NHCOCH$_3$, —NHCOCF$_3$, —NHCOCH$_2$CF$_3$, —OH, and

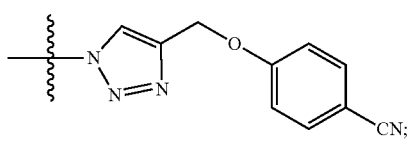

and

R³ is selected from —H, —OH, —CH₃, —OCH₃, and —OCH₂CH=CH₂.

Clause 42. The conjugate of clause 41, wherein X is:

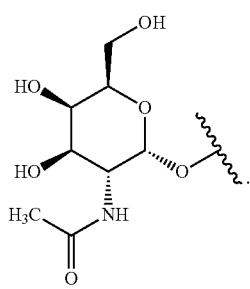

Clause 43. The conjugate of clause 41, wherein X is:

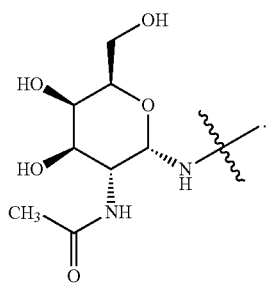 [SMILES: *N[C@H]1O[C@H](CO)[C@H](O)[C@H](O)[C@H]1NC(C)=O]

Clause 44. A conjugate of the following formula (IVa):

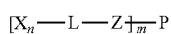 (IVa)

or a pharmaceutically acceptable salt thereof,
wherein:
X is a moiety that binds to a ASGPR cell surface receptor;
L is a linker of the following formula (IIa):

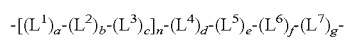 (IIa); and wherein
each L¹ is independently

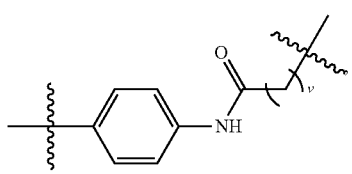

-continued

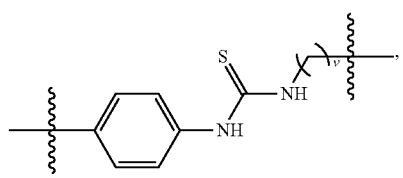

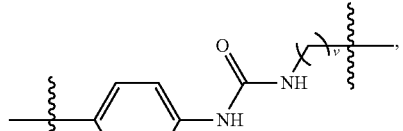

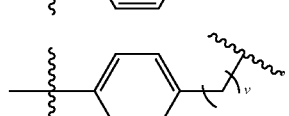

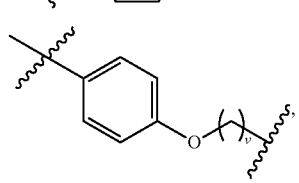

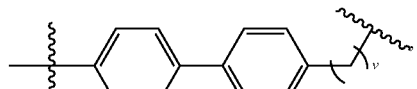

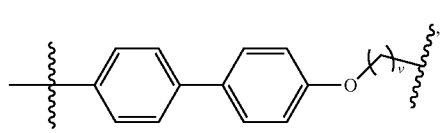

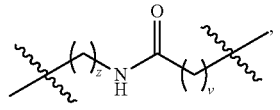

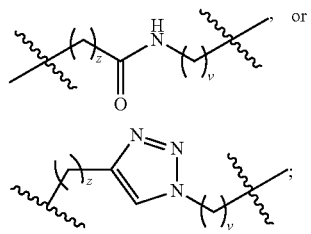

each L² is independently —C₁₋₆-alkylene-, —NHCO—C₁₋₆-alkylene-, —CONH—C₁₋₆-alkylene-, —(OCH₂)ₚ—, or —(OCH₂CH₂)ₚ—;

each L³ is independently

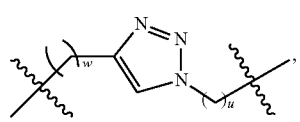

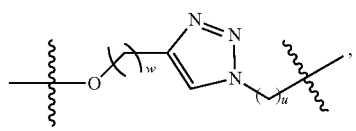

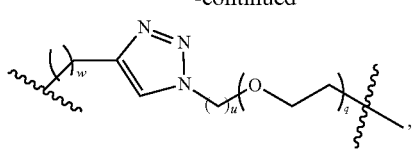

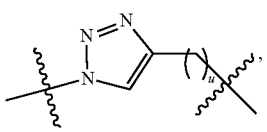

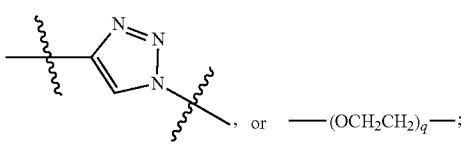, or —(OCH$_2$CH$_2$)$_q$—;

each L$^4$ is independently

—OCH$_2$CH$_2$—,

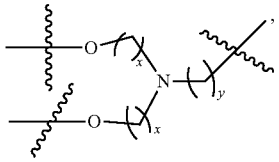

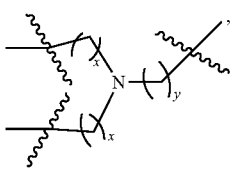

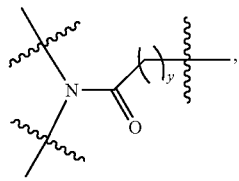

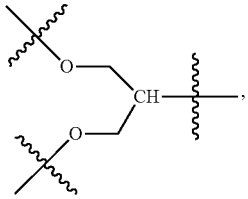

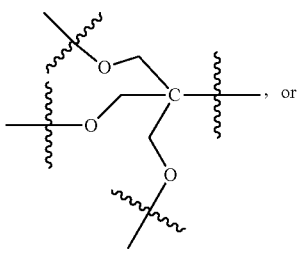, or

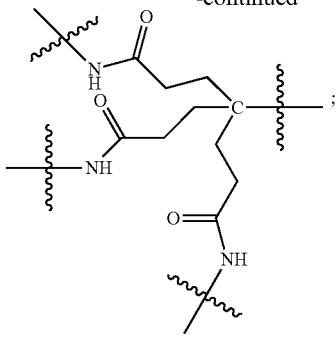

each L$^5$ is independently —NHCO—C$_{1-6}$-alkylene-, —CONH—C$_{1-6}$-alkylene-, —C$_{1-6}$-alkylene-,

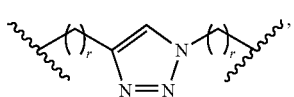

or —(OCH$_2$CH$_2$)$_r$—;

each L$^6$ is independently —NHCO—C$_{1-6}$-alkylene-, —CONH—C$_{1-6}$-alkylene-, —C$_{1-6}$-alkylene-, or —(OCH$_2$CH$_2$)$_s$—;

each L$^7$ is independently —NHCO—C$_{1-6}$-alkylene-, —CONH—C$_{1-6}$-alkylene-, C$_{1-6}$-alkylene-, —(OCH$_2$CH$_2$)$_t$—, or —OCH$_2$—;

p, q, r, s, and t are each independently an integer of 1 to 20; a is 1 or 2; b, c, d, e, f, and g are each independently 0, 1, or 2; u, v, w, x, y, and z are each independently an integer of 1 to 10;

n is an integer of 1 to 5; wherein when d is 0, n is 1, when d is 1, n is an integer of 1 to 3, and when d is 2, n is an integer of 1 to 5;

Z is selected from the group consisting of

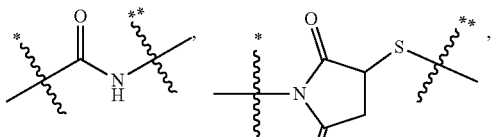

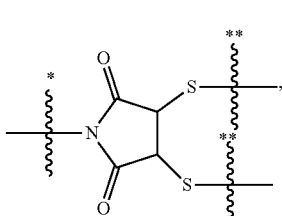

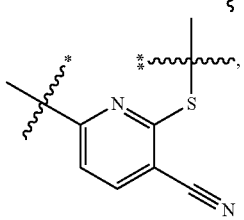

-continued

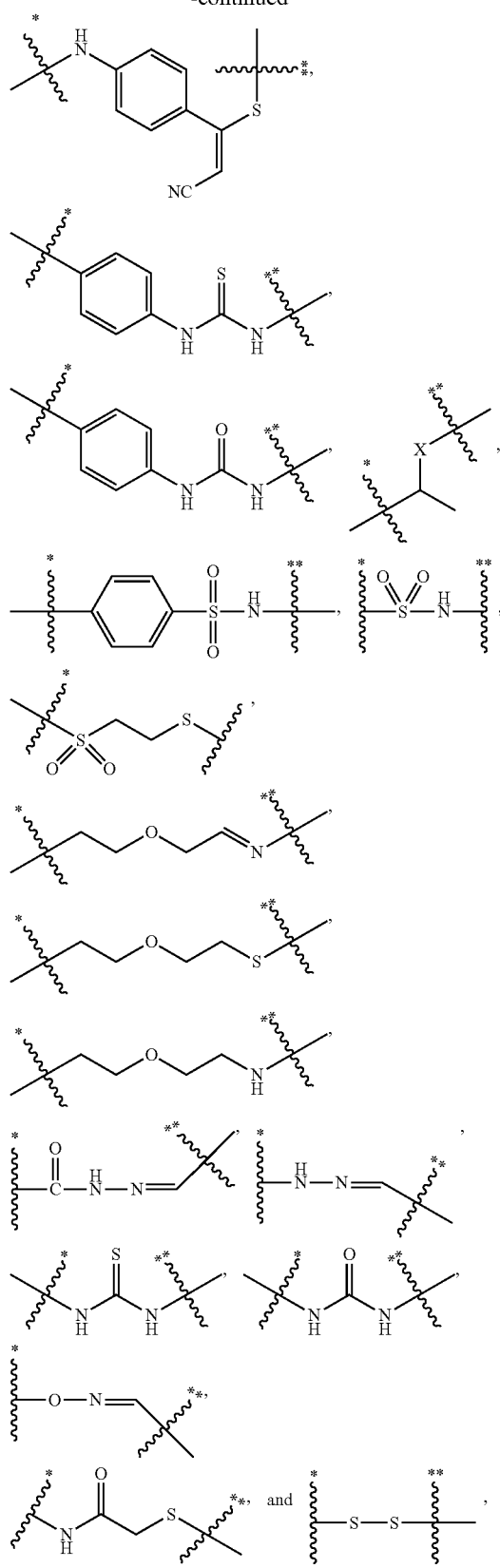

wherein ⟩ represents the point of attachment to L, wherein ** ⟩ represents the point of attachment to P,
X is CH$_2$, NH, O or S; and
P is a polypeptide.

Clause 45. The conjugate of clause 44, wherein P comprises an antibody or an antigen-binding fragment of an antibody.

Clause 46. A conjugate of the following formula (Va):

$$[X_n-L-Z]_m-\boxed{Ab} \quad ; \qquad (Va)$$

or a pharmaceutically acceptable salt thereof,
wherein:
X is a moiety that binds to a ASGPR cell surface receptor;
L is a linker of the following formula (IIa):

$$-[(L^1)_a\text{-}(L^2)_b\text{-}(L^3)_c]_n\text{-}(L^4)_d\text{-}(L^5)_e\text{-}(L^6)_f\text{-}(L^7)_g\text{-} \qquad (IIa); \text{ and}$$

wherein
each L$^1$ is independently

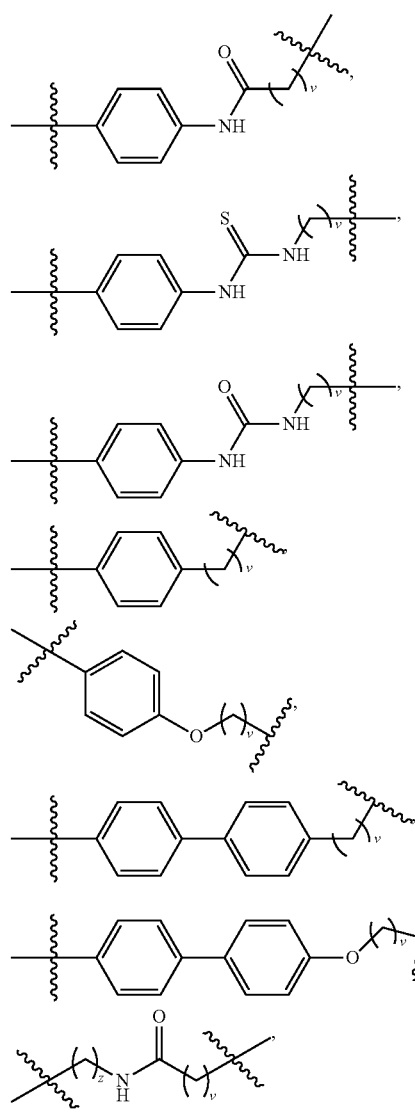

-continued

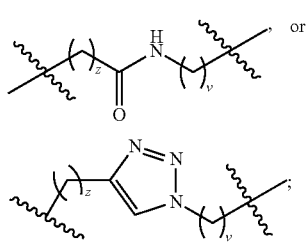

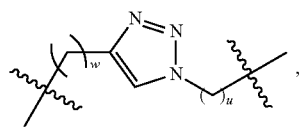

each L² is independently —C₁₋₆-alkylene-, —NHCO—C₁₋₆-alkylene-, —CONH—C₁₋₆-alkylene-, —(OCH₂)$_p$—, or —(OCH₂CH₂)$_p$—;

each L³ is independently

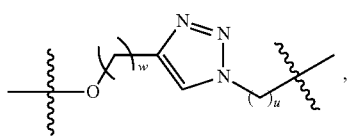

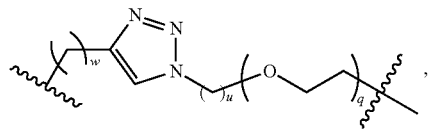

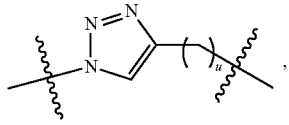

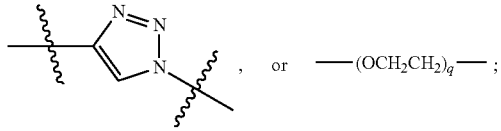

each L⁴ is independently

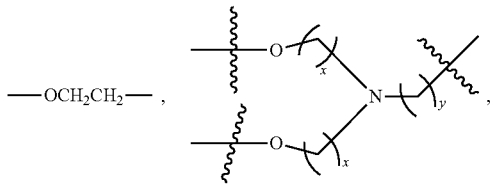

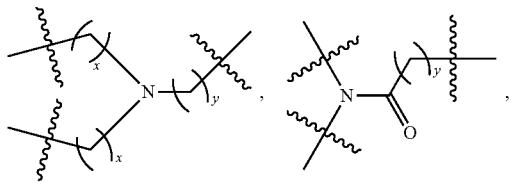

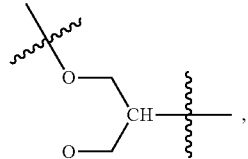

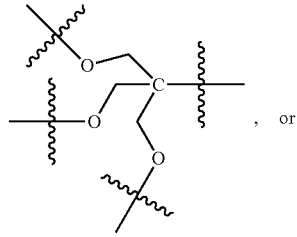

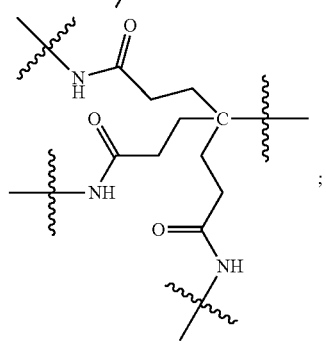

each L⁵ is —NHCO—C₁₋₆-alkylene-, —CONH—C₁₋₆-alkylene-, —C₁₋₆-alkylene-,

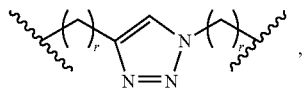

or —(OCH₂CH₂)$_r$—;

each L⁶ is —NHCO—C₁₋₆-alkylene-, —CONH—C₁₋₆-alkylene-, —C₁₋₆-alkylene-, or —(OCH₂CH₂)$_s$—;

each L⁷ is —NHCO—C₁₋₆-alkylene-, —CONH—C₁₋₆-alkylene-, —C₁₋₆-alkylene-, —(OCH₂CH₂)$_t$—, or —OCH₂—;

p, q, r, s, and t are each independently an integer of 1 to 20; a is 1 or 2; b, c, d, e, f, and g are each independently 0, 1, or 2; u, v, w, x, y, and z are each independently 1, 2, 3, 4, 5, or 6;

n is an integer of 1 to 5; wherein when d is 0, n is 1, when d is 1, n is an integer of 1 to 3, and when d is 2, n is an integer of 1 to 5;

m is an integer from 1 to 8;

Z is selected from the group consisting of

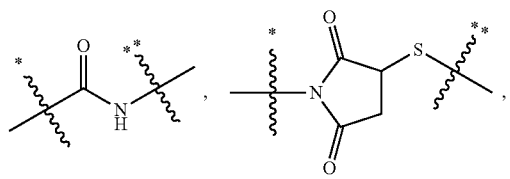

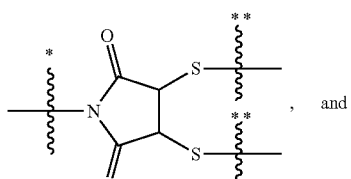
, and
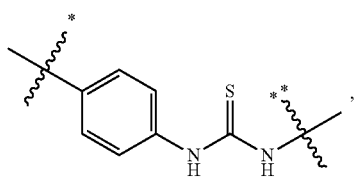
,
wherein ⸸ represents the point of attachment to L, wherein ** ⸸ represents the point of attachment to
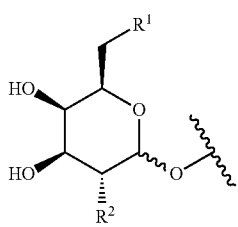
;
and
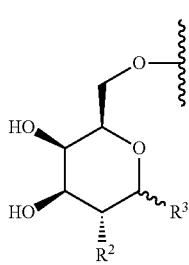
is an antibody.
Clause 47. The conjugate of any one of clauses 44 to 46, wherein each X is independently selected from formula (III-a) to (III-j):
(III-a)
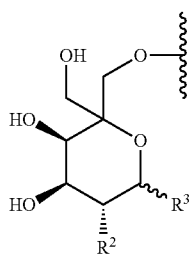
(III-b)
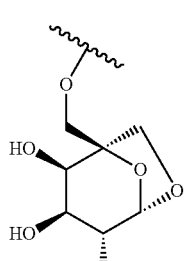
(III-c)
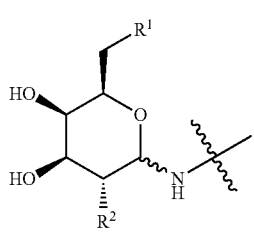
(III-d)
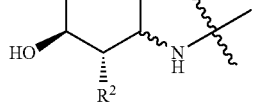
(III-e)
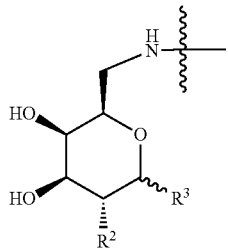
(III-f)
(III-g)
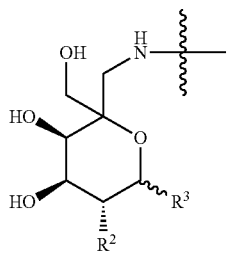
(III-h)
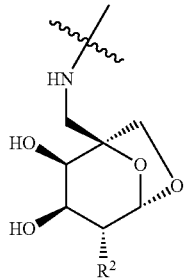

-continued

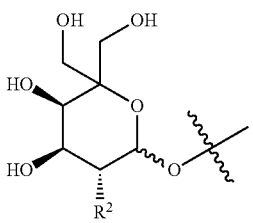
(III-i)

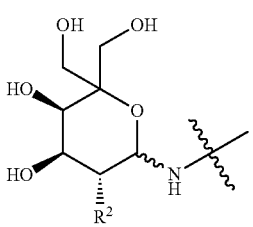
(III-j)

wherein:

R¹ is selected from —OH, —OC(O)R, and

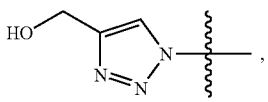

wherein R is $C_{1-6}$ alkyl;

R² is selected from —NHCOCH₃, —NHCOCF₃, —NHCOCH₂CF₃, —OH, and

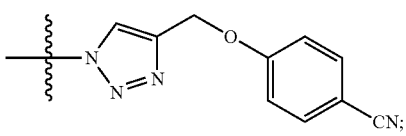

and

R³ is selected from —H, —OH, —CH₃, —OCH₃, and —OCH₂CH=CH₂.

Clause 48. The conjugate of clause 47, wherein X is:

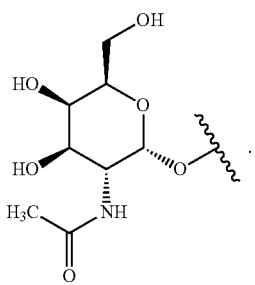 [SMILES: *O[C@H]1O[C@H](CO)[C@H](O)[C@H](O)[C@H]1NC(C)=O]

Clause 49. The conjugate of clause 47, wherein X is:

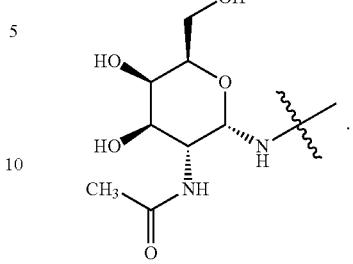

Clause 50. A pharmaceutical composition comprising the conjugate or pharmaceutically acceptable salt of any one of clauses 44 to 50, and a pharmaceutically acceptable carrier.

Clause 51. The pharmaceutical composition of clause 50, wherein m is an integer of 4 to 8.

Clause 52. The pharmaceutical composition comprising the conjugate or pharmaceutically acceptable salt of clause 51, wherein m is 4.

Clause 53. The conjugate of any one of clauses 44 to 49, wherein the antibody is an IgG antibody.

Clause 54. The conjugate of any one of clauses 44 to 49, wherein the antibody is a humanized antibody.

Clause 55. The conjugate of any one of clauses 44 to 49, wherein the antibody specifically binds to a secreted or soluble protein.

Clause 56. The conjugate of any one of clauses 44 to 49, wherein the antibody specifically binds to a cell surface receptor.

Clause 57. The conjugate of any one of clauses 44 to 49, wherein the antibody specifically binds to programmed death ligand-1 (PD-L¹) protein.

Clause 58. The conjugate of any one of clauses 44 to 49, wherein the antibody specifically binds to Vascular Endothelial Growth Factor (VEGF) protein.

Clause 59. The conjugate of any one of clauses 44 to 49, wherein the antibody specifically binds to a Fibroblast Growth Factor Receptor 2 (FGFR2) protein or a Fibroblast Growth Factor Receptor 3 (FGFR3) protein.

Clause 60. The conjugate of any one of clauses 44 to 49, wherein the antibody is cetuximab.

Clause 61. The conjugate of any one of clauses 44 to 49, wherein the antibody is matuzumab.

Clause 62. The conjugate of any one of clauses 44 to 49, wherein the antibody is atezolizumab.

Clause 63. A method of treating a disease or disorder by administering to a subject in need thereof an effective amount of the conjugate or pharmaceutically acceptable salt of any one of clauses 44 to 49 or the pharmaceutical composition of any one of clauses 50 to 52.

Clause 64. The method of clause 63, wherein the disease or disorder is an inflammatory disease.

Clause 65. The method of clause 63, wherein the disease or disorder is an autoimmune disease.

Clause 66. The method of clause 63, wherein the disease or disorder is a cancer.

Clause 67. A cell surface ASGPR binding compound of formula (I):

$$X_n\text{-L-Y} \qquad (I)$$

or a prodrug thereof, or a salt thereof, wherein:

Y is a moiety of interest;
n is 1 to 500;
L is a linker; and

X is a moiety that binds to a cell surface asialoglycoprotein receptor (ASGPR) of formula (Ia):

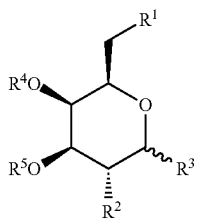

(Ia)

wherein:
  $R^1$ is selected from —OH, —OC(O)R, —C(O)NHR, —$Z^1$—*, and optionally substituted triazole, where R is optionally substituted $C_{1-6}$ alkyl or optionally substituted aryl;
  $R^2$ is selected from —NHCOCH$_3$, —NHCOCF$_3$, —NHCOCH$_2$CF$_3$, —OH, optionally substituted triazole, and —$Z^1$—*;
  $R^3$ is selected from —H, —OH, —CH$_3$, —OCH$_3$, —OCH$_2$CH=CH and —$Z^1$—*;
  one of $R^1$ to $R^3$ is —$Z^1$—*, wherein "*" represents a point of attachment of $Z^1$ to the linker (L);
  $R^4$ and $R^5$ are each independently selected from H, and a promoiety (e.g., an ester promoiety);
  $Z^1$ is a linking moiety selected from $Z^{11}$, optionally substituted $Z^{11}$-heteroaryl, optionally substituted $Z^{11}$-aryl, optionally substituted heteroaryl, optionally substituted aryl, optionally substituted amide, optionally substituted sulfonamide, optionally substituted urea, and optionally substituted thiourea;
  $Z^{11}$ is selected from —O—, —S—, $NR^{21}$—, and —$C(R^{22})_2$,
  each $R^{21}$ is independently selected from H, and optionally substituted ($C_1$-$C_6$)alkyl; and
  each $R^{22}$ is independently selected from H, halogen (e.g., F) and optionally substituted ($C_1$-$C_6$)alkyl;
wherein:
  i) when n is 3, $R^1$ is OH, $R^2$ is —NHCOCH$_3$, $R^4$-$R^5$ are H, and $R^3$ is $Z^1$, then $Z^1$ is not O;
  ii) when n is 2 or 3, $R^1$ is OAc, $R^2$ is —NHCOCH$_3$, $R^4$-$R^5$ are Ac, and $R^3$ is $Z^1$, then $Z^1$ is not O;
  iii) when n is 2 or 3, $R^1$ is OBz, $R^2$ is —NHCOCH$_3$, $R^4$-$R^5$ are Bz, and $R^3$ is $Z^1$, then $Z^1$ is not O;
  iv) when n is 3, $R^1$ is OH, $R^2$ is —NHCOCH$_3$, $R^4$-$R^5$ are H, and $R^3$ is $Z^1$, and $Z^1$ is O, then L comprises a backbone of at least 16 consecutive atoms to a branching point; and/or
  v) when n is 3, $R^1$ is $Z^1$, where $Z^1$ is O, and $R^4$-$R^5$ are H, then $R^3$ is not —CH$_3$.

6. EXAMPLES

The examples in this section are offered by way of illustration, and not by way of limitation.

6.1. Preparation of Compounds

The following are illustrative schemes and examples of how the compounds described herein can be prepared and tested. Although the examples can represent only some embodiments, it should be understood that the following examples are illustrative and not limiting. All substituents, unless otherwise specified, are as previously defined. The reagents and starting materials are readily available to one of ordinary skill in the art. The specific synthetic steps for each of the routes described may be combined in different ways, or in conjunction with steps from different schemes, to prepare the compounds described herein.

Examples 1-54: Preparation of ASGPR Ligand-Linker Examples

Example 1: Synthesis of [(2R,3R,4R,5R,6R)-3,4-bis(acetyloxy)-6-(but-3-yn-1-yloxy)-5-acetamidooxan-2-yl]methyl acetate (Intermediate A)

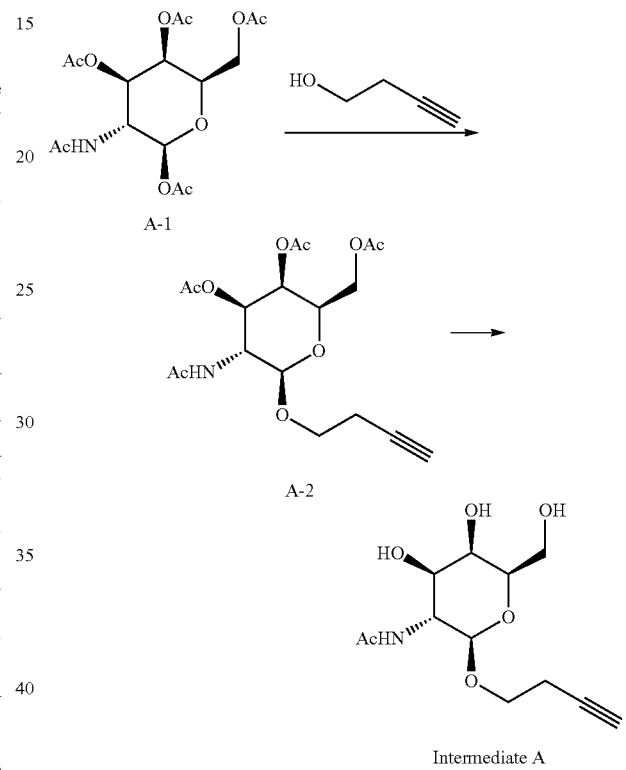

Intermediate A

To an activated 4 Å molecular sieves (5.0 g) and [(2R,3R,4R,5R,6S)-3,4,6-tris(acetyloxy)-5-acetamidooxan-2-yl]methyl acetate (A-1) (5.0 g, 12.8 mmol), was added dichloromethane (50 mL) and stirred at room temperature for 5 min followed by addition of but-3-yn-1-ol (2.92 mL, 3.0 eq., 38.5 mmol). Stirred the reaction mixture for 10 min at room temperature and then cooled to 0° C. Diethyl trifluoroborinate (4.75 mL, 38.5 mmol) added dropwise to above reaction mixture and again stirred for 10 min at room temperature followed by 5 h refluxing at 51° C. TLC checked for the completion of reaction and triethylamine added to quench the diethyl trifluoroborinate (up to neutral pH) and filtered through celite bed followed by concentration on rotary evaporator. Obtained thick residue was purified by silica gel column purification with 60-75% ethyl acetate in dichloromethane as eluent that afforded Intermediate A-2 as an off white foam. Yield: 4.50 g, 87%; $R_f$=0.45 (7.5% methanol in dichloromethane); LC-MS m/z 400.0 [M+1]$^+$; $^1$H NMR (400 MHz, CDCl$_3$) δ 5.44 (d, J=8.6 Hz, 1H), 5.35 (d, J=7.0 Hz, 1H), 5.30 (dd, J=11.2, 3.0 Hz, 1H), 4.79 (d, J=8.2 Hz, 1H), 4.14-4.09 (m, 2H), 3.99-3.90 (m, 3H), 3.71-3.65 (m, 1H), 2.49-2.47 (m, 2H), 2.14 (s, 3H), 2.05 (s, 3H), 2.00 (s, 3H), 1.96 (s, 3H).

Intermediate A-2 (7.8 g, 17.5 mmol) was dissolved in methanol (50 mL) and cooled to 0° C. Sodium methoxide 25% w/v (2.48 mL, 11.3 mmol) in methanol added dropwise to this solution and reaction maintained at room temperature for 3 h. TLC Checked and after completion of reaction 1N HCl was added drop-wise to quench the sodium methoxide. Methanol evaporated and obtained residue was washed with diethyl ether (30 mL×4). The crude residue obtained was purified with preparative HPLC (5-20% acetonitrile in water with 0.1% TFAH) to afford Intermediate A as a white solid. Yield: 2.6 g, 84%; LC-MS m/z 274.0 [M+1]$^+$; $^1$H NMR (400 MHz, D$_2$O) δ 4.58 (d, J=8.4 Hz, 1H), 3.97-3.86 (m, 3H), 3.82-3.73 (m, 5H), 2.49-2.44 (m, 2H), 2.04 (s, 3H).

Example 2: Synthesis of N-((2R,3R,4R,5R,6R)-6-((but-3-yn-1-yloxy)methyl)-2,4,5-trihydroxytetrahydro-2H-pyran-3-yl)acetamide (Intermediate B)

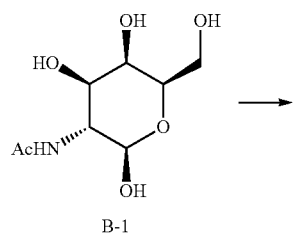

B-1

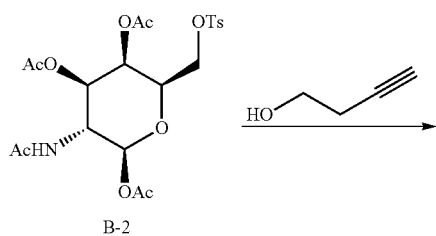

B-2

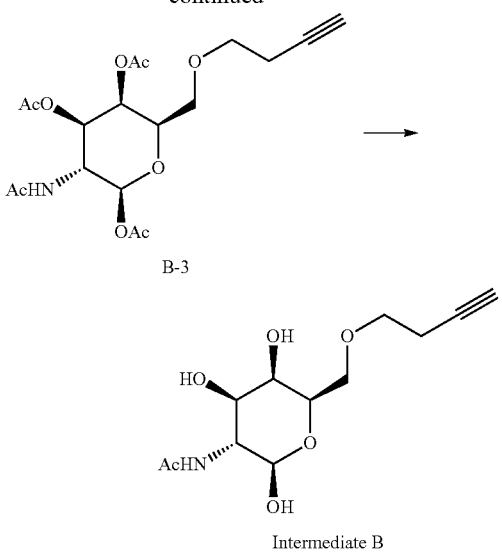

B-3

Intermediate B

A solution of p-toluenesulfonyl chloride (1.1 eq.) in dichloromethane is added slowly to a stirred solution of N-((2R,3R,4R,5R,6R)-2,4,5-trihydroxy-6-(hydroxymethyl)tetrahydro-2H-pyran-3-yl)acetamide (B-1) (1 eq.) in dichloromethane at 0° C. The reaction mixture is warmed to room temperature and monitored by LC-MS to indicate complete formation of the desired primary alcohol tosylate. Pyridine (3.5 eq.) is added followed by acetic anhydride (3.1 eq.). The reaction mixture is stirred at room temperature and monitored by LC-MS to indicate complete formation of Intermediate B-2, which is isolated by silica gel chromatography. Sodium hydride (1.1 eq.) is added to a stirred solution of but-3-yn-1-ol (1.1 eq.) in tetrahydrofuran at 0° C. After stirring at 0° C. for 10 min a solution of Intermediate B-2 (1 eq.) in tetrahydrofuran is added. The resulting mixture is warmed to room temperature and monitored by LC-MS to indicate complete formation of Intermediate B-3, which is isolated by silica gel chromatography. Sodium methoxide in methanol (3 eq.) is added to a stirred solution of Intermediate B-3 (1 eq.) in methanol at 0° C. The resulting mixture is stirred at 0° until LC-MS indicates complete conversion to Intermediate B, which is isolated by reverse phase chromatography.

Example 3: Synthesis of Trivalent GalNAc Ligand a Perfluorophenyl Ester (Compound I-107)

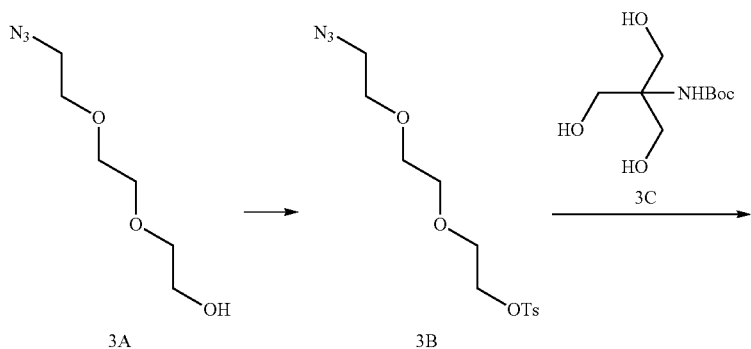

-continued
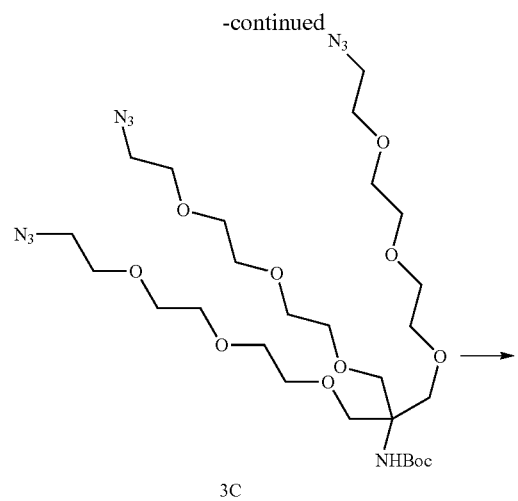
3C
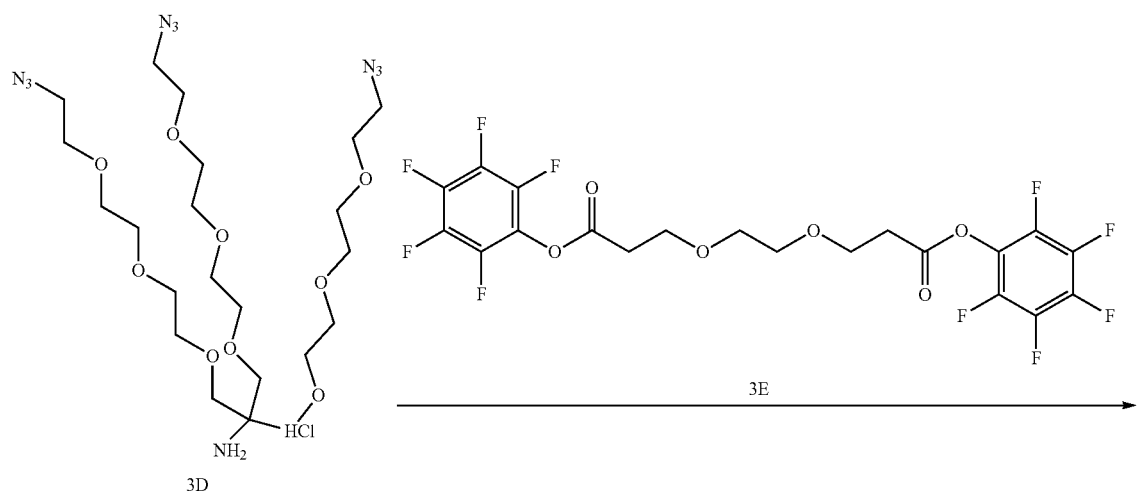
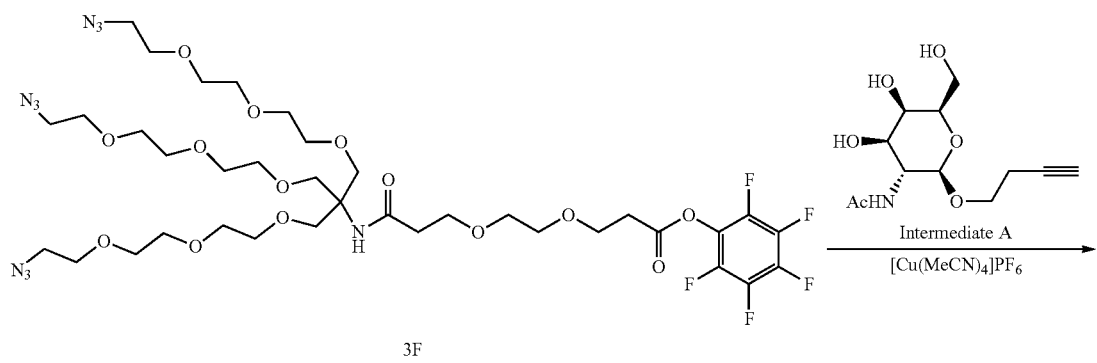

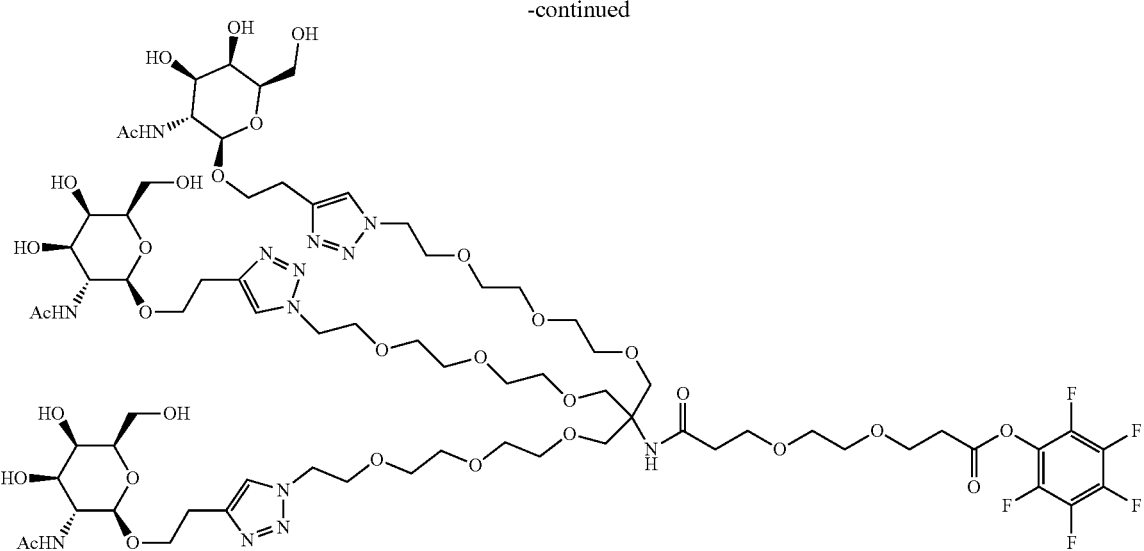

I-107

A solution of p-toluenesulfonyl chloride (1.1 eq.) in dichloromethane is added to a stirred solution of 2-(2-(2-azidoethoxy)ethoxy)ethan-1-ol (3A) (1 eq.) and pyridine (1.2 eq.) in dichloromethane. The resulting mixture is stirred at room temperature and monitored by LC-MS to indicate complete formation of Compound 3B, which is isolated by silica gel chromatography. Sodium hydride is added to a stirred mixture of tert-butyl (1,3-dihydroxy-2-(hydroxymethyl)propan-2-yl)carbamate (3C) (1 eq.) and Compound 3B (3.3 eq.) in THF at −78° C. The cold bath is removed and the resulting mixture is stirred at room temperature until LC-MS indicates complete conversion to Compound 3C, which is isolated by silica gel chromatography. HCl in diethyl ether (3 eq.) is added to a stirred solution of tert-Compound 3C (1 eq.) in dichloromethane at room temperature. The resulting mixture is stirred at room temperature until LC-MS indicates complete conversion and then volatiles are removed on a rotary evaporator to afford Compound 3D. Diisopropylethylamine (2 eq.) is added to a stirred solution of Compound 3D (1 eq.) in dichloromethane at room temperature. Bis (perfluorophenyl) 3,3'-(ethane-1,2-diylbis(oxy))dipropionate (3E) (1.1 eq.) is added and the resulting mixture is stirred at room temperature until LC-MS indicates complete conversion to Compound 3F, which is isolated by silica gel chromatography. Compound 3F (1 eq.) and Intermediate A (1 eq.) are dissolved with stirring in DMSO at room temperature. Tetrakis(acetonitrile)copper(I) tetrafluoroborate (3 eq.) is added and the resulting mixture is stirred at room temperature until LC-MS indicates complete conversion to Compound I-107, which is purified via reverse-phase preparatory HPLC followed by lyophilization.

Example 4: Synthesis of Trivalent GalNAc Ligand B Perfluorophenyl Ester (Compound I-108)

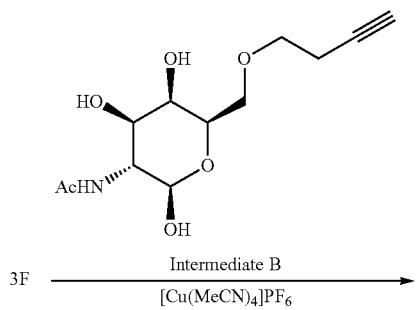

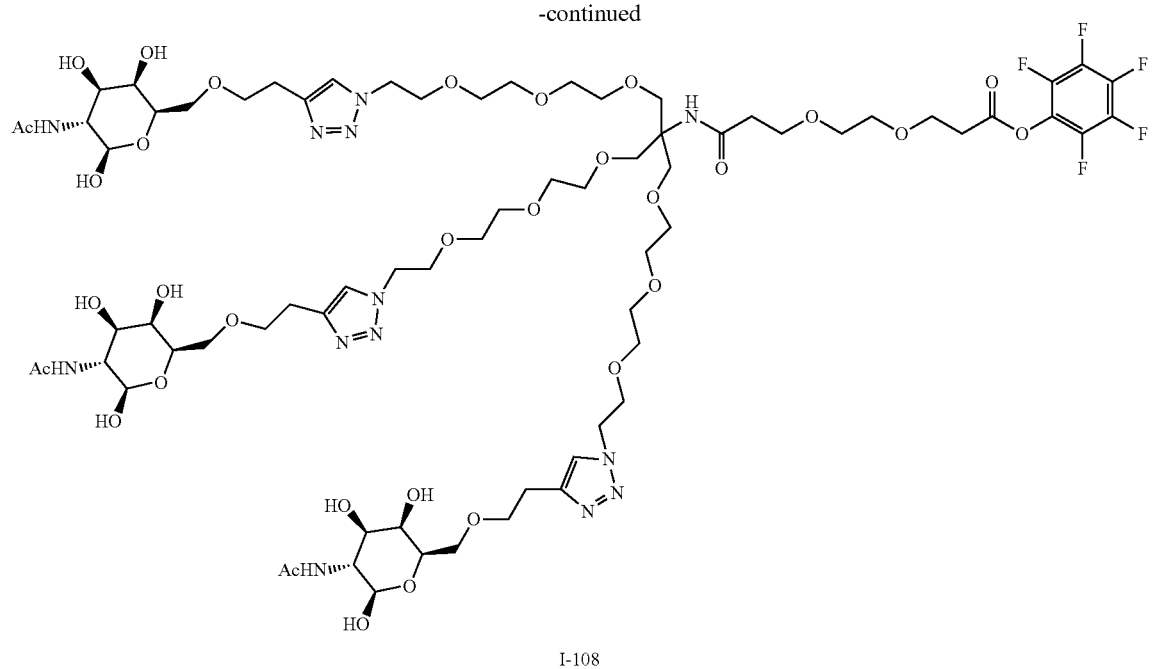

I-108

Compound 3F (1 eq.) and Intermediate B (1 eq.) are dissolved with stirring in DMSO at room temperature. Tetrakis(acetonitrile)copper(I) tetrafluoroborate (3 eq.) is added and the resulting mixture is stirred at room temperature until LC-MS indicates complete conversion to Compound I-108, which is purified via reverse-phase preparatory HPLC followed by lyophilization.

Example 5: Synthesis of Divalent GalNAc Ligand a Perfluorophenyl Ester (Compound I-109)

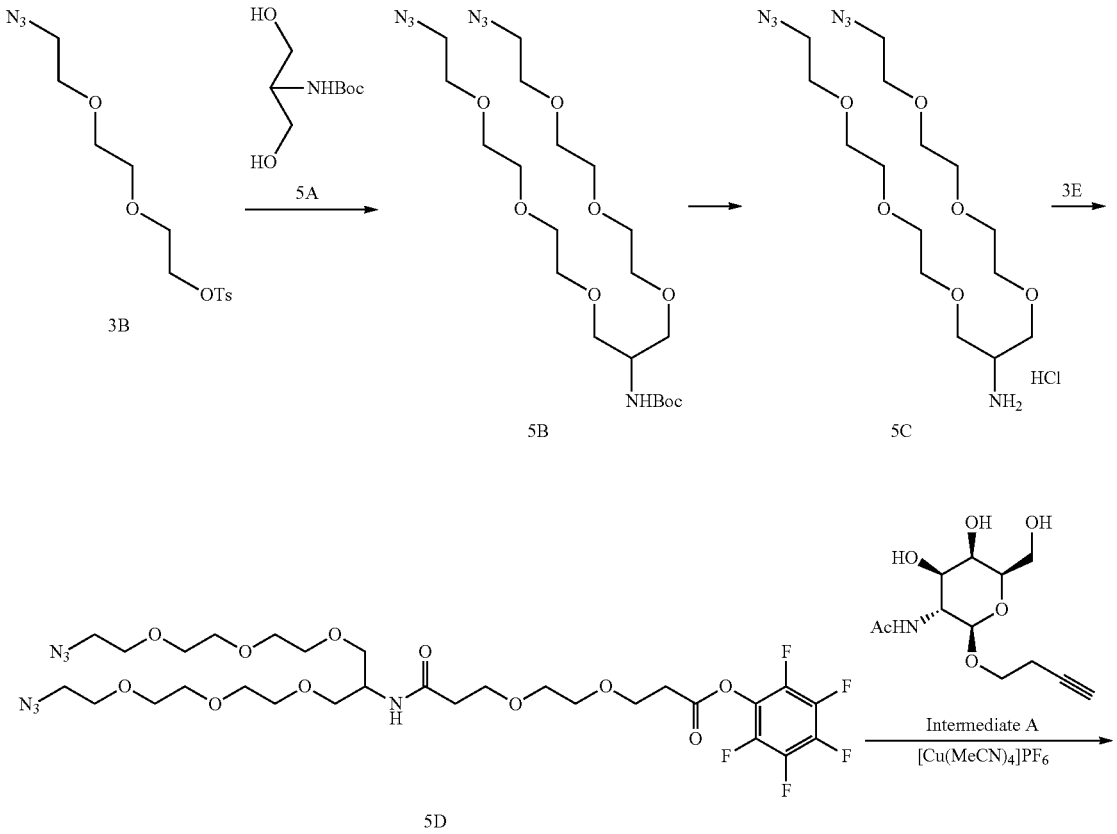

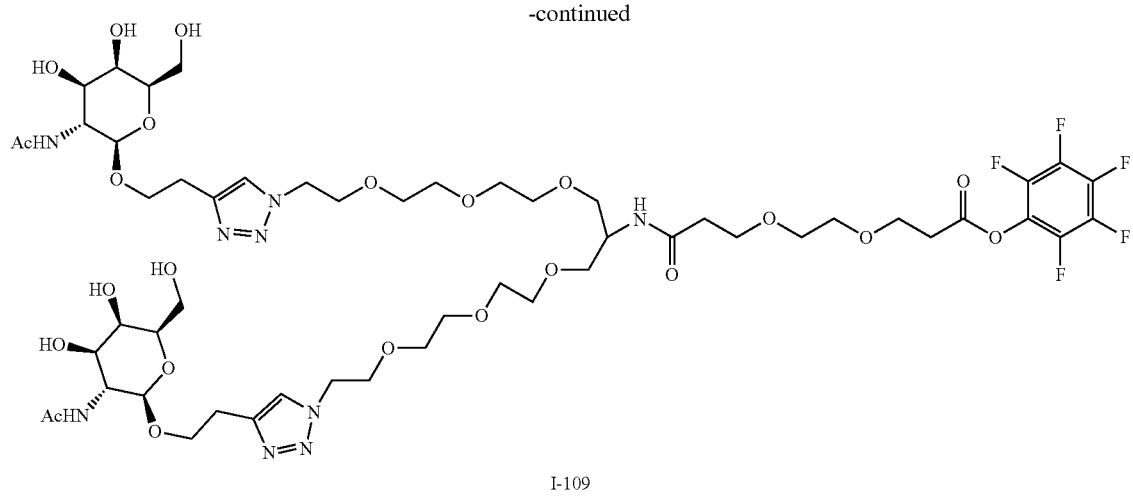

I-109

Sodium hydride is added to a stirred mixture of tert-butyl (1,3-dihydroxypropan-2-yl)carbamate (5A) (1 eq.) and Compound 3B (3.3 eq.) in THF at −78° C. The cold bath is removed and the resulting mixture is stirred at room temperature until LC-MS indicates complete conversion to Compound 5B, which is isolated by silica gel chromatography. HCl in diethyl ether (3 eq.) is added to a stirred solution of Compound 5B (1 eq.) in dichloromethane at room temperature. The resulting mixture is stirred at room temperature until LC-MS indicates complete conversion and then volatiles are removed on a rotary evaporator to afford Compound 5C. Diisopropylethylamine (2 eq.) is added to a stirred solution of Compound 5C (1 eq.) in dichloromethane at room temperature. Bis(perfluorophenyl) 3,3'-(ethane-1,2-diylbis(oxy))dipropionate (Compound 3E) (1.1 eq.) is added and the resulting mixture is stirred at room temperature until LC-MS indicates complete conversion to Compound 5D, which is isolated by silica gel chromatography. Compound 5D (1 eq.) and Intermediate A (1 eq.) are dissolved with stirring in DMSO at room temperature. Tetrakis(acetonitrile)copper(I) tetrafluoroborate (3 eq.) is added and the resulting mixture is stirred at room temperature until LC-MS indicates complete conversion to Compound I-5, which is purified via reverse-phase preparatory HPLC followed by lyophilization.

Following the above synthesis, 41 mg of Compound I-109 was obtained. LC-MS m/z 1336.7 [M+1]+; 1 HNMR (400 MHz, $D_2O$) d 7.87 (s, 2H), 4.65-4.61 (m, 4H), 4.47 (d, J=8.0 Hz, 2H), 4.23-4.11 (m, 2H), 4.01-3.91 (m, 10H), 3.88-3.82 (m, 10H), 3.81 (s, 1H), 3.79-3.77 (m, 4H), 3.76-3.73 (m, 12H), 3.72-3.68 (m, 14H). 3.63-3.55 (m, 6H), 3.09 (t, J=6.0 Hz, 2H), 3.00 (t, J=6.4 Hz, 4H), 1.88 (s, 6H).

Example 6: Synthesis of Divalent GalNAc Ligand B Perfluorophenyl Ester (Compound I-110)

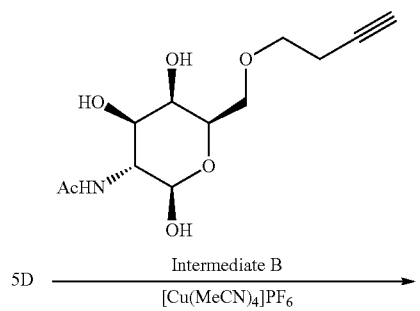

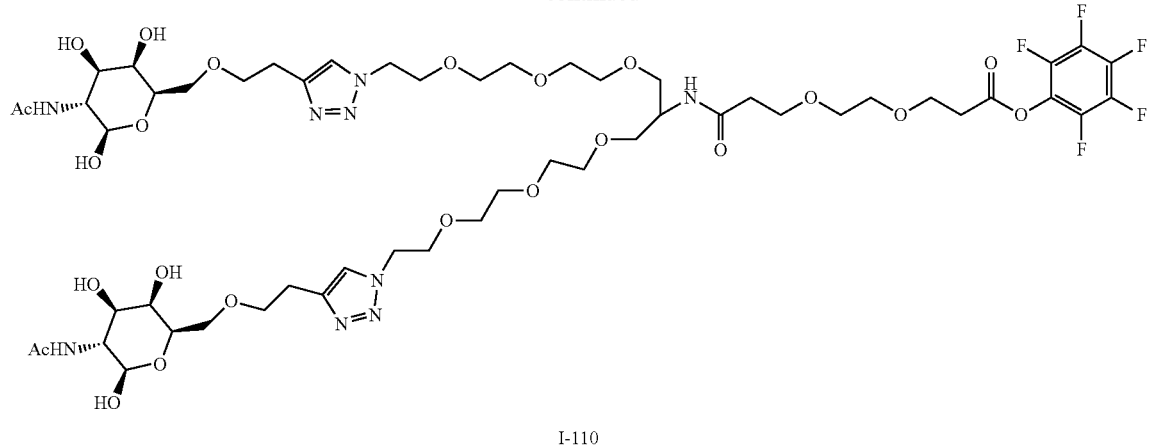

I-110

Compound 5D (1 eq.) and Intermediate B (1 eq.) are dissolved with stirring in DMSO at room temperature. Tetrakis(acetonitrile)copper(I) tetrafluoroborate (3 eq.) is added and the resulting mixture is stirred at room temperature until LC-MS indicates complete conversion to Compound I-110, which is purified via reverse-phase preparatory HPLC followed by lyophilization.

Example 7: Synthesis of perfluorophenyl 1-(4-(2-(42R,3R,4R,5R,6R)-3-acetamido-4,5-dihydroxy-6-(hydroxymethyl)tetrahydro-2H-pyran-2-yl)oxy)ethyl)-1H-1,2,3-triazol-1-yl)-12-(2-(2-(2-(2-(4-(2-(((2R,3R,4R,5R,6R)-3-acetamido-4,5-dihydroxy-6-(hydroxymethyl)tetrahydro-2H-pyran-2-yl)oxy)ethyl)-1H-1,2,3-triazol-1-yl)ethoxy)ethoxy)ethoxy)ethyl)-3,6,9,15,18,21-hexaoxa-12-azatetracosan-24-oate (divalent GalNAc ligand A perfluorophenyl ester, Compound I-111)

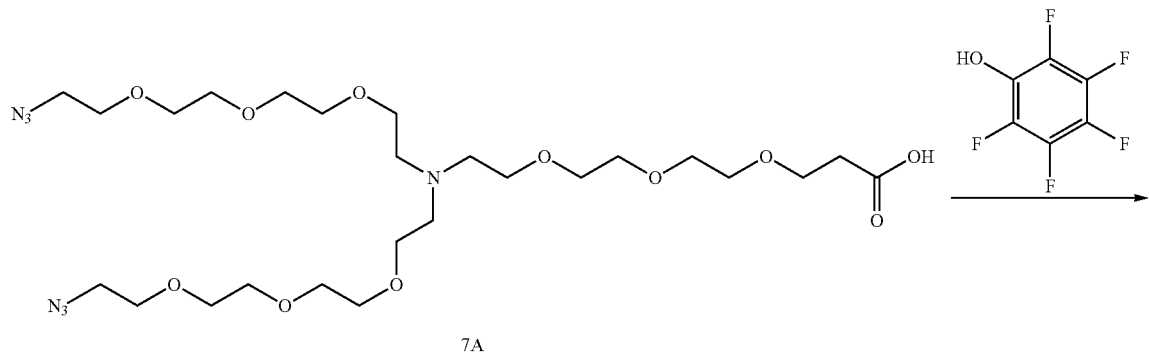

7A

7B  →  Intermediate A
(PFP ester of 7A)  [Cu(MeCN)₄]PF₆

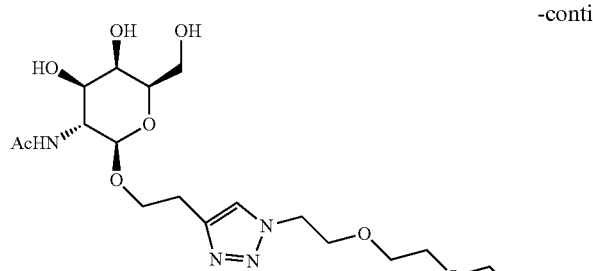

I-111

To a solution of perfluorophenyl 1-azido-12-(2-(2-(2-(2-azidoethoxy)ethoxy)ethoxy)ethyl)-3,6,9,15,18,21-hexaoxa-12-azatetracosan-24-oate (7B, 1.0 eq, 0.050 g, 0.063 mmol) and N-42R,3R,4R,5R,6R)-2-(but-3-yn-1-yloxy)-4,5-dihydroxy-6-(hydroxymethyl)tetrahydro-2H-pyran-3-yl)acetamide (Intermediate A, 2.0 eq, 0.034 g, 0.127 mmol) in dimethyl sulfoxide (2 mL), tetrakis(acetonitrile)copper(I) hexafluorophosphate (5.0 eq, 0.118 g, 0.317 mmol) was added and reaction mixture was stirred at room temperature for 1 h. After completion, reaction mixture was diluted with acetonitrile and purified by prep HPLC (45-75% acetonitrile in water with 0.1% trifluoroacetic acid). Fractions containing the desired compound were combined and lyophilized to afford perfluorophenyl 1-(4-(2-(42R,3R,4R,5R,6R)-3-acetamido-4,5-dihydroxy-6-(hydroxymethyl)tetrahydro-2H-pyran-2-yl)oxy)ethyl)-1H-1,2,3-triazol-1-yl)-12-(2-(2-(2-(2-(4-(2-(((2R,3R,4R,5R,6R)-3-acetamido-4,5-dihydroxy-6-(hydroxymethyl)tetrahydro-2H-pyran-2-yl)oxy)ethyl)-1H-1,2,3-triazol-1-yl)ethoxy)ethoxy)ethoxy)ethyl)-3,6,9,15,18,21-hexaoxa-12-azatetracosan-24-oate (Compound I-111) as a thick syrup. Yield: 0.044 g, 52.01%; LCMS m/z 1336.70 [M+1]$^+$; $^1$H-NMR (400 MHz, D$_2$O) δ 7.86 (s, 2H), 4.65-4.61 (m, 4H), 4.47 (d, J=8.0 Hz, 2H), 4.22-4.16 (m, 2H), 4.10-3.91 (m, 10H), 3.92-3.82 (m, 10H), 3.82-3.79 (m, 4H), 3.75-3.62 (m, 26H), 3.59-3.57 (m, 6H), 4.47 (t, J=6.0 Hz, 2H), 2.99 (t, J=5.6 Hz, 4H), 1.87 (s, 6H).

Example 8: Synthesis of GalNac Ligand a Perfluorophenyl Ester (Compound I-112)

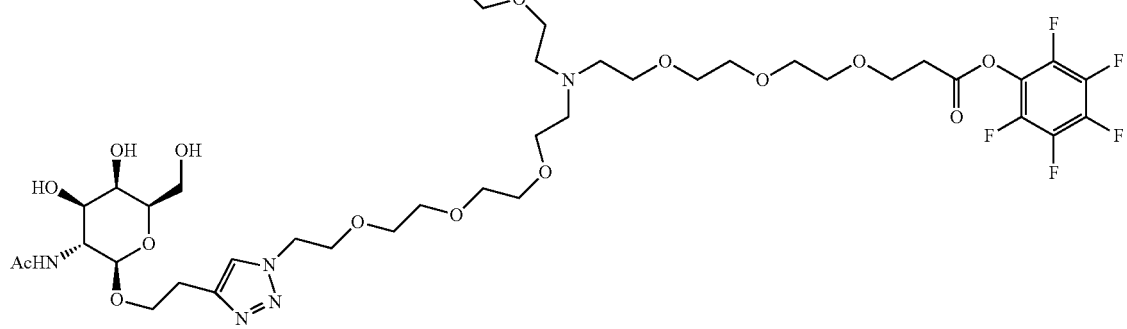

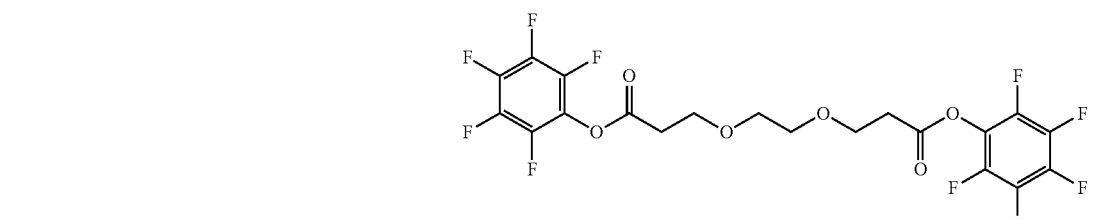

8A

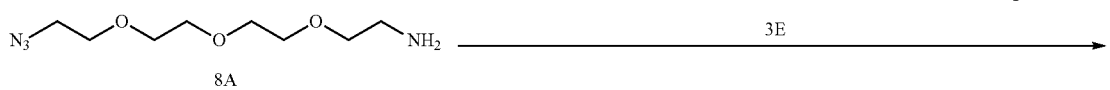

8B

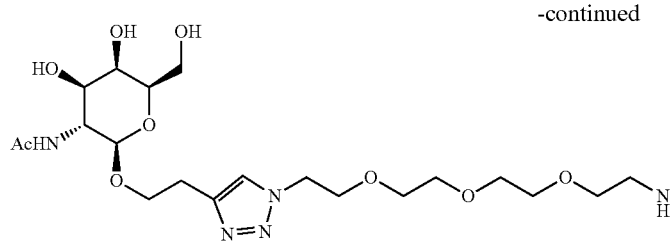

I-112

To a solution of Compound 3E (1.0 eq, 0.50 g, 0.929 mmol) in tetrahydrofuran (5 mL, 10 vol.) was added Compound 8A (1.0 eq, 0.203 g, 0.929 mmol) and N,N-diisopropylethylamine (2.0 eq, 0.34 mL, 1.86 mmol). The reaction mixture was allowed to stir at room temperature for 2 h. The progress of reaction was monitored by LCMS. When complete, the reaction mixture was diluted with acetonitrile and purified by reverse-phase preparative HPLC (55-65% acetonitrile in water with 0.1% TFA). Fractions containing the desired product were combined and lyophilized to dryness to afford perfluorophenyl 1-azido-13-oxo-3,6,9,16,19-pentaoxa-12-azadocosan-22-oate (Compound 8B) as a colorless viscous liquid. Yield: 0.130 g, 23%; LCMS m/z 573.25 [M+1]+.

To a solution of Compound 8B (1.0 eq, 0.070 g, 0.122 mmol) in dimethyl sulfoxide (2 mL) was added Intermediate A (1.0 eq, 0.0334 g, 0.122 mmol). The reaction mixture was stirred for 5 minutes prior to addition of tetrakis(acetonitrile)copper(I) hexafluorophosphate (2.5 eq, 0.100 g, 0.306 mmol). The reaction mixture was stirred at room temperature for 1 h. The progress of reaction was monitored by LCMS. After completion, reaction mixture was diluted with acetonitrile and purified by preparative HPLC (35-55% acetonitrile in water with 0.1% TFA). Fractions containing the desired product were combined and lyophilized to dryness to afford the Compound I-112 as a colorless viscous liquid. Yield: 0.015 g, 14.5%; LCMS m/z 846.33 [M+1]+; 1H NMR (400 MHz, $D_2O$) 7.83 (s, 1H), 4.60-4.58 (m, 2H), 4.43 (d, J=8.4 Hz, 1H), 4.17-4.13 (m, 1H), 3.97-3.90 (m, 5H), 3.88-3.72 (m, 6H), 3.70-3.49 (m, 16H), 3.37-3.34 (m, 2H), 3.05 (t, J=6.0 Hz, 2H), 2.96 (t, J=6.0 Hz, 2H), 2.50 (t, J=6.0 Hz, 2H), 1.84 (s, 3H).

Example 9: Synthesis of perfluorophenyl 1-(4-(2-(((2R,3R,4R,5R,6R)-5-acetamido-3,4,6-trihydroxytetrahydro-2H-pyran-2-yl)methoxy)ethyl)-1H-1,2,3-triazol-1-yl)-13-oxo-3,6,9,16,19-pentaoxa-12-azadocosan-22-oate (Compound I-113)

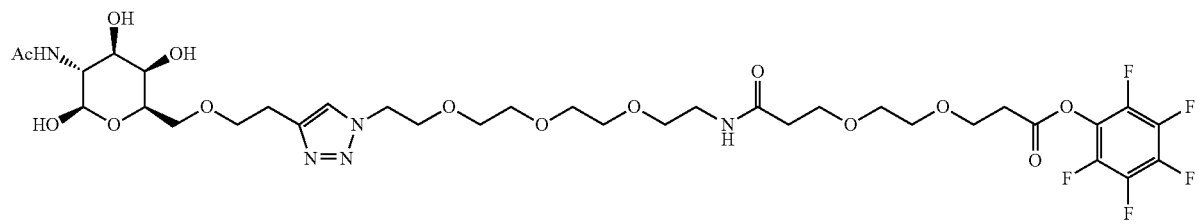

I-113

Compound I-113 is prepared by adapting the procedure for the synthesis of I-112 to substitute Intermediate A for Intermediate B.

Example 10: Synthesis of Compounds I-114-I-118

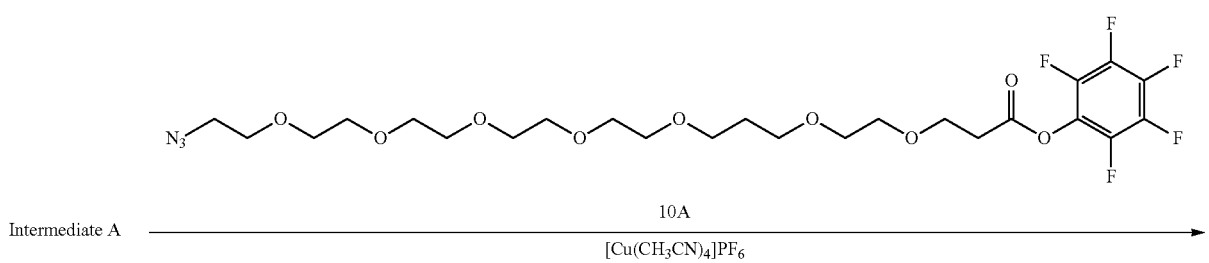

-continued

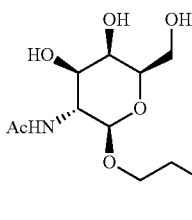 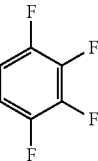

I-114

To a solution of perfluorophenyl 1-azido-3,6,9,12,15,18-hexaoxahenicosan-21-oate (10A) (1.0 eq, 0.0998 g, 0.183 mmol) in dimethyl sulfoxide (1 mL), Intermediate A (1.0 eq, 0.050 g, 0.183 mmol) was added and stirred for 5 minutes. Then, tetrakis(acetonitrile)copper(I) hexafluorophosphate (2.5 eq, 0.170 g, 0.457 mmol) was added and reaction mixture was stirred at room temperature for 1 h. The progress of reaction was monitored by LC-MS. After completion, reaction mixture was diluted with acetonitrile and purified by preparative HPLC (30-45% acetonitrile in water with 0.1% acetic acid). Fractions containing the desired product were combined and lyophilized to dryness to afford Compound I-114 as an off white solid. Yield: 0.022 g, 14.1%; LC-MS m/z 819.24 [M+1]$^+$; $^1$H NMR (400 MHz, D$_2$O) δ 7.81 (s, 1H), 4.57-4.55 (m, 2H), 4.40 (d, J=19.2 Hz, 1H), 4.16-4.11 (m, 1H), 3.94-3.85 (m, 6H), 3.80-3.73 (m, 3H), 3.71-3.59 (m, 22H), 3.04 (t, J=5.6 Hz, 2H), 2.94 (t, J=6.0 Hz, 2H), 1.81 (s, 3H).

Compounds I-115-I-118 were prepared by adapting the procedure for compound I-114. The structure and corresponding data for each of compounds I-115-I-118 is presented below:

| Compound # | Structure and Data |
|---|---|
| I-115 | 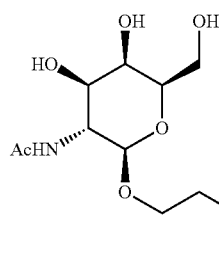 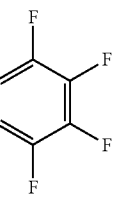<br>I-115<br>LC-MS m/z 731.2 [M + 1]$^+$<br>$^1$H NMR (400 MHz, D$_2$O) δ 7.82 (2, 1H), 4.60-4.57 (m, 2H), 4.43 (d, J = 8.1 Hz, 1H), 4.20-4.12 (m, 1H), 3.96-3.90 (m, 4H), 3.85-3.57 (m, 17H), 3.25-3.15 (m, 1H), 3.08-3.04 (m, 2H), 2.98-2.94 (m, 2H), 1.83 (s, 3H), 1.27 (t, J = 7.16, 2H) |
| I-116 | 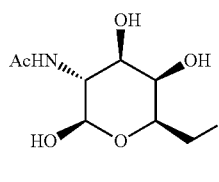 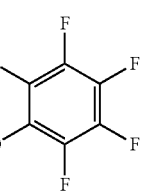<br>I-116 |

| Compound # | Structure and Data |
|---|---|
| I-117 | 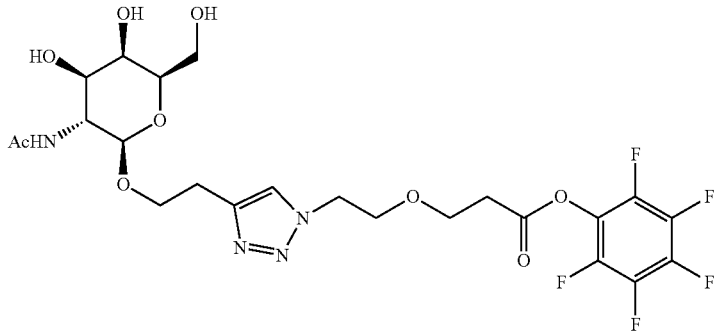

I-117

LC-MS m/z 599.1 [M + 1]$^+$ $^1$H NMR (400 MHz, D$_2$O) δ 7.75 (s, 1H), 4.78-4.57 (m, 2H), 4.39 (d, J = 8.1 Hz, 1H), 4.15-4.08 (m, 2H), 3.99 (t, J = 4.6 Hz, 2H), 3.90-3.86 (m, 3H), 3.81-3.72 (m, 4H), 3.67-3.64 (m, 2H), 2.97 (t, J = 5.6 Hz, 2H), 2.86 (t, J = 6.4 Hz, 2H), 1.83 (s, 3H). |
| I-118 | 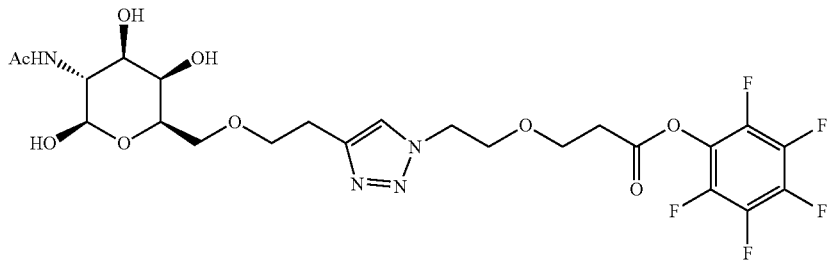

I-118 |

Example 11: Synthesis of Intermediate C

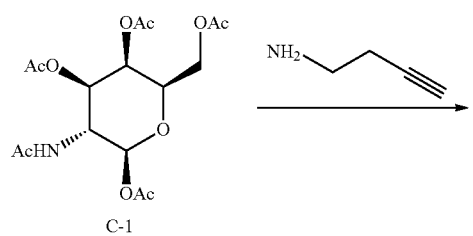

C-1

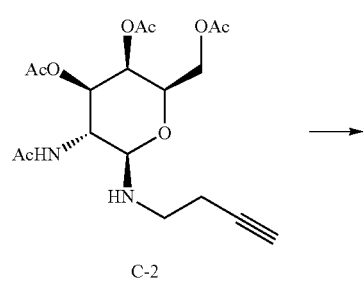

C-2

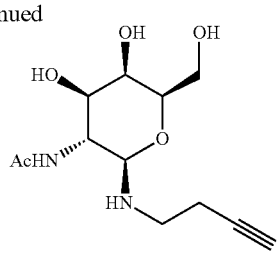

Intermediate C

To activated 4 Å molecular sieves and [(2R,3R,4R,5R, 6S)-3,4,6-tris(acetyloxy)-5-acetamidooxan-2-yl]methyl acetate (C-1) (1 eq.) is added dichloromethane. To the reaction solution is added but-3-yn-1-amine (3 eq). The reaction mixture is allowed to cool to 0° C. prior to the addition of diethyl trifluoroborinate (2 eq). The reaction is stirred at room temperature and then heated to refluxing for 16 h. Aqueous NaHCO$_3$ is added to quench the diethyl trifluoroborinate and the DCM layer is partitioned and dried over MgSO$_4$. The solution is filtered and concentrated on a rotary evaporator. Silica gel column purification with 60-75% ethyl acetate in dichloromethane as eluent is used to obtain Intermediate C-2.

Intermediate C-2 (1 eq.) is dissolved in methanol and cooled to 0° C. Sodium methoxide 25% w/v (10 eq) in methanol is added dropwise to this solution. The reaction is maintained at room temperature for 3 h. After completion of reaction IN HCl is added dropwise to quench the sodium methoxide. Methanol is evaporated and the obtained residue is washed with diethyl ether. The crude residue obtained is purified with preparative HPLC HPLC (5-20% acetonitrile in water with 0.1% TFAH) to afford Intermediate C.

Example 12: Synthesis of Compound I-120

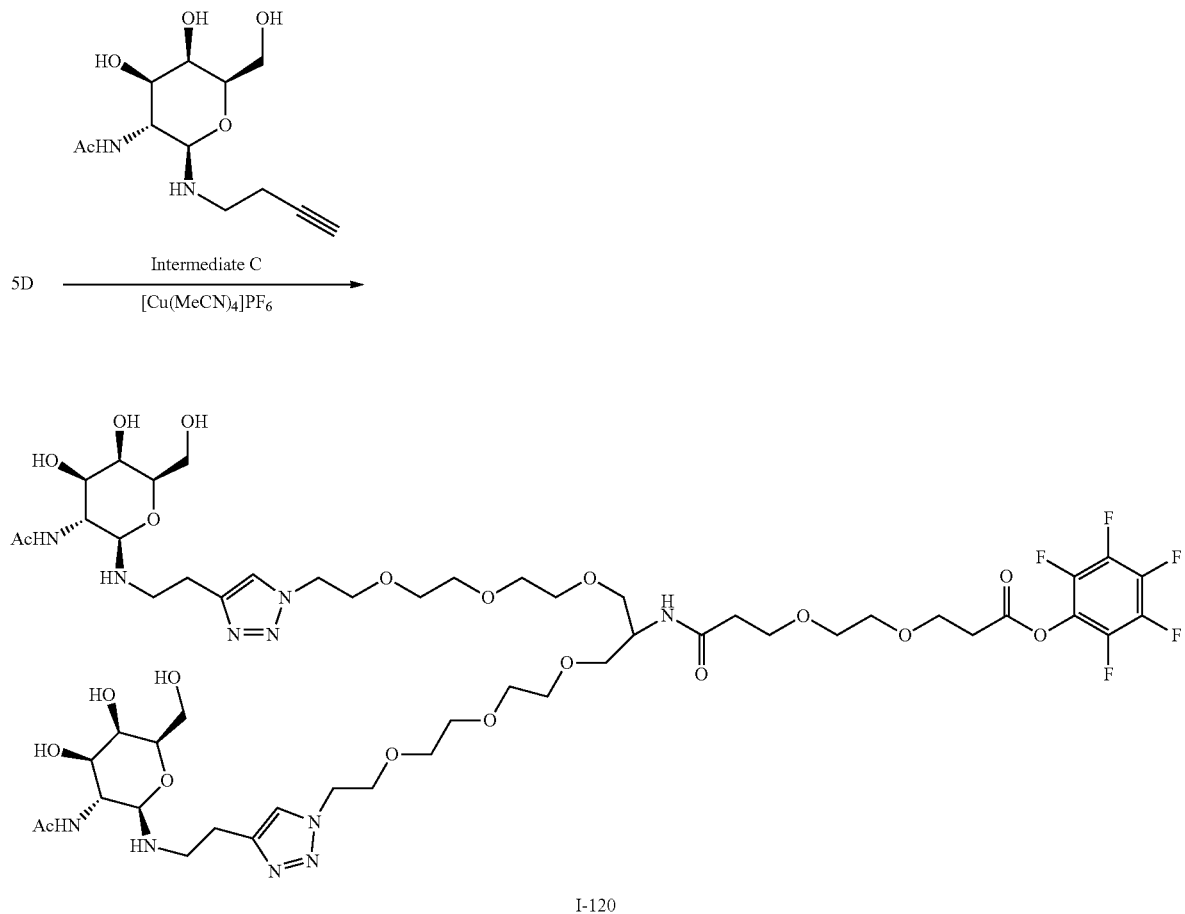

Compound 5D (1 eq.) and Intermediate C (1 eq.) are dissolved with stirring in DMSO at room temperature. Tetrakis(acetonitrile)copper(I) tetrafluoroborate (3 eq.) is added and the resulting mixture is stirred at room temperature until LC-MS indicates complete conversion to Compound I-120, which is purified via reverse-phase preparatory HPLC followed by lyophilization.

Example 13: Synthesis of Compound I-146

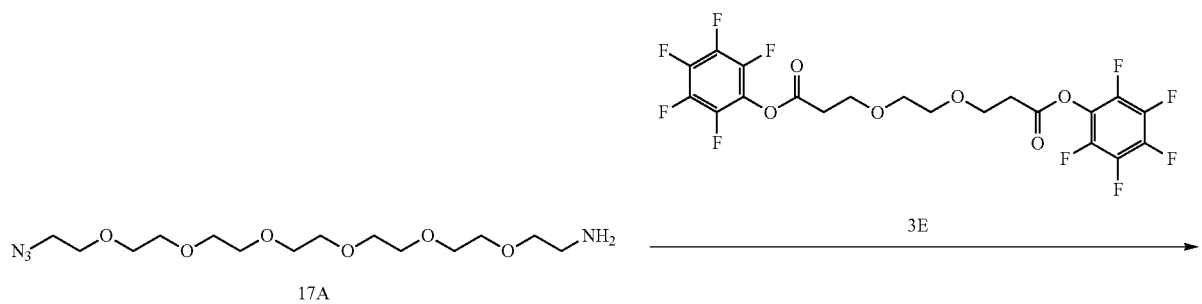

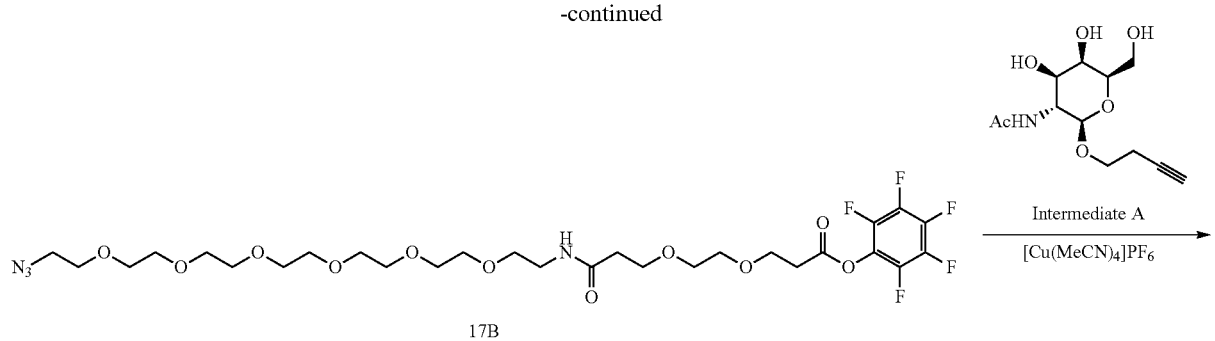
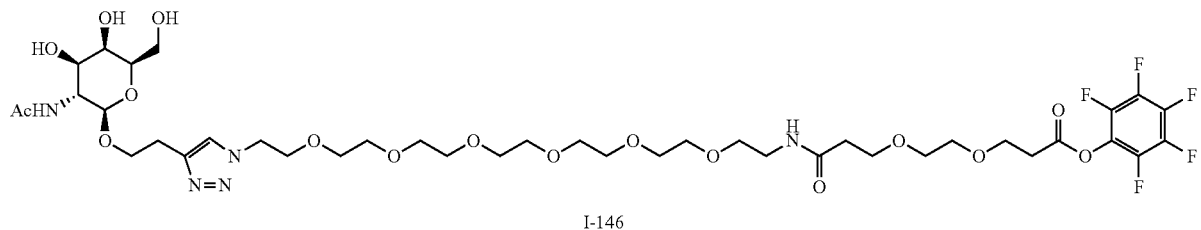
Compound 17B was synthesized employing the procedures described for Compound 8B using Compound 17A in lieu of Compound 8A. Compound I-146 was synthesized employing the procedures described for Compound I-8 using Compound 17B in lieu of Compound 8B (32 mg). LC-MS m/z 978.3 [M+1]$^+$.
Example 14: Synthesis of Compound I-122
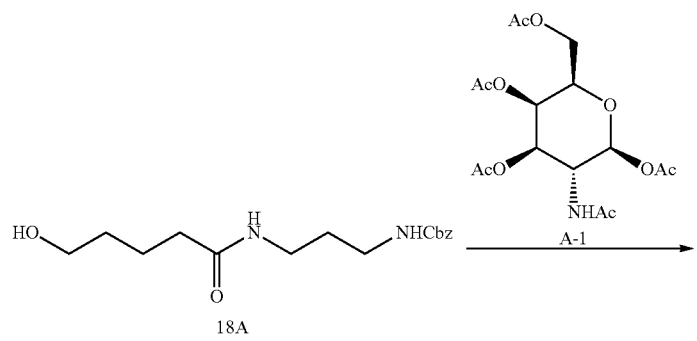
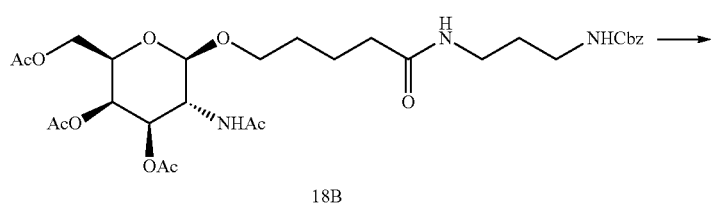

-continued
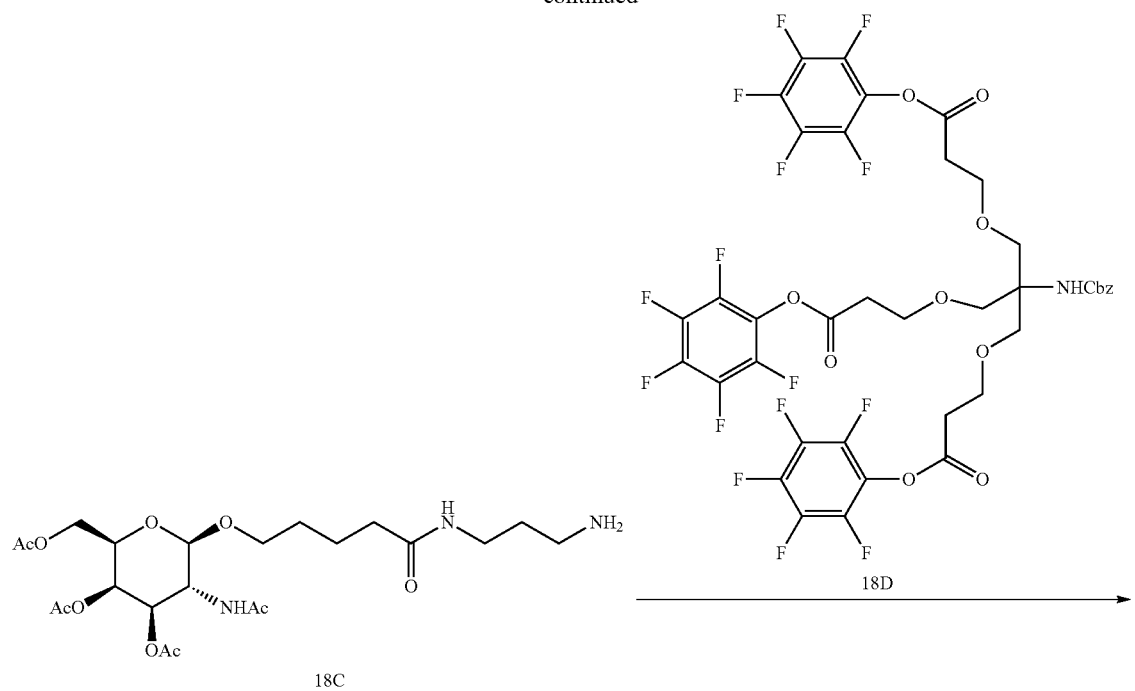
18C
18D
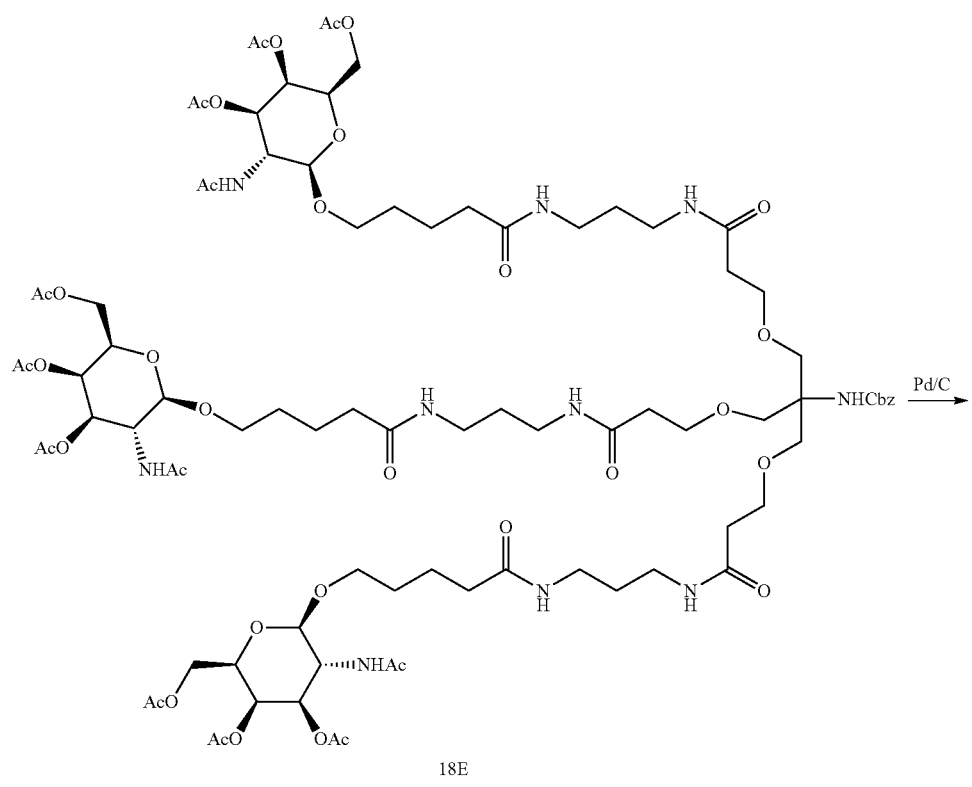
18E

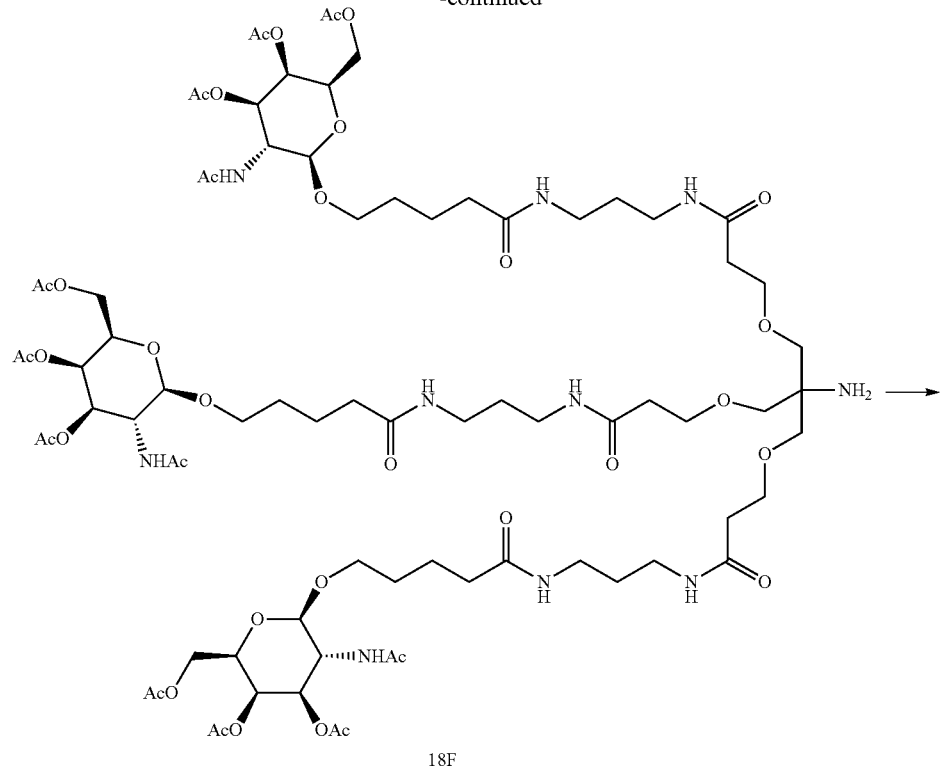
-continued
18F
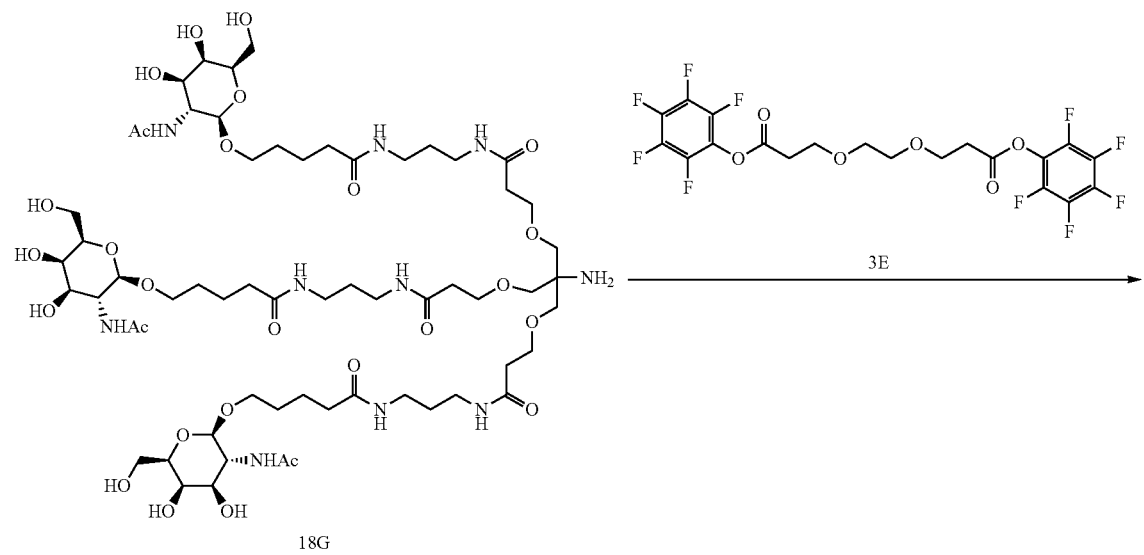
18G

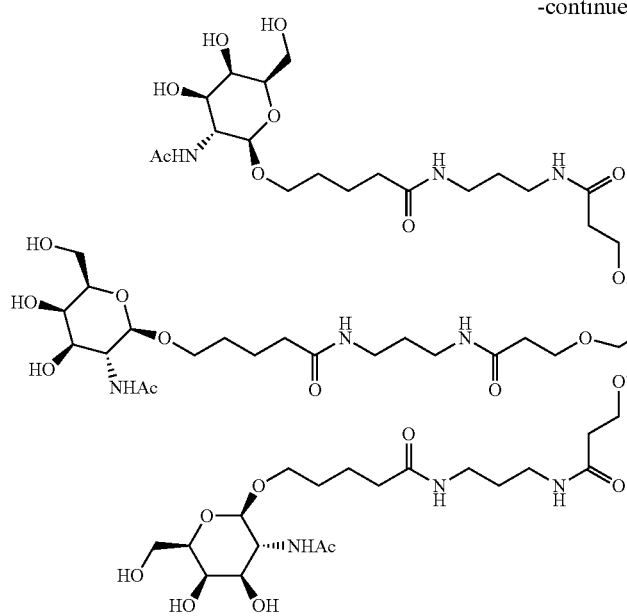
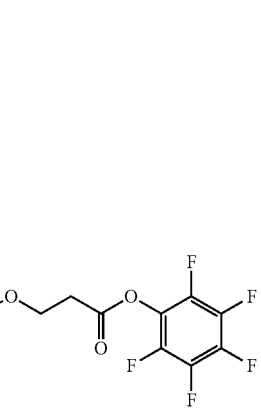

I-122

To the solution of Compound A-1 (1.0 eq, 5.05 g, 13.0 mmol) and benzyl N-[3-(5-hydroxypentanamido) propyl] carbamate (Compound 18A) (1.0 eq, 4.00 g, 13.0 mmol) in dichloromethane (50.0 mL), trimethylsilyl trifluoromethanesulfonate (1.1 eq, 2.52 mL, 14.3 mmol) was added dropwise at room temperature. The reaction mixture was stirred at 40° C. for 5 h. After completion, the reaction mixture was quenched with saturated sodium bicarbonate solution and extracted with dichloromethane. The organic layer was dried over sodium sulfate, filtered, and concentrated under high vacuum to get crude. The crude was purified by reverse phase chromatography using 0-30% acetonitrile in water to afford Compound 18B as yellow viscous liquid, Yield: (5.80 g, 70.12%), LCMS m/z 638.2 [M+1]$^+$ To a solution of Compound 18B (1.0 eq, 4.80 g, 7.53 mmol) in methanol (40.0 mL), 10% Palladium on carbon (1.60 g) was added and stirred at room temperature under hydrogen atmosphere for 4 h. After completion, the reaction mixture was filtered through syringe filter, filtrate was concentrated and dried to get crude. The crude was triturated with diethyl ether to afford Compound 18C as a pale yellow viscous liquid. Yield: (3.4 g, 80.73%); LCMS m/z 504.37 [M+1]$^+$.

A solution of 2,3,4,5,6-pentafluorophenyl 3-(2-{[(benzyloxy)carbonyl]amino}-3-[3-oxo-3-(2,3,4,5,6-pentafluorophenoxy)propoxy]-2-{[3-oxo-3-(2,3,4,5,6-pentafluorophenoxy)propoxy]methyl}propoxy)propanoate (18D) (1.0 eq, 1.20 g, 1.24 mmol) and Compound 18C (3.0 eq, 1.87 g, 3.71 mmol) in N,N-dimethylformamide (30.0 mL) was stirred at room temperature for 1 h. After completion, the reaction mixture was concentrated and dried to get crude. The crude was purified by flash column chromatography using 20% methanol in dichloromethane to afford Compound 18E as pale yellow viscous liquid. Yield: (1.60 g; 67.05%); LCMS m/z 1926.78 [M−1]$^-$.

To a solution of Compound 18E (1.0 eq, 1.60 g, 0.830 mmol) in methanol (20 mL) and acetic acid (1.0 mL), 10% Palladium on carbon (250 mg) was added. The reaction mixture was stirred at room temperature under hydrogen atmosphere for 16 h. After completion, the reaction mixture was filtered through celite bed, filtrate was concentrated and dried to afford Compound 18F as pale yellow viscous liquid. Yield: 1.45 g (Crude); LCMS m/z 1794.05 [M+1]$^+$.

To a solution of Compound 18F (1.0 eq, 1.45 g, 0.808 mmol) in methanol (10 mL), 25% sodium methanolate solution (8.0 eq, 1.45 mL, 6.47 mmol) was added at 0° C. The reaction mixture was stirred at room temperature for 1 h. After completion reaction, reaction mixture was concentrated and dry to get crude. The crude was diluted with acetonitrile and purified by preparative HPLC (30% acetonitrile in water with 0.1% TFA). Fractions containing the desired product were combined and lyophilized to dryness to afford Compound 18G as an off white semi solid. Yield: (0.20 g, 17.4%); LCMS m/z 1415.77 [M+1]$^+$.

To a solution of Compound 18G (1.0 eq, 0.090 g, 0.0636 mmol) in dimethyl sulfoxide (1.00 mL), Compound 3E (1.0 eq, 0.030 g, 0.0636 mmol) was added and stirred at room temperature for 16 h. After completion, reaction mixture was diluted with acetonitrile and purified by preparative HPLC (42% acetonitrile in water with 0.1% Acetic acid (0-13 min)). Fractions containing the desired product were combined and lyophilized to dryness to afford Compound I-122 as off white solid. Yield: 0.004 g, 3.55%; LC-MS m/z 1769.93 [M+1]$^+$; $^1$H NMR (400 MHz, DMSO-d$_6$) δ 7.84 (bs, 3H), 7.73 (bs, 3H), 7.63 (d, J=9.2 Hz, 3H), 7.13 (s, 1H), 4.58-4.54 (m, 4H), 4.47 (bs, 3H), 4.22 (d, J=8.8 Hz, 3H), 3.77-3.67 (m, 12H), 3.53-3.52 (m, 30H), 3.32-3.27 (m, 4H), 3.02 (bs, 14H), 2.29 (t, J=6.0 Hz, 6H), 2.05 (t, J=7.2 Hz, 6H), 1.79 (s, 9H), 1.50-1.41 (m, 18H).

Example 15: Synthesis of N-[1,3-bis(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propan-2-yl]-12-(2,5-dioxo-2,5-dihydro-1H-pyrrol-1-yl)dodecanamide (Compound I-123)
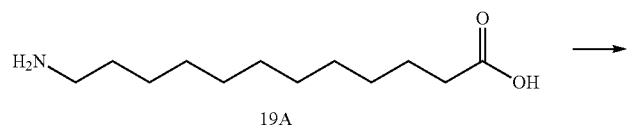
19A
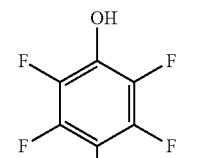
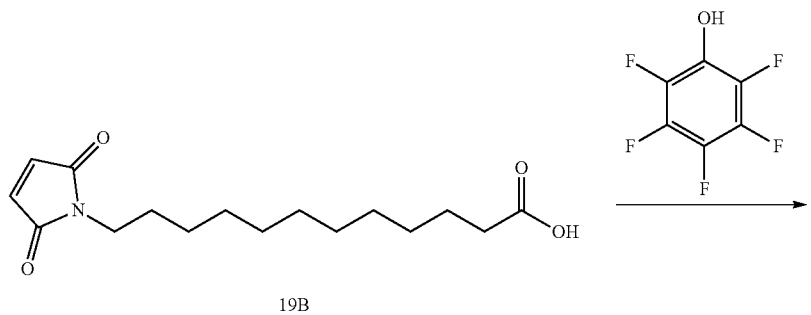
19B
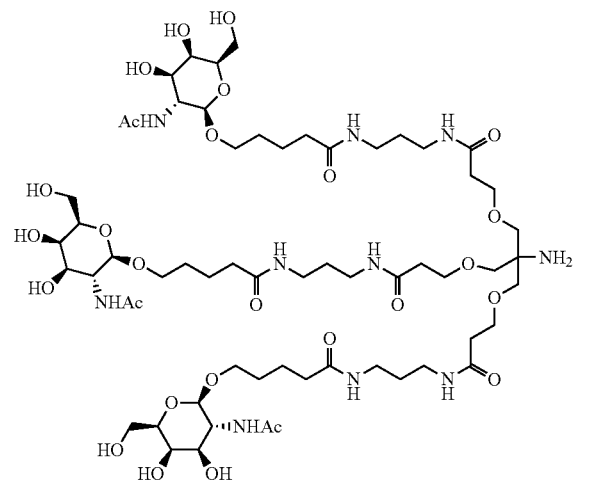
18G
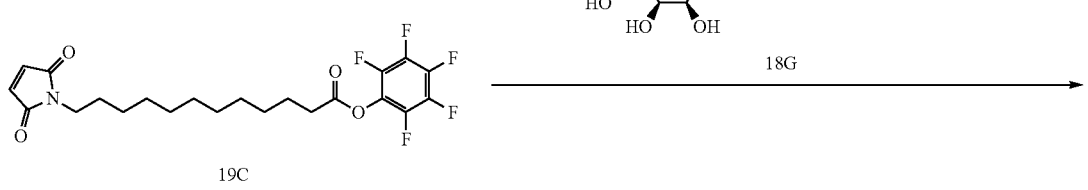
19C -continued

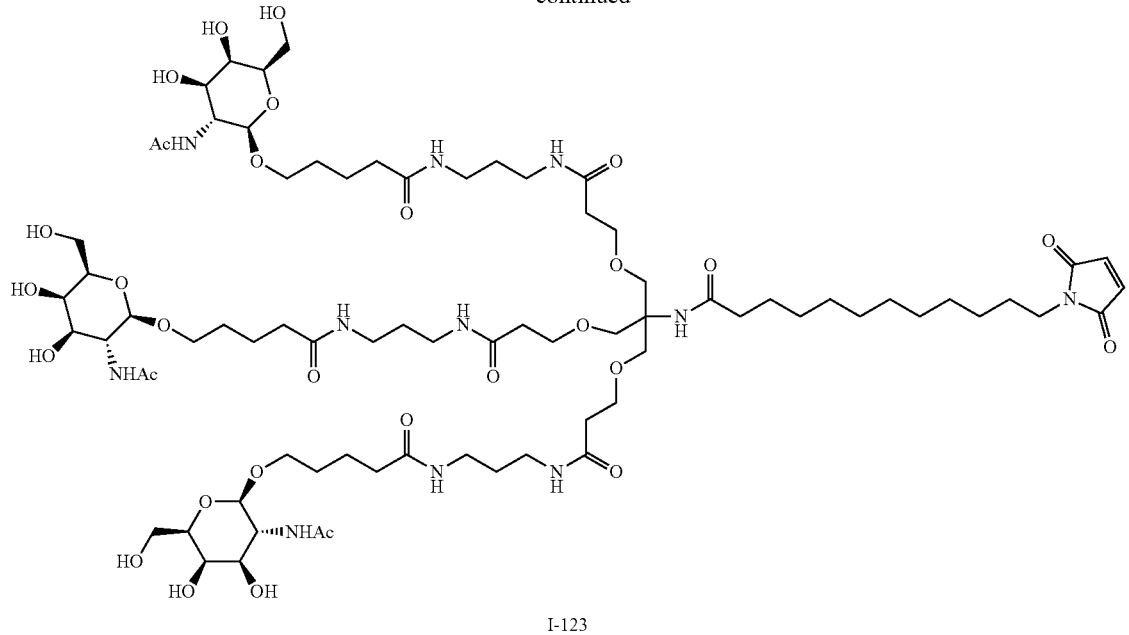

I-123

To a solution of 12-aminododecanoic acid (19A) (2.00 g, 9.29 mmol) in acetic acid (15.00 ml) was added 2,5-dihydrofuran-2,5-dione (1.09 g, 11.1 mmol) and reaction mixture was refluxed at 120° C. for 16 h. After completion, reaction mixture was concentrated under vacuum to get crude compound which was purified by flash column chromatography using silica gel and 5% methanol in dichloromethane as eluents to afford Compound 19B as off white solid. Yield: 1.60 g (57.17%); LCMS m/z 294.3 [M−1]⁻.

To a solution of Compound 19B (0.300 g, 1.02 mmol) in tetrahydrofuran (15.00 mL) at 0° C. were added pentafluorophenol (168 mg, 0.914 mmol) and diisopropylmethanediimine (0.192 mL, 1.22 mmol). Reaction mixture was then stirred at room temperature for 1 h. After completion reaction mixture was concentrated to get crude product which was purified by flash column chromatography using silica gel and 5% to 7% ethyl acetate in hexanes as eluents to afford Compound 19C as off white solid. Yield: 0.250 g (53.34%) LCMS m/z 479.0[M+18]⁺.

Compound 18G (0.060 g, 0.04 mmol) in dimethylsulfoxide (1.0 mL), N,N-diisopropylethylamine (0.015 mL, 0.084 mmol) and Compound 19C (0.019 g, 0.04 mmol) were added and reaction mixture was stirred at room temperature for 16 h. After completion, reaction mixture was diluted with acetonitrile and purified by preparative HPLC (25-45% acetonitrile in water with 0.1% TFA). Fractions containing the desired product were combined and lyophilized to dryness to afford Compound I-123 as an off-white solid. Yield: 0.0035 g, 4.88%; LC-MS m/z 1692.93[M+1]⁺; ¹H NMR (400 MHz, DMSO-d6) δ 7.83 (t, J=5.2 Hz, 3H), 7.73 (t, J=6.0 Hz, 3H), 7.61 (d, J=9.6 Hz, 3H), 6.98 (s, 3H), 4.57-4.53 (m, 7H), 4.22 (d, J=8.4 Hz, 3H), 3.72-3.63 (m, 9H), 3.55-3.51 (m, 20H), 3.37-3.27 (m, 10H), 3.04-3.01 (m, 12H), 2.29 (t, J=6.4 Hz, 6H), 2.05 (t, J=6.8 Hz, 6H), 1.81 (bs, 8H), 1.51-1.41 (m, 24H), 1.21 (s, 14H).

Example 16: Synthesis of Compound I-124 and I-132

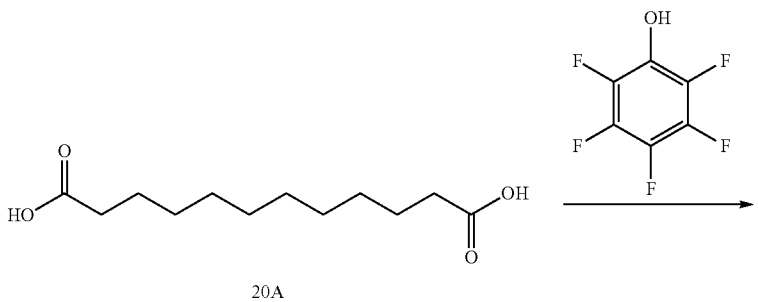

20A

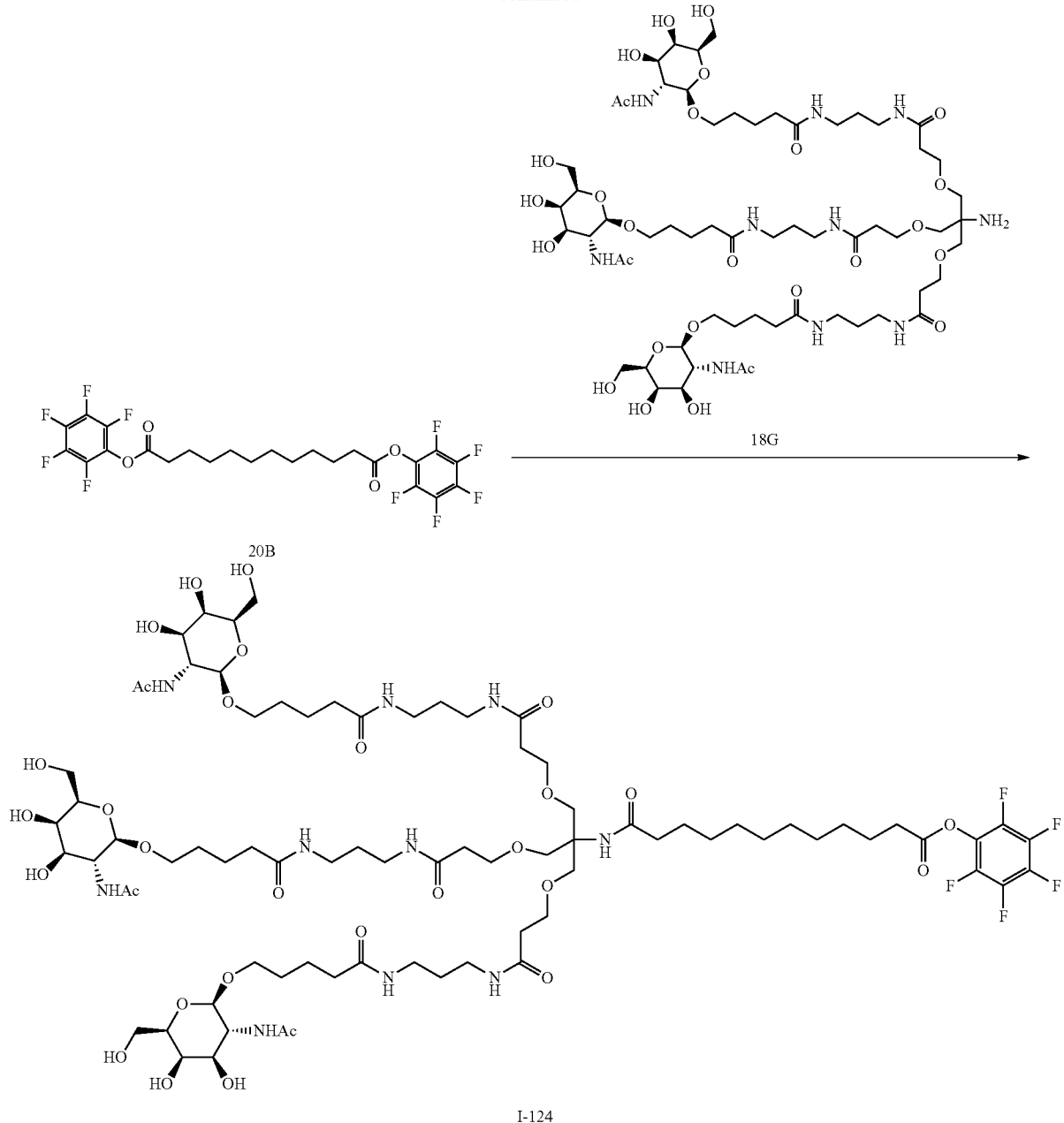

I-124

To the solution of dodecanedioic acid (20A) (1.00 g, 4.34 mmol) in ethyl acetate (10.00 mL) at 0° C., pentafluorophenol (1.60 g, 8.68 mmol) and diisopropylmethanediimine (1.91 mL, 13.0 mmol) were added and reaction mixture stirred at room temperature for 1 h. After completion, reaction mixture was filtered through celite bed and filtrate was concentrated under reduced pressure to get crude compound. Crude compound obtained was purified by flash column chromatography on silica gel column using 5% ethyl acetate in hexanes as eluents to afford Compound 20B as off white solid. Yield: 1.00 g (40.95%); LCMS m/z 580.39 [M+18]+.

To a solution Compound 18G (45.0 mg, 0.031 mmol) in dimethyl sulfoxide (1.0 mL) was added N,N-diisopropylethylamine (0.016 mL, 0.093 mmol) and Compound 20B (17.9 mg, 0.031 mmol). Reaction mixture was stirred at room temperature for 2 h. After completion, the reaction mixture was purified via preparatory HPLC (40-60% acetonitrile in water with 0.1% trifluoroacetic acid). Fractions containing the desired product were combined and lyophilized to dryness to afford Compound I-124 as an off white solid. Yield: 0.006 g (10.52%); LCMS m/z 1793.94 [M+1]+, 897.99 [M/2+1]+. $^1$H NMR (400 MHz, DMSO-d6) δ 7.83 (t, J=5.6 Hz, 3H), 7.73 (t, J=5.2 Hz, 3H), 7.60 (d, J=9.2 Hz, 3H), 6.99 (s, 1H), 4.57-4.47 (m, 6H), 4.46 (d, J=4.4 Hz, 3H), 4.21 (d, J=8.4 Hz, 3H), 3.70-3.63 (m, 9H), 3.55-3.49 (m, 21H), 3.32-3.28 (m, 4H), 3.02 (t, J=5.6 Hz, 12H), 2.76 (t, J=5.6 Hz, 2H), 2.27 (t, J=6.4 Hz, 6H), 2.03 (t, J=7.2 Hz, 8H), 1.79 (s, 9H), 1.70-1.67 (m, 2H), 1.52-1.41 (m, 20H), 1.23 (bs, 14H).

Compound I-132 is synthesized by adapting the procedure for compound I-124. The structure for compound I-132 is presented below:

I-132

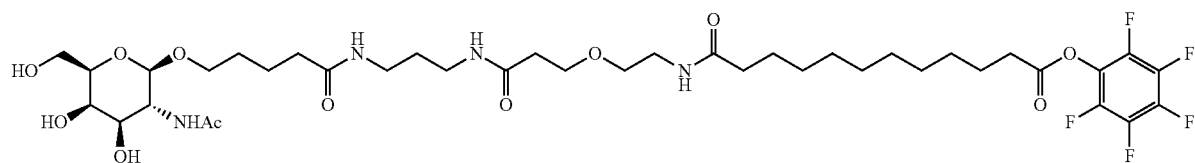

Example 17: Synthesis of Compound I-163

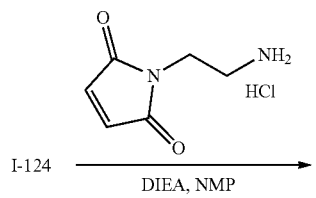

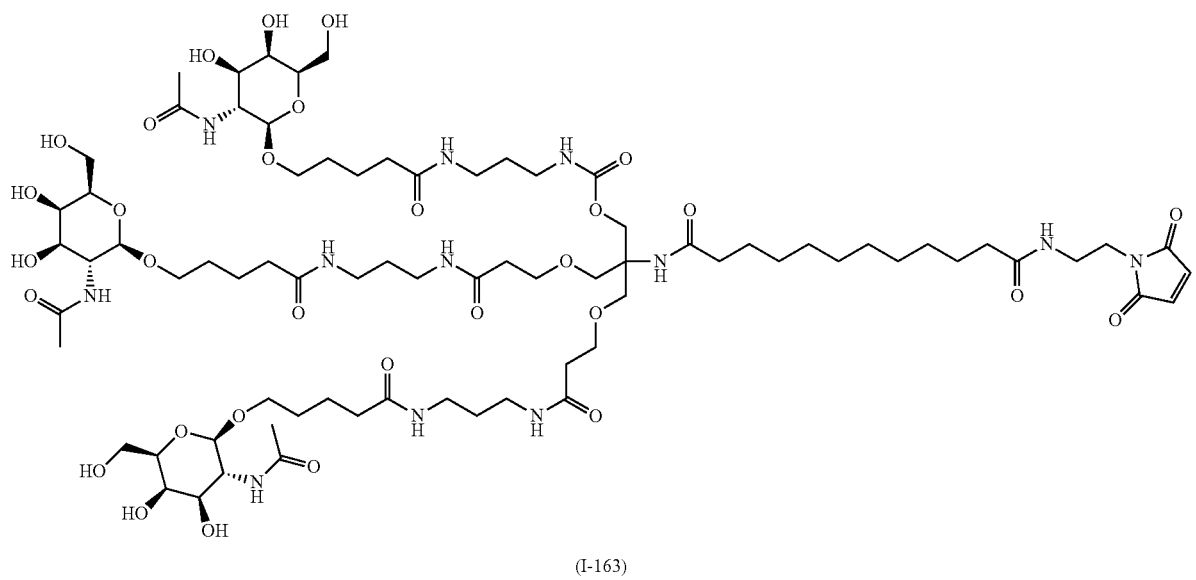

(I-163)

To a mixture of Compound I-124 (1 eq, 17.2 mg. 0.00959 mmol) and 1-(2-aminoethyl)pyrrole-2,5-dione; hydrochloride (1.1 eq, 1.86 mg, 0.00105 mmol) in NMP (0.5 mL) was added DIEA (3 eq, 5 uL, 0.0288 mmol). The mixture was stirred at rt for 10 minutes and acetic acid (4 uL) was added. The mixture was purified by prep. HPLC (10-40% MeCN/water with 0.1% TFA) to give compound I-163 as a white solid (10.1 mg, yield 64%). (purity: 99%). LCMS m/z 1751.0 [M+H]+.

Example 18: Synthesis of Compound I-125 and I-145

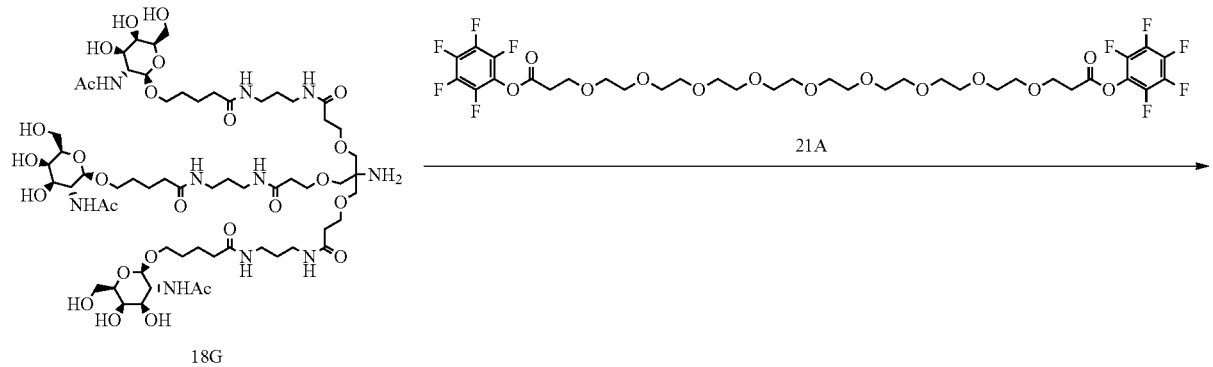

18G

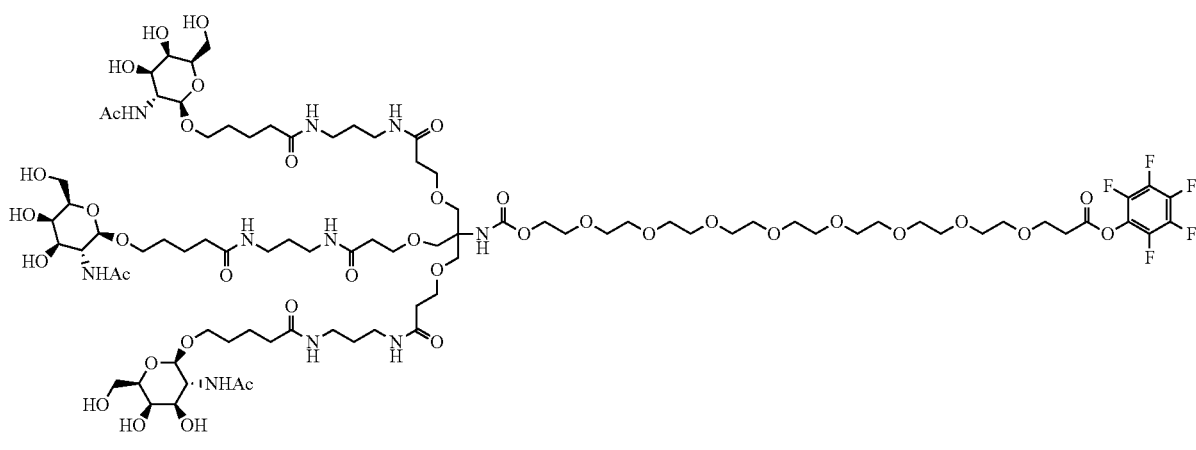

I-125

To a solution of Compound 18G (1.0 eq, 0.10 g, 0.070 mmol) in dimethyl sulfoxide (1.00 mL), ethylbis(propan-2-yl)amine (3.0 eq, 39.1 µL, 0.212 mmol) and bis(2,3,4,5,6-pentafluorophenyl) 4,7,10,13,16,19,22,25,28-nonaoxahentriacontanedioate (21A) (1.0 eq, 0.0598 g, 0.070 mmol) were added and stirred at room temperature for 16 h. After completion, reaction mixture was diluted with acetonitrile and purified by preparative HPLC (50% acetonitrile in water with 0.1% Acetic acid (0-10 min)). Fractions containing the desired product were combined and lyophilized to dryness to afford Compound I-125 as off white solid. Yield: 0.006 g, 4.09%; LC-MS m/z 1039.74 [M/2+1]$^+$; $^1$HNMR (400 MHz, D$_2$O) δ 4.45 (d, J=8.4 Hz, 3H), 3.96-3.83 (m, 11H), 3.80-3.58 (m, 61H), 3.24-3.19 (m, 12H), 3.10 (t, J=5.6 Hz, 2H), 2.52-2.47 (m, 8H), 2.27 (t, J=6.0 Hz, 6H), 2.02 (s, 9H), 1.75-1.70 (m, 6H), 1.58-1.50 (m, 12H), 1.35-1.34 (m, 1H).

Compound I-145 was synthesized by adapting the procedure for the synthesis of compound I-125. The structure and data for compound I-145 are presented below.

I-145
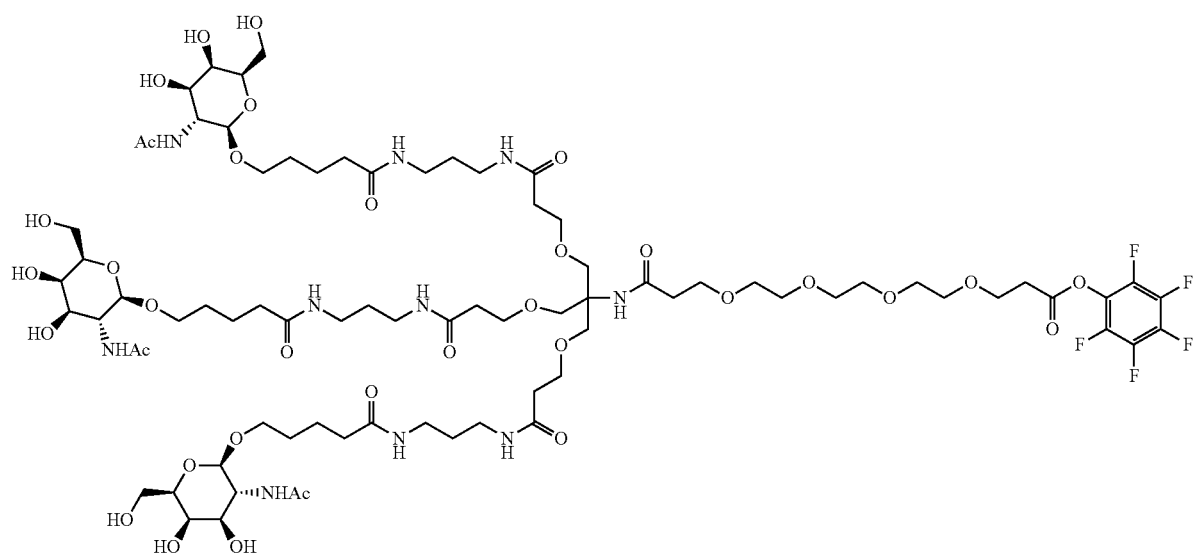
MS (ESI) m/z, 1858 [M+1]$^+$, 729 [M/2+1]$^+$.
$^1$H NMR (400 MHz, DMSO-d6) δ 7.83 (t, J=5.6 Hz, 3H), 7.35 (t, J=5.2 Hz, 3H), 7.61 (d, J=8.8 Hz, 3H), 7.13 (s, 1H), 4.59-4.54 (m, 6H), 4.46 (d, J=4.4 Hz, 3H), 4.21 (d, J=8.4 Hz, 3H), 3.76-3.70 (m, 2H), 3.67-3.63 (m, 10H), 3.55-3.46 (m, 34H), 3.14 (s, 2H), 3.32-3.28 (m, 2H), 3.02 (t, J=6 Hz, 16H), 2.27 (t, J=6 Hz, 6H), 2.03 (t, J=7.2 Hz, 6H), 1.79 (s, 9H), 1.51-139 (m, 20H).
Example 19: Synthesis of Compounds I-159 and I-170
Compound I-159 was synthesised according to the procedure for compound I-125, replacing intermediate 21-A with intermediate 22-B.
22-B
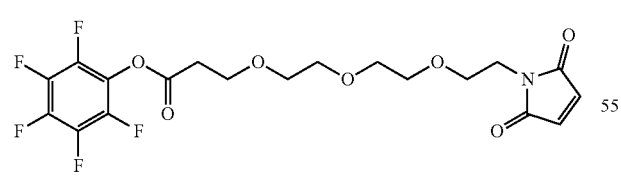
The structure and data for compound I-159 is presented below:

(I-159)
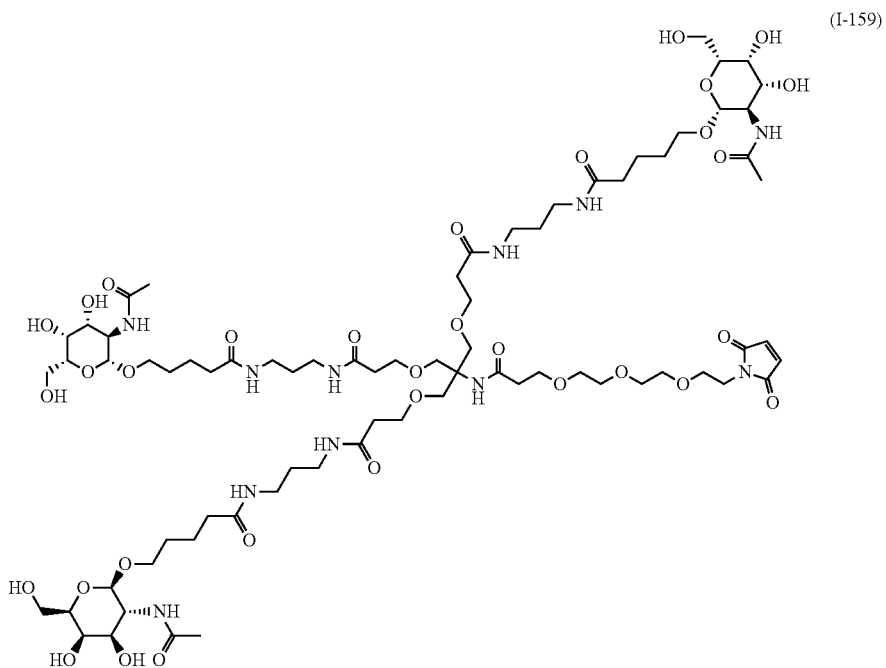 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCOCCOCCOCCN2C(=O)C=CC2=O)O[C@H](CO)[C@H](O)[C@@H]1O]
LCMS m/z 1698.9 [M+H]+.
Compound I-170 was synthesised according to the procedure for compound I-125 and I-159 replacing intermediate 22-B ((2,3,4,5,6-pentafluorophenyl) 3-[2-[2-[2-(2,5-dioxopyrrol-1-yl)ethoxy]ethoxy]ethoxy]propanoate) with (2,3,4,5,6-pentafluorophenyl) 3-[2-[2-[2-[2-[2-[2-(2,5-dioxopyrrol-1-yl)ethoxy]ethoxy]ethoxy]ethoxy]ethoxy]ethoxy]propanoate.
The structure and data for compound I-170 is presented below:
(I-170)
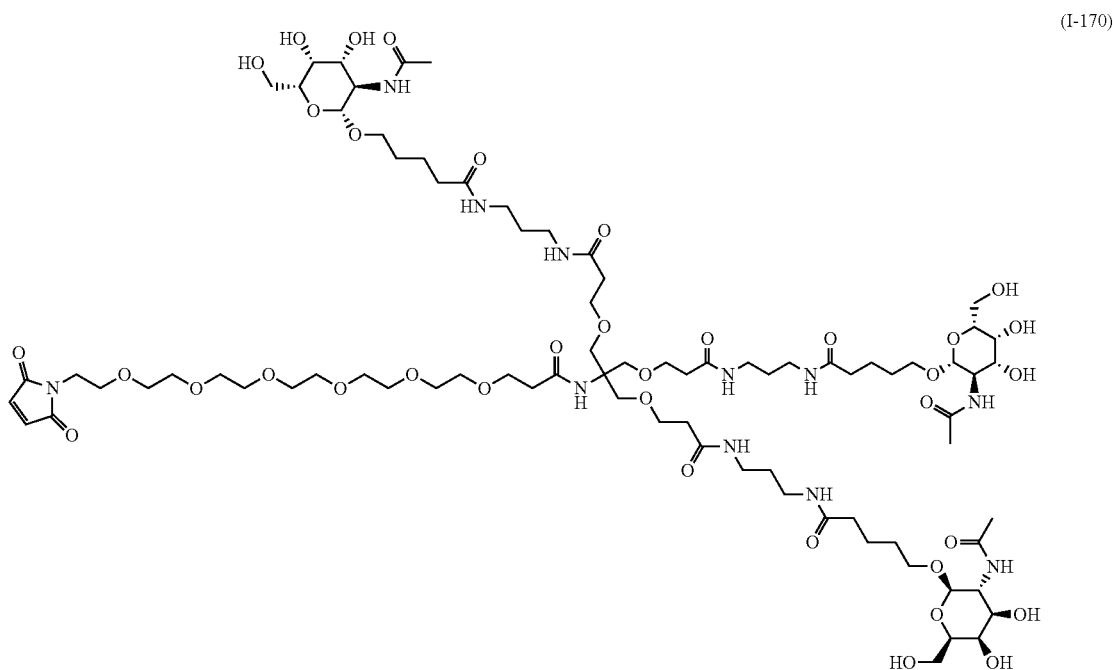 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCOCCOCCOCCOCCOCCOCCN2C(=O)C=CC2=O)O[C@H](CO)[C@H](O)[C@@H]1O]
LCMS m/z 1831.7 [M+H]+.

Example 20: Synthesis of Compound I-127 and I-129
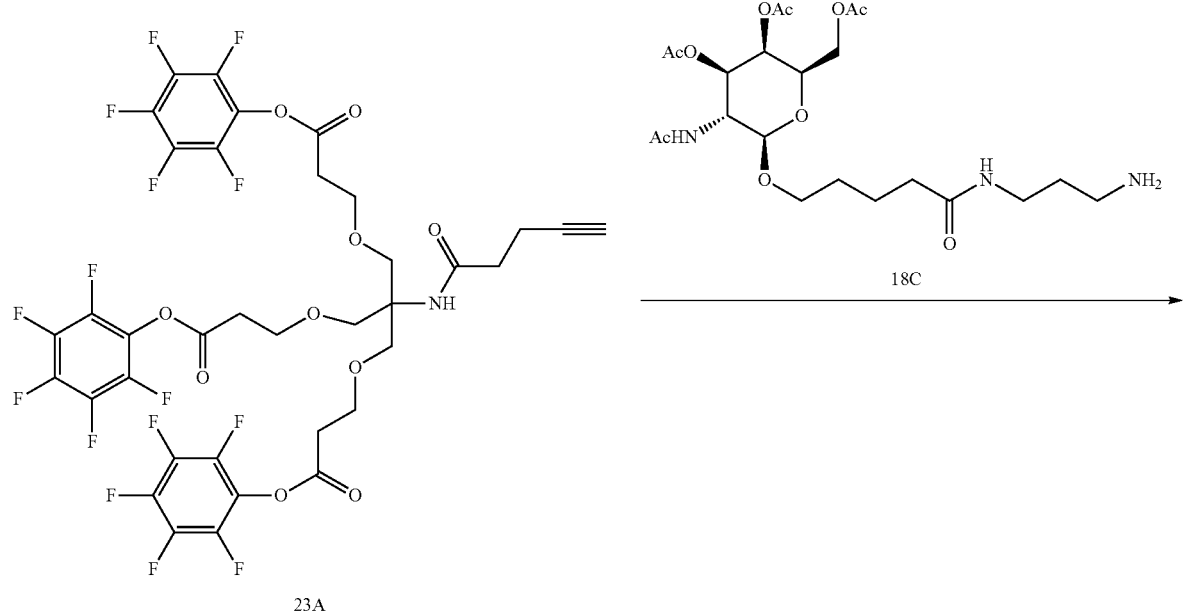
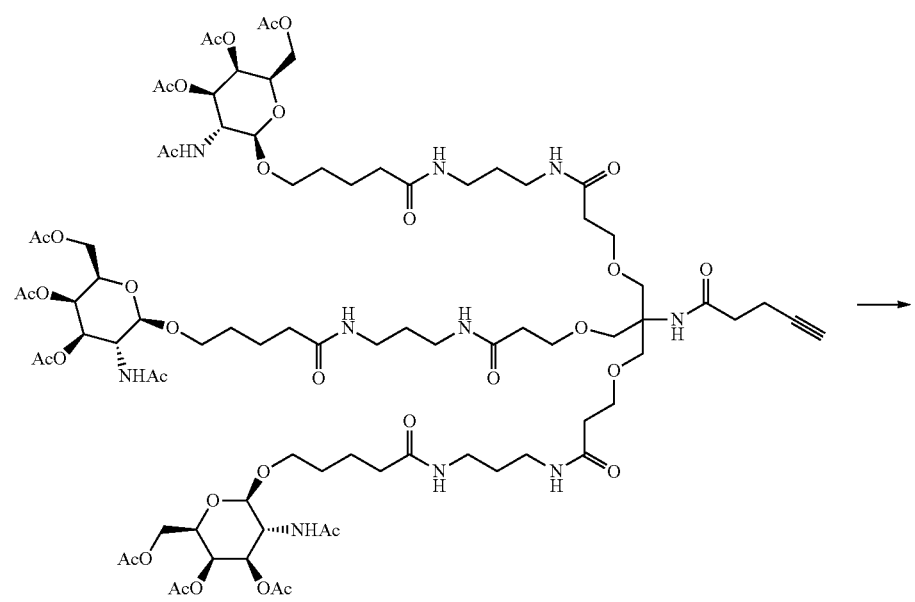

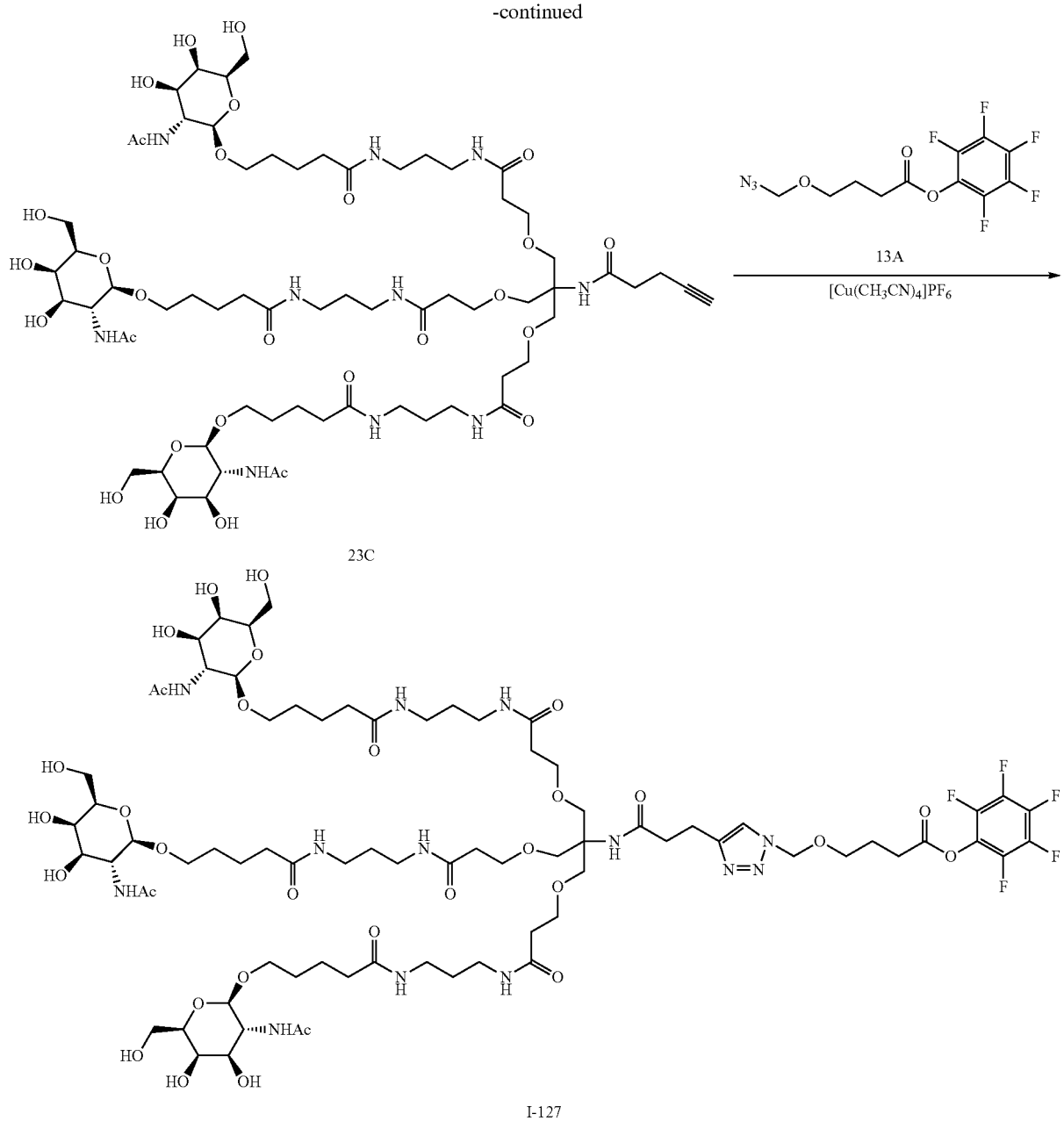

I-127

To a solution of bis(perfluorophenyl) 3,3'-((2-((3-oxo-3-(perfluorophenoxy)propoxy)methyl)-2-(pent-4-ynamido)propane-1,3-diyl)bis(oxy))dipropionate (23A) (1.0 eq, 0.500 g, 0.54 mmol) and Compound 18C (4.0 eq, 1.3 g, 2.16 mmol) in N,N-dimethylformamide (10 mL), N,N-diisopropylethylamine (6.0 eq, 0.59 mL, 3.24 mmol) was added and reaction mixture was stirred at room temperature for 16 h. After completion, reaction mixture was concentrated and dried to afford Compound 23B as a light brown viscous liquid. Yield: 3.0 g (Crude), LCMS m/z 937.4 [M+2H]++.

To a solution of Compound 23B (1.0 eq, 3.0 g, 1.60 mmol) in methanol (10 mL), sodium methoxide (25% solution in methanol) (10.0 eq, 3.92 mL, 16.0 mmol) was added and reaction mixture was stirred at room temperature for 1 h. The reaction was monitored by ELSD. After completion, reaction mixture was neutralized with Dowex 50WX8 hydrogen form (200-400 mesh) and filtered. The filtrate was concentrated to afford crude which was diluted with acetonitrile and purified by preparative HPLC (13-25% acetonitrile in water). Fractions containing the desired product were combined and lyophilized to dryness to afford Compound 23C as an off white solid. Yield: 0.380 g, 15.45%; LCMS m/z 748.35 [M+2H]++.

To a solution of Compound 23C (1.0 eq, 0.040 g, 0.026 mmol) in dimethylsulfoxide (1.0 mL), Compound 13A (1.2 eq, 0.010 g, 0.032 mmol) was added and stirred for 5 minutes. Then, tetrakis(acetonitrile)copper(I) hexafluorophosphate (2.8 eq., 0.027 g, 0.074 mmol) was added and reaction mixture was stirred at room temperature for 15 minutes. After completion, reaction mixture was diluted with acetonitrile and purified by preparative HPLC (20-45% acetonitrile in water with 0.1% TFA). Fractions containing the desired product were combined and lyophilized to dryness to afford Compound I-127 as an off white solid. Yield: 0.008 g, 16.6%; LCMS m/z 911.31 [M+2H]++; $^1$H NMR (400 MHz, D$_2$O) δ 7.71 (s, 1H), 4.57-4.54 (m, 3H), 4.39 (d, J=8.4 Hz, 4H), 3.94 (t, J=8.4 Hz, 2H), 3.91-3.79 (m, 10H), 3.76-3.72 (m, 5H), 3.69-3.67 (m, 2H), 3.65-3.63 (m, 10H), 3.58 (bs, 5H), 3.55-3.52 (m, 4H), 3.18-3.13 (m, 12H), 2.95 (t, J=5.2 Hz, 2H), 2.81 (t, J=6.8 Hz, 2H), 2.49-2.46 (m, 2H), 2.44-2.41 (m, 6H), 2.19-2.17 (m, 6H), 1.98 (s, 9H), 1.69-1.62 (m, 6H), 1.60-1.49 (m, 12H).

Compound I-129 was synthesised by adapting the synthetic procedure for compound I-127. The structure and data for compound I-129 are presented below.

I-129

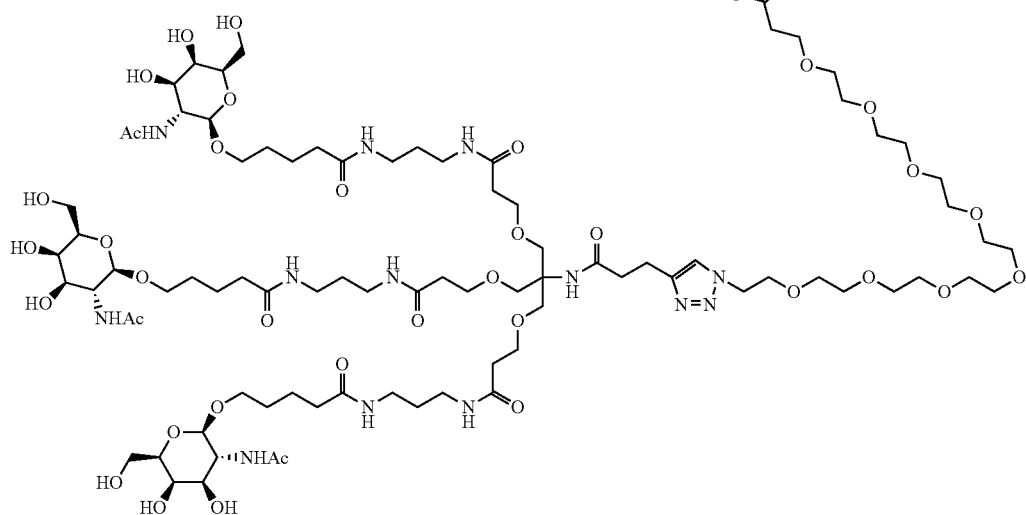

LCMS m/z 1065.25 [M+2H]++.

$^1$H NMR (400 MHz, D$_2$O) δ 7.81 (s, 1H), 4.55 (bs, 2H), 4.39 (d, J=8.4 Hz, 3H), 3.89-3.82 (m, 12H), 3.78-3.74 (m, 5H), 3.71-3.58 (m, 51H), 3.19-3.14 (m, 12H), 3.04 (t, J=5.2 Hz, 2H), 2.91 (t, J=7.2 Hz, 2H), 2.56 (t, J=7.6 Hz, 2H), 2.42 (bs, 6H), 2.21-2.10 (m, 6H), 1.98 (s, 9H), 1.66 (t, J=6.8 Hz, 6H), 1.53 (bs, 12H).

Example 21: Synthesis of perfluorophenyl 1-(((2R,3R,4R,5R,6R)-3-acetamido-4,5-dihydroxy-6-(hydroxymethyl)tetrahydro-2H-pyran-2-yl)oxy)-16-((3-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oate (Compound I-144)

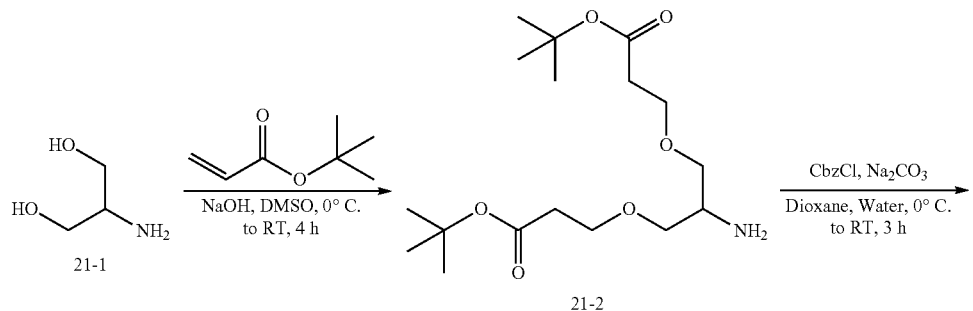

-continued
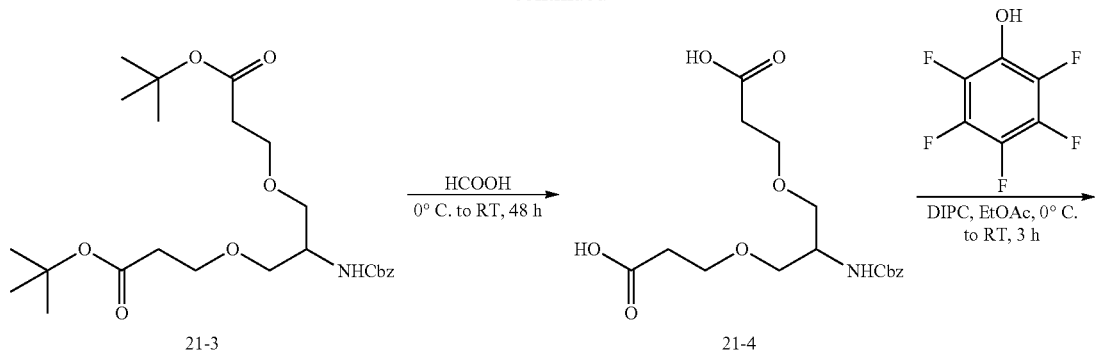
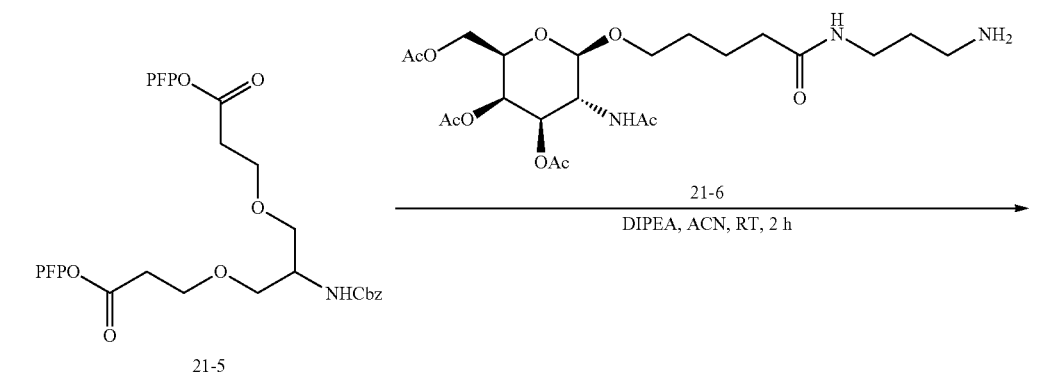
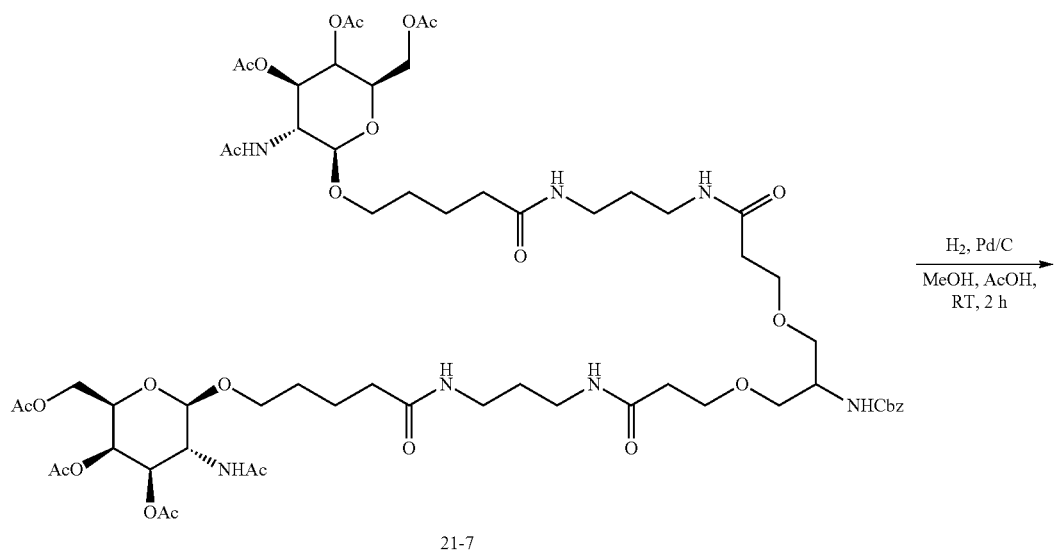

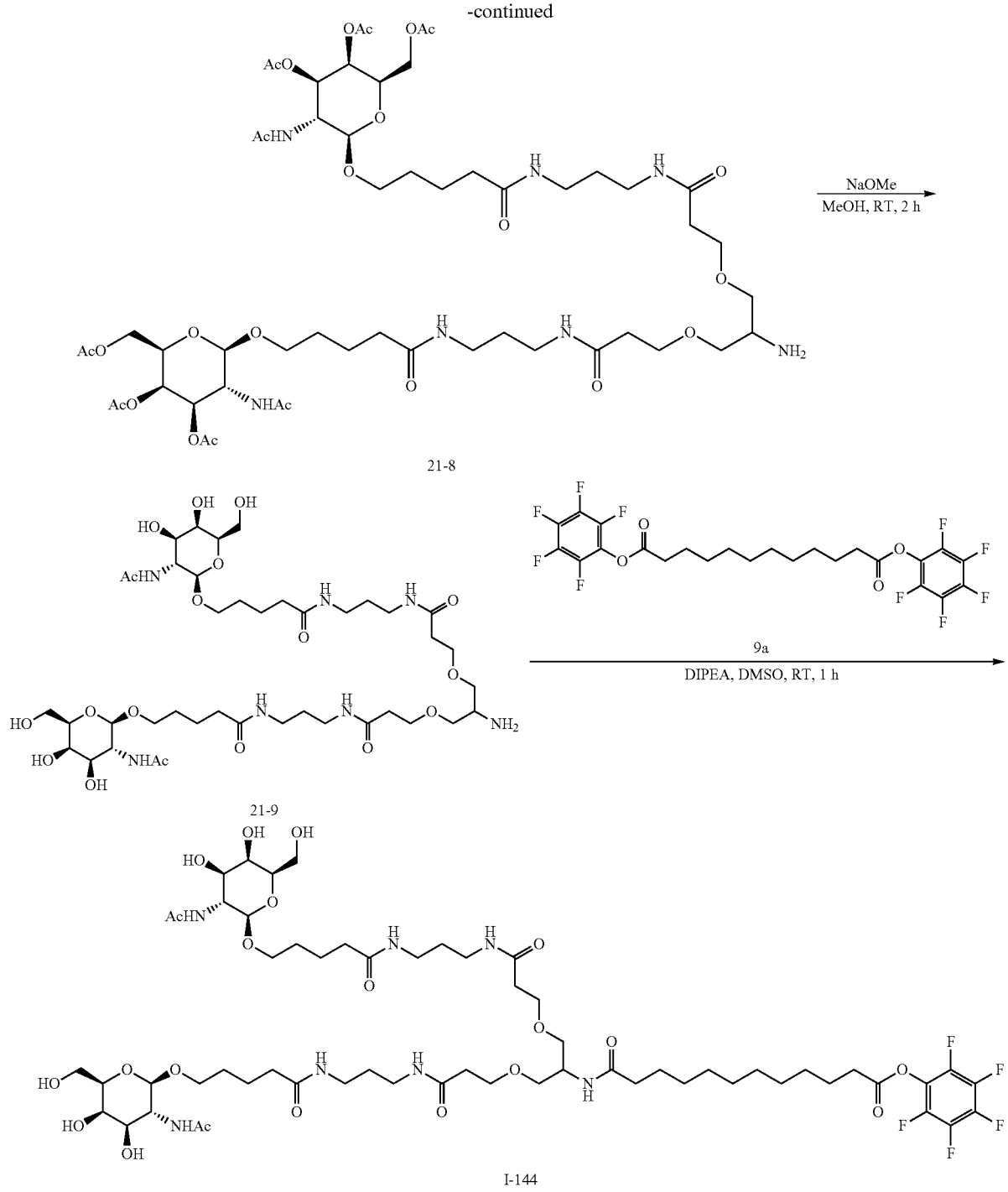

To a stirred solution of 2-aminopropane-1,3-diol (21-1, 1.00 g, 11.0 mmol) in dimethyl sulfoxide (27 mL) was added aqueous sodium hydroxide solution (3.62 mmol/L, 4 mL) at 0° C. tert-butyl acrylate (3.52 g, 27.4 mmol) dissolved in dimethyl sulfoxide (4.0 mL) was gradually added, and the reaction mixture was stirred at room temperature for 4 h. Water was added to the reaction mixture, followed by extraction with ethyl acetate. The organic layer was washed with brine and dried over anhydrous sodium sulfate, filtered and concentrated under reduced pressure to get crude, which was purified by silica gel column chromatography using 30% ethyl acetate in hexane to afford di-tert-butyl 3,3'-((2-aminopropane-1,3-diyl)bis(oxy))dipropionate (21-2). yield: 1.20 g, 32%. ESI-MS m/z: 348.0 (M+H)$^+$ To a stirred solution of di-tert-butyl 3,3'-((2-aminopropane-1,3-diyl)bis(oxy))dipropionate (21-2, 1.20 g, 3.45 mmol) in 1,4-dioxane (20.0 mL) was added sodium carbonate (0.54 g, 5.18 mmol) dissolved in water (4.0 mL). Reaction mixture was then placed at ice bath, and benzyl chloroformate (0.74 mL, 5.18 mmol) was added it. After 10 minutes, the ice bath was removed and stirred at room temperature for further 3 h. Reaction mixture diluted with water and extracted with ethyl acetate. The organic layer was dried over anhydrous sodium sulfate, filtered and concentrated under reduced pressure to get crude product which was purified by flash column chromatography using 4 to 7% methanol in dichloromethane to afford di-tert-butyl 3,3'-((2-(((benzyloxy)carbonyl)amino)propane-1,3-diyl)bis(oxy))dipropionate (21-3). Yield: 1.0 g, 60.12%; LCMS m/z 482.0 [M+1]$^+$.

A solution of di-tert-butyl 3,3'-((2-(((benzyloxy)carbonyl)amino)propane-1,3-diyl)bis(oxy))dipropionate (21-3, 1.00 g, 11.0 mmol) in formic acid (5.0 mL) was stirred at room temperature for 48 h. Reaction mixture was concentrated under reduced pressure to get crude 3,3'-((2-(((benzyloxy)carbonyl)amino)propane-1,3-diyl)bis(oxy))dipropionic acid (21-4). The obtained crude product was used as such for next reaction. Yield: 0.380 g, 49.29%; $^1$H NMR (400 MHz, DMSO-d$_6$) δ 7.38-7.29 (m, 5H), 7.14 (d, J=8 Hz, 1H), 5.01 (s, 1H), 3.72 (t, J=6.8 Hz, 4H) 3.34 (d, J=6 Hz., 4H), 2.42 (t, J=6 Hz 4H).

To a stirred solution of 3,3'-((2-(((benzyloxy)carbonyl)amino)propane-1,3-diyl)bis(oxy))dipropionic acid (21-4, 0.750 g, 2.03 mmol) in ethyl acetate (10.0 mL), diisopropylmethanediimine (0.894 mL, 3.0 eq., 6.09 mmol) and a solution of pentafluorophenol (5.86 g, 5.0 eq., 31.8 mmol) in ethyl acetate (10.0 mL) were added and reaction mixture was stirred at room temperature for 3 h. After completion, reaction mixture was filtered over celite pad and filtrate was concentrated under reduced pressure to get crude. The crude was purified by column chromatography using silica gel (100-200 mesh) and eluting in 20-30% ethyl acetate in hexane to afford bis(perfluorophenyl) 3,3'-((2-(((benzyloxy)carbonyl)amino)propane-1,3-diyl)bis(oxy))dipropionate (21-5) as off white solid. Yield: 0.69 g, 47.96% $^1$H NMR (400 MHz, DMSO-d$_6$) δ 7.32 (s, 5H), 7.13 (d, J=8 Hz, 1H), 4.99 (s, 2H), 4.10-3.94 (m, 5H) 3.42 (t, J=6 Hz., 4H), 3.00 (t, J=5.6 Hz 4H).

To a stirred solution of bis(perfluorophenyl) 3,3'-((2-(((benzyloxy)carbonyl)amino)propane-1,3-diyl)bis(oxy))dipropionate (21-5, 0.680 g, 1.0 eq, 0.969 mmol) and (2R,3R,4R,5R,6R)-5-acetamido-2-(acetoxymethyl)-6-((5-((3-aminopropyl)amino)-5-oxopentyl)oxy)tetrahydro-2H-pyran-3,4-diyl diacetate (21-6, 1.95 g, 4.0 eq., 3.88 mmol) in acetonitrile and reaction mixture was stirred at room temperature for 2 h. The solvent was evaporated under reduced pressure to get the crude which was purified by flash chromatography using 10% methanol in dichloromethane to afford (2R,2'R,3R,3'R,4R,4'R,5R,5'R,6R,6'R)-((16-(((benzyloxy)carbonyl)amino)-5,11,21,27-tetraoxo-14,18-dioxa-6,10,22,26-tetraazahentriacontane-1,31-diyl)bis(oxy))bis(5-acetamido-2-(acetoxymethyl)tetrahydro-2H-pyran-6,3,4-triyl) tetraacetate (21-7) as a colorless liquid. Yield: 1.10 g, 62.94%; LCMS m/z 670.8[M/2+1]+.

To a stirred solution of ((2R,2'R,3R,3'R,4R,4'R,5R,5'R,6R,6'R)-((16-(((benzyloxy)carbonyl)amino)-5,11,21,27-tetraoxo-14,18-dioxa-6,10,22,26-tetraazahentriacontane-1,31-diyl)bis(oxy))bis(5-acetamido-2-(acetoxymethyl) tetrahydro-2H-pyran-6,3,4-triyl) tetraacetate (21-7, 1.10 g, 0.821 mmol) in methanol (10.0 mL), was added acetic acid (0.0469 mL, 0.821 mmol), and 10% palladium on carbon (0.300 g), and reaction mixture was stirred at room temperature for 2 h under hydrogen gas atmosphere. Then reaction mixture was passed through celite pad and the filtrate was evaporated under reduced pressure to get crude (2R,2'R,3R,3'R,4R,4'R,5R,5'R,6R,6'R)-((16-amino-5,11,21,27-tetraoxo-14,18-dioxa-6,10,22,26-tetraazahentriacontane-1,31-diyl)bis(oxy))bis(5-acetamido-2-(acetoxymethyl)tetrahydro-2H-pyran-6,3,4-triyl) tetraacetate (21-8) as a colorless liquid. Yield: 0.850 g (Crude); LCMS m/z 1206.20 [M+1]$^+$.

To a stirred solution of (2R,2'R,3R,3'R,4R,4'R,5R,5'R,6R,6'R)-((16-amino-5,11,21,27-tetraoxo-14,18-dioxa-6,10,22,26-tetraazahentriacontane-1,31-diyl)bis(oxy))bis(5-acetamido-2-(acetoxymethyl)tetrahydro-2H-pyran-6,3,4-triyl) tetraacetate (21-8, 0.830 g, 0.688 mmol) in methanol (10.0 mL) was added sodium methanolate (25% solution in methanol, 0.330 mL, 12.0 eq., 8.26 mmol) at room temperature and reaction mixture was stirred at same temperature for 30 mins. Thereafter, reaction mixture was quenched with 1 N hydrochloric acid and the solution was dried under lypholization to get N,N'-(10-amino-5,15-dioxo-8,12-dioxa-4,16-diazanonadecane-1,19-diyl)bis(5-(((2R,3R,4R,5R,6R)-3-acetamido-4,5-dihydroxy-6-(hydroxymethyl)tetrahydro-2H-pyran-2-yl)oxy)pentanamide) (21-9) as a light brown solid. Yield: 0.700 g, 98.10%; LCMS m/z 954.2 [M+1]+.

To a stirred solution of N,N'-(10-amino-5,15-dioxo-8,12-dioxa-4,16-diazanonadecane-1,19-diyl)bis(5-(((2R,3R,4R,5R,6R)-3-acetamido-4,5-dihydroxy-6-(hydroxymethyl)tetrahydro-2H-pyran-2-yl)oxy)pentanamide) (21-9, 0.200 g, 0.210 mmol) in dimethyl sulphoxide (2.00 mL), 2,3,4,5,6-pentafluorophenyl 12-oxo-12-(2,3,4,5,6-pentafluorophenyl) dodecanoate (9a, 0.172 g, 1.5 eq., 0.314 mmol) and N,N-diisopropylethylamine (0.0366 mL, 0.210 mmol) was added at room temperature and reaction mixture was stirred at same temperature for 1 h. The progress reaction was monitored by LC-MS, after completion, reaction mixture was purified by prep HPLC (45-55% acetonitrile in water with 0.5% TFA buffer) to afford perfluorophenyl 1-(((2R,3R,4R,5R,6R)-3-acetamido-4,5-dihydroxy-6-(hydroxymethyl)tetrahydro-2H-pyran-2-yl)oxy)-16-((3-((3-(5-(((2R,3R,4R,5R,6R)-3-acetamido-4,5-dihydroxy-6-(hydroxymethyl) tetrahydro-2H-pyran-2-yl)oxy)pentanamido)propyl)amino)-3-oxopropoxy)methyl)-5,11,18-trioxo-14-oxa-6,10,17-triazanonacosan-29-oate (Compound I-144) as white solid. Yield: 0.026 g, 9.0%; LCMS m/z 1332.98 [M+1]+; $^1$H NMR (400 MHz, DMSO-d$_6$ with D$_2$O) δ 4.20 (d, J=8.4 Hz, 2H), 3.92-3.90 (m, 2H), 3.67-3.62 (m, 6H), 3.55-3.50 (m, 3H), 3.41-3.38 (m, 3H), 3.35-3.25 (m, 8H), 3.05-2.95 (m, 8H), 2.74 (t, J=7.2 Hz, 2H), 2.30-2.25 (m, 4H), 2.17 (t, J=6.8 Hz, 1H), 2.05-1.98 (m, 6H), 1.85 (s, 6H), 1.68-1.60 (m, 2H), 1.55-1.38 (m, 16H), 1.37-1.14 (m, 15H).

Example 22: Synthesis of Compounds I-131 and I-133

N,N'-(10-(12-(2,5-dioxo-2,5-dihydro-1H-pyrrol-1-yl)do-decanamido)-5,15-dioxo-8,12-dioxa-4,16-diazanonade-cane-1,19-diyl)bis(5-(((2R,3R,4R,5R,6R)-3-acetamido-4,5-dihydroxy-6-(hydroxymethyl)tetrahydro-2H-pyran-2-yl)oxy)pentanamide) (Compound I-131)

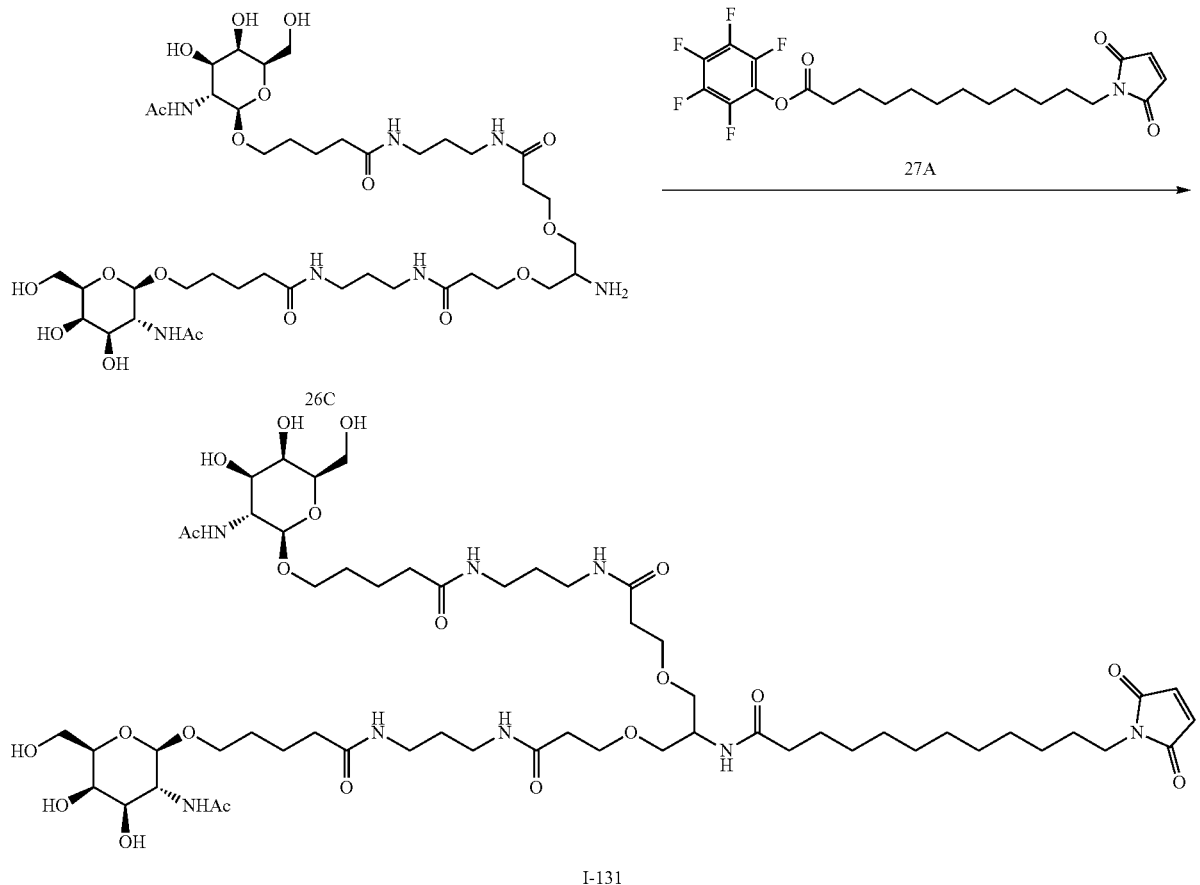

I-131

Compound I-131 was synthesized by employing the procedures described for Compound I-144 using Compound 27A in lieu of Compound 9A to afford N,N'-(10-(12-(2,5-dioxo-2,5-dihydro-1H-pyrrol-1-yl)dodecanamido)-5,15-dioxo-8,12-dioxa-4,16-diazanonadecane-1,19-diyl)bis(5-(((2R,3R,4R,5R,6R)-3-acetamido-4,5-dihydroxy-6-(hydroxymethyl)tetrahydro-2H-pyran-2-yl)oxy)pentanamide) (Compound I-131) as white solid. Yield: 0.026 g, 9.0%; LCMS m/z 1231.91 [M+1]$^+$, $^1$H NMR (400 MHz, DMSO-d$_6$, D$_2$O exchange) δ 6.94 (s, 1H), 4.20 (d, J=8.4 Hz, 2H), 3.90 (t, J=10.8 Hz, 1H), 3.70-3.63 (m, 4H) 3.56-3.40 (m, 8H), 3.37-3.29 (m, 13H) 3.02-3.00 (m, 8H) 2.27 (t, J=11.6 Hz, 4H), 2.05 (t, J=6.4 Hz, 4H), 1.79 (s, 6H), 1.49-1.41 (m, 16H), 1.19 (s, 15H).

N-(2-(3-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-3-oxopropoxy)ethyl)-12-(2,5-dioxo-2,5-dihydro-1H-pyrrol-1-yl)dodecanamide (Compound I-133) can be synthesized by adapting the procedure for compound I-131. The structure of compound and data for compound I-133 is presented below.

I-133

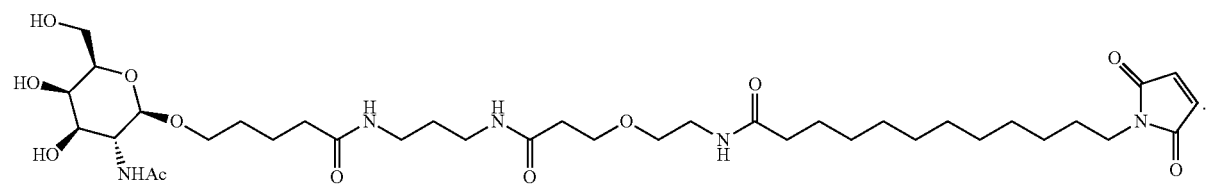

LC-MS; m/z 770.43 [M + 1]$^+$ $^1$H NMR (400 MHz, DMSO-d$_6$ with D$_2$O exchange) δ 6.93 (s, 2H), 4.19 (d, J=8.4 Hz, 1H), 3.60-3.57 (m, 2H), 3.57 (t, J=6.4 Hz, 2H), 3.53-3.44 (m, 2H), 3.40-3.27 (m, 7H), 3.15-3.13 (m, 2H), 3.01 (brs, 4H), 2.28 (t, J=6 Hz, 2H), 2.02 (br t, J=7 Hz, 4H), 1.78 (s, 3H), 1.46 (m, 9H), 1.18 (br m, 15H).

Example 23: Perfluorophenyl 1-(((2R,3R,4R,5R,6R)-3-acetamido-4,5-dihydroxy-6-(hydroxymethyl)tetrahydro-2H-pyran-2-yl)oxy)-5,16-dioxo-9,12-dioxa-6,15-diazaheptacosan-27-oate (I-150)

A mixture of 5-[(2R,3R,4R,5R,6R)-3-acetamido-4,5-diacetoxy-6-(acetoxymethyl)tetrahydropyran-2-yl]oxypentanoic acid (Int C) (1.00 eq, 109 mg, 0.244 mmol) and HATU (1.45 eq, 134 mg, 0.353 mmol) were dissolved in DMF (1.2 mL) before adding N,N-diisopropylethylamine (2.00 eq, 85 µL, 0.487 mmol) followed by azido-PEG2-amine (1.10 eq, 42 µL, 0.268 mmol). After 30 minutes, the reaction was filtered then purified directly by reversed-phase HPLC (10-80% acetonitrile in water w/0.1% formic acid) to give [(2R,3R,4R,5R,6R)-5-acetamido-3,4-diacetoxy-6-[5-[2-[2-(2-azidoethoxy)ethoxy]ethylamino]-5-oxo-pentoxy]

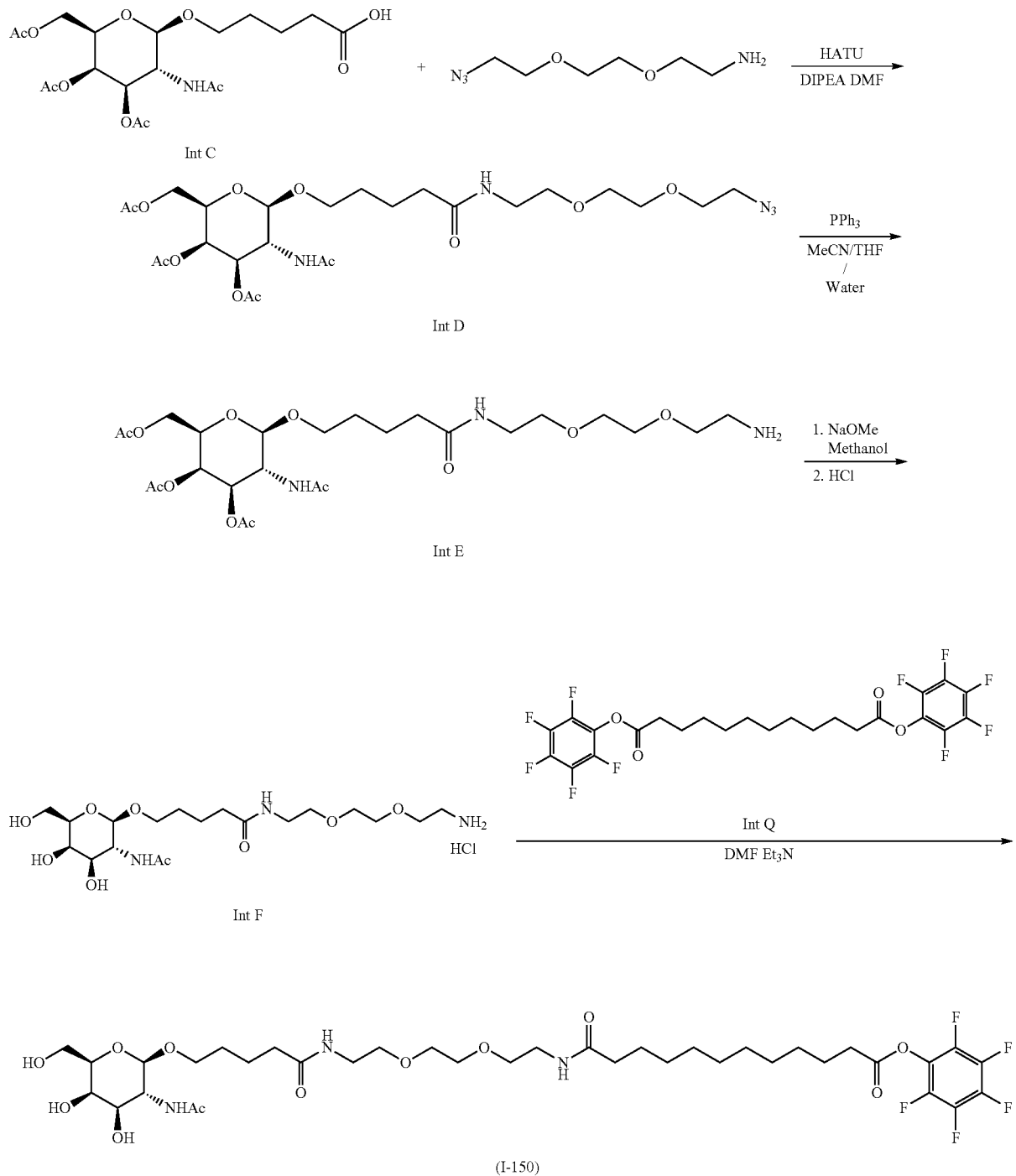

(I-150)

tetrahydropyran-2-yl]methyl acetate (Int D). Yield: 136 mg, 92.5%. LCMS m/z 604.3 [M+H]⁺.

A solution of [(2R,3R,4R,5R,6R)-5-acetamido-3,4-diacetoxy-6-[5-[2-[2-(2-azidoethoxy)ethoxy]ethylamino]-5-oxo-pentoxy]tetrahydropyran-2-yl]methyl acetate (Int D) (1.00 eq, 130 mg, 0.215 mmol) in acetonitrile (1 mL) and THF (0.500 mL) was treated with triphenylphosphine (3.00 eq, 169 mg, 0.646 mmol) for 2 hours before adding water (0.500 mL). The reaction was stirred overnight at room temperature. Volatile components were removed under reduced pressure and the residue purified by reversed-phase HPLC (10-100% acetonitrile in water w/0.1% TFA) to give [(2R,3R,4R,5R,6R)-5-acetamido-3,4-diacetoxy-6-[5-[2-[2-(2-aminoethoxy)ethoxy]ethylamino]-5-oxo-pentoxy]tetrahydropyran-2-yl]methyl acetate (Int E) as the TFA salt. Yield: 40 mg, 26%. LCMS m/z 578.2 [M+H]⁺.

A solution of [(2R,3R,4R,5R,6R)-5-acetamido-3,4-diacetoxy-6-[5-[2-[2-(2-aminoethoxy)ethoxy]ethylamino]-5-oxo-pentoxy]tetrahydropyran-2-yl]methyl acetate; 2,2,2-trifluoroacetic acid (Int E) (1.00 eq, 40.0 mg, 0.0463 mmol) in methanol (116 µL) was treated with a solution of sodium methoxide, 0.75M in methanol (1.00 eq, 62 µL, 0.0463 mmol) until a pH>8 was achieved (5 eq) then another charge of sodium methoxide, 0.75M in methanol (1.00 eq, 62 µL, 0.0463 mmol) was added and the reaction was stirred at room temperature. After 24 h, the reaction was acidified with 4M HCl in dioxane (1.00 eq, 0.046 mL, 0.0463 mmol) then volatile components were removed under reduced pressure. The crude material was used in the next step without further purification. LCMS m/z 488.2 [M+H]⁺.

A slurry of 5-(((2R,3R,4R,5R,6R)-3-acetamido-4,5-dihydroxy-6-(hydroxymethyl)tetrahydro-2H-pyran-2-yl)oxy)-N-(2-(2-(2-aminoethoxy)ethoxy)ethyl)pentanamide hydrochloride (Int F) (1.00 eq, 20.0 mg, 0.0410 mmol) and triethylamine (2.00 eq, 11 µL, 0.0820 mmol) in DMF (0.439 mL) was added to a solution of bis(2,3,4,5,6-pentafluorophenyl) dodecanedioate (2.50 eq, 57.6 mg, 0.102 mmol) in DMF (0.439 mL) and the reaction was stirred at room temp. After 30 minutes, the reaction was diluted with DMSO, filtered, then purified by reversed-phase HPLC (20-80% acetonitrile in water) to give the title compound (2,3,4,5,6-pentafluorophenyl) 12-[2-[2-[2-[5-[(2R,3R,4R,5R,6R)-3-acetamido-4,5-dihydroxy-6-(hydroxymethyl)tetrahydropyran-2-yl]oxypentanoylamino]ethoxy]ethoxy]ethylamino]-12-oxo-dodecanoate (I-150) as a white solid, Yield: 13 mg, 34%. LCMS m/z 830.2 [M+H]⁺.

Compounds I-149, and I-151 can be obtained by adapting the procedure for the synthesis of compound I-150. The structures and LCMS data for I-149 and I-151 are presented below.

(I-149)

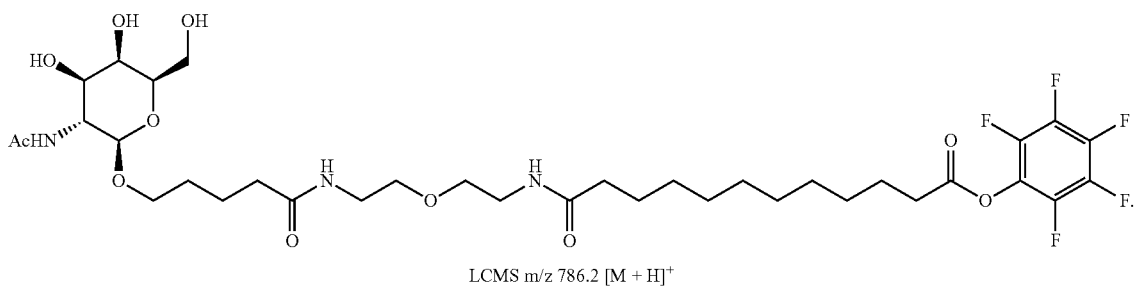

LCMS m/z 786.2 [M + H]⁺

(I-151)

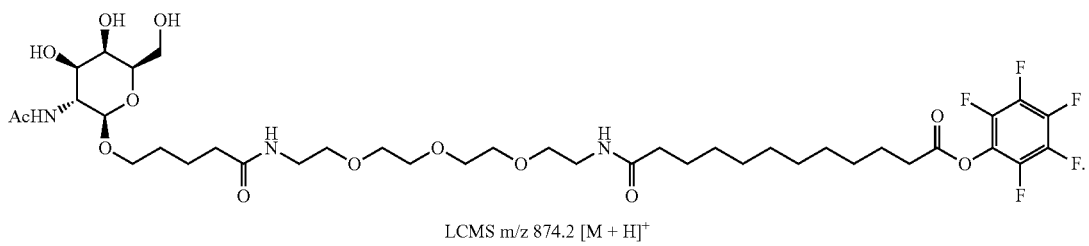

LCMS m/z 874.2 [M + H]⁺

Example 24: Synthesis of Perfluorophenyl 12-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-12-oxododecanoate (I-164)

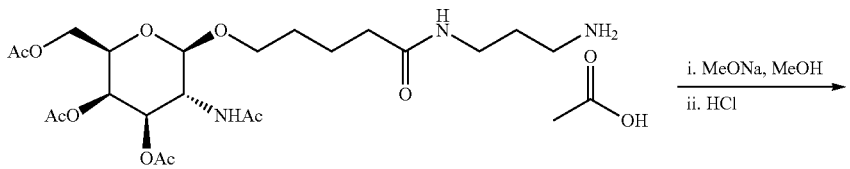

ISP2-99-3a

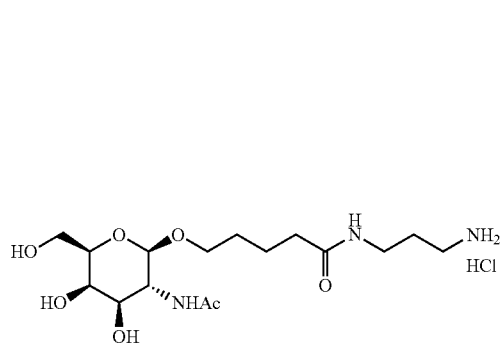

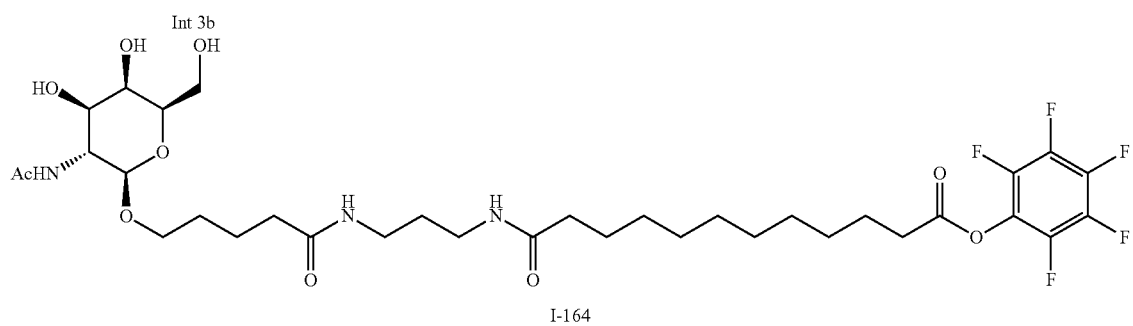

I-164

A solution of (2R,3R,4R,5R,6R)-5-acetamido-2-(acetoxymethyl)-6-((5-((3-aminopropyl)amino)-5-oxopentyl)oxy)tetrahydro-2H-pyran-3,4-diyl diacetate acetate (ISP2-99-3a) (1.00 eq, 80.0 mg, 0.159 mmol) in methanol (530 uL) was treated with a 1M solution of sodium methoxide (1.40 eq, 223 μL, 0.223 mmol) in methanol. After 18 hours, the reaction was acidified with 1M aqueous HCl (0.500 eq, 79 μL, 0.0794 mmol) until the solution became acidic (pH ~3). The reaction was concentrated under reduced pressure to give crude 5-(((2R,3R,4R,5R,6R)-3-acetamido-4,5-dihydroxy-6-(hydroxymethyl)tetrahydro-2H-pyran-2-yl)oxy)-N-(3-aminopropyl)pentanamide (Int 3b) as the HCl salt. This material was used in the next step without further purification. Yield: 90 mg. LCMS m/z 378.2 [M+H]+.

A solution of 5-(((2R,3R,4R,5R,6R)-3-acetamido-4,5-dihydroxy-6-(hydroxymethyl)tetrahydro-2H-pyran-2-yl)oxy)-N-(3-aminopropyl)pentanamide (Int 3b) (1.00 eq, 10.0 mg, 0.0265 mmol) and N,N-diisopropylethylamine (1.00 eq, 4.6 μL, 0.0265 mmol) in DMF (265 μL) was added to an ice cold solution of bis(2,3,4,5,6-pentafluorophenyl) dodecanedioate (2.00 eq, 29.8 mg, 0.0530 mmol) in DMF (265 μL) and the reaction was stirred at 0° C. for 1 hour. The reaction solution was acidified with a drop of formic acid then purified directly by reversed-phase HPLC (10-100% acetonitrile in water w/0.1% formic acid) to give perfluorophenyl 12-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-12-oxododecanoate (I-164) as a white solid. Yield: 6.5 mg, 32%. LCMS m/z 778.34 [M+Na]+.

Example 25: perfluorophenyl 1-(4-(3-(((2R,3R,4R,5R,6R)-3-acetamido-4,5-dihydroxy-6-(hydroxymethyl)tetrahydro-2H-pyran-2-yl)oxy)propyl)-1H-1,2,3-triazol-1-yl)-13,13-bis(3-((2-(2-(2-(4-(3-(((2R,3R,4R,5R,6R)-3-acetamido-4,5-dihydroxy-6-(hydroxymethyl)tetrahydro-2H-pyran-2-yl)oxy)propyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-135)

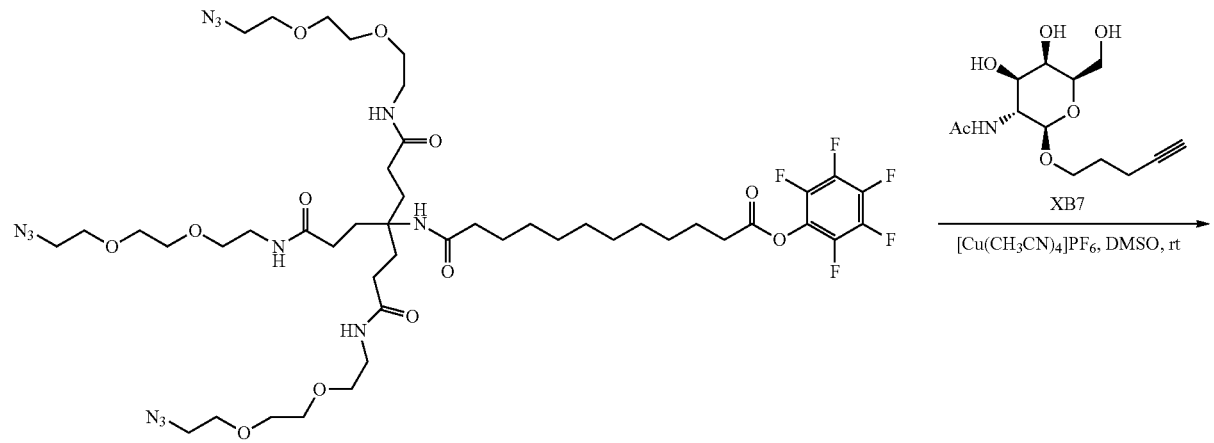

131A

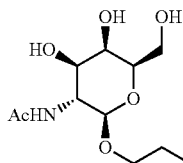
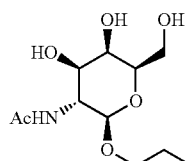
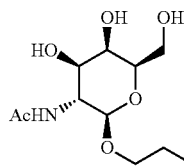
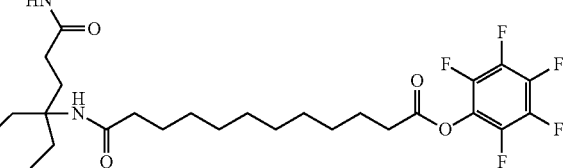

I-135

To a solution of perfluorophenyl 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oate (131A, 1.0 eq, 0.095 g, 0.086 mmol) in dimethylsulfoxide (2.0 mL), N-((2R,3R,4R,5R,6R)-4,5-dihydroxy-6-(hydroxymethyl)-2-(pent-4-yn-1-yloxy)tetrahydro-2H-pyran-3-yl)acetamide (XB7, 3.0 eq, 0.074 g, 0.26 mmol) was added and stirred for 5 minutes. Then, tetrakis(acetonitrile)copper(I) hexafluorophosphate (8.4 eq., 0.272 g, 0.729 mmol) was added and reaction mixture was stirred at room temperature for 1 h. After completion, reaction mixture was diluted with acetonitrile and purified by preparative HPLC (33-53% acetonitrile in water with 0.1% TFA). Fractions containing the desired product were combined and lyophilized to dryness to afford perfluorophenyl 1-(4-(3-(((2R,3R,4R,5R,6R)-3-acetamido-4,5-dihydroxy-6-(hydroxymethyl)tetrahydro-2H-pyran-2-yl)oxy)propyl)-1H-1,2,3-triazol-1-yl)-13,13-bis(3-((2-(2-(2-(4-(((2R,3R,4R,5R,6R)-3-acetamido-4,5-dihydroxy-6-(hydroxymethyl)tetrahydro-2H-pyran-2-yl)oxy)propyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-135) as an off white solid. Yield: 0.036 g, 19.2%; LCMS m/z 978.89 [M+2H]++; $^1$H NMR (400 MHz, DMSO-d$_6$ with D$_2$O) δ 7.76 (s, 3H), 4.42 (t, J=5.2 Hz, 6H), 4.22 (d, J=8.8 Hz, 3H), 3.75-3.68 (m, 11H), 3.63-3.62 (m, 3H), 3.54-3.46 (m, 13H), 3.43-3.42 (m, 8H), 3.40-3.37 (m, 4H), 3.35-3.24 (m, 10H), 3.12 (t, J=5.6 Hz, 6H), 2.71 (t, J=7.2 Hz, 2H), 2.61-2.57 (m, 6H), 2.05-1.92 (m, 7H), 1.79 (s, 9H), 1.76-1.73 (m, 10H), 1.62-1.60 (m, 2H), 1.45-1.41 (m, 2H), 1.36-1.29 (m, 2H), 1.25-1.16 (m, 10H).

Example 26: perfluorophenyl 1-(4-((((2R,3R,4R,5R,6R)-5-acetamido-3,4-dihydroxy-6-methoxytetrahydro-2H-pyran-2-yl)methoxy)methyl)-1H-1,2,3-triazol-1-yl)-13,13-bis(3-((2-(2-(2-(4-((((2R,3R,4R,5R,6R)-5-acetamido-3,4-dihydroxy-6-methoxytetrahydro-2H-pyran-2-yl)methoxy)methyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-136)

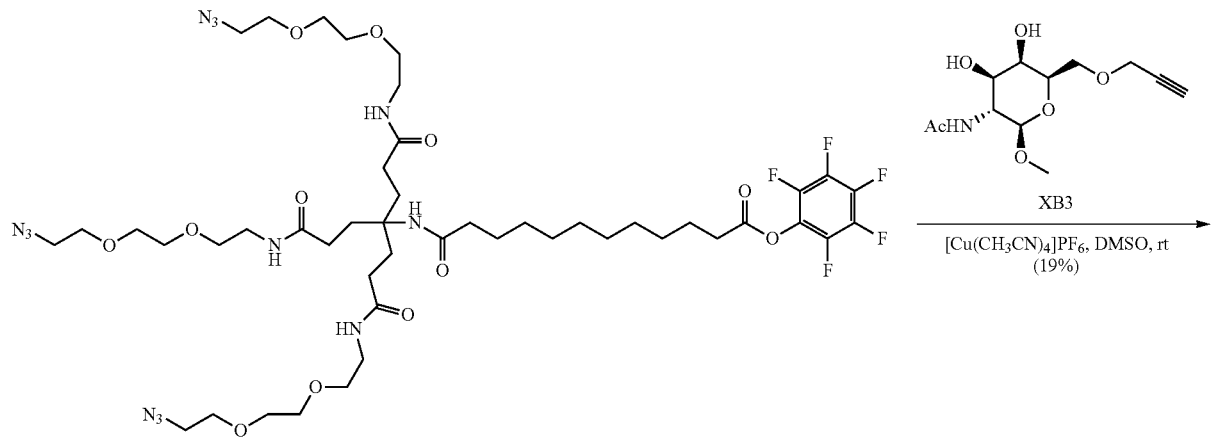

132A

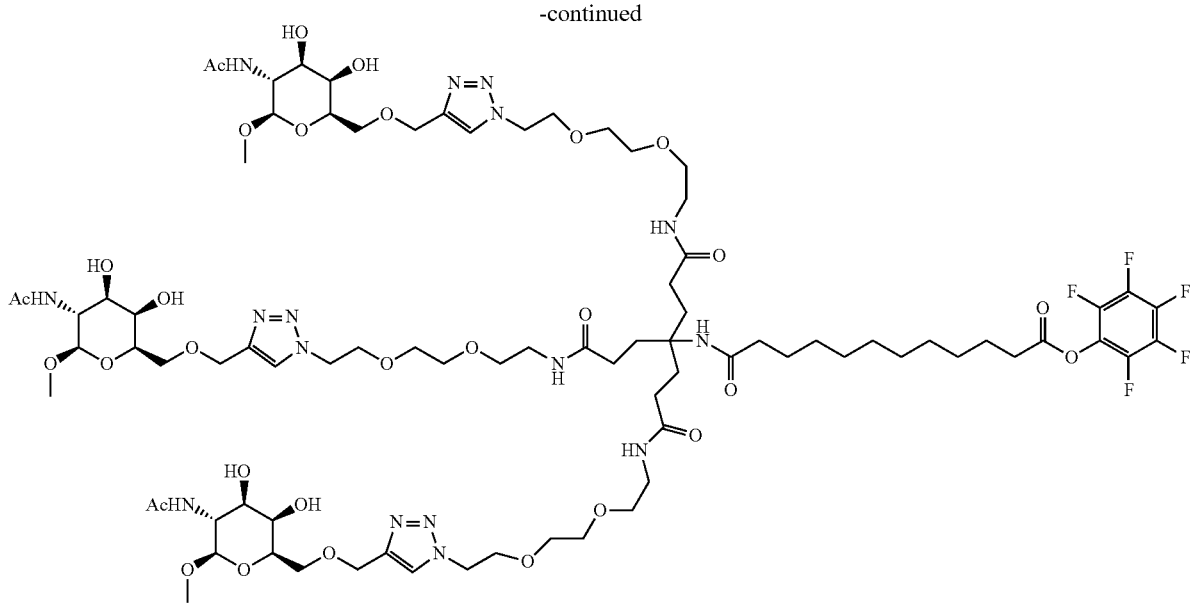

I-136

To a solution of perfluorophenyl 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oate (132A, 1.0 eq, 0.160 g, 0.146 mmol) in dimethyl sulfoxide (3 mL), N-((2R,3R,4R,5R,6R)-4,5-dihydroxy-2-methoxy-6-((prop-2-yn-1-yloxy)methyl)tetrahydro-2H-pyran-3-yl)acetamide (XB3, 3.0 eq, 0.120 g, 0.439 mmol) and tetrakis(acetonitrile)copper(I) hexafluorophosphate (8.4 eq, 0.458 g, 1.23 mmol) were added and reaction mixture was stirred at room temperature for 1 h. After completion, reaction mixture was diluted with acetonitrile and purified by preparative HPLC (eluting from a C18 column with 30-57% acetonitrile in water with 0.1% TFA). Fractions containing the desired product were combined and lyophilized to dryness to afford perfluorophenyl 1-(4-((((2R,3R,4R,5R,6R)-5-acetamido-3,4-dihydroxy-6-methoxytetrahydro-2H-pyran-2-yl)methoxy)methyl)-1H-1,2,3-triazol-1-yl)-13,13-bis(3-((2-(2-(2-(4-((((2R,3R,4R,5R,6R)-5-acetamido-3,4-dihydroxy-6-methoxytetrahydro-2H-pyran-2-yl)methoxy)methyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-136) as an off white solid. Yield: 0.055 g, 19.6%; LCMS m/z 957.74 [M+2H]++; 1H NMR (400 MHz, DMSO-d6) δ 8.04 (s, 3H), 7.81-7.80 (m, 2H), 7.63 (d, J=8.8 Hz, 2H), 7.11 (s, 1H), 4.54 (d, J=4.4 Hz, 5H), 4.50 (t, J=5.2 Hz, 6H), 4.16 (d, J=8.4 Hz, 3H), 3.80 (t, J=5.2 Hz, 8H), 3.76-3.69 (m, 4H), 3.63-3.56 (m, 12H), 3.52-3.49 (m, 14H), 3.47-3.44 (m, 11H), 3.29 (s, 9H), 3.20 (s, 1H), 3.15 (d, J=6.0 Hz, 8H), 2.76 (t, J=6.8 Hz, 2H), 2.03-1.96 (m, 9H), 1.83-1.76 (m, 11H), 1.71-1.63 (m, 2H), 1.45-1.40 (m, 2H), 1.36-1.32 (m, 2H), 1.28-1.20 (m, 12H).

Example 27: 2,3,4,5,6-pentafluorophenyl 1-[4-(2-{[1,3-bis(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propan-2-yl]carbamoyl}ethyl)-1H-1,2,3-triazol-1-yl]-3,6,9,12,15,18,21,24,27,30,33,36,39,42,45,48,51,54,57,60,63,66,69,72-tetracosaoxapentaheptacontan-75-oate Cpd. No. I-137)

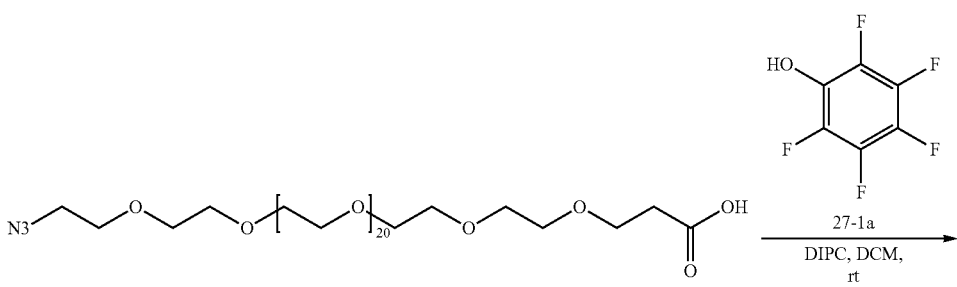

-continued

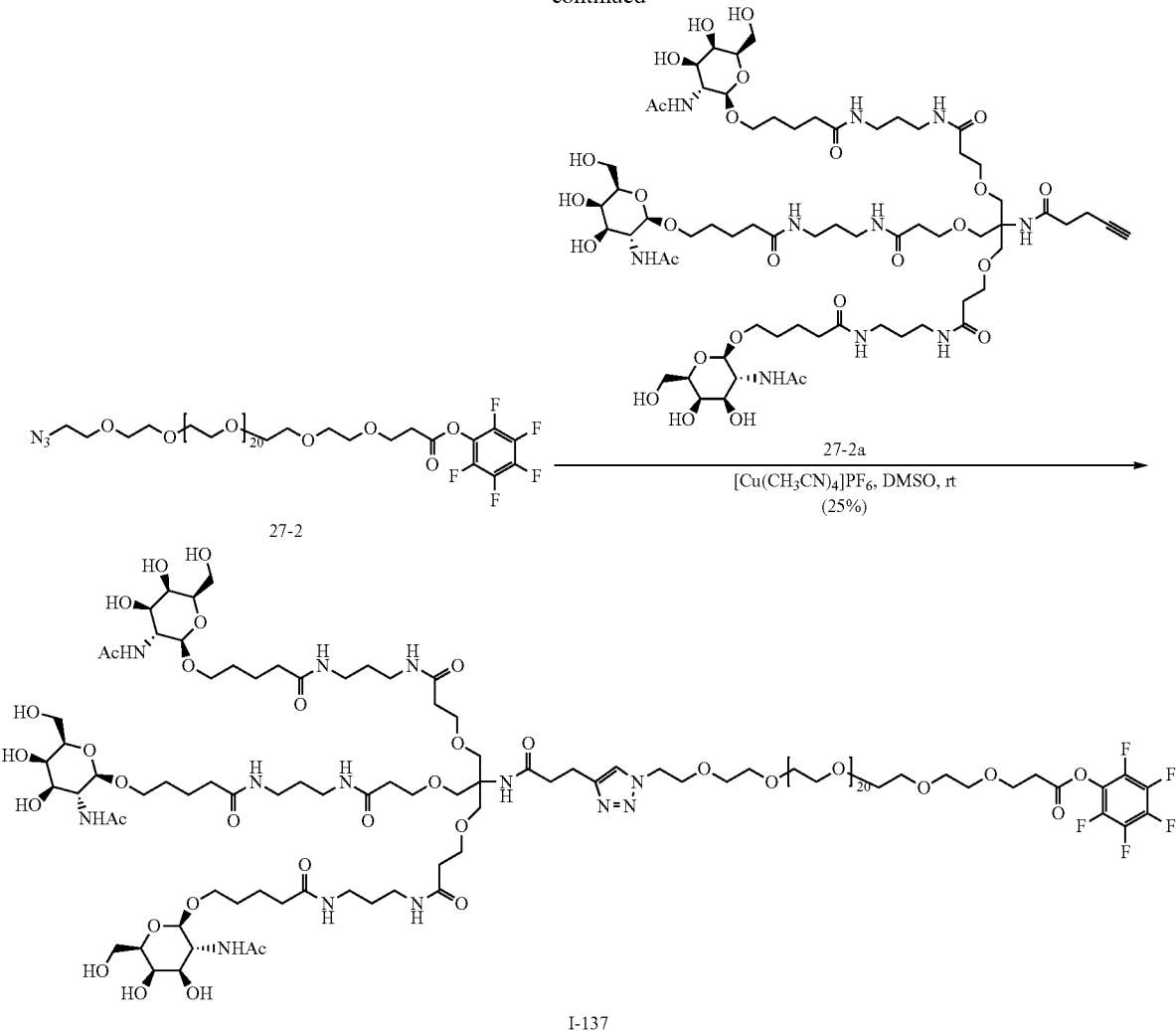

I-137

To a solution of 1-azido-3,6,9,12,15,18,21,24,27,30,33,36,39,42,45,48,51,54,57,60,63,66,69,72-tetracosaoxapentaheptacontan-75-oic acid (27-1, 1.0 eq, 0.050 g, 0.042 mmol) in dichloromethane (1.0 mL), pentafluorophenol (27-Ia, 1.1 eq, 0.008 g, 0.046 mmol) and N,N'-diisopropylcarbodiimide (1.5 eq, 0.008 g, 0.064 mmol) were added and reaction mixture was stirred at room temperature for 2 h. After completion, reaction mixture was diluted with dichloromethane, filtered through syringe filter, filtrate was concentrated and dried to afford 2,3,4,5,6-pentafluorophenyl 1-azido-3,6,9,12,15,18,21,24,27,30,33,36,39,42,45,48,51,54,57,60,63,66,69,72-tetracosaoxapentaheptacontan-75-oate (27-2) as a colourless sticky solid. Yield: 0.070 g (Crude), LCMS m/z 669.8 [M+2H]++.

To a solution of [(2R,3R,4R,5R,6R)-3,4-bis(acetyloxy)-6-{4-[(3-{3-[3-(2-{[3-(5-{[(2R,3R,4R,5R,6R)-4,5-bis(acetyloxy)-6-[(acetyloxy)methyl]-3-acetamidooxan-2-yl]oxy}pentanamido)propyl]carbamoyl}ethoxy)-2-[(2-{[3-(5-{[(2R,3R,4R,5R,6R)-4,5-bis(acetyloxy)-6-[(acetyloxy)methyl]-3-acetamidooxan-2-yl]oxy}pentanamido)propyl]carbamoyl}ethoxy)methyl]-2-(pent-4-ynamido)propoxy]propanamido}propyl)carbamoyl]butoxy}-5-acetamidooxan-2-yl]methyl acetate (27-2a, 1.0 eq, 0.030 g, 0.016 mmol) in dimethylsulfoxide (0.5 mL), 2,3,4,5,6-pentafluorophenyl 1-azido-3,6,9,12,15,18,21,24,27,30,33,36,39,42,45,48,51,54,57,60,63,66,69,72-tetracosaoxapentaheptacontan-75-oate (27-2, 2.0 eq, 0.042 g, 0.032 mmol) was added and stirred for 5 minutes. Then, tetrakis(acetonitrile)copper(I) hexafluorophosphate (2.8 eq., 0.016 g, 0.044 mmol) was added and reaction mixture was stirred at room temperature for 15 minutes. After completion, reaction mixture was diluted with acetonitrile and purified by preparative HPLC (27-62% acetonitrile in water with 0.1% TFA). Fractions containing the desired product were combined and lyophilized to dryness to afford 2,3,4,5,6-pentafluorophenyl 1-[4-(2-{[1,3-bis(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propan-2-yl]carbamoyl}ethyl)-1H-1,2,3-triazol-1-yl]-3,6,9,12,15,18,21,24,27,30,33,36,39,42,45,48,51,54,57,60,63,66,69,72-tetracosaoxapentaheptacontan-75-oate (Cpd. No. I-137) as a colourless sticky solid. Yield: 0.012 g, 25.93%; LCMS m/z 1417.18 [M+2H]++; $^1$H NMR (400 MHz, D$_2$O) δ 7.82 (s, 1H), 4.56 (bs, 3H), 4.40 (d, J=8.4 Hz, 4H), 3.90-3.82 (m, 14H), 3.75-3.70 (m, 5H), 3.67-3.49 (m, 111H), 3.17 (d, J=6.4 Hz, 12H), 3.05 (t, J=5.2 Hz, 2H), 2.92 (t, J=7.6 Hz, 2H), 2.57 (t, J=6.0 Hz, 2H), 2.43 (bs, 6H), 2.20 (bs, 6H), 1.99 (s, 9H), 1.71-1.66 (m, 6H), 1.54 (bs, 12H).

Example 28: 2,3,4,5,6-pentafluorophenyl 11-{[1,5-bis({[2-(2-{2-[4-(3-{[(2R,3R,4R,5R,6R)-3-acet-amido-5-hydroxy-6-(hydroxymethyl)-4-[(2-methyl-propanoyl)oxy]oxan-2-yl]oxy}propyl)-1H-1,2,3-triazol-1-yl]ethoxy}ethoxy)ethyl]carbamoyl})-3-(2-{[2-(2-{2-[4-(3-{[(2R,3R,4R,5R,6R)-3-acetamido-5-hydroxy-6-(hydroxymethyl)-4-[(2-methylpropanoyl)oxy]oxan-2-yl]oxy}propyl)-1H-1,2,3-triazol-1-yl]ethoxy}ethoxy)ethyl]carbamoyl}ethyl)pentan-3-yl]carbamoyl}undecanoate (Cpd. No. I-138)

ethyl)-2-(pent-4-yn-1-yloxy)tetrahydro-2H-pyran-4-yl isobutyrate (XB4, 3.0 eq, 0.098 g, 0.274 mmol) and tetrakis (acetonitrile)copper(I) hexafluorophosphate (8.4 eq., 0.286 g, 0.768 mmol) were added and reaction mixture was stirred at room temperature for 1 h. After completion, reaction mixture was quenched with acetic acid and purified by preparative HPLC (42-60% acetonitrile in water with 0.1% TFA). Fractions containing the desired product were combined and lyophilized to dryness to afford 2,3,4,5,6-pentafluorophenyl 11-{[1,5-bis({[2-(2-{2-[4-(3-{[(2R,3R,4R,5R,6R)-3-acetamido-5-hydroxy-6-(hydroxymethyl)-4-[(2-methylpropanoyl)oxy]oxan-2-yl]oxy}propyl)-1H-1,2,3-triazol-1-yl]ethoxy}ethoxy)ethyl]carbamoyl})-3-(2-{[2-(2-{2-[4-(3-{[(2R,3R,4R,5R,6R)-3-acetamido-5-hydroxy-6-

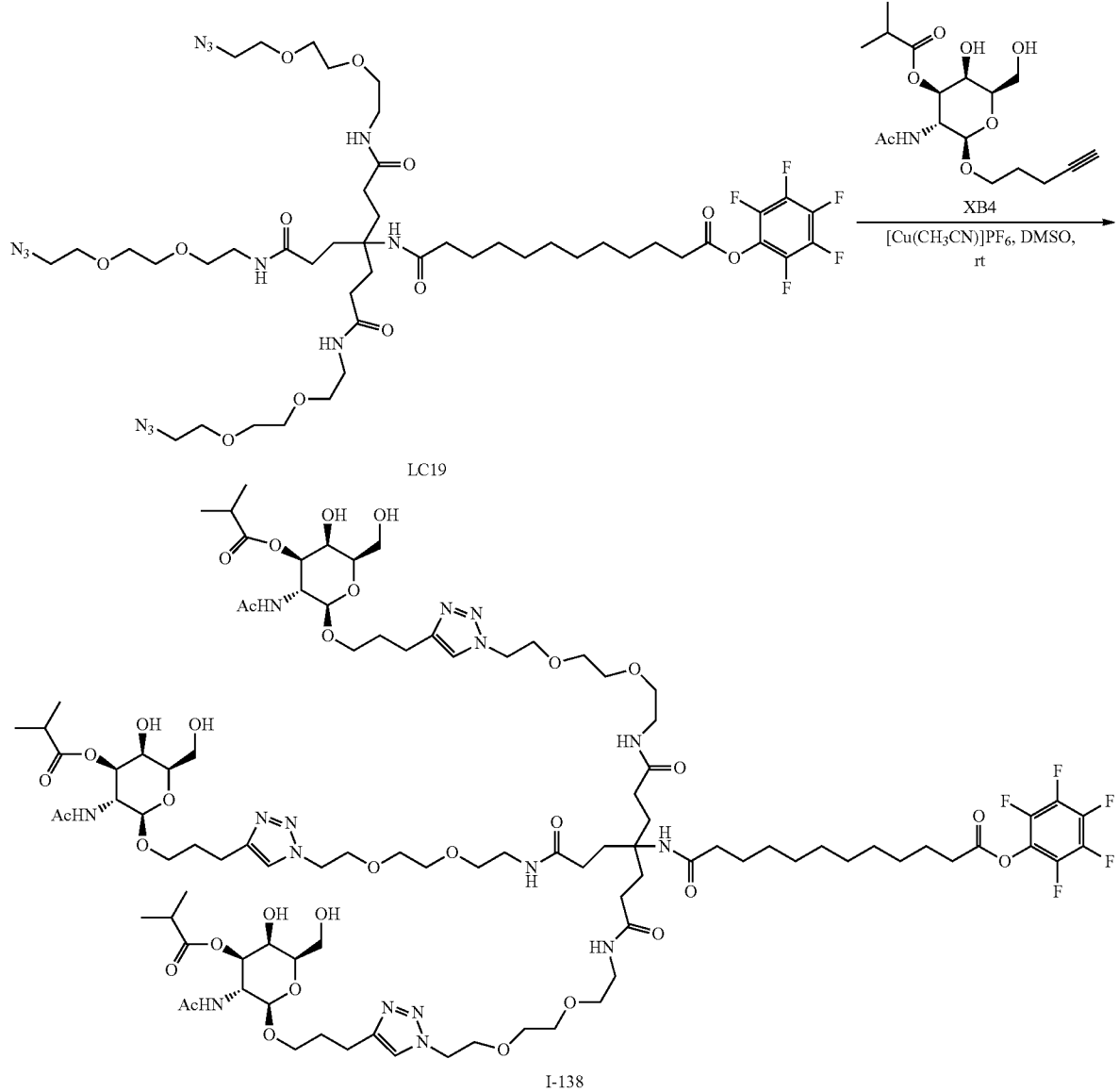

To a solution of perfluorophenyl 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oate (LC19, 1.0 eq, 0.100 g, 0.091 mmol) in dimethyl sulfoxide (1 mL), (2R,3R,4R,5R,6R)-3-acetamido-5-hydroxy-6-(hydroxym-ethyl)-4-[(2-methylpropanoyl)oxy]oxan-2-yl]oxy}propyl)-1H-1,2,3-triazol-1-yl]ethoxy}ethoxy)ethyl]carbamoyl}ethyl)pentan-3-yl]carbamoyl}undecanoate (Cpd. No. I-138) as an off white solid. Yield: 0.040 g, 20.2%; LCMS m/z 1083.15 [M$^+$2H]$^{++}$; 1H NMR (400 MHz, DMSO-d$_6$ with D$_2$O exchange) δ 7.76 (s, 3H), 4.65-4.61 (m, 3H), 4.41 (t, J=4.8 Hz, 6H), 4.35 (d, J=8.4 Hz, 3H), 4.01 (dd, J=8.4, 10.8 Hz, 3H), 3.80 (d, J=2.8 Hz, 3H), 3.75 (t, J=5.2 Hz, 6H), 3.72-3.65 (m, 3H), 3.54-3.49 (m, 6H), 3.47-3.45 (m, 6H), 3.43-3.40 (m, 12H), 3.32 (t, J=6.0 Hz, 6H), 3.12 (t, J=5.6 Hz, 6H), 2.70-2.67 (m, 2H), 2.58 (t, J=5.6 Hz, 6H), 2.53-2.47 (m, 26H), 2.45-2.43 (m, 2H), 2.02-1.95 (m, 8H), 1.79-1.72 (m, 20H), 1.61-1.60 (m, 2H), 1.48-1.38 (m, 2H), 1.27-1.17 (m, 14H), 1.08-1.05 (m, 1H), 1.03-0.99 (m, 18H).

Example 29: N-(3-{3-[2-(3-{2-[2-({12-[2-(4-{1-[(2,5-dimethylphenyl)methyl]-2-[hydroxy(pyridin-4-yl)methyl]-1H-1,3-benzodiazol-6-yl}-1H-pyrazol-1-yl)ethoxy]dodecyl}carbamoyl)ethoxy]ethoxy}propanamido)-3-(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propoxy]propanamido}propyl)-5-{[(2R,3R,4R,5R,6R)-3-acetamido-4,5-dihydroxy-6-(hydroxymethyl)oxan-2-yl]oxy}pentanamide (Cpd. No. I-139)

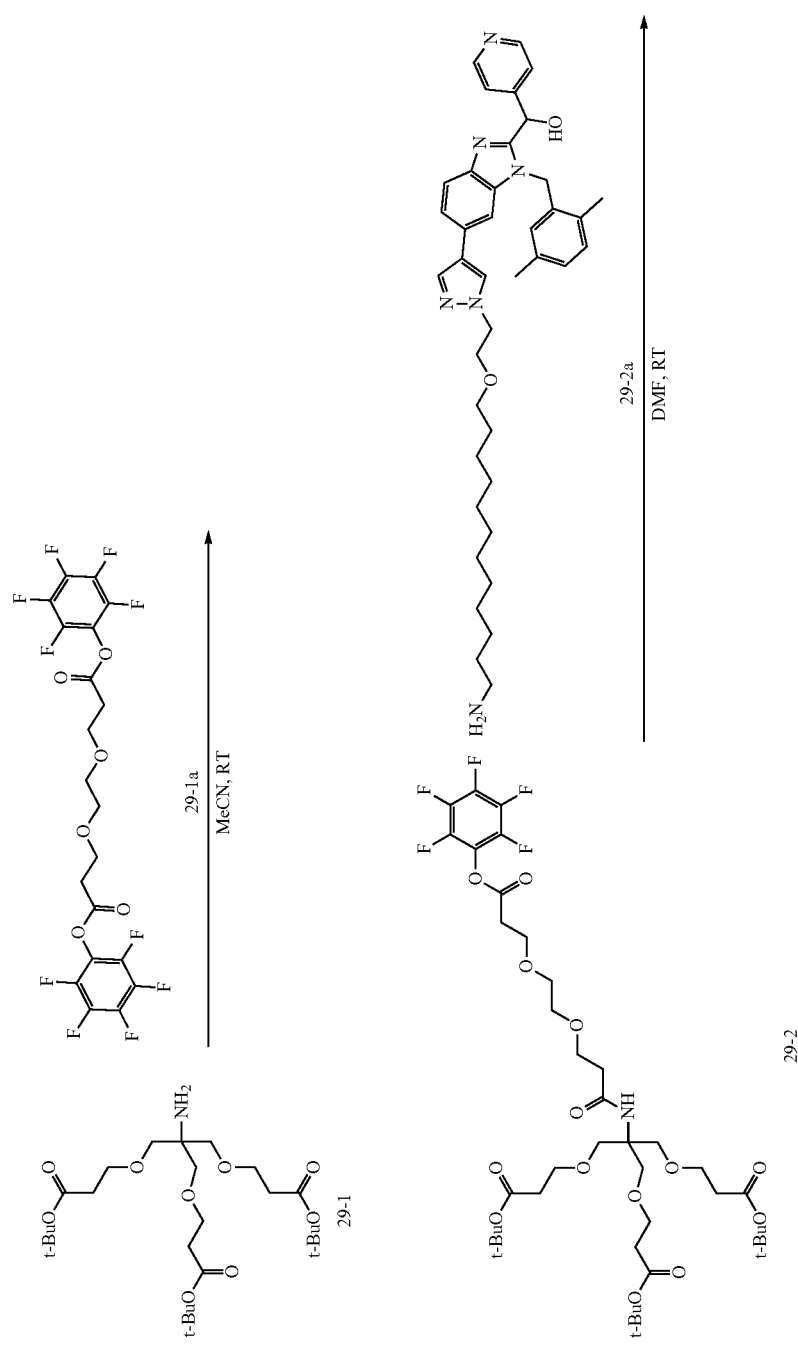

-continued
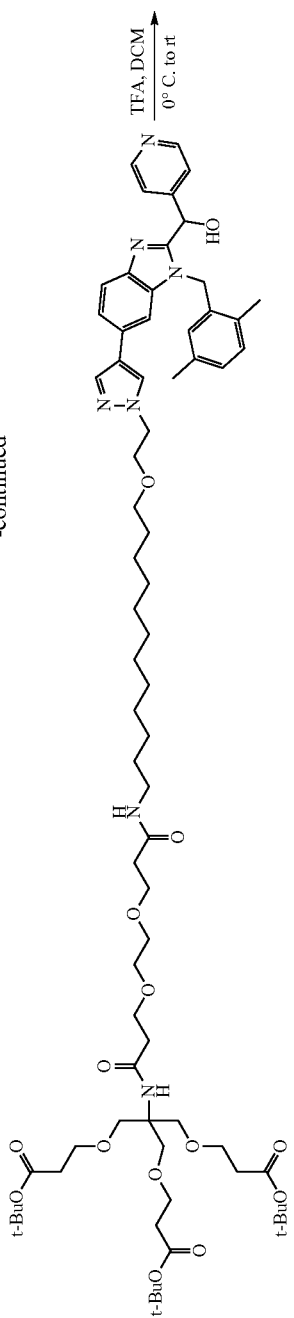
29-3
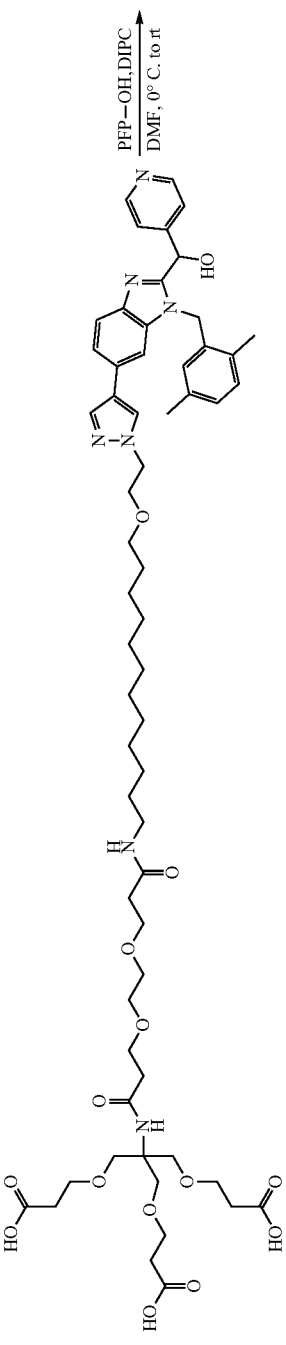
29-4
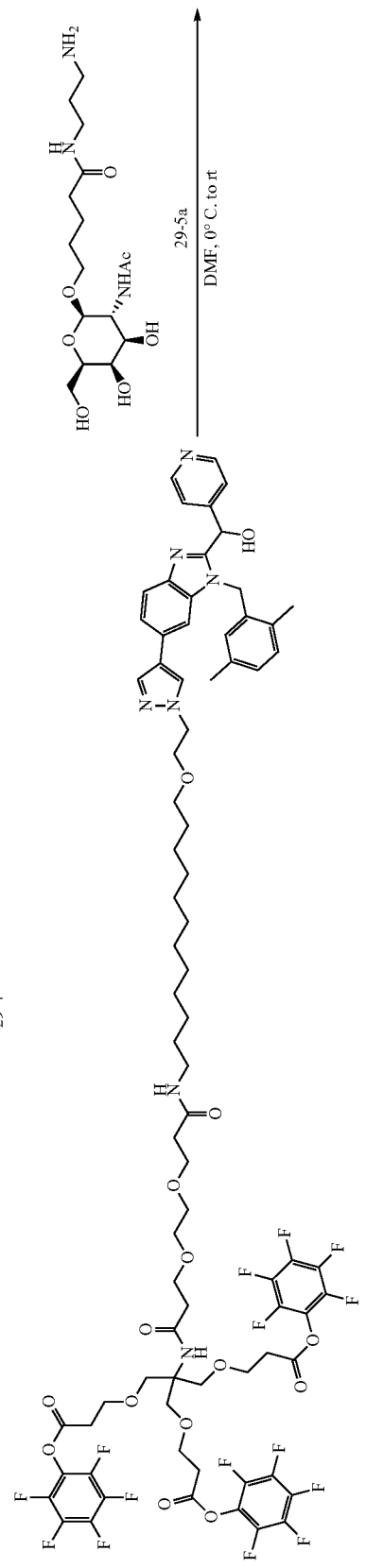
29-5

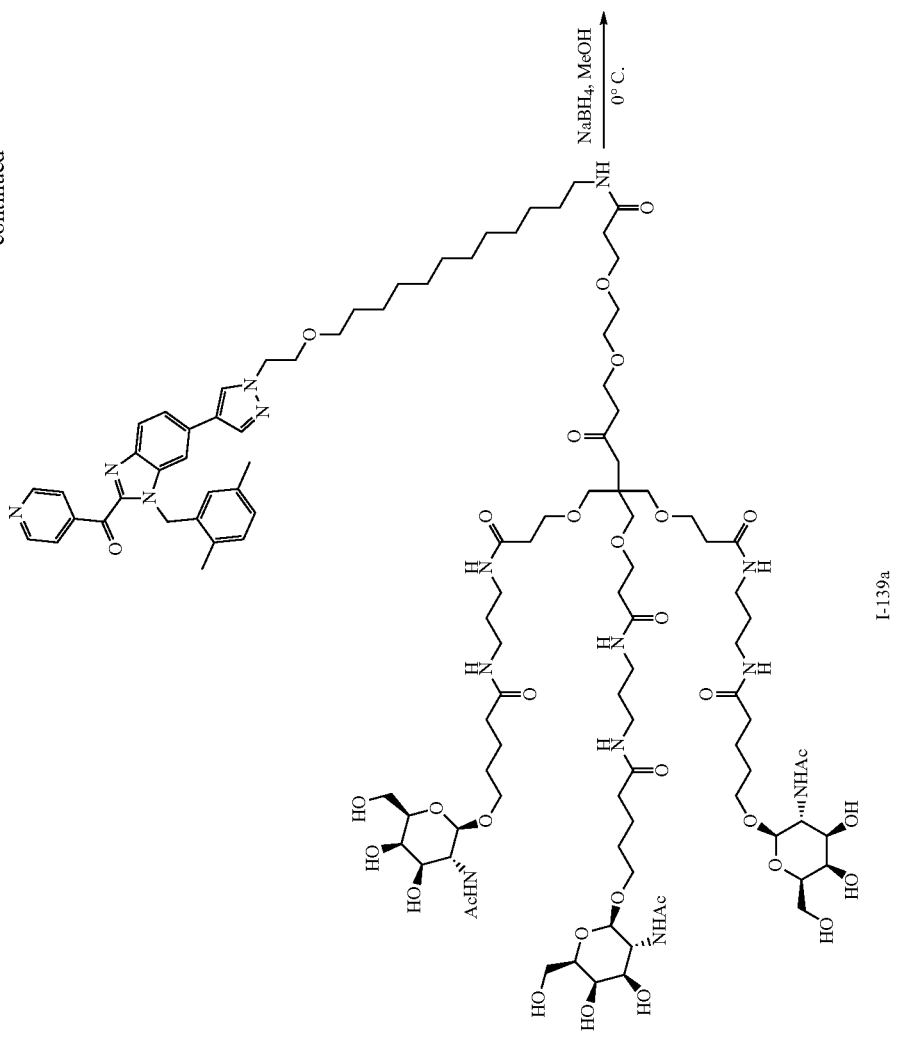
I-139a

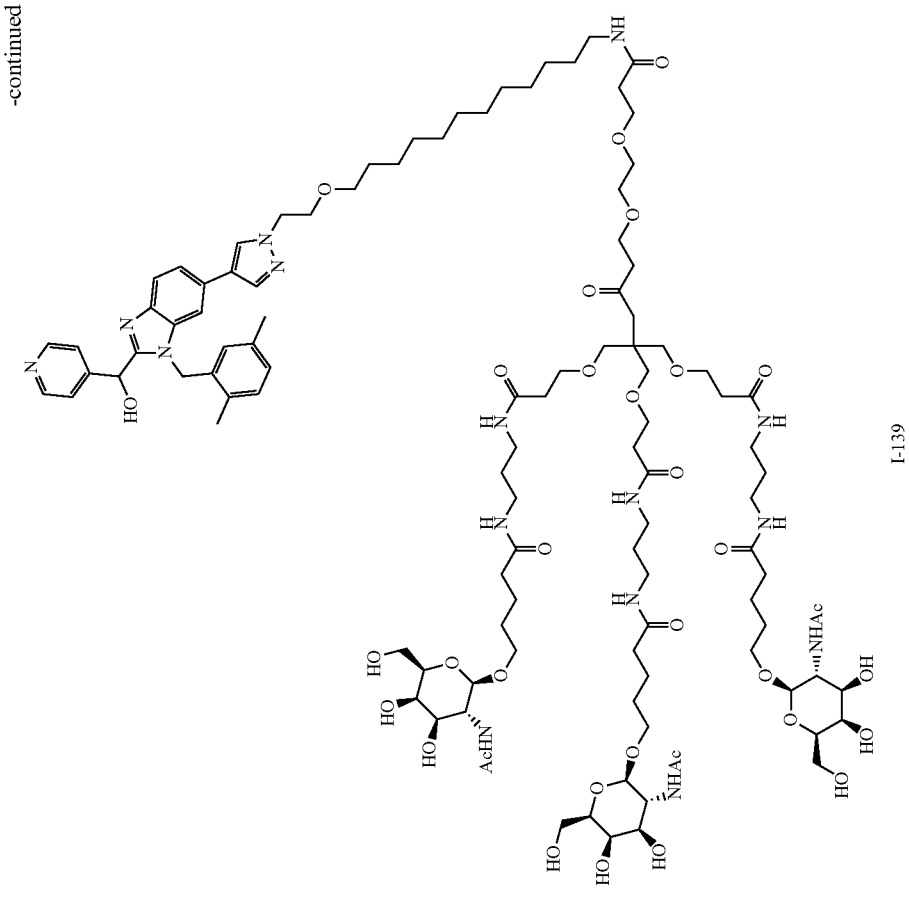
I-139

To a solution of di-tert-butyl 3,3'-((2-amino-2-((3-(tert-butoxy)-3-oxopropoxy)methyl)propane-1,3-diyl)bis(oxy)) dipropionate (29-1, 1.0 g, 1.0 eq, 1.98 mmol) in acetonitrile (15.0 mL) at 0° C. was added bis(perfluorophenyl) 3,3'-(ethane-1,2-diylbis(oxy))dipropionate (0.958 g, 1.0 eq, 1.78 mmol) solution in acetonitrile (15.0 mL) and reaction mixture stirred at room temperature for 16 h. Reaction mixture was then concentrated under reduced pressure at 20 to 25° C. and purified by reverse phase preparative HPLC using 50 to 90% acetonitrile in water and 0.1% acetic acid as buffer. Desired fractions were combined and concentrated under reduced pressure (at 20 to 25° C.) to remove most of acetonitrile and lyophilized to afford 1-(tert-butyl) 17-(perfluorophenyl) 6,6-bis((3-(tert-butoxy)-3-oxopropoxy)methyl)-8-oxo-4,11,14-trioxa-7-azaheptadecanedioate (29-2) as colorless sticky gum. Yield: 0.45 g (26.46%). LCMS m/z 861.25 [M+1]$^+$.

To a solution of 1-(tert-butyl) 17-(perfluorophenyl) 6,6-bis((3-(tert-butoxy)-3-oxopropoxy)methyl)-8-oxo-4,11,14-trioxa-7-azaheptadecanedioate (29-2, 0.400 g, 1.0 eq., 0.465 mmol) in N,N-dimethylformamide (3.0 mL), (6-(1-(2-((12-aminododecyl)oxy)ethyl)-1H-pyrazol-4-yl)-1-(2,5-dimethylbenzyl)-1H-benzo[d]imidazol-2-yl)(pyridin-4-yl)methanol (29-2a, 0.296 g, 1.0 eq., 0.465 mmol) dissolved in N,N-dimethylformamide (2.0 mL) was added at 0° C. and the reaction mixture was stirred at room temperature for 1 h, Thereafter, reaction mixture was quenched with water and extracted with ethyl acetate, organic layer was washed with water and concentrated to get crude compound which was purified by column chromatography using 7 to 10% methanol in dichloromethane as eluent to afford tert-butyl 28,28-bis((3-(tert-butoxy)-3-oxopropoxy)methyl)-1-(4-(1-(2,5-dimethylbenzyl)-2-(hydroxy(pyridin-4-yl)methyl)-1H-benzo[d]imidazol-6-yl)-1H-pyrazol-1-yl)-17,26-dioxo-3,20,23,30-tetraoxa-16,27-diazatritriacontan-33-oate (29-3) as colorless sticky gum. Yield: 0.400 g (65.5%). LCMS m/z 1313.14 [M+1]+.

To a solution of tert-butyl 28,28-bis((3-(tert-butoxy)-3-oxopropoxy)methyl)-1-(4-(1-(2,5-dimethylbenzyl)-2-(hydroxy(pyridin-4-yl)methyl)-1H-benzo[d]imidazol-6-yl)-1H-pyrazol-1-yl)-17,26-dioxo-3,20,23,30-tetraoxa-16,27-diazatritriacontan-33-oate (29-3, 0.400 g 1.0 eq, 0.345 mmol) in dichloromethane (10.00 mL) at 0° C., trifluoroacetic acid (1.00 mL) was added and reaction mixture stirred at room temperature 16 h. Reaction mixture was concentrated under reduce pressure co-evaporated with dichloromethane to remove residual trifluoroacetic acid to afford 28,28-bis((2-carboxyethoxy)methyl)-1-(4-(1-(2,5-dimethylbenzyl)-2-(hydroxy(pyridin-4-yl)methyl)-1H-benzo[d]imidazol-6-yl)-1H-pyrazol-1-yl)-17,26-dioxo-3,20,23,30-tetraoxa-16,27-diazatritriacontan-33-oic acid (29-4) as pale yellow sticky gum. Yield:0.400 g (99.9%). LCMS m/z 1144.15 [M+1]$^+$.

To a solution of 28,28-bis((2-carboxyethoxy)methyl)-1-(4-(1-(2,5-dimethylbenzyl)-2-(hydroxy(pyridin-4-yl)methyl)-1H-benzo[d]imidazol-6-yl)-1H-pyrazol-1-yl)-17,26-dioxo-3,20,23,30-tetraoxa-16,27-diazatritriacontan-33-oic acid (29-4, 0.380 g, 1.0 eq, 0.332 mmol) in N,N dimethylformamide (7.0 mL) was added pentafluorophenol (0.61 g, 10 eq., 3.32 mmol) and N,N'-diisopropylcarbodiimide (0.505 mL, 10 eq., 3.32 mmol) at 0° C. and reaction mixture was stirred at room temperature for 12 h. LCMS showed presence of intermediates so again pentafluorophenol (0.61 g, 10 eq., 3.32 mmol) and N,N'-diisopropylcarbodiimide (0.505 mL, 10 eq., 3.32 mmol) at 0° C. were added and reaction mixture stirred at room temperature for 4 h. Reaction mixture was directly purified by Preparative HPLC (eluting in 50 to 93% Acetonitrile in water). Desired fractions were concentrated under reduced pressure to remove most of acetonitrile and lyophilized to afford perfluorophenyl 1-(4-(1-(2,5-dimethylbenzyl)-2-isonicotinoyl-1H-benzo[d]imidazol-6-yl)-1H-pyrazol-1-yl)-17,26-dioxo-28,28-bis((3-oxo-3-(perfluorophenoxy)propoxy)methyl)-3,20,23,30-tetraoxa-16,27-diazatritriacontan-33-oate (29-5) as pale yellow solid. Yield; 0.18 g (33.04%). LCMS m/z 1641.05 [M+1]$^+$.

Synthesis of N-(3-{3-[2-(3-{2-[2-({12-[2-(4-{1-[(2,5-dimethylphenyl)methyl]-2-(pyridine-4-carbonyl)-1H-1,3-benzodiazol-6-yl}-1H-pyrazol-1-yl)ethoxy]dodecyl}carbamoyl)ethoxy]ethoxy}propanamido)-3-(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propoxy]propanamido}propyl)-5-{[(2R,3R,4R,5R,6R)-3-acetamido-4,5-dihydroxy-6-(hydroxymethyl)oxan-2-yl]oxy}pentanamide (I-139a)

To a solution of perfluorophenyl 1-(4-(1-(2,5-dimethylbenzyl)-2-(hydroxy(pyridin-4-yl)methyl)-1H-benzo[d]imidazol-6-yl)-1H-pyrazol-1-yl)-17,26-dioxo-28,28-bis((3-oxo-3-(perfluorophenoxy)propoxy)methyl)-3,20,23,30-tetraoxa-16,27-diazatritriacontan-33-oate (5, 0.170 g, 1.0 eq, 0.103 mmol) in N,N-dimethyl formamide (2.0 mL) at 0° C. was added 5-(((2R,3R,4R,5R,6R)-3-acetamido-4,5-dihydroxy-6-(hydroxymethyl)tetrahydro-2H-pyran-2-yl)oxy)-N-(3-aminopropyl)pentanamide (29-5a, 0.156 g, 4 eq., 0.414 mmol) in N,N-dimethyl formamide (1.0 mL). Reaction mixture was then stirred at room temperature for 30 minutes. After that, reaction mixture was diluted with acetonitrile and purified by preparative HPLC (35 to 54% acetonitrile in water with 0.1% trifluoroacetic acid) to afford N-(3-{3-[2-(3-{2-[2-({12-[2-(4-{1-[(2,5-dimethylphenyl)methyl]-2-(pyridine-4-carbonyl)-1H-1,3-benzodiazol-6-yl}-1H-pyrazol-1-yl)ethoxy]dodecyl}carbamoyl)ethoxy]ethoxy}propanamido)-3-(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propoxy]propanamido}propyl)-5-{[(2R,3R,4R,5R,6R)-3-acetamido-4,5-dihydroxy-6-(hydroxymethyl)oxan-2-yl]oxy}pentanamide (I-139a) as pale yellow solid. Yield: 90.0 mg (39.16%). LCMS m/z 1111.12 [m/2+1]$^+$ To a solution of N-(3-{3-[2-(3-{2-[2-({12-[2-(4-{1-[(2,5-dimethylphenyl)methyl]-2-(pyridine-4-carbonyl)-1H-1,3-benzodiazol-6-yl}-1H-pyrazol-1-yl)ethoxy]dodecyl}carbamoyl)ethoxy]ethoxy}propanamido)-3-(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propoxy]propanamido}propyl)-5-{[(2R,3R,4R,5R,6R)-3-acetamido-4,5-dihydroxy-6-(hydroxymethyl)oxan-2-yl]oxy}pentanamide (Cpd. No I-139a, 0.080 g, 1.0 eq, 0.036 mmol) in methanol (4.0 mL) at 0° C. was added sodium borohydride (0.0012 g, 1.0 eq, 0.036 mmol) and reaction mixture stirred at 0° C. for 5 minutes. LCMS showed formation of desired compound. Reaction mixture was then directly submitted for HPLC Preparative HPLC purification. Reaction mixture purified by preparative HPLC using 28 to 50% acetonitrile in water with 0.1% Trifluoroacetic acid.

Desired fractions were mixed and lyophilized to get N-(3-{3-[2-(3-{2-[2-({12-[2-(4-{1-[(2,5-dimethylphenyl)methyl]-2-[hydroxy(pyridin-4-yl)methyl]-1H-1,3-benzodiazol-6-yl}-1H-pyrazol-1-yl)ethoxy]dodecyl}carbamoyl)ethoxy]ethoxy}propanamido)-3-(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propoxy]propanamido}propyl)-5-{[(2R,3R,4R,5R,6R)-3-acetamido-4,5-dihydroxy-6-(hydroxymethyl)oxan-2-yl]oxy}pentanamide (Cpd. No I-139) as off white solid. Yield: 0.035 g (43.71%). LC-MS m/z 1111.91 [m/2+1]+ $^1$H-NMR (400 MHz, DMSO-d6) δ 8.55 (bs, 1H), 8.07 (s, 1H), 7.83-7.79 (m, 2H), 7.73-7.49 (m, 8H), 7.13 (s, 1H), 7.06 (d, J=8.0 Hz, 1H), 6.87 (d, J=8.0 Hz, 1H), 6.23 (bs, 1H), 5.78 (s, 1H), 5.64 (1H, J=18.4 Hz, 1H), 5.53 (1H, J=18.4 Hz, 1H), 4.22-4.20 (m, 4H), 3.70-3.27 (m, 71H), 3.03-3.00 (m, 13H), 2.34 (s, 3H), 2.29-2.27 (m, 8H), 2.07-2.02 (m, 6H), 1.90 (s, 3H), 1.85 (s, 1H), 1.79 (s, 8H), 1.52-1.49 (m, 11H). 1.45-1.37 (m, 9H), 1.24-1.14 (m, 16H).

Example 30: perfluorophenyl 1-(4-(((2S,3R,4R,5R,6R)-3-acetamido-4,5-dihydroxy-6-(hydroxymethyl)tetrahydro-2H-pyran-2-yl)methyl)-1H-1,2,3-triazol-1-yl)-16,16-bis(1-(4-(((2S,3R,4R,5R,6R)-3-acetamido-4,5-dihydroxy-6-(hydroxymethyl)tetrahydro-2H-pyran-2-yl)methyl)-1H-1,2,3-triazol-1-yl)-13-oxo-3,6,9-trioxa-12-azapentadecan-15-yl)-13,18-dioxo-3,6,9-trioxa-12,17-diazanonacosan-29-oate (Cpd. No. I-140)

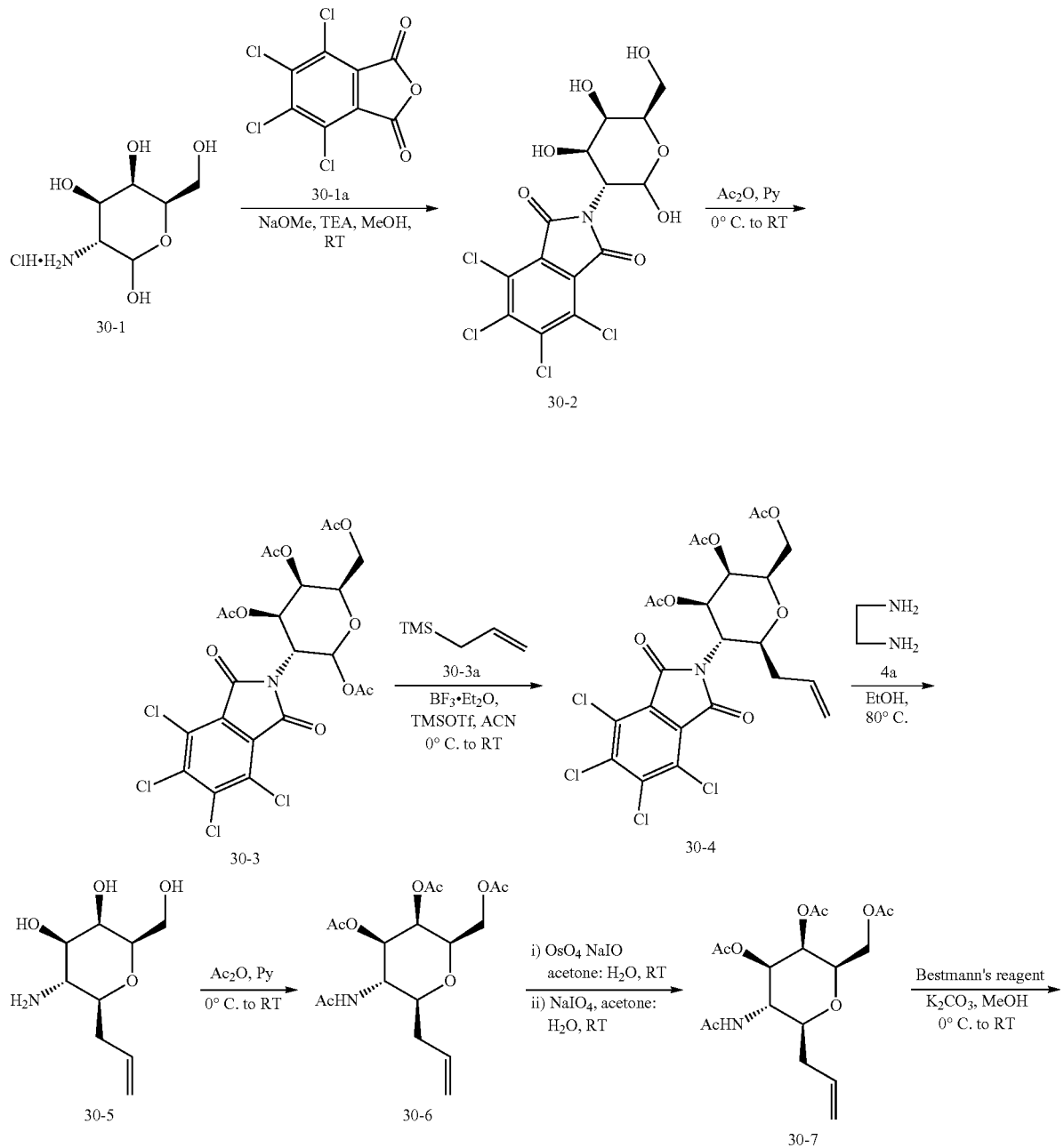

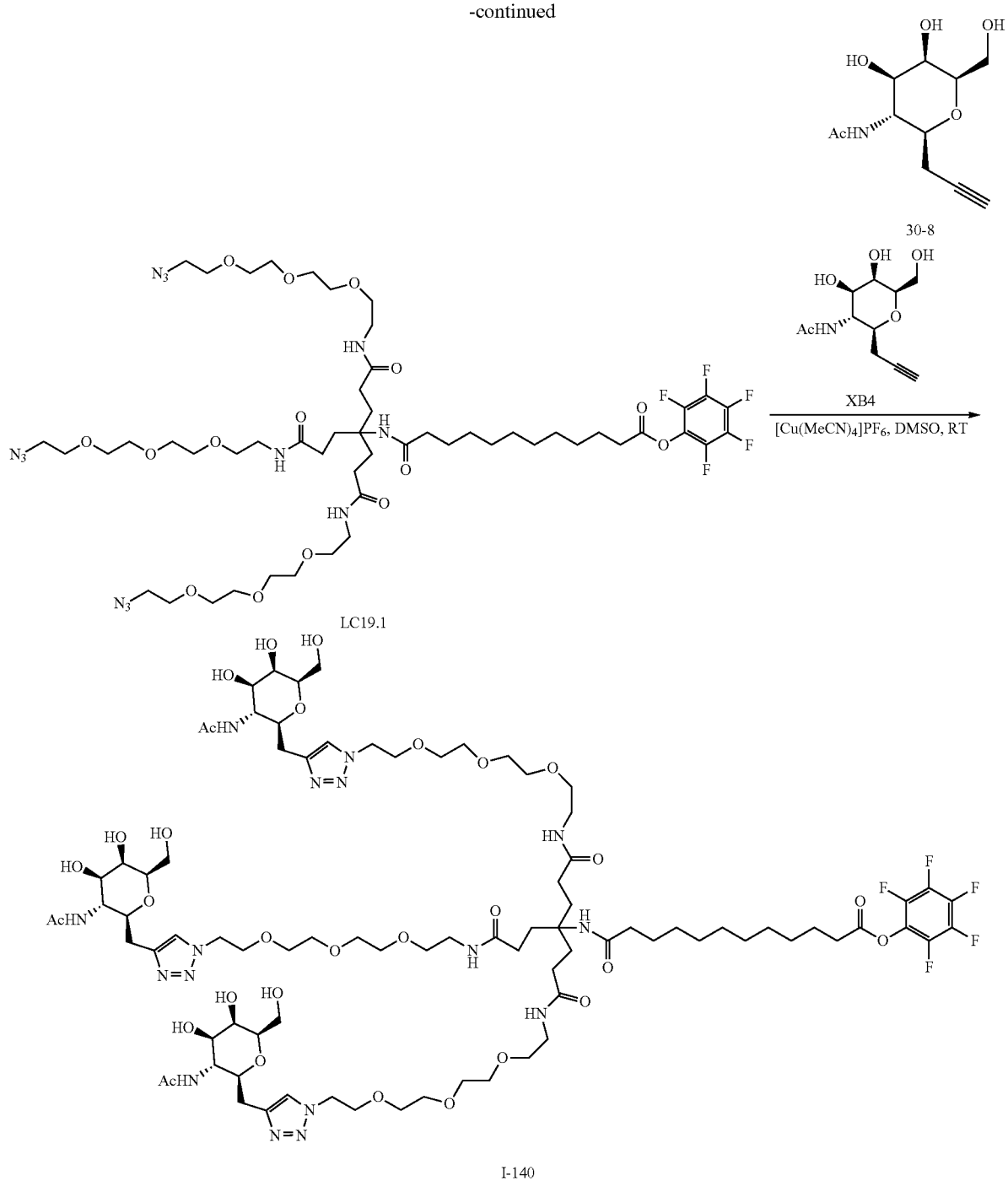

To a solution of 0.25 M sodium methoxide (4.95 mL) in methanol (90.0 mL) was added D-Galactosamine hydrochloride (30-1, 1.0 eq, 5.0 g, 23.2 mmol) in small portions. After stirring for 15 minutes, 3,4,5,6-tetrachloropthalic anhydride (30-1a, 0.6 eq, 4.0 g, 14.0 mmol) was added and the reaction mixture was vigorously stirred for 20 minutes at room temperature. Triethylamine (1.4 eq, 4.5 mL, 32.5 mmol) and a second lot of 3,4,5,6-tetrachloropthalic anhydride (30-1a, 0.6 eq, 4.0 g, 14.0 mmol) was added and the reaction mixture was stirred at room temperature for 24 h. After completion (monitored by LCMS), methanol was concentrated under reduced pressure to obtain 4,5,6,7-tetrachloro-2-((3R,4R,5R,6R)-2,4,5-trihydroxy-6 (hydroxymethyl)tetrahydro-2H-pyran-3-yl)isoindoline-1,3-dione (30-2) as orange syrup which was used as such for next step without any further purification. Yield: 10.0 g (crude); LC-MS m/z 447.8 [M+1]+.

To a solution of 4,5,6,7-tetrachloro-2-((3R,4R,5R,6R)-2, 4,5-trihydroxy-6 (hydroxymethyl)tetrahydro-2H-pyran-3-yl)isoindoline-1,3-dione (30-2, 1.0 eq, 10.0 g, 22.4 mmol) in pyridine (100.0 mL) was added acetic anhydride (15.0 eq, 31.7 mL, 335.5 mmol) at 0° C. The reaction mixture was stirred at room temperature for 16 h. After completion (monitored by TLC), reaction mixture was poured onto ice water and extracted with dichloromethane. The organic layer was washed with 5% aqueous hydrochloric acid solution, saturated solution of sodium bicarbonate and water. The organic layer was dried over sodium sulfate, filtered and concentrated under reduced pressure to obtain crude. The crude was purified by column chromatography (silica mesh: 100-200; elution: 30-40% ethyl acetate in hexane) to afford (3R,4R,5R,6R)-6-(acetoxymethyl)-3-(4,5,6,7-tetrachloro-1,3-dioxoisoindolin-2-yl)tetrahydro-2H-pyran-2,4,5-triyl triacetate (30-3) as white fluffy solid as anomeric mixture. Yield: 6.8 g, 49.4%; LC-MS m/z 631.31 [M$^+$17]$^+$.

To a solution of (3R,4R,5R,6R)-6-(acetoxymethyl)-3-(4,5,6,7-tetrachloro-1,3-dioxoisoindolin-2-yl)tetrahydro-2H-pyran-2,4,5-triyl triacetate (30-3, 1.0 eq., 6.0 g, 9.76 mmol) in acetonitrile (40.0 mL) were added allyltrimethylsilane (30-3a, 4.0 eq, 3.1 mL, 19.5 mmol) followed by boron trifluoride diethyl etherate (4.0 eq, 2.4 mL, 19.5 mmol) and trimethylsilyl trifluoromethanesulfonate (0.3 eq, 0.26 mL, 1.46 mmol) sequentially at 0° C. under nitrogen. The reaction mixture was stirred at room temperature for 16 h. After completion (monitored by TLC), reaction mixture was poured onto ice-cold saturated sodium bicarbonate solution and extracted with dichloromethane. The organic layer was dried over sodium sulfate, filtered and concentrated under reduced pressure to obtain crude. The crude was purified by column chromatography (silica mesh: 100-200; elution: 30-40% ethyl acetate in hexane) to afford (2R,3R,4R,5S,6S)-2-(acetoxymethyl)-6-allyl-5-(4,5,6,7-tetrachloro-1,3-dioxoisoindolin-2-yl)tetrahydro-2H-pyran-3,4-diyl diacetate (30-4) as yellow liquid. Yield: 4.3 g, 73.8%; LC-MS m/z 598.2 [M+1]+.

To a solution of (2R,3R,4R,5S,6S)-2-(acetoxymethyl)-6-allyl-5-(4,5,6,7-tetrachloro-1,3-dioxoisoindolin-2-yl)tetrahydro-2H-pyran-3,4-diyl diacetate (30-4, 1.0 eq, 4.3 g, 7.2 mmol) in ethanol (4.0 mL) was added ethane-1,2-diamine (10.0 eq, 4.8 mL, 72 mmol). The reaction mixture was heated at 80° C. for 8 h. After completion, the reaction mixture was concentrated under reduced pressure and dried to afford (2R,3R,4R,5R,6S)-6-allyl-5-amino-2-(hydroxymethyl)tetrahydro-2H-pyran-3,4-diol (30-5) as crude (3.0 g). To a solution of (2R,3R,4R,5S,6S)-2-(acetoxymethyl)-6-allyl-5-aminotetrahydro-2H-pyran-3,4-diyl diacetate (1.0 eq, 3.0 g (crude), 9.1 mmol) in pyridine (30.0 mL) was acetic anhydride (3.0 eq, 2.6 mL, 27.0 mmol) at 0° C. The reaction mixture was stirred at room temperature for 16 h. After completion (monitored by TLC), reaction mixture was poured onto ice water and extracted with dichloromethane. The organic layer was washed with 5% aqueous hydrochloric acid solution, saturated solution of sodium bicarbonate and water. The organic layer was dried over sodium sulfate, filtered and concentrated under reduced pressure to obtain crude. The crude was purified by column chromatography (silica mesh: 100-200; elution: 50-60% ethyl acetate in hexane) to afford (2R,3R,4R,5S,6S)-5-acetamido-2-(acetoxymethyl)-6-allyltetrahydro-2H-pyran-3,4-diyl diacetate (30-6) as viscous liquid. Yield: 0.84 g (Peak-1) and 0.24 g (Peak-2), 42%; LC-MS m/z 372.1 [M+1]$^+$.

To a solution of (2R,3R,4R,5S,6S)-5-acetamido-2-(acetoxymethyl)-6-allyltetrahydro-2H-pyran-3,4-diyl diacetate (30-6, Peak-1, 1.0 eq, 0.78 g, 2.09 mmol) in acetone: water (5:1) (10.0 mL) were added N-methylmorpholine N-oxide (1.5 eq, 0.4 mL, 3.1 mmol) and osmium tetraoxide (4% in water) (0.1 eq, 1.33 mL, 0.210 mmol). The reaction mixture was stirred at room temperature for 2 h. After completion (monitored by TLC), the reaction mixture was diluted with ethyl acetate and the layers were separated. The organic layer was dried over sodium sulfate, filtered and concentrated under reduced pressure to obtain crude. The crude was dissolved in acetone: water (2:1) (20 mL) and sodium Meta periodate (2.0 eq, 0.9 g, 4.2 mmol) was added. After completion (monitored by TLC), the reaction mixture was diluted with ethyl acetate and the layers were separated. The organic layer was dried over sodium sulfate, filtered and concentrated under reduced pressure to afford (2R,3R,4R,5S,6S)-5-acetamido-2-(acetoxymethyl)-6-(2-oxoethyl)tetrahydro-2H-pyran-3,4-diyl diacetate (30-7) as sticky solid which was used as such for next step without any further purification. Yield: 0.85 g (crude); LCMS: 374.0 [M+1]+.

To a solution of (2R,3R,4R,5S,6S)-5-acetamido-2-(acetoxymethyl)-6-(2-oxoethyl)tetrahydro-2H-pyran-3,4-diyl diacetate (0.85 g, 1.0 eq, 2.30 mmol) in methanol (20.0 mL) at 0° C., were added potassium carbonate (0.950 g, 3.0 eq, 6.89 mmol) and dimethyl (1-diazo-2-oxopropyl)phosphonate (0.88 g, 2.0 eq, 4.59 mmol). The reaction mixture was stirred at room temperature for 3 h. After completion (monitored by TLC), the reaction mixture was concentrated under reduced pressure to obtain crude. The crude was purified by reverse phase preparative HPLC, fractions containing desired product were lyophilized to afford N-((2S,3R,4R,5R,6R)-4,5-dihydroxy-6-(hydroxymethyl)-2-(prop-2-yn-1-yl)tetrahydro-2H-pyran-3-yl)acetamide (30-8) as white solid. Yield: 0.13 g, 20.89%; LCMS: 244.0 [M+1]$^+$.

To a solution of perfluorophenyl 1-azido-16,16-bis(1-azido-13-oxo-3,6,9-trioxa-12-azapentadecan-15-yl)-13,18-dioxo-3,6,9-trioxa-12,17-diazanonacosan-29-oate (LC19.1, 1.0 eq, 0.07 g, 0.0571 mmol) and N-((2S,3R,4R,5R,6R)-4,5-dihydroxy-6-(hydroxymethyl)-2-(prop-2-yn-1-yl)tetrahydro-2H-pyran-3-yl)acetamide (XB4, 3.6 eq, 0.050 g, 0.205 mmol) in dimethylsulfoxide (2.0 mL), tetrakis(acetonitrile)copper(I) hexafluorophosphate (8.4 eq, 0.179 g, 0.479 mmol) was added. The reaction mixture was stirred at room temperature for 1 h and reaction mixture was directly purified by preparative HPLC (30-45% acetonitrile in water with 0.1% TFA). Fractions containing the desired product were combined and lyophilized to dryness to afford perfluorophenyl 1-(4-(((2S,3R,4R,5R,6R)-3-acetamido-4,5-dihydroxy-6-(hydroxymethyl)tetrahydro-2H-pyran-2-yl)methyl)-1H-1,2,3-triazol-1-yl)-16,16-bis(1-(4-(((2S,3R,4R,5R,6R)-3-acetamido-4,5-dihydroxy-6-(hydroxymethyl)tetrahydro-2H-pyran-2-yl)methyl)-1H-1,2,3-triazol-1-yl)-13-oxo-3,6,9-trioxa-12-azapentadecan-15-yl)-13,18-dioxo-3,6,9-trioxa-12,17-diazanonacosan-29-oate (Cpd. No. I-140) as a cream solid. Yield: 0.011 g; 9.85%: LCMS; m/z 978.93 [M$^+$2H]$^{++}$; $^1$H NMR (400 MHz, DMSO-d6) δ 7.84-7.81 (m, 6H), 7.68 (d, J=8.8 Hz, 3H), 7.12 (s, 1H), 4.50-4.43 (m, 13H), 3.82-3.77 (m, 9H), 3.63 (s, 1H), 3.49-3.46 (m, 10H), 3.42-3.36 (m, 27H), 3.25-3.21 (m, 6H), 3.16-3.15 (m, 6H), 2.86-2.82 (m, 3H), 2.76 (t, J=7.2 Hz, 2H), 2.01-1.98 (m, 8H), 1.83 (s, 9H), 1.77 (s, 5H), 1.65-1.63 (m, 2H), 1.44 (s, 2H), 1.23 (s, 14H).

Example 31: Compound I-160

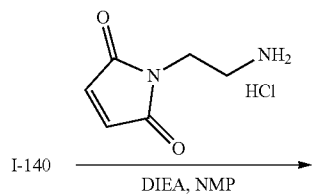

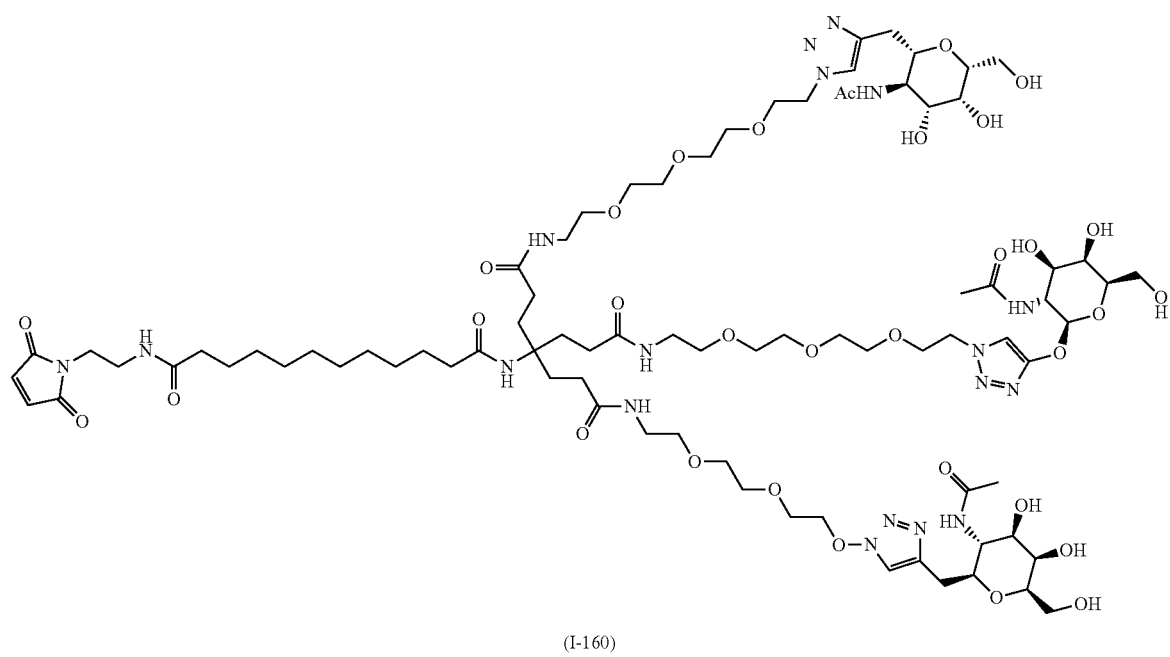

To a mixture of compound I-140 (1.00 eq, 26.3 mg, 0.0127 mmol) and 1-(2-aminoethyl)pyrrole-2,5-dione; hydrochloride (1.15 eq, 2.6 mg, 0.0146 mmol) in NMP (0.6 mL) was added Diisopropylethylamine (DIPEA) (3.50 eq, 0.0077 mL, 0.0445 mmol). The mixture was stirred at rt for 1 h and acetic acid (6 uL) was added. The mixture was purified by prep. HPLC (5-30% MeCN/water with 0.1% TFA) to give compound I-160 as a white solid (17.8 mg, yield 73%). (purity: 99%). LCMS m/z 1912.3 [M+H]+.

Example 32: perfluorophenyl 1-(((2S,3R,4R,5R, 6R)-3-acetamido-4,5-dihydroxy-6-(hydroxymethyl) tetrahydro-2H-pyran-2-yl)thio)-16,16-bis((3-(((2S,3R,4R,5R,6R)-3-acetamido-4,5-dihydroxy-6-(hydroxymethyl)tetrahydro-2H-pyran-2-yl)thio) propanamido)pentyl)amino)-3-oxopropoxy)methyl)-3,11,18-trioxo-14-oxa-4,10,17-triazanonacosan-29-oate (Cpd. No. I-141)

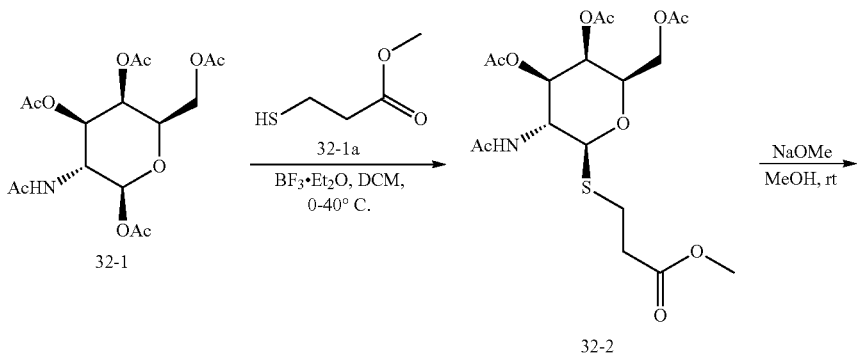

347 348
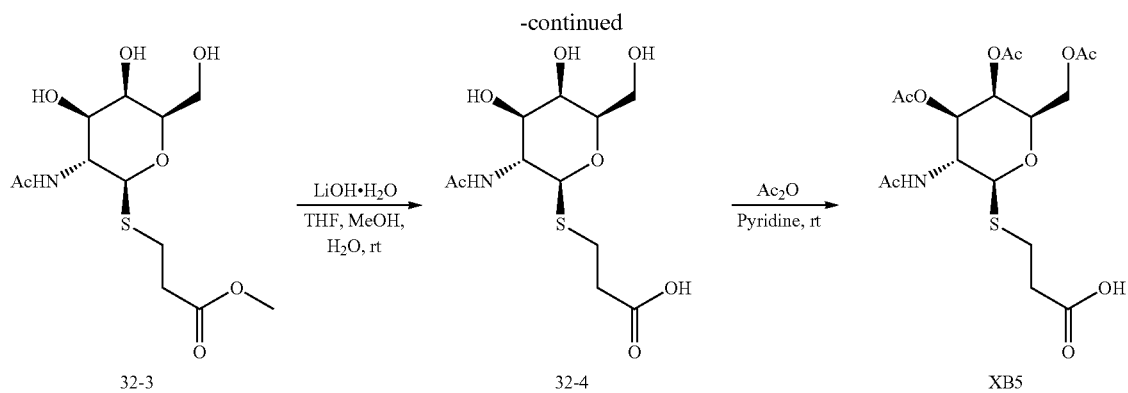
-continued
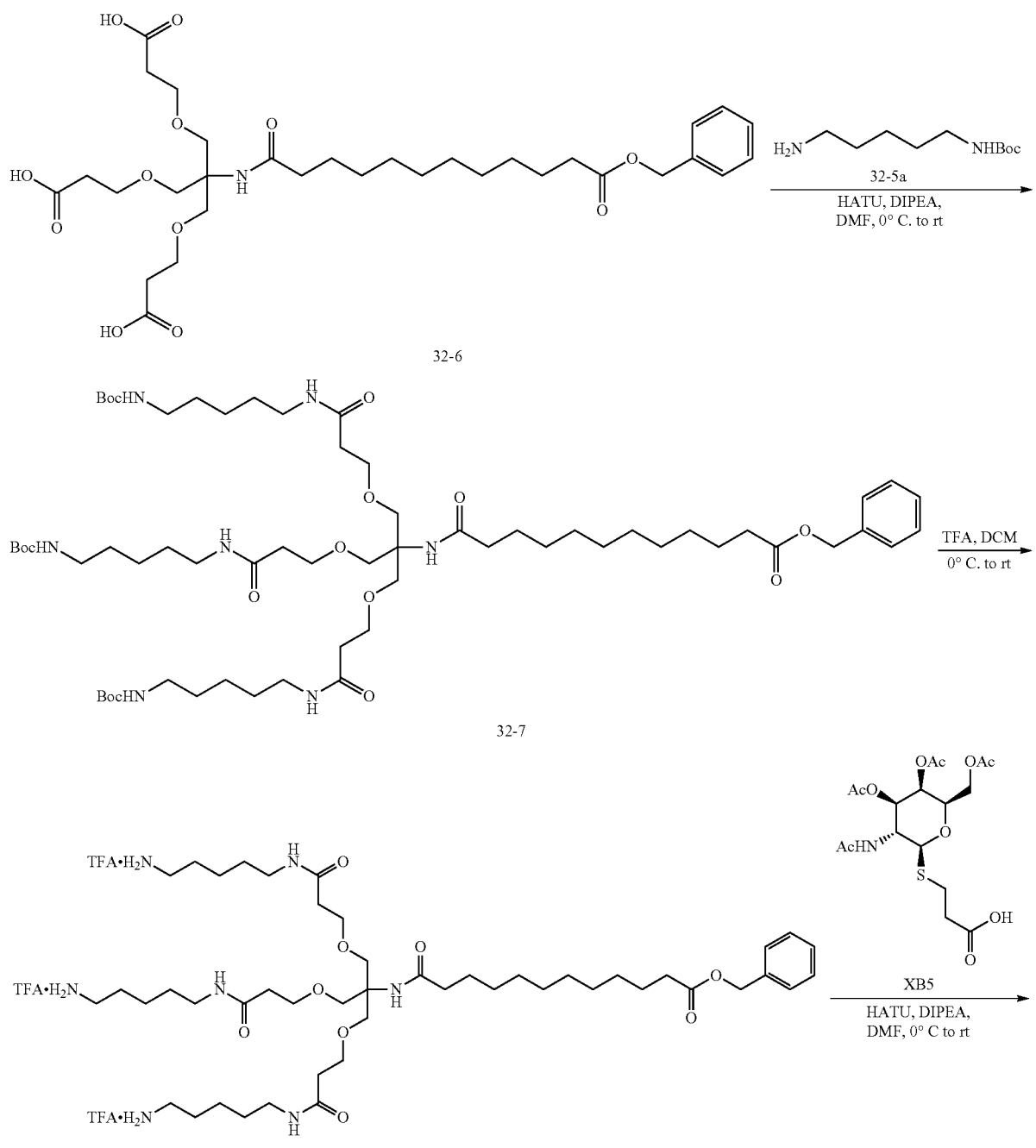

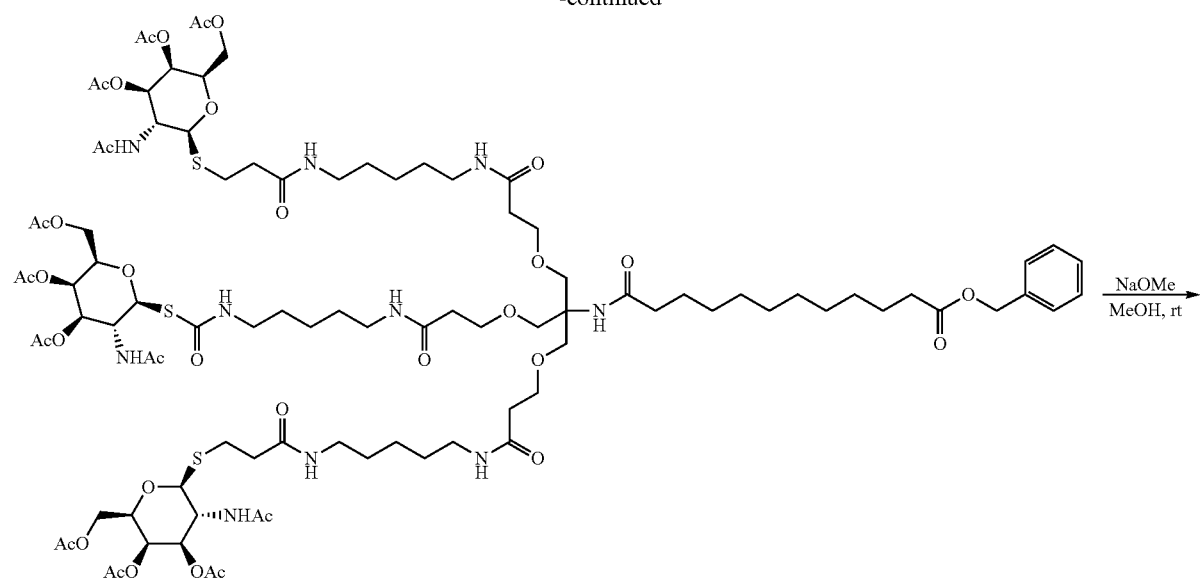
32-9
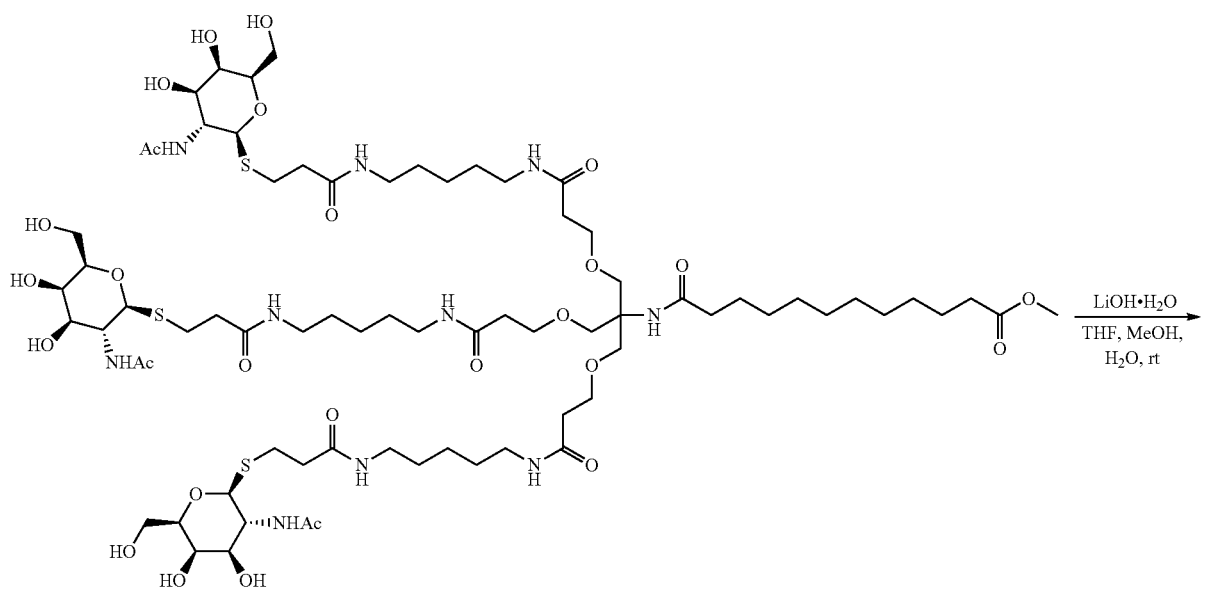
32-10

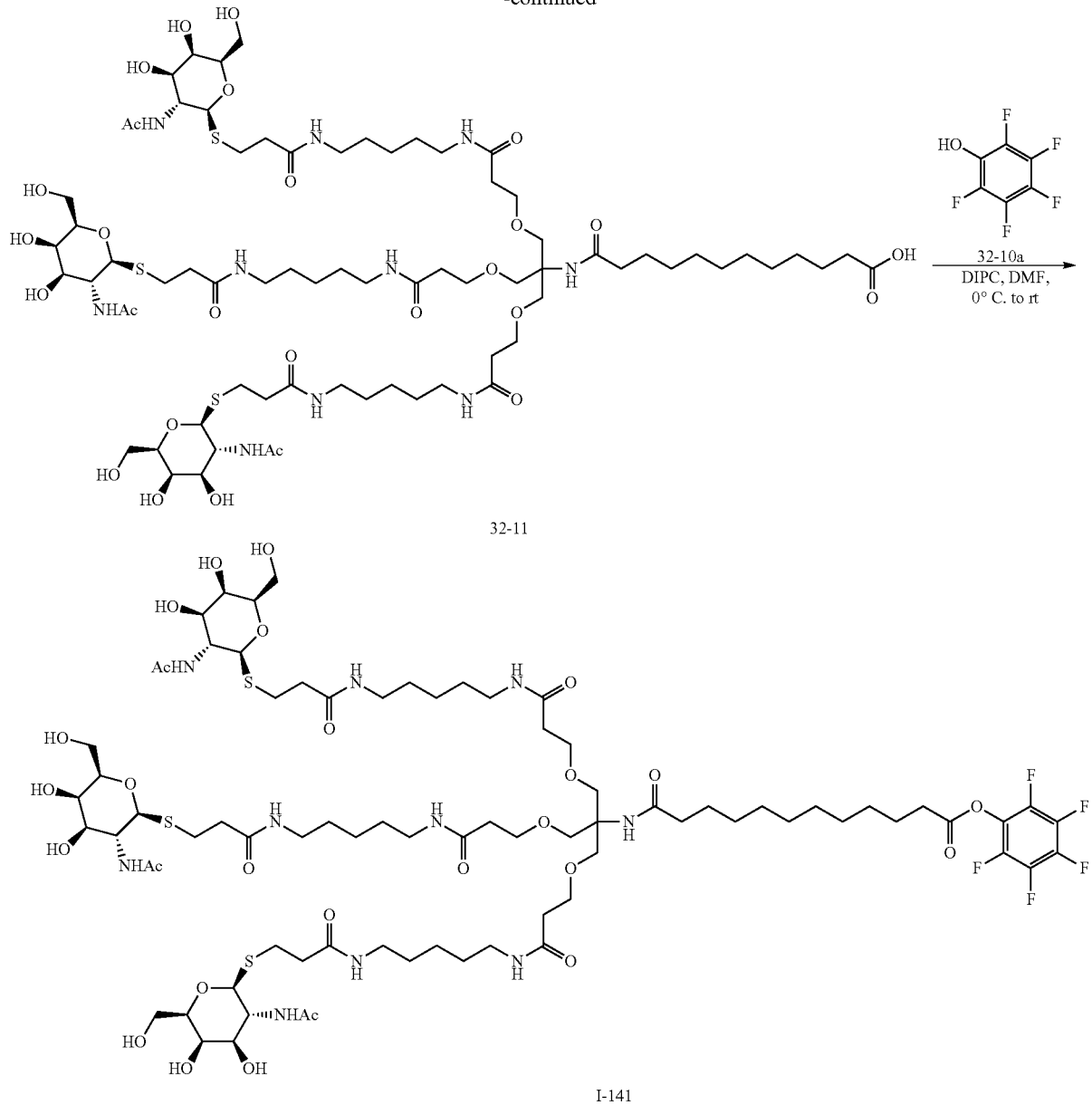

32-11

I-141

A solution of (2S,3R,4R,5R,6R)-3-acetamido-6-(acetoxymethyl)tetrahydro-2H-pyran-2,4,5-triyl triacetate (32-1, 1.0 eq, 5.0 g, 12.8 mmol) and methyl 3-mercaptopropanoate (32-1a, 2.0 eq, 3.09 mL, 25.7 mmol) in dichloromethane (50 mL) was cooled at 0° C., boron trifluoride diethyl etherate (5.0 eq, 8.28 mL, 64.2 mmol) was added dropwise and reaction mixture was heated at 40° C. for 16 h. Reaction was monitored by LCMS. After completion, reaction mixture was cooled, diluted with dichloromethane, washed with saturated aqueous sodium bicarbonate solution and water. The organic layer was dried over anhydrous sodium sulfate, filtered and concentrated to get crude which was purified by column chromatography using silica gel (100-200 mesh) and 0-5% methanol in dichloromethane to afford (2R,3R,4R,5R,6S)-5-acetamido-2-(acetoxymethyl)-6-((3-methoxy-3-oxopropyl)thio)tetrahydro-2H-pyran-3,4-diyl diacetate (32-2) as a colourless viscous liquid. Yield: 5.2 g, 87.39%; LCMS m/z 450.1 [M+1]$^+$.

To a solution of (2R,3R,4R,5R,6S)-5-acetamido-2-(acetoxymethyl)-6-((3-methoxy-3-oxopropyl)thio)tetrahydro-2H-pyran-3,4-diyl diacetate (32-2, 1.0 eq, 4.0 g, 8.9 mmol) in methanol (40 mL), sodium methoxide (25% solution in methanol) (0.1 eq, 0.21 mL, 0.89 mmol) was added and reaction mixture was stirred at room temperature for 3 h. After completion, reaction mixture was neutralized with Dowex 50WX8 hydrogen form (200-400 mesh) and filtered through sintered funnel (without celite). The filtrate was concentrated and dried to afford methyl 3-(((2S,3R,4R,5R, 6R)-3-acetamido-4,5-dihydroxy-6-(hydroxymethyl)tetrahydro-2H-pyran-2-yl)thio)propanoate (32-3) as an off white solid. Yield: 1.7 g, 59.0%; LCMS m/z 324.0 [M+1]$^+$.

To a solution of methyl 3-(((2S,3R,4R,5R,6R)-3-acetamido-4,5-dihydroxy-6-(hydroxymethyl)tetrahydro-2H-pyran-2-yl)thio)propanoate (32-3, 1.0 eq, 2.0 g, 6.19 mmol) in tetrahydrofuran (18 mL), methanol (12 mL) and water (6 mL), lithium hydroxide monohydrate (2.0 eq, 0.519 g, 12.4 mmol) was added and reaction mixture was stirred at room temperature for 2 h. After completion, reaction mixture was concentrated, methanol was added, neutralized with Dowex 50WX8 hydrogen form (200-400 mesh) and filtered through sintered funnel (without celite). The filtrate was concentrated and dried to afford 3-(((2S,3R,4R,5R,6R)-3-acetamido-4,5-dihydroxy-6-(hydroxymethyl)tetrahydro-2H-pyran-2-yl)thio)propanoic acid (32-4) as an off white sticky solid. Yield: 2.4 g (Crude); LCMS m/z 310.0 [M+1]$^+$.

To a solution of 3-(((2S,3R,4R,5R,6R)-3-acetamido-4,5-dihydroxy-6-(hydroxymethyl)tetrahydro-2H-pyran-2-yl)thio)propanoic acid (32-4, 1.0 eq, 1.1 g, 3.56 mmol) in pyridine (11 mL), acetic anhydride (10.0 eq, 3.36 mL, 35.6 mmol) was added and reaction mixture was stirred at room temperature for 16 h. After completion, reaction mixture was concentrated to get crude which was purified by column chromatography using silica gel (100-200 mesh) and 0-7% methanol in dichloromethane to afford 3-(((2S,3R,4R,5R,6R)-3-acetamido-4,5-diacetoxy-6-(acetoxymethyl)tetrahydro-2H-pyran-2-yl)thio)propanoic acid (XB5) as a colourless viscous liquid. Yield: 1.25 g, 76.74%; LCMS m/z 436.0 [M+1]$^+$.

A solution of 3,3'-((2-(12-(benzyloxy)-12-oxododecanamido)-2-((2-carboxyethoxy)methyl)propane-1,3-diyl)bis(oxy))dipropionic acid (32-6, 1.0 eq, 1.0 g, 1.56 mmol) in N,N-dimethylformamide (20 mL) was cooled at 0° C., tert-butyl (5-aminopentyl)carbamate (32-5a, 3.3 eq, 1.04 g, 5.16 mmol), N,N-diisopropylethylamine (10.0 eq, 2.77 mL, 15.6 mmol) and 1-[bis(dimethylamino)methylene]-1H-1,2,3-triazolo[4,5-b]pyridinium 3-oxid hexafluorophosphate (HATU) (4.5 eq, 2.67 g, 7.03 mmol) were added and reaction mixture was stirred at room temperature for 16 h. After completion, water was added to reaction mixture and extracted with ethyl acetate. The organic layer was washed with water, dried over anhydrous sodium sulfate, filtered and concentrated to get crude which was purified by column chromatography using silica gel (100-200 mesh) and 0-4% methanol in dichloromethane to afford benzyl 17,17-bis(15,15-dimethyl-5,13-dioxo-2,14-dioxa-6,12-diazahexadecyl)-2,2-dimethyl-4,12,19-trioxo-3,15-dioxa-5,11,18-triazatriacontan-30-oate (32-7) as a light brown viscous liquid. Yield: 1.3 g, 69.74%; LCMS m/z 1192.8 [M+1]$^+$.

A solution of benzyl 17,17-bis(15,15-dimethyl-5,13-dioxo-2,14-dioxa-6,12-diazahexadecyl)-2,2-dimethyl-4,12,19-trioxo-3,15-dioxa-5,11,18-triazatriacontan-30-oate (32-7, 1.0 eq, 0.100 g, 0.083 mmol) in dichloromethane (0.5 mL) was cooled at 0° C., trifluoroacetic acid (0.5 mL) was added and reaction mixture was stirred at room temperature for 3 h. After completion, reaction mixture was concentrated, azeotroped with dichloromethane (2-3 times), washed with diethyl ether (2-3 times) and dried to afford benzyl 11-{1,3-bis(2-{[5-(2,2,2-trifluoroacetamido)pentyl]carbamoyl}ethoxy)-2-[(2-{[5-(2,2,2-trifluoroacetamido)pentyl]carbamoyl}ethoxy)methyl]propan-2-yl]carbamoyl}undecanoate (32-8) as a light brown viscous liquid. Yield: 0.110 g (Crude); LCMS m/z 892.6 [M+1]$^+$.

A solution of benzyl 11-{1,3-bis(2-{[5-(2,2,2-trifluoroacetamido)pentyl]carbamoyl}ethoxy)-2-[(2-{[5-(2,2,2-trifluoroacetamido)pentyl]carbamoyl}ethoxy)methyl]propan-2-yl]carbamoyl}undecanoate (32-8, 1.0 eq, 0.220 g, 0.18 mmol) in N,N-dimethylformamide (4 mL) was cooled at 0° C., 3-(((2S,3R,4R,5R,6R)-3-acetamido-4,5-diacetoxy-6-(acetoxymethyl)tetrahydro-2H-pyran-2-yl)thio)propanoic acid (XB5, 3.0 eq, 0.235 g, 0.54 mmol), N,N-diisopropylethylamine (10.0 eq, 0.33 mL, 1.8 mmol) and 1-[Bis(dimethylamino)methylene]-1H-1,2,3-triazolo[4,5-b]pyridinium 3-oxid hexafluorophosphate (HATU) (4.5 eq, 0.308 g, 0.81 mmol) were added and reaction mixture was stirred at room temperature for 16 h. After completion, water was added to the reaction mixture and extracted with ethyl acetate. The organic layer was washed with water, dried over anhydrous sodium sulfate, filtered and concentrated to afford benzyl 11-{[1,3-bis(2-{[5-(3-{[(2S,3R,4R,5R,6R)-4,5-bis(acetyloxy)-6-[(acetyloxy)methyl]-3-acetamidooxan-2-yl]sulfanyl}propanamido)pentyl]carbamoyl}ethoxy)-2-[(2-{[5-(3-{[(2S,3R,4R,5R,6R)-4,5-bis(acetyloxy)-6-[(acetyloxy)methyl]-3-acetamidooxan-2-yl]sulfanyl}propanamido)pentyl]carbamoyl}ethoxy)methyl]propan-2-yl]carbamoyl}undecanoate (32-9) as light yellow viscous liquid. Yield: 0.230 g (Crude); LCMS m/z 1072.8 [M$^+$2H]$^{++}$.

To a solution of benzyl 11-{[1,3-bis(2-{[5-(3-{[(2S,3R,4R,5R,6R)-4,5-bis(acetyloxy)-6-[(acetyloxy)methyl]-3-acetamidooxan-2-yl]sulfanyl}propanamido)pentyl]carbamoyl}ethoxy)-2-[(2-{[5-(3-{[(2S,3R,4R,5R,6R)-4,5-bis(acetyloxy)-6-[(acetyloxy)methyl]-3-acetamidooxan-2-yl]sulfanyl}propanamido)pentyl]carbamoyl}ethoxy)methyl]propan-2-yl]carbamoyl}undecanoate (32-9, 1.0 eq, 0.180 g, 0.083 mmol) in methanol (4 mL), sodium methoxide (25% solution in methanol) (0.2 eq, 0.003 mL, 0.016 mmol) was added and reaction mixture was stirred at room temperature for 3 h. After completion, reaction mixture was neutralized with Dowex 50WX8 hydrogen form (200-400 mesh) and filtered through syringe filter. The filtrate was concentrated and dried to afford methyl 1-(((2S,3R,4R,5R,6R)-3-acetamido-4,5-dihydroxy-6-(hydroxymethyl)tetrahydro-2H-pyran-2-yl)thio)-16,16-bis((3-((5-(3-(((2S,3R,4R,5R,6R)-3-acetamido-4,5-dihydroxy-6-(hydroxymethyl)tetrahydro-2H-pyran-2-yl)thio)propanamido)pentyl)amino)-3-oxopropoxy)methyl)-3,11,18-trioxo-14-oxa-4,10,17-triazanonacosan-29-oate (32-10) as a colourless viscous liquid. Yield: 0.130 g (Crude); LCMS m/z 845.6 [M$^+$2H]$^{++}$.

To a solution of methyl 1-(((2S,3R,4R,5R,6R)-3-acetamido-4,5-dihydroxy-6-(hydroxymethyl)tetrahydro-2H-pyran-2-yl)thio)-16,16-bis((3-((5-(3-(((2S,3R,4R,5R,6R)-3-acetamido-4,5-dihydroxy-6-(hydroxymethyl)tetrahydro-2H-pyran-2-yl)thio)propanamido)pentyl)amino)-3-oxopropoxy)methyl)-3,11,18-trioxo-14-oxa-4,10,17-triazanonacosan-29-oate (32-10, 1.0 eq, 0.160 g, 0.094 mmol) in tetrahydrofuran:methanol:water (3:2:1) (2 mL), lithium hydroxide monohydrate (2.0 eq, 0.007 g, 0.189 mmol) was added and reaction mixture was stirred at room temperature for 3 h. After completion, reaction mixture was concentrated, methanol was added, neutralized with Dowex 50WX8 hydrogen form (200-400 mesh) and filtered through syringe filter. The filtrate was concentrated and dried to afford 1-(((2S,3R,4R,5R,6R)-3-acetamido-4,5-dihydroxy-6-(hydroxymethyl)tetrahydro-2H-pyran-2-yl)thio)-16,16-bis((3-((5-(3-(((2S,3R,4R,5R,6R)-3-acetamido-4,5-dihydroxy-6-(hydroxymethyl)tetrahydro-2H-pyran-2-yl)thio)propanamido)pentyl)amino)-3-oxopropoxy)methyl)-3,11,18-trioxo-14-oxa-4,10,17-triazanonacosan-29-oic acid (32-11) as a light yellow solid. Yield: 0.140 g, 88.23%; LCMS m/z 838.6 [M$^+$2H]$^{++}$.

A solution of 1-(((2S,3R,4R,5R,6R)-3-acetamido-4,5-dihydroxy-6-(hydroxymethyl)tetrahydro-2H-pyran-2-yl)thio)-16,16-bis((3-((5-(3-(((2S,3R,4R,5R,6R)-3-acetamido-4,5-dihydroxy-6-(hydroxymethyl)tetrahydro-2H-pyran-2-yl)thio)propanamido)pentyl)amino)-3-oxopropoxy)methyl)-3,11,18-trioxo-14-oxa-4,10,17-triazanonacosan-29-oic acid (32-11, 1.0 eq, 0.140 g, 0.083 mmol) in N,N-dimethylformamide (2 mL) was cooled at 0° C., 2,3,4,5,6-pentafluorophenol (32-10a, 2.0 eq, 0.030 g, 0.166 mmol)

and N,N'-diisopropylcarbodiimide (3.0 eq, 0.038 mL, 0.249 mmol) were added and reaction mixture was stirred at room temperature for 16 h. After completion, reaction mixture was directly purified by preparative HPLC (32-53% acetonitrile in water with 0.1% TFA) to afford perfluorophenyl 1-(((2S, 3R,4R,5R,6R)-3-acetamido-4,5-dihydroxy-6-(hydroxymethyl)tetrahydro-2H-pyran-2-yl)thio)-16,16-bis((3-((5-(3-(((2S,3R,4R,5R,6R)-3-acetamido-4,5-dihydroxy-6-(hydroxymethyl)tetrahydro-2H-pyran-2-yl)thio) propanamido)pentyl)amino)-3-oxopropoxy)methyl)-3,11, 18-trioxo-14-oxa-4,10,17-triazanonacosan-29-oate (Cpd. No. I-141) as a white solid. Yield: 0.020 g, 13.1%; LCMS m/z 921.89 [M$^+$2H]$^{++}$; $^1$H NMR (400 MHz, DMSO-d$_6$ with D$_2$O) δ 4.29 (d, J=10.4 Hz, 3H), 3.82-3.79 (m, 3H), 3.66 (s, 3H), 3.50-3.47 (m, 19H), 3.41-3.35 (m, 6H), 2.99-2.97 (m, 12H), 2.75-2.70 (m, 6H), 2.33-2.31 (m, 6H), 2.26-2.24 (m, 6H), 2.03-2.01 (m, 3H), 1.78 (m, 9H), 1.63-1.61 (m, 2H), 1.40-1.30 (m, 16H), 1.35-1.20 (m, 16H).

Example 33: Synthesis of Compound I-162

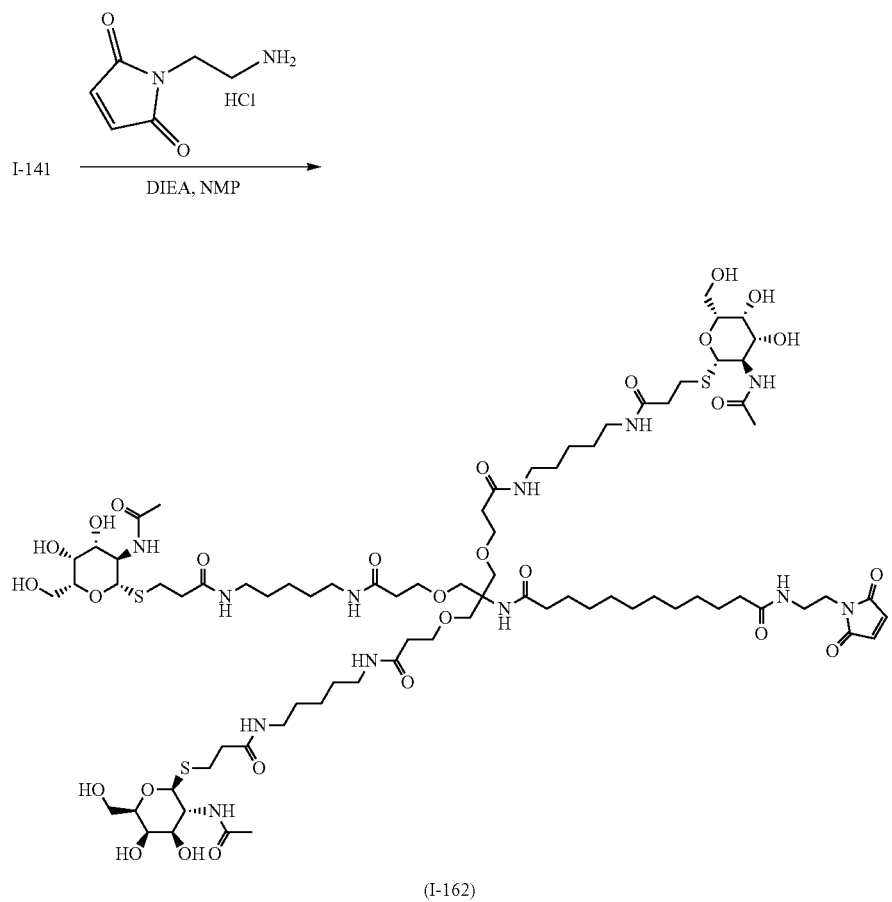

To a mixture of compound I-141 (1.00 eq, 10.9 mg, 0.00592 mmol) and 1-(2-aminoethyl)pyrrole-2,5-dione; hydrochloride (1.15 eq, 1.2 mg, 0.00680 mmol) in NMP (0.3 mL) was added Diisopropylethylamine (DIPEA) (2.50 eq, 0.0026 mL, 0.0148 mmol). The mixture was stirred at rt for 1 h and TFA (4 uL) was added. The mixture was purified by prep. HPLC (5-30% MeCN/water with 0.1% TFA) to give compound I-162 as a white solid (8.2 mg, yield 77%). (purity: 99%). LCMS m/z 1797.8 [M+H]+.

Example 34: Synthesis of N$^1$-(1,25-bis(4-(3-(((2S, 3S,4S,5S,6S)-3-acetamido-4,5-dihydroxy-6-(hydroxymethyl)tetrahydro-2H-pyran-2-yl)oxy)propyl)-1H-1,2,3-triazol-1-yl)-13-(3-((2-(2-(2-(4-(3-(((2S,3S, 4S,5S,6S)-3-acetamido-4,5-dihydroxy-6-(hydroxymethyl)tetrahydro-2H-pyran-2-yl)oxy) propyl)-1H-1,2,3-triazol-1-yl)ethoxy)ethoxy)ethyl) amino)-3-oxopropyl)-10,16-dioxo-3,6,20,23-tetraoxa-9,17-diazapentacosan-13-yl)-N$^{12}$-(12-(2-(4-(1-(2,5-dimethylbenzyl)-2-(hydroxy(pyridin-4-yl) methyl)-1H-benzo[d]imidazol-6-yl)-1H-pyrazol-1-yl)ethoxy)dodecyl)dodecanediamide (Cpd. No. 142)

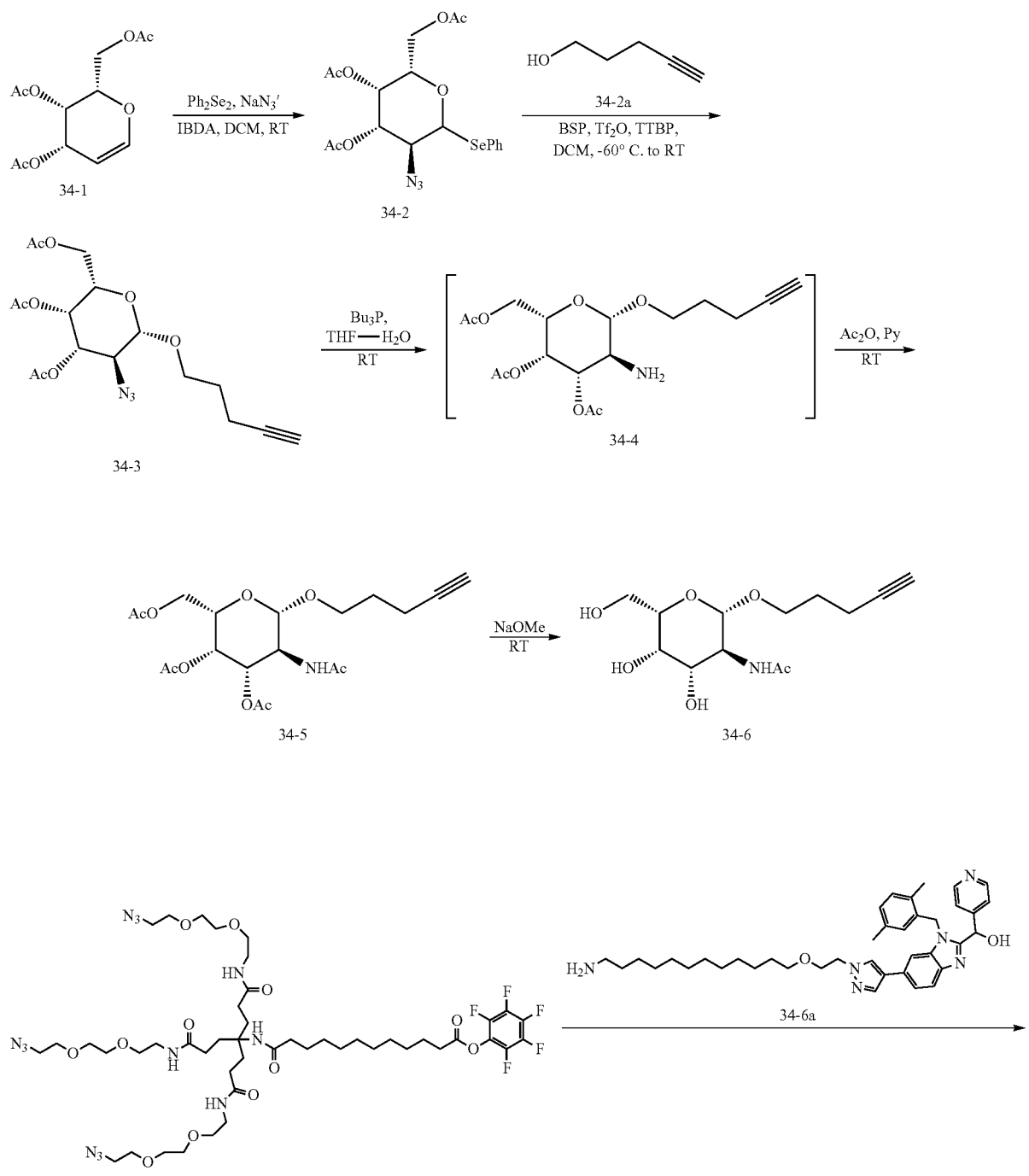

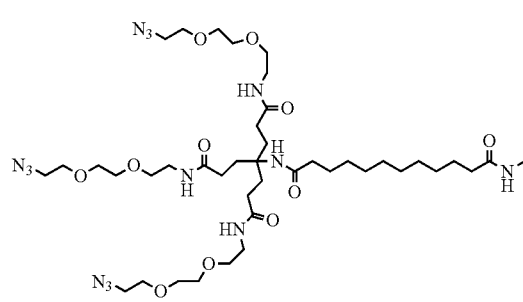
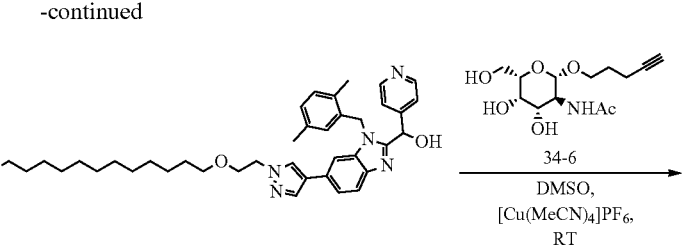

34-7

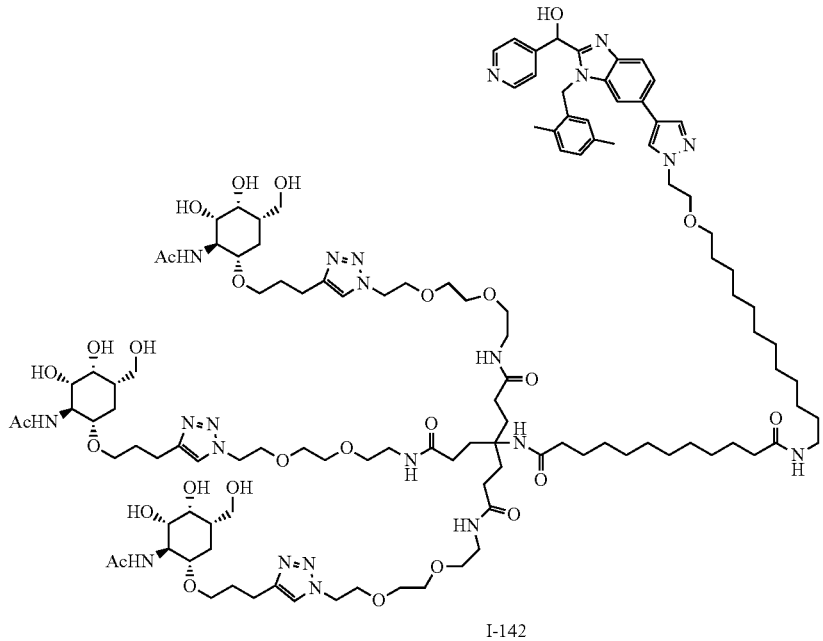

I-142

To a stirred solution of (2S,3S,4S)-2-(acetoxymethyl)-3,4-dihydro-2H-pyran-3,4-diyl diacetate (34-1, 0.860 g, 1 eq, 3.16 mmol) in dichloromethane (100 mL), were added (phenyldiselanyl)benzene (1.73 g, 1.75 eq, 5.53 mmol), sodium azide (0.4719 g, 3.5 eq, 11.1 mmol) and (Diacetoxy) iodobenzene (2.24 g, 2.2 eq, 6.95 mmol) at room temperature under nitrogen atmosphere. After 18 h, TLC analysis (ethyl acetate/light petroleum 1:2) showed complete consumption of the starting compound. The reaction mixture was poured into a saturated aqueous solution of sodium bicarbonate, the phases were separated and the aqueous phase was extracted twice with dichloromethane. The combined organic phases were dried over anhydrous sodium sulphate, filtered and concentrated in vacuo. Column chromatography (20% ethyl acetate in hexane) afforded (2S,3S, 4S,5S,6S)-2-(acetoxymethyl)-5-azido-6-(phenylselanyl)tetrahydro-2H-pyran-3,4-diyl diacetate (34-2) as colorless syrup. Yield: 0.560 g, 37.69%. LCMS; m/z 488.9 [M+18]+

Trifluoromethanesulfonyl trifluoromethanesulfonate (0.260 mL, 1.3 eq, 1.55 mmol) was added to a stirred solution of (2S,3S,4S,5S,6S)-2-(acetoxymethyl)-5-azido-6-(phenylselanyl)tetrahydro-2H-pyran-3,4-diyl diacetate (34-2, 0.560 g, 1 eq, 1.19 mmol), 1-(benzenesulfinyl)piperidine (BSP) (0.299 g, 1.2 eq, 1.43 mmol) and 2,4,6-tri-tert-butylpyrimidine (0.651 g, 2.2 eq, 2.62 mmol) in dichloromethane (5.00 mL) containing 4A molecular sieves (0.500 g) at −60° C. The reaction mixture was stirred at this temperature for 30 min, after which pent-4-yn-1-ol (34-2a, 0.222 mL, 2.0 eq, 2.38 mmol) was added. The mixture was allowed to warm to room temperature gradually. After 2 h, the reaction mixture was quenched by addition of triethylamine. After filtration, the organic phase was washed with saturated aqueous sodium bicarbonate, dried over sodium sulphate, filtered, concentrated in vacuo. The crude compound was purified by flash column chromatography (using 20% ethyl acetate in hexane) to afford (2S,3S,4S,5S,6S)-2-(acetoxymethyl)-5-azido-6-(pent-4-yn-1-yloxy)tetrahydro-2H-pyran-3,4-diyl diacetate (34-3) as colorless oil. Yield: 0.30 g, 60.87%. LCMS; m/z 415.1 [M+18]+

(2S,3S,4S,5S,6S)-3,4-bis(acetyloxy)-5-azido-6-(pent-4-yn-1-yloxy)oxan-2-yl methyl acetate (34-3, 0.3 g, 1 eq, 0.755 mmol) was dissolved in tetrahydrofuran (4.00 mL), and tributylphosphine (0.56 mL, 3 eq, 2.26 mmol) and water (0.400 mL) were added and the mixture was stirred at room temperature for 3 days. ELSD-MS data was recorded for crude compound which showed full conversion. Subsequently, the mixture was concentrated and co-concentrated with toluene to get crude (2S,3S,4S,5S,6S)-2-(acetoxymethyl)-5-amino-6-(pent-4-yn-1-yloxy)tetrahydro-2H-pyran-3,4-diyl diacetate (34-4) as brown oil. which was dissolved in pyridine (4.0 mL), and acetic anhydride (2.0 mL) was added at room temperature. After stirring for 24 h, the mixture was concentrated and the resulting crude product was co-evaporated with toluene. Column chromatography (using 5% methanol in dichloromethane) afforded (2S,3S,4S,5S,6S)-5-acetamido-2-(acetoxymethyl)-6-(pent-4-yn-1-yloxy)tetrahydro-2H-pyran-3,4-diyl diacetate (34-5) as a slightly yellow syrup. Yield: 0.185 g, 59.28%.; LCMS; m/z 414.1 [M+1]$^+$ (2S,3S,4S,5S,6S)-5-acetamido-2-(acetoxymethyl)-6-(pent-4-yn-1-yloxy)tetrahydro-2H-pyran-3,4-diyl diacetate (34-5, 0.185 g, 1 eq, 0.447 mmol) was dissolved in methanol (5 mL) and 25% solution of sodium methoxide in methanol (0.295 mL, 3 eq, 1.34 mmol) was added and the reaction mixture was stirred at room temperature for 30 min and the ELSD-MS data showed full conversion. Thereafter, Dowex-50w-hydrogen form added up to neutral pH, the reaction mass was then filtered through sintered and concentrated in vacuo to get crude mass which was purified by preparative HPLC (using 65-70% acetonitrile in water with 0.1% TFA) to give N-((2S,3S,4S,5S,6S)-4,5-dihydroxy-6-(hydroxymethyl)-2-(pent-4-yn-1-yloxy)tetrahydro-2H-pyran-3-yl)acetamide (34-6) as white solid. Yield: 0.070 g, 54.45%.; LCMS; m/z 288.0 [M+1]$^+$ In an inert atmosphere N-(1,25-diazido-13-(3-((2-(2-(2-azidoethoxy)ethoxy)ethyl)amino)-3-oxopropyl)-10,16-dioxo-3,6,20,23-tetraoxa-9,17-diazapentacosan-13-yl)-N$^{12}$-(12-(2-(4-(1-(2,5-dimethylbenzyl)-2-(hydroxy(pyridin-4-yl)methyl)-1H-benzo[d]imidazol-6-yl)-1H-pyrazol-1-yl)ethoxy)dodecyl)dodecanediamide (34-7, 0.100 g, 1 eq, 0.0646 mmol) dissolved in dimethylsulfoxide (2.00 mL) at room temperature and stirred for 5 mins at room temperature. Then, N-((2S,3S,4S,5S,6S)-4,5-dihydroxy-6-(hydroxymethyl)-2-(pent-4-yn-1-yloxy)tetrahydro-2H-pyran-3-yl)acetamide (34-6, 66.9 mg, 3.6 eq., 0.233 mmol) was added and again stirred for more 5 mins followed by addition of Tetrakis(acetonitrile)copper(I) hexafluorophosphate (0.178 g, 8.4 eq., 0.543 mmol). After 30 mins, the reaction mixture was quenched with acetic acid (0.5 mL) and directly used for preparative HPLC purification (using 30-40% acetonitrile in water with 0.1% TFA). All the fractions containing desired compound were combined and lyophilized to afford N$^1$-(1,25-bis(4-(3-(((2S,3S,4S,5S,6S)-3-acetamido-4,5-dihydroxy-6-(hydroxymethyl)tetrahydro-2H-pyran-2-yl)oxy)propyl)-1H-1,2,3-triazol-1-yl)-13-(3-((2-(2-(2-(4-(3-(((2S,3S,4S,5S,6S)-3-acetamido-4,5-dihydroxy-6-(hydroxymethyl)tetrahydro-2H-pyran-2-yl)oxy)propyl)-1H-1,2,3-triazol-1-yl)ethoxy)ethoxy)ethyl)amino)-3-oxopropyl)-10,16-dioxo-3,6,20,23-tetraoxa-9,17-diazapentacosan-13-yl)-N$^{12}$-(12-(2-(4-(1-(2,5-dimethylbenzyl)-2-(hydroxy(pyridin-4-yl)methyl)-1H-benzo[d]imidazol-6-yl)-1H-pyrazol-1-yl)ethoxy)dodecyl)dodecanediamide (I-142) as off-white solid. Yield: 0.032 g, 20.55%, LC-MS; m/z 803.2 [M/3+1]+; $^1$H NMR (400 MHz, DMSO-d$_6$) δ 8.65 (d, J=5.2 Hz, 2H), 8.10 (s, 1H), 7.85-7.78 (m, 8H), 7.71-7.65 (m, 4H), 7.55 (d, J=8.4 Hz, 1H), 7.13 (bs, 1H), 7.06 (d, J=7.6 Hz, 1H), 6.87 (d, J=7.2 Hz, 1H), 6.37 (s, 1H), 5.74 (s, 1H), 5.62 (AB$_q$, J$_{ab}$=17.6 Hz, 2H), 4.47-4.44 (m, 10H), 4.25-4.22 (m, 7H), 3.79-3.77 (m, 6H), 3.72-3.70 (m, 7H), 3.64 (d, J=2.8 Hz, 3H), 3.52-3.30 (m, 36H), 3.15-3.14 (m, 6H), 3.05-2.95 (m, 2H), 2.62-261 (m, 6H), 2.35 (s, 3H), 2.01-1.99 (m, 10H), 1.89 (s, 4H), 1.79-1.76 (m, 21H), 1.50-1.32 (m, 8H), 1.20-1.13 (m, 29H).

Example 35: Synthesis of perfluorophenyl 1-(1-((2R,3R,4R,5R,6R)-3-acetamido-4,5-dihydroxy-6-(hydroxymethyl)tetrahydro-2H-pyran-2-yl)-1H-1,2,3-triazol-4-yl)-15,15-bis(1-(1-((2R,3R,4R,5R,6R)-3-acetamido-4,5-dihydroxy-6-(hydroxymethyl)tetrahydro-2H-pyran-2-yl)-1H-1,2,3-triazol-4-yl)-12-oxo-2,5,8-trioxa-11-azatetradecan-14-yl)-12,17-dioxo-2,5,8-trioxa-11,16-diazaoctacosan-28-oate (Cpd. No. 143)

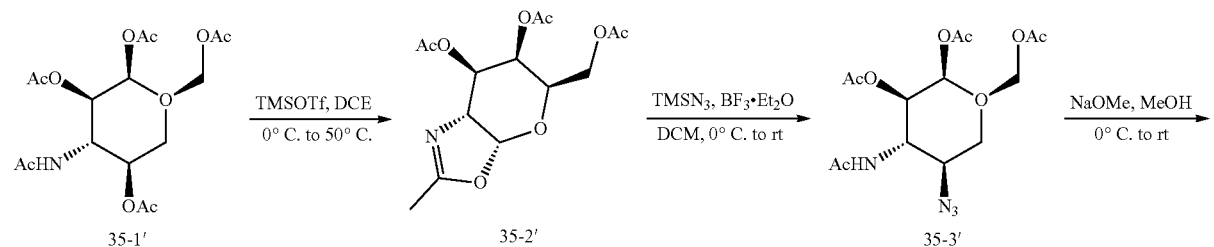

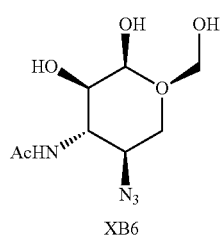

XB6

-continued
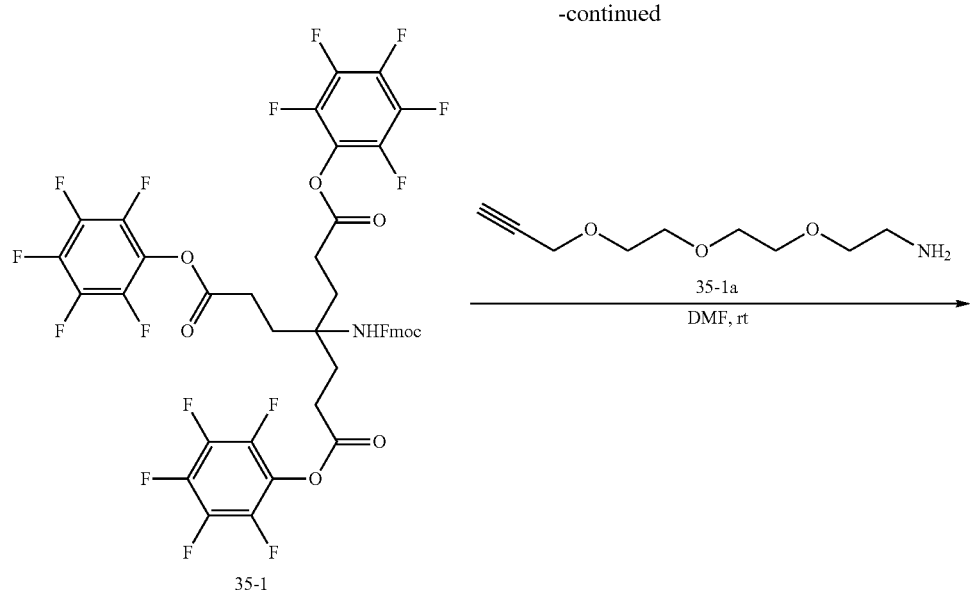
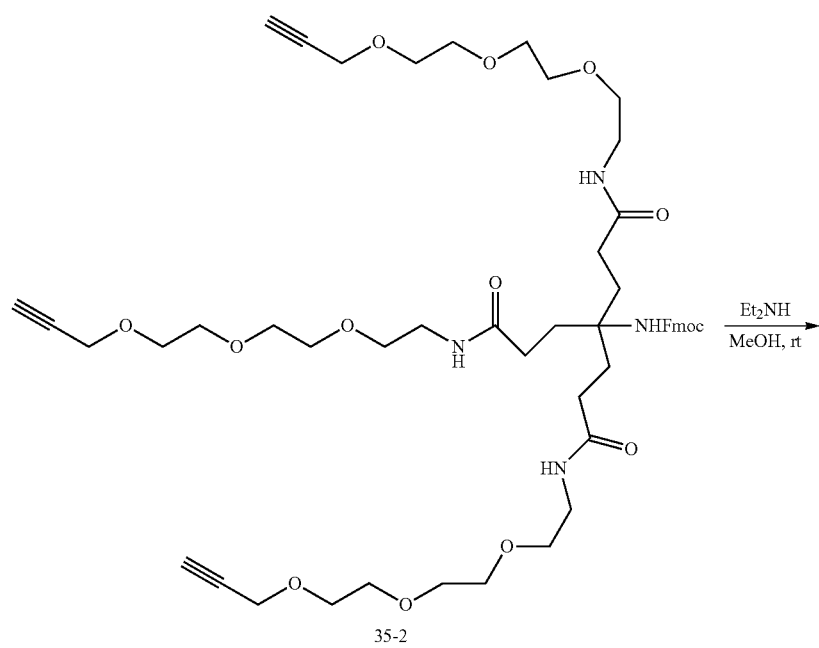

-continued
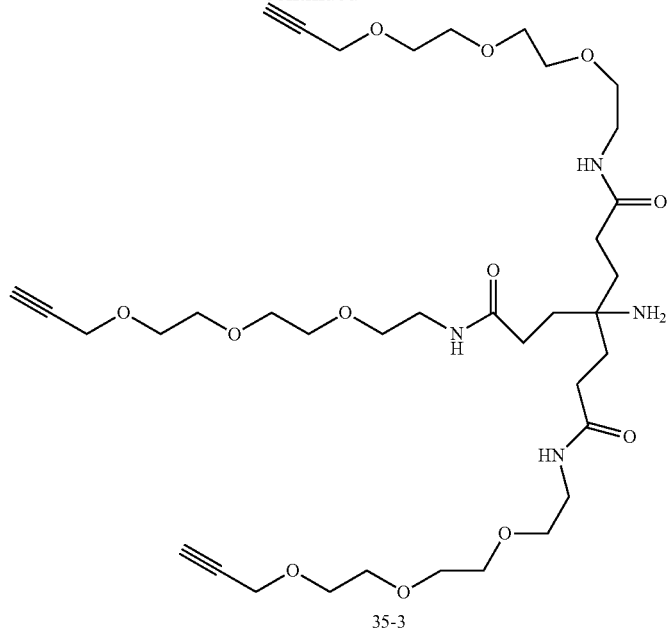
35-3
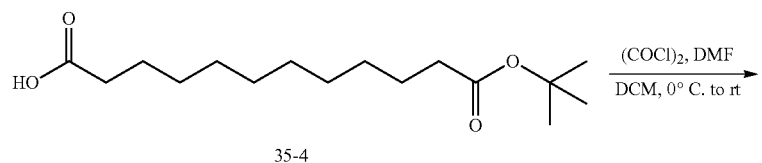
35-4
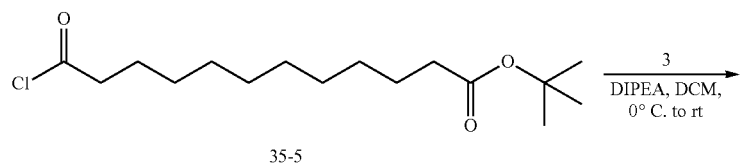
35-5
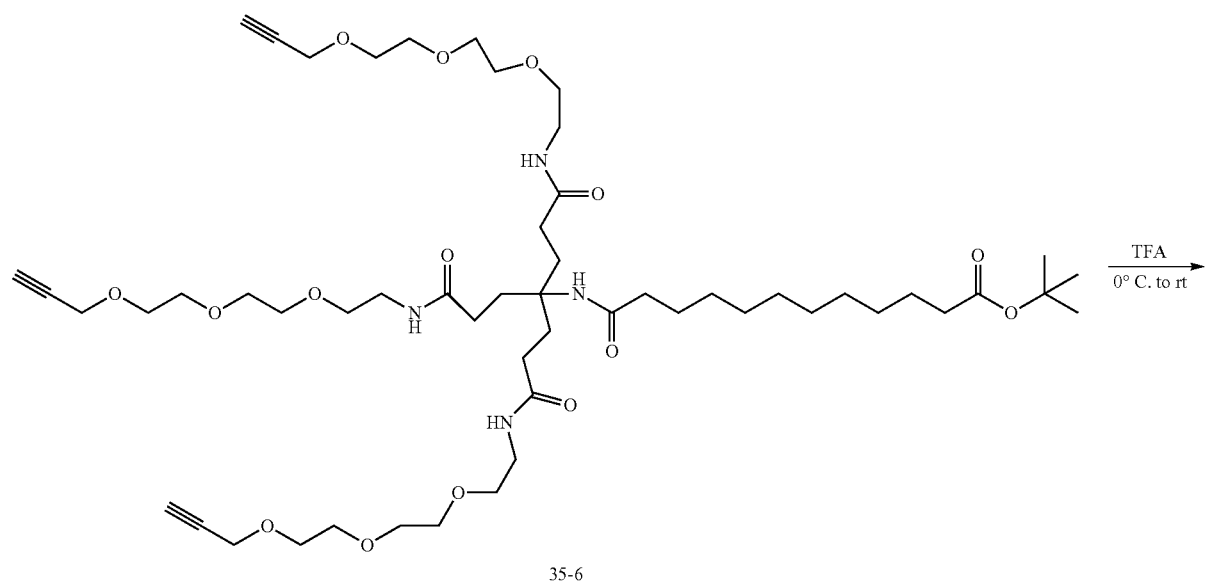
35-6

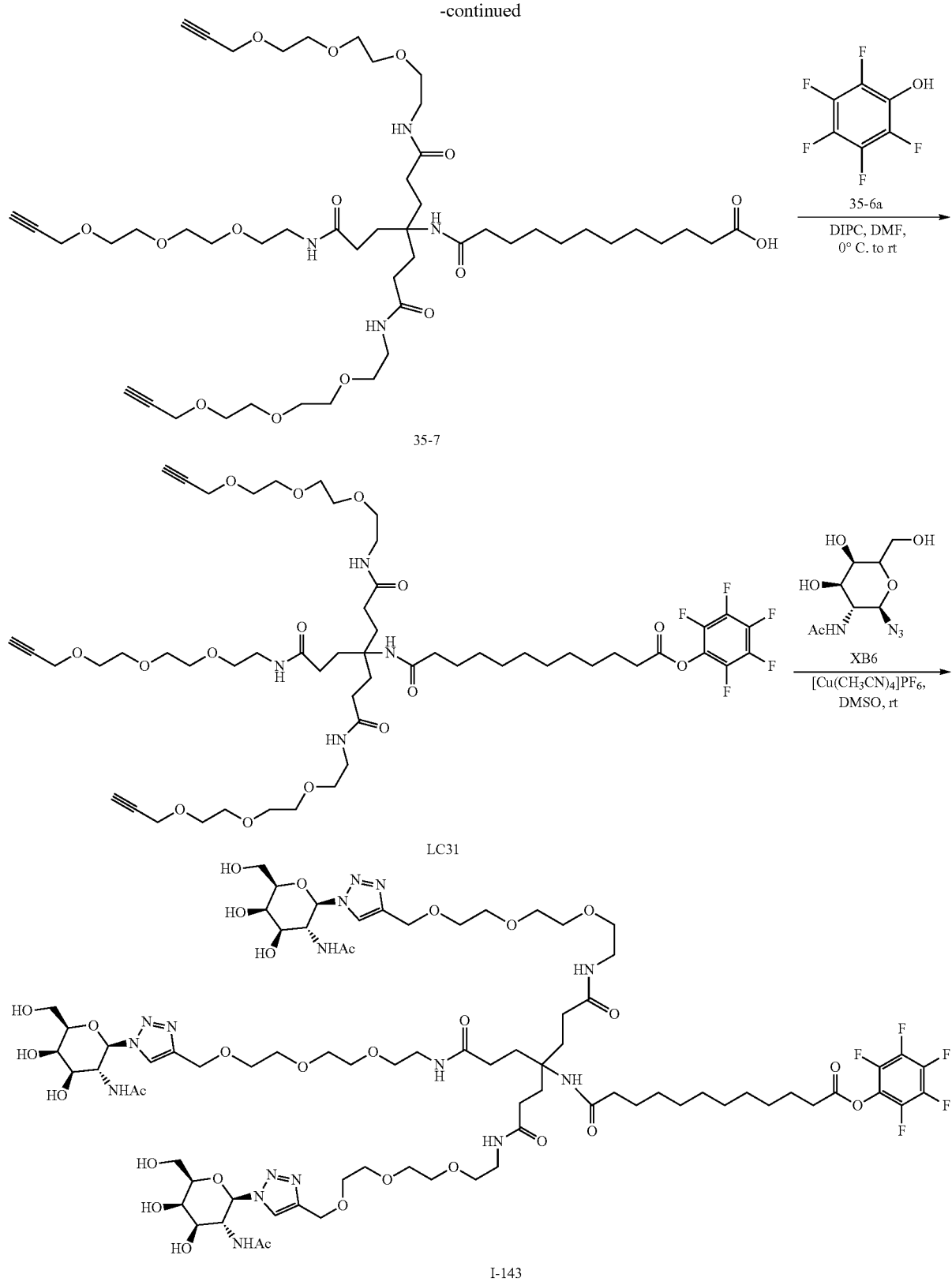
A solution of (2S,3R,4R,5R,6R)-3-acetamido-6-(acetoxymethyl)tetrahydro-2H-pyran-2,4,5-triyl triacetate (35-1', 1.0 eq, 2.0 g, 5.14 mmol) in 1,2-dichloroethane (20 mL) was cooled at 0° C. and trimethylsilyl trifluoromethanesulfonate (1.5 eq, 1.4 mL, 7.71 mmol) was added and reaction mixture was heated at 50° C. for 1.5 h and then stirred at room temperature for 3 h. After completion, reaction mixture was quenched with trimethylamine, concentrated and dried to afford (3aR,5R,6R,7R,7aR)-5-(acetoxymethyl)-2-methyl-3a,6,7,7a-tetrahydro-5H-pyrano[3,2-d]oxazole-6,7-diyl diacetate (35-2') as a brown liquid. Yield: 1.6 g (Crude); LCMS m/z 330.0 [M+1]+.

A solution of (3aR,5R,6R,7R,7aR)-5-(acetoxymethyl)-2-methyl-3a,6,7,7a-tetrahydro-5H-pyrano[3,2-d]oxazole-6,7-diyl diacetate (35-2', 1.0 eq, 1.6 g, 4.86 mmol) in dichloromethane (20 mL) was cooled at 0° C., trimethylsilyl azide (2.0 eq, 1.28 mL, 9.72 mmol) and boron trifluoride diethyl etherate (6.0 eq, 3.69 mL, 29.2 mmol) were added dropwise and reaction mixture was stirred at room temperature for 16 h. After completion, reaction mixture was quenched with ice (very small amount), diluted with saturated aqueous sodium bicarbonate solution and extracted with dichloromethane. The organic layer was dried over anhydrous sodium sulfate, filtered and concentrated to get crude which was purified by column chromatography using silica gel (100-200 mesh) and 0-10% methanol in dichloromethane to afford (2R,3R,4R,5R,6R)-5-acetamido-2-(acetoxymethyl)-6-azidotetrahydro-2H-pyran-3,4-diyl diacetate (35-3') as an off white solid. Yield: 0.600 g, 33.17%; LCMS m/z 372.8 [M+1]+.

A solution of (2R,3R,4R,5R,6R)-5-acetamido-2-(acetoxymethyl)-6-azidotetrahydro-2H-pyran-3,4-diyl diacetate (35-3', 1.0 eq, 0.600 g, 1.61 mmol) in methanol (6 mL) was cooled to 0° C. sodium methoxide (25% solution in methanol) (0.2 eq, 0.07 mL, 0.322 mmol) was added and reaction mixture was stirred at room temperature for 2 h. After completion, reaction mixture was neutralized with Dowex 50WX8 hydrogen form (200-400 mesh) and filtered through sintered (without celite). The filtrate was concentrated to get crude which was purified by preparative HPLC (16-30% acetonitrile in water with 0.1% trifluoroacetic acid). Fractions containing the desired product were combined and lyophilized to dryness to afford N-((2R,3R,4R,5R,6R)-2-azido-4,5-dihydroxy-6-(hydroxymethyl)tetrahydro-2H-pyran-3-yl)acetamide (XB6) as an off white solid. Yield: 0.218 g, 54.94%; LCMS m/z 247.0 [M+1]+.

A solution of bis(perfluorophenyl) 4-((((9H-fluoren-9-yl)methoxy)carbonyl)amino)-4-(3-oxo-3-(perfluorophenoxy)propyl)heptanedioate (35-1, 1.0 eq, 1.87 g, 1.93 mmol) and 2-(2-(2-(prop-2-yn-1-yloxy)ethoxy)ethoxy)ethan-1-amine (35-1a, 3.0 eq, 1.09 g, 5.80 mmol) in N,N-dimethylformamide (18 mL) was stirred at room temperature for 16 h. After completion, water was added to reaction mixture and extracted with ethyl acetate. The organic layer was washed with water, dried over anhydrous sodium sulfate, filtered and concentrated to get crude which was purified by column chromatography using silica gel (100-200 mesh) and 0-5% methanol in dichloromethane to afford (9H-fluoren-9-yl)methyl (14,20-dioxo-17-(3-oxo-7,10,13-trioxa-4-azahexadec-15-yn-1-yl)-4,7,10,24,27,30-hexaoxa-13,21-diazatritriaconta-1,32-diyn-17-yl)carbamate (35-2) as a colourless viscous liquid. Yield: 1.67 g, 88.43%; LCMS m/z 977.36 [M+1]+.

To a solution of (9H-fluoren-9-yl)methyl (14,20-dioxo-17-(3-oxo-7,10,13-trioxa-4-azahexadec-15-yn-1-yl)-4,7,10,24,27,30-hexaoxa-13,21-diazatritriaconta-1,32-diyn-17-yl)carbamate (35-2, 1.0 eq, 1.57 g, 1.61 mmol) in methanol (20 mL), diethylamine (20.0 eq, 3.36 mL, 32.1 mmol) was added and reaction mixture was stirred at room temperature for 16 h. After completion, reaction mixture was concentrated to get crude which was triturated with diethyl ether (2-3 times) to afford 4-amino-4-(3-oxo-7,10,13-trioxa-4-azahexadec-15-yn-1-yl)-N1,N7-bis(2-(2-(2-(prop-2-yn-1-yloxy)ethoxy)ethoxy)ethyl)heptanediamide (35-3) as a light yellow viscous liquid. Yield: 1.2 g, 98.93%; LCMS m/z 755.2 [M+1]+.

A solution of 12-(tert-butoxy)-12-oxododecanoic acid (35-4, 1.0 eq, 1.4 g, 4.89 mmol) in dichloromethane (14 mL) was cooled at 0° C., oxalyl chloride (1.5 eq, 0.66 mL, 7.33 mmol) and N,N-dimethylformamide (0.14 mL) were added and reaction mixture was stirred at room temperature for 1 h. Reaction was monitored by TLC (TLC was checked after diluted with methanol). After completion, reaction mixture was concentrated under nitrogen gas atmosphere and dried to afford tert-butyl 12-chloro-12-oxododecanoate (35-5) as a light brown viscous liquid which was directly used as such for next reaction. Yield: 1.5 g (Crude).

A solution of tert-butyl 12-chloro-12-oxododecanoate (35-5, 2.0 eq, 0.808 g, 2.65 mmol) in dichloromethane (5 mL) was cooled at 0° C., then a solution of 4-amino-4-(3-oxo-7,10,13-trioxa-4-azahexadec-15-yn-1-yl)-N1,N7-bis(2-(2-(2-(prop-2-yn-1-yloxy)ethoxy)ethoxy)ethyl)heptanediamide (35-3, 1.0 eq, 1.0 g, 1.32 mmol) and N,N-diisopropylethylamine (5.0 eq, 1.22 mL, 6.62 mmol) in dichloromethane (10 mL) was added dropwise and reaction mixture was stirred at room temperature for 3 h. After completion, water was added to reaction mixture and extracted with dichloromethane. The organic layer was dried over anhydrous sodium sulfate, filtered and concentrated to get crude which was purified by column chromatography using silica gel (100-200 mesh) and 0-8% methanol in dichloromethane to afford tert-butyl 14,19-dioxo-17,17-bis(3-oxo-7,10,13-trioxa-4-azahexadec-15-yn-1-yl)-4,7,10-trioxa-13,18-diazatriacont-1-yn-30-oate (35-6) as a light brown viscous liquid. Yield: 1.2 g, 88.53%; LCMS m/z 1023.5 [M+1].

tert-butyl 14,19-dioxo-17,17-bis(3-oxo-7,10,13-trioxa-4-azahexadec-15-yn-1-yl)-4,7,10-trioxa-13,18-diazatriacont-1-yn-30-oate (35-6, 1.0 eq, 1.2 g, 1.17 mmol) was cooled at 0° C., trifluoroacetic acid (15 mL) was added and reaction mixture was stirred at room temperature for 3 h. After completion, reaction mixture was concentrated, azeotroped with dichloromethane (2-3 times), washed with diethyl ether (3 times) and lyophilized to dryness to afford 14,19-dioxo-17,17-bis(3-oxo-7,10,13-trioxa-4-azahexadec-15-yn-1-yl)-4,7,10-trioxa-13,18-diazatriacont-1-yn-30-oic acid (35-7) as a brown viscous liquid. Yield: 1.1 g, 96.98%; LCMS m/z 967.2 [M+1]+.

Perfluorophenyl 14,19-dioxo-17,17-bis(3-oxo-7,10,13-trioxa-4-azahexadec-15-yn-1-yl)-4,7,10-trioxa-13,18-diazatriacont-1-yn-30-oate (35-7, 1.0 eq, 0.900 g, 0.930 mmol) and triethylamine (3.0 eq, 0.324 mL, 2.79 mmol)) were dissolved in N,N-dimethylformamide (10 mL) and perfluorophenyl 2,2,2-trifluoroacetate (35-6a, 2.0 eq, 0.326 mL, 1.86 mmol) was added. After 1 h, LCMS analysis showed that the reaction was completed. N,N-dimethylformamide was removed under reduced pressure at 50° C. The residue was diluted with dichloromethane and the solution thus obtained was washed with sodium bisulfate (80 mL), saturated aqueous sodium bicarbonate solution and brine, dried over anhydrous sodium sulfate, filtered and concentrated to dryness to afford perfluorophenyl 14,19-dioxo-17,17-bis(3-oxo-7,10,13-trioxa-4-azahexadec-15-yn-1-yl)-4,7,10-trioxa-13,18-diazatriacont-1-yn-30-oate (LC31) as a yellow thick syrup. Yield: 0.110 g, 10.43%; LCMS m/z 1133.0 [M+1]+.

To a solution of perfluorophenyl 14,19-dioxo-17,17-bis(3-oxo-7,10,13-trioxa-4-azahexadec-15-yn-1-yl)-4,7,10-trioxa-13,18-diazatriacont-1-yn-30-oate (LC31, 1.0 eq, 0.107 g, 0.094 mmol) in dimethylsulfoxide (3 mL), N-((2R,3R, 4R,5R,6R)-2-azido-4,5-dihydroxy-6-(hydroxymethyl)tetrahydro-2H-pyran-3-yl)acetamide (XB6, 3.3 eq, 0.076 g, 0.311 mmol) and tetrakis(acetonitrile)copper(I) hexafluorophosphate (8.4 eq., 0.296 g, 0.793 mmol) were added and reaction mixture was stirred at room temperature for 1 h. After completion, acetic acid (0.3 mL) was added and reaction mixture was purified by preparative HPLC (20-35% acetonitrile in water with 0.1% trifluoroacetic acid). Fractions containing the desired product were combined and lyophilized to dryness to afford perfluorophenyl 1-(1-((2R, 3R,4R,5R,6R)-3-acetamido-4,5-dihydroxy-6-(hydroxymethyl)tetrahydro-2H-pyran-2-yl)-1H-1,2,3-triazol-4-yl)-15, 15-bis(1-(1-((2R,3R,4R,5R,6R)-3-acetamido-4,5-dihydroxy-6-(hydroxymethyl)tetrahydro-2H-pyran-2-yl)-1H-1,2,3-triazol-4-yl)-12-oxo-2,5,8-trioxa-11-azatetradecan-14-yl)-12,17-dioxo-2,5,8-trioxa-11,16-diazaoctacosan-28-oate (Cpd. No. I-143) as an off white solid. Yield: 0.121 g, 68.46%; $^1$H NMR (400 MHz, DMSO-$d_6$ with $D_2O$) δ 8.09 (s, 3H) 5.60 (d, J=10.0 Hz, 3H), 4.48 (s, 6H), 4.36 (t, J=10.0 Hz, 3H), 3.80-3.75 (m, 6H), 3.70-3.66 (m, 6H), 3.55-3.46 (m, 31H), 3.37-3.35 (m, 6H), 3.16-3.13 (m, 6H), 2.72-2.69 (m, 2H), 2.02-1.95 (m, 9H), 1.80-1.75 (m, 6H), 1.60 (s, 12H), 1.45-1.40 (m, 2H), 1.35-1.15 (m, 14H).

Example 36: Synthesis of Compound I-161

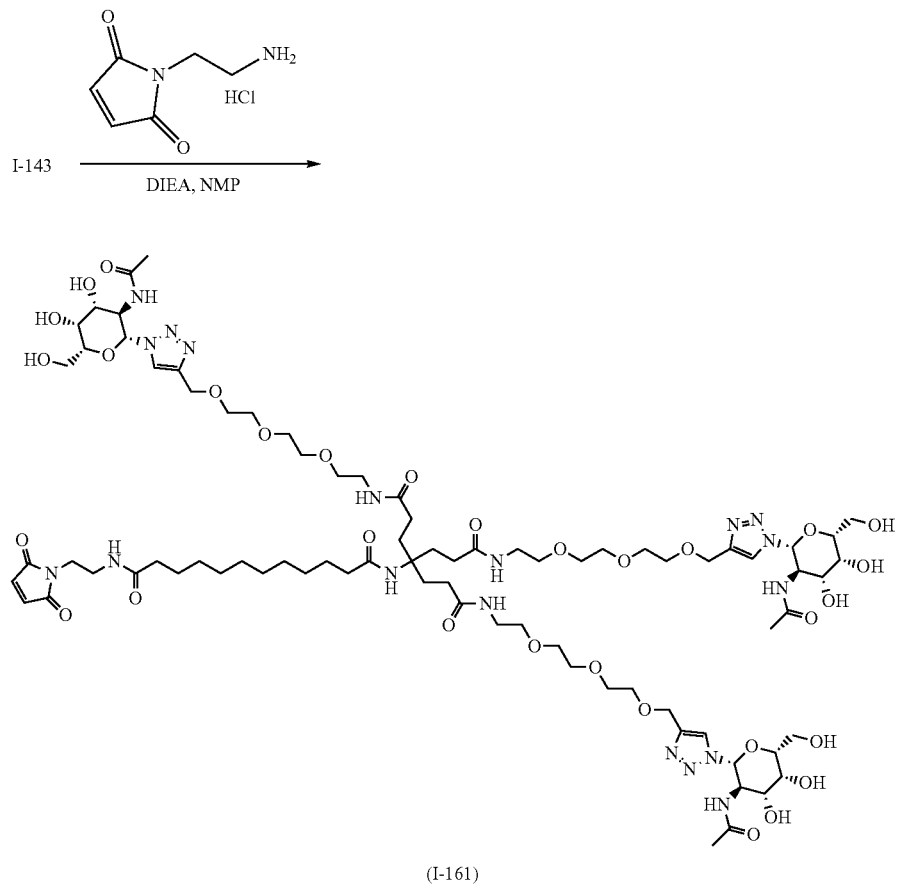

To a mixture compound I-143 (1.00 eq, 25.3 mg, 0.0135 mmol) and 1-(2-aminoethyl)pyrrole-2,5-dione; hydrochloride (1.15 eq, 2.7 mg, 0.0155 mmol) in NMP (0.6 mL) was added Diisopropylethylamine (DIPEA) (2.50 eq, 0.0059 mL, 0.0338 mmol). The mixture was stirred at rt for 1 h and acetic acid (5 uL) was added. The mixture was purified by prep. HPLC (5-30% MeCN/water with 0.1% TFA) and the impure fractions were re-purified by prep. HPLC (5-30% MeCN/water with 0.1% TFA) to give compound I-161 as a white solid (14.8 mg, yield 60%). (purity: 99%). LCMS m/z 1829.0 [M+H]$^+$.

373

Example 37: Synthesis of perfluorophenyl 1-(1-((2R,3R,4R,5R,6R)-4,5-dihydroxy-6-(hydroxymethyl)-2-methoxytetrahydro-2H-pyran-3-yl)-1H-1,2,3-triazol-4-yl)-15,15-bis(1-(1-((2R,3R,4R,5R,6R)-4,5-dihydroxy-6-(hydroxymethyl)-2-methoxytetrahydro-2H-pyran-3-yl)-1H-1,2,3-triazol-4-yl)-12-oxo-2,5,8-trioxa-11-azatetradecan-14-yl)-12,17-dioxo-2,5,8-trioxa-11,16-diazaoctacosan-28-oate (Cpd. No. I-153)

374

To a solution of (2R,3R,4R,5R,6R)-2-(acetoxymethyl)-5-azido-6-methoxytetrahydro-2H-pyran-3,4-diyl diacetate (37-1, 1.0 eq, 1.1 g, 3.19 mmol) in methanol (10 mL), sodium methoxide (25% solution in methanol) (0.1 eq, 0.073 mL, 0.319 mmol) was added and reaction mixture was stirred at room temperature for 1 h. After completion, reaction mixture was neutralized with Dowex 50WX8 hydrogen form (200-400 mesh) and filtered through sintered funnel (without celite). The filtrate was concentrated to get

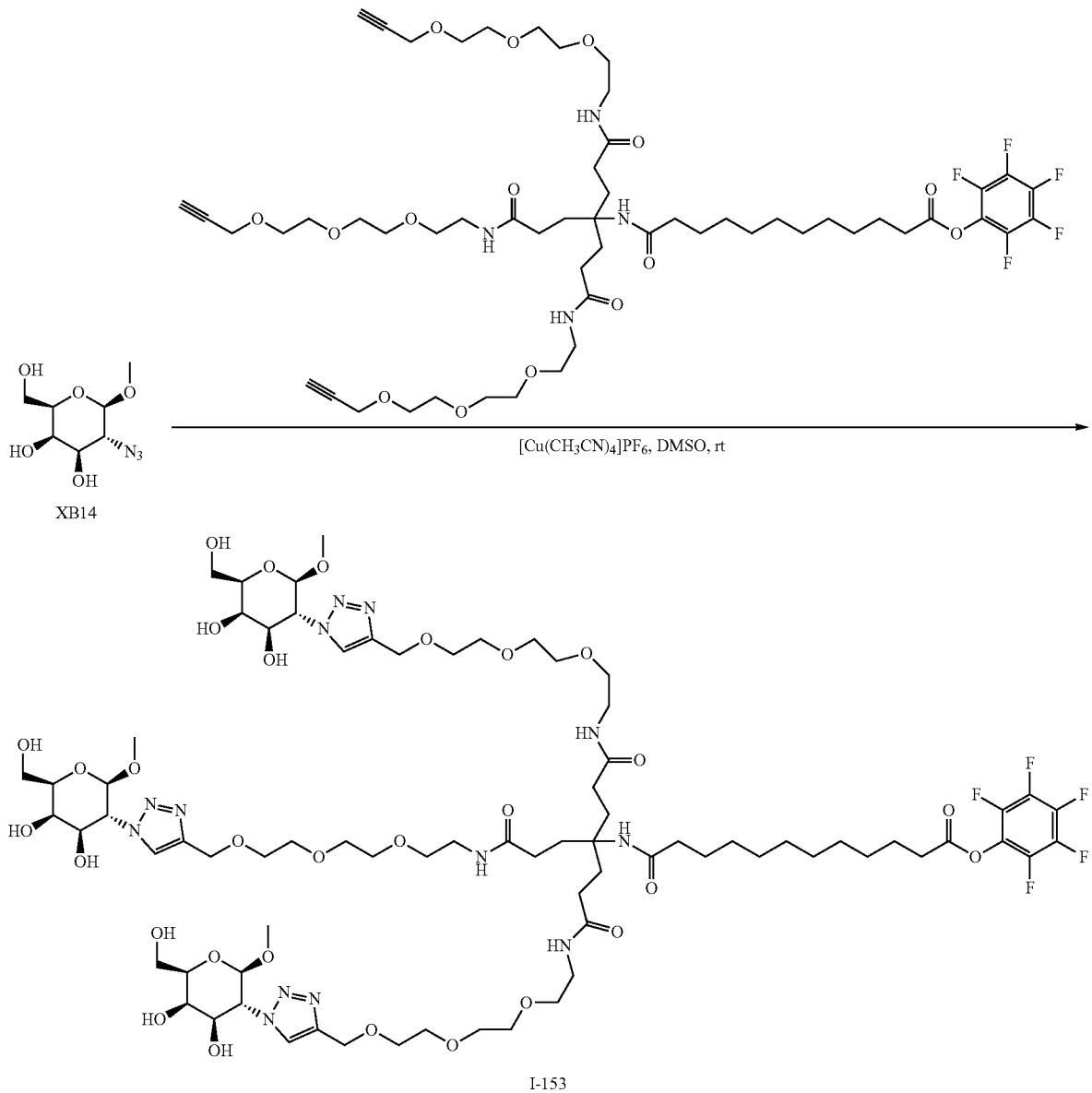

crude which was purified by preparative HPLC (5-20% acetonitrile in water with 0.1% TFA). Fractions containing the desired product were combined and lyophilized to dryness to afford (2R,3R,4R,5R,6R)-5-azido-2-(hydroxymethyl)-6-methoxytetrahydro-2H-pyran-3,4-diol (Cpd. No. XB14) as a white solid. Yield: 0.400 g, 57.28%. LCMS, m/z 218.1 [M−1]⁻.

To a solution of perfluorophenyl 14,19-dioxo-17,17-bis(3-oxo-7,10,13-trioxa-4-azahexadec-15-yn-1-yl)-4,7,10-trioxa-13,18-diazatriacont-1-yn-30-oate (Cpd. No. LC31, 1.0 eq, 0.047 g, 0.041 mmol) and (2R,3R,4R,5R,6R)-5-azido-2-(hydroxymethyl)-6-methoxytetrahydro-2H-pyran-3,4-diol (Cpd. No. XB14, 3.5 eq, 0.031 g, 0.145 mmol) in dimethylsulfoxide (2 mL), tetrakis(acetonitrile)copper(I) hexafluorophosphate (2.5 eq., 0.038 g, 0.104 mmol) was added and reaction mixture was stirred at room temperature for 1 h. After completion, reaction mixture was quenched with acetic acid (0.2 mL) and purified by preparative HPLC (23-41% acetonitrile in water with 0.1% TFA). Fractions containing the desired product were combined and lyophilized to dryness to afford {perfluorophenyl 1-(1-((2R,3R,4R,5R,6R)-4,5-dihydroxy-6-(hydroxymethyl)-2-methoxytetrahydro-2H-pyran-3-yl)-1H-1,2,3-triazol-4-yl)-15,15-bis(1-(1-((2R,3R,4R,5R,6R)-4,5-dihydroxy-6-(hydroxymethyl)-2-methoxytetrahydro-2H-pyran-3-yl)-1H-1,2,3-triazol-4-yl)-12-oxo-2,5,8-trioxa-11-azatetradecan-14-yl)-12,17-dioxo-2,5,8-trioxa-11,16-diazaoctacosan-28-oate (Cpd. No. I-153) as an off white solid. Yield: 0.028 g, 37.7%; LCMS m/z 896.28 [M⁺2H]⁺⁺; ¹H NMR (400 MHz, DMSO-d₆ with D₂O) δ 8.05 (s, 3H), 4.77 (s, 1H), 4.70 (d, J=8.4 Hz, 3H), 4.33 (t, J=10.8 Hz, 3H), 4.02 (dd, J=10.8, 3.2 Hz, 3H), 3.76 (d, J=3.2 Hz, 4H), 3.57 (s, 8H), 3.54-3.49 (m, 14H), 3.46 (s, 13H), 3.36 (t, J=8.4 Hz, 7H), 3.27 (s, 1H), 3.21 (s, 9H), 3.15-3.14 (m, 8H), 2.71 (d, J=6.8 Hz, 2H), 2.00-1.95 (m, 9H), 1.81-1.69 (m, 7H), 1.63-1.60 (m, 2H), 1.45-1.35 (m, 3H), 1.34-1.15 (m, 15H).

Example 38: Synthesis of perfluorophenyl 1-(4-((2-(3-((2R,3R,4R,5R,6R)-4,5-dihydroxy-6-(hydroxymethyl)-2-methoxytetrahydro-2H-pyran-3-yl)ureido)ethoxy)methyl)-1H-1,2,3-triazol-1-yl)-13,13-bis(3-((2-(2-(2-(4-((2-(3-((2R,3R,4R,5R,6R)-4,5-dihydroxy-6-(hydroxymethyl)-2-methoxytetrahydro-2H-pyran-3-yl)ureido)ethoxy)methyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-154)

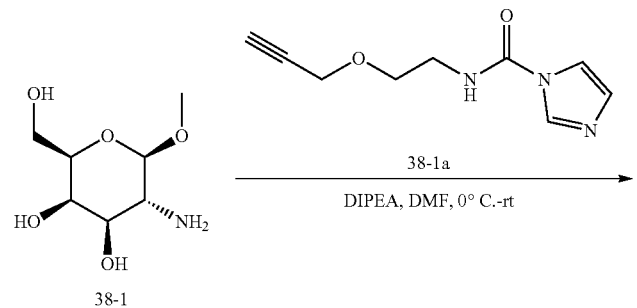

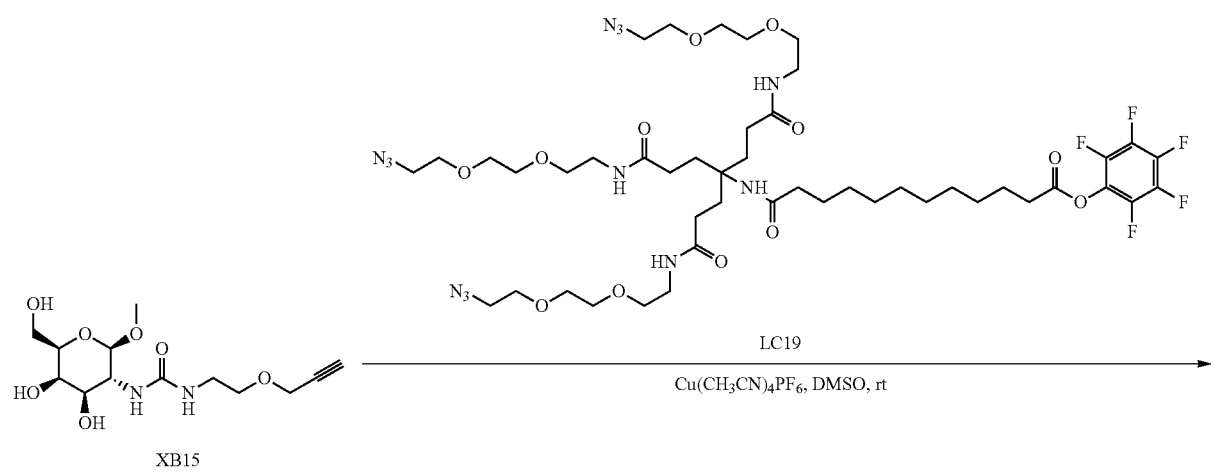

-continued

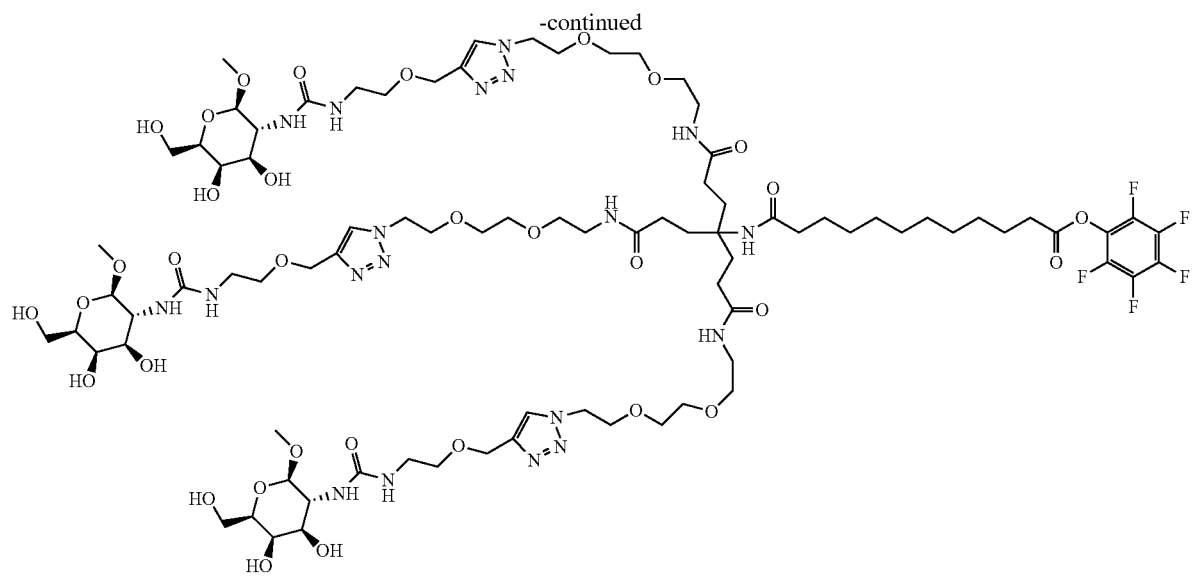

I-154

To a solution of (2R,3R,4R,5R,6R)-5-amino-2-(hydroxymethyl)-6-methoxytetrahydro-2H-pyran-3,4-diol (38-1, 1.0 eq., 0.200 g, 1.04 mmol) in anhydrous N,N-dimethylformamide (2.0 mL), N,N-diisopropylethylamine (4.0 eq., 0.721 mL, 4.14 mmol) and N-(2-(prop-2-yn-1-yloxy)ethyl)-1H-imidazole-1-carboxamide (1.2 eq., 0.240 g, 1.24 mmol) were added at 0° C. and the reaction mixture was stirred at room temperature for 16 h. After completion, the reaction mixture was diluted with ethyl acetate and extracted. The aqueous layer was extracted twice with ethyl acetate. The combined organic layer was washed with water, dried over anhydrous sodium sulfate, filtered and concentrated to get crude which was purified by flash column chromatography (using 15% methanol in dichloromethane as eluent) to afford 1-((2R,3R,4R,5R,6R)-4,5-dihydroxy-6-(hydroxymethyl)-2-methoxytetrahydro-2H-pyran-3-yl)-3-(2-(prop-2-yn-1-yloxy)ethyl)urea (Cpd. No. XB15) as a white solid. Yield: 0.115 g, 35.0%; LCMS m/z 319.0 [M+1]$^+$.

To a solution of 1-((2R,3R,4R,5R,6R)-4,5-dihydroxy-6-(hydroxymethyl)-2-methoxytetrahydro-2H-pyran-3-yl)-3-(2-(prop-2-yn-1-yloxy)ethyl)urea (XB15, 3.3 eq, 0.0403 g, 0.127 mmol) in dimethyl sulfoxide (1.5 mL), perfluorophenyl 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oate (LC19, 1.0 eq., 0.042 g, 0.038 mmol) and tetrakis(acetonitrile)copper(I) hexafluorophosphate (2.8 eq, 0.120 g, 0.322 mmol) were added and reaction mixture was stirred at room temperature for 30 minutes. After completion, the reaction mixture was quenched with acetic acid (0.3 mL) and purified by preparative HPLC (20-48% acetonitrile in water with 0.1% TFA). Fractions containing the desired product were combined and lyophilized to dryness to afford perfluorophenyl 1-(4-((2-(3-((2R,3R,4R,5R,6R)-4,5-dihydroxy-6-(hydroxymethyl)-2-methoxytetrahydro-2H-pyran-3-yl)ureido)ethoxy)methyl)-1H-1,2,3-triazol-1-yl)-13,13-bis(3-((2-(2-(2-(4-((2-(3-((2R,3R,4R,5R,6R)-4,5-dihydroxy-6-(hydroxymethyl)-2-methoxytetrahydro-2H-pyran-3-yl)ureido)ethoxy)methyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-154) as white fluffy solid. Yield: 0.025 g, 31.78%; LCMS m/z 1025.2, [M$^+$2H]$^{++}$; $^1$H-NMR (400 MHz, DMSO-d$_6$ with D$_2$O) δ 8.02 (s, 2H), 4.55-4.45 (m, 12H), 4.09 (d, J 8.0 Hz, 3H), 3.80-3.75 (m, 6H), 3.62-3.60 (m, 3H), 3.48-3.41 (m, 28H), 3.34-3.29 (m, 20H), 3.19-3.13 (m, 13H), 2.71-2.67 (m, 1H), 2.16 (t, J=7.6 Hz, 2H), 2.05-1.95 (m, 8H), 1.80-1.70 (m, 6H), 1.67-1.60 (m, 1H), 1.47-1.37 (m, 3H), 1.35-1.15 (m, 14H).

Example 39: Synthesis of perfluorophenyl 1-(4-(2-(2-(((2R,3R,4R,5R,6R)-4,5-dihydroxy-6-(hydroxymethyl)-2-methoxytetrahydro-2H-pyran-3-yl)amino)-2-oxoethoxy)ethyl)-1H-1,2,3-triazol-1-yl)-13,13-bis(3-((2-(2-(2-(4-(2-(2-(((2R,3R,4R,5R,6R)-4,5-dihydroxy-6-(hydroxymethyl)-2-methoxytetrahydro-2H-pyran-3-yl)amino)-2-oxoethoxy)ethyl)-1H-1,2,3-triazol-1-yl)ethoxy)ethoxy)ethyl)amino)-3-oxopropyl)-10,15-dioxo-3,6-dioxa-9,14-diazahexacosan-26-oate (Cpd. No. I-155)

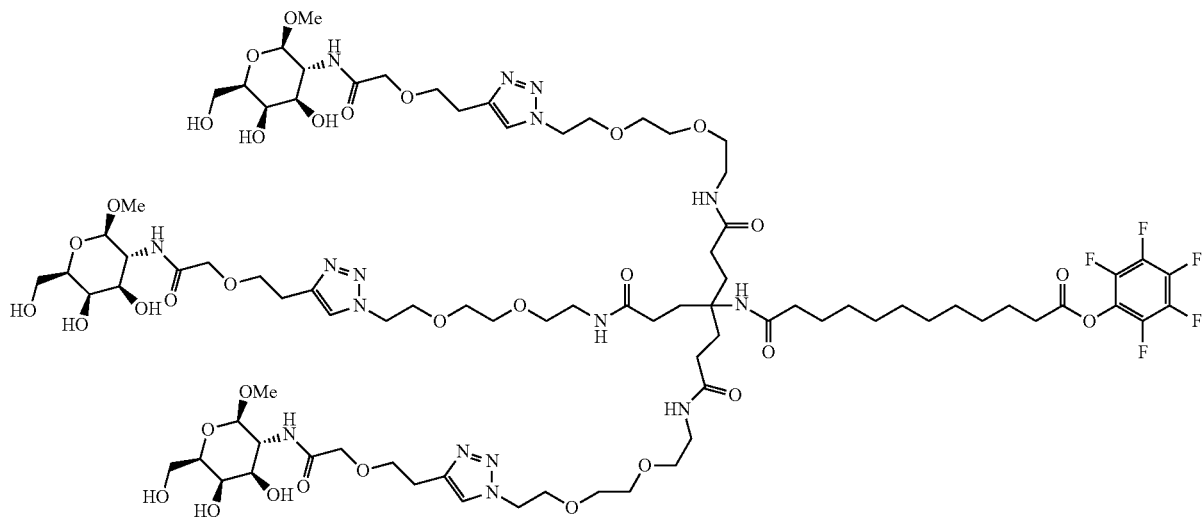

I-155

The title compound was synthesized analogously to example 41 (Cpd. No. I-154). LCMS m/z 1002.9, [M+2H]++

Example 40: Synthesis of 1-[4-(2-{[1,3-bis(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propan-2-yl]carbamoyl}ethyl)-1H-1,2,3-triazol-1-yl]-N-[2-(2,5-dioxo-2,5-dihydro-1H-pyrrol-1-yl)ethyl]-3,6,9,12,15,18,21,24-octaoxaheptacosan-27-amide (Compound I-158)

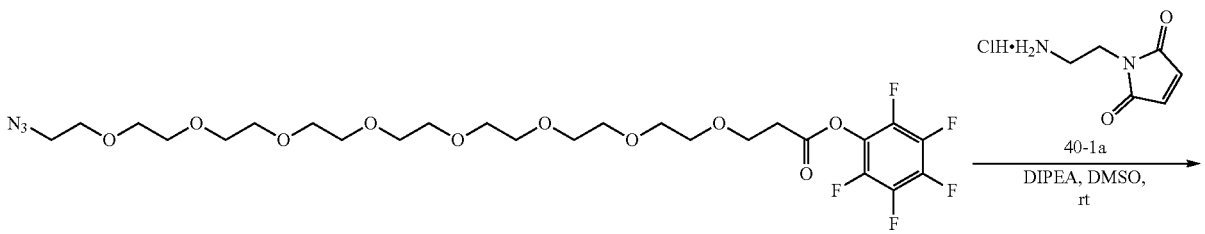

-continued

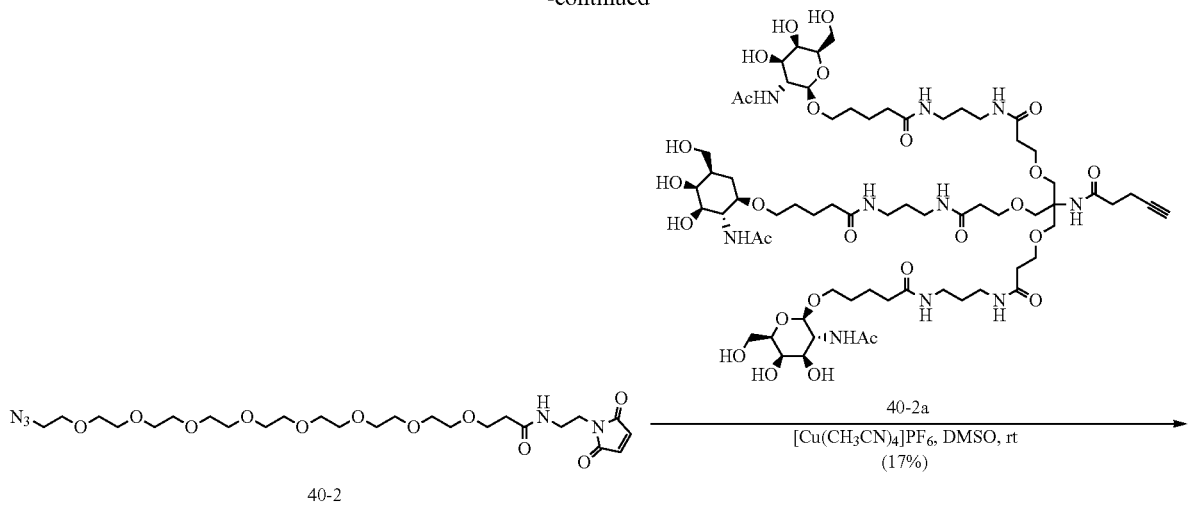
40-2a

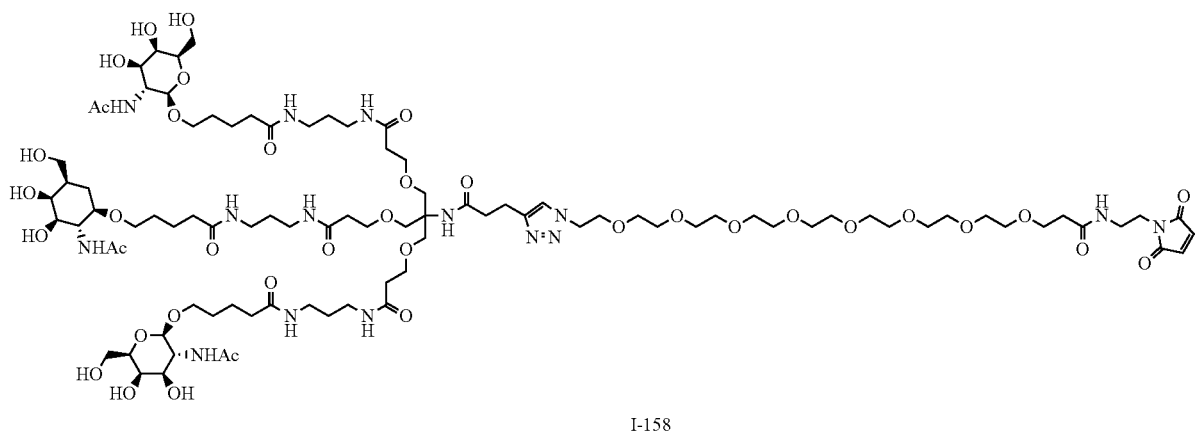
I-158

To a solution of perfluorophenyl 1-azido-3,6,9,12,15,18, 21,24-octaoxaheptacosan-27-oate (40-1, 1.0 eq., 0.040 g, 0.063 mmol) and 1-(2-aminoethyl)-1H-pyrrole-2,5-dione hydrochloride (40-1a, 1.2 eq., 0.013 g, 0.075 mmol) in dimethylsulfoxide (1 mL), N,N-diisopropylethylamine (2.0 eq, 0.023 mL, 0.126 mmol) was added and reaction mixture was stirred at room temperature for 1 h. Reaction was monitored by LCMS. After completion of reaction, the solution of crude 1-azido-N-(2-(2,5-dioxo-2,5-dihydro-1H-pyrrol-1-yl)ethyl)-3,6,9,12,15,18,21,24-octaoxaheptacosan-27-amide (40-2) was used as such for next reaction. To this solution, N-[1,3-bis(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propan-2-yl]pent-4-ynamide (40-2a, 0.53 eq, 0.050 g, 0.033 mmol) and tetrakis(acetonitrile)copper(I) hexafluorophosphate (2.8 eq., 0.065 g, 0.177 mmol) were added and reaction mixture was stirred at room temperature for 1 h. Reaction was monitored by LCMS. After completion, reaction mixture was diluted with acetonitrile and purified by prep HPLC (16-35% acetonitrile in water with 0.1% acetic acid). Fractions containing the desired product were combined and lyophilized to dryness to afford 1-[4-(2-{[1,3-bis(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)-2-[(2-{[3-(5-{[(2R,3R,4R,5R,6R)-3-acetamido-4,5-dihydroxy-6-(hydroxymethyl)oxan-2-yl]oxy}pentanamido)propyl]carbamoyl}ethoxy)methyl]propan-2-yl]carbamoyl}ethyl)-1H-1,2,3-triazol-1-yl]-N-[2-(2,5-dioxo-2,5-dihydro-1H-pyrrol-1-yl)ethyl]-3,6,9,12,15,18,21,24-octaoxaheptacosan-27-amide (Compound I-158) as a colourless sticky solid. Yield: 0.024 g, 17.93%; LCMS m/z 1043.72 [(M/2)+1]$^+$; $^1$H NMR (400 MHz, DMSO-d$_6$) δ 7.94-7.93 (m, 1H), 7.86-7.84 (m, 4H), 7.76-7.73 (m, 3H), 7.62 (d, J=6.0 Hz, 3H), 7.17 (bs, 1H), 7.00 (s, 2H), 4.62-4.44 (m, 9H), 4.20 (d, J=8.8 Hz, 3H), 3.78 (t, J=5.2 Hz, 2H), 3.71-3.67 (m, 6H), 3.63 (bs, 3H), 3.53-3.48 (m, 37H), 3.45-3.39 (m, 10H), 3.33-3.28 (m, 4H), 3.20-3.16 (m, 2H), 3.02-2.97 (m, 12H), 2.79-2.75 (m, 2H), 2.53-2.49 (m, 8H), 2.43-2.40 (m, 4H), 2.27 (t, J=5.6 Hz, 6H), 2.21 (t, J=6.8 Hz, 2H), 2.03 (t, J=7.2 Hz, 6H), 1.79 (s, 9H), 1.49-1.45 (m, 12H), 1.42-1.36 (m, 6H).

Example 41: Synthesis of Synthesis of (2R,3R,4R,5R,6R)-3-acetamido-5-hydroxy-6-(hydroxymethyl)-2-(pent-4-yn-1-yloxy)tetrahydro-2H-pyran-4-yl isobutyrate (Intermediate D)

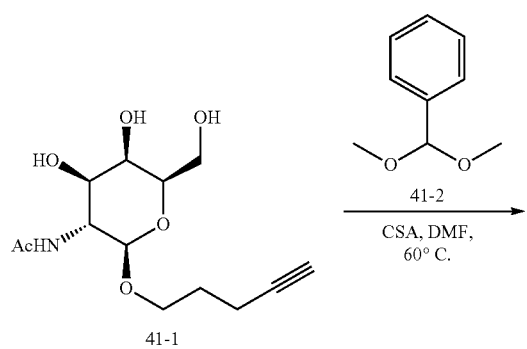

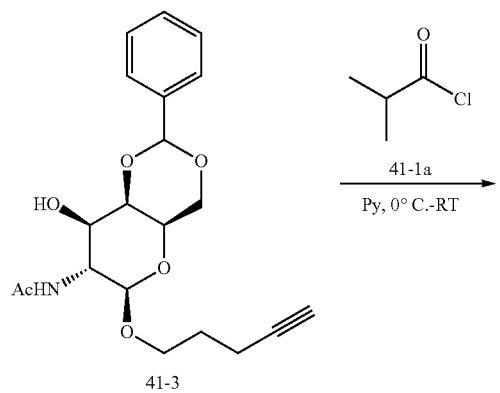

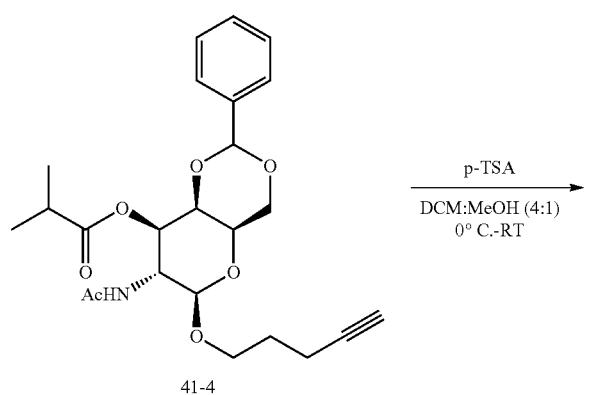

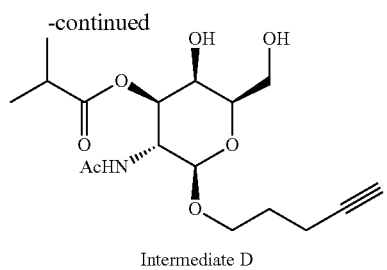

Intermediate D

In an inert atmosphere, N-[(2R,3R,4R,5R,6R)-4,5-dihydroxy-6-(hydroxymethyl)-2-(pent-4-yn-1-yloxy)oxan-3-yl]acetamide (41-1, 2.00 g, 6.97 mmol) was dissolved in N,N-dimethylformamide (20.0 mL). The reaction vessel then cooled to 0° C. followed by addition of (dimethoxymethyl)benzene (41-2, 1.53 mL, 1.5 eq., 10.5 mmol) and {7,7-dimethyl-2-oxobicyclo[2.2.1]heptan-1-yl}methanesulfonic acid (323 mg, 0.2 eq., 1.39 mmol). Thereafter, the reaction was stirred at 60° C. for 6 h and monitored by TLC and LC-MS. After completion of reaction, triethylamine added to up to neutral pH and N,N-dimethylformamide was evaporated that gave thick residue, which was purified with silica gel column chromatography using 10% methanol in dichloromethane as mobile phase to afford N-((4aR,6R,7R,8R,8aR)-8-hydroxy-6-(pent-4-yn-1-yloxy)-2-phenylhexahydropyrano[3,2-d][1,3]dioxin-7-yl)acetamide (41-3) as white solid. Yield: 1.60 g (61.22%); LCMS m/z 374.5 [M−1]⁻.

To a solution of N-[(4aR,6R,7R,8R,8aR)-8-hydroxy-6-(pent-4-yn-1-yloxy)-2-phenyl-hexahydropyrano[3,2-d][1,3]dioxin-7-yl]acetamide (41-3, 1.0 g, 2.66 mmol) in pyridine (10.0 mL) was added 2-methylpropanoyl chloride (41-1a, 0.334 mL, 1.2 eq., 3.20 mmol) at 0° C. The reaction was stirred at room temperature for 1 h and TLC checked. After completion of reaction, pyridine was evaporated to dryness and the observed crude was purified by silica gel column chromatography using 5% methanol in dichloromethane as mobile phase to afford (4aR,6R,7R,8R,8aR)-7-acetamido-6-(pent-4-yn-1-yloxy)-2-phenylhexahydropyrano[3,2-d][1,3]dioxin-8-yl isobutyrate (41-4) as white solid. Yield: 0.91 g (76.68%); LCMS m/z 444.25 [M−1]⁻.

To a solution of (4aR,6R,7R,8R,8aR)-7-acetamido-6-(pent-4-yn-1-yloxy)-2-phenylhexahydropyrano[3,2-d][1,3]dioxin-8-yl isobutyrate (41-4, 0.91 g, 2.04 mmol) in DCM:MeOH (4:1, 10 mL) was added 4-methylbenzene-1-sulfonic acid (0.035 g, 0.1 eq., 0.204 mmol) at 0° C. The reaction was stirred at room temperature for 3 h and was monitored by TLC. After completion of reaction, triethylamine was added up to neutral pH. Reaction mixture was concentrated on rotary evaporator and observed thick syrup was purified in prep-HPLC (using 45-75% acetonitrile in water with 0.10% TFA) to get (2R,3R,4R,5R,6R)-3-acetamido-5-hydroxy-6-(hydroxymethyl)-2-(pent-4-yn-1-yloxy)tetrahydro-2H-pyran-4-yl isobutyrate (Intermediate D) as white solid. Yield: 0.18 g (24.66%); LCMS m/z 330.2 [M+1]⁺.

Example 42: Synthesis of Perfluorophenyl 1-(4-(3-(((2R,3R,4R,5R,6R)-3-acetamido-5-hydroxy-6-(hydroxymethyl)-4-(isobutyryloxy)tetrahydro-2H-pyran-2-yl)oxy)propyl)-1H-1,2,3-triazol-1-yl)-3,6,9,12,15,18-hexaoxahenicosan-21-oate (Compound I-148)

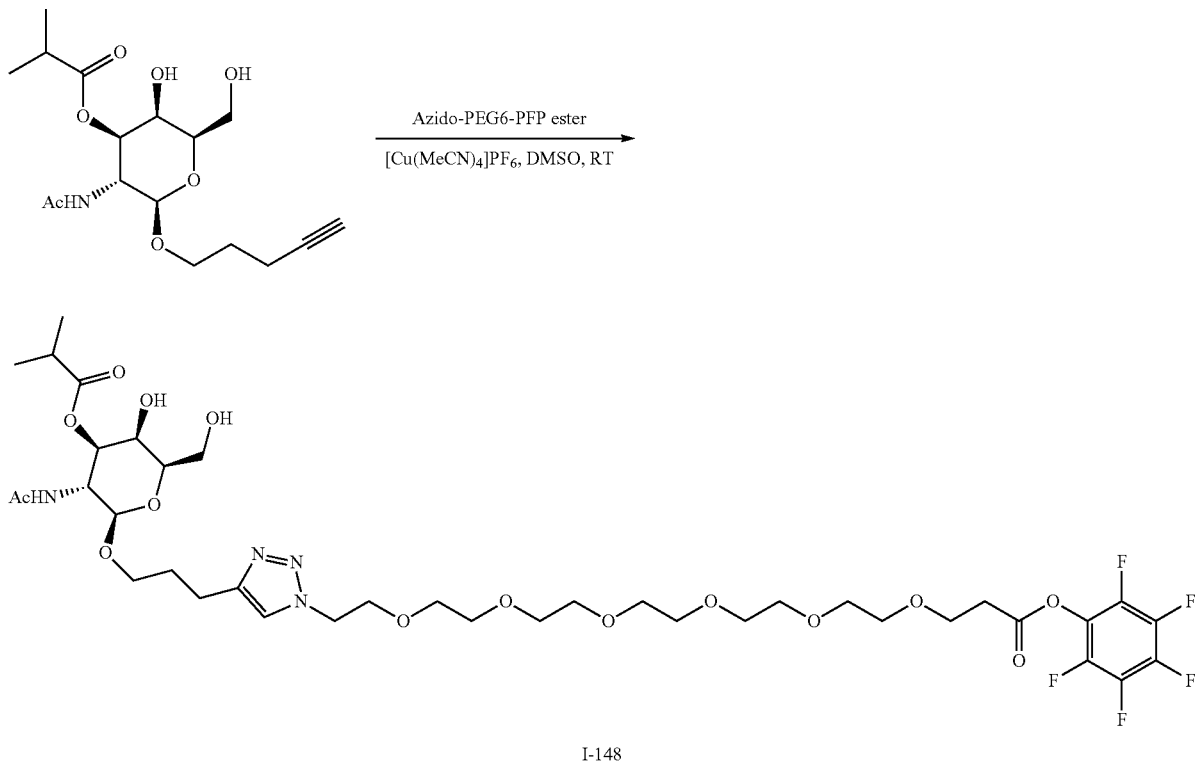

I-148

To a stirred solution of (2R,3R,4R,5R,6R)-3-acetamido-5-hydroxy-6-(hydroxymethyl)-2-(pent-4-yn-1-yloxy)tetrahydro-2H-pyran-4-yl isobutyrate (Intermediate D, 0.30 g, 1.0 eq., 0.0839 mmol) in dimethylsulfoxide (2.0 mL) was 2,3,4,5,6-pentafluorophenyl 1-azido-3,6,9,12,15,18-hexaoxahenicosan-21-oate (0.045 g, 1.0 eq, 0.0839 mmol) at room temperature and stirred for 5 min. Tetrakis(acetonitrile)copper(I) hexafluorophosphate (0.060 g, 2.2 eq., 0.185 mmol) was then added to the reaction mixture at room temperature. The progress of the reaction was monitored by LC-MS. After 15 min, the reaction mixture was directly used for prep-HPLC purification (0.1% TFA, 13-40% acetonitrile in water). The fractions containing desired compound were lyophilized to afford perfluorophenyl 1-(4-(3-(((2R,3R,4R,5R,6R)-3-acetamido-5-hydroxy-6-(hydroxymethyl)-4-(isobutyryloxy)tetrahydro-2H-pyran-2-yl)oxy)propyl)-1H-1,2,3-triazol-1-yl)-3,6,9,12,15,18-hexaoxahenicosan-21-oate (Compound I-148) as a white solid. Yield: 0.021 g (27.71%). LC-MS: m/z 903.29 [M+1]+. $^1$H NMR (DMSO-$d_6$, $D_2O$ exchange.): 7.64 (s, 1H), 4.63 (dd, J=10.8, 2.8 Hz 1H), 4.42 (t, J=4.8 Hz, 2H), 4.34 (d, J=8.4 Hz, 1H), 4.04-4.01 (m, 1H), 3.77-3.71 (m, 5H), 3.50-3.39 (m, 26H), 2.95 (t, J=11.6 Hz, 2H), 2.57 (d, J=8.0 Hz, 2H), 2.49-2.46 (s, 1H), 1.72-1.76 (m, 5H), 1.01 (dd, J=6.8, 2.4 Hz, 6H).

Example 43: Synthesis of Perfluorophenyl 1-(4-(3-(((2R,3R,4R,5R,6R)-3-acetamido-5-hydroxy-6-(hydroxymethyl)-4-(isobutyryloxy)tetrahydro-2H-pyran-2-yl)oxy)propyl)-1H-1,2,3-triazol-1-yl)-13-oxo-3,6,9,16,19-pentaoxa-12-azadocosan-22-oate (Compound I-147)

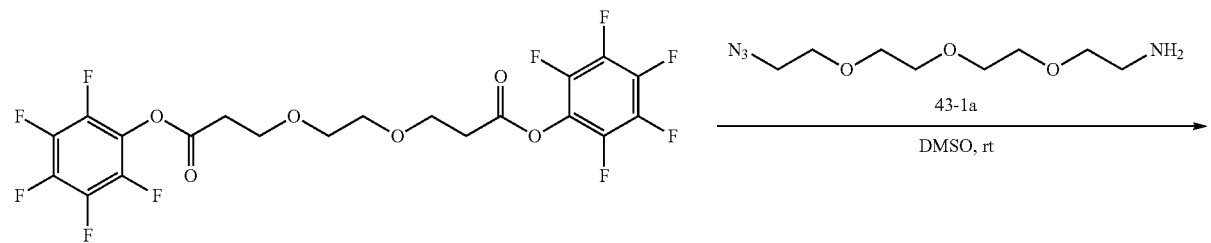

43-1

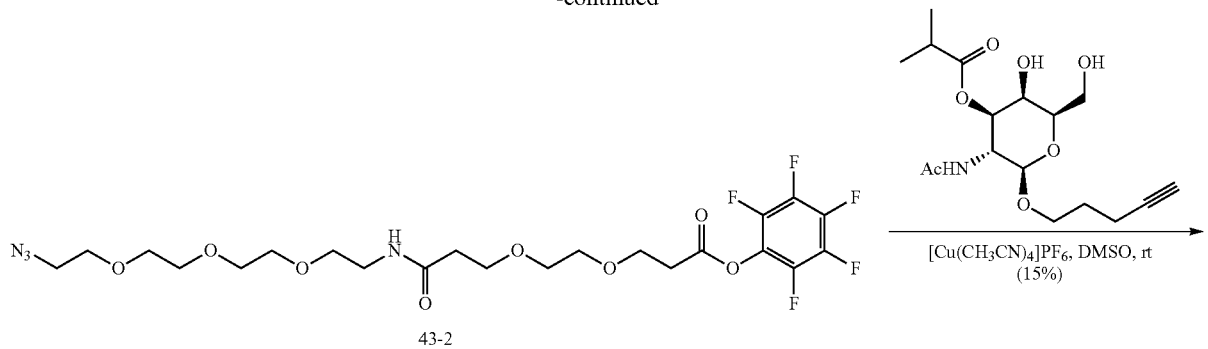

43-2

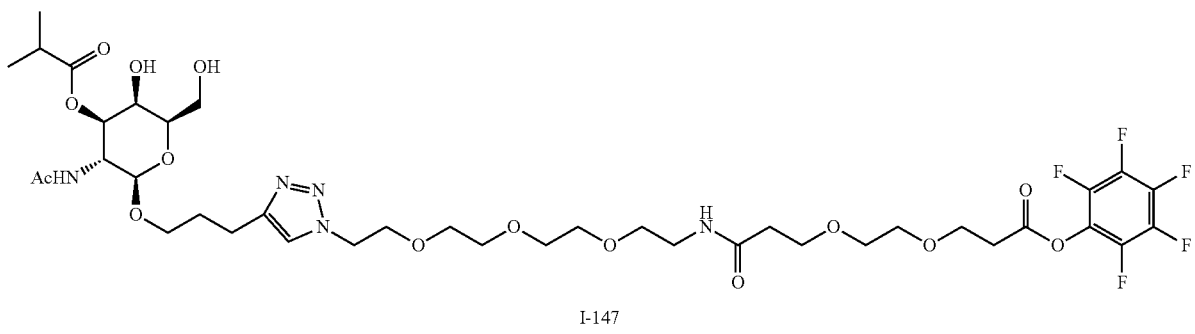

I-147

A solution of bis(perfluorophenyl) 3,3'-(ethane-1,2-diyl-bis(oxy))dipropionate (43-1, 1.0 eq, 0.100 g, 0.186 mmol) and 2-(2-(2-(2-azidoethoxy)ethoxy)ethoxy)ethan-1-amine (43-1a, 0.9 eq, 0.036 g, 0.167 mmol) in dimethyl sulfoxide (2.0 mL) was stirred at room temperature for 2 h. Thereafter, crude perfluorophenyl 1-azido-13-oxo-3,6,9,16,19-pentaoxa-12-azadocosan-22-oate (43-2) obtained, was used as such for next reaction. Yield: 0.110 g (Crude), LCMS m/z 573.05 [M+1]⁺.

A solution of (2R,3R,4R,5R,6R)-3-acetamido-5-hydroxy-6-(hydroxymethyl)-2-(pent-4-yn-1-yloxy)tetrahydro-2H-pyran-4-yl isobutyrate (Intermediate D, 1.0 eq, 0.050 g, 0.140 mmol), perfluorophenyl 1-azido-13-oxo-3,6,9,16,19-pentaoxa-12-azadocosan-22-oate (43-2, 1.3 eq, 0.104 g, 0.182 mmol) and tetrakis(acetonitrile)copper(I) hexafluorophosphate (2.8 eq, 0.146 g, 0.392 mmol) in dimethyl sulfoxide (2 mL) was stirred at room temperature for 1 h. Thereafter, reaction mixture was diluted with acetonitrile and purified by prep HPLC (37-48% acetonitrile in water with 0.1% TFA). Fractions containing the desired product were combined and lyophilized to dryness to afford perfluorophenyl 1-(4-(3-(((2R,3R,4R,5R,6R)-3-acetamido-5-hydroxy-6-(hydroxymethyl)-4-(isobutyryloxy)tetrahydro-2H-pyran-2-yl)oxy)propyl)-1H-1,2,3-triazol-1-yl)-13-oxo-3,6,9,16,19-pentaoxa-12-azadocosan-22-oate (Compound I-147) as a colourless viscous liquid. Yield: 0.023 g, 15.65%; LCMS m/z 930.20 [M+1]+; ¹H NMR (400 MHz, DMSO-d₆) δ 7.86 (t, J=5.6 Hz, 1H), 7.80 (s, 1H), 7.71 (d, J=9.6 Hz, 1H), 4.65 (dd, J=11.2 Hz, 3.2 Hz, 1H), 4.45 (t, J=5.6 Hz, 2H), 4.36 (d, J=8.4 Hz, 1H), 4.08-4.03 (m, 1H), 3.83 (s, 1H), 3.80-3.74 (m, 5H), 3.59-3.52 (m, 7H), 3.49-3.47 (m, 10H), 3.40-3.36 (m, 5H), 3.19-3.16 (m, 2H), 3.02 (t, J=4.0 Hz, 2H), 2.61 (t, J=6.4 Hz, 2H), 2.53 (s, 1H), 2.32-2.28 (m, 2H), 1.79-1.75 (m, 5H), 1.06-1.03 (m, 6H).

Example 44: Synthesis of 2-(((4-(1-((2R,3R,4R,5R,6R)-3-acetamido-4,5-dihydroxy-6-(hydroxymethyl)tetrahydro-2H-pyran-2-yl)-1H-1,2,3-triazol-4-yl)butanoyl)oxy)methyl)-2-(12-oxo-12-(perfluorophenoxy)dodecanamido)propane-1,3-diyl bis(4-(1-((2R,3R,4R,5R,6R)-3-acetamido-4,5-dihydroxy-6-(hydroxymethyl)tetrahydro-2H-pyran-2-yl)-1H-1,2,3-triazol-4-yl)butanoate) (Compound I-157)

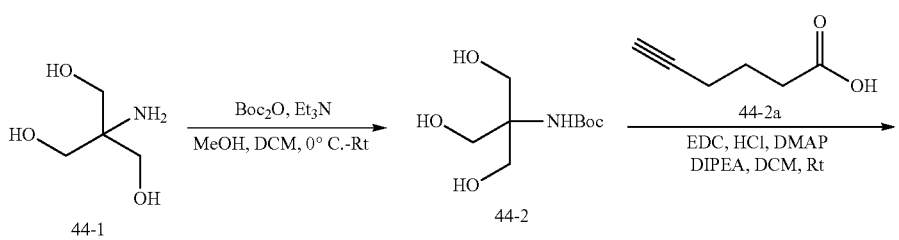

-continued
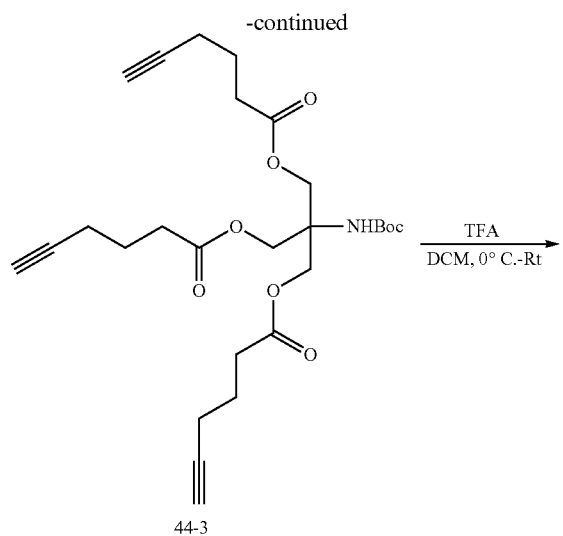
44-3
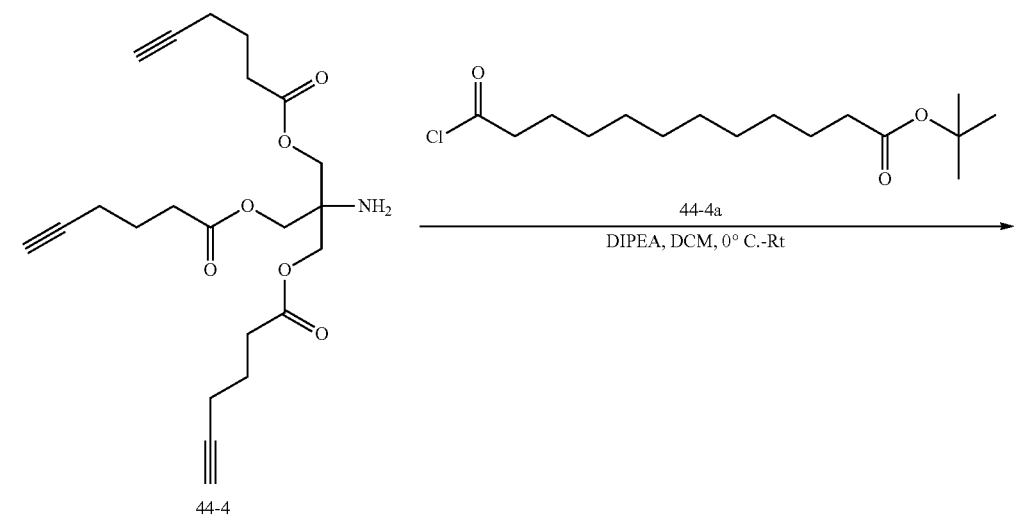
44-4
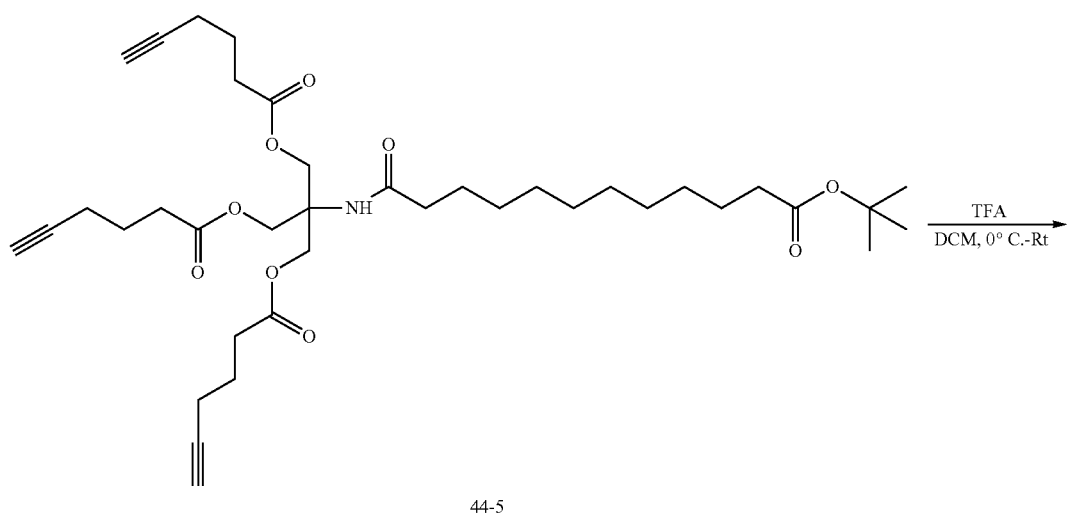
44-5

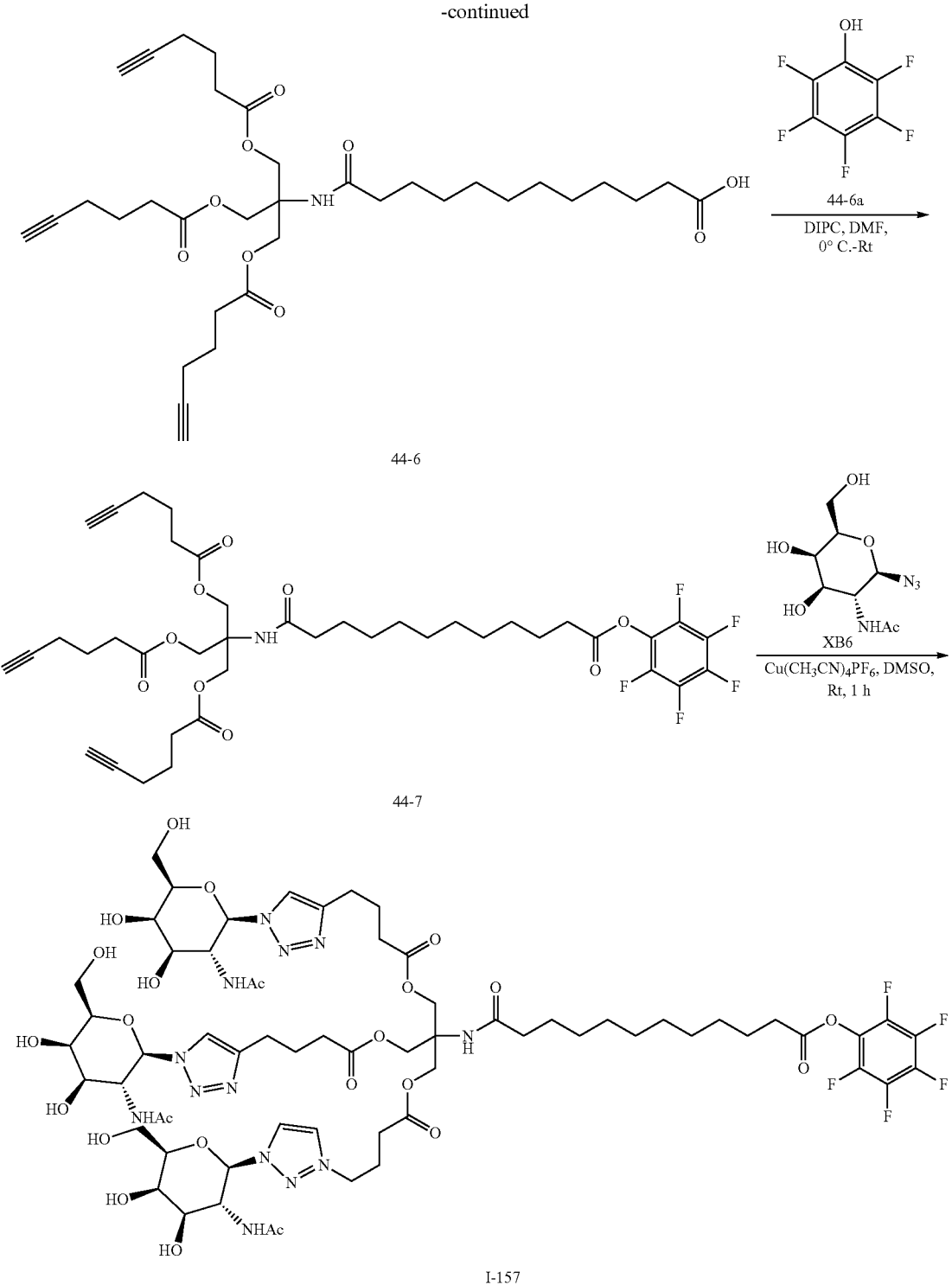

To a solution of 2-amino-2-(hydroxymethyl)propane-1,3-diol (44-1, 5.00 g, 1.0 eq, 41.3 mmol) in methanol (25.0 mL)/dichloromethane (25.0 mL) mixture, were added di-tert-butyl dicarbonate (19.0 mL, 2.0 eq, 82.6 mmol.) and triethylamine (20.3 mL, 3.5 eq 144 mmol.) at 0° C. and then reaction mixture was stirred at room temperature for 12 h. After completion, the mixture was evaporated to dryness under reduced pressure and resulted residue was recrystallized from ethylacetate to afford tert-butyl (1, 3-dihydroxy-2-(hydroxymethyl)propan-2-yl)carbamate (44-2), white solid. Yield: 4.0 g, 43.8%; ELSD-MS m/z 222.0 [M+1].

To a solution of tert-butyl (1, 3-dihydroxy-2-(hydroxymethyl)propan-2-yl)carbamate (2, 3.0 g, 1.0 eq, 13.6 mmol,), 5-hexynoic acid (44-2a, 4.73 ml, 3.3 eq, 44.7 mmol,) in dichloromethane (30 ml), N-ethyl-N-(3-dimethylaminopropyl)carbodiimide hydrochloride (EDC·HCl) (8.58 g, 3.3 eq, 44.7 mmol.)N,N-diisopropylethylamine (8.03 ml, 3.3 eq, 44.7 mmol) and 4-dimethylaminopyridine (0.82 g, 0.5 eq, and 6.78 mmol) were added to the reaction mixture and stirred at ambient conditions for 24 h. The mixture was washed with brine and saturated sodium bicarbonate. The organic layer was dried over anhydrous sodium sulphate and evaporated to dryness under reduced pressure to give crude product which was purified by column chromatography on silica gel using ethyl acetate in hexane (10-40%) as eluent to afford 2-((tert-butoxycarbonyl)amino)-2-((pentanoyloxy)methyl)propane-1,3-diyl bis(hex-5-ynoate) (44-3). Yield: 2.0 g, 29.29%; ELSD-MS m/z 502.0 [M−1]⁻.

To a stirred solution of 2-((tert-butoxycarbonyl)amino)-2-((pentanoyloxy)methyl)propane-1,3-diyl bis(hex-5-ynoate) (44-3, 0.60 g, 1.0 eq, 1.19 mmol)) in dry dichloromethane (2 mL), trifluoroacetic acid (0.5 mL) was added dropwise at 0° C. The reaction mixture was stirred at room temperature for 5 h. Then reaction mixture was evaporated to dryness under reduced pressure followed by triturated with dichloromethane (2 times), and diethyl ether (2 times) to give 2-amino-2-((hex-5-ynoyloxy)methyl)propane-1,3-diyl bis(hex-5-ynoate) (44-4) as pale yellow solid. Yield: 0.33 g, Crude; ELSD-MS m/z 404.0 [M+1]⁺.

To a stirred solution of tert-butyl 12-chloro-12-oxododecanoate (44-4a, 0.49 g, 2.0 eq 1.64 mmol) in dichloromethane (5 mL), was added a solution of 2-amino-2-((hex-5-ynoyloxy)methyl)propane-1,3-diyl bis(hex-5-ynoate) (44-4, 0.330 g, 1.0 eq, 0.818 mmol) and N,N-diisopropylethylamine (0.755 mL, 5.0 eq, 4.09 mmol) in dichloromethane (5.0 mL) at 0° C., then a was added dropwise and reaction mixture was stirred at room temperature for 1 h. After completion, water was added to reaction mixture and extracted with dichloromethane. The organic layer was dried over anhydrous sodium sulfate, filtered and concentrated to get crude which was purified by column chromatography on silica gel using 0-8% methanol in dichloromethane to afford 2-(12-(tert-butoxy)-12-oxododecanamido)-2-((hex-5-ynoyloxy)methyl)propane-1,3-diyl bis(hex-5-ynoate) (44-5) as a light brown viscous liquid. Yield: 0.28 g, 50.95%; LCMS m/z 672.50 [M+1]⁺.

To a stirred solution of 2-(12-(tert-butoxy)-12-oxododecanamido)-2-((hex-5-ynoyloxy)methyl)propane-1,3-diyl bis(hex-5-ynoate) (44-5, 0.50 g, 0.744 mmol) in dry dichloromethane (4 mL), trifluoroacetic acid (4 mL) was added dropwise at 0° C. The reaction mixture was stirred at room temperature for 5 h. Then reaction mixture was evaporated to dryness under reduced pressure followed by triturated with dichloromethane (2 times), and diethyl ether (2 times) to afford. 12-((1,3-bis(hex-5-ynoyloxy)-2-((hex-5-ynoyloxy)methyl)propan-2-yl)amino)-12-oxododecanoic acid (44-6) as pale yellow solid. Yield: 0.40 g, Crude. ELSD-MS m/z 614.20[M+1]⁺.

To a stirred solution of 12-((1,3-bis(hex-5-ynoyloxy)-2-((hex-5-ynoyloxy)methyl)propan-2-yl)amino)-12-oxododecanoic acid (44-6, 0.40 g, 1.0 eq, 0.650 mmol) in N,N-dimethylformamide (4 mL), was added pentafluorophenol (44-6a, 0.10 g, 0.9 eq., 0.580 mmol) dissolved in N,N-dimethylformamide (0.5 mL) and N,N'-diisopropylcarbodiimide (0.16 g, 2.0 eq, 1.30 mmol) and the reaction mixture was stirred at room temperature for 18 h. After completion, reaction mixture was concentrated under reduced pressure to get crude which was purified by flash column chromatography on silica gel using 30-50% ethyl acetate in hexane to afford 2-((hex-5-ynoyloxy)methyl)-2-(12-oxo-12-(perfluorophenoxy)dodecanamido)propane-1,3-diyl bis(hex-5-ynoate) (44-7) as off white semi-solid. Yield: 0.350 g, 68%; ELSD-MS m/z 782.0 [M+1]+.

To a stirred solution of 2-((hex-5-ynoyloxy)methyl)-2-(12-oxo-12-(perfluorophenoxy)dodecanamido)propane-1,3-diyl bis(hex-5-ynoate) (44-7, 0.10 g, 1.0 eq, 0.128 mmol), and N-((2R,3R,4R,5R,6R)-2-azido-4,5-dihydroxy-6-(hydroxymethyl)tetrahydro-2H-pyran-3-yl)acetamide (XB6, 3.3 eq, 0.10 g, 0.422 mmol) in dimethyl sulfoxide (3 mL), tetrakis(acetonitrile)copper(I) hexafluorophosphate (0.40 g, 8.4 eq., 1.07 mmol) was added and reaction mixture was stirred at room temperature for 1 h. After completion, reaction mixture was purified by prep HPLC (using 23-41% acetonitrile in water with 0.1% TFA). Fractions containing the desired product were combined and lyophilized to dryness to afford 2-(((4-(1-((2R,3R,4R,5R,6R)-3-acetamido-4,5-dihydroxy-6-(hydroxymethyl)tetrahydro-2H-pyran-2-yl)-1H-1,2,3-triazol-4-yl)butanoyl)oxy)methyl)-2-(12-oxo-12-(perfluorophenoxy)dodecanamido)propane-1,3-diyl bis(4-(1-((2R,3R,4R,5R,6R)-3-acetamido-4,5-dihydroxy-6-(hydroxymethyl)tetrahydro-2H-pyran-2-yl)-1H-1,2,3-triazol-4-yl)butanoate) (Compound I-157) as an off white solid. Yield: 0.14 g, 72% LCMS m/z 1520.60 [M+1]+. ¹H NMR (400 MHz, DMSO-d₆ with D₂O exchange) δ 7.85 (s, 3H), 5.55 (d, J=9.6 Hz, 3H), 4.35 (t, J=10.0 Hz, 3H), 4.26 (s, 6H), 3.77 (d, J=2.4, Hz, 3H), 3.69-3.66 (m, 6H), 3.55-3.46 (m, 6H), 2.72 (t, J=7.0 Hz, 2H), 2.58 (t, J=7.2 Hz, 6H), 2.29 (t, J=7.2 Hz, 6H), 2.02 (t, J=6.8 Hz, 2H), 1.81-1.74 (m, 6H), 1.64-1.58 (m, 11H), 1.41-1.39 (m, 2H), 1.30-1.38 (m, 13H).

Example 45: Synthesis of 1-(4-(3-(((3S,4S,5R,6R)-4,5-dihydroxy-6-(hydroxymethyl)tetrahydro-2H-pyran-3-yl)oxy)propyl)-1H-1,2,3-triazol-1-yl)-13,13-bis(3-((2-(2-(2-(4-(3-(((3S,4S,5R,6R)-4,5-dihydroxy-6-(hydroxymethyl)tetrahydro-2H-pyran-3-yl)oxy)propyl)-1H-1,2,3-triazol-1-yl)ethoxy)ethoxy)ethyl)amino)-3-oxopropyl)-10,15-dioxo-3,6-dioxa-9,14-diazahexacosan-26-oic acid (Compound I-165)

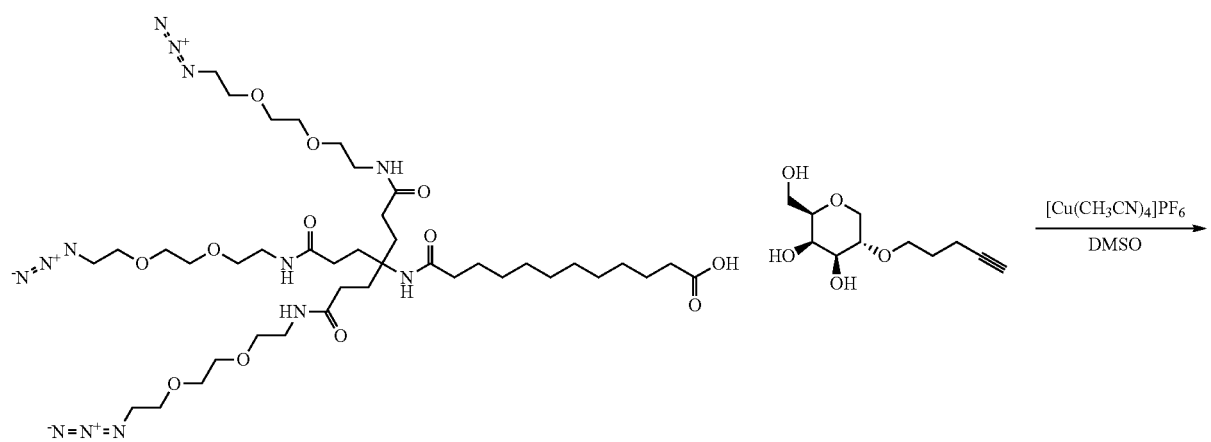

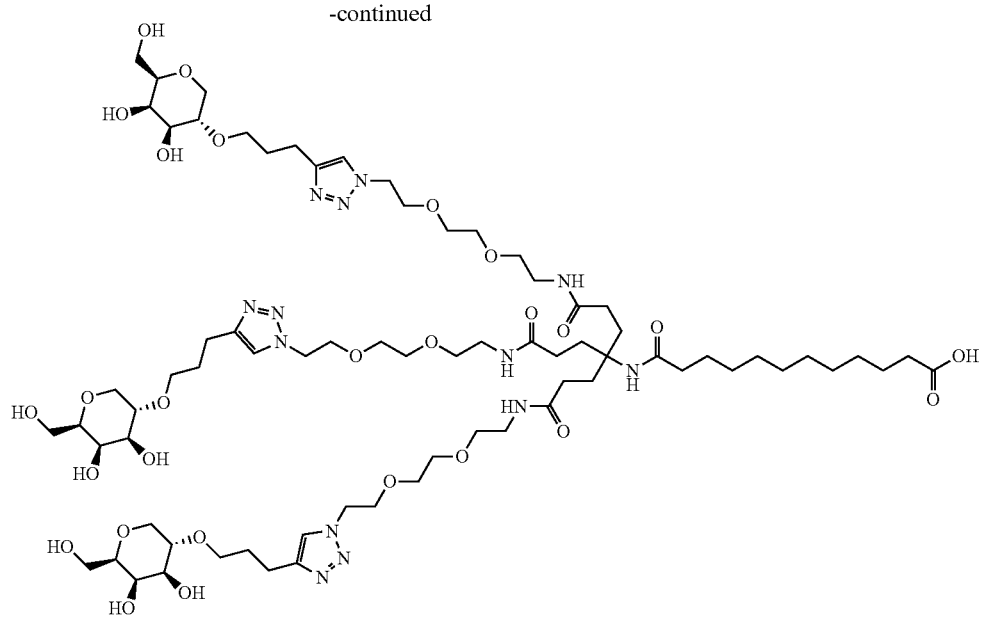

I-165

A solution of 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oic acid (1.00 eq, 8.0 mg, 0.00862 mmol) and (2R,3R,4S,5S)-2-(hydroxymethyl)-5-pent-4-ynoxy-tetrahydropyran-3,4-diol (3.30 eq, 6.5 mg, 0.0284 mmol) in DMSO (200 L) under nitrogen was treated with tetrakis(acetonitrile)copper(I) hexafluorophosphate (3.10 eq, 10.0 mg, 0.0267 mmol) and the reaction was stirred at room temperature for 1 hour. The reaction was acidified with TFA then purified twice by reversed-phase HPLC (10-50% acetonitrile in water w/0.1% TFA) to give Compound I-165 (2.2 mg, 0.00129 mmol, 15% yield). LCMS m/z 1616.2 [M−H]⁻.

Example 46: Synthesis of 1-(4-(((2-(((3S,4R,5R,6R)-4,5-dihydroxy-6-(hydroxymethyl)tetrahydro-2H-pyran-3-yl)amino)-6-(trifluoromethyl)pyrimidin-4-yl)oxy)methyl)-1H-1,2,3-triazol-1-yl)-13,13-bis(3-((2-(2-(2-(4-(((2-(((3S,4R,5R,6R)-4,5-dihydroxy-6-(hydroxymethyl)tetrahydro-2H-pyran-3-yl)amino)-6-(trifluoromethyl)pyrimidin-4-yl)oxy)methyl)-1H-1,2,3-triazol-1-yl)ethoxy)ethoxy)ethyl)amino)-3-oxopropyl)-10,15-dioxo-3,6-dioxa-9,14-diazahexacosan-26-oic acid (I-166)

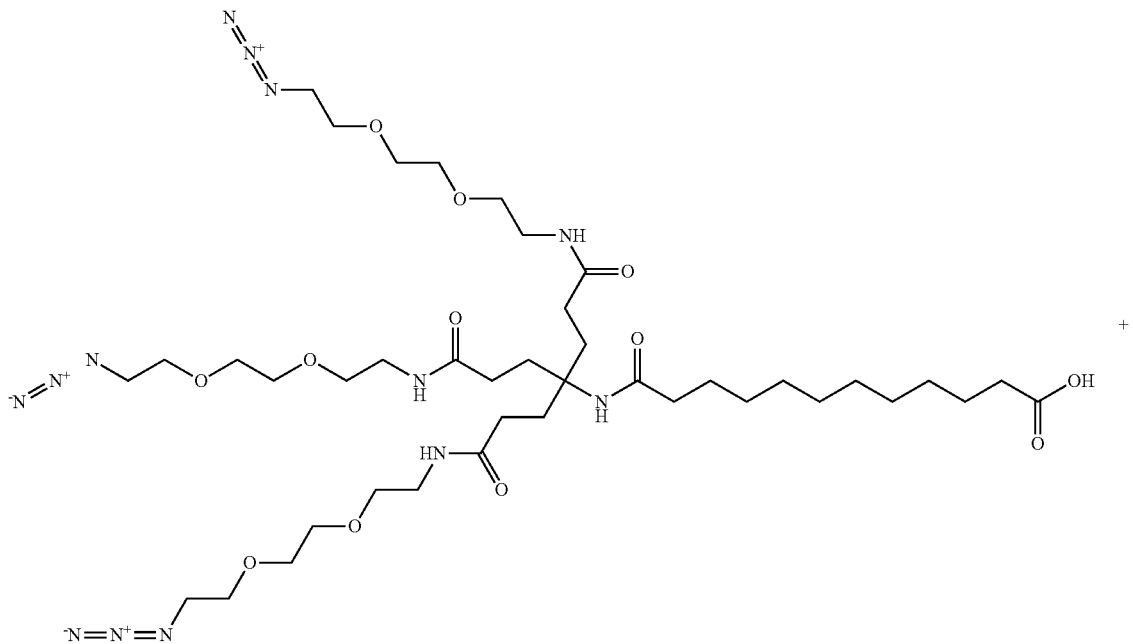

-continued

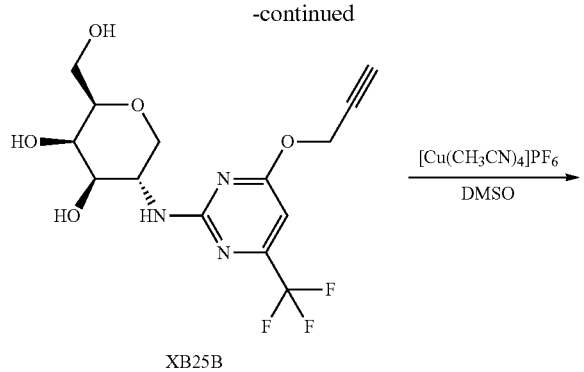

XB25B

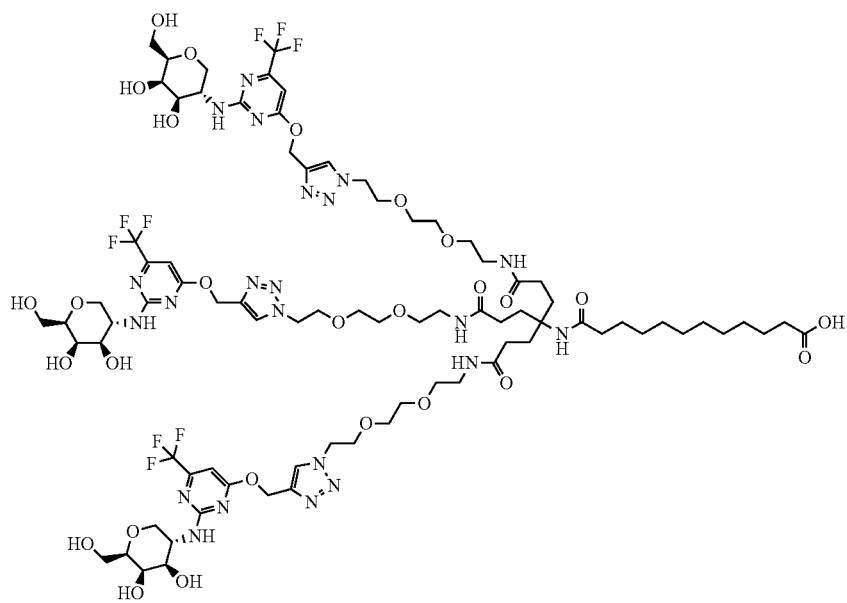

I-166

A solution of 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oic acid (1.00 eq, 7.6 mg, 0.00819 mmol) and (2R,3R,4R,5S)-2-(hydroxymethyl)-5-((4-(prop-2-yn-1-yloxy)-6-(trifluoromethyl)pyrimidin-2-yl)amino)tetrahydro-2H-pyran-3,4-diol (XB25B, 3.30 eq, 9.8 mg, 0.0270 mmol) in DMSO (200 µL) under nitrogen was treated with tetrakis(acetonitrile)copper(I) hexafluorophosphate (3.10 eq, 9.5 mg, 0.0254 mmol) and the reaction was stirred at room temperature for 1 hour. The reaction was acidified with TFA then purified directly by revers-phase HPLC (10-50% acetonitrile in water w/0.1% TFA) to give Compound I-166 (11 mg, 0.00555 mmol, 68% yield). LCMS m/z 1007.4 [(M−2H)/2]⁻.

Compound I-167 was synthesized by adapting the procedure for compound I-166, replacing intermediate XB25B with intermediate XB25A (e.g., as described herein). The structure, name and data for compound I-167 are provided below.

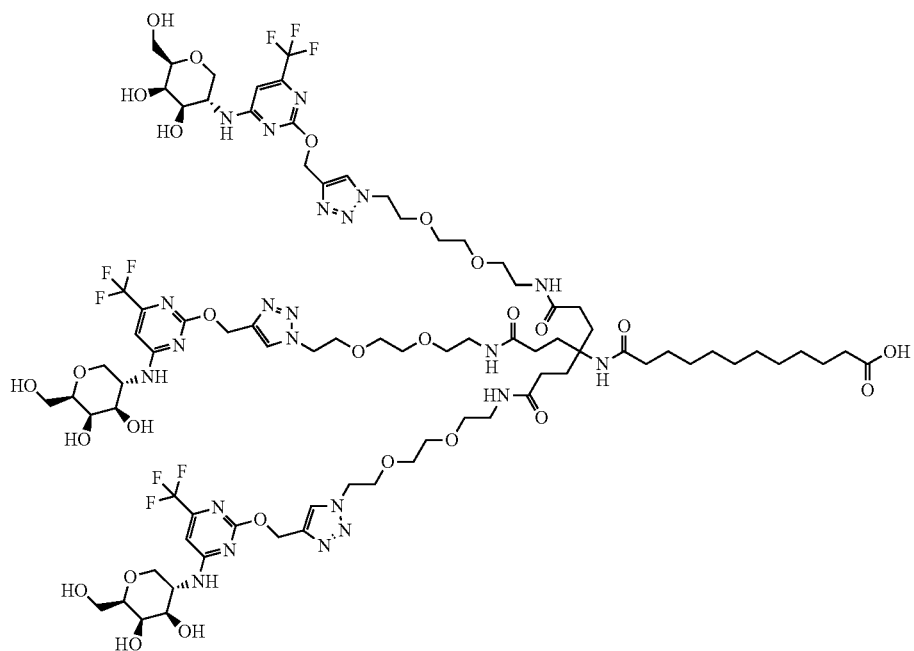

(I-167)

1-(4-(((4-(((3S,4R,5R,6R)-4,5-dihydroxy-6-(hydroxymethyl)tetrahydro-2H-pyran-3-yl)amino)-6-(trifluoromethyl)pyrimidin-2-yl)oxy)methyl)-1H-1,2,3-triazol-1-yl)-13,13-bis(3-((2-(2-(2-(4-(((4-(((3S,4R,5R,6R)-4,5-dihydroxy-6-(hydroxymethyl)tetrahydro-2H-pyran-3-yl)amino)-6-(trifluoromethyl)pyrimidin-2-yl)oxy)methyl)-1H-1,2,3-triazol-1-yl)ethoxy)ethoxy)ethyl)amino)-3-oxopropyl)-10,15-dioxo-3,6-dioxa-9,14-diazahexacosan-26-oic acid (I-167).

LCMS m/z 1007.4 [(M−2H)/2]⁻.

Example 47: Synthesis of N1-(1-(4-(((2R,3R,4R,5R,6R)-3-acetamido-4,5-dihydroxy-6-(hydroxymethyl)tetrahydro-2H-pyran-2-yl)methyl)-1H-1,2,3-triazol-1-yl)-13-oxo-3,6,9-trioxa-12-azahexadecan-16-yl)-N12-(2-(2,5-dioxo-2,5-dihydro-1H-pyrrol-1-yl)ethyl)dodecanediamide (Compound I-168)

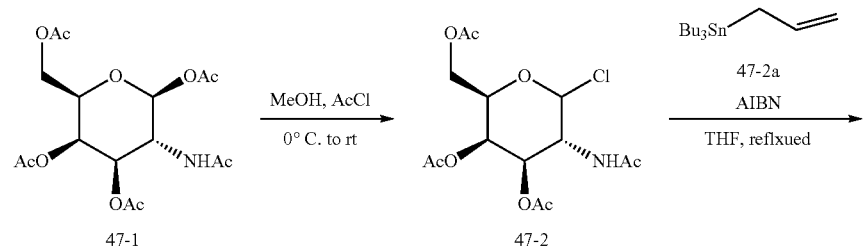

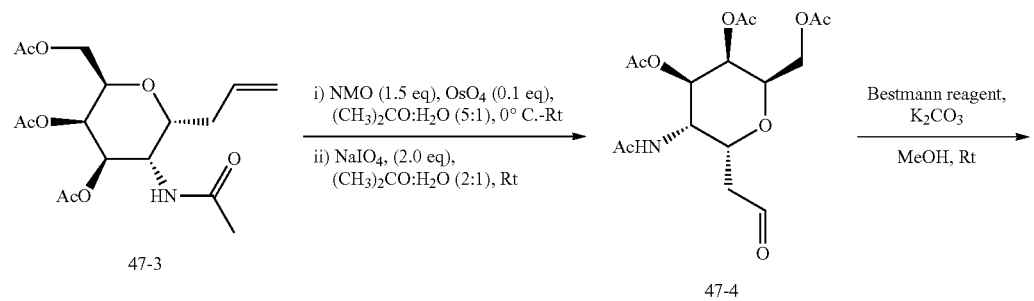

-continued

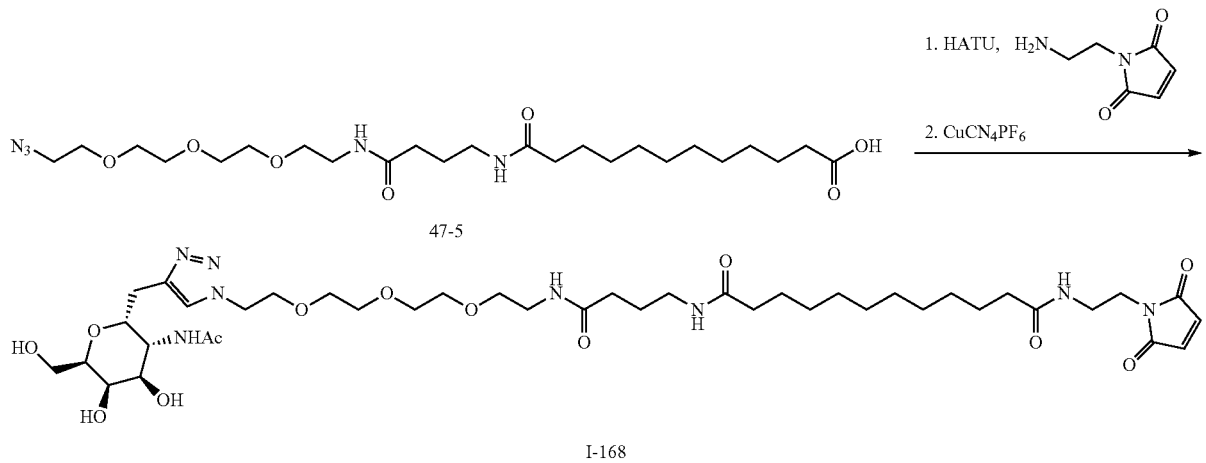

I-168

A solution of (2S,3R,4R,5R,6R)-3-acetamido-6-(acetoxymethyl)tetrahydro-2H-pyran-2,4,5-triyl triacetate (47-1, 1.0 eq, 20.0 g, 51.4 mmol) in acetyl chloride (60 mL) was cooled at 0° C., methanol (2.4 eq, 4.98 mL, 123.3 mmol) was added and reaction mixture was stirred at room temperature for 48 h. After completion, reaction mixture was concentrated, washed with 10% diethyl ether in ethyl acetate and dried to afford (2R,3R,4R,5R)-5-acetamido-2-(acetoxymethyl)-6-chlorotetrahydro-2H-pyran-3,4-diyl diacetate (47-2) as a white solid. Yield: 16.0 g, 85.16%; $^1$H NMR (400 MHz, CDCl$_3$) δ 6.08 (d, J=2.0 Hz, 1H), 5.36-5.31 (m, 2H), 5.26-5.25 (m, 1H), 5.29-5.25 (m, 1H), 4.15-4.02 (m, 3H), 2.16 (d, J=3.2 Hz, 3H), 2.09 (s, 3H), 2.07 (s, 3H), 2.00 (s, 3H).

To a stirred solution of (2R,3R,4R,5R)-5-acetamido-2-(acetoxymethyl)-6-chlorotetrahydro-2H-pyran-3,4-diyl diacetate (47-2, 5.0 g, 1.0 eq., 13.7 mmol) in dry tetrahydrofuran (50 mL) was added allyltributylstannane (47-2a, 42.7 mL, 10.0 eq., 137 mmol) and azobisisobutyronitrile (AIBN) (0.673 g, 0.3 eq., 4.1 mmol). Reaction mixture was then purged with argon, and refluxed for 12 h. Thereafter, volatiles were removed in vacuo, and the remaining residue was partitioned between acetonitrile and pentane. Acetonitrile layer was extracted with pentane (3 times) to remove the remaining organotin compounds and then concentrated to dryness to get crude which was purified by silica gel flash column chromatography eluting with 45-50% ethyl acetate in hexane to afford (2R,3R,4R,5S,6R)-5-acetamido-2-(acetoxymethyl)-6-allyltetrahydro-2H-pyran-3,4-diyl diacetate (47-3) as sticky colorless syrup. Yield: 2.4 g, 47.0%; ELSD-MS m/z 372.21 [M+H]$^+$.

To a stirred solution of (2R,3R,4R,5S,6R)-5-acetamido-2-(acetoxymethyl)-6-allyltetrahydro-2H-pyran-3,4-diyl diacetate (1.5 g, 1 eq., 4.03 mmol) in acetone:water (5:1) (15 mL) was added N-methylmorpholine-N-oxide (0.708 g, 1.5 eq, 6.04 mmol) followed by osmium tetraoxide (4.0 wt % in water, 0.274 mL, 0.1 eq, 0.0403 mmol) at 0° C., and stirred for 2 h at room temperature. After completion, the reaction mixture was extracted with ethyl acetate. The organic part was then dried over anhydrous sodium sulphate, filtered, and concentrated to give crude product which was again dissolved in acetone:water (2:1) (15 mL), and added sodium periodate (1.55 g, 2.0 eq., 8.06 mmol), stirred for another 3 h at room temperature. Thereafter, reaction mixture was extracted with ethyl acetate, and the collected ethyl acetate was dried over anhydrous sodium sulphate, filtered, and concentrated to give crude (2R,3R,4R,5S,6R)-5-acetamido-2-(acetoxymethyl)-6-(2-oxoethyl)tetrahydro-2H-pyran-3,4-diyl diacetate (47-4) as colorless syrup. This was immediately used for next step without purification. Yield: 1.4 g (Crude); ELSD-MS m/z 374.19 [M+H]$^+$.

To a stirred solution of (2R,3R,4R,5S,6R)-5-acetamido-2-(acetoxymethyl)-6-(2-oxoethyl)tetrahydro-2H-pyran-3,4-diyl diacetate (1.0 g, 1.00 eq, 2.68 mmol) in methanol (25.0 mL) at 0° C., were added potassium carbonate (1.11 g, 3.0 eq., 8.04 mmol), dimethyl (1-diazo-2-oxopropyl)phosphonate (1.03 g, 2.0 eq., 5.36 mmol) and stirred at room temperature for 5 h. Thereafter, volatiles were evaporated in vacuo to get crude which was purified by prep-HPLC (70% acetonitrile in water with 0.1% trifluoroacetic acid). Fractions containing the desired product were combined and lyophilized to dryness to afford N-((2R,3R,4R,5R,6R)-4,5-dihydroxy-6-(hydroxymethyl)-2-(prop-2-yn-1-yl)tetrahydro-2H-pyran-3-yl)acetamide (XB4B) as an off-white solid. Yield: 0.112 g, 17.04%. LCMS m/z 244.11 [M+H]$^+$. $^1$H NMR (400 MHz, DMSO-d$_6$ with D$_2$O exchange) δ 4.05-4.00 (m, 2H), 3.73 (bs, 1H), 3.58-3.45 (m, 4H), 2.60 (t, J=2.4 Hz, 1H), 2.46-2.41 (m, 1H), 2.33-2.27 (m, 1H), 1.82 (s, 3H).

To a mixture of compound 47-5 (1.00 eq, 14.7 mg, 0.0285 mmol) in DMSO (0.5 mL) were added DIEA (4.00 eq, 0.020 mL, 0.114 mmol) and HATU (1.10 eq, 11.9 mg, 0.0314 mmol), followed by addition of 2-Maleimidoethylamine hydrochloride (1.00 eq, 5.0 mg, 0.0285 mmol). The mixture was stirred at room temperature for 30 minutes and to this mixture was added compound XB4B (1.00 eq, 6.9 mg, 0.0285 mmol). The mixture was purged with nitrogen and Tetrakis(acetonitrile)copper(I) hexafluorophosphate (2.00 eq, 21.5 mg, 0.0570 mmol) was added. The mixture was stirred at room temperature for 3 h. The mixture was purified by prep. HPLC (10-40% MeCN/water with 0.1% TFA) to give I-168 as a white solid (11.8 mg, yield: 47%). LCMS m/z 881.2 [M+H]$^+$.

Example 48: Synthesis of (2R,3R,4R,5S)-5-((5-(but-3-yn-1-yl)-1,3,4-thiadiazol-2-yl)amino)-2-(hydroxymethyl)tetrahydro-2H-pyran-3,4-diol (XB26)

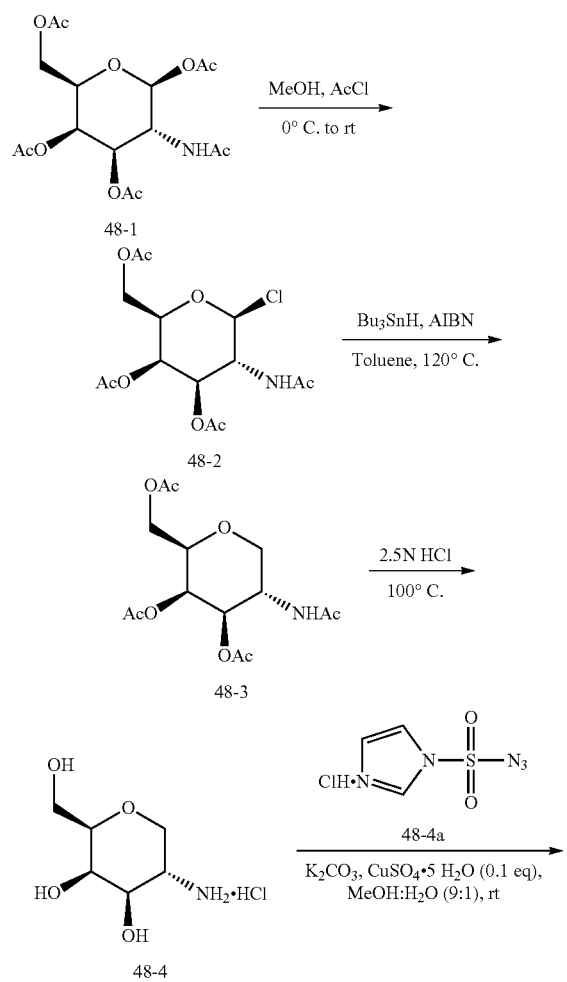

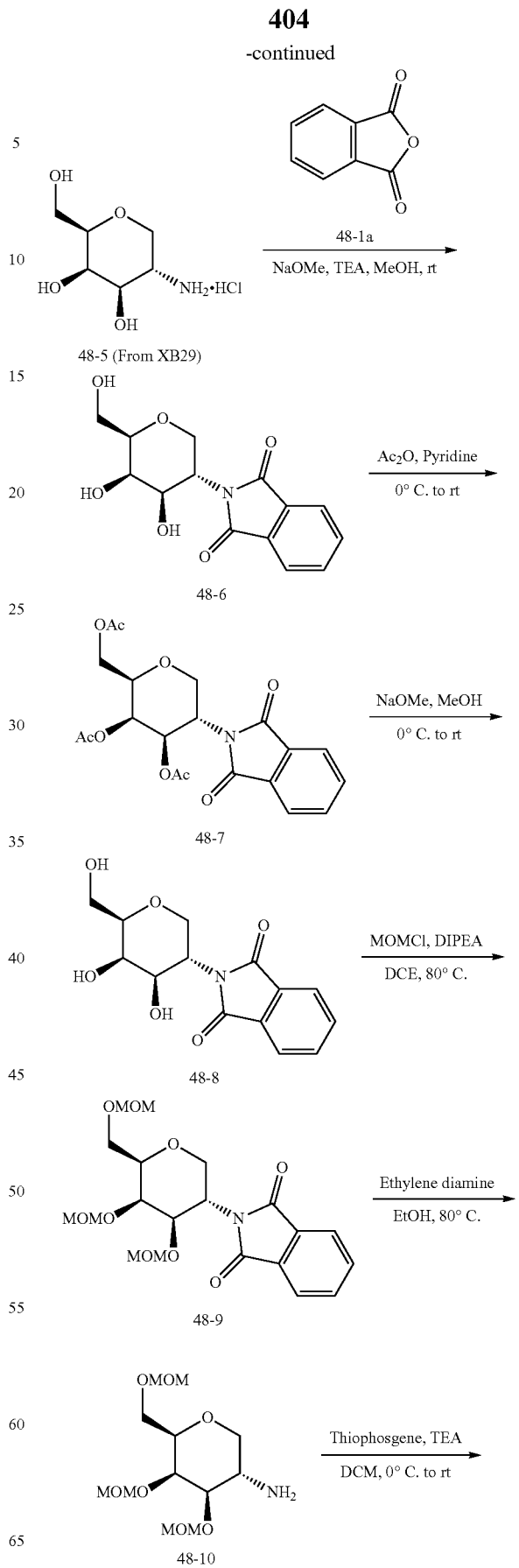

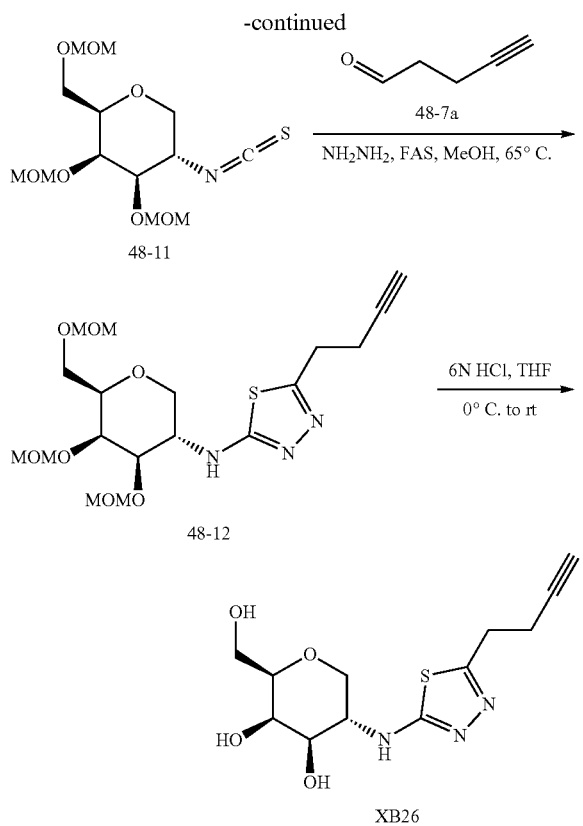

A solution of (2S,3R,4R,5R,6R)-3-acetamido-6-(acetoxymethyl)tetrahydro-2H-pyran-2,4,5-triyl triacetate (48-1, 1.0 eq, 20.0 g, 51.4 mmol) in acetyl chloride (60 mL) was cooled at 0° C., methanol (2.4 eq, 4.98 mL, 123.3 mmol) was added and reaction mixture was stirred at room temperature for 48 h. After completion, reaction mixture was concentrated, washed with 10% diethyl ether in ethyl acetate and dried to afford (2R,3R,4R,5R)-5-acetamido-2-(acetoxymethyl)-6-chlorotetrahydro-2H-pyran-3,4-diyl diacetate (48-2) as a white solid. Yield: 16.0 g, 85.16%; $^1$H NMR (400 MHz, CDCl$_3$) δ 6.08 (d, J=2.0 Hz, 1H), 5.36-5.31 (m, 2H), 5.26-5.25 (m, 1H), 5.29-5.25 (m, 1H), 4.15-4.02 (m, 3H), 2.16 (d, J=3.2 Hz, 3H), 2.09 (s, 3H), 2.07 (s, 3H), 2.00 (s, 3H).

To a solution of (2R,3R,4R,5R)-5-acetamido-2-(acetoxymethyl)-6-chlorotetrahydro-2H-pyran-3,4-diyl diacetate (48-2, 1.0 eq, 10.0 g, 27.3 mmol) in toluene (100 mL), tributyl tin hydride (1.2 eq, 8.84 mL, 32.8 mmol) and azobisisobutyronitrile (AIBN) (0.1 eq, 0.449 g, 2.73 mmol) were added and reaction mixture was heated at 120° C. for 16 h. After completion, reaction mixture was cooled and concentrated to get crude which was purified by column chromatography using silica gel (100-200 mesh) and 0-80% ethyl acetate in hexane to afford (2R,3R,4R,5S)-5-acetamido-2-(acetoxymethyl)tetrahydro-2H-pyran-3,4-diyl diacetate (48-3) as a colorless sticky solid. Yield: 8.7 g, 84.52%; ELSD m/z 330.0 [M−1]$^−$.

A solution of (2R,3R,4R,5S)-5-acetamido-2-(acetoxymethyl)tetrahydro-2H-pyran-3,4-diyl diacetate (48-3, 1.0 eq, 4.0 g, 12.1 mmol) in 2.5 M aqueous hydrochloric acid solution (25 mL) was heated at 100° C. for 16 h. After completion, reaction mixture was cooled, concentrated, washed with methanol, diethyl ether and dried to afford (2R,3R,4R,5S)-5-amino-2-(hydroxymethyl)tetrahydro-2H-pyran-3,4-diol hydrochloride (48-4) as a light brown solid. Yield: 1.6 g, 81.22%; ELSD m/z 164.15 [M+1]$^+$.

To a solution of (2R,3R,4R,5S)-5-amino-2-(hydroxymethyl)tetrahydro-2H-pyran-3,4-diol hydrochloride (48-4, 1.0 eq, 2.1 g, 12.9 mmol) in methanol:water (9:1) (21 mL), copper sulfate pentahydrate (0.1 eq, 0.320 g, 1.29 mmol) and potassium carbonate (5.0 eq, 8.89 g, 64.3 mmol) were added, cooled at 0° C., 1H-imidazole-1-sulfonyl azide hydrochloride (1.2 eq, 3.24 g, 15.4 mmol) was added and reaction mixture was stirred at room temperature for 16 h. After completion, reaction mixture was concentrated, water was added and extracted with ethyl acetate. The organic layer was dried over anhydrous sodium sulfate, filtered and concentrated to get crude which was purified by column chromatography using silica gel and 0-15% methanolic ammonia in dichloromethane to afford (2R,3R,4R,5S)-5-azido-2-(hydroxymethyl)tetrahydro-2H-pyran-3,4-diol (XB29) as a cream solid. Yield: 1.6 g, 65.72%; LCMS m/z 188.05 [M−1]$^−$; $^1$H NMR (400 MHz, MeOD) δ 7.82 (bs, 1H), 7.12 (bs, 2H), 3.98-3.91 (m, 1H), 3.84-3.83 (m, 1H), 3.74-3.62 (m, 3H), 3.52-3.47 (m, 1H), 3.39-3.36 (m, 1H), 3.07 (t, J=10.8 Hz, 1H).

To a solution of (2R,3R,4R,5S)-5-amino-2-(hydroxymethyl)tetrahydro-2H-pyran-3,4-diol hydrochloride (48-5, 1.0 eq, 2.0 g, 10.0 mmol) in methanol (40 mL), sodium methoxide (25% in methanol) (1.2 eq, 2.89 mL, 12.0 mmol) was added and reaction mixture was stirred at room temperature for 30 minutes. Then, phthalic anhydride (48-1a, 1.2 eq, 1.78 g, 12.0 mmol) was added and reaction mixture was stirred at room temperature for 30 minutes. Then, triethylamine (1.4 eq, 2.03 mL, 14.0 mmol) and a second portion of phthalic anhydride (48-1a, 1.2 eq, 1.78 g, 12.0 mmol) was added and reaction mixture was stirred at room temperature for 16 h. After that, reaction mixture was concentrated, washed with diethyl ether and dried to afford 2-((3S,4R,5R,6R)-4,5-dihydroxy-6-(hydroxymethyl)tetrahydro-2H-pyran-3-yl)isoindoline-1,3-dione (48-6) as a light purple solid which was used as such for next reaction. Yield: 7.0 g (Crude).

A solution of 2-((3S,4R,5R,6R)-4,5-dihydroxy-6-(hydroxymethyl)tetrahydro-2H-pyran-3-yl)isoindoline-1,3-dione (48-6, 1.0 eq, 7.0 g, 23.9 mmol), in pyridine (70 mL) was cooled at 0° C., acetic anhydride (10.0 eq, 24.4 mL, 239.0 mmol) was added and reaction mixture was stirred at room temperature for 16 h. After completion, reaction mixture was diluted with 1N hydrochloric acid and extracted with ethyl acetate. The organic layer was washed with saturated aqueous sodium bicarbonate solution and brine, dried over anhydrous sodium sulfate, filtered and concentrated to get crude which was purified by column chromatography using silica gel (100-200 mesh) and 0-50% ethyl acetate in hexane to afford (2R,3R,4R,5S)-2-(acetoxymethyl)-5-(1,3-dioxoisoindolin-2-yl)tetrahydro-2H-pyran-3,4-diyl diacetate (48-7) as an off white sticky solid. Yield: 1.1 g, 10.99%; ELSD m/z 437.45 [M+18]+.

A solution of (2R,3R,4R,5S)-2-(acetoxymethyl)-5-(1,3-dioxoisoindolin-2-yl)tetrahydro-2H-pyran-3,4-diyl diacetate (48-7, 1.0 eq, 1.1 g, 2.62 mmol) in methanol (11 mL) was cooled at 0° C., sodium methoxide (25% solution in methanol) (0.1 eq, 0.06 mL, 0.262 mmol) was added and reaction mixture was stirred at room temperature for 3 h. After completion, reaction mixture was neutralized with Dowex 50WX8 hydrogen form (200-400 mesh) and filtered through sintered funnel (without celite). The filtrate was concentrated, washed with diethyl ether and dried to afford 2-((3S,4R,5R,6R)-4,5-dihydroxy-6-(hydroxymethyl)tetrahydro-2H-pyran-3-yl)isoindoline-1,3-dione (48-8) as an off white solid. Yield: 0.640 g, 83.2%; ELSD m/z 294.15 [M+1]+.

A solution of 2-((3S,4R,5R,6R)-4,5-dihydroxy-6-(hydroxymethyl)tetrahydro-2H-pyran-3-yl)isoindoline-1,3-dione (48-8, 1.0 eq, 0.900 g, 3.07 mmol) in dichloroethane (9 mL) was cooled at 0° C., N,N-disopropylethylamine (8.0 eq, 4.53 mL, 24.6 mmol) and chloromethyl methyl ether (6.0 eq, 1.48 mL, 18.4 mmol) were added and reaction mixture was heated at 80° C. for 16 h. After completion, reaction mixture was cooled, water was added and extracted with dichloromethane. The organic layer was dried over anhydrous sodium sulfate, filtered and concentrated to get crude which was purified by column chromatography using silica gel (100-200 mesh) and 0-25% ethyl acetate in hexane to afford 2-((3S,4R,5R,6R)-4,5-bis(methoxymethoxy)-6-((methoxymethoxy)methyl)tetrahydro-2H-pyran-3-yl)isoindoline-1,3-dione (48-9) as a colourless viscous liquid. Yield: 0.600 g, 45.96%; ELSD m/z 443.25 [M+18]+.

To a solution of 2-((3S,4R,5R,6R)-4,5-bis(methoxymethoxy)-6-((methoxymethoxy)methyl)tetrahydro-2H-pyran-3-yl)isoindoline-1,3-dione (48-9, 1.0 eq, 0.580 g, 1.36 mmol) in ethanol (6 mL), ethylene diamine (10.0 eq, 0.91 mL, 13.6 mmol) was added and reaction mixture was heated at 80° C. for 16 h. After completion, reaction mixture was cooled and concentrated to get crude which was purified by column chromatography using silica gel (100-200 mesh) and 0-5% methanol in dichloromethane to afford (3S,4R,5R,6R)-4,5-bis(methoxymethoxy)-6-((methoxymethoxy)methyl)tetrahydro-2H-pyran-3-amine (48-10) as a colourless viscous liquid. Yield: 0.310 g, 76.99%; ELSD m/z 296.20 [M+1]+.

A solution of (3S,4R,5R,6R)-4,5-bis(methoxymethoxy)-6-((methoxymethoxy)methyl)tetrahydro-2H-pyran-3-amine (48-10, 1.0 eq, 0.100 g, 0.339 mmol) in dichloromethane (3 mL) was cooled at 0° C., triethylamine (2.0 eq, 0.097 mL, 0.677 mmol) and thiophosgene (1.0 eq, 0.038 g, 0.339 mmol) were added and reaction mixture was stirred at room temperature for 16 h. Reaction was monitored by ELSD. After completion, reaction mixture was diluted with dichloromethane and washed with saturated aqueous sodium bicarbonate solution. The organic layer was dried over anhydrous sodium sulfate, filtered, concentrated and dried to afford (2R,3R,4R,5S)-5-isothiocyanato-3,4-bis(methoxymethoxy)-2-((methoxymethoxy)methyl)tetrahydro-2H-pyran (48-11) as a light brown viscous liquid. Yield: 0.110 g (Crude); ELSD m/z 355.15 [M+18]+.

To a solution of (2R,3R,4R,5S)-5-isothiocyanato-3,4-bis(methoxymethoxy)-2-((methoxymethoxy)methyl)tetrahydro-2H-pyran (7, 1.0 eq, 0.300 g, 0.889 mmol) and pent-4-ynal (48-7a, 1.0 eq, 0.073 g, 0.889 mmol) in methanol (12 mL), hydrazine hydrate (1.0 eq, 0.044 g, 0.889 mmol) was added and reaction mixture was heated at 65° C. for 3 h. After that, reaction mixture was cooled to room temperature, ammonium iron (III) sulfate dodecahydrate (3.0 eq, 1.29 g, 2.67 mmol) was added and reaction mixture was heated at 65° C. for 16 h. After completion, reaction mixture was cooled, filtered through sintered funnel (without celite) and filtrate was concentrated to get crude which was purified by column chromatography using silica gel (100-200 mesh) and 0-3% methanol in dichloromethane to afford N-((3S,4R,5R,6R)-4,5-bis(methoxymethoxy)-6-((methoxymethoxy)methyl)tetrahydro-2H-pyran-3-yl)-5-(but-3-yn-1-yl)-1,3,4-thiadiazol-2-amine (48-12) as a colourless viscous liquid. Yield: 0.180 g, 45.41%; LCMS m/z 432.15 [M+1]+.

A solution of N-((3S,4R,5R,6R)-4,5-bis(methoxymethoxy)-6-((methoxymethoxy)methyl)tetrahydro-2H-pyran-3-yl)-5-(but-3-yn-1-yl)-1,3,4-thiadiazol-2-amine (48-12, 1.0 eq, 0.025 g, 0.057 mmol) in tetrahydrofuran (0.5 mL) was cooled at 0° C., 6N aqueous hydrochloric acid solution (0.5 mL) was added and reaction mixture was stirred at room temperature for 16 h. After completion, reaction mixture was concentrated and purified by prep HPLC (11-23% acetonitrile in water with 0.05% trifluoroacetic acid). Fractions containing the desired product were combined and lyophilized to dryness to afford (2R,3R,4R,5S)-5-((5-(but-3-yn-1-yl)-1,3,4-thiadiazol-2-yl)amino)-2-(hydroxymethyl)tetrahydro-2H-pyran-3,4-diol (XB26) as a cream solid. Yield: 0.003 g, 17.64%; LCMS m/z 300.10 [M+1]+; $^1$H NMR (400 MHz, MeOD) δ 4.17-4.13 (m, 1H), 3.97-3.89 (m, 2H), 3.77-3.72 (m, 1H), 3.70-3.66 (m, 1H), 3.63-3.57 (m, 1H), 3.48-3.43 (m, 1H), 3.20 (t, J=10.8 Hz, 1H), 3.08 (t, J=7.2 Hz, 2H), 2.62-2.58 (m, 2H), 2.38 (t, J=2.4 Hz, 1H).

Example 49: Synthesis of 4-amino-4-(1-(1-(((1S,2R, 3R,4R,5S)-2,3-dihydroxy-1-(hydroxymethyl)-6,8-dioxabicyclo[3.2.1]octan-4-yl)-1H-1,2,3-triazol-4-yl)-12-oxo-2,5,8-trioxa-11-azatetradecan-14-yl)-N1, N7-bis(2-(2-(2-((1-(((1S,2R,3R,4R,5S)-2,3-dihydroxy-1-(hydroxymethyl)-6,8-dioxabicyclo [3.2.1]octan-4-yl)-1H-1,2,3-triazol-4-yl)methoxy)ethoxy)ethoxy)ethyl)heptanediamide (XB40)

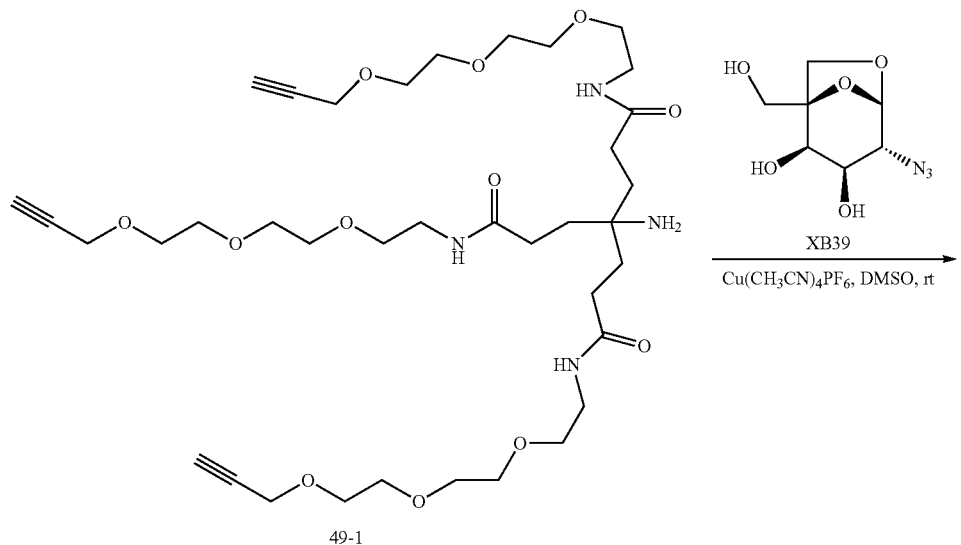

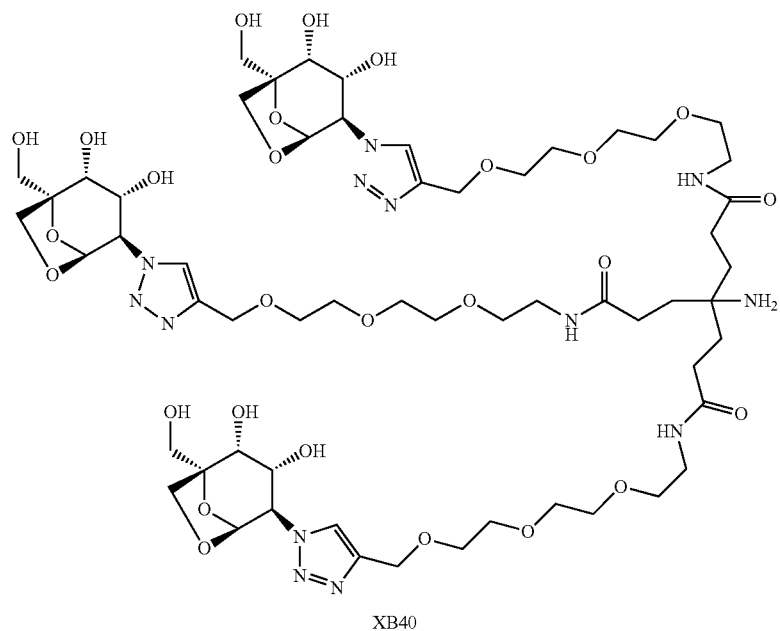

Compound XB40 was synthesized from compounds 49-1 and XB39 (Sanhueza, J. Am. Chem. Soc. 2017, 139, 3528-3536.) analogously to compound I-142 in example 34 to give compound XB40 in 23% yield. Purity 99%. LCMS m/z 1406.8 [M+H]$^+$.

Example 50: 13,13-bis((3-((4-(3-((1-((3S,4R,5R, 6R)-4,5-dihydroxy-6-(hydroxymethyl)tetrahydro-2H-pyran-3-yl)-1H-1,2,3-triazol-4-yl)methoxy)benzamido)butyl)amino)-3-oxopropoxy)methyl)-1-(3-((1-((3S,4R,5R,6R)-4,5-dihydroxy-6-(hydroxymethyl)tetrahydro-2H-pyran-3-yl)-1H-1,2,3-triazol-4-yl)methoxy)phenyl)-1,8,15-trioxo-11-oxa-2,7,14-triazahexacosan-26-oic acid (Compound I-171)
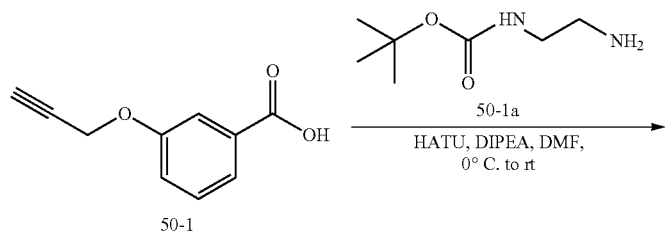
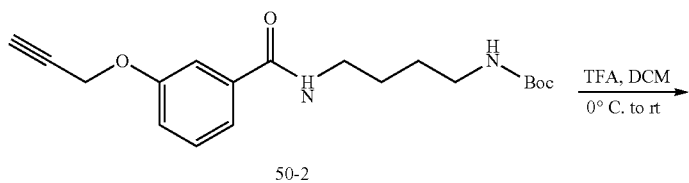
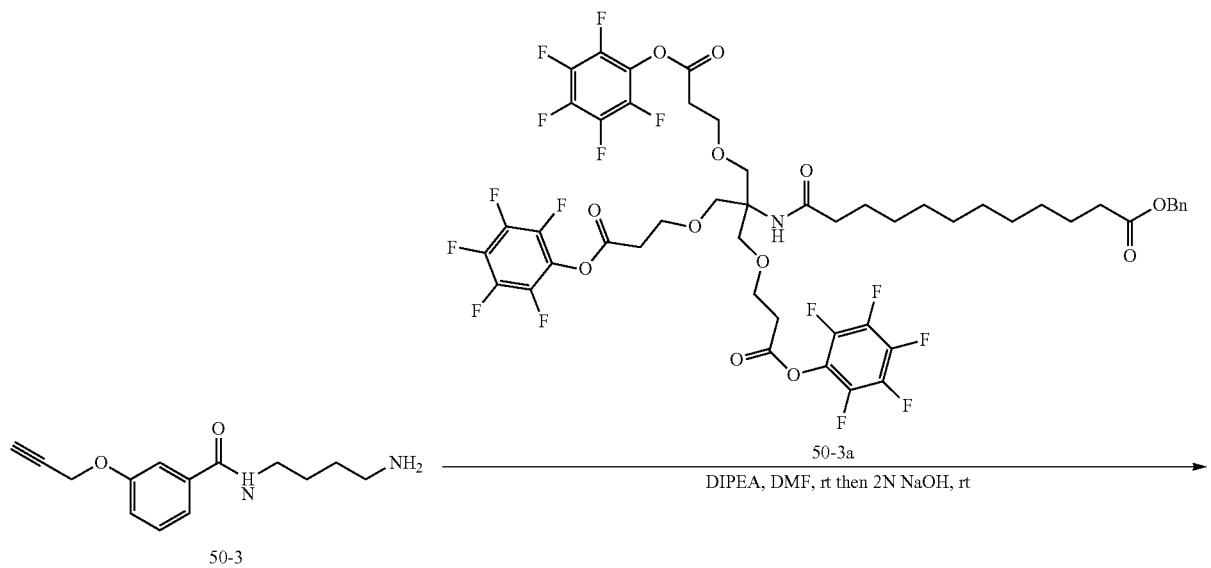

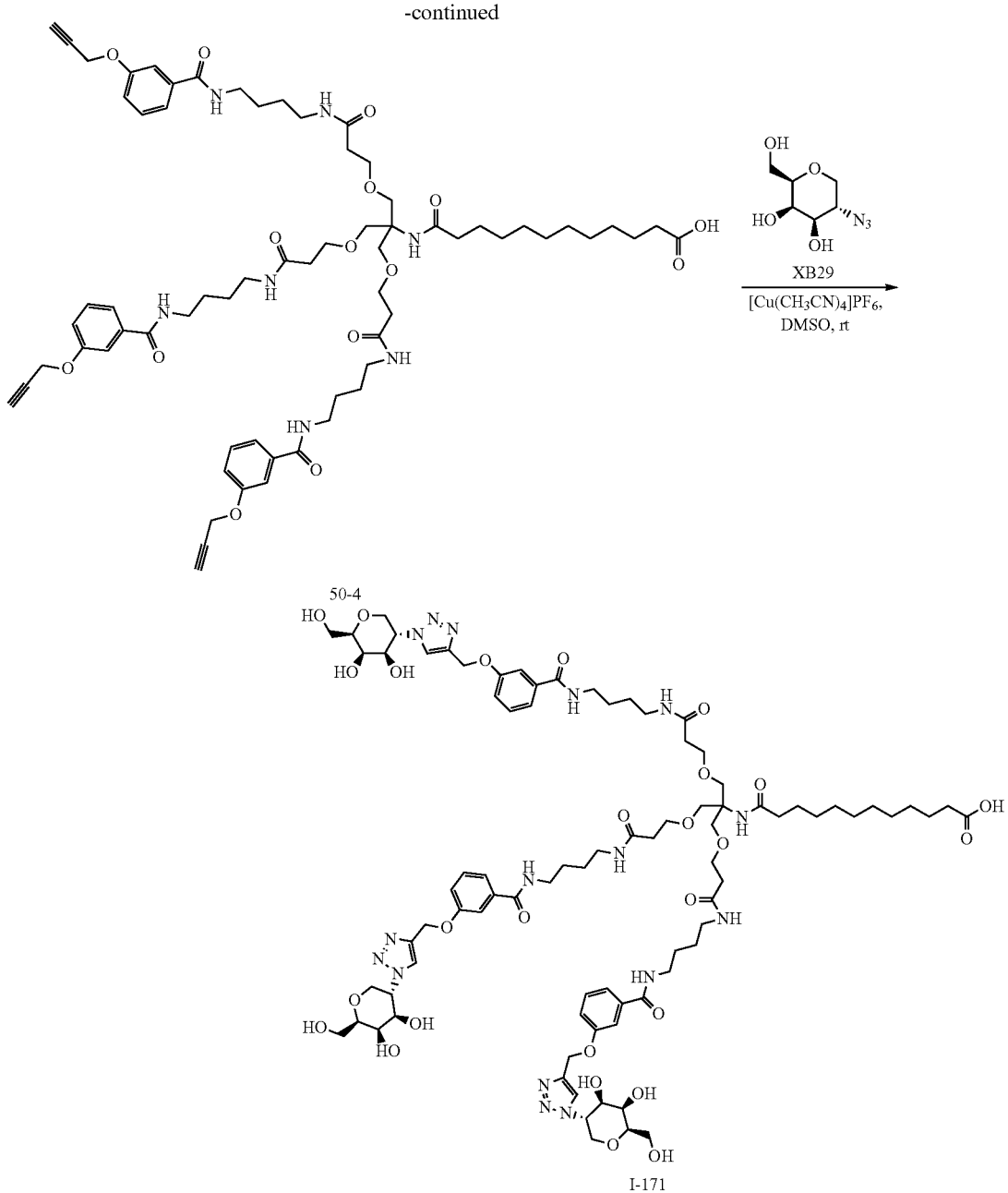

A solution of 3-(prop-2-yn-1-yloxy)benzoic acid (50-1, 1.0 eq, 1.0 g, 5.68 mmol) and tert-butyl (4-aminobutyl) carbamate (50-1a, 1.5 eq, 1.6 g, 8.51 mmol) in N,N-dimethylformamide (10 mL) was cooled at 0° C., N,N diisopropylethylamine (3.0 eq, 3.12 mL, 17.0 mmol) and 1-[bis(dimethylamino)methylene]-1H-1,2,3-triazolo[4,5-b]pyridinium 3-oxid hexafluorophosphate (HATU) (1.5 eq, 3.24 g, 8.51 mmol) were added and reaction mixture was stirred at room temperature for 3 h. After completion, water was added to reaction mixture and extracted with ethyl acetate. The organic layer was washed with water, dried over anhydrous sodium sulfate, filtered and concentrated to get crude which was purified by column chromatography using silica gel (100-200 mesh) and 0-30% ethyl acetate in hexane to afford tert-butyl (4-(3-(prop-2-yn-1-yloxy)benzamido) butyl)carbamate (50-2) as a white solid. Yield: 1.5 g, 76.28%; LCMS m/z 347.10 [M+1]$^+$.

A solution of tert-butyl (4-(3-(prop-2-yn-1-yloxy)benzamido)butyl)carbamate (50-2, 1.0 eq, 1.5 g, 4.33 mmol) in dichloromethane (8 mL) was cooled at 0° C., trifluoroacetic acid (8 mL) was added and reaction mixture was stirred at room temperature for 1 h. After completion, reaction mixture was concentrated, azeotroped with dichloromethane (2-3 times), washed with diethyl ether (2-3 times) and dried to afford N-(4-aminobutyl)-3-(prop-2-yn-1-yloxy)benzamide (50-3) as a white solid. Yield: 1.8 g (Crude); LCMS m/z 247.15 [M+1]$^+$.

To a solution of bis(perfluorophenyl) 3,3'-((2-(12-(benzyloxy)-12-oxododecanamido)-2-((3-oxo-3-(perfluorophenoxy)propoxy)methyl)propane-1,3-diyl)bis(oxy))dipropionate (50-3a, 1.0 eq, 0.250 g, 0.22 mmol) and N-(4-aminobutyl)-3-(prop-2-yn-1-yloxy)benzamide (50-3, 3.6 eq, 0.195 g, 0.792 mmol) in N,N-dimethylformamide (2.5 mL), N,N diisopropylethylamine (10.0 eq, 0.4 mL, 2.2 mmol) was added and reaction mixture was stirred at room temperature for 16 h. After that, 2N aqueous sodium hydroxide solution (2.5 mL) was added and reaction mixture was stirred at room temperature for 1 h. After completion, reaction mixture directly purified by prep HPLC (22-35% acetonitrile in water with 0.05% trifluoroacetic acid). Fractions containing the desired product were combined and lyophilized to dryness to afford 1,8,15-trioxo-13,13-bis((3-oxo-3-((4-(3-(prop-2-yn-1-yloxy)benzamido)butyl)amino)propoxy)methyl)-1-(3-(prop-2-yn-1-yloxy)phenyl)-11-oxa-2,7,14-triazahexacosan-26-oic acid (50-4) as a white solid. Yield: 0.022 g, 8.87%; LCMS m/z 618.52 [(M/2)+1]$^+$.

To a solution of 1,8,15-trioxo-13,13-bis((3-oxo-3-((4-(3-(prop-2-yn-1-yloxy)benzamido)butyl)amino)propoxy)methyl)-1-(3-(prop-2-yn-1-yloxy)phenyl)-11-oxa-2,7,14-triazahexacosan-26-oic acid (50-4, 1.0 eq, 0.025 g, 0.020 mmol) and (2R,3R,4R,5S)-5-azido-2-(hydroxymethyl)tetrahydro-2H-pyran-3,4-diol (XB29, 3.0 eq, 0.011 g, 0.060 mmol) in dimethylsulfoxide (1 mL), tetrakis(acetonitrile)copper(I) hexafluorophosphate (4.5 eq., 0.033 g, 0.091 mmol) was added and reaction mixture was stirred at room temperature for 1 h. After completion, reaction mixture was quenched with acetic acid (0.1 mL) and purified by prep HPLC (33-45% acetonitrile in water with 0.05% trifluoroacetic acid). Fractions containing the desired product were combined and lyophilized to dryness to afford 13,13-bis((3-((4-(3-((1-((3S,4R,5R,6R)-4,5-dihydroxy-6-(hydroxymethyl)tetrahydro-2H-pyran-3-yl)-1H-1,2,3-triazol-4-yl)methoxy)benzamido)butyl)amino)-3-oxopropoxy)methyl)-1-(3-((1-((3S,4R,5R,6R)-4,5-dihydroxy-6-(hydroxymethyl)tetrahydro-2H-pyran-3-yl)-1H-1,2,3-triazol-4-yl)methoxy)phenyl)-1,8,15-trioxo-11-oxa-2,7,14-triazahexacosan-26-oic acid (I-171) as a white solid. Yield: 0.005 g, 13.7%; LCMS m/z 902.27 [(M/2)+1]$^+$; $^1$H NMR (400 MHz, DMSO-d$_6$ with D$_2$O) δ 8.18 (s, 3H), 7.37-7.33 (m, 9H), 7.15-7.12 (m, 3H), 5.10 (s, 6H), 4.67-4.63 (m, 3H), 4.02-3.95 (m, 6H), 3.81 (d, J=3.2 Hz, 3H), 3.62 (t, J=10.8 Hz, 3H), 3.54-3.45 (m, 21H), 3.20 (t, J=6.0 Hz, 6H), 3.02 (t, J=6.4 Hz, 6H), 2.22 (t, J=5.6 Hz, 6H), 2.08 (t, J=7.6 Hz, 2H), 1.99-1.97 (m, 2H), 1.45-1.35 (m, 16H), 1.08 (s, 12H).

Compound I-172 was synthesized in accordance with the procedure for compound I-171, substituting compound 50-1 for 4-(prop-2-yn-1-yloxy)benzoic acid of the following structure:

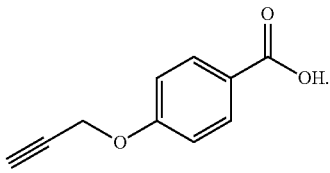

The structure, name and data for compound I-172 is provided below.

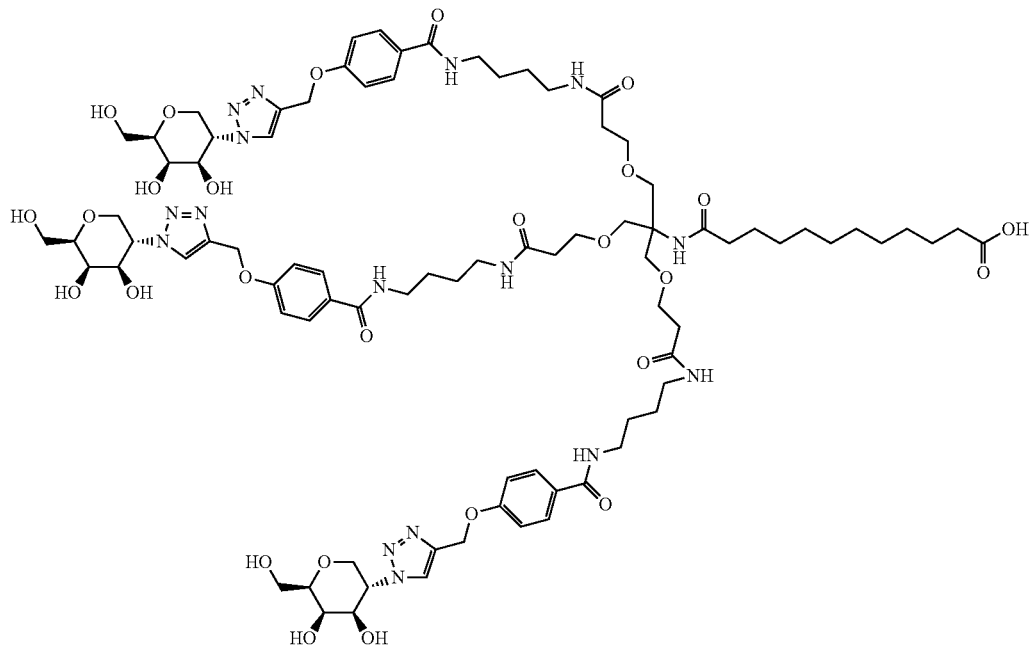

I-172

13,13-bis((3-((4-(4-((1-((3S,4R,5R,6R)-4,5-dihydroxy-6-(hydroxymethyl)tetrahydro-2H-pyran-3-yl)-1H-1,2,3-triazol-4-yl)methoxy)benzamido)butyl)amino)-3-oxopropoxy)methyl)-1-(4-((1-((3S,4R,5R,6R)-4,5-dihydroxy-6-(hydroxymethyl)tetrahydro-2H-pyran-3-yl)-1H-1,2,3-triazol-4-yl)methoxy)phenyl)-1,8,15-trioxo-11-oxa-2,7,14-triazahexacosan-26-oic acid (I-172).

LCMS m/z 902.36 [(M/2)+1]$^+$.

$^1$H NMR (400 MHz, DMSO-d$_6$ with D$_2$O) δ 8.20 (s, 3H), 7.74 (d, J=8.8 Hz, 6H), 7.04 (d, J=8.8 Hz, 6H), 5.13 (s, 6H), 4.70-4.64 (m, 3H), 4.00-3.95 (m, 6H), 3.81 (d, J=3.2 Hz, 3H), 3.62 (t, J=10.8 Hz, 3H), 3.53-3.47 (m, 21H), 3.19-3.17 (m, 6H), 3.02 (t, J=6.4 Hz, 6H), 2.23 (t, J=5.2 Hz, 6H), 2.10 (t, J=7.2 Hz, 2H), 2.00 (t, J=6.8 Hz, 2H), 1.45-1.38 (m, 16H), 1.11 (s, 12H).

Example 51: 4-amino-4-(1-(1-((3S,4R,5R,6R)-4,5-dihydroxy-6-(hydroxymethyl)tetrahydro-2H-pyran-3-yl)-1H-1,2,3-triazol-4-yl)-12-oxo-2,5,8-trioxa-11-azatetradecan-14-yl)-N1,N7-bis(2-(2-(2-((1-((3S,4R,5R,6R)-4,5-dihydroxy-6-(hydroxymethyl)tetrahydro-2H-pyran-3-yl)-1H-1,2,3-triazol-4-yl)methoxy)ethoxy)ethoxy)ethyl)heptanediamide (XB32)

purified by prep HPLC (15-20% acetonitrile in water with 0.1% FA). Fractions containing the desired product were combined and lyophilized to dryness to afford 4-amino-4-(1-(1-((3S,4R,5R,6R)-4,5-dihydroxy-6-(hydroxymethyl)tetrahydro-2H-pyran-3-yl)-1H-1,2,3-triazol-4-yl)-12-oxo-2,5,8-trioxa-11-azatetradecan-14-yl)-N1,N7-bis(2-(2-(2-((1-((3S,4R,5R,6R)-4,5-dihydroxy-6-(hydroxymethyl)

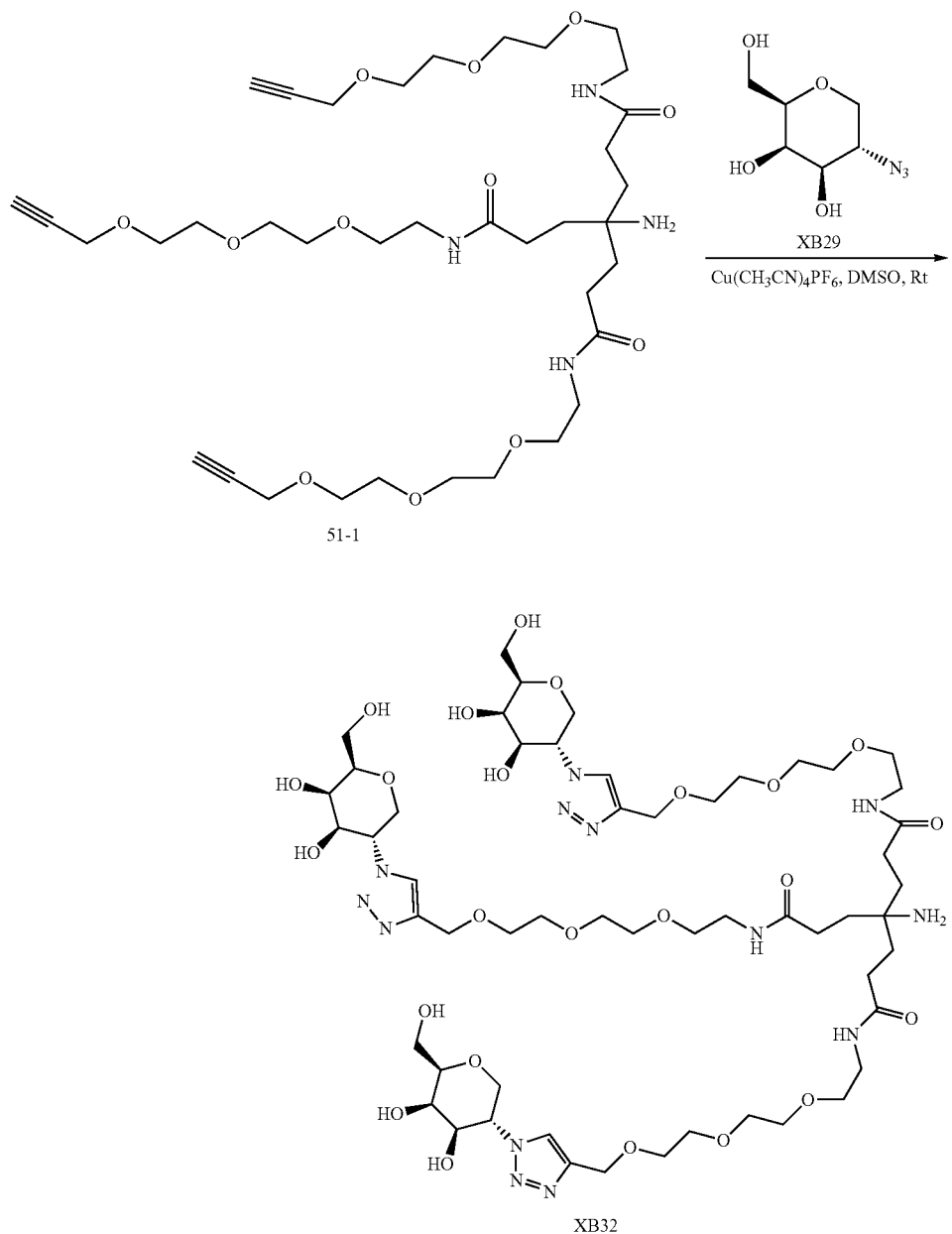

To a solution of (4-amino-4-(3-oxo-7,10,13-trioxa-4-azahexadec-15-yn-1-yl)-N1,N7-bis(2-(2-(2-(prop-2-yn-1-yloxy)ethoxy)ethoxy)ethyl)heptanediamide (51-1, 1.0 eq, 0.20 g, 0.265 mmol) and (2R,3R,4R,5S)-5-azido-2-(hydroxymethyl)tetrahydro-2H-pyran-3,4-diol (XB29, 3.6 eq, 0.180 g, 0.954 mmol) in dimethylsulfoxide (2 mL), tetrakis(acetonitrile)copper(I) hexafluorophosphate (7.5 eq, 0.741 g, 1.99 mmol) was added. The reaction mixture was stirred at room temperature for 1 h and reaction mixture was directly tetrahydro-2H-pyran-3-yl)-1H-1,2,3-triazol-4-yl)methoxy)ethoxy)ethoxy)ethyl)heptanediamide (XB32) as a bluish solid. Yield: 0.18 g; 51.38%: LCMS; m/z 1322.50 [M+H]$^+$; $^1$H-NMR (400 MHz, DMSO-d$_6$ with D$_2$O exchange) δ 8.05 (s, 3H), 4.68-4.61 (m, 3H), 4.48 (s, 6H), 3.99-3.93 (m, 6H), 3.80 (d, J=3.2 Hz, 3H), 3.63-3.58 (m, 3H), 3.54-3.46 (m, 33H), 3.38 (t, J=5.6 Hz, 6H), 3.17 (t, J=5.6 Hz, 6H), 2.15-2.11 (m, 6H), 1.99 (s, 1H), 1.72 (bs, 6H).

Example 52: Synthesis of 3-((1-((3S,4R,5R,6R)-4,5-dihydroxy-6-(hydroxymethyl)tetrahydro-2H-pyran-3-yl)-1H-1,2,3-triazol-4-yl)methoxy)benzoic acid (XB20)

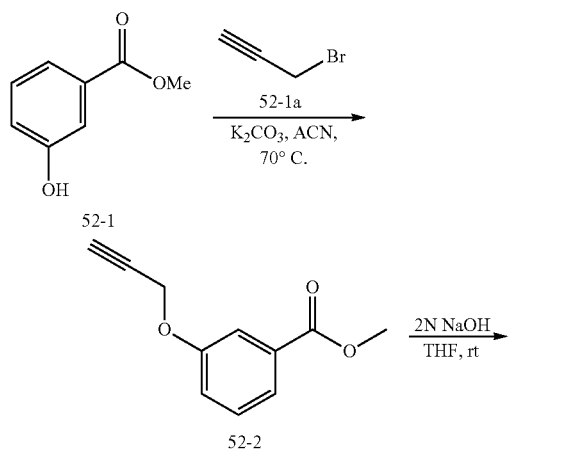

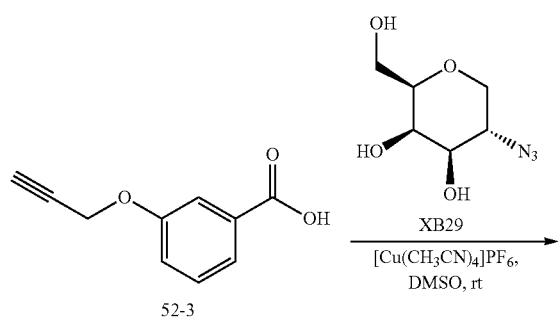

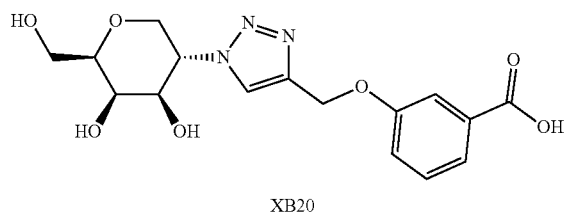

To a solution of methyl 3-hydroxybenzoate (52-1, 1.0 eq, 3.0 g, 19.7 mmol) and 3-bromoprop-1-yne (52-1a, 2.0 eq, 4.69 g, 39.4 mmol) in acetonitrile (30 mL), potassium carbonate (2.5 g, 6.81 g, 49.3 mmol) was added and reaction mixture was heated at 70° C. for 16 h. After completion, water was added to reaction mixture and extracted with ethyl acetate. The organic layer was dried over anhydrous sodium sulfate, filtered and concentrated to get crude product, which was purified by column chromatography using silica gel (100-200 mesh) and 0-25% ethyl acetate in hexane to afford methyl 3-(prop-2-yn-1-yloxy)benzoate (52-2) as a white solid. Yield: 3.6 g, 95.99%; LCMS m/z 189.05 [M−1]⁻.

To a solution of methyl 3-(prop-2-yn-1-yloxy)benzoate (52-2, 1.0 eq, 3.6 g, 18.9 mmol) in tetrahydrofuran (18 mL), 2 N aqueous sodium hydroxide solution (18 mL) was added and reaction mixture was stirred at room temperature for 16 h. After completion, reaction mixture was concentrated, water was added, acidify with 1 N aqueous hydrochloric acid solution to get solid which was filtered off and dried to afford 3-(prop-2-yn-1-yloxy)benzoic acid (52-3) as a white solid. Yield: 2.7 g, 80.97%; LCMS m/z 175.05 [M−1]⁻.

To a solution of (2R,3R,4R,5S)-5-azido-2-(hydroxymethyl)tetrahydro-2H-pyran-3,4-diol (XB29, 1.0 eq, 0.200 g, 1.05 mmol) and 3-(prop-2-yn-1-yloxy)benzoic acid (52-3, 1.0 eq, 0.186 g, 1.05 mmol) in dimethylsulfoxide (4 mL), tetrakis(acetonitrile)copper(I) hexafluorophosphate (1.5 eq, 0.588 g, 1.58 mmol) was added and reaction mixture was stirred at room temperature for 1 h. After completion, reaction mixture was quenched with acetic acid (0.4 mL) and purified by prep HPLC (20-45% acetonitrile in water with 0.05% trifluoroacetic acid). Fractions containing the desired product were combined and lyophilized to dryness to afford 3-((1-((3S,4R,5R,6R)-4,5-dihydroxy-6-(hydroxymethyl)tetrahydro-2H-pyran-3-yl)-1H-1,2,3-triazol-4-yl)methoxy)benzoic acid (XB20) as a white solid. Yield: 0.078 g, 20.25%; LCMS m/z 366.10 [M+1]⁺; $^1$H NMR (400 MHz, DMSO-$d_6$ with $D_2O$) δ 8.22 (s, 1H), 7.54-7.51 (m, 2H), 7.42 (t, J=8.0 Hz, 1H), 7.29-7.26 (m, 1H), 5.15 (s, 2H), 4.75-4.62 (m, 1H), 4.01-3.95 (m, 2H), 3.80 (d, J=2.8 Hz, 1H), 3.63 (t, J=10.8 Hz, 1H), 3.53-3.48 (m, 3H).

Compound XB21 was synthesized by adapting the procedure for the synthesis of compound XB20, substituting compound 52-3 for 4-(prop-2-yn-1-yloxy)benzoic acid, the structure of which is reproduced below:

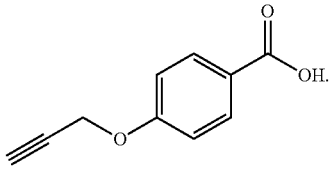

The structure, name and data for Compound XB21 is provided below.

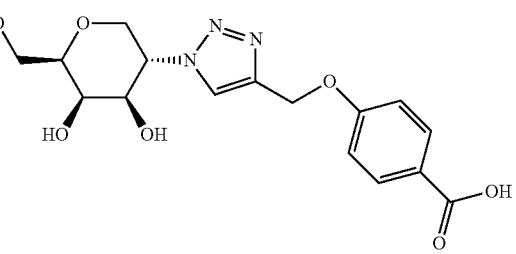

XB21

4-((1-((3S,4R,5R,6R)-4,5-dihydroxy-6-(hydroxymethyl)tetrahydro-2H-pyran-3-yl)-1H-1,2,3-triazol-4-yl)methoxy)benzoic acid.

LCMS m/z 366.19 [M+1]⁺.

$^1$H NMR (400 MHz, DMSO-$d_6$ with $D_2O$) δ 8.24 (s, 1H), 7.92-7.88 (m, 2H), 7.15-7.11 (m, 2H), 5.17 (s, 2H), 4.71-4.65 (m, 1H), 4.01-3.95 (m, 2H), 3.80 (d, J=2.8 Hz, 1H), 3.63 (t, J=11.2 Hz, 1H), 3.53-3.46 (m, 3H).

Example 53: Synthesis of perfluorophenyl 12-((3-(5-(((3aR,4R,6R,7R,7aR)-7-acetamido-4-(hydroxymethyl)-2-oxotetrahydro-4H-[1,3]dioxolo[4,5-c]pyran-6-yl)oxy)pentanamido)propyl)amino)-12-oxododecanoate (Compound I-173)

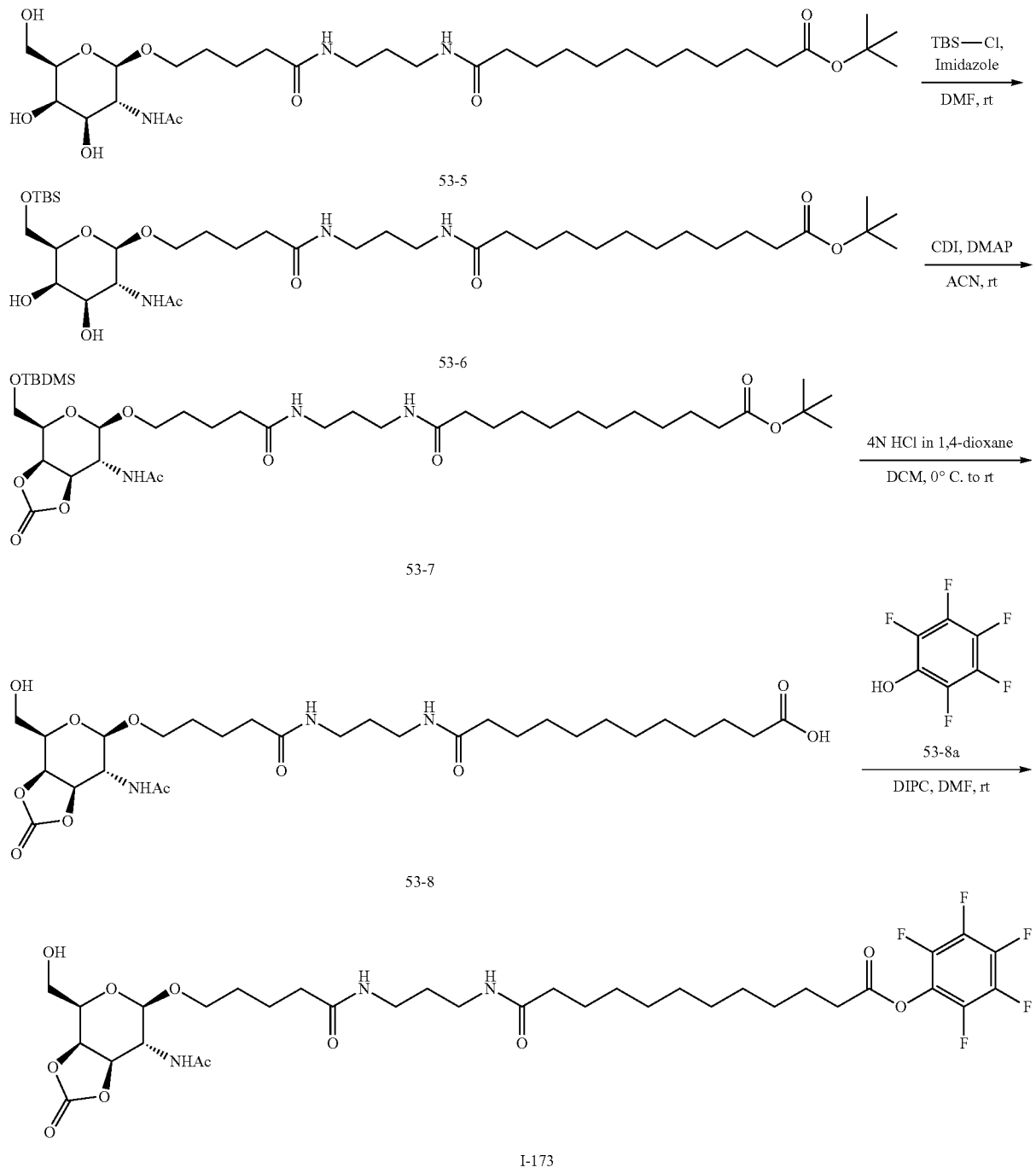

To a solution of tert-butyl 12-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-12-oxododecanoate (53-5, 1.0 eq, 0.400 g, 0.619 mmol) in N,N-dimethylformamide (4 mL), imidazole (2.0 eq, 0.084 g, 1.24 mmol) and tert-butyldimethylsilyl chloride (1.5 eq, 0.140 g, 0.929 mmol) were added and reaction mixture was stirred at room temperature for 16 h. After completion, reaction mixture was diluted with water and extracted with ethyl acetate. The organic layer was dried over anhydrous sodium sulfate, filtered and concentrated to get crude which was purified by column chromatography using silica gel (100-200 mesh) and 0-4% methanol in dichloromethane to afford tert-butyl 12-((3-(5-(((2R,3R,4R,5R,6R)-3-acetamido-6-(((tert-butyldimethylsilyl)oxy)methyl)-4,5-dihydroxytetrahydro-2H-pyran-2-yl)oxy)pentanamido)propyl)amino)-12-oxododecanoate (53-6) as an off white solid. Yield: 0.300 g, 63.73%; LCMS m/z 760.30 [M+1]$^+$.

To a solution of tert-butyl 12-((3-(5-(((2R,3R,4R,5R,6R)-3-acetamido-6-((((tert-butyldimethylsilyl)oxy)methyl)-4,5-dihydroxytetrahydro-2H-pyran-2-yl)oxy)pentanamido)propyl)amino)-12-oxododecanoate (53-6, 1.0 eq, 0.300 g, 0.395 mmol) and 1,1'-carbonyldiimidazole (CDI) (1.5 eq, 0.096 g, 0.592 mmol) in acetonitrile (6 mL), 4-dimethylaminopyridine (0.1 eq, 0.004 g, 0.039 mmol) was added and reaction mixture was stirred at room temperature for 16 h. After completion, water was added to reaction mixture and extracted with ethyl acetate. The organic layer was dried over anhydrous sodium sulfate, filtered and concentrated to get crude which was purified by column chromatography using silica gel (100-200 mesh) and 0-5% methanol in dichloromethane to afford tert-butyl 12-((3-(5-(((3aR,4R,6R,7R,7aR)-7-acetamido-4-(((tert-butyldimethylsilyl)oxy)methyl)-2-oxotetrahydro-4H-[1,3]dioxolo[4,5-c]pyran-6-yl)oxy)pentanamido)propyl)amino)-12-oxododecanoate (53-7) as an off white sticky solid. Yield: 0.200 g, 64.46%; LCMS m/z 786.25 [M+1]$^+$.

A solution of tert-butyl 12-((3-(5-(((3aR,4R,6R,7R,7aR)-7-acetamido-4-(((tert-butyldimethylsilyl)oxy)methyl)-2-oxotetrahydro-4H-[1,3]dioxolo[4,5-c]pyran-6-yl)oxy)pentanamido)propyl)amino)-12-oxododecanoate (53-7, 1.0 eq, 0.050 g, 0.063 mmol) in dichloromethane (0.25 mL) was cooled at 0° C., 4N hydrochloric acid in 1,4-dioxane (0.25 mL) was added and reaction mixture was stirred at room temperature for 3 h. After completion, reaction mixture was concentrated, azeotroped with dichloromethane (2-3 times), dried and lyophilized to dryness to afford 12-((3-(5-(((3aR,4R,6R,7R,7aR)-7-acetamido-4-(hydroxymethyl)-2-oxotetrahydro-4H-[1,3]dioxolo[4,5-c]pyran-6-yl)oxy)pentanamido)propyl)amino)-12-oxododecanoic acid (53-8) as an off white sticky solid. Yield: 0.035 g (Crude); LCMS m/z 616.30 [M+1]$^+$.

To a solution of 12-((3-(5-(((3aR,4R,6R,7R,7aR)-7-acetamido-4-(hydroxymethyl)-2-oxotetrahydro-4H-[1,3]dioxolo[4,5-c]pyran-6-yl)oxy)pentanamido)propyl)amino)-12-oxododecanoic acid (53-8, 1.0 eq, 0.030 g, 0.048 mmol) and pentafluorophenol (53-8a, 1.2 eq, 0.010 g, 0.058 mmol) in N,N-dimethylformamide (1 mL), N,N'-diisopropylcarbodiimide (2.0 eq, 0.012 g, 0.097 mmol) was added and reaction mixture was stirred at room temperature for 16 h. After completion, reaction mixture was directly purified by prep HPLC (20-35% acetonitrile in water with 0.05% trifluoroacetic acid). Fractions containing the desired compound were combined and lyophilized to afford perfluorophenyl 12-((3-(5-(((3aR,4R,6R,7R,7aR)-7-acetamido-4-(hydroxymethyl)-2-oxotetrahydro-4H-[1,3]dioxolo[4,5-c]pyran-6-yl)oxy)pentanamido)propyl)amino)-12-oxododecanoate (Compound I-173) as a white solid. Yield: 0.008 g, 21.0%; LCMS m/z 782.72 [M+1]$^+$; $^1$H NMR (400 MHz, DMSO-d$_6$ with D$_2$O exchange) δ 4.88-4.81 (m, 2H), 4.49 (d, J=7.2 Hz, 1H), 3.86-3.83 (m, 2H), 3.70-3.64 (m, 1H), 3.58-3.55 (m, 3H), 3.39-3.35 (m, 1H), 2.99 (t, J=6.4 Hz, 4H), 2.71-2.67 (m, 1H), 2.16 (t, J=7.2 Hz, 1H), 2.03-2.00 (m, 4H), 1.83 (s, 3H), 1.65-1.58 (m, 1H), 1.49-1.43 (m, 9H), 1.32-1.28 (m, 3H), 1.25-1.19 (m, 8H).

Example 54: Synthesis of perfluorophenyl 1-(4-(3-((2S,3R,4R,5R,6R)-5-acetamido-3,4-dihydroxy-6-methoxytetrahydro-2H-pyran-2-carboxamido)propyl)-1H-1,2,3-triazol-1-yl)-13,13-bis(3-((2-(2-(2-(4-(3-((2S,3R,4R,5R,6R)-5-acetamido-3,4-dihydroxy-6-methoxytetrahydro-2H-pyran-2-carboxamido)propyl)-1H-1,2,3-triazol-1-yl)ethoxy)ethoxy)ethyl)amino)-3-oxopropyl)-10,15-dioxo-3,6-dioxa-9,14-diazahexacosan-26-oate (Compound I-152)

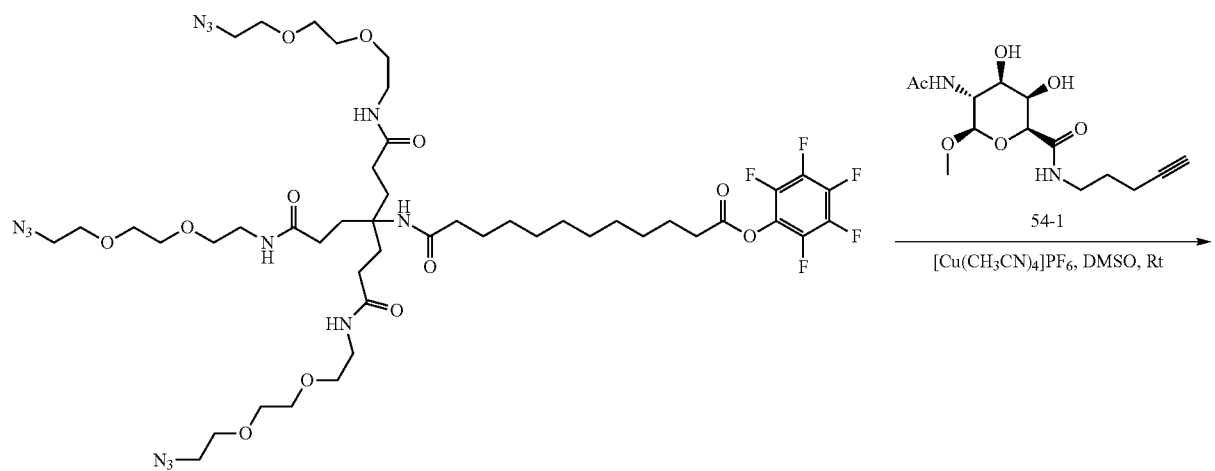

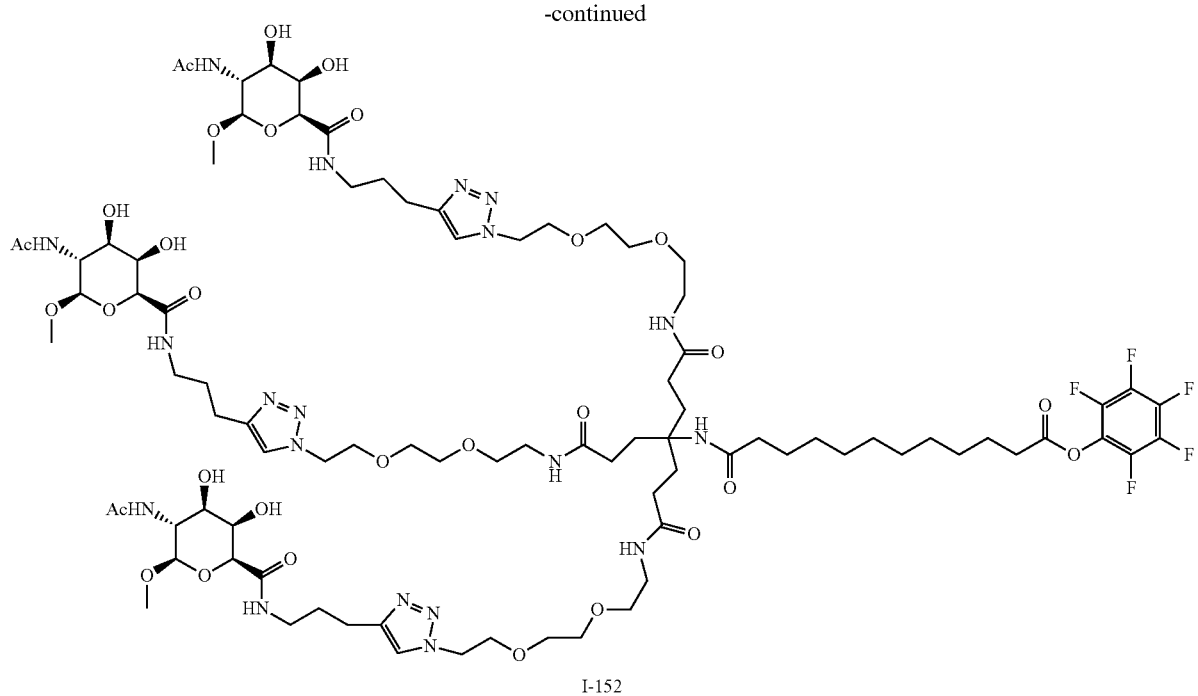

I-152

To a solution of perfluorophenyl 1-azido-13,13-bis(3-((2-(2-(2-azidoethoxy)ethoxy)ethyl)amino)-3-oxopropyl)-10,15-dioxo-3,6-dioxa-9,14-diazahexacosan-26-oate (LC19, 1.0 eq, 0.030 g, 0.027 mmol) and (2S,3R,4R,5R,6R)-5-acetamido-3,4-dihydroxy-6-methoxy-N-(pent-4-yn-1-yl) tetrahydro-2H-pyran-2-carboxamide (54-1, 3.5 eq, 0.0298 g, 0.0947 mmol) in dimethyl sulfoxide (2 mL), tetrakis(acetonitrile)copper(I) hexafluorophosphate (8.4 eq, 0.0848 g, 0.227 mmol) was added and reaction mixture was stirred at room temperature for 1 h. After completion, reaction mixture was diluted with acetonitrile and purified by prep HPLC (35-45% acetonitrile in water with 0.1% trifluoroacetic acid). Fractions containing the desired compound were combined and lyophilized to afford perfluorophenyl 1-(4-(3-((2S,3R,4R,5R,6R)-5-acetamido-3,4-dihydroxy-6-methoxytetrahydro-2H-pyran-2-carboxamido)propyl)-1H-1,2,3-triazol-1-yl)-13,13-bis(3-((2-(2-(2-(4-(3-((2S,3R,4R,5R,6R)-5-acetamido-3,4-dihydroxy-6-methoxytetrahydro-2H-pyran-2-carboxamido)propyl)-1H-1,2,3-triazol-1-yl)ethoxy)ethoxy)ethyl)amino)-3-oxopropyl)-10,15-dioxo-3,6-dioxa-9,14-diazahexacosan-26-oate (I-152) as white solid. Yield: 0.016 g, 28.64%; LCMS m/z 1019.39 [M/2+1]$^+$; $^1$H-NMR (400 MHz, with D$_2$O exchange) δ 7.80 (s, 3H), 4.43 (t, J=4.8 Hz, 6H), 4.24 (d, J=8.8 Hz, 3H), 3.93 (d, J=2.4 Hz, 3H), 3.86 (s, 3H), 3.79-3.74 (m, 9H), 3.49-3.43 (m, 15H), 3.38 (s, 9H), 3.34 (t, J=6.0 Hz, 6H), 3.15-3.12 (m, 12H), 2.73 (t, J=7.2 Hz, 2H), 2.59 (t, J=7.2 Hz, 2H), 2.03-1.96 (m, 8H), 1.80 (s, 9H), 1.77-1.70 (m, 12H), 1.65-1.62 (m, 2H), 1.43-1.41 (m, 1H), 1.32-1.13 (m, 14H).

6.2. Preparation of Conjugates

Example 55: Conjugation of Isothiocyanate-Based Ligand-Linker Compounds with Anti-EGFR and Anti-PD-L$^1$ Antibodies This example provides a general protocol for the conjugation of the isothiocyanate-based ligand-linker compounds with the primary amines on lysine residues of anti-EGFR antibodies (e.g., matuzumab, cetuximab) and anti-PD-L$^1$ antibodies (e.g., atezolizumab, anti-PD-L$^1$(29E.2A3)).

The antibody is buffer exchanged into 100 mM sodium bicarbonate buffer pH 9.0 at 5 mg/mL concentration, after which about 30 equivalents of the isothiocyanate-based ligand-linker compound (e.g., freshly prepared as 20 mM stock solution in DMSO) is added and incubated overnight at ambient temperature in a tube revolver at 10 rpm.

The conjugates are purified using a PD-10 desalting column (GE Healthcare) and followed by formulating the final conjugate into PBS pH 7.4 with Amicon Ultra 15 mL Centrifugal Filters with 30 kDa molecular weight cutoff.

Example 56: Conjugation of Perfluorophenoxy-Based Ligand-Linker Compounds with Anti-EGFR and IgG Antibodies This example provides a general protocol for the conjugation of the perfluorophenoxy-based ligand-linker compounds (e.g., Compound I-141) with the primary amines on lysine residues of anti-EGFR antibodies (e.g., matuzumab, cetuximab) and IgG antibodies (e.g., IgG2a-UNLB).

The antibody is buffer exchanged into 50 mM sodium phosphate buffer pH 8.0 at 5 mg/mL concentration, after which about 22 equivalents of perfluorophenoxy-based ligand-linker compound (e.g., Compound I-141; freshly prepared as 20 mM stock solution in DMSO) is added and incubated for 3 hours at ambient temperature in a tube revolver at 10 rpm.

The conjugates containing on average four ligand-linker moieties per antibody are purified using a PD-10 desalting column (GE Healthcare) and followed with formulating the final conjugate into PBS pH 7.4 with Amicon Ultra 15 mL Centrifugal Filters with 30 kDa molecular weight cutoff.

Example 57: Determination of DAR Values by Mass Spectrometry

This example provides the method for determining DAR values for the conjugates prepared as described in Examples 55 and 56. To determine the DAR value, 10 μg of the antibody (unconjugated or conjugated) was treated 2 μL of non-reducing denaturing buffer (10×, New England Biolabs) for 10 minutes at 75° C. The denatured antibody solution was then deglycosylated by adding 1.5 μL of Rapid-PNGase F (New England Biolabs) and incubated for 10 minutes at 50° C. Deglycosylated samples were diluted 50-fold in water and analyzed on a Waters ACQUITY UPLC interfaced to Xevo G2-S QToF mass spectrometer. Deconvoluted masses were obtained using Waters MassLynx 4.2 Software. DAR values were calculated using a weighted average of the peak intensities corresponding to each loading species using the formula below:

DAR=Σ(drug load distribution (%) each Ab with drug load $n$)($n$)/100

DAR values for the conjugates prepared are shown in Tables 15 to 18.

Example 58: Determination of Purity of Conjugates by SEC Method

Purity of the conjugates prepared as described in Examples 55 and 56 was determined through size exclusion high performance liquid chromatography (SEC-HPLC) using a 20 minute isocratic method with a mobile phase of 0.2 M sodium phosphate, 0.2 M potassium chloride, 15 w/v isopropanol, pH 6.8. An injection volume of 10 μL was loaded to a TSKgel SuperSW3000 column, at a constant flow rate of 0.35 mL/min. Chromatographs were integrated based on elution time to calculate the purity of monomeric conjugate species.

Example 59: Antibody Disulfide Reduction and Thiol-Reactive Ligand-Linker Conjugation to Antibody This example provides an exemplary protocol for reduction of the disulfides of the antibodies described herein, and conjugation of the reduced antibodies to thiol-reactive ligand-linker compounds described herein, e.g., containing a maleimide chemoselective ligation group.

Protocol: Antibody Disulfide Reduction
  A) Dilute antibody to 15 mg/mL (0.1 mM IgG) in PBS, pH 7.4.
  B) Prepare a fresh 20 mM (5.7 mg/mL) stock solution of tris(2 carboxyethyl)phosphine (TCEP) in $H_2O$.
  C) Add 25 μL of TCEP stock solution from step B) above to 1 mL of antibody from step A) above (0.5 mM final concentration TCEP).
  D) Incubate at 37° C. for 2 hours (check for free thiols using 5,5'-dithiobis-(2-nitrobenzoic acid) (DTNB) test).
  E) Aliquot the reduced antibody into 4 tubes (250 μL each).

Ligand-Linker Conjugation to Antibody
  A) Prepare 10 mM stock solution of thiol-reactive ligand-linker compound in DMSO (DMA, DMF or $CH_3CN$ are also acceptable).
  B) Add 5 equivalents of 12.5 μL stock solution from step A) above to each tube of reduced antibody (0.5 mM final concentration ligand-linker compound stock solution).
  C) Incubate overnight at 4° C. for 4 hours at room temperature; check for free thiols using DTNB test.
  D) Run analytical hydrophobic interaction chromatography (HIC) to determine DAR and homogeneity.

Example 60: Preparation of Omalizumab Conjugates

A series of conjugates of the exemplary antibody omalizumab (an anti-IgE antibody) with a series of perfluorophenyl ester containing ligand-linker compounds were prepared and characterized using methods similar to those described in Examples 55 to 58.

These conjugates were assessed for cell uptake activity as described in Example 67.

TABLE 22

Figure 2A:
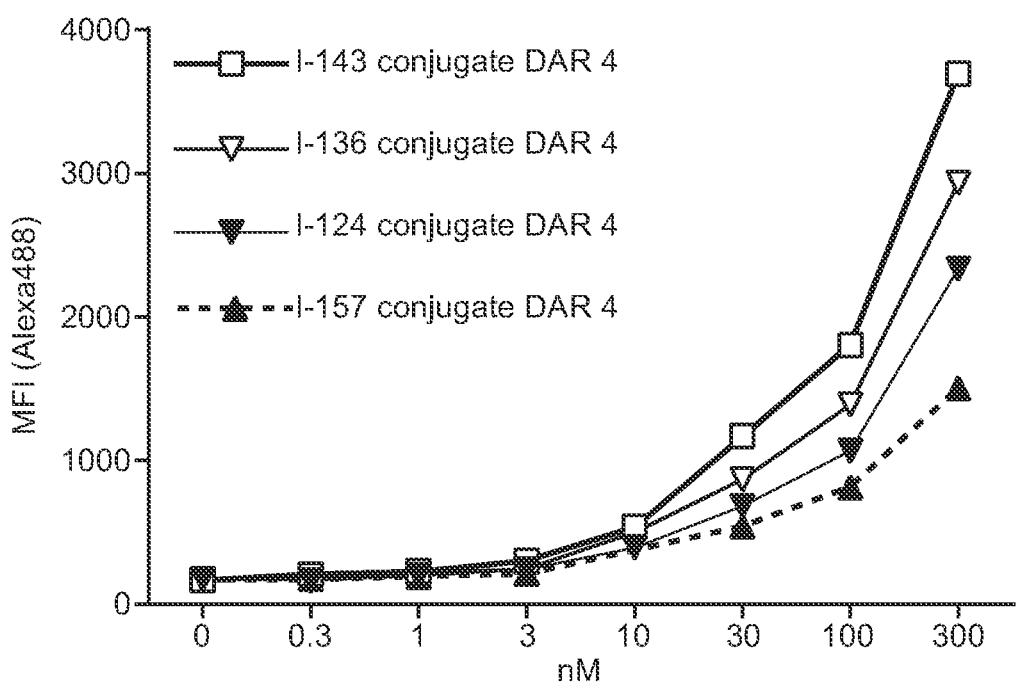
FIG. 2A-2D shows graphs of cell fluorescence versus antibody conjugate concentration indicating that various antibody conjugates of exemplary ASGPR binding compounds exhibited robust uptake into HepG2 cells after one hour incubation.

Omalizumab Conjugate Set 1 (see FIG. 2A)

| Ligand-Linker (Compd. No.) | Chemoselective ligation group | DAR (by MS) | Purity (by SEC) |
|---|---|---|---|
| I-143 | PFP ester | 4 | >95% |
| I-136 | PFP ester | 4 | >95% |
| I-124 | PFP ester | 4 | >95% |
| I-157 | PFP ester | 4 | >95% |

TABLE 23

Figure 2B:
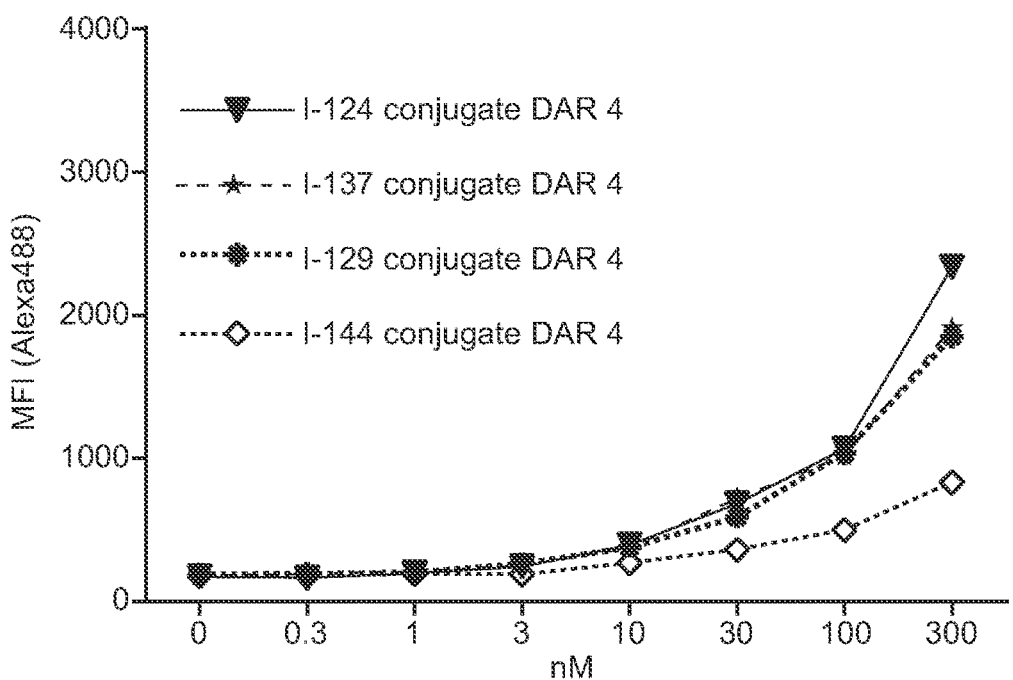

Omalizumab Conjugate Set 2 (see FIG. 2B)

| Ligand-Linker (Compd. No.) | Chemoselective ligation group | DAR (by MS) | Purity (by SEC) |
|---|---|---|---|
| I-124 | PFP ester | 4 | >95% |
| I-137 | PFP ester | 4 | >95% |
| I-129 | PFP ester | 4 | >95% |
| I-144 | PFP ester | 4 | >95% |

TABLE 24

Figure 2C:
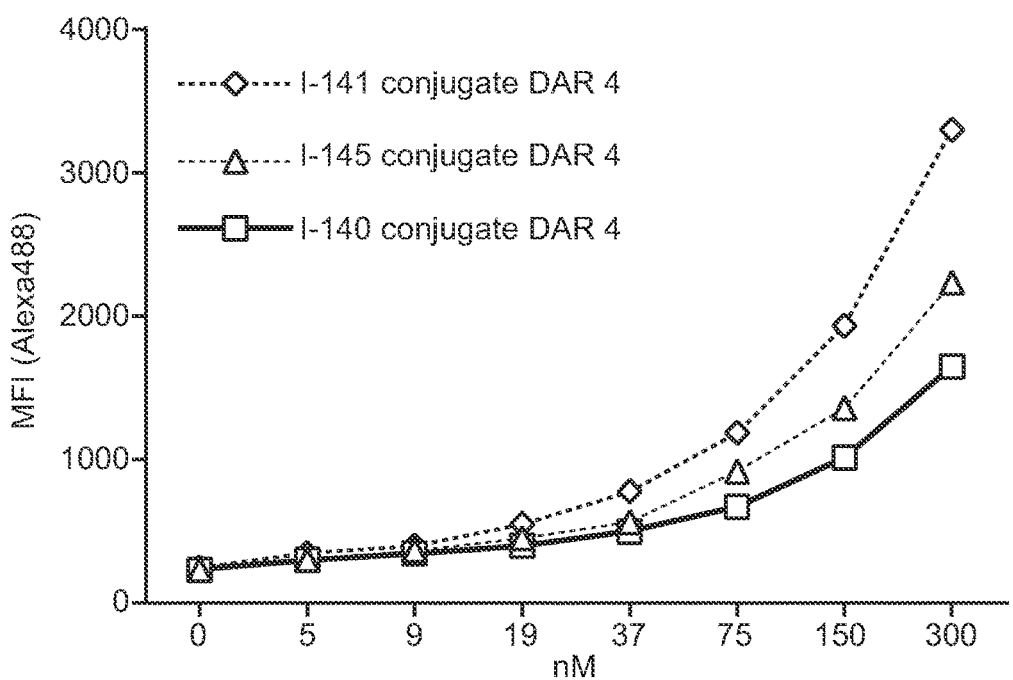

Omalizumab Conjugate Set 3 (see FIG. 2C)

| Ligand-Linker (Compd. No.) | Chemoselective ligation group | DAR (by MS) | Purity (by SEC) |
|---|---|---|---|
| I-141 | PFP ester | 4 | >95% |
| I-145 | PFP ester | 4 | >95% |
| I-140 | PFP ester | 4 | >95% |

TABLE 25

Figure 2D:
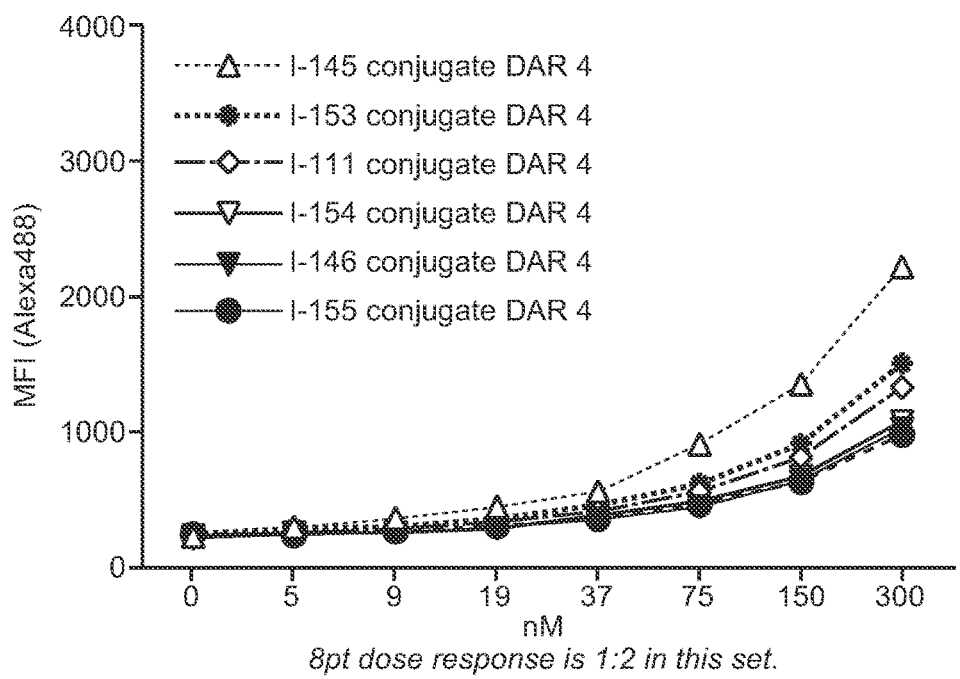

Omalizumab Conjugate Set 4 (see FIG. 2D)

| Ligand-Linker (Compd. No.) | Chemoselective ligation group | DAR (by MS) | Purity (by SEC) |
|---|---|---|---|
| I-145 | PFP ester | 4 | >95% |
| I-153 | PFP ester | 4 | >95% |
| I-111 | PFP ester | 4 | >95% |
| I-154 | PEP ester | 4 | >95% |
| I-146 | PEP ester | 4 | >95% |
| I-155 | PFP ester | 4 | >95% |

6.3. Assessment of Activity of Compounds and Conjugates

Example 61: Alexa Fluor Labelling

Cetuximab, matuzumab and human IgG isotype antibodies are conjugated to Alexa Fluor 647 using Alexa Fluor™ Protein Labeling Kit (Invitrogen) per the manufacturer's protocol. In brief, antibodies to be labeled are diluted to 2 mg/mL in PBS to a total volume of 500 μL. A 15 DOL (degree of labeling) is used for the conjugation with the fluorophore. Free dye is removed by pre-wetting an Amicon 30 kDa filter with PBS. After incubation, the conjugation reaction is then added to the filter and spun at high speed for 10 minutes. Retained solution is then resuspended in PBS to a final volume of 1 mL and stored at 4° C. indefinitely.

The above procedure can be adapted to fluorescently label a variety of antibodies or target proteins of interest with alternative dyes such as Alexa Fluor™ 488 using e.g., NHS-lysine conjugation chemistry.

Example 62: Measurement of EGFR/IgG Levels by Surface Staining

This example provides a protocol for the measurement of the time course activity of cetuximab, and matuzumab conjugates on surface EGFR and IgG levels in Hela parental cells measured by surface staining.

Day −1

1e6 Hela parental cells are plated in 2 mL of media in 6 well plates.

Day 0

Media are replaced with 1.5 mL of fresh media.

PBS, unconjugated antibodies and conjugated antibodies are added to respective wells at a final concentration of 20 nM.

Day 1/2/3

Media is aspirated from wells and washed thrice with PBS. 750 μL of Enzyme-Free Dissociation buffer is added and cells are allowed to detach on ice.

Cell are collected in tubes and spun down at 300×g for 5 mins @ 4° C.

Cells are resuspended in PBS and volume is split equally into two tubes.

All tubes are spun at 300×g for 5 mins at 4° C. One set, the PBS is aspirated and pellets are frozen at −80° C.

The other set, the PBS is aspirated and washed 2× with cold FACS buffer.

After final wash, pellets are resuspended in 300 μL FACS buffer.

The 300 μL suspension is split into three wells (100 μL each) of a 96 well plate.

Set 1: Ctx::AF647 at 1:100 dilution and incubated on ice in the dark for 1 h.

Set 2: Mtz::AF647 at 1:100 dilution and incubated on ice in the dark for 1 h.

Set 3: Goat anti-human IgG PE at 2 μg/mL and incubated on ice in the dark for 1 h.

Cells are spun down at 1000×g at 4° C. for 3 minutes and liquid is decanted. Cell pellets are resuspended in 200 μL of cold FACS buffer. Repeated 3× total.

After final wash and decant, cells are resuspended in 100 μL cold FACS buffer with DAPI (25 ug/mL final).

Stained cells are then analyzed on Biorad ZE5.

Example 63: Live-Cell EGFR Surface Staining by Flow Cytometry

This example provides an alternate protocol for the determination of the effect of matuzumab conjugates on surface EGFR levels measured by surface staining using flow cytometry.

Hela parental cells are plated in 6 well plates and treated with vehicle (PBS), unconjugated anti-EGFR antibody (matuzumab, Mtz), or matuzumab conjugates for the indicated period of time.

After incubation, media is aspirated and cells are washed three times with PBS, lifted using Accutase and pelleted by centrifugation at 300×g for 5 minutes. Cells are resuspended in cold FACS buffer and kept cold for the remainder of the staining procedure. A portion of cells are excluded from staining procedure as an unstained control. Cells are stained with either human IgG Isotype-AF647 or cetuximab-AF647 conjugates for 1 h on ice in the dark. Cells are then spun at 300×g for 5 min at 4° C. and washed with cold FACS buffer for a total of three washes. After the final wash, cells are resuspended in 100 μL of FACS buffer with DAPI added at a final concentration of 5 μg/mL. Cells are analyzed using a BioRad ZE5 flow cytometer and data is analyzed using FlowJo software. Cells are first gated to remove debris, doublets and dead cells (DAPI negative). EGFR cell surface levels are determined based on AF647 mean fluorescence intensity (MFI).

In parental Hela cells, treatment with the conjugated antibodies can result in reduced cell surface levels of EGFR compared to cells treated with unconjugated antibodies (Ctx or Mtz).

Treatment of cells with the conjugates described herein can induce reduction in targeted cell surface receptors.

Example 64: Measurement of Total EGFR Levels by Western Blotting

This example provides the protocol for the measurement of the time course activity of cetuximab, and matuzumab conjugates on total EGFR levels in Hela parental cells measured by traditional Western blotting.

Once all time-points from Example above are collected, all cell pellets are resuspended in 50 μL of radioimmunoprecipitation assay (RIPA) buffer (+protease/phosphatase inhibitor+nuclease).

Lysates are incubated on ice for 1 h.

Lysates are then spun at high-speed for 10 min at 4° C.

40 μL of cleared lysate is transferred to a 96 well plate.

All lysate concentrations are calculated using BCA assay (1:3 dilution).

All lysates are equalized to 2 mg/mL using RIPA as diluent.

Equal volumes (15 μL) of lysate are then mixed with LDS sample buffer (3×LDS+2.5× reducing agent).

Samples are incubated at 98° C. for mins and allowed to cool.

Samples are vortexed and spun down.

15 μL of sample is loaded onto a 26-well bis-tris 4-12% midi-gel.

Gel is allowed to run at 180V for 20 mins.

Gels are transferred to nitrocellulose membrane using iBlot 2 (20V constant, 7 mins).

Membranes are washed 1× in PBS and then placed in Odyssey blocking buffer for 1 h RT with shaking.

Primary antibodies mouse anti-β-actin (SCB) and rabbit anti-EGFR (CST) are diluted 1:1000 in blocking buffer and allowed to incubate overnight at 4° C. with shaking.

Membranes are washed thrice with PBS-T (Tween20 0.1%), at least 5 mins each wash.

Secondary antibodies anti-mouse 680rd and anti-rabbit 800cw are diluted 1:5000 in blocking buffer and allowed to incubate for 1 h at RT with shaking.

Membranes are washed thrice with PBS-T (Tween20 0.1%), at least 5 mins each wash.

Membranes are imaged using licor odyssey scanner.

Example 65: Measurement of Total EGFR Levels by In-Cell Western Blotting

This example provides a protocol for the measurement of the dose response of cetuximab and matuzumab conjugates on total EGFR levels in Hela parental measured by in-cell Western blotting.

Day −1
  3e4 Hela parental cells are plated 100 μL per well in a clear bottom black walled 96 well plate (Costar 3603)
Day 0
  Media is decanted and 100 μL of fresh media is added back to wells.
  50 μL of a 3× dose response of unconjugated and conjugated antibodies are added to respective wells.
  80 nM final starting concentration, 1:2 dilution. EGF is added in 3 wells at a concentration of 50 ng/mL final.
Day 2
  Media is decanted and wells are washed thrice with PBS.
  Wells are fixed with 4% PFA in PBS for 15 minutes at RT.
  Wells are washed thrice with PBS.
  Cells are permeabilized with 0.2% triton-x100 in PBS for 15 mins. Repeated 3× total.
  Cells are blocked in Odyssey blocking buffer with 0.2% triton-x100 for 1 h at RT.
  Cells are stained with goat anti-EGFR (AF231, R&D, 1 μg/mL final) in block buffer overnight at 4° C.
  Cells are washed 3× with PBS-T (Tween20 0.1%).
  Cells are stained with donkey anti-goat 800CW secondary (1:200) and CellTag700 (1:500) in blocking buffer for 1 h at RT in dark.
  Cells are washed 3× with PBS-T (Tween20 0.1%).
  Last wash is decanted and plates are blotted on paper towel to remove residual liquid.
  Plates are imaged on Licor scanner (3 mm offset).

Example 66: Conjugates of M6PR or ASGPR Binding Compounds Mediate Uptake of IgG2a into Human Liver Cancer Cells The uptake of antibody conjugates of exemplary M6PR or ASGPR binding compounds was assessed in Hep G2 cells, using a method similar to that described in Example above. FIG. 1 shows a graph of cell fluorescence versus antibody conjugate concentration indicating that various antibody conjugates of exemplary ASGPR binding compounds, and an example M6PR binding compound (see, e.g., PCT US21/12846, herein incorporated by reference) exhibited robust uptake into HepG2 cells after one hour incubation. Conjugates of compound 1209 (ASGPR binding compound I-124) (average loading DAR6), compound 1210 (ASGPR binding compound I-123) (average loading DAR4) and M6PR binding compound 520 (average loading DAR4) exhibited comparable HepG2 cellular uptake.

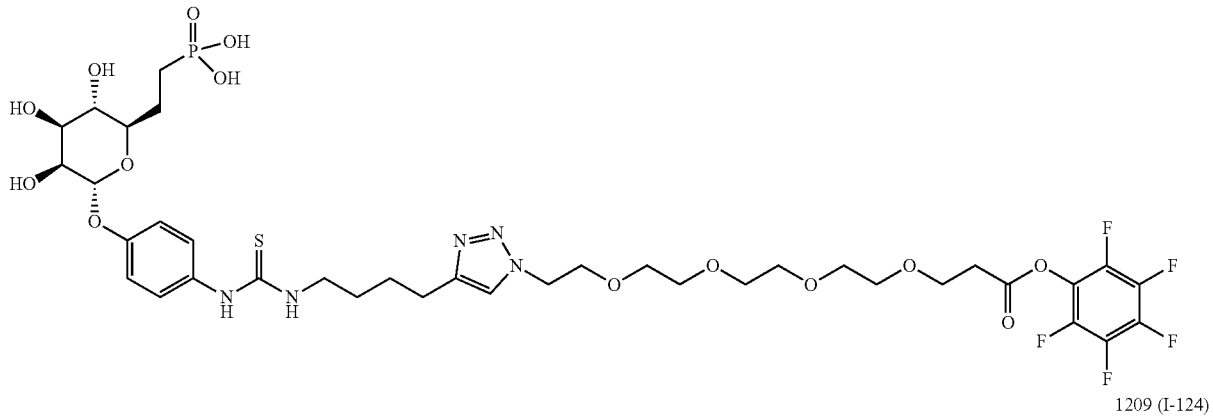

1209 (I-124)

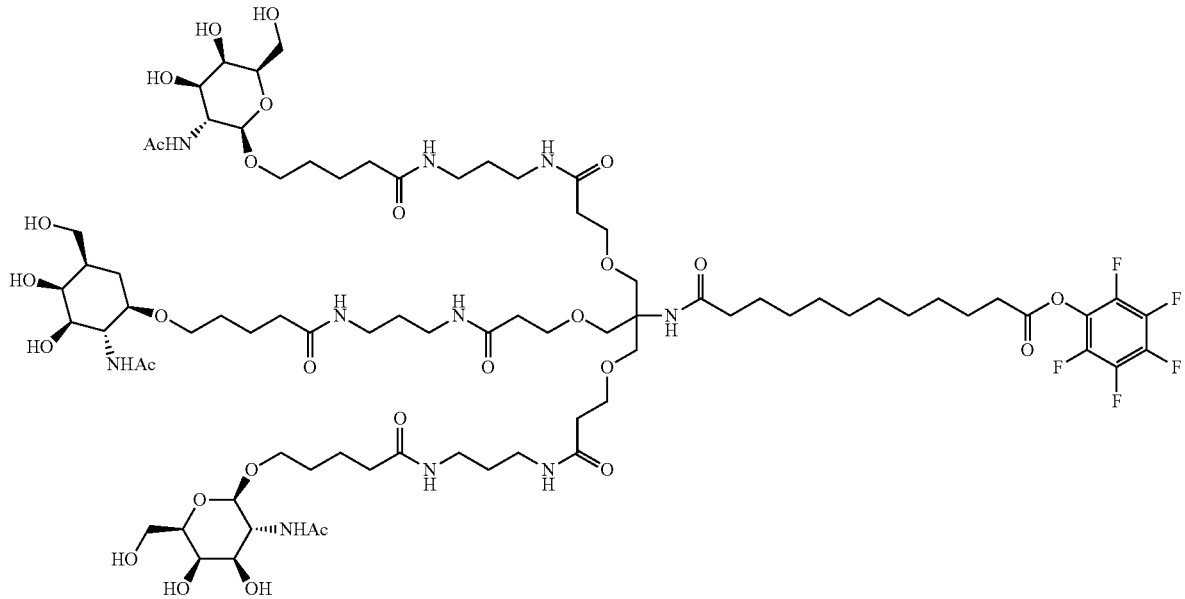

520

1210 (I-123)

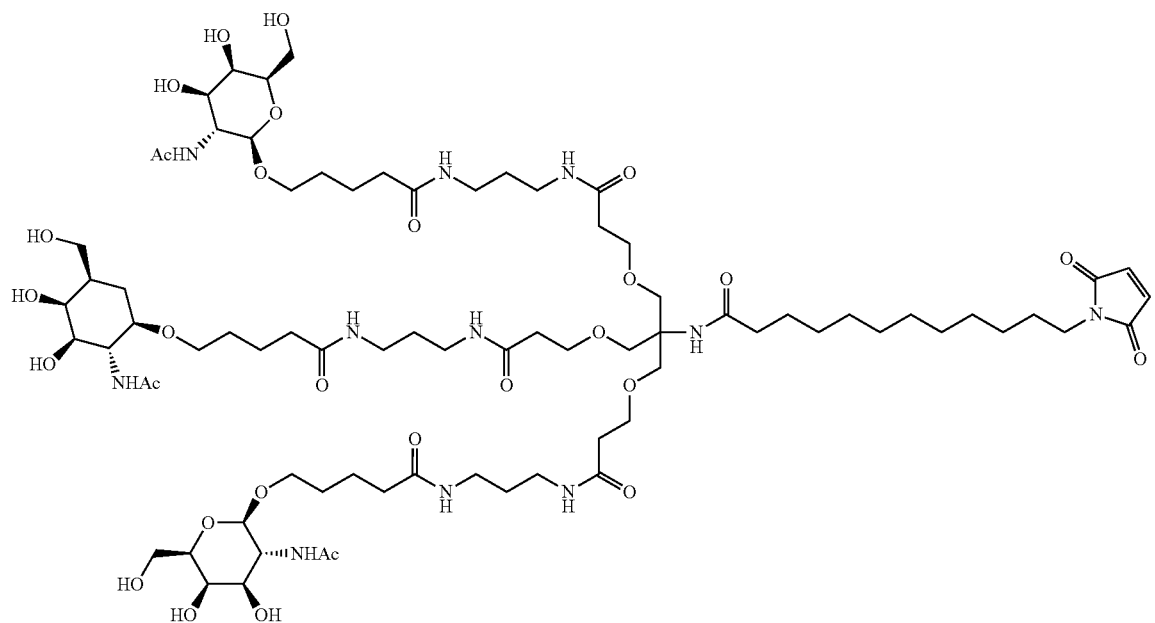

Example 67: Uptake of Target Protein in HepG2 Cells

The omalizumab conjugates of Example 60 were bound to IgE-Alexa488 (prepared according to Example 62), as follows: equal molar ratios of omalizumab (anti-IgE) conjugate and IgE-Alexa488 were added in tissue culture media for 30 minutes at room temperature. The resulting anti-IgE conjugate:IgE antibody-Alexa488 compositions were added to HepG2 cells (100 k cells/50 ul per well, n=2), and Alexa488 fluorescence levels in the cells were measured at 1 hour by flow cytometry. As the fluorescently labelled target (IgE antibody) accumulates in cells, the fluorescence presents a way to measure total intracellular uptake by cells over time.

FIG. 2A shows a graph of cellular uptake of various conjugates of omalizumab (anti-IgE) with exemplary ASGPR ligand-linkers of Table 26, bound to Alexa488 labeled-target IgE in HepG2 cells. The conjugates are ordered in Table 26 according to the relative uptake activity as shown in FIG. 2A.

TABLE 26

Omalizumab Conjugates

| Ligand-Linker (Compd. No.) | ASGPR ligand (see Tables 1-3) | Linker (Table 5-7) | Length (atoms) ($Z^1$ to branching atom) | m | n (DAR) |
|---|---|---|---|---|---|
| I-143 | X4 | L28 | 14 | 3 | 4 |
| I-136 | X8 | L25 | 16 | 3 | 4 |
| I-124 (reference) | X1 | L29 | 15 | 3 | 4 |
| I-157 | X4 | L30 | 6 | 3 | 4 |

As seen in FIG. 2A all of the conjugates include multivalent compounds (e.g., n=3). The conjugate having a 1-triazole moiety (I-143, ASGPR ligand X4) has superior activity to the reference conjugate having a 1-oxygen moiety (I-124, ASGPR ligand X1).

The conjugate having a 6-position oxygen linkage (I-136, ASGPR ligand X8) has superior activity to the reference conjugate I-124.

The conjugate having a 1-triazole moiety and a shorter linkage from the ASGPR ligand to the branching point of the ligand (I-157, linker length of 6 atoms to branching point) exhibits less activity than the conjugate having a 1-triazole moiety and a longer linkage from the ASGPR ligand to the branching point (I-143, length of 14 atoms).

FIG. 2B shows a graph of cellular uptake of various conjugates of omalizumab (anti-IgE) with exemplary ASGPR ligand-linkers of Table 27, bound to Alexa488 labeled-target IgE in HepG2 cells. The conjugates are ordered in Table 27 according to the relative uptake activity as shown in FIG. 2B

TABLE 27

Omalizumab Conjugates

| Ligand-Linker (Compd. No.) | ASGPR ligand (see Tables 1-3) | Linker (Tables 5-7) | Length (atoms) (branching point to Y) | m | n (DAR) |
|---|---|---|---|---|---|
| I-124 (reference) | X1 | L29 | 12 | 3 | 4 |
| I-137 | X1 | L29 | 81 | 3 | 4 |
| I-129 | X1 | L29 | 33 | 3 | 4 |
| I-144 | X1 | L30 | 12 | 2 | 4 |

As seen in FIG. 2B all of the conjugates include the ASGPR ligand X1 and branched trivalent linker $L^{29}$, or its divalent equivalent $L^{30}$. The conjugates having longer linkers between the ASGPR linker and Y (e.g., conjugates of compounds I-137 and I-129) exhibit comparable activity to the reference conjugate (e.g., conjugate of compound I-124).

The reference conjugate (I-124, n=3) showed superior activity to the divalent conjugate (I-144, n=2).

FIG. 2C shows a graph of cellular uptake of various conjugates of omalizumab (anti-IgE) with exemplary ASGPR ligand-linkers of Table 28, bound to Alexa488 labeled-target IgE in HepG2 cells. The conjugates are ordered in Table 28 according to the relative uptake activity as shown in FIG. 2C.

TABLE 28

Omalizumab Conjugates

| Ligand-Linker (Compd. No.) | ASGPR ligand (see Tables 1-3) | Linker (Tables 5-7) | Length (atoms) ($Z^1$ to branching atom) | m | n (DAR) |
|---|---|---|---|---|---|
| I-141 | X2 | L32 | 15 | 3 | 4 |
| I-145 | X1 | L33 | 15 | 3 | 4 |
| I-140 | X3 | L34 | 18 | 3 | 4 |

As seen in FIG. 2C the conjugate having an S-glycoside (I-141, ASGPR ligand X2) shows superior uptake to that of the O-glycoside (I-145, ASGPR ligand X1).

The conjugates having a 1-methylene moiety (I-140, ASGPR ligand X3) has comparable activity to the conjugate having the O-glycoside (I-145, ASGPR ligand X1).

FIG. 2D shows a graph of cellular uptake of various conjugates of omalizumab (anti-IgE) with exemplary ASGPR ligand-linkers of Table 29, bound to Alexa488 labeled-target IgE in HepG2 cells. The conjugates are ordered in Table 29 according to the relative uptake activity as shown in FIG. 2D.

TABLE 29

Omalizumab Conjugates

| Ligand-Linker (Compd. No.) | ASGPR ligand (see Tables 1-3) | Linker (Tables 5-7) | Length (atoms) ($Z^1$ to branching atom or Y) | m | n (DAR) |
|---|---|---|---|---|---|
| I-145 | X1 | L33 | 15 | 3 | 4 |
| I-153 | X10 | L28 | 14 | 3 | 4 |
| I-111 | X1 | L21 | 16 | 2 | 4 |
| I-154 | X11 | L26 | 19 | 3 | 4 |
| I-146 | X1 | L9 | 35 (to Y) | 1 | 4 |
| I-155 | X12 | L26 | 19 | 3 | 4 |

As seen in FIG. 2D the conjugate having a valency of 3 (I-145, n=3) shows superior uptake to conjugates having a valency of 2 or 1 (I-111, n=2; and I-146, n=1).

The conjugates having the linker attached to the ASGPR ligand at the 2-position (e.g., I-153, ASGPR ligand X10; I-154, ASGPR ligand X11; and I-155, ASGPR ligand X12) also exhibit activity in this assay, however, are less active than the 1-position linked conjugate (e.g., 1-145, ASGPR ligand X1).

Example 68: Binding Affinity Assessment of Trivalent compounds by Fluorescence Polarization Assay Example trivalent compounds (1901 (I-171), 1902 (I-172), (see Table 19), XB32 (see Table 6) and 2101 (see Table 21)) were assessed for binding affinity to ASGPR by fluorescence polarization assay as compared to a reference compound 18G (e.g., intermediate compound 18G in Example 14, structure below) as a positive control, and the corresponding carboxylic acid of compound I-124 (I-124 acid, structure below) as a second reference compound.

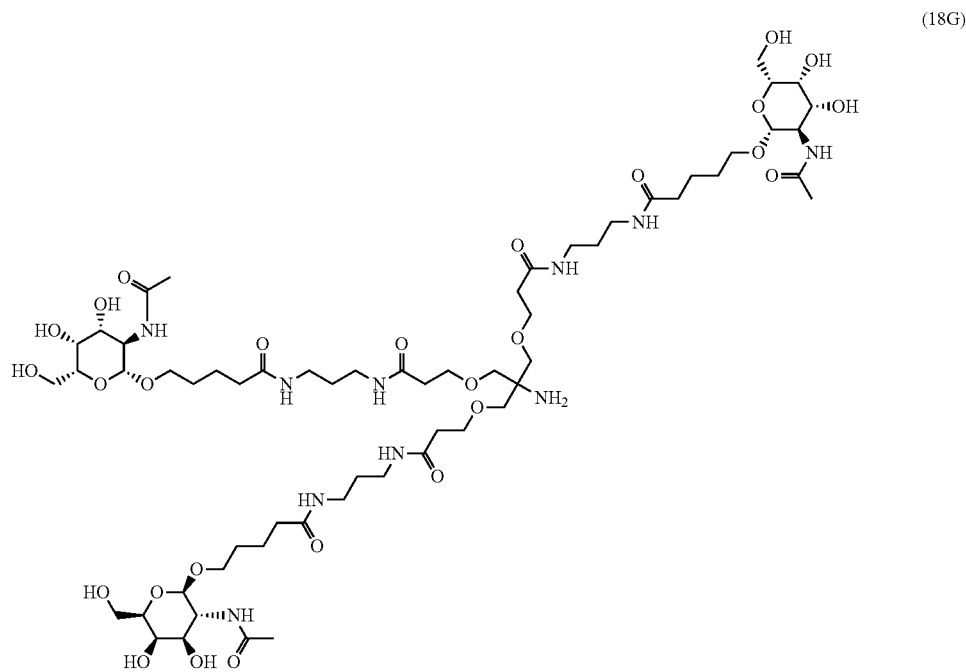

(18G)

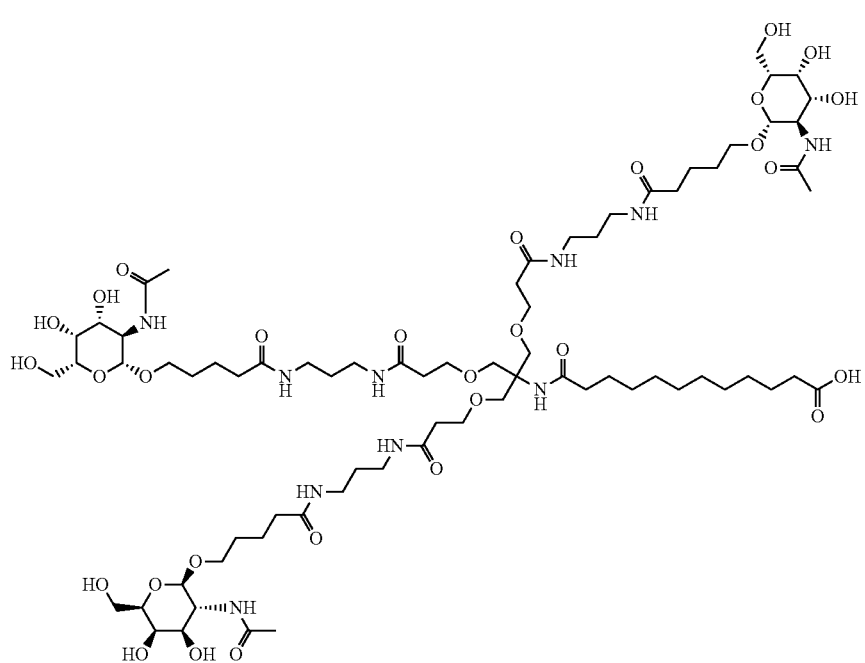

(I-124acid)

Assay Procedure: ASGPR binding was measured in black 96-well plates using a fluorescence polarization assay. A fluorescent probe consisting of a tri-GalNAc linked to Cy5 (GalNac-Cy5, depicted below) was custom synthesized. Example compounds were resuspended in DMSO and 3-fold serial dilutions were made at 100× final concentrations. Binding reactions were conducted in 100 µl final volume in 20 mM Hepes (pH 7.5) 50 mM NaCl 5 mM $CaCl_2$ 0.015% Triton X-100 1% DMSO with 80 nM ASGPR (Acro Biosystems) and 1 nM probe. Fluorescence polarization was measured using λex=620 nm, λem=688 nm on an Envision plate reader (Perkin Elmer) after 2 hr incubation time. Dose responses were conducted in duplicate and normalized to the response with DMSO (high) and 1 µM reference compound 18G (low) on each plate. $IC_{50}$ values were determined by fitting to 4-parameter curves in GraphPad Prism.

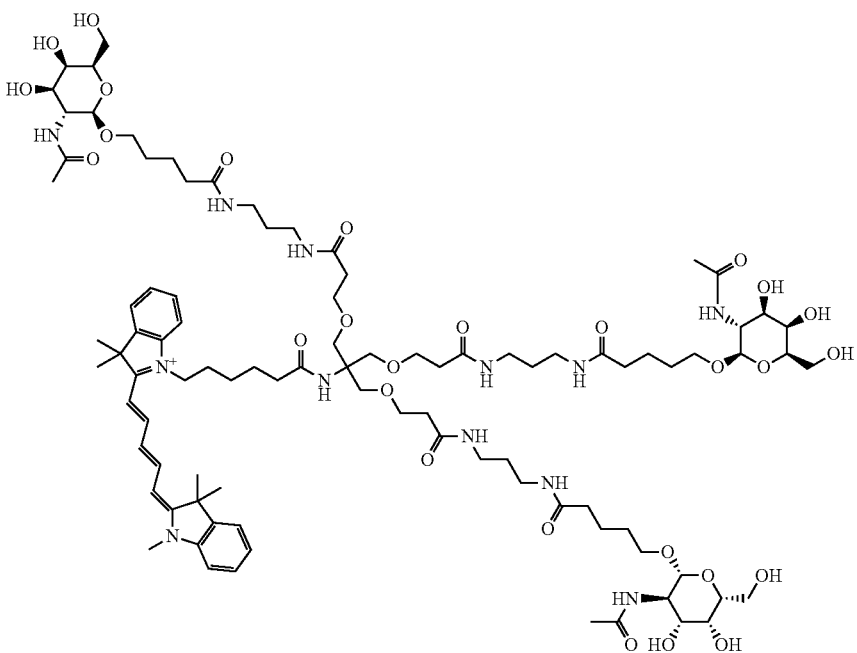

(GalNac-Cy5)

Dose response curves were measured for example compounds. It was observed that Compounds 1901 (I-171), 1902 (I-172) and XB32 bind ASGPR with comparable affinity as reference compound 18G. The other reference compound I-124acid had reduced ASGPR binding affinity as compared to other trivalent compounds assayed.

Figure 3:
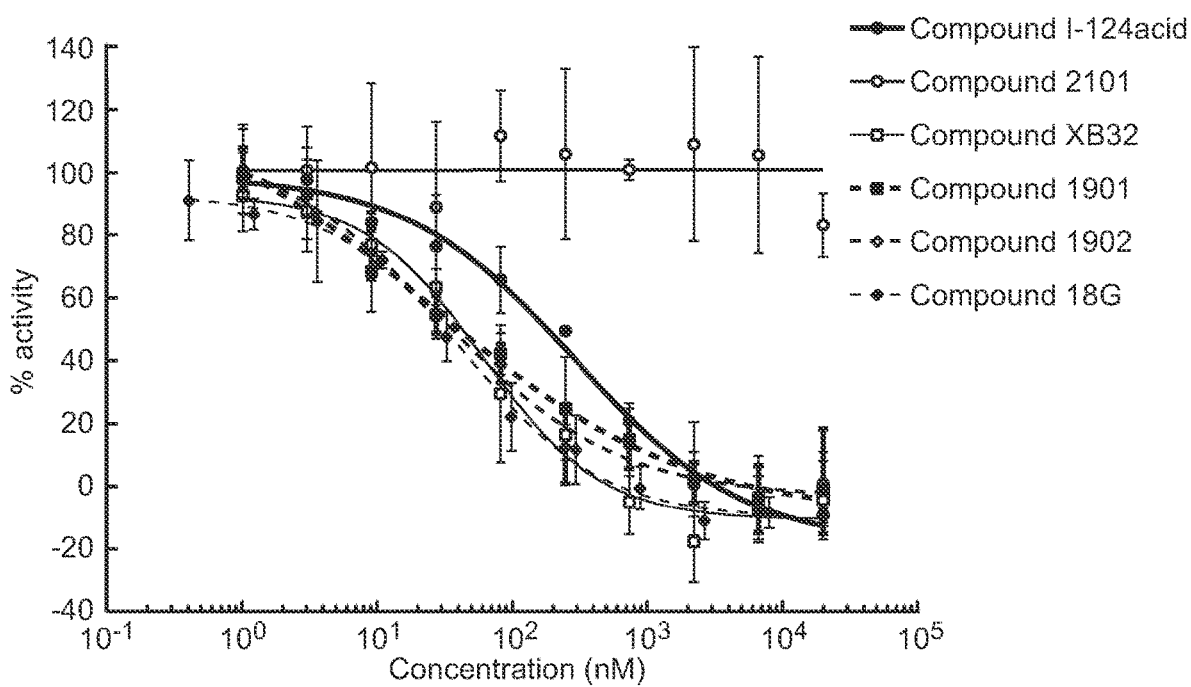
FIG. 3 illustrates the fluorescence polarization screening results for example trivalent compounds (1901 (I-171), 1902 (I-172), XB32 and 2101).

FIG. 3 illustrates the fluorescence polarization screening results for example trivalent compounds (1901 (I-171), 1902 (I-172), XB32 and 2101).

The IC$_{50}$ ranges for the compounds assayed are presented in Table 30. In Table 30, A: IC$_{50}$≤50 nM; B: 50 nM<IC$_{50}$≤100 nM; and C: IC$_{50}$>100 nM

TABLE 30

IC$_{50}$ ranges for example compounds

| Compound | IC$_{50}$ (nM) |
| --- | --- |
| 18G | A |
| 1901 (I-171) | A |
| 1902 (I-172) | A |
| XB32 | B |
| I-124acid | C |
| 2101 | — |
| 1216-acid | C |
| 1216A-acid | A |
| XB40 | A |
| 1920 | C |
| 1905 acid | A |

Example 69: Binding Affinity Assessment of Monomer Compounds by Fluorescence Polarization Assay Example monovalent compounds (depicted below) were assessed at 100 μM as compared to a reference compound 18G (e.g., intermediate compound 18G in Example 14) as a positive control, following the assay procedure outlined in Example 68.

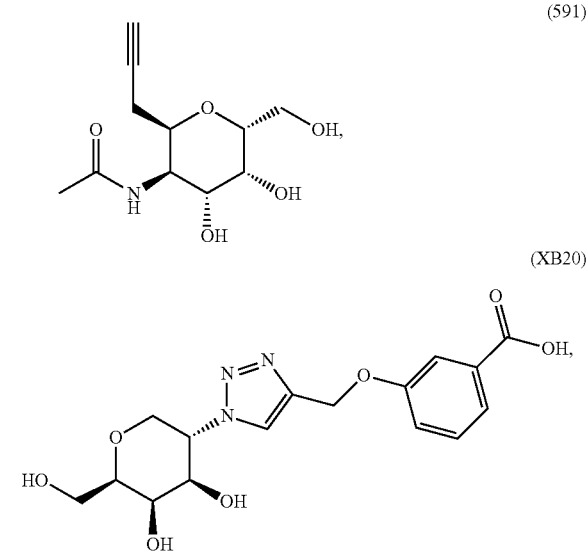

(591)

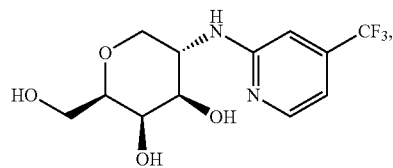

(XB23)

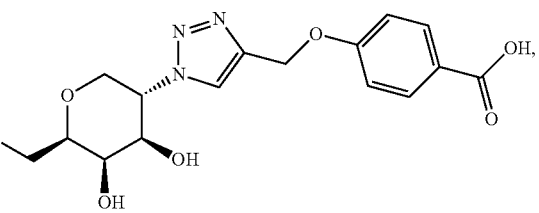

(XB21)

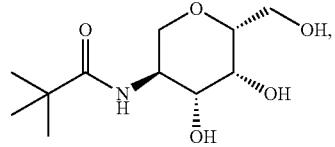

(592)

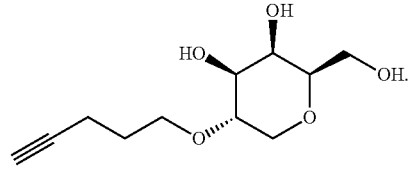

(593)

It was observed that all monovalent compounds screened, with the exception of compound 593, bind with at least 50% of the activity of reference compound 18G.

Figure 4:
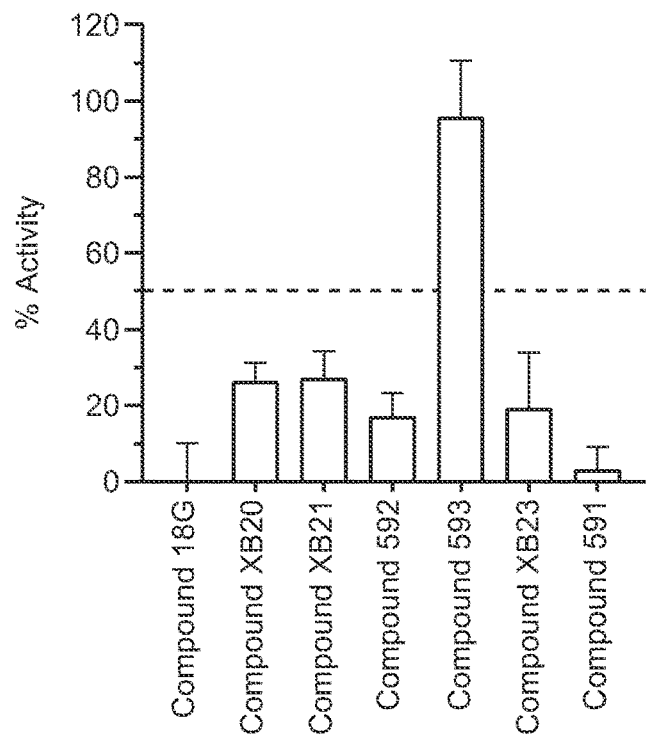
FIG. 4 illustrates the binding of example monovalent compounds (591, XB20, XB23, XB21, 592 and 593) as a percentage of the activity of reference compound 18G.

FIG. 4 illustrates the binding of example monovalent compounds (591, XB20, XB23, XB21, 592 and 593) as a percentage of the activity of reference compound 18G.

Dose response curves were measured for example compounds. It was observed that Compound 591 binds ASGPR with the highest affinity of the tested monomers.

Figure 5:
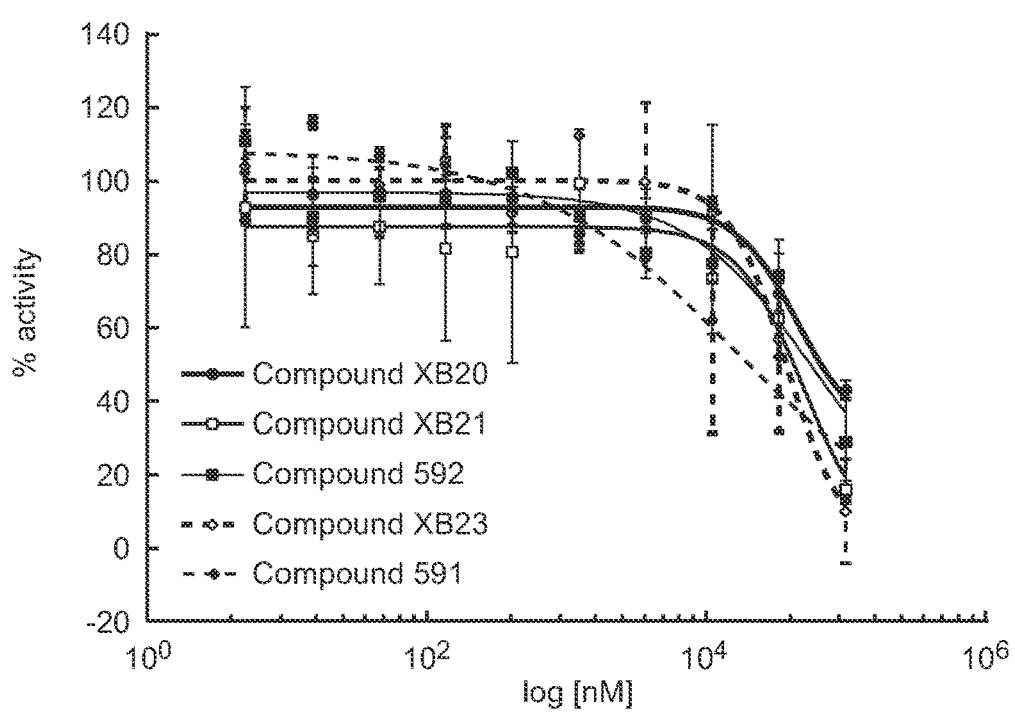
FIG. 5 illustrates the fluorescence polarization screening results for example monovalent compounds (XB20, XB21, 592, XB23, 591).

FIG. 5 illustrates the fluorescence polarization screening results for example monovalent compounds (XB20, XB21, 592, XB23, 591).

The IC$_{50}$ ranges for the monovalent compounds assayed are presented in Table 31. In Table 31, A: IC$_{50}$≤1 μM; B: 1 μM<IC$_{50}$≤50 μM; and C: IC$_{50}$>50 μM

TABLE 31

IC$_{50}$ ranges for example compounds

| Compound | IC$_{50}$ (MM) |
| --- | --- |
| 18G | A |
| 591 | B |
| XB20 | B |
| XB23 | B |
| XB21 | B |
| 592 | C |
| 593 | — |

Example 70: Comparison of Trivalent Compounds of Formula (Ib) with Atom Variations at the Anomeric Position (1-Position, Z$^1$ Group)

To investigate the merits of alternative glycoside linkages at the anomeric position of the ASGPR ligand (e.g., S-glycoside linkage and C-glycoside linkages), compounds having various alternative linkages at the anomeric position (1-position) of the ASGPR ligand were compared to reference compound having a 1-position 0-glycoside linkage (compound I-163).

OMA Ab conjugates of example compounds I-160-I-163 and I-141 were bound to IgE-Alexa488 (prepared by adapting procedure in Example 61), as follows: equal molar ratios of OMA(anti-IgE) conjugate and IgE-Alexa488 were added in tissue culture media for 30 minutes at room temperature. The resulting anti-IgE conjugate:IgE antibody-Alexa488 compositions were added to HepG2 cells (100 k cells/50 ul per well, n=2), and Alexa488 fluorescence levels in the cells were measured at 1 hour by flow cytometry. As the fluorescently labelled target (IgE antibody) accumulates in cells, the fluorescence presents a way to measure total intracellular uptake by cells over time.

Figure 6:
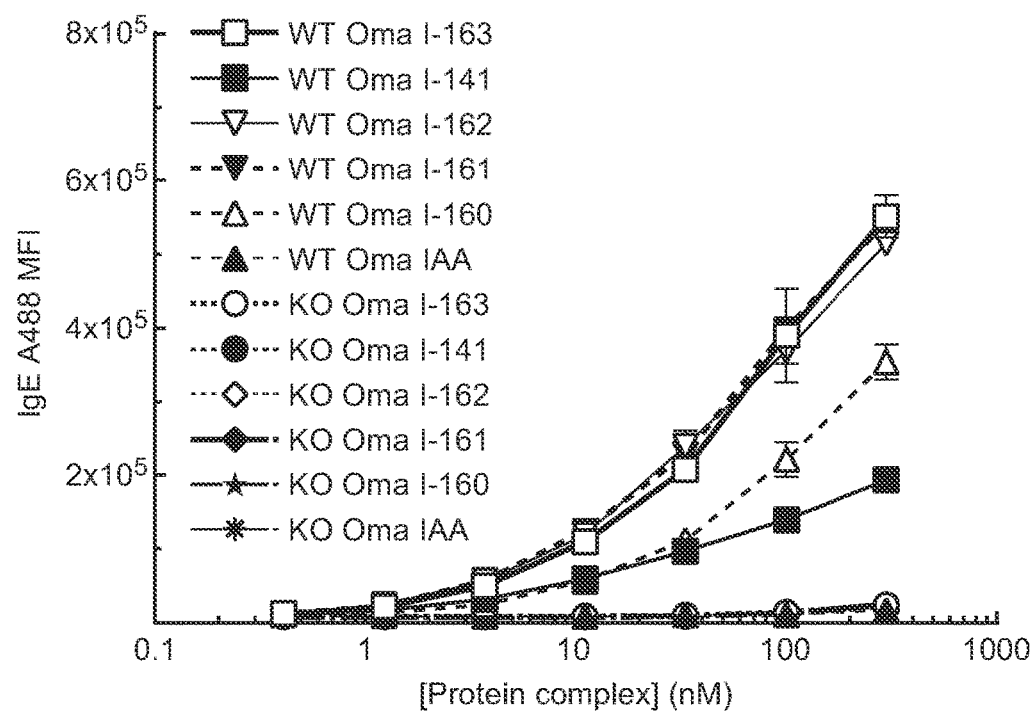
FIG. 6 shows a graph of cellular uptake of various conjugates of OMA (anti-IgE) with example compounds I-160 to I-163 and I-141 bound to Alexa488 labeled-target IgE in HepG2 cells.

FIG. 6 shows a graph of cellular uptake of various conjugates of OMA (anti-IgE) with example compounds of table 32 bound to Alexa488 labeled-target IgE in HepG2 cells. The conjugates are ordered in Table 32 according to the relative uptake activity as shown in FIG. 6.

TABLE 32

Oma Conjugate Set (see FIG. 6)

| Ligand-Linker (Compd. No.) | Chemoselective ligation group | Anomeric Position glycoside linkage |
|---|---|---|
| I-163 | maleimide | —O— |
| I-161 | maleimide | (triazole structure with N=N) |
| I-162 | maleimide | —S— |
| I-160 | maleimide | —CH$_2$— |
| I-141 | PFP ester | —S— |

As seen in FIG. 6 all of the conjugates include multivalent compounds (e.g., n=3) linked to the linker through the anomeric position (1-position of the ASGPR ligand). The conjugate having a 1-triazole moiety (I-161) has essentially identical activity to the reference conjugate having a 1-oxygen moiety (I-163). The conjugate having a 1-position —S-glycoside linkage has similar activity to compounds I-163 and I-161.

In Vivo Comparison of Example Compounds Having Atom Variations at the Anomeric Position The three most active anomeric position variants (I-161, 1-162 and 1-160) identified in the HepG2 uptake assay were evaluated in comparison to the 0-glycoside linked compound I-163 in vivo.

Pharmacokinetic Studies

Pharmacokinetic (PK) studies were undertaken to determine the pharmacokinetic profile of various OMA linked example compounds (I-161-I-163).

Protocol: Female C57BL/6 mice are dosed via IV with 5 mg/kg of OMA-example compounds, and OMA-reference. Serum samples are collected at 0.083, 0.25, 0.5, 1, 2, 4, 8, 24, 48, 72, and 168 hours after dosing with 3 animals per timepoint.

Serum hIgG concentrations were measured by ELISA.

Figure 7:
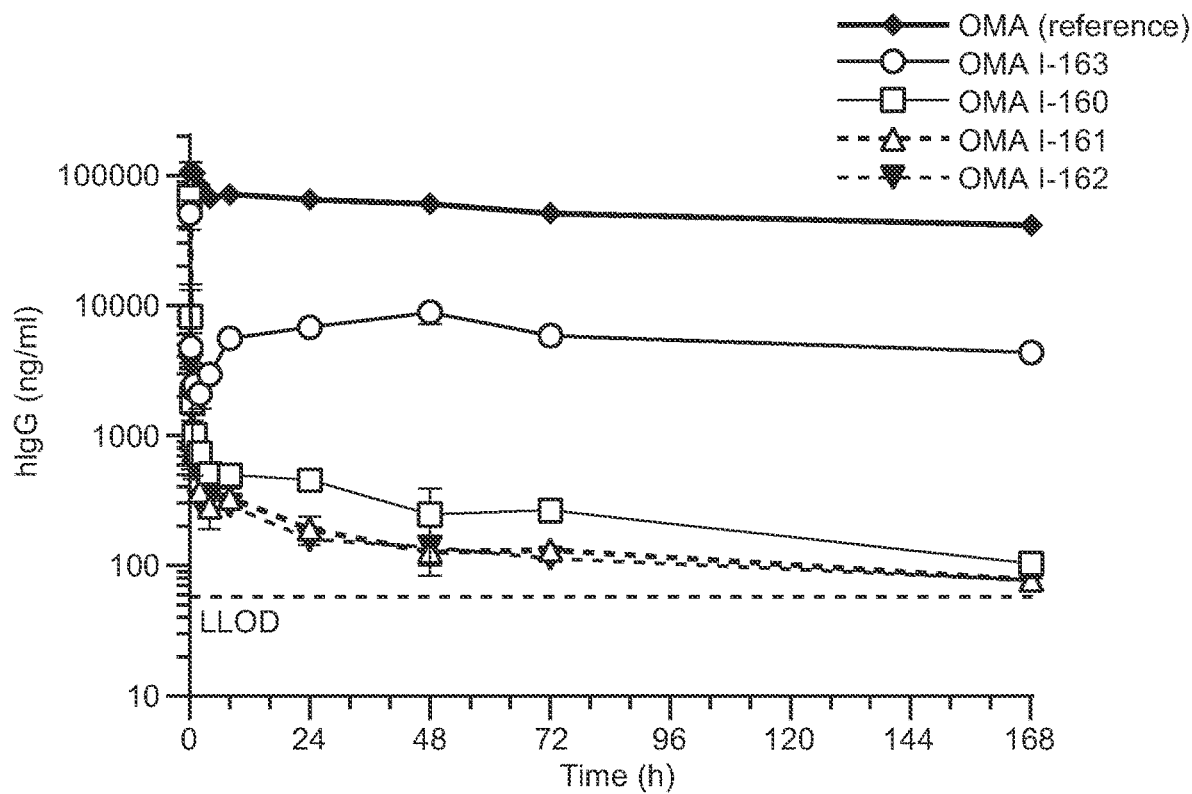
FIG. 7 illustrates affinity-dependent clearance of OMA-example compounds (I-160 to I-163) as compared to OMA (reference).

FIG. 7 illustrates affinity-dependent clearance of OMA-linked example compounds (I-160 to 1-163) as compared to OMA IgG antibody alone (reference).

These results demonstrate that compounds with alternative anomeric position glycoside linkages to oxygen (e.g., 1-position —S— (I-162), —CH$_2$— (I-160) and -triazole- (I-161)) have distinct PK profiles from reference compound I-163 (1-position —O— linkage), with near complete depletion of particular OMA linked compounds to lower limit of detection (LLOD) by day 7.

Pharmacodynamic Studies

A dose titration of the effect of OMA-linked compound I-163 on target IgE clearance was undertaken to determine the pharmacodynamic (PD) parameters of IgE and OMA-I-163 in mice.

Protocol: Female C57BL/6 mice were IV dosed 1 mg/kg of IgE followed by 0.1, 0.3, 1, or 3 mg/kg of OMA-I-163 16 hours later. Serum samples were collected at 0 (pre-bleed), 1, 4, and 24 hours after OMA-I-163 dose with 3 animals per timepoint.

Serum hIgE and hIgG concentrations were measured by ELISA.

Figure 8:
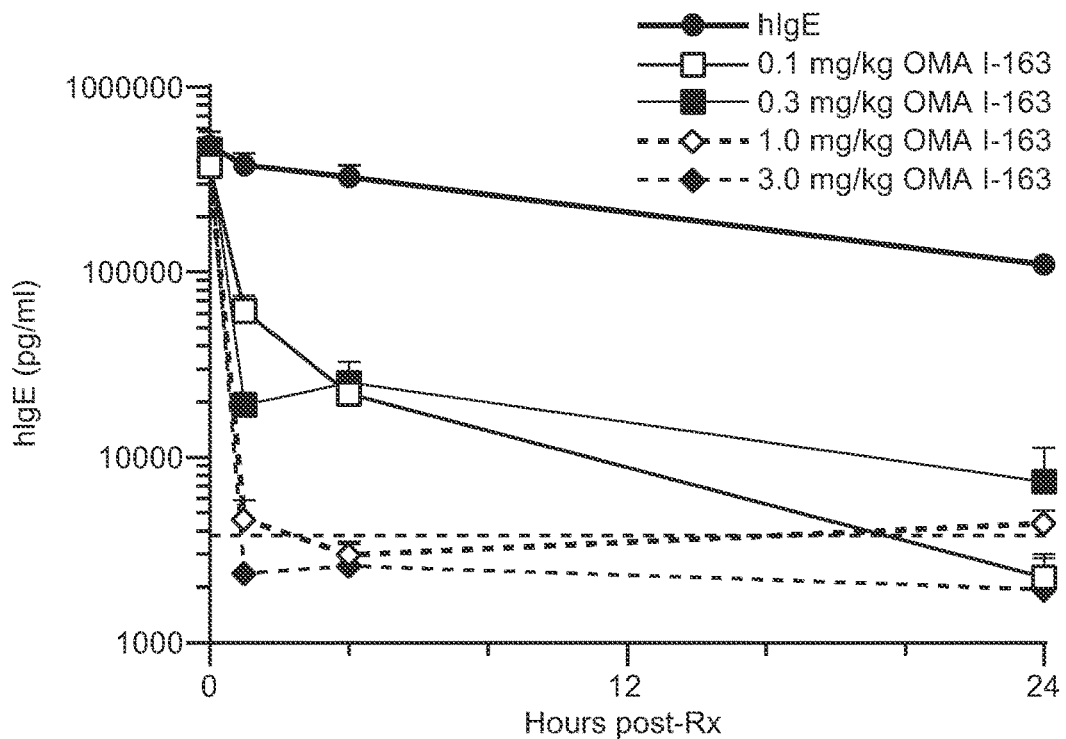
FIG. 8 illustrates dose titration OMA-I-163 IgE clearance.

FIG. 8 illustrates dose titration OMA-I-163 IgE clearance.

These results demonstrate that compound OMA-I-163 at 0.1 mg/kg gave partial clearance of IgE dosed at 1 mg/kg at 2 and 4 h, and complete clearance at 24 h. From these results the limiting dose of IgE and OMA-I-163 in mice was determined to be 0.1 mg/kg.

Next, the effect of example compound conjugate on IgE clearance was investigated at the determined limiting dose to compare the PD activity of OMA-I-163 (reference compound) to OMA-linked compounds I-160, I-161 and I-162.

Protocol: Female C57BL/6 mice were IV dosed 1 mg/kg of IgE followed by 0.1 mg/kg of OMA-I-163, OMA-I-162, OMA-I-161, and OMA-I-160 16 hours later. Serum samples were collected at 0 (pre-bleed), 1, 4, and 24 hours after LYTAC dose with 3 animals per timepoint.

Serum concentrations were measured by Elisa.

Figure 9:
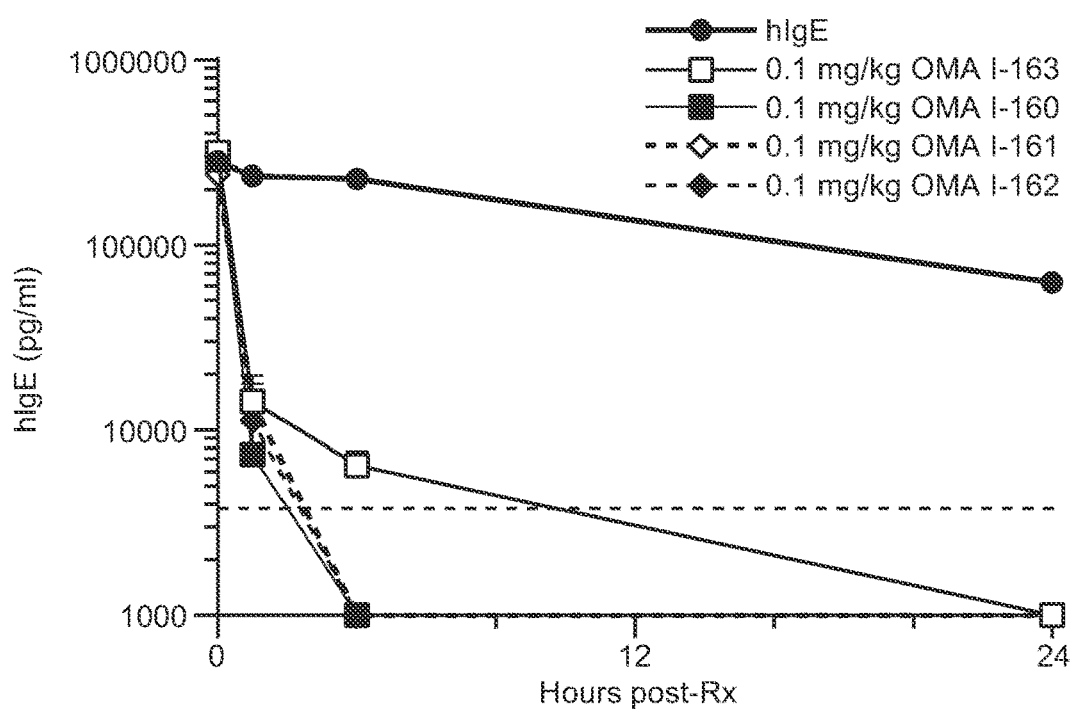
FIG. 9 illustrates affinity-dependent clearance of OMA-example compounds (I-160 to I-163) as compared to hIgE (reference).

FIG. 9 illustrates the clearance of target IgE via OMA-example compounds (I-160 to I-163) as compared to hIgE (reference) was affinity-dependent.

These results demonstrate that at low dose (0.1 mg/kg of the example OMA conjugate) OMA example compounds with alternative anomeric position glycoside linkages to oxygen (e.g., 1-position —S— (I-162), —CH$_2$— (I-160) and -triazole- (I-161)) clear IgE more efficiently than the reference compound with an oxygen linkage at the anomeric position (OMA-I-163). All of compounds OMA-I-60, OMA-I-161 and OMA-I-162 cleared IgE completely within 4 hours.

Summary

In summary, in vivo and in vitro data set for ASGPR compounds with alternative anomeric position glycoside linkages to oxygen indicates that increased target clearance can be attained by replacing the 1-position oxygen atom, e.g., by —S—, —CH$_2$— or -triazole-.

7. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A compound of formula (I):

$$X_n\text{-L-Y} \quad (I)$$

or a prodrug thereof, or a salt thereof,
wherein:
  Y is an antibody or antibody fragment that binds a target protein;
  n is 1 to 500;
  L is a linker; and
  X is a moiety that binds to a cell surface asialoglycoprotein receptor (ASGPR) of formula:

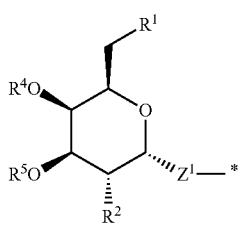

wherein:
  $R^1$ is selected from —OH, —OC(O)R, —C(O)NHR, and triazole, where R is $C_{1-6}$ alkyl or aryl;
  $R^2$ is selected from —NHCOCH$_3$, —NHCOCF$_3$, —NHCOCH$_2$CF$_3$, —OH, and triazole;
  wherein "*" represents a point of attachment of $Z^1$ to the linker (L);
  $R^4$ and $R^5$ are H;
  each $Z^1$ is a linking moiety selected from $Z^{11}$, $Z^{11}$-heteroaryl, $Z^{11}$-aryl, and alkyl;
  $Z^{11}$ is —C(R$^{22}$)$_2$—; and
  each $R^{22}$ is independently selected from H, halogen, and (C$_1$-C$_6$) alkyl.

2. The compound of claim 1, wherein each X is independently of formula:

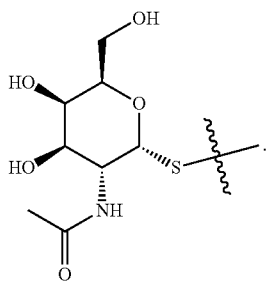 [SMILES: *S[C@H]1O[C@H](CO)[C@H](O)[C@H](O)[C@H]1NC(C)=O]

3. The compound of claim 1, wherein $Z^1$ is $Z^{11}$-Ar, wherein Ar is heteroaryl or aryl.

4. The compound of claim 3, wherein each X is

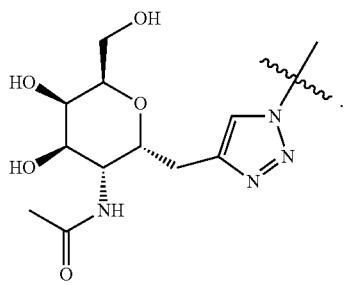 [SMILES: *n1cc(C[C@H]2O[C@H](CO)[C@H](O)[C@H](O)[C@H]2NC(C)=O)nn1]

5. The compound of claim 1, wherein n is 1, and L comprises a linear linker having a backbone of 20 to 50 consecutive atoms covalently linking X to Y via $Z^1$.

6. The compound of claim 1, wherein n is 2 or 3, and L is a branched linker that covalently links each X moiety to Y via the linking moiety $Z^1$ and a chain of 21 to 50 consecutive atoms.

7. The compound of claim 1, wherein L is of formula (II):

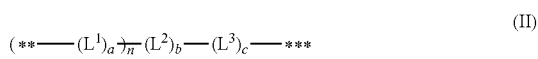

wherein
  n is 1 to 20;
  $L^1$ and $L^3$ are independently a linker, and $L^2$ is a branched linking moiety, wherein $L^1$ to $L^3$ together provide a linear or branched linker between X and Y;
  a is 1;
  b is 0 or 1;
  c is 1;
  ** represents the point of attachment to $L^1$ of X via $Z^1$; and
  *** represents the point of attachment to Y;
wherein:
  when n is 1, then b is 0;
  when n is >1, then b is 1.

8. The compound of claim 7, wherein $L^1$ to $L^3$ each independently comprise one or more linking moieties independently selected from —C$_{1-20}$-alkylene-, —NHCO—C$_{1-6}$-alkylene-, —CONH—C$_{1-6}$-alkylene-, —NH—C$_{1-6}$-alkylene-, —NHCONH—C$_{1-6}$-alkylene-, —NHCSNH—C$_{1-6}$-alkylene-, —C$_{1-6}$-alkylene-NHCO—, —C$_{1-6}$-alkylene-CONH—, —C$_{1-6}$-alkylene-NH—, —C$_{1-6}$-alkylene-NHCONH—, —C$_{1-6}$-alkylene-NHCSNH—, —O(CH$_2$)$_p$—, —(OCH$_2$CH$_2$)$_p$—, —NHCO—, —CONH—, —NHSO$_2$—, —SO$_2$NH—, —CO—, —SO$_2$—, —O—, —S—, pyrrolidine-2,5-dione, 1,2,3-triazole, —NH—, and —NMe-, wherein each p is independently 1 to 50;
  $L^2$ is a polypeptide, or is selected from:

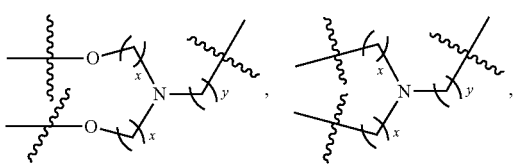

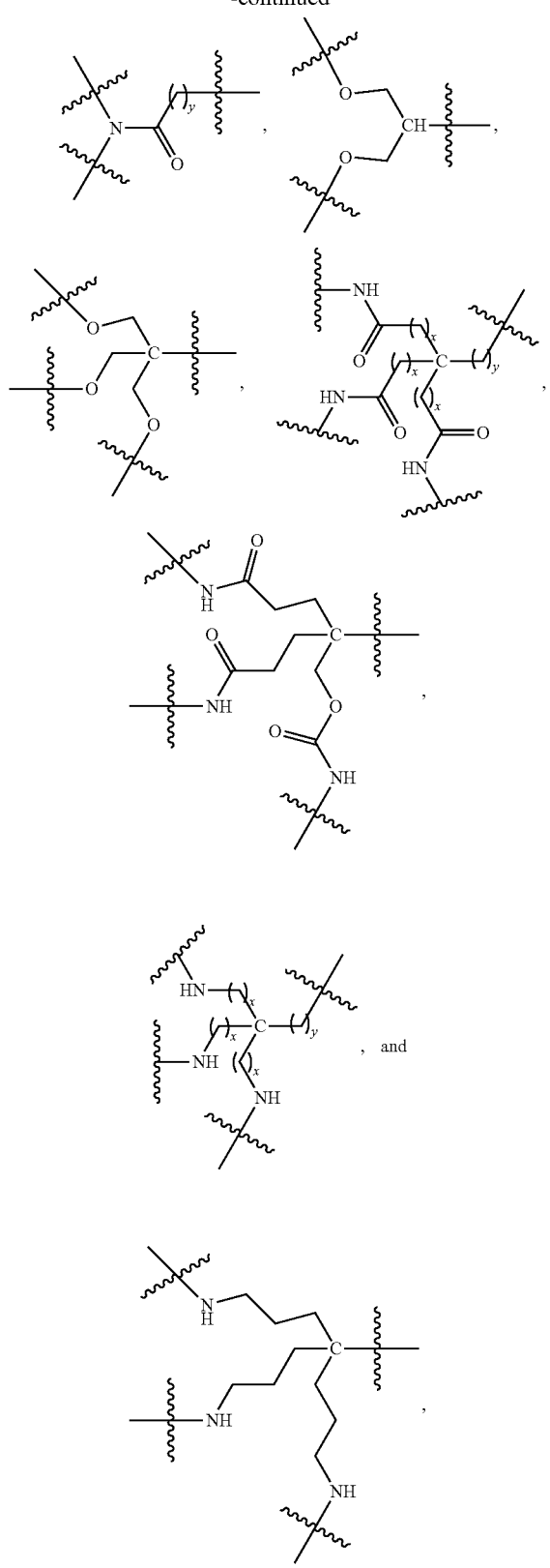

wherein each x and y is independently 1 to 10.

9. The compound of claim 7, wherein —Z¹-L¹- comprises a group selected from:

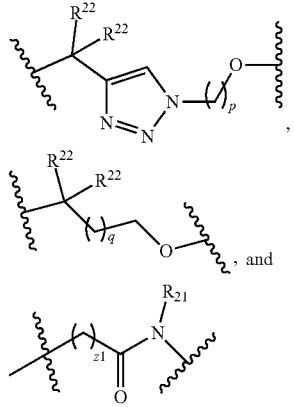

wherein p, q, and z1 are each independently 1 to 6.

10. A conjugate of formula (III):

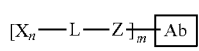

wherein:
n is 1 to 20;
m is an average loading of 1 to 80;
each X is a moiety that binds to a cell surface ASGPR of formula:

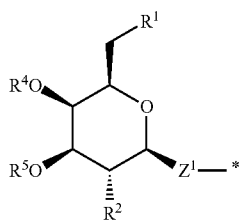

wherein:
R¹ is selected from —OH, —OC(O)R, —C(O)NHR, and triazole, where R is $C_{1-6}$ alkyl or aryl;
R² is selected from —NHCOCH₃, —NHCOCF₃, —NHCOCH₂CF₃, —OH, and triazole;
wherein "*" represents a point of attachment of Z¹ to the linker (L);
R⁴ and R⁵ are each H;
Z¹ is a linking moiety selected from Z¹¹, Z¹¹-heteroaryl, Z¹¹-aryl, and alkyl;
Z¹¹ is —C(R²²)₂—; and
each R²² is independently selected from H, halogen, and ($C_1$-$C_6$) alkyl;
each L is a linker;
each Z is a residual moiety resulting from the covalent linkage of a chemoselective ligation group to a compatible group of Ab; and
Ab is an antibody or antibody fragment that binds a target protein.

11. The compound of claim 10, wherein n is 1 to 6, and m is 1 to 20.

12. The compound of claim 10, wherein Z is a residual moiety resulting from the covalent linkage of a thiol-reactive chemoselective ligation group to one or more cysteine residue(s) of Ab; or Z is a residual moiety resulting from the covalent linkage of an amine-reactive chemoselective ligation group to one or more lysine residue(s) of Ab.

13. The compound of claim 10, wherein L is of the formula:

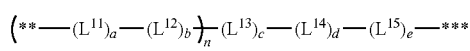

wherein n is 1, 2, or 3;

each $L^{11}$ to $L^{15}$ is independently a linking moiety which together provide a linear or branched linker between $Z^1$ and Ab;

a, b, c, d, and e are each independently 0, 1, or 2;

** represents the point of attachment to $L^1$ to X via $Z^1$; and

* represents the point of attachment to Ab.

14. The compound of claim 13, wherein:

each linking moiety of $L^{11}$, $L^{12}$, $L^{14}$ and $L^{15}$ is independently selected from —$C_{1-20}$-alkylene-, —NHCO—$C_{1-6}$-alkylene-, —CONH—$C_{1-6}$-alkylene-, —NH$C_{1-6}$-alkylene-, —NHCONH—$C_{1-6}$-alkylene-, —NHCSNH—$C_{1-6}$-alkylene-, —$C_{1-6}$-alkylene-NHCO—, —$C_{1-6}$-alkylene-CONH—, —$C_{1-6}$-alkylene-NH—, —$C_{1-6}$-alkylene-NHCONH—, —$C_{1-6}$-alkylene-NHCSNH—, —O(CH$_2$)$_p$—, —(OCH$_2$CH$_2$)$_p$—, —NHCO—, —CONH—, —NHSO$_2$—, —SO$_2$NH—, —CO—, —SO$_2$—, —O—, —S—, monocyclic heteroaryl, monocyclic aryl, monocyclic heterocycle, amino acid residue, —NH—, and —NMe-, wherein each p is independently 1 to 50; and each $L^{13}$ is a branched linking moiety independently selected from amino acid residue, polypeptide,

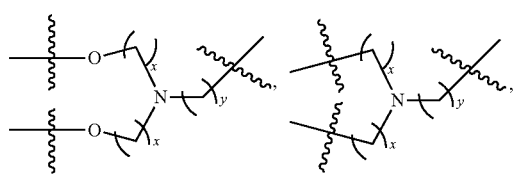

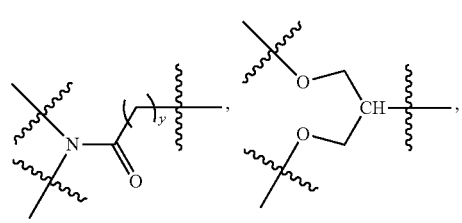

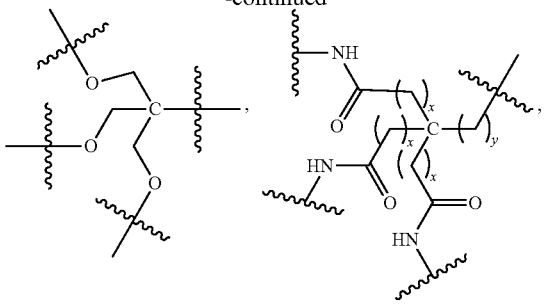

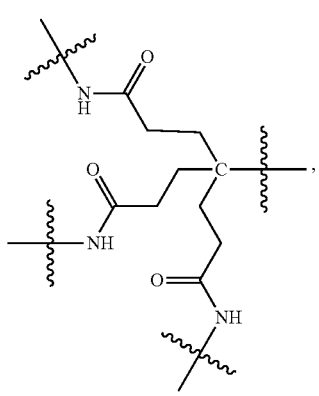

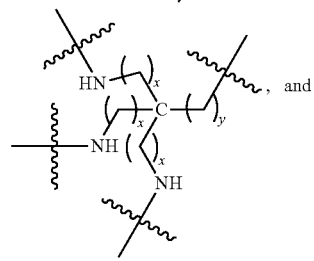

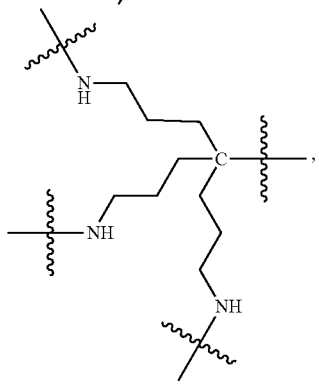

wherein each x and y is independently 1 to 10.

15. The compound of claim 13, wherein n is 1 and the linker comprises a linking moiety selected from:

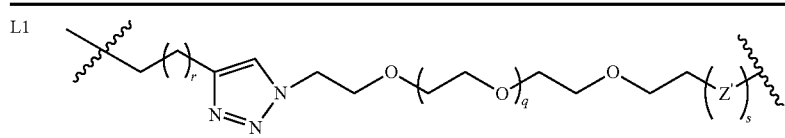

wherein r is 0 to 10, q is 0 to 20, s is 0 or 1, Z' is CO, NHCO, CONH or NH

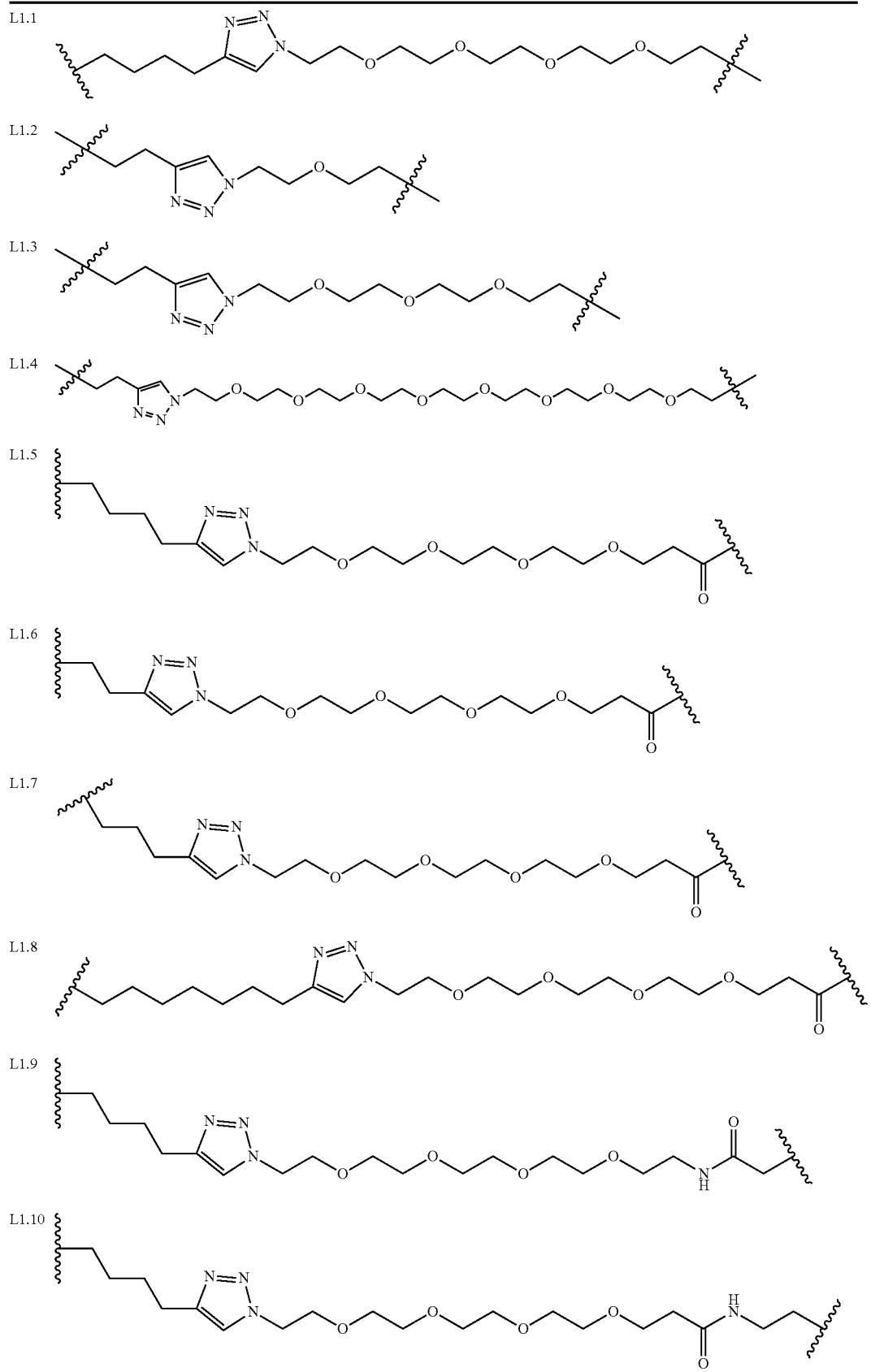

L1.11 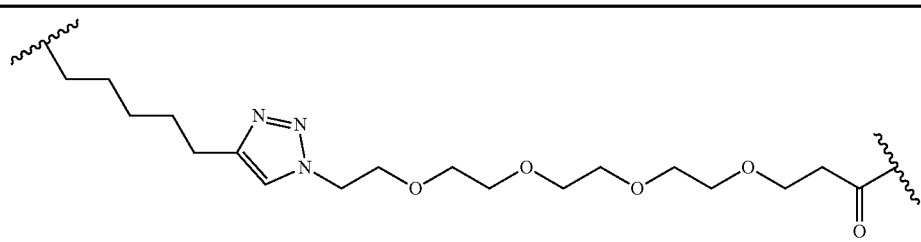
L2 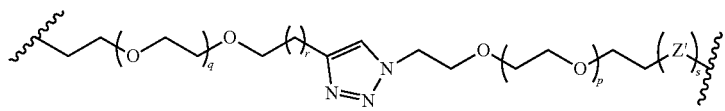
wherein r is 0 to 10, p and q are 0 to 20, s is 0 or 1, Z' is CO, NHCO, CONH, or NH
L2.1 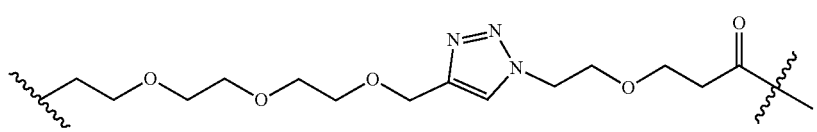 [SMILES: *CCOCCOCCOCc1cn(CCOCCC(*)=O)nn1]
L3 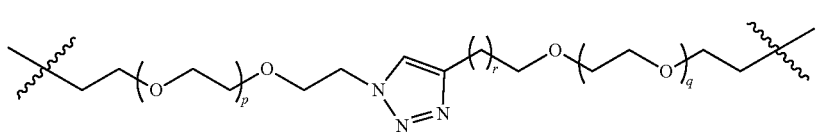
wherein r is 0 to 10, p and q are independently 0 to 20
L4 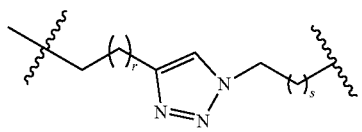
wherein r is 0 to 10, s is 1 to 10
L5 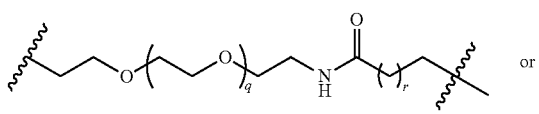 or
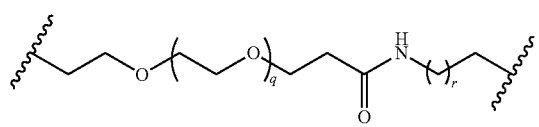
wherein r is 0 to 10, q is 0 to 20
L5.1 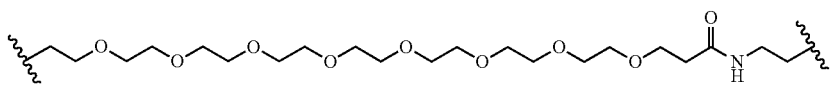 [SMILES: *CCNC(=O)CCOCCOCCOCCOCCOCCOCCOCCOCC*]
L6 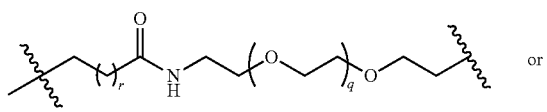 or
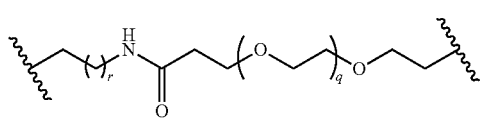
wherein r is 0 to 10, q is 0 to 20

L7 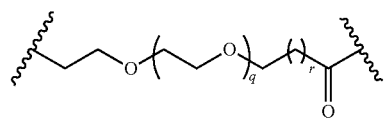
wherein r is 0 to 10, q is 0 to 20
L7.1 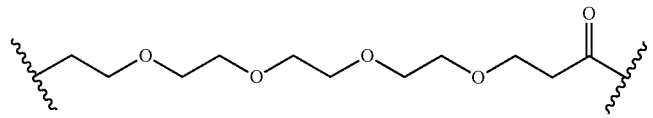 [SMILES: *CCOCCOCCOCCOCCC(*)=O]
L7.2 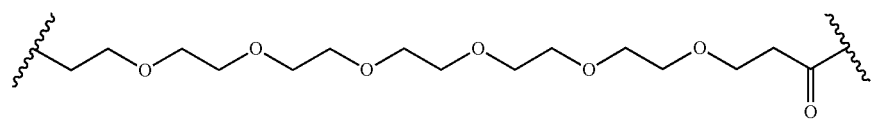 [SMILES: *CCOCCOCCOCCOCCOCCOCCC(*)=O]
L7.3 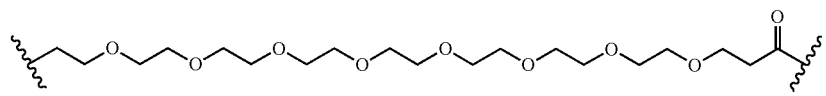 [SMILES: *CCOCCOCCOCCOCCOCCOCCOCCOCCC(*)=O]
L8 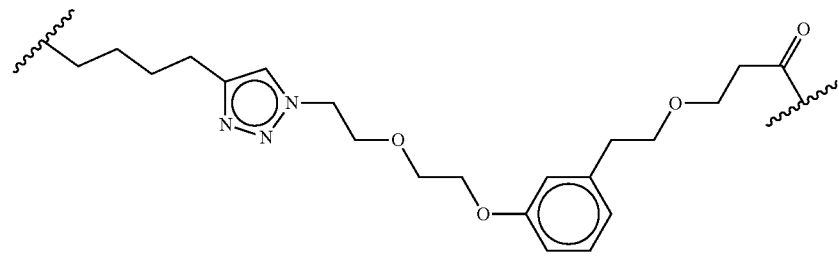
L9 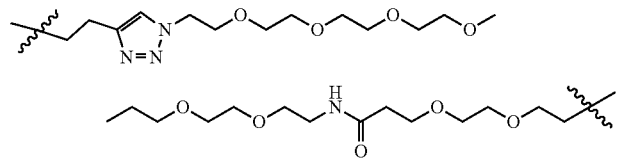
L10 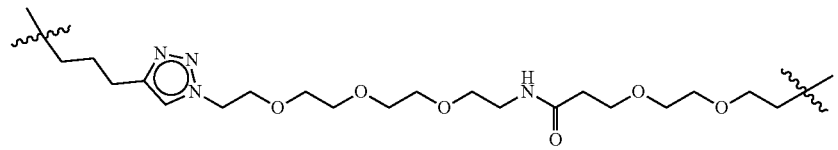
L11 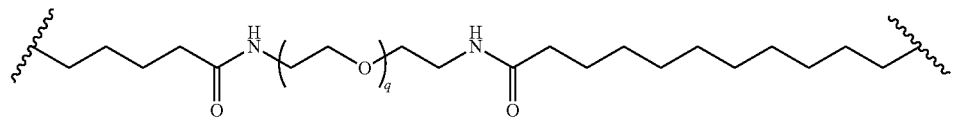
wherein q is 0 to 10.

16. The compound of claim 14, wherein:
n is 2 or 3;
c is 1; and
$L^{13}$ is
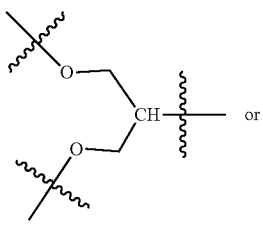 or
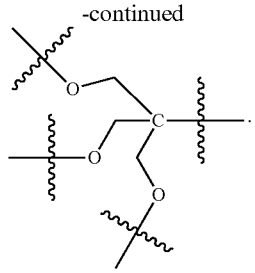
17. The compound of claim 10, wherein each X moiety is covalently linked to Ab via L-Z having a chain of 21 to 50 consecutive atoms.
18. The compound of claim 10, wherein the linker is selected from:
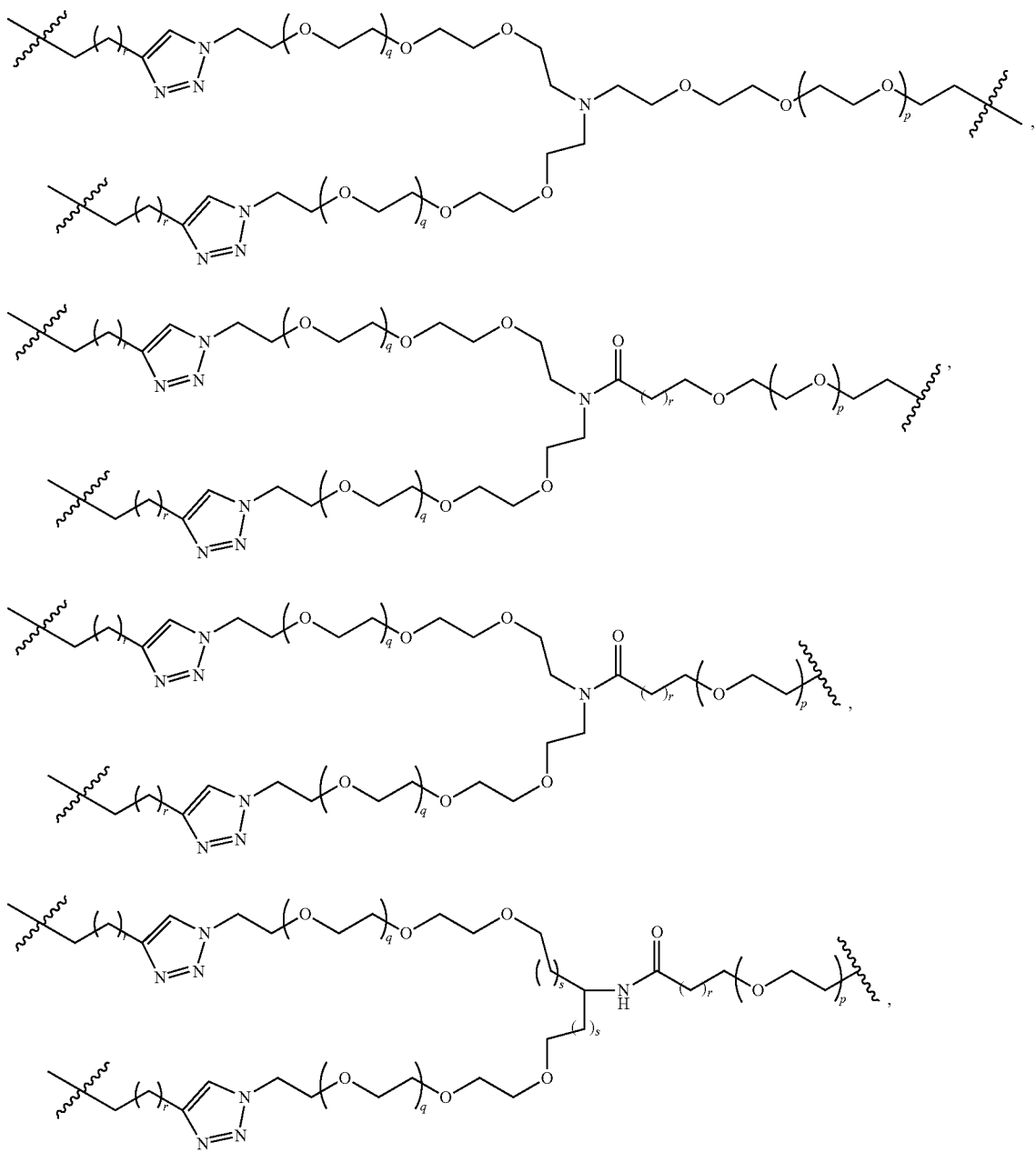

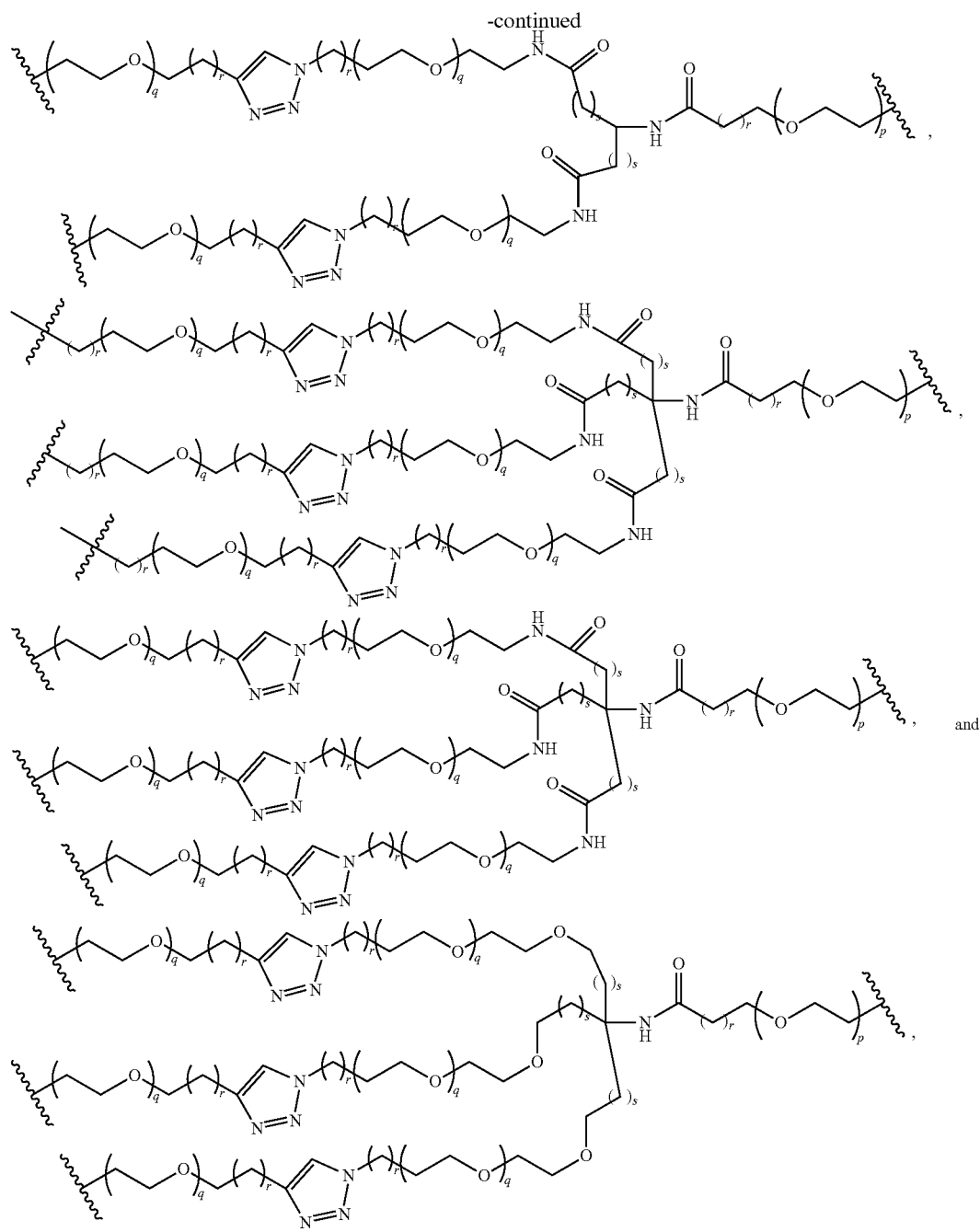
-continued
wherein:
 each r is independently 0 to 10;
 each s is independently 0 or 1; and
 each q and p is independently 0 to 20.
* * * * *